United States Patent
Williams et al.

(10) Patent No.: US 8,168,588 B2
(45) Date of Patent: May 1, 2012

(54) COMPOSITIONS COMPRISING FGF-9 AND BETACELLULIN AND METHODS FOR TREATING CARDIAC CONDITIONS

(75) Inventors: Lewis T. Williams, Mill Valley, CA (US); Hongbing Zhang, Albany, CA (US); Yan Wang, Redwood City, CA (US); Loriane Masuoka, Oakland, CA (US); Stephen Doberstein, San Francisco, CA (US)

(73) Assignee: Five Prime Therapeutics, Inc., South San Francisco, CA (US)

( * ) Notice: Subject to any disclaimer, the term of this patent is extended or adjusted under 35 U.S.C. 154(b) by 922 days.

(21) Appl. No.: 11/795,915

(22) PCT Filed: Jan. 25, 2006

(86) PCT No.: PCT/US2006/002313
§ 371 (c)(1),
(2), (4) Date: May 19, 2008

(87) PCT Pub. No.: WO2006/081190
PCT Pub. Date: Aug. 3, 2006

(65) Prior Publication Data
US 2009/0018061 A1 Jan. 15, 2009

Related U.S. Application Data

(60) Provisional application No. 60/646,520, filed on Jan. 25, 2005, provisional application No. 60/675,086, filed on Apr. 27, 2005, provisional application No. 60/675,859, filed on Apr. 29, 2005, provisional application No. 60/701,474, filed on Jul. 22, 2005, provisional application No. 60/716,491, filed on Sep. 14, 2005, provisional application No. 60/739,815, filed on Nov. 25, 2005.

(51) Int. Cl.
*A61K 38/18* (2006.01)
*A61K 38/00* (2006.01)
*A61K 39/00* (2006.01)

(52) U.S. Cl. ......... 514/7.6; 514/9.1; 514/9.6; 514/16.4; 424/198.1; 424/192.1

(58) Field of Classification Search .................. None
See application file for complete search history.

(56) References Cited

U.S. PATENT DOCUMENTS

| | | | |
|---|---|---|---|
| 6,451,303 B1 | 9/2002 | Whitehouse et al. | |
| 6,737,404 B2 | 5/2004 | Springer et al. | |
| 7,214,369 B2 * | 5/2007 | Wolff et al. | 424/93.2 |
| 2003/0008351 A1 | 1/2003 | Deisher et al. | |
| 2003/0054973 A1 | 3/2003 | Anversa | |

FOREIGN PATENT DOCUMENTS

| | | | |
|---|---|---|---|
| GB | 2332373 | * | 6/1999 |
| WO | WO 98/06420 A1 | | 2/1998 |
| WO | WO 99/49015 A2 | | 9/1999 |

OTHER PUBLICATIONS

International Search Report and Written Opinion of the International Searching Authority, mailed Jan. 2, 2008, in International Application No. PCT/US2006/002313.
Nag et al., "Factors Controlling Embryonic Heart Cell Proliferation in Serum-Free Synthetic Media," *In Vitro Cellular & Developmental Biology*, 21(10): 553-562 (1985).
Queen, M. M. et al., "Breast Cancer Cells Stimulate Neutrophils to Produce Oncostatin M: Potential Implications for Tumor Progression," Abstract only of Cancer Res., vol. 65, No. 19, pp. 8896-904 (1 Sheet), (Oct. 1, 2005).
Song, H. et al., "Oncostatin M Induces Proliferation of Human Adipose Tissue-Derived Mesenchymal Stem Cells," Abstract only of Int. J. Biochem. Cell Biol., vol. 37, No. 11, pp. 2357-2365 (1 Sheet), (Nov. 2005).
Fouladi-Nashta, A. A. et al., "Characterization of the Uterine Phenotype During the Peri-Implantation Period for LIF-null, MF1 Strain Mice," Abstract only of Dev. Biol., vol. 281, No. 1, pp. 1-21 (1 Sheet), (May 1, 2005).
Baus-Locar, M. et al., "Trefoil Factor 2 (TFF2) Deficiency in Murine Digestive Tract Influences the Immune System," Abstract only of Cell Physio Biochem, vol. 16, No. 1-3, pp. 31-42 (1 Sheet), (2005).
Chwieralski, C. E. et al., "Epidermal Growth Factor and Trefoil Factor Family 2 Synergistically Trigger Chemotaxis on BEAS-2B Cells via Different Signaling Cascades," Abstract only of Am. J. Respir. Cell Mol. Biol., vol. 31, No. 5, pp. 528-37 (1 Sheet), (Nov. 2004).
Examiner's first report on Australian Patent Application No. 2006208241, mailed Jun. 22, 2010 (2 pages).
Reply to Jun. 22, 2010 Examination Report in Australian Patent Application No. 2006208241 submitted Jul. 8, 2011, including claims 1-17 (14 pages).
Notice of Acceptance for Australian Patent Application No. 2006208241 mailed Jul. 20, 2011 (3 pages).

* cited by examiner

*Primary Examiner* — Elly-Gerald Stoica
(74) *Attorney, Agent, or Firm* — Finnegan, Henderson, Farabow, Garrett & Dunner, L.L.P.

(57) ABSTRACT

Pharmaceutical polypeptide compositions promote the survival of cardiac cells, recruit cardiac cells to the cardiac area, stimulate the differentiation of cardiac cells, stimulate the proliferation of cardiac cells, and promote the activity of cardiac cells, thereby treating cardiac conditions. Methods of providing these compositions to the cardiac area include catheterization and direct injection. In preferred embodiments, the compositions comprise one of more of the following growth factors: EGF, bFGF, cardiotrophin-1, thrombin, PDGF-BB, amphiregulin, epiregulin, HB-EGF, TGFalpha, betacellulin, heregulin alpha, NRG-1-beta1-HRG-beta1, FGF 9.

18 Claims, 22 Drawing Sheets

FIGURE 8A
| Therapeutic Agent | pAkt | pERK | pSTAT3 | Cardiosphere |
|---|---|---|---|---|
| Betacellulin | yes | yes | no | yes |
| NRG1-β1 | yes | yes | no | no |
FIGURE 8B
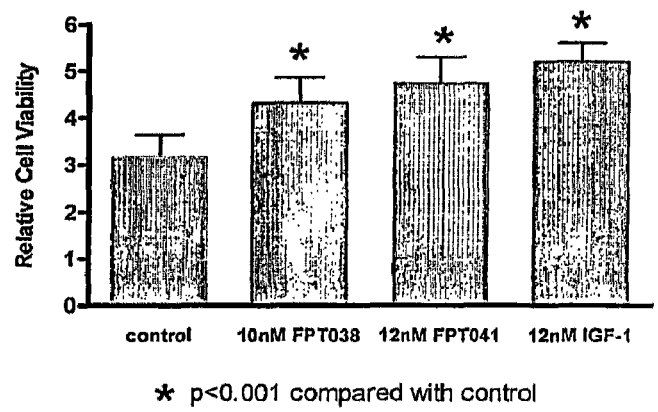
* $p<0.001$ compared with control
FIGURE 8C
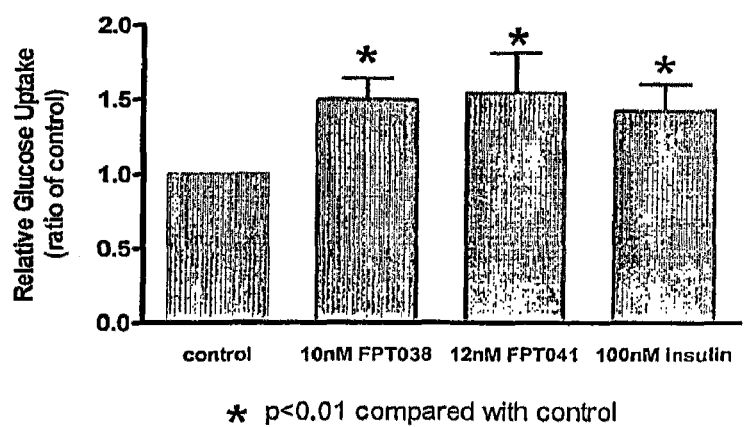
* $p<0.01$ compared with control

A.

B.

C.

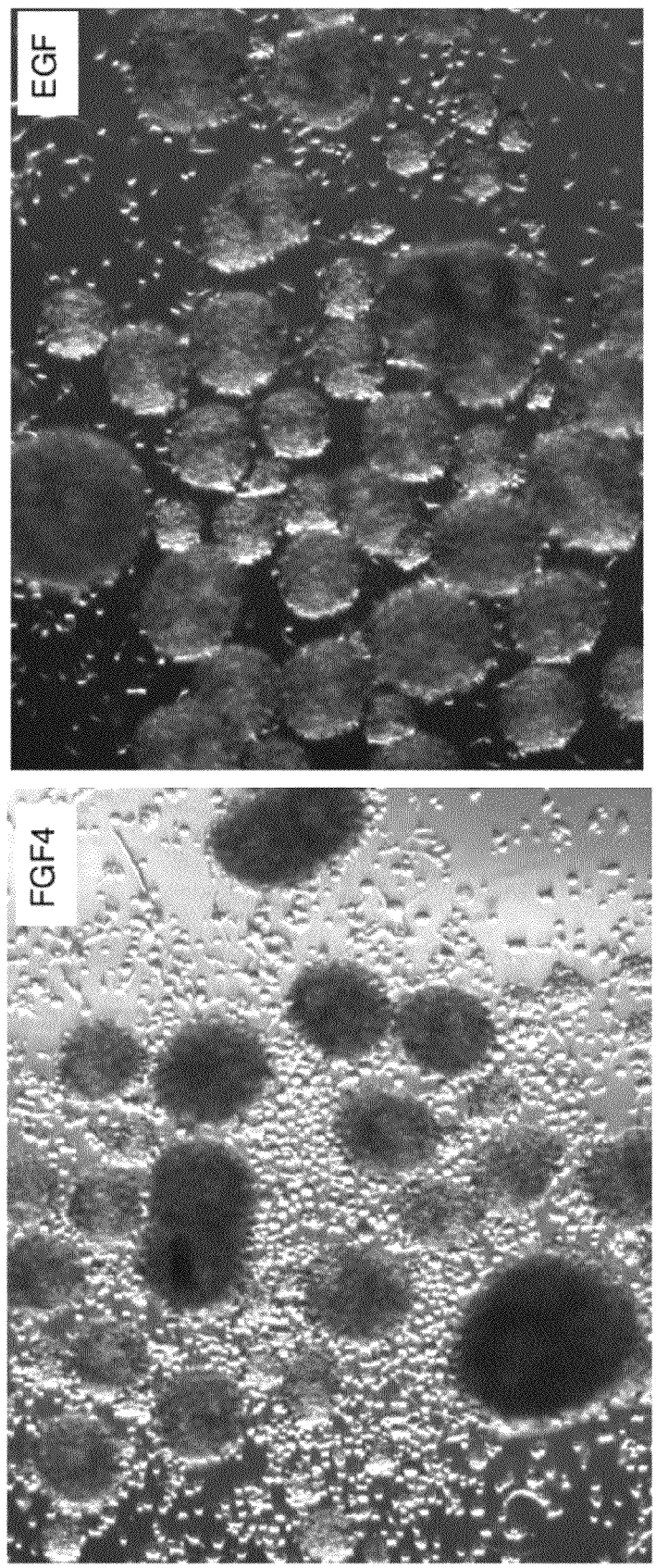
FIGURE 10, CONTINUED

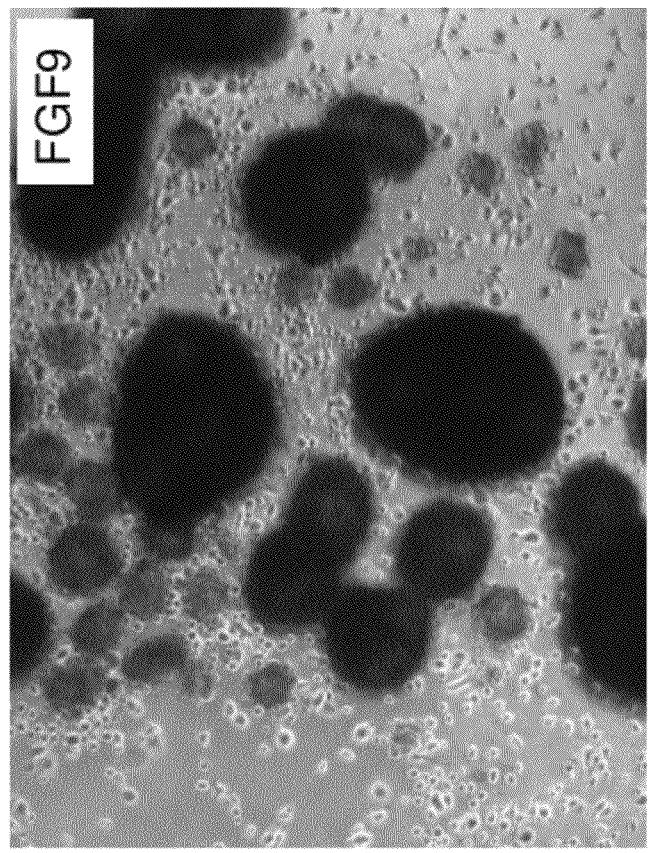
FIGURE 10, CONTINUED

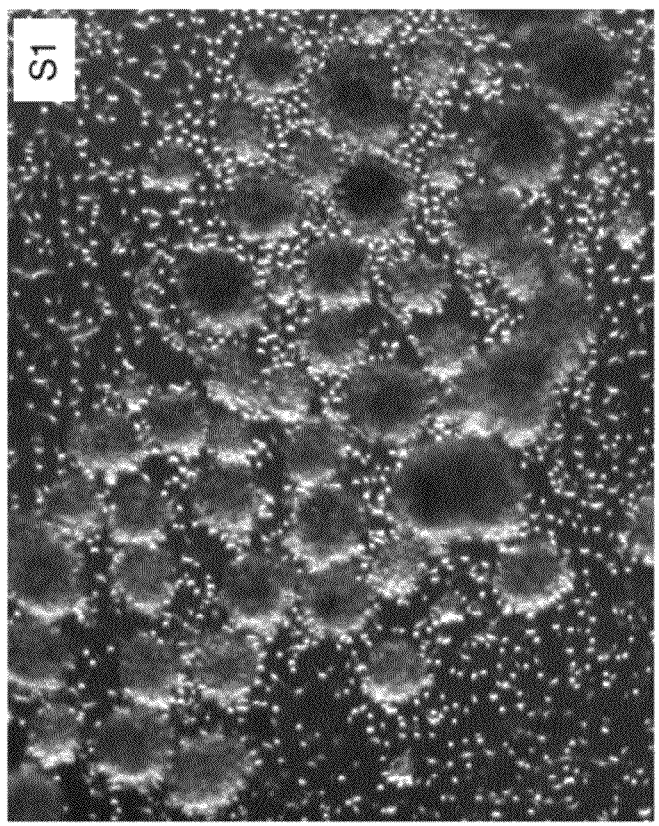
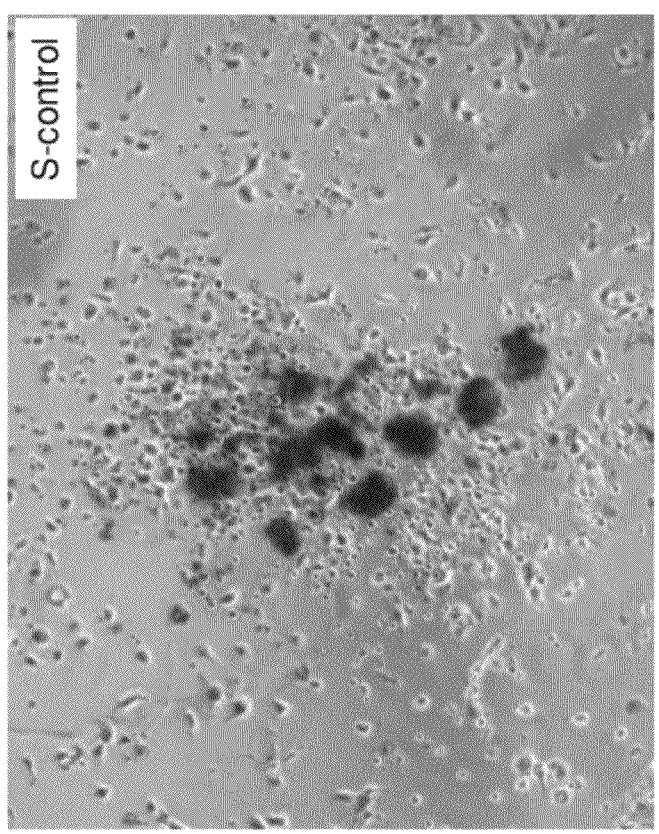
FIGURE 10, CONTINUED

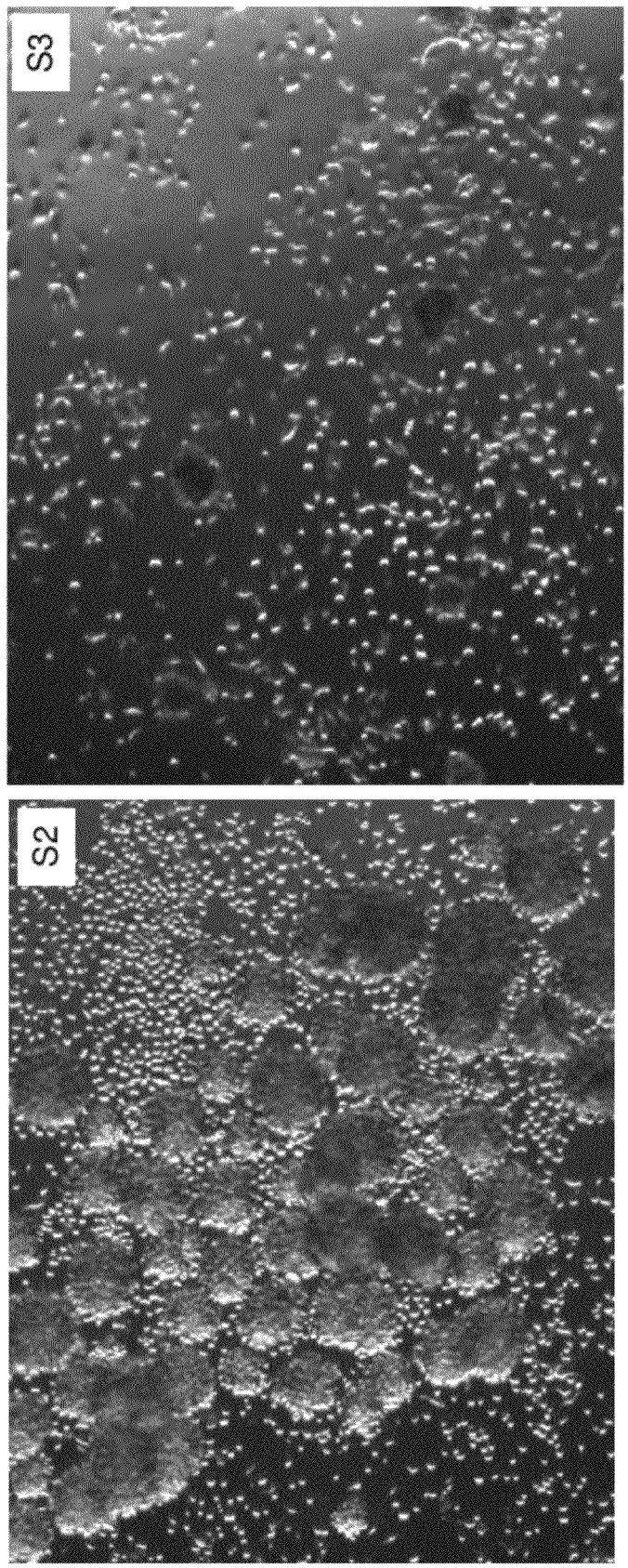
FIGURE 10, CONTINUED

COMPOSITIONS COMPRISING FGF-9 AND BETACELLULIN AND METHODS FOR TREATING CARDIAC CONDITIONS

This application claims the benefit of priority to U.S. Provisional Application Nos. 60/646,520, "Method of Delivering Substances to the Heart to Treat Ischemic Cardiac Injury," filed Jan. 25, 2005; 60/675,086, "Method of Delivering Substances to the Heart to Treat Ischemic Cardiac Injury," filed Apr. 27, 2005; 60/675,859, "Method of Delivering Substances to the Heart to Treat Ischemic Cardiac Injury," filed Apr. 29, 2005; 60/701,474, "Compositions and Methods for Treatment of Pathological Cardiac Conditions and Promotion of Cell Survival, Differentiation, Proliferation, and Regeneration," filed Jul. 22, 2005; 60/716,491, "Compositions and Methods for Treatment of Pathological Cardiac Conditions and Promotion of Cell Survival, Differentiation, Proliferation, and Regeneration," filed Sep. 14, 2005; and 60/739,815, "Compositions and Methods for Treatment of Cardiac Conditions and Promotion of Cell Survival, Differentiation, Proliferation, and Regeneration," filed Nov. 25, 2005, the disclosures of which are all incorporated herein by reference in their entireties. Further, this application is related to PCT/US05/14963, "Novel Stromal Cell-Derived Factor-1 Polypeptides, Polynucleotides, Modulators Thereof, and Methods of Use," filed under the Patent Cooperation Treaty on Apr. 29, 2005; and PCT/US05/19491, "Novel G-CSF Polypeptides, Polynucleotides, Modulators Thereof, and Methods of Use," filed under the Patent Cooperation Treaty on Jun. 3, 2005, the disclosures of which are both incorporated herein by reference in their entireties.

TECHNICAL FIELD

This application generally relates to compositions and methods for treating cardiac conditions by delivering one or more therapeutic agents to the heart.

BACKGROUND ART

Cardiac Ischemia

Cardiac ischemia arises when the blood flow inside a coronary artery is restricted. The restricted blood flow is most commonly caused by plaque build-up on the inner walls or lining of the artery. Unable to obtain optimal amounts of oxygen and nutrients because of the reduced blood flow, cardiomyocytes function at sub-optimal levels and may die. The heart eventually is not able to pump blood efficiently. Episodes of cardiac ischemia can cause abnormal heart rhythms (arrhythmias), which can lead to either fainting or cardiac arrest and sudden cardiac death. Weakening of the heart muscle (cardiomyopathy) may also result. When a blood clot completely obstructs blood flow through an artery already narrowed by plaque, a heart attack may occur.

A number of options for treating cardiac ischemia are available. Some are based on reducing the heart's need for oxygen commensurate to the reduction in oxygen and nutrients that the heart receives because of reduced blood flow. These treatment options involve taking medications that slow the heart rate, reduce blood pressure, and relax the blood vessels. Such medications include beta-blockers, calcium channel blockers, and nitrates. Beta-blockers block the effects of adrenaline on the body's beta receptors. As a result, the heart does not have to work as hard because it needs less blood and oxygen. Calcium channel blockers block the movement of calcium ions into heart cells, thus relaxing and dilating the arteries. By this mechanism, calcium channel blockers lower blood pressure. Nitrate medicines, including glyceryl trinitrate (GTN), isosorbide dinitrate, and isosorbide mononitrate, also relax and dilate the coronary arteries. Other medications, like aspirin and other antiplatelet agents, may decrease the chance of blood clot formation in an already narrowed artery. Exercise and/or stress management techniques are also recommended. More invasive procedures, such as balloon angioplasty or bypass surgery, may be used to clear the blockage in the coronary arteries. Drug-coated stents may reduce the rates of re-narrowing (restenosis) of the arteries following angioplasty.

Gene therapy is showing promise as an option to improve blood supply to the heart and relieve angina in patients with cardiac ischemia. In the area of therapeutic angiogenesis, experimental treatments that promote creation of new blood vessels are being developed. Injection of Ad5FGF-4, a replication-deficient serotype 5 adenovirus containing the gene for fibroblast growth factor-4, has been found to improve ischemic areas of the heart, with significant numbers of patients reporting relief of symptoms of angina (Grines et al., J. Am. Coll. Cardiol. (2003) 42:1339-1347; Grines et al., Am. J. Cardiol. (2003) 92:24 N-31N). However, the concept of introducing a growth factor gene into the heart and the potential for the introduced gene to do harm has raised concern.

Ischemic Cardiac Injury

Ischemic cardiac injury is sustained by the myocardium as a result of cardiac ischemia. At the cellular level, ischemic cardiac injury is characterized by a central region of cellular necrosis, surrounded by a penumbra or "volume at risk" (VAR) where cells typically undergo a delayed death. A substantial portion of cardiomyocyte loss after myocardial infarction and reperfusion has been shown to arise from apoptosis within this region. In addition, further injury occurs as a result of recruiting inflammatory cells into the infarcted region. The inflammatory cells release chemotactic and cytotoxic cytokines and other inflammatory molecules, thus expanding the volume of injury (Calvillo et al., Proc. Natl. Acad. Sci. USA (2003) 100:4802-4806). These forms of cell death and injury eventually may lead to heart failure.

Changes in gene expression after ischemia have been observed. Using a cDNA array approach, Lyn et al., Physiol. Genomics (2000) 2:93-100 showed that myocardial ischemia induced transcription of the apoptosis regulator BAX gene, the early growth response factor Egr-1 and Egr-3 genes, and genes associated with cardiac muscle development such as those encoding α-myosin heavy chain (α-MHC) and fetal myosin alkali light chain (MLC). Glutathione S-transferase gene transcription, on the other hand, decreased in response to ischemia.

There is currently no available therapy that replaces lost cardiomyocytes, aside from heart transplantation, which has obvious risks, limitations, and disadvantages. Heart transplantation is able to resolve the problems of heart failure and relieve patients' symptoms, but its utility is severely limited by suitable donor organ availability and problems of organ rejection (Lovell and Mathur, Cell Prolif. (2004) 37:67-87). Further, the ability of pharmacological agents to improve cardiac function to date is limited as these agents do not address the fundamental issue of cell loss. There thus remains a need for alternative treatment options for ischemic cardiac injury.

Congestive Heart Failure

Congestive heart failure is a consequence of most serious cardiac conditions. This pathological state is characterized by abnormal myocardial function, which causes the heart to fail to pump blood at a rate commensurate with the needs of the metabolizing tissues. It can result from primary damage to the heart muscle or secondary damage to the heart muscle due to a chronically excessive workload. In either case, the basis of congestive heart failure is defective myocardial contraction.

Treating cardiac ischemia, the resulting injury, and other cardiac conditions, such as congestive heart failure, remains a major public health challenge in the industrialized world. Cardiac conditions are a complication of atherosclerosis, which is a major cause of death and disability in industrialized nations. Therapies that prevent cardiomyocyte death or replace dead cardiomyocytes are currently severely limited. Treatments based on stem cell transplantation and gene transfer are still being investigated (Dawn et al., Proc. Natl. Acad. Sci. (2005) 102(10):3766-3771; Mariani et al., Ital. Heart J. (2004) 5:340-342; Matsui & Rosenzweig, Curr. Atheroscler. Rep. (2003) 5:191-195). Treatments based on delivery of growth factors have not yet overcome the potential side effect of growth factor-induced tumorigenesis. Methods that effectively cure heart failure by restoring the function of injured cardiomyocytes, or by stimulating myocardial cells to proliferate or differentiate in a way that improves cardiac function, are yet to be established. Accordingly, there remains a need to develop new methods, compositions, and agents for treating heart conditions.

BRIEF DESCRIPTION OF THE FIGURES AND TABLES

Brief Description of the Figures

In FIGS. 1A, 1B, and 1C, the y-axis indicates the luminescent signal of pERK, pAkt, and pSTAT3, which represents the protein expression of phosphor-ERK, phosphor-Akt1, and phosphor-STAT3, respectively. In FIGS. 1A-1C, each vertical bar represents a signal from one well in a 96-well plate with 12 columns and 8 rows. The x-axis indicates the 12 columns; and in each column the 8 bars indicate 8 wells from rows A to H. A vector only control was used as a negative control in wells E1-H1 (second 4 bars in column 1); rhIGF-1 at 300 ng/ml diluted in the vector control was used as a positive control for pAkt in wells A1-D1 (first 4 bars in column 1); and rhLIF (recombinant human leukemia inhibitory factor) at 20 ng/ml diluted in a vector control was used as a positive control for pERK and pSTAT3 in wells A12-H12 (last 8 bars in column 12). In the inner 80-wells of the 96 well plate(s) (columnns 2-11), the labeled proteins which produced signals that exceed the 2 sigma value (which is indicated by a horizontal line labeled "2 sigma" in the Figures) are the ones that showed over a 2 sigma signal in duplicate assay plates. Well G10 represents a hypothetical protein XP_098916, SEQ ID NO: 20, which has an almost 2 sigma signal for pERK.

FIG. 8A summarizes the results for the therapeutic agents betacellulin and neuregulin-β1 (NRG1-β1) in the phospho-Akt, phospho-ERK, phospho-STAT3, and cardiosphere proliferation assays. Both agents increased cell viability and glucose uptake in rat neonatal cardiomyocytes in vitro, as shown in FIGS. 8B and 8C.

FIG. 8B shows the effects of recombinant betacellulin and NRG1-beta1 on rat neonatal cardiomyocyte viability in ischemic buffer were studied, as further described in Example 6. Rat neonatal cardiomyocytes were treated with control ischemic buffer or ischemic buffer with the indicated concentration of recombinant betacellulin (FPT038), recombinant NRG1-beta1 (FPT041), or the positive control recombinant IGF-1 for three hours. Each bar represents the results of 24 replicate luminescent ATP assays of the indicated recombinant protein. The height of the bar (y-axis) indicates cell viability as a percentage of the control. All three proteins enhanced cardiomyocyte survival in ischemic buffer to a statistically significant extent; * denotes ($p<0.001$).

FIG. 8C shows the effects of recombinant betacellulin and NRG1-beta1 on rat neonatal cardiomyocyte glucose uptake, as further described in Example 8. Rat neonatal cardiomyocytes were treated with control medium or medium with the indicated concentration of recombinant betacellulin (FPT038), recombinant NRG1-beta1 (FPT041), or the positive control recombinant insulin for 20 minutes. The height of the bar (y-axis) indicates relative glucose uptake, which is the ratio of glucose uptake observed in the treatment compared to the glucose uptake observed in the control. All three proteins enhanced glucose uptake to a statistically significant extent; * denotes ($p<0.01$).

BRIEF DESCRIPTION OF THE TABLES

Figure 1A:
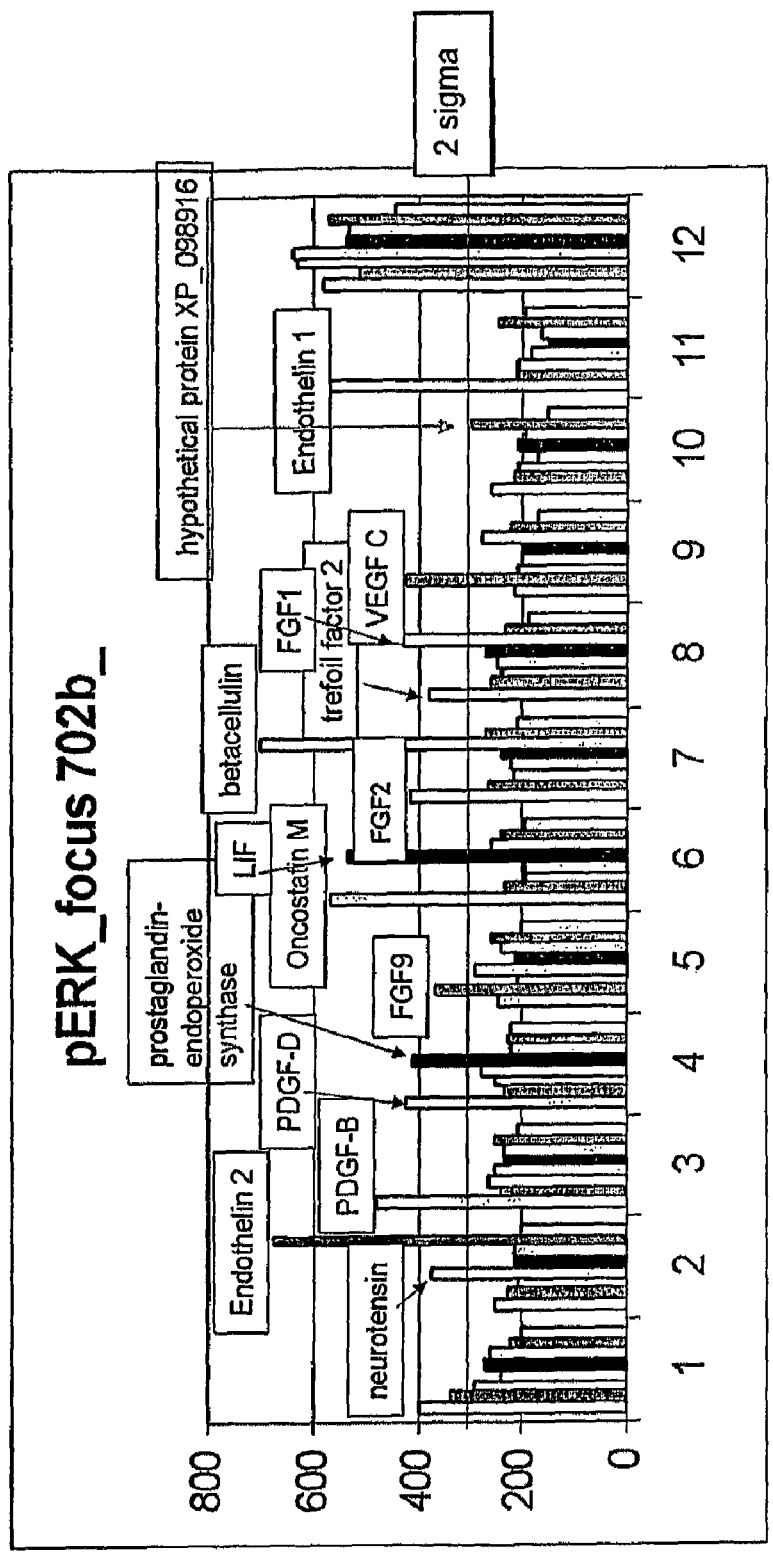
FIGS. 1A-1C show 3-plex luminex phosphor-protein expression(s) including pERK (FIG. 1A), pAkt (FIG. 1B), and pSTAT3 (FIG. 1C) in rat neonatal cardiomyocytes treated with a protein supernatant, as further described in Example 6. Based on the results from the 3-plex luminex screen, clones were identified that showed more than a 2 sigma. These clones were subsequently retested in duplicate assay plates, and from at least one transfection using protein supernatant, produced in-house, referred to as a focus protein plate (number 702). The protein supernatant from the 702 focus plate was applied to duplicate assay plates, identified as assay plates 702a and 702b.
Figure 1B:
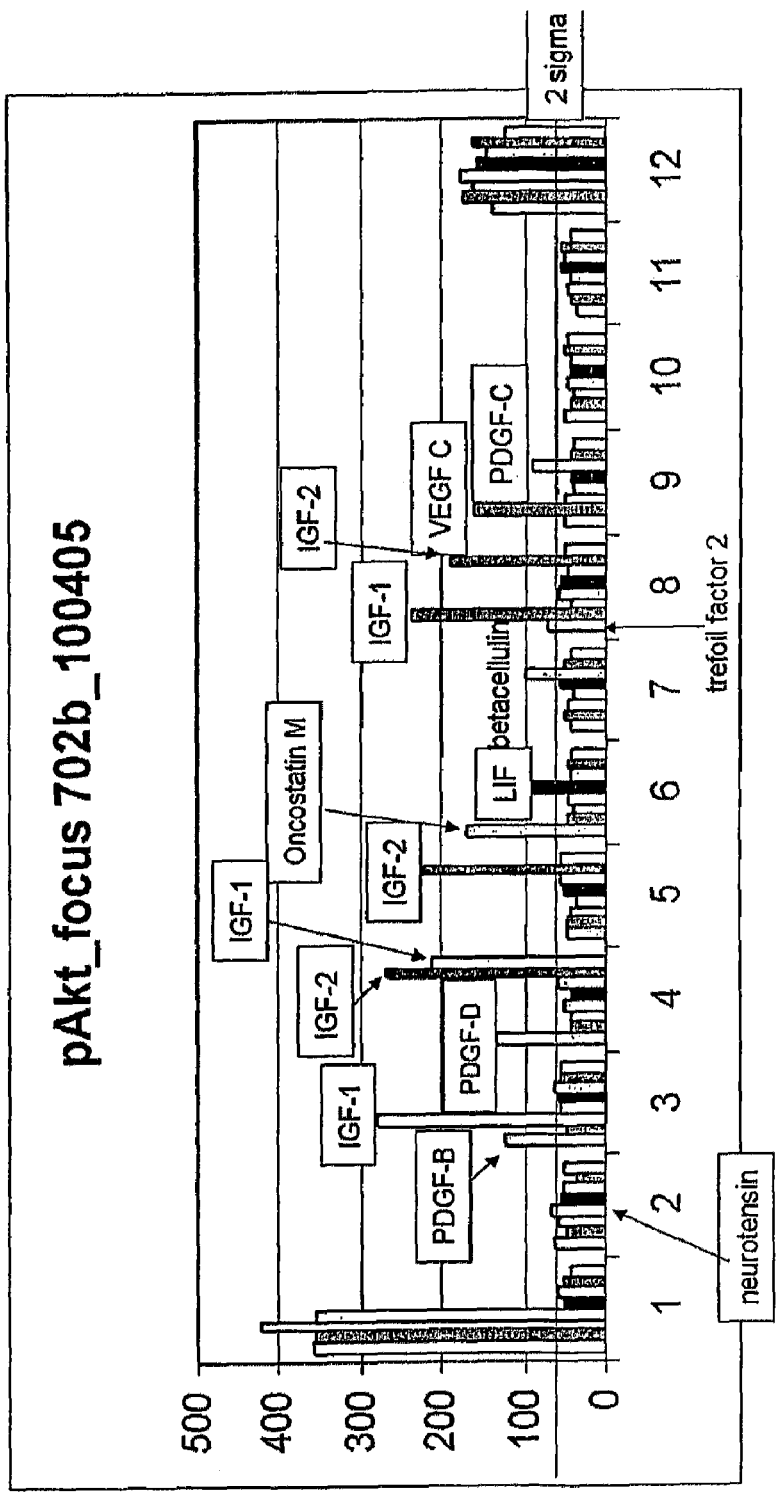
Figure 1C:
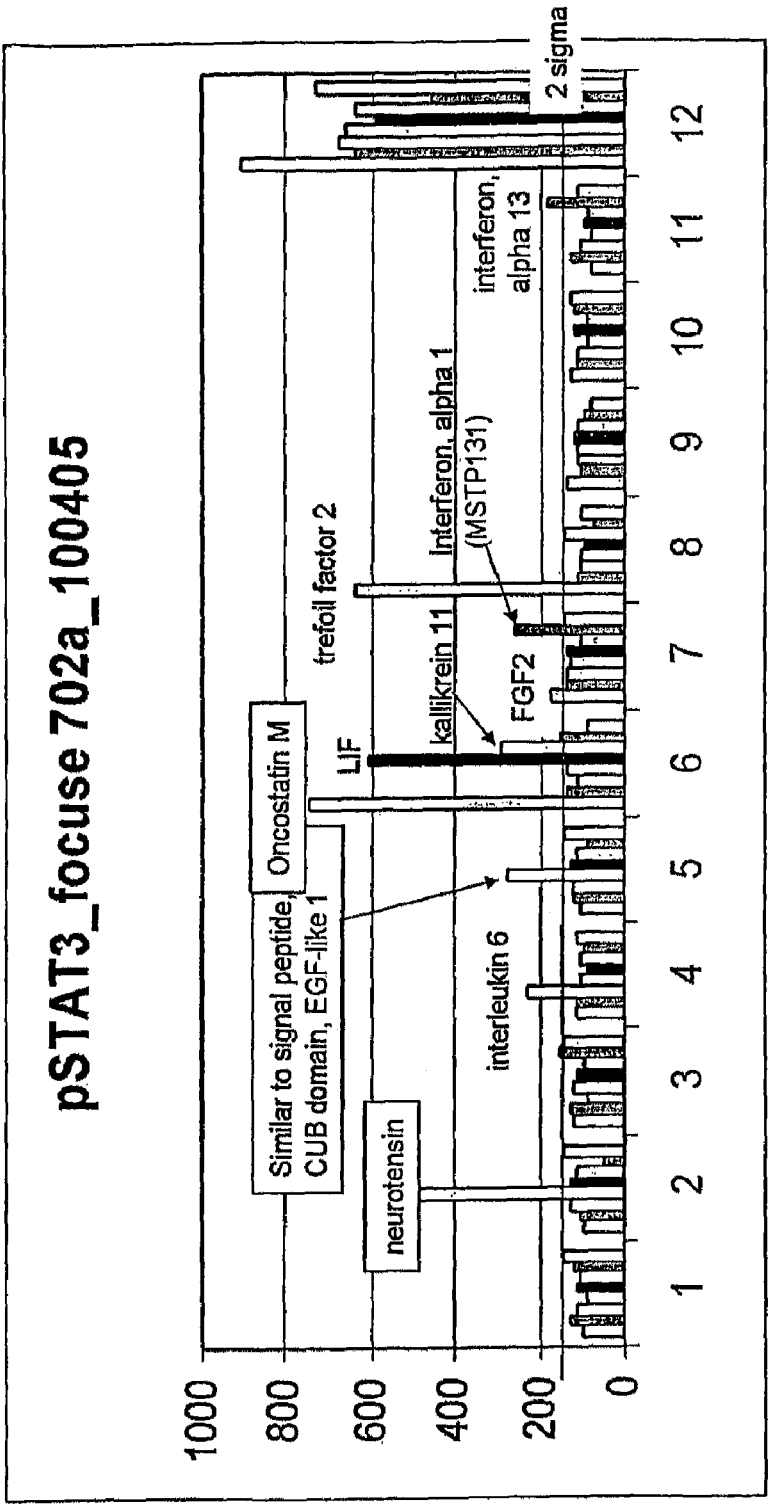
Figure 2:
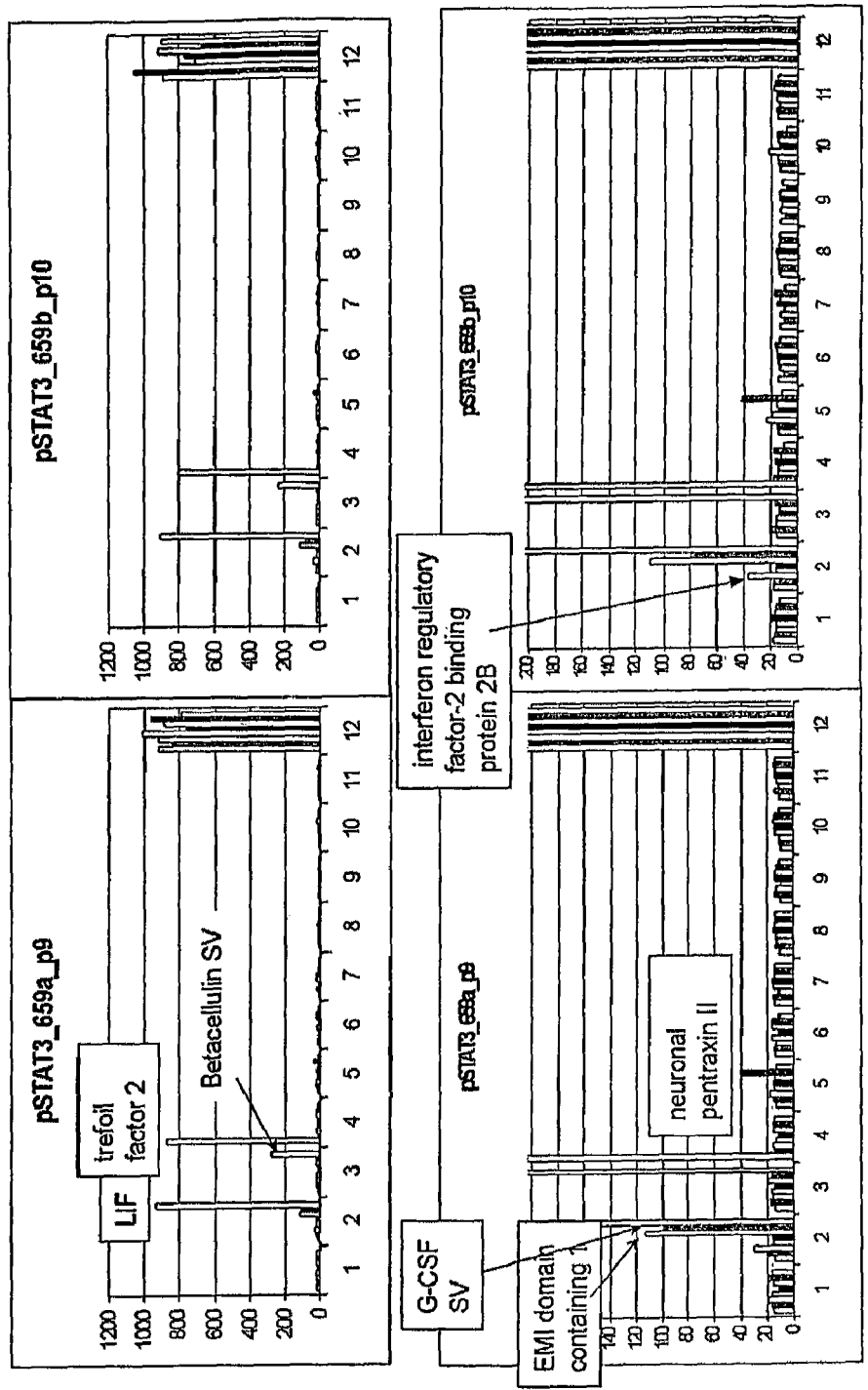
FIG. 2 shows phosphor-STAT3 (pSTAT3) expression in a 3-plex luminex screen in rat neonatal cardiomyocytes treated with an in-house protein supernatant from protein plate number 659. The upper two panels, duplicate assay plates, show the betacellulin splice variant SEQ ID NO: 180 (Betacellulin SV), in well H3, increased pSTAT3 dramatically with over 7 sigma. The lower two panels, in duplicate, show a modification in the y-axis scale from 0-1200 to 0-200. Here, the G-CSF splice variant (G-CSF SV, SEQ ID NO: 183) located in well G2 increased pERK over 2 sigma (data not shown) and pSTAT3 over 2 sigma (shown).
Figure 3A:
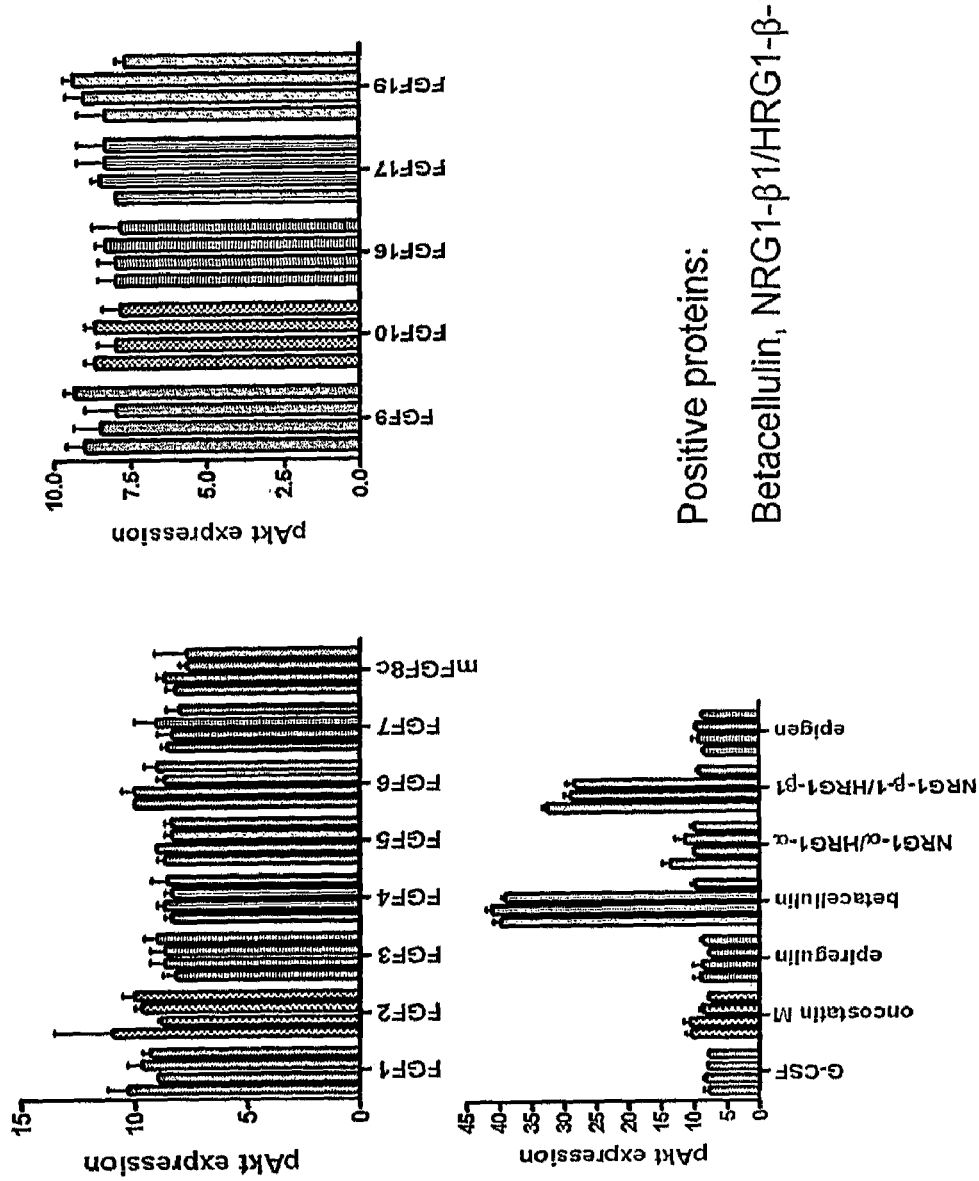
FIGS. 3A-3C show 3-plex luminex phosphor-protein expression(s) including pAkt (FIG. 3A), pERK (FIG. 3B), and pSTAT3 (FIG. 3C) in rat neonatal cardiomyocytes treated with recombinant proteins at the same dosages shown in FIGS. 1A-1C. For each recombinant protein treatment, four bars represent different protein concentrations from the left at 100 ng/ml, 33 ng/ml, 11 ng/ml, and 0 ng/ml. The proteins that showed clear positive signals are labeled accordingly.
Figure 3B:
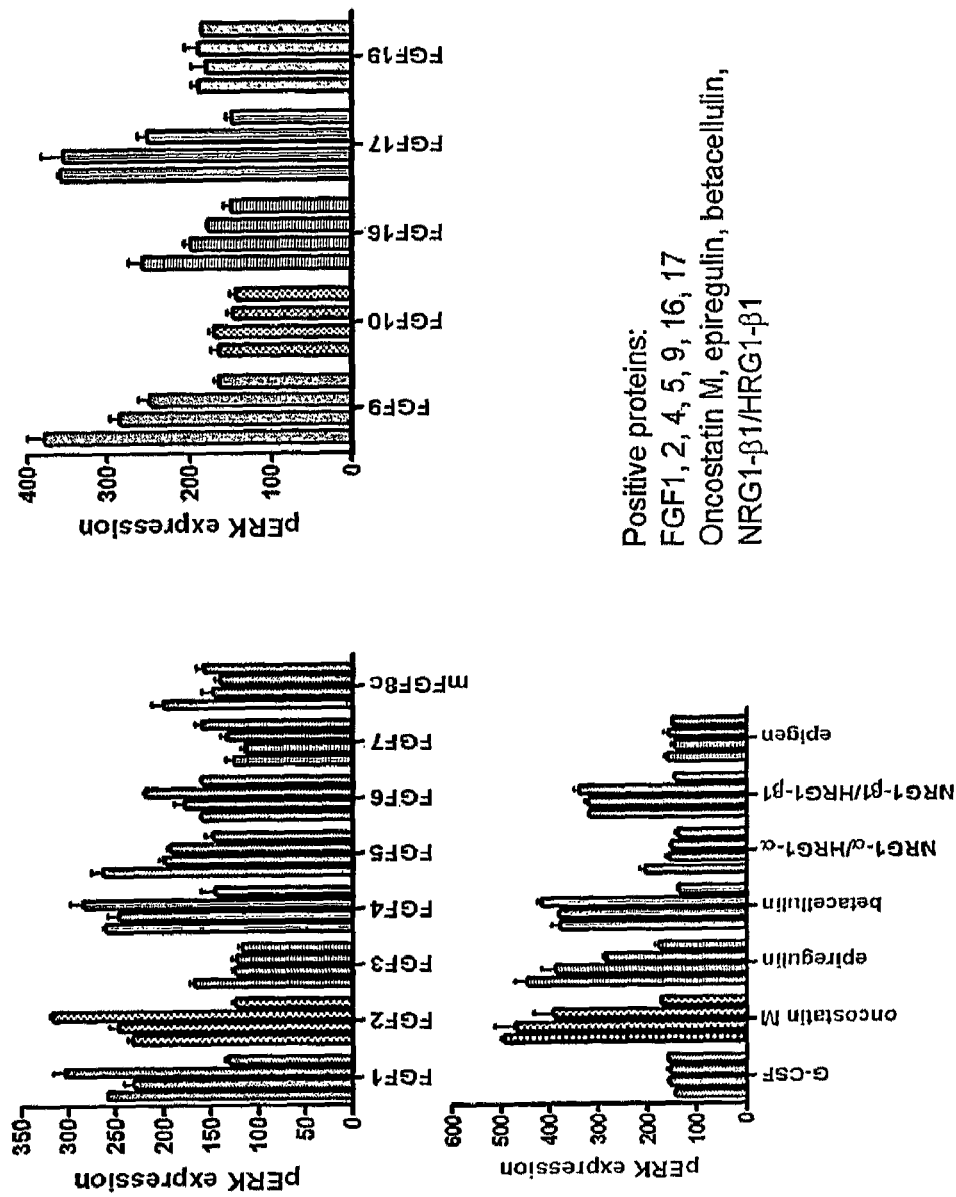
Figure 3C:
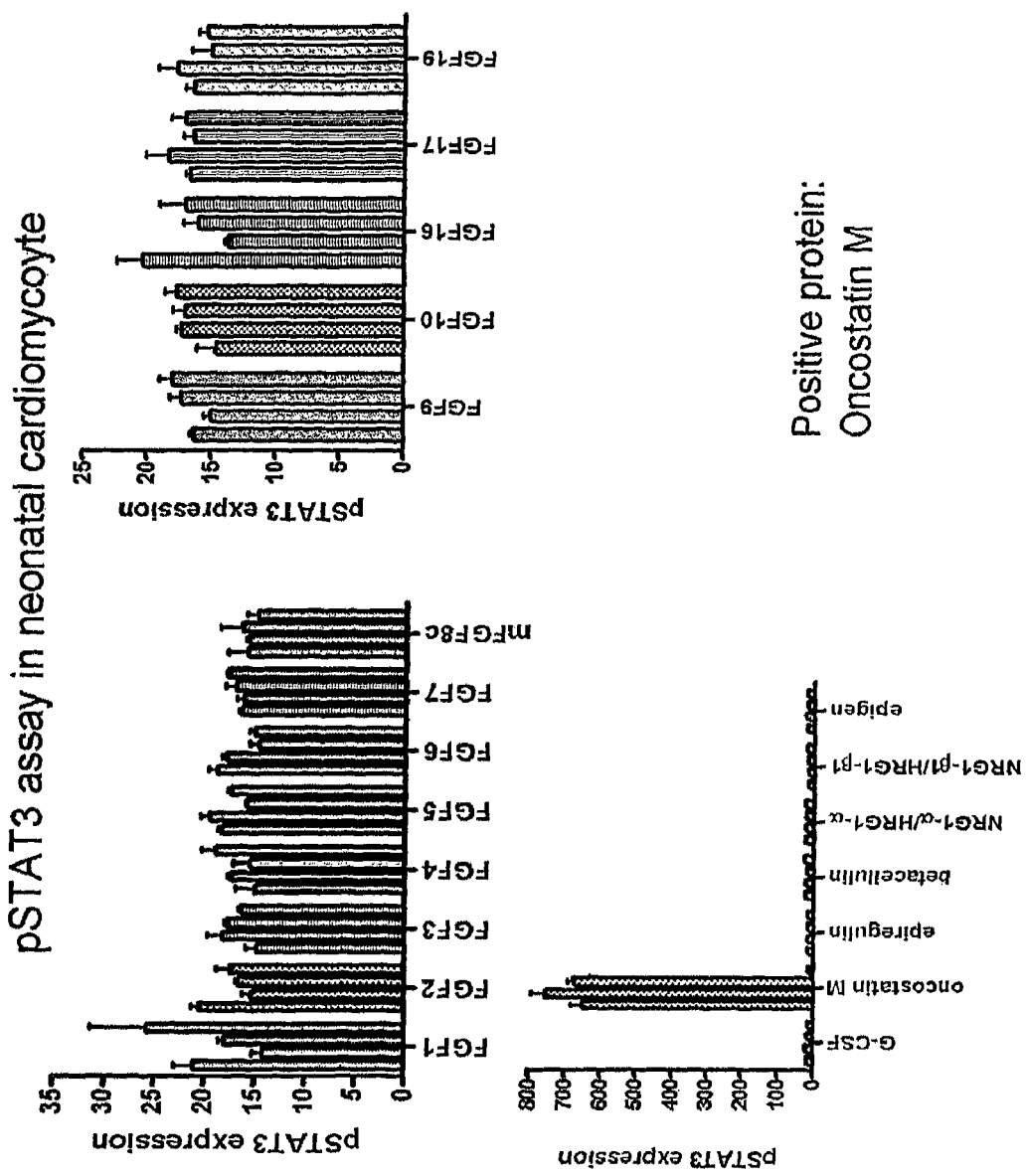

Table 1 shows the SEQ. ID. NOS. for molecules of the invention (SEQ ID NOS: 1-348). Column 1 shows an internal designation identification number (FP ID). Column 2 shows the nucleotide sequence identification number for the open reading frame of the nucleic acid sequence (SEQ. ID. NO.: N1). Column 3 shows the amino acid sequence identification number for the polypeptide sequence (SEQ. ID. NO.:P1). Column 4 shows the polypeptide identification number of the source clone or sequence (Source ID).

Table 2 shows the Pfam coordinates of the molecules of the invention. Column 1 shows an internal designation identification number of the polypeptide (FP ID). Column 2 shows the source identification number of the polypeptide (Source ID). Column 3 shows the name of the Pfam domain when present, and Column 4 shows the coordinates of the domains.

Table 3 shows characteristics of the polypeptides of the invention. Column 1 shows an internal designation identification number of the polypeptide (FP ID). Column 2 shows the predicted protein length. Column 3 shows an internal parameter (tree vote) which designates whether a polypeptide is secreted. A tree vote of 1 denotes a high likelihood the polypeptide is secreted and a tree vote of 0 denotes a low likelihood the polypeptide is secreted. Column 4 shows the signal peptide coordinates. Column 5 shows the mature protein coordinates. Column 6 shows the alternative signal peptide coordinates. Column 7 shows an alternate prediction of the mature protein coordinates. Column 8 shows the hydrophobicity coordinates. Column 9 shows the number of transmembrane domains (TM). Column 10 shows the TM coordinates. Column 11 shows the non-TM coordinates.

Table 4 shows the public annotation of the polypeptide sequences of the invention. Column 1 shows either an internal designation identification number of the polypeptide (FP ID) or the commercial source of the polypeptide. Column 2 shows the polypeptides confirmed in the pAkt assay. Column 3 shows the polypeptides confirmed in the pERK assay. Column 4 shows the polypeptides confirmed in the pSTAT3 assay. Column 5 shows the SwissProt ID. Column 6 shows the WT (wild-type) protein ID. Column 7 shows the assayed clone ID. Column 8 shows the representative protein of the clone. Column 9 shows the cluster ID number. Column 10 shows the cluster annotation.

Table 5 shows three groups of clones that have been tested and identified in cardiomyocyte screens. The first group of clones has been tested and identified in two different transfections, the second group of clones has been tested and identified in one transfection, and the third group of clones has been tested with recombinant proteins. Column 1 shows the expressed protein ID. Column 2 shows the clone ID. Column 3 shows a representative annotation of the protein. Column 4 shows the sigma from median for each signal. Column 5 shows the activity percentage. Column 6 shows the protein well position (in a 96 well plate). Column 7 shows the read category, i.e., pAkt, pERK, or pSTAT3. Several proteins, including chromosome 10 open reading frame 58 (chro10orf58), sushi-repeat-containing protein-X-linked 2, and a G-CSF splice variant (SEQ ID NO: 183), showed up in more than one readout, such as in pERK and pSTAT3 for the G-CSF splice variant.

INDUSTRIAL APPLICABILITY

The compositions and methods and kits of the invention are useful in the treatment of cardiac conditions, including, but not limited to, ischemia, ischemic cardiac injury, heart failure, congestive heart failure, myocardial infarction, coronary artery disease, and cardiomyopathy. They are also useful in promoting cell survival, differentiation, proliferation, and regeneration.

SUMMARY OF THE INVENTION

The present invention provides compositions for treating cardiac conditions and methods for treating cardiac conditions by delivering compositions comprising one or more therapeutic agents to the site of cardiac injury. Delivery may be local to the cardiac area or may be intravenous. Both local and intravenous delivery can provide a therapeutically effective concentration of the agents to the site where therapeutic action is needed. In some embodiments, local delivery can avoid potential undesirable systemic side effects.

The invention provides methods to precisely deliver therapeutic agents to the volume at risk (VAR) region at the injury site that will restore the function of injured cardiomyocytes, thereby providing a therapy or cure for an undesirable cardiac condition, for example, ischemic cardiac injury or other cardiac myopathies. In an embodiment, the delivery method employs cardiac catheterization. This involves, for example, the use of a catheter to deliver agents to the (VAR) region that will prevent cardiomyocyte death in the region during or following ischemic cardiac injury, or will stimulate cardiomyocyte regeneration. Other local delivery methods include, for example, direct injection guided with a suitable device or means.

Compositions that can be used in the instant invention include pharmaceutical compositions and comprise one or more therapeutic agents that can treat cardiac conditions. The therapeutic agents of the instant invention can operate in at least two ways. The therapeutic agent can be a survival factor that prevents cardiomyocyte cell death in the VAR region or presumptive VAR region. Alternatively, the therapeutic agent can mobilize and/or stimulate progenitor cells (for example, cardiac stem cells) to replace dead or dying cardiomyocytes. Both types of therapeutic agents increase heart function and provide a prophylactic, a treatment, or a cure for cardiac conditions. Agents of the invention include, but are not limited to, therapeutic polypeptides.

The invention also provides certain proteins or fragments thereof that have the ability to recruit cardiac progenitor cells and/or to promote survival, differentiation, and/or proliferation of cardiomyocytes or cardiomyocyte progenitors and are useful for treating cardiac conditions including, but not limited to, ischemic cardiac injury, myocardial infarction, heart failure, coronary artery disease, other cardiomyopathies, and the like.

The present application is directed to a pharmaceutical composition for local delivery to heart of a subject other than to a coronary artery of the subject for treating a cardiac condition comprising at least a first therapeutic agent, wherein the first therapeutic agent comprises at least a first isolated polypeptide, wherein the first isolated polypeptide is effective, solely or in combination with at least a second therapeutic agent, in producing a desired biological activity, wherein the desired biological activity comprises promoting survival of cardiac cells; promoting differentiation of cardiac cells; and/or promoting proliferation of cardiac cells. The pharmaceutical composition can further comprise a second therapeutic agent, which, in turn, can comprise thymosin β4.

In some embodiments of the invention, the first therapeutic agent is effective in promoting survival and/or proliferation of cardiac cells. The first therapeutic agent can comprise any one or more of a member of FGF family, a member of PDGF family, a member of EGF family, a member of IGF family, a member of TNF family, a member of TGF family, a member of interferon (IFN) family, a member of trefoil factor (TTF) family, a member of IL-6 family, a member of endothelin family, a member of IL-1 family, a member of IL-11 family, a member of VEGF family, a splice variant of G-CSF family, a member of LIF family, a polypeptide comprising SEQ ID NO: 180, a polypeptide comprising SEQ ID NO: 183, a polypeptide comprising SEQ ID NO: 20, or splice variants thereof, or an active fragment thereof.

The pharmaceutical composition can be adapted for delivery by a catheter or by direct injection. The pharmaceutical composition can contain at least one therapeutic agent that inhibits cardiomyocyte death, for example, in a volume at risk.

The cardiac condition according to the invention can be ischemia. In other embodiments, the cardiac condition can be ischemic cardiac injury, heart failure, congestive heart failure, myocardial infarction, coronary artery disease, or cardiomyopathy. The cardiac cells according to the invention can be cardiac stem cells or cardiac progenitor cells. The subject can be human.

The pharmaceutical composition can further comprise at least a second therapeutic agent, at least a third therapeutic agent, or at least a fourth therapeutic agent. The first, second, third and/or fourth therapeutic agent in the pharmaceutical composition can be a polypeptide chosen from IGF family, FGF family, EGF family and/or PDGF family or an active fragment thereof. The first, second, third and/or fourth therapeutic agent in the pharmaceutical composition can be a member of the FGF family, including, but not limited to, FGF-1, FGF-2, FGF-4, FGF-5, FGF-6, FGF-8, FGF-9, FGF-16, or FGF-17, or an active fragment thereof.

The first, second, third and/or fourth therapeutic agent can be a member of the EGF family, including, but not limited to, amphiregulin, Epigen, epiregulin, HB-EGF, EGF, betacellulin, or a splice variant of betacellulin, or an active fragment thereof. The splice variant of betacellulin can comprise SEQ ID NO: 180. In other embodiments, the member of the EGF family can be a member of neuregulin family, including, but not limited to, NRG1-α or NRG1-β, or an active fragment thereof.

The first, second, third and/or fourth therapeutic agent can be a member of the PDGF family, including, but not limited to, PDGF-A, PDGF-B, PDGF-C, or PDGF-D, or an active fragment thereof. The first, second, third and/or fourth therapeutic agent also can be a member of the IGF family, including, but not limited to, IGF-1 or IGF-2, or an active fragment thereof.

The first therapeutic agent can be a member of the TNF family, including, but not limited to, TNF-α or TNF-β, or an active fragment thereof. The first therapeutic agent also can be a member of the TGF family, including, but not limited to, TGF-α or a member of TGF-β family, or an active fragment thereof. The member of the TGF-β family can be TGF-β2 or TGF-β3. The first therapeutic agent can be a member of the IL-1 family, including, but not limited to, IL-1α, or an active fragment thereof. In other embodiments, the first therapeutic agent can be a member of the IL-6 family, including, but not limited to, oncostatin M or IL-6, or an active fragment thereof. The first therapeutic agent can also be a splice variant of G-CSF, which can comprise SEQ ID NO: 183, or an active fragment thereof. The first therapeutic agent can be a member of the interferon (IFN) family, including, but not limited to, interferon-α1, or an active fragment thereof. The first therapeutic agent can be a member of the trefoil factor family, including, but not limited to, trefoil factor 2, or an active fragment thereof. The first therapeutic agent also can be a polypeptide comprising SEQ ID NO: 20 or an active fragment thereof. The first therapeutic agent can be a member of the VEGF family, including, but not limited to, VEGF-C, or an active fragment thereof. The first therapeutic agent can be a member of the endothelin family, including, but not limited to, endothelin-1 or endothelin-2, or an active fragment thereof. The first therapeutic agent also can be a member of the LIF family, including, but not limited to, LIF, or an active fragment thereof.

At least one of the therapeutic agents can be a fusion molecule. The fusion molecule can comprise a fusion partner. The fusion partner can confer a half-life to the therapeutic agent that is longer in the subject than the half-life of the therapeutic agent in the subject in the absence of the fusion partner. The half-life of the therapeutic agent can be at least one-half hour, one hour, two hours, three hours, four hours, five hours, twelve hours, twenty four hours, forty eight hours, seventy two hours or longer in the subject than the half-life of the therapeutic agent in the absence of the fusion partner. The fusion partner can comprise a polymer, an immunoglobulin molecule, a succinyl group, fetuin A, fetuin B, albumin, a leucine zipper domain, a tetranectin trimerization domain, a mannose binding protein, a macrophage scavenger protein, an Fc region, or an active fragment of any of these. The polymer can be a polyethylene glycol moiety. The polyethylene glycol moiety can be attached to the therapeutic agent through an amino group of the therapeutic agent. The polyethylene glycol moiety can be a branched or linear chain polymer. The immunoglobulin molecule can comprise at least a portion of an Fc region. The albumin can comprise an albumin molecule, one or more fragments of albumin, a peptide that binds albumin, an albumin molecule that conjugates with a lipid, or an albumin molecule that binds to another molecule.

In other embodiments, the fusion partner can comprise an oligomerization domain. The oligomerization domain can comprise a coiled-coil domain, a collagen domain, a collagen-like domain, or a dimeric immunoglobulin domain. The coiled-coil domain can comprise a tetranectin coiled-coil domain, a coiled-coil domain found in a cartilage oligomeric matrix protein, an angiopoietin coiled-coil domain, or a leucine zipper domain. The collagen or collagen-like domain can comprise a collagen or collagen-like domain found in collagen, mannose-binding lectin, lung surfactant protein A, lung surfactant protein D, adiponectin, ficolin, conglutinin, macrophage scavenger receptor, or emilin. The dimeric immunoglobulin domain can comprise an antibody CH3 domain. In some embodiments, the fusion molecule can have improved receptor binding in a lysosome.

The pharmaceutically acceptable carrier in the composition can comprise a biodegradable carrier. The biodegradable carrier can comprise a polysaccharide, which, in turn, can comprise hyaluronic acid, dextran, dextran sulfate, chondroitin sulfate, dermatan sulfate, keratan sulfate, heparin, heparan sulfate, or alginate. The pharmaceutical composition of the invention also can further comprise an extracellular matrix, which can comprise collagen.

The composition can comprise a biomarker in some embodiments of the invention. The biomarker can be tracked to track or monitor the location of the therapeutic agent in the subject. The composition in accordance with the invention can be a gel composition.

In particular embodiments of the invention, the first therapeutic agent in the pharmaceutical composition can increase viability of cells in an in vitro cardiosphere survival assay. In some embodiments, the first therapeutic agent can increase viability of cells in an in vitro cardiosphere proliferation assay. In other embodiments, at least one of the therapeutic agents can stabilize β-catenin in the cardiomyocytes of the volume at risk.

The present invention is also directed to kits for treating a cardiac condition in a subject, comprising any one of the aforementioned compositions and further comprising a device to deliver the composition to the heart. The device can be a catheter and/or can deliver the composition to the volume at risk.

The present invention provides methods of treating a cardiac condition in a subject comprising: providing any one of the aforementioned pharmaceutical compositions; and administering the composition to the subject. Administering the composition can comprise administering the composition to a volume at risk in some embodiments. Administering the composition also can comprise delivering the composition by a device, which can be a catheter.

Administering the composition can comprise injecting the composition. Administering the composition to the subject can comprise administering at least two injections or two doses; at least three injections or three doses; at least four injections or four doses; or more than four injections or four doses. The injections can be given around the edge of the volume at risk. Intracardiac injections of the composition can be performed once a week until the desired result is achieved. Systemic injections (e.g., subcutaneous, intraperitoneal, tail-vein injections) can be performed once a day until the desired result is achieved.

In some embodiments, administering the composition to the subject can recruit cardiac progenitor cells or cardiac stem cells to the area of administration. In other embodiments, administering the composition to the subject can stimulate differentiation of cardiac progenitor cells or cardiac stem cells. In yet other embodiments, administering the composition to the subject can stimulate proliferation of cardiac progenitor cells when administered one or more times, and/or promote activity of cardiac progenitor cells or cardiac stem cells.

The pharmaceutical composition also can include at least any of the following combinations: (1) a member of the FGF family and a member of the EGF family; (2) a member of the FGF family and a member of the PDGF family; (3) a member of the FGF family and a member of the IGF family; (4) a member of the EGF family and a member of the PDGF family; (5) a member of the EGF family and a member of the IGF family; (6) a member of the PDGF family and a member of the IGF family; (7) a member of the FGF family, a member of the EGF family, and a member of the PDGF family; (8) a member of the FGF family, a member of the EGF family, and a member of the IGF family; (9) a member of the FGF family, a member of the PDGF family, and a member of the IGF family; (10) a member of the EGF family, a member of the PDGF family, and a member of the IGF family.

The invention also provides a pharmaceutical composition for local delivery to a heart of a human subject for treating a cardiac condition comprising at least a first therapeutic agent, wherein the first therapeutic agent comprises at least a first isolated polypeptide, wherein the first isolated polypeptide, solely or in combination with at least a second therapeutic agent, produces a desired biological activity, wherein the desired biological activity comprises promoting survival of cardiac cells; and/or promoting differentiation of cardiac cells; and/or promoting proliferation of cardiac cells; and wherein the composition is not delivered to a coronary artery, the first or second therapeutic agent comprises one or more of a member of FGF family, a member of VEGF family, a member of IGF family, a member of endothelin family, a member of LIF family, a member of EGF family, a member of PDGF family, a member of TGF family, a of IL-11 family, a member of TNF family, a member of interferon family, hypothetical protein XP_098916, or chro10 orf58 or splice variants or active fragments thereof, provided that the first therapeutic agent is other than FGF1 or FGF2 when it is the sole therapeutic agent in the composition. The pharmaceutical composition can further comprise a second therapeutic agent. The composition can be a composition wherein the first or second therapeutic agent promotes survival and/or proliferation of cardiac cells. In another embodiment, at least one therapeutic agent can inhibit cardiomyocyte death. The first or second therapeutic agent can comprise FGF5, FGF9, FGF16, neuregulin 1-β1, or betacellulin. Where there is a second therapeutic agent in the composition, the second therapeutic agent can comprise a member of the PDGF family, a member of the IGF family and/or thymosin β4.

The pharmaceutical composition of the invention can be adapted for delivery by a catheter. In another embodiment, the composition can be adapted for delivery by direct injection.

The composition of the invention can have a first therapeutic agent other than VEGF or PDGF when it is the sole therapeutic agent.

The cardiac cells can be cardiac stem cells or cardiac progenitor cells. The cardiac condition can be ischemia, ischemic cardiac injury, congestive heart failure, myocardial infarction, coronary artery disease, and/or cardiomyopathy.

The composition can further comprise at least a third therapeutic agent. The third therapeutic agent can comprise a member of the EGF family, the IGF family, or the PDGF family. The composition can also further comprise at least a fourth therapeutic agent. The fourth therapeutic agent can be a polypeptide or an active fragment thereof, chosen from the IGF family, FGF family, EGF family, or PDGF family.

The first, second, third, or fourth therapeutic agent, if any, can be a member of the FGF family, including, but not limited to, FGF-1, FGF-2, FGF-4, FGF-5, FGF-6, FGF-8, FGF-9, FGF-16, and FGF-17, or an active fragment thereof. The first, second, third, or fourth therapeutic agent, if any, can be a member of the EGF family, including, but not limited to, amphiregulin, Epigen, epiregulin, HB-EGF, EGF, betacellulin, a member of the neuregulin family (such as NRG1-α or NRG1-β1), and a splice variant thereof, or an active fragment thereof. The splice variant of betacellulin can comprise SEQ ID NO: 180.

The first, second, third, or fourth therapeutic agent, if any, can be a member of the PDGF family, including, but not limited to, PDGF-A, PDGF-B, PDGF-C, PDGF-D, PDGF-AA, PDGF-BB, and PDGF-AB, or an active fragment thereof. The first, second, third, or fourth therapeutic agent, if any, can be a member of the IGF family, including, but not limited to, IGF-1 and IGF-2, or an active fragment thereof.

The first therapeutic agent can be a member of the TNF family or an active fragment thereof and the second, third, or fourth therapeutic agent, if any, can be a polypeptide or an active fragment thereof, chosen from the IGF family, FGF family, EGF family, and/or PDGF family. The member of the TNF family can be TNF-β or an active fragment thereof.

The first therapeutic agent can be a member of the TGF family or an active fragment thereof and the second, third, or fourth therapeutic agent, if any, is a polypeptide or an active fragment thereof, chosen from the IGF family, FGF family, EGF family, and/or PDGF family. The member of the TGF family can be TGF-α. In another embodiment, the member of the TGF family can be a member of the TGF-β family, including, but not limited to, TGF-β2 and TGF-β3.

The first therapeutic agent can be a member of the interleukin family or an active fragment thereof and the second, third, or fourth therapeutic agent, if any, can be a polypeptide or an active fragment thereof, chosen from the IGF family, FGF family, EGF family, and/or PDGF family. The member of the interleukin family can be IL-11 or oncostatin M.

The first therapeutic agent can be a member of the interferon family or an active fragment thereof and the second, third, or fourth therapeutic agent, if any, can be a polypeptide or an active fragment thereof, chosen from the IGF family, FGF family, EGF family, and/or PDGF family. The member of the interferon family can be interferon-α1.

The first therapeutic agent can be a polypeptide comprising SEQ ID NO:20 or an active fragment thereof, and the second, third, or fourth therapeutic agent, if any, is a polypeptide, or an active fragment thereof, chosen from the IGF family, FGF family, EGF family, and/or PDGF family.

The first therapeutic agent can be a member of the VEGF family or an active fragment thereof, and the second, third, or fourth therapeutic agent, if any, is a polypeptide or an active fragment thereof, chosen from the IGF family, FGF family, EGF family, and/or PDGF family. The member of the VEGF family can be VEGF-C.

The first therapeutic agent can be a member of the endothelin family or an active fragment thereof, and the second, third, or fourth therapeutic agent, if any, can be a polypeptide or an active fragment thereof, chosen from the IGF family, FGF family, EGF family, and/or PDGF family. The member of the endothelin family can be endothelin-1 or an active fragment thereof.

The first therapeutic agent can be a member of the LIF family or an active fragment thereof, and the second, third, or fourth therapeutic agent, if any, can be a polypeptide or an active fragment thereof, chosen from the IGF family, FGF family, EGF family, and/or PDGF family. The member of the LIF family can be LIF or an active fragment thereof.

At least one of the therapeutic agents in the composition of the invention can be a fusion molecule. The fusion molecule can comprise a fusion partner. The fusion partner can confer a half-life to the therapeutic agent that is longer in the subject than the half-life of the therapeutic agent in the subject in the absence of the fusion partner. The half-life of the therapeutic agent can be at least one-half hour, one hour, two hours, three hours, four hours, five hours, twelve hours, twenty four hours, forty eight hours, seventy two hours or longer in the subject than the half-life of the therapeutic agent in the absence of the fusion partner. The fusion partner can comprise a polymer, an immunoglobulin molecule, a succinyl group, fetuin A, fetuin B, albumin, a leucine zipper domain, an oligomerization domain, a mannose binding protein, a macrophage scavenger protein, an Fc region, or an active fragment of any of these. The polymer can be a polyethylene glycol moiety; the immunoglobulin molecule can comprise at least a portion of an Fc region; the oligomerization domain can comprise a tetranectin trimerization domain, a coiled-coil domain, a collagen domain, a collagen-like domain, or a dimeric immunoglobulin domain; the albumin can comprise an albumin molecule, one or more fragments of albumin, a peptide that binds albumin, an albumin molecule that conjugates with a lipid, or an albumin molecule that binds to another molecule. The polyethylene glycol moiety can be a branched or linear chain polymer or is attached to the therapeutic agent through an amino group of the therapeutic agent; the coiled-coil domain can comprise a tetranectin coiled-coil domain, a coiled-coil domain found in a cartilage oligomeric matrix protein, an angiopoietin coiled-coil domain, or a leucine zipper domain; the collagen or collagen-like domain can comprise a collagen or collagen-like domain found in collagen, mannose-binding lectin, lung surfactant protein A, lung surfactant protein D, adiponectin, ficolin, conglutinin, macrophage scavenger receptor, or emilin; and the dimeric immunoglobulin domain can comprise an antibody CH3 domain. The fusion molecule can have improved receptor binding in a lysosome.

At least one of the therapeutic agents can stabilize β-catenin in the cardiomyocytes of the volume at risk.

The composition of the invention can further comprise a pharmaceutically acceptable carrier comprising a biodegradable carrier. The biodegradable carrier can comprise a polysaccharide. The polysaccharide can comprise hyaluronic acid, dextran, dextran sulfate, chondroitin sulfate, dermatan sulfate, keratan sulfate, heparin, heparan sulfate, and/or alginate. In another embodiment, the composition of the invention can further comprise an extracellular matrix. The extracellular matrix can comprise collagen.

The composition of the invention can also comprise a biomarker, wherein tracking the biomarker tracks the location of the therapeutic agent in the subject. The composition can also be a gel composition.

The first therapeutic agent in the composition can increase the viability of cells in an in vitro cardiosphere survival assay and/or an in vitro cardiosphere proliferation assay.

The invention also provides a kit for treating a cardiac condition in a subject, comprising the composition of the invention, a device for delivering the composition to the heart, and instructions for injecting the composition into the heart other than to a coronary artery. The device can be a catheter. The device can deliver the composition to the volume at risk.

In another aspect, the invention relates to a method of treating a cardiac condition in a subject comprising the steps of: (a) providing the pharmaceutical composition of the invention as described herein; and (b) administering the composition to the subject by local administration to heart of the subject other than to a coronary artery of the subject. The step of administering the composition can comprise administering the composition to a volume at risk. The step of administering the composition can comprise delivering the composition by a device, which can be a catheter. The step of administering the composition can also comprise injecting the composition. The step of administering the composition to the subject can comprise administering at least two, three, four, or more than four injections; or two, three, four, or more than four doses. The step of administering the composition to the subject can recruit cardiac progenitor cells or cardiac stem cells to the area of administration; can stimulate differentiation of cardiac progenitor cells or cardiac stem cells; can stimulate proliferation of cardiac progenitor cells; and/or can promote activity of cardiac progenitor cells or cardiac stem cells. The step of administering the composition to the subject can comprise injecting the composition into one, two, three, four, or more than four and up to ten sites around ischemic area or edge of volume at risk of subject's heart or myocardium during one session. The step of administering the composition to the subject can comprise injecting the composition in one or more sessions.

The method of treating a cardiac condition in a subject in accordance with the invention can further comprise the step of administering the composition systemically. The composition can be administered to the subject once a day or once every other day for up to one, two, three, four, five times, or more than five times. The composition can be administered to the subject once a day for up to one, two, three, four, or five times a week. The composition can be administered to the subject once a week for up to one, two, three, four, five, or more than five, weeks. The composition can be administered to the subject once a week, once a month, once every other month, once every three months, once every six months, or once a year.

In the method of treating a cardiac condition in a subject in accordance with the present invention, the subject can be administered a dose in the range of about 1 nanogram to about 10 milligrams. The first therapeutic agent can be present in the composition in an amount of about 1 nanogram to about 50 milligrams.

DETAILED DESCRIPTION OF THE INVENTION

Definitions

A "cardiac condition" is a state of the heart that can be identified by symptoms or other identifying factors as diverging from a healthy or a normal state. The term "cardiac condition" includes disorders, syndromes, diseases, and injuries that affect the heart. Cardiac conditions include, but are not limited to, cardiac failure, for example, congestive heart failure; ischemic conditions, for example, myocardial infarction; hypertensive conditions; congenital conditions; infectious conditions, for example, endocarditis; proliferative diseases, including benign and malignant tumors; and coronary artery disease. Cardiac conditions also include myocardial diseases, for example, myocarditis, cardiomyopathy, and fibrosis; pericardial diseases, for example, pericarditis; and endocardial and valvular diseases, for example, stenosis and prolapse.

"Ischemic cardiac injury" is damage to the heart that results from a deficiency of oxygen. It may occur as the result of a deficiency of blood supply to the heart muscle due, for example, to obstruction or constriction of the coronary arteries.

A "cardiomyocyte" is a cardiac muscle cell.

A "cardiac progenitor cell" is a precursor to any of the cell types found in the cardiac area. Cardiac progenitor cells include stem cells. They also include precursors of connective tissue cells, nerve cells, and all other types of cells present in the cardiac area.

A "cardiac stem cell" is an undifferentiated cell found in the prenatal or postnatal heart that has the capacity to differentiate into a cardiomyocyte.

The "cardiac area" refers to the anatomical and functional region of the heart. It includes the myocardium, the pericardium, the conduction system, and the blood vessels in the anatomical region of the heart, including the coronary circulation.

The "volume at risk" (VAR) is a region of the myocardium that is adjacent to the region of cellular necrosis formed by the cells that die as a result of ischemic cardiac injury. Cells in the VAR typically undergo a delayed death, which follows the period of ischemia.

A "growth factor" is an extracellular hormone or polypeptide signaling molecule that stimulates a cell to grow or proliferate. Many types of growth factors exist, including protein hormones and steroid hormones. Growth factors of the invention include variants and muteins. Examples of growth factors include fibroblast growth factors (FGF), epidermal growth factors (EGF), and platelet-derived growth factors (PDGF). These include, but are not limited to, FGF-2, FGF-4, FGF-9, IGF, IGF-I, PDGF, PDGF-BB, amphiregulin, epiregulin, Epigen, EGF, HB-EGF, and betacellulin.

A "member of the EGF family" is a growth factor that has a conserved domain known as the EGF motif, typically characterized by six conserved cysteine residues. Members of the EGF family are described in greater detail below.

A "member of the FGF family" is a growth factor that interacts with heparin sulfate glycosaminoglycans and the extracellular domains of FGF cell surface receptors (FGFRs) to trigger receptor activation and biological responses, for example, as described in Olsen et al., J. Biol. Chem. (2003) 278(36):34,226-34,236 and Ornitz et al., Genome Biol. 2001 2:3005.1-3005.12. Members of the FGF family are described in greater detail below.

A "member of the PDGF family" is a growth factor that binds to a PDGF receptor. Examples of members of the PDGF family include PDGF-BB and PDGF-DD, which are composed of two polypeptide B chains and D chains, respectively. Members of the PDGF family are described in greater detail below. For example, PDGF-BB induces increased synthesis of both PDGF α- and β-receptor protein, and binds the PDGF β-receptor with high affinity (Eriksson et al., J. Biol. Chem. (1991) 266:21138-21144).

A "member of the IGF family" is a growth factor that binds to an IGF receptor and shows a high degree of sequence homology with other members of the IGF family. Examples of members of the IGF family include IGF-1 and IGF-2. Members of the IGF family are described in greater detail below.

A "gel composition" is a gel comprising a biocompatible polymer and a solvent that dissolves the polymer. Viscosity of a gel composition can be adjusted to accommodate desired release kinetics and to sustain or control the release of a therapeutic agent in the gel composition. With the use of a temperature-sensitive polymer, a gel composition can be a liquid before administration to the patient and become a gel within the patient.

A "biodegradable carrier" comprises a composition that is capable of being decomposed by biological agents, such as bacteria.

A "biomarker" is a biologically-compatible substance whose presence inside a patient can be visualized or detected by any of a variety of methods, including, but not limited to, x-rays, computed tomography (CT), magnetic resonance imaging (MRI), molecular imaging, and positron emission tomography (PET).

A "variant" of a protein includes both naturally occurring and artificially produced, for example, genetically engineered proteins, that differ from the wild-type protein. Differences from the wild-type protein may include, but are not limited to, substitutions, truncations, deletions, insertions, and repetitions. They can be conservative or non-conservative.

A "fusion molecule" is a molecule, for example, a polynucleotide, polypeptide, or other polymer, that represents the joining of all or portions of more than one gene. For example, a fusion protein can be the product from splicing strands of recombinant DNA and expressing the hybrid gene. A fusion molecule can be made by genetic engineering, for example, by removing the stop codon from the DNA sequence of the first protein, then appending the DNA sequence of the second protein in-frame. That DNA sequence will then be expressed by a cell as a single protein. Typically this is accomplished by cloning a cDNA into an expression vector in frame with an existing gene.

A "fusion partner" is a molecule fused to a therapeutic or prophylactic polypeptide. A fusion partner can also be a polynucleotide, or polypeptide, or other polymer. For example, a polypeptide can be fused in-frame at the N-terminus and/or C-terminus of, or internally to, a therapeutic or prophylactic polypeptide. For example, the fusion partner may be albumin, any variant of albumin, or any fragment thereof. Another fusion partner may be any variant of fetuin, or any fragment thereof. Yet another fusion partner may be the Fc domain or a variant thereof. See, e.g., U.S. Pat. Nos. 5,116,964; 5,225,538; 5,428,130; 5,455,165; 5,514,582; 5,714,147; and 6,406,697.

The terms "agent," "substance," "modulator," and "compound" are used interchangeably herein. These terms refer to a substance that binds to and/or modulates a level or activity of a polypeptide or a level of mRNA encoding a polypeptide or nucleic acid, or that modulates the activity of a cell containing a polypeptide or nucleic acid. These terms also encompass a substance that can be used to treat ischemic cardiac injury or other cardiac conditions. Where the agent modulates a level of mRNA encoding a polypeptide, agents include ribozymes, antisense, and RNAi molecules. Where the agent is a substance that modulates a level of activity of a polypeptide, agents include antibodies specific for the polypeptide, peptide aptamers, small molecule drugs, agents that bind a ligand-binding site in the polypeptide, natural ligands, soluble receptors, agonists, antagonists, and the like. Antibody agents include antibodies that specifically bind a subject polypeptide and activate the polypeptide, such as receptor-ligand binding that initiates signal transduction; antibodies that specifically bind a subject polypeptide and inhibit binding of another molecule to the polypeptide, thus preventing activation of a signal transduction pathway; antibodies that bind a subject polypeptide to modulate transcription; antibodies that bind a subject polypeptide to modulate translation; as well as antibodies that bind a subject polypeptide on the surface of a cell to initiate antibody-dependent cytotoxicity (ADCC) or to initiate cell killing or cell growth. Small molecule drug modulators also include those that bind the polypeptide to modulate activity of the polypeptide or a cell containing the polypeptide.

A "long-acting therapeutic agent" refers to a therapeutic agent modified to have a longer in vivo half-life than the agent in the absence of the modification.

"Treatment," as used herein, covers any administration or application of remedies for disease in a mammal, including a human, and includes inhibiting the disease, arresting its development, or relieving the disease, for example, by causing regression, or restoring or repairing a lost, missing, or defective function; or stimulating an inefficient process.

"Prophylaxis," as used herein, includes preventing a disease from occurring or recurring in a subject that may be predisposed to the disease but is not currently symptomatic.

Treatment and prophylaxis can be administered to an organism, or to a cell in vivo, in vitro, or ex vivo, and the cell subsequently administered to the subject.

A "therapeutically effective amount" refers to a dose of a therapeutic agent capable of treating a particular condition or disease, for example, a cardiac condition. A therapeutically effective amount may be effective upon the first administration or it may require more than one administration to achieve therapeutic effect.

"Cardiomyopathy" is defined herein as any abnormal condition of the heart muscle. It may be manifest as a dilated heart with poor pumping power. It may include symptoms of arrhythmia, emboli, and/or valvular insufficiency. Cardiomyopathy may be restrictive and impair the ability of the heart to fill. It may also be hypertrophic (enlarged heart).

"Heart failure" is a condition where the heart muscle weakens and cannot pump blood efficiently.

"Myocardial infarction" refers to destruction of heart tissue resulting from obstruction of the blood supply to the heart muscle.

"Coronary artery disease" is characterized by a narrowing or stenosis of the coronary arteries resulting in inadequate blood flow to the heart muscle.

"Half-life" is the time needed for the concentration of a foreign substance in a body fluid to decrease to half of its original value.

An "Fc molecule" refers to that region in the immunoglobulin molecule that binds to a cell when the antigen binding sites of the antibody are occupied or the antibody is aggregated.

An "antibody CH3 domain" refers to the C-terminal immunoglobulin domain of a heavy chain of an immunoglobulin molecule. Folding and assembly of the non-covalent homodimer formed by antibody CH3 domains have been studied. See Thies et al., J. Mol. Biol. (1999) 293:67-79.

A "pharmaceutically acceptable carrier" refers to a non-toxic solid, semisolid or liquid filler, diluent, encapsulating material or formulation auxiliary of any conventional type. A "pharmaceutically acceptable carrier" is non-toxic to recipients at the dosages and concentrations employed and is compatible with other ingredients of the formulation. For example, the carrier for a formulation containing polypeptides suitably does not include oxidizing agents and other compounds that are known to be deleterious to polypeptides. Suitable carriers include, but are not limited to, water, dextrose, glycerol, saline, ethanol, and combinations thereof. The carrier may contain additional agents such as wetting or emulsifying agents, pH buffering agents, or adjuvants which enhance the effectiveness of the formulation. Topical carriers include liquid petroleum, isopropyl palmitate, polyethylene glycol, ethanol (95%), polyoxyethylene monolaurate (5%) in water, or sodium lauryl sulfate (5%) in water. Other materials such as anti-oxidants, humectants, viscosity stabilizers, and similar agents may be added as necessary. Percutaneous penetration enhancers such as Azone may also be included.

A "device" is an appliance or piece of equipment, for example, a mechanical or electronic appliance, designed to serve a special purpose or perform a special function.

A "catheter" is a tubular instrument which allows the passage of fluid into or from a blood vessel or body cavity.

"Injection" is the introduction of a substance into the body. Injection may introduce substances into muscular tissue, for example, cardiac muscle; subcutaneous tissue; a vascular lumen, for example a vein or artery; or other cavities or canals of the body. The term "injection" includes the use of any suitable device to effect the introduction. The term includes, for example, introduction by catheter. The term also includes, for example, the direct injection of a substance to the cardiac area.

The terms "subject," "host," "individual," "animal," and "patient," used interchangeably herein, refer to mammals, including humans, and also include, but are not limited to, murines, simians, felines, canines, equines, bovines, porcines, ovines, caprines, rabbits, mammalian farm animals, mammalian sport animals, and mammalian pets. In many embodiments, the hosts will be humans. Animal models are of interest for experimental investigations, providing a model for treatment of human disease.

Described herein, are compositions and methods that are useful in treating cardiac conditions, including, for example, AMI and CHF in a subject that support cardiomyocyte survival and decrease apoptosis/necrosis of cardiomyocytes in response to ischemic damage, which aides in the preservation of the myocardium and cardiac pump function. The molecules of the invention were identified by employing several in vitro cell-based assays. As the phosphorylation of Akt, STAT3 and ERK1/2 are known to be involved in the cell survival pathways in cardiomyocytes, the phosphor-Akt (pAkt), phosphor-STAT3 and phosphor-ERK1/2 were employed as the surrogate makers for cell survival using the multiplex luminex technology, see, for example, Rhyne et al., Biotechniques (2003) 35(3):624-9, to detect pAkt, pSTAT3, and pERK in rat neonatal cardiomyocytes treated with a protein supernatant.

Pharmaceutical Compositions

The present invention provides compositions, including pharmaceutical compositions, comprising the polypeptides, polynucleotides, and other therapeutic agents of the invention. The compositions may include a buffer, which is selected according to the desired use of the polypeptide, polynucleotide, or other therapeutic agent, and may also include other substances appropriate to the intended use. Those skilled in the art can readily select an appropriate buffer, a wide variety of which are known in the art, suitable for an intended use. In some instances, the composition can comprise a pharmaceutically acceptable carrier or excipient, a variety of which are known in the art and need not be discussed in detail herein. Pharmaceutically acceptable excipients have been amply described in a variety of publications, including, for example, Gennaro, A. R. (2003) Remington: The Science and Practice of Pharmacy with Facts and Comparisons: Drugfacts Plus. $20^{th}$ ed., Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed., Amer. Pharmaceutical Assoc.

The pharmaceutically acceptable excipients, such as vehicles, adjuvants, carriers, and diluents, are readily available to the public. Moreover, pharmaceutically acceptable auxiliary substances, such as pH adjusting and buffering agents, tonicity adjusting agents, stabilizers, wetting agents and the like, are readily available to the public.

The therapeutic agents may be obtained from naturally occurring sources or synthetically produced. Where obtained from naturally occurring sources, the source chosen will generally depend on the species from which the protein is to be derived. The subject proteins may also be derived from synthetic means, e.g., by expressing a recombinant gene encoding protein of interest in a suitable host. Any convenient protein purification procedures may be employed. Suitable protein purification methodologies are described in Guide to Protein Purification, Deuthser ed. (Academic Press, 1990).

For example, a lysate may be prepared from the original source and purified using HPLC, exclusion chromatography, gel electrophoresis, affinity chromatography, and the like.

Therapeutic compositions of the invention may comprise polypeptides, small organic molecules, carbohydrates, and lipids. These may, in appropriate circumstances, take the form of monomers or polymers.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant, and animal extracts are available or readily produced. Additionally, natural or synthetically produced libraries and compounds are readily modified through conventional chemical, physical, and biochemical means, and may be used to produce combinatorial libraries. Known pharmacological agents may be subjected to directed or random chemical modifications, such as acylation, alkylation, esterification, amidification, etc. to produce structural analogs.

Candidate agents may be obtained from a study of changes in gene expression profiles brought about by cardiac ischemia. Gene expression profiling may be accomplished by a variety of techniques, including, but not limited to, differential display, serial analysis of gene expression (SAGE), subtractive hybridization, and gene microarrays (gene chips). Gene expression profiling may be used in the study of myocardial ischemia, as described by Simkhovich et al., Cardiovasc. Pathol. (2003) 12:180-185. Gene expression microarrays and DNA chips have been discussed in a number of publications, e.g., Hardiman, Pharmacogenomics (2004) 5:487-502. These techniques enable rapid identification of genes whose expression levels are affected by cardiac ischemia. Such genes and their gene products are candidate agents for treating ischemic cardiac injury and other cardiac conditions.

Where the screening assay to identify candidate agents is a binding assay, one or more of the molecules may be joined to a label, where the label can directly or indirectly provide a detectable signal. Various labels include radioisotopes, fluorescers, chemiluminescers, enzymes, specific binding molecules, particles, e.g., magnetic particles, and the like. Specific binding molecules include pairs, such as biotin and streptavidin, digoxin and antidigoxin, etc. For the specific binding members, the complementary member would normally be labeled with a molecule that provides for detection, in accordance with known procedures.

A variety of other reagents may be included in the screening assay. These include reagents like salts, detergents, neutral proteins, e.g. albumin, etc., that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components is added in any order that provides for the requisite binding. Incubations are performed at any suitable temperature, typically between 4° C. and 40° C. Incubation periods are selected for optimum activity, but may also be optimized to facilitate rapid high-throughput screening. Typically between 0.1 and 1 hour will be sufficient.

A cardiosphere assay can be used to identify factors that affect cardiac myocytes, for example, factors which stimulate or inhibit their survival and/or proliferation. Cardiomyocytes, long considered as terminally differentiated cells, have potential to proliferate in animal models and in heart transplant patients. For example, the modest proliferation of cardiomyocytes in heart failure patients is due to the proliferation and differentiation of resident cardiac stem cells, which are not sufficient to overcome the cardiomyocyte destruction. Therefore, certain growth factors or other polypeptides may help to promote cardiac regeneration both in vitro and in vivo. A cardiosphere assay can identify such polypeptides and can be used to assess the effect of growth factors or other polypeptides on the biological activities of cardiomyocytes. Biological activities suitable for cardiosphere assay include, but are not limited to, cardiac cell survival, recruiting cardiac progenitor cells to the cardiac area, stimulating differentiation of cardiac progenitor cells, stimulating proliferation of cardiac progenitor cells, and promoting one or more activity of cardiac progenitor cells. It is generally performed by dissociating cardiac tissue, for example, adult mouse cardiac tissue and producing stem cells and/or cardiospheres, as further described in the Examples and by Laugwitz et al., Nature (2005) 433:647-653; Messina et al., Circ. Res. (2004) 95:911-921; Lovell and Mathur, Cell Prolif. (2004) 37:67-87); Beltrami et al., Cell (2003) 114:763-776; and Oh et al., Proc. Natl. Acad. Sci. (2003) 100:12,313-12,318.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be provided in unit dosage forms, i.e., physically discrete units suitable as unitary dosages for human and animal subjects, each unit containing a predetermined quantity of compounds of the present invention calculated in an amount sufficient to produce the desired effect in association with a pharmaceutically acceptable diluent, carrier, or vehicle. The specifications for the novel unit dosage forms of the present invention depend on the particular compound employed and the effect to be achieved, and the pharmacodynamics associated with each compound in the host.

An effective amount of the active agent (e.g., small molecule, antibody specific for a subject polypeptide, or a subject polypeptide) is administered to the host at a dosage sufficient to produce a desired result. In some embodiments, the desired result is at least a reduction in a given biological activity of a subject polypeptide as compared to a control. In other embodiments, the desired result is an increase in the level of active subject polypeptide (in the individual, or in a localized anatomical site in the individual), as compared to a control. In some embodiments, the desired result is at least a reduction in enzymatic activity of a subject polypeptide as compared to a control. In other embodiments, the desired result is an increase in the level of enzymatically active subject polypeptide (in the individual, or in a localized anatomical site in the individual), as compared to a control. In still other embodiments, the desired result is a decrease in ischemic cardiac injury or severity of a cardiac condition as compared to a control. A decrease in ischemic cardiac injury or severity of a cardiac condition may be indicated by a variety of indicia known in the art or described herein (e.g., decrease in cardiomyocyte loss/death).

Typically, the compositions of the instant invention will contain from less than 1% to about 95% of the active ingredient, in some embodiments, about 10% to about 50%. Generally, between about 100 mg and 500 mg of the compositions will be administered to a child and between about 500 mg and 5 grams will be administered to an adult. Administration is generally by injection and often by injection to a localized area. The frequency of administration will be determined by the care given based on patient responsiveness. Other effective dosages can be readily determined by one of ordinary skill in the art through trials establishing dose response curves.

In order to calculate the amount of therapeutic agent to be administered, those skilled in the art could use readily available information with respect to the amount of agent necessary to have the desired effect. The amount of an agent necessary to increase a level of active subject polypeptide can be calculated from in vitro experimentation. The amount of agent will, of course, vary depending upon the particular agent used.

Regarding pharmaceutical dosage forms, the agents may be administered in the form of their pharmaceutically acceptable salts, or they may also be used alone or in appropriate association, as well as in combination, with other pharmaceutically active compounds or treatment procedures. The following methods and excipients are merely exemplary and are in no way limiting.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Gennaro, A. R. (2003) Remington: The Science and Practice of Pharmacy with Facts and Comparisons: Drugfacts Plus. $20^{th}$ ed., Lippincott, Williams, & Wilkins. The composition or formulation to be administered will, in any event, contain a quantity of the therapeutic agent adequate to achieve the desired state in the subject being treated.

The polypeptide compositions of the invention will be formulated and dosed in a fashion consistent with good medical practice, taking into account the clinical condition of the individual subject, the site of delivery of the polypeptide composition, the method of administration, the scheduling of administration, and other factors known to practitioners. The effective amount of polypeptide for purposes herein is thus determined by such considerations.

Therapeutic Polynucleotides

The invention covers nucleic acid compositions that encode the therapeutic polypeptides or fragments thereof. Polynucleotides of the invention include those encoding FGFs, EGFs, PDGFs, and IGFs, as described herein.

By nucleic acid composition is meant a composition comprising a sequence of DNA or RNA, including one having an open reading frame that encodes the therapeutic polypeptide and is capable, under appropriate conditions, of being expressed as one of the therapeutic polypeptides of the instant invention. However, the term encompasses genomic DNA, cDNA, mRNA, splice variants, antisense RNA, RNAi, DNA comprising one or more single-nucleotide polymorphisms (SNPs), and vectors comprising the subject nucleic acid sequences. Also encompassed in this term are nucleic acids that are homologous or substantially similar or identical to the nucleic acids encoding the therapeutic proteins. Thus, the subject invention provides genes encoding a subject protein, and homologs thereof.

Polynucleotides or nucleic acids of the invention refer to polymeric forms of nucleotides of any length. The polynucleotides can contain deoxyribonucleotides, ribonucleotides, and/or their analogs or derivatives. For example, nucleic acids can be naturally occurring DNA or RNA, or can be synthetic analogs, as known in the art. Polynucleotides of the invention also encompass genomic DNA, genes, gene fragments, exons, introns, regulatory sequences, or regulatory elements, such as promoters, enhancers, initiation and termination regions, other control regions, expression regulatory factors, and expression controls; DNA comprising one or more single-nucleotide polymorphisms (SNPs), allelic variants, isolated DNA of any sequence, and cDNA; mRNA, tRNA, rRNA, ribozymes, splice variants, antisense RNA, antisense conjugates, RNAi, and isolated RNA of any sequence; recombinant polynucleotides, heterologous polynucleotides, branched polynucleotides, labeled polynucleotides, hybrid DNA/RNA, polynucleotide constructs, vectors comprising the subject nucleic acids, nucleic acid probes, primers, and primer pairs.

Polynucleotides of the invention encompass modified nucleic acid molecules, with alterations in the backbone, sugars, or heterocyclic bases, such as methylated nucleic acid molecules, peptide nucleic acids, and nucleic acid molecule analogs, which may be suitable as, for example, probes if they demonstrate superior stability and/or binding affinity under assay conditions. They also encompass single-stranded, double-stranded, and triple helical molecules that are either DNA, RNA, or hybrid DNA/RNA and that may encode a full-length gene or a biologically active fragment thereof.

Polynucleotides of the invention include single nucleotide polymorphisms. Single nucleotide polymorphisms (SNPs) occur frequently in eukaryotic genomes. Nature (2001) 409: 860-921. The nucleotide sequence determined from one individual of a species may differ from other allelic forms present within the population. The present invention encompasses such SNPs.

The subject polynucleotides include those that encode variants of the polypeptides described in the instant specification. Thus, in some embodiments, a subject polynucleotide encodes variant polypeptides that include insertions, deletions, or substitutions compared with the polypeptides described herein. Conservative amino acid substitutions include serine/threonine, valine/leucine/isoleucine, asparagine/histidine/glutamine, glutamic acid/aspartic acid, etc. See, e.g., Gonnet et al. (1992) Science 256:1443-1445.

Nucleic acids encoding the proteins and polypeptides of the subject invention may be cDNA or genomic DNA or a fragment thereof. The term "gene" shall be intended to mean the open reading frame encoding specific proteins and polypeptides of the subject invention, and introns, as well as adjacent 5' and 3' non-coding nucleotide sequences involved in the regulation of expression, up to about 20 kb beyond the coding region, but possibly further in either direction. The gene may be introduced into an appropriate vector for extra-chromosomal maintenance or for integration into a host genome.

The subject polynucleotides are isolated and obtained in substantial purity, generally as other than an intact chromosome. Usually, the DNA will be obtained substantially free of other nucleic acid sequences that do not include a sequence or fragment thereof of the subject genes, generally being at least about 50%, usually at least about 90% pure and are typically "recombinant," i.e., flanked by one or more nucleotides with which it is not normally associated on a naturally occurring chromosome.

The invention provides plasmids, i.e., small, independently replicating pieces of extrachromosomal cytoplasmic DNA that can be transferred from one organism to another, comprising the therapeutic polynucleotides of the invention. Plasmids can become incorporated into the genome of a host or can remain independent. Artificially constructed plasmids are commonly used as cloning vectors. The invention also provides vectors, i.e., plasmids that can be used to transfer DNA sequences from one organism to another. Expression vectors can be used to express the therapeutic gene products of the invention and typically comprise restriction sites to provide for the insertion of nucleic acid sequences encoding heterologous protein or RNA molecules.

The subject genes and gene fragments are useful in therapy to treat ischemic cardiac injury and other cardiac conditions. Expression vectors may be used to introduce the gene into a cell. Such vectors generally have convenient restriction sites located near the promoter sequence to provide for the insertion of nucleic acid sequences. Transcription cassettes may be prepared comprising a transcription initiation region, the subject gene or fragment thereof, and a transcriptional termination region. The transcription cassettes may be introduced into a variety of vectors, e.g., plasmid; retrovirus, e.g., lentivirus; adenovirus; and the like, where the vectors are able to transiently or stably be maintained in the cells, usually for a period of at least about one day, more usually for a period of at least several days to several weeks.

An adenoviral vector preparation can be administered in combination with a vasoactive agent to enhance gene delivery as described in Pub. No. US 2003/0148968 A1, published Aug. 7, 2003 and PCT application WO 99/40945, published Aug. 19, 1999. The vector can be delivered into a blood vessel such as an artery or into a tissue that is pre-infused and/or co-infused with a vasoactive agent. Vasoactive agent, as used herein, refers to a natural or synthetic substance that induces increased vascular permeability and/or enhances transfer of macromolecules such as gene delivery vectors from blood vessels, e.g. across capillary endothelia. By making the vascular system more permeable to macromolecules or otherwise more amenable to the transfer of macromolecules into the capillary bed perfused by an artery, vasoactive agents can enhance delivery of these vectors to the targeted sites and thus effectively enhance overall expression of the transgene in the target tissue. Vasoactive agents that can be used in the instant invention include histamine; histamine derivatives and agonists, such as those that interact with histamine H receptors, which include, for example, 2-methylhistamine, 2-pyridylethylamine, betahistine, and thiazolylethylamine; vascular endothelial growth factors (VEGFs) and VEGF agonists (as described herein and in the cited references); and nitric oxide donors, such as sodium nitroprusside (SNP). Histamine agonists that can be used in the instant invention are described, for example, in Goodman and Gilman's The Pharmacological Basis of Therapeutics (1990) A. G. Gilman et al., eds., 8$^{th}$ ed., Pergamon Press (pp. 575-582) and in other pharmacological treatises.

Where the agent introduced into the heart is a polynucleotide and the polynucleotide's gene product acts to treat ischemic cardiac injury or other cardiac conditions, optimal expression of the polynucleotide is desired. The use of appropriate promoters can drive expression of the polynucleotide. Where the agent is delivered locally to areas of the heart where expression is desired, constitutive promoters, such as the cytomegalovirus promoter, can be used. Additionally, cardiac-specific promoters can be used to ensure limiting expression of the polynucleotide in cardiac cells. This may be important in instances where the mode of delivery used involves contacting the therapeutic polynucleotide with tissues other than cardiac tissue. For expression exclusively limited to cardiomyocytes, tissue-specific transcriptional control sequences in the myosin light chain (MLC-2) gene may be used (Lee et al., J. Biol. Chem. (1992) 267:15875-15885; Pub. No. US 2004/0132190 A1). Other cardiac-specific promoter segments are known in the art, including those found in the promoters of the atrial natriuretic factor gene, cardiac troponin T gene, and the proximal human brain natriuretic peptide gene (LaPointe et al., Am. J. Physiol. Heart Circ. Physiol. (2002) 283: H1439-1445; Ma et al., Am. J. Physiol. Cell Physiol. (2004) 286:C556-564; Plageman & Yutzey, J. Biol. Chem. (2004) 279:19026-19034; Chen et al., Cell (2002) 110:713-723). Development of efficient and strong vectors using cell-specific regulatory elements for cardiovascular gene transfer is described in Beck et al., Curr. Gene Ther. (2004) 4:457-467.

Specifically, the invention provides compositions and methods for treating a cardiac condition, for example, ischemic cardiac injury, in a patient by providing a composition comprising a therapeutic polynucleotide, or biologically active fragment thereof, which encodes a fibroblast growth factor (FGF), such as FGF-1, FGF-2, FGF-4, FGF-5, FGF-6, FGF-8, FGF-9, FGF-16, and FGF-17; an insulin-like growth factor (IGF), such as IGF-1, IGF-2, IGF1e and MGF; a vascular endothelial growth factor (VEGF), such as VEGF-C; an epidermal growth factor (EGF) family member such as a neuregulin (NRG), such as NRG-1α, NRG-1β, amphiregulin, Epigen, epiregulin, HB-EGF, EGF, betacellulin and a betacellulin splice variant (SEQ ID NO: 180); a platelet-derived growth factor (PDGF) such as PDGF-A, PDGF-B, PDGF-C, PDGF-D, and a PDGF composed of two polypeptides of A, B, C, or D polypeptides, such as PDGF-AA, PDGF-BB, PDGF-CC, PDGF-DD, and PDGF-AB; oncostatin M; a hepatocyte growth factor (HGF); a transforming growth factor (TGF) such as TGFα, TGFβ2 and TGFβ3; endothelin-1; hypothetical protein XP-098916 (SEQ ID NO: 20); TNF-α and TNFβ; interferon-α1; a member of the trefoil factor family, such as trefoil factor 2; leukemia inhibitory factor (LIF); an interleukin, such as IL-1α, IL-1β, IL-6, and IL-11; a G-CSF splice variant (SEQ ID NO: 183); chro10orf58; sushi-repeat-containing protein-X-linked 2; thymosin β4; and/or angiotensin-II; and administering the composition to the patient, for example, with a catheter to deliver the composition specifically to a VAR for treating ischemic cardiac injury.

Therapeutic Polypeptides

The invention provides polypeptides that are useful in treating cardiac conditions. Polypeptides of the invention include a polymeric form of amino acids of any length, which can include naturally-occurring amino acids, coded and non-coded amino acids, chemically or biochemically modified, derivatized, or designer amino acids, amino acid analogs, peptidomimetics, and depsipeptides, and polypeptides having modified, cyclic, bicyclic, depsicyclic, or depsibicyclic peptide backbones. They include single chain proteins as well as multimers. They also include conjugated proteins, fusion proteins, including, but not limited to, glutathione S-transferase (GST) fusion proteins, fusion proteins with a heterologous amino acid sequence, fusion proteins with heterologous and homologous leader sequences, fusion proteins with or without N-terminal methionine residues, pegolyated proteins, and immunologically tagged, or his-tagged proteins. Also included in the polypeptides of the invention are variations of naturally occurring proteins, where such variations are homologous or substantially similar to the naturally occurring protein, as well as corresponding homologs from different species. Variants of polypeptide sequences include insertions, additions, deletions, or substitutions compared with the subject polypeptides. The polypeptides of the invention also include peptide aptamers.

Polypeptides useful in treating ischemic cardiac injury and other cardiac conditions that can be used in accordance with the present invention include growth factors. Some growth factors have a broad specificity, and some have a narrow specificity. Examples of growth factors with broad specificity include platelet-derived growth factor (PDGF), epidermal growth factor, insulin like growth factor I (IGF-1), transforming growth factor β, and fibroblast growth factor, which act on many classes of cells. Examples of growth factors with narrow specificity include erythropoietin, which induces proliferation of precursors of red blood cells; interleukin-2, which stimulates proliferation of activated T-lymphocytes; interleukin-3, which stimulates proliferation and survival of various types of blood cell precursors; and nerve growth factor, which promotes the survival and the outgrowth of nerve processes from specific classes of neurons. Other examples of growth factors include keratinocyte growth factor (KGF), brain-derived neurotrophic factor (BDNF), granulocyte colony-stimulating factor (G-CSF), and granulocyte-macrophage colony-stimulating factor (GM-CSF).

The molecule oncostatin M is also useful in the present invention. Oncostatin M is a pleiotropic cytokine belonging to the interleukin-6 family that is expressed by several cell types including activated human T lymphocytes, macrophages, and neutrophils. Whereas oncostatin M can inhibit the proliferation of breast cancer cells in vitro, recent studies suggest that oncostatin M may promote tumor progression by enhancing angiogenesis and metastasis (Queen et al., Cancer Res. (2005) 65(19):8896-904). In addition, granulocyte-macrophage colony-stimulating factor produced by breast cancer cells and cell-cell contact may both be necessary for the release of oncostatin M from neutrophils. Importantly, neutrophil-derived oncostatin M induces vascular endothelial growth factor from breast cancer cells in coculture and increases breast cancer cell detachment and invasive capacity, suggesting that neutrophils and oncostatin M may promote tumor progression in vivo.

Another molecule useful in the present invention is leukemia inhibitory factor or "LIF." LIF, like oncostatin M and IL-6, has been implicated in a variety of physiological responses, such as cell growth, differentiation, and inflammation. In one study, it was shown that both OSM and LIF stimulated the proliferation of human adipose tissue-derived mesenchymal stem cells (hATSCs), however, IL-6 had no effect on cell proliferation (Song et al., Int. J. Biochem Cell Biol. (2005) 37(11):2357-65). LIF has also been shown to play a significant role in the uterus and in its absence embryos fail to implant. However, knowledge of the targets for LIF and the consequences of LIFs absence is still very incomplete (Fouladi-Nashta et al., Dev Biol. (2005) 281(1):1-21).

Another useful molecule in the present invention is trefoil factor 2 or "TFF2." The gastrointestinal trefoil factor family (TFF1, TFF2, TFF3) are considered to play an important role in maintaining the integrity of the mucosa. In one study, the physiological role of trefoil factor 2 (TFF2) in the protection of the GI tract was investigated in TFF2 deficiency and it was observed that several mouse defensin (cryptdin) genes coding important intestinal microbicidal proteins were up-regulated as a consequence of TFF2 deficiency (Baus-Loncar et al., Cell Physiol Biochem. (2005) 16(1-3):31-42). The motogenic effect of TFF2 has been demonstrated to depend on ERK1/2 and protein kinase C activation; whereas the EGF-triggered motogenic response was shown to be completely independent of ERK1/2 activation but sensitive to the inhibition of phosphoinositide 3-kinase, p38, protein kinase C, or nuclear factor kappaB (Chwieralski et al., Am J Respir Cell Mol. Biol. (2004) 31(5):528-37). However, the motogenic effects of EGF and TFF2 are additive. These data suggest that luminal EGF and TFF peptides can act synergistically in the human respiratory epithelium to enhance rapid repair processes in the course of diseases such as asthma.

Other growth factors that can be used in accordance with the invention are various fibroblast growth factors. Fibroblast growth factors (FGFs) are a family of proteins that interact with heparin sulfate glycosaminoglycans and the extracellular domains of FGF cell surface receptors (FGFRs) to trigger receptor activation and biological responses, as described in Olsen et al., J. Biol. Chem. (2003) 278(36):34226-34236 (Epub 2003 June). Other factors, known as FGF homologous factors (FHF1-FHF4, also known as FGF-11-FGF-14), are related to the FGFs by substantial sequence homology, and by their ability to bind heparin with high affinity, but fail to activate any of the seven principal FGFRs. FGFs are also called heparin binding growth factors (HBGF). Expression of different members of these proteins is found in various tissues and is under particular temporal and spatial control. These proteins are generally potent mitogens for a variety of cell types, such as those of mesodermal, ectodermal, and endodermal origin including, for example, fibroblasts, corneal and vascular endothelial cells, granulocytes, adrenal cortical cells, chondrocytes, myoblasts, vascular smooth muscle cells, lens epithelial cells, melanocytes, keratinocytes, oligodendrocytes, astrocytes, osteoblasts, and hematopoietic cells.

An overview of the FGF gene family and its evolution is provided by Itoh and Ornitz, Trends in Genetics (2004) 20:563-569 and Ornitz and Itoh, Genome Biology (2001) 2:1-12. Each member of the FGF family has its unique spectrum of functions as well as functions that overlap with other members of the family or that require interaction with other members of the family. For example, two of the family members, FGF-1 and FGF-2, have been characterized under many names, but most often as acidic and basic fibroblast growth factor, respectively. The normal gene products influence the general proliferative capacity of the majority of mesoderm and neuroectoderm-derived cells. They are capable of inducing angiogenesis in vivo and may play important roles in early development, as described in Burgess and Maciag, Ann. Rev. Biochem. (1989) 58:575-606. Further, both FGF-1 and FGF-2 have the ability to stimulate proliferation and chemotaxis of vascular endothelial cells. In addition, intramyocardial administration of FGF-2 has been reported to prevent ischemia-induced myocardial cell death and arrhythmias (Nishida et al., Circ. J. (2003) 67:334-9). The next several paragraphs illustrate the diverse roles different FGFs play in cell proliferation, migration, differentiation, tissue repair, response to injury, and signal transduction.

Many other members of the FGF family share similar activities with FGF-1 and FGF-2, such as promoting angiogenesis and wound healing. In addition, certain FGFs have been implicated in promoting tumorigenesis in carcinomas and sarcomas by promoting tumor vascularization and as transforming proteins when their expression is deregulated. For example, Pickles and Chir, Audiol. Neurootol. (2002) 7(1):36-39, described the activities of FGFs in inner ear development including: the activity of FGF-19 in inducing otocyst followed by the activity of FGF-3 in inducing further development of the otocyst; the activities of FGF-1 and FGF-2, acting as trophic factors for the developing cochlear nerve fibers; and the activities of FGF-3 and FGF-10 in the development of the walls of the cochlear spaces. The FGF-3 molecule has been described to be longer than both FGF-1 and FGF-2, with five locations of amino acid insertions compared to FGF-1 and FGF-2 (Dickson et al., Nature (1987) 326:833).

FGF-4 was reported by Yoshida et al. (Proc. Natl. Acad. Sci. 84:7305-7309 (1987)) to comprise 206 amino acids, with those in the C-terminal half of the molecule sharing approximately 40% homology with FGF-1, FGF-2, and FGF-3. FGF-4 has been reported to be active in vitro in maintaining trophoblast stem cells and was found to be absolutely required for periimplantation mouse development, as described in Goldin and Papaioannou, Genesis (2003) 36(1): 40-47.

FGF-5 cDNA, the deduced amino acid sequence of FGF-5, methods for its expression, and sequence comparison with FGF-1, FGF-2, FGF-3, and FGF-4 were reported by Zhan et al., Molec. Cell Biol. (1987)8:3487-3495. Clase et al., Dev. Dyn. (2000) 219(3):368-380 expressed FGF-5 ectopically and found that it significantly stimulated proliferation and expansion of tenascin-expressing, connective tissue fibroblast lineage throughout the developing hind limb.

FGF-6 cDNA, the deduced amino acid sequence of FGF-6, and a method for expression were reported by Coulier et al., Oncogene (1991) 6:1437-1444. FGF-6 was found to accumulate almost exclusively in the myogenic lineage. Injection of a single dose of recombinant FGF-6 was found to upregulate the expression of cyclin D1 mRNA, increase the expression of differentiation markers such as CdkIs, MHCI, and TnI, and accelerate cellular differentiation, as described in Armand, Biochim. Biophys. Acta (2003) 1642(1-2):97-105.

The amino acid sequence of FGF-7 was disclosed by Miyamoto et al., Molec. Cell Biol. (1993) 13:4251-4259 and compared therein to the sequences of FGF-1 through FGF-6. FGF-7 was found to interact exclusively with one isoform of the FGFR family, FGFR2IIIb, through interaction between the FGFR2IIIb unique exon and the beta4/beta5 loop of FGF-7, as described in Sher et al., FEBS Lett. (2003) 552(2-3): 150-4. Kinkl et al., Mol. Cell. Neurosci. (2003) 23(1):39-53, examined the effects of FGFR-3 and its preferred ligand, FGF-9 on survival of adult mammalian retinal ganglion cells ("RGC") and neurite outgrowth and suggested that the ligand-receptor couple might function to promote survival of adult mammalian retinal ganglion cells.

The cDNA, deduced amino acid sequence, and a method of making recombinant FGF-8 was reported by Tanaka et al., Proc. Natl. Acad. Sci. (1992) 89(19):8928-8932. FGF-8, also known as AIGF, was purified from a conditioned medium of mouse mammary carcinoma cells (SC-3) simulated with testosterone. FGF-8 is a distinctive FGF-like growth factor, having a putative signal peptide and sharing 30-40% homology with known members of the FGF family. FGF-8 mediates androgen-induced growth of SC-3 cells, and perhaps other cells, since it is secreted by the tumor cells themselves (Tanaka et al., Proc. Natl. Acad. Sci. (1992) 89(19):8928-8932).

The cDNA, deduced amino acid sequence, and a method of making recombinant FGF-9 was reported by Santos-Ocampo et al., J. Biol. Chem. (1996) 271:1726-1731; U.S. Pat. No. 5,155,214. FGF-9 has approximately 30% sequence similarity to other members of the FGF family. Two cysteine residues and other consensus sequences in family members were well-conserved in the FGF-9 sequence. FGF-9 was found to have no typical signal sequence in its N terminus, such as those observed in acidic and basic FGF. However, FGF-9 was observed to be secreted from cells after synthesis (Miyamoto et al., Mol. and Cell. Biol. (1993) 13:4251-4259). FGF-9, along with other FGFs, may find application in the generation of synchronous populations of cells, for example, propagating embryoid bodies into a synchronous population of neural stem cells in the presence of FGF-2, FGF-8, FGF-9, or FGF-4 (WO 05/021720).

The cDNA, deduced amino acid sequence, and a method of making recombinant FGF-10 was reported by Emoto et al., J. Biol. Chem. (1997) 272(37):23,191-23,194. Hart et al., Dev. Dyn. (2003) 228(2):185-193, suggested a role for FGF-10 and FGFR-2b signaling in regulation of pancreatic cell proliferation and differentiation.

FGF-11, FGF-12, FGF-13, and FGF-14, also known as FHF-3, FHF-1, FHF-2, and FHF-4, respectively, were cloned as described by Wang et al., J. Biol. Chem. (1996) 271:4468 and their deduced amino acid sequences reported by Smallwood et al., Proc. Natl. Acad. Sci. (1996) 93:9850-9857. Smallwood et al. also reported these FGFs to be expressed in the developing and adult nervous systems. FGF-12 and FGF-13 RNAs were detected in the developing central nervous system in mice in cells outside the proliferating ependymal layer. FGF-13 RNA was found throughout the peripheral nervous system. FGF-12 was found to be expressed in developing soft connective tissue of the limb skeleton of mice.

Both FGF-12 and FGF-13 were reported to be expressed in the myocardium, with FGF-12 RNA found only in the atrial chamber and FGF-13 RNA detected in both atrium and ventricle, as described in Hartung et al., Mech. Dev. (1997) 64(1-2):31-39. Moreover, Leung et al., Biochem. Biophys. Res. Commun. (1998) 250(1):137-142, found that FGF-13 induced cell growth of human lung fibroblasts and aortic smooth muscle cells but had no effect on dermal vascular endotherial cells. In contrast, FGF-2 induced cell growth in all three cell types.

A cDNA clone corresponding to FGF-15 and its deduced amino acid sequence were reported by McWhirter et al., Development (1997) 124:3221-3232. Recently, FGF-15 was found to be required for proper morphogenesis of the mouse cardiac outflow tract (Vincentz et al., Genesis (2005) 41:192-201).

FGF-16 has been identified as a polypeptide containing 207 amino acids (Miyake et al., Biochem. Biophys. Res. Commun. (1998) 243(1):148-152) and appears to have some similarity to FGF-9, with approximately 73% amino acid identity. In a comparison of the activities of FGF-10, FGF-16, FGF-17, and FGF-18 on the human embryonal carcinoma derived cell line Tera-2, it was observed that all four of these FGFs enhanced the survival rate of Tera-2 cells by counteracting apoptosis at concentrations in the interval of approximately 1-10 ng/ml (Granerus and Engstrom, Anticancer Res. (2000) 20(5B):3527-3531). Higher concentrations of all four of these FGFs exhibited a preferential effect on cell motility.

The cDNA, deduced amino acid sequence, and a method of making recombinant FGF-17 was reported by Hoshikawa et al., Biochem. Biophys. Res. Commun. (1998) 244(1):187-191. FGF-17 has been reported to be overexpressed in prostate cancer and benign prostatic hyperplasia by Polnaszek et al., Prostate (2004) Jun 60(1):18-24. It has also been found to play a role in the growth of large blood vessels (Xu et al., Mech. Dev. (1999) 83(1-2):165-178.

The cDNA, deduced amino acid sequence, and a method of making recombinant FGF-18, also known as FGF-98, was reported in WO 2001/13031. It is prominently expressed in developing tissues and adult lung (Ohbayashi et al., J. Biol. Chem. (1998) 273(29):18,161-18,164.

The cDNA, deduced amino acid sequence, and a method of making recombinant FGF-19 was reported by Mie et al., Cytokine (1999) 11(10):729-735. Human FGF-19 may be an orthologous gene (Ornitz et al., Genome Biol. (2001) 2:3005.1-3005.12).

The cDNA, deduced amino acid sequence, and a method of making recombinant FGF-20 was reported by Kirikoshi et al., Biochem. Biophys. Res. Commun. (2000) 274(2):337-343. FGF-20 was found to be expressed in the endocardium and epicardium (Lavine et al., Dev. Cell (2005) 8:85-95) and in another study, was found to act synergistically with FGF-2 to increase the number of dopaminergic neurons in ES cell-derived neurospheres (Takagi et al., J. Clin. Invest. (2005) 115:23-25).

The cDNA, deduced amino acid sequence, and a method of making recombinant FGF-21 was reported by Nishimura et al., Biochim. Biophys. Acta (2000) 1492:203-206. FGF-21 was initially characterized as most abundantly expressed in the liver and is most similar (approximately 35% amino acid identity) to FGF-19 (Nishimura et al., Biochim. Biophys. Acta (2000) 1492:203-206).

The cDNA, deduced amino acid sequence, and a method of making recombinant FGF-22 was reported by Naketake et al, Biochim. Biophys Acta (2001), who characterized it as a homolog of FGF-7 and FGF-10. FGF-22 has been observed to interact with fibroblast growth factor-binding protein (FGF-BP), which regulates its activity (Beer et al., Oncogene (2005) 24(34):5269-5277). FGF-BP is known to bind and activate FGF-1 and FGF-2, thereby contributing to tumor angiogenesis (Beer et al., Oncogene (2005) 24(34):5269-5277). FGF-22 has also been reported to act as a presynaptic organizing molecule in the mammalian brain (Umemori et al., Cell (2004) 118:257-270).

The cDNA, deduced amino acid sequence, and a method of making recombinant FGF-23 was reported by Yamashita et al., Biochem. Biophys. Res. Commun. (2000) 277:494-498). FGF-23 was found to be preferentially expressed in the ventrolateral thalamic nucleus of the brain, suggesting a role for FGF-23 in this particular location (Yamashita et al., Biochem. Biophys. Res. Commun. (2000) 277:494-498).

EGFs can also be used to treat cardiac conditions in accordance with the invention. As described in more detail in the Examples, EGF family members amphiregulin, Epigen, epiregulin, HB-EGF, TGFα, EGF, and betacellulin promote cardiosphere development. EGF family members can thus be used to stimulate proliferation of cardiomyocyte progenitor cells and treat ischemic cardiac injury or other cardiac condition in a patient. Epidermal growth factor (EGF) stimulates a variety of tissues in vitro including normal and malignant rodent mammary epithelium and human breast epithelial cells and fibroadenoma (Osborne et al. (1980) Cancer Res. 40:2361-2366; Gray et al., Nature (1983) 303:722-725). Amphiregulin is a glycoprotein that has been shown to inhibit growth of several human carcinoma cells and stimulate proliferation of human fibroblasts and certain tumor cells (Shoyab et al., Proc. Natl. Acad. Sci. USA (1988) 85:6528-6532). Epigen is able to promote the growth of epithelial cells and stimulates the phosphorylation of c-erbB-1 and MAP kinase proteins in epithelial cells (Strachan et al., J. Biol. Chem. (2001) 276:18,265-18,271). Epiregulin inhibits the growth of several epithelial tumor cells and stimulates the growth of fibroblasts and various other types of cells (Toyoda et al., J. Biol. Chem. (1995) 270:7495-7500; Takahashi et al., Circulation (2003) 108:2524-2529). Heparin-binding EGF-like growth factor (HB-EGF) is mitogenic for BALB-3T3 fibroblasts and smooth muscle cells, but not endothelial cells (Higashiyama et al., Science (1991) 251:936-939). Transforming growth factor α (TGFα) is a 50-residue polypeptide that can induce a reversible phenotypic transformation of normal mammalian cells (Winkler et al. (1986) J. Biol. Chem. 261:13,838-13,843; Derynck et al. (1984) Cell 38:287-297). TGFα and related polypeptides may find application in expanding populations of cells (US Patent Applications 2002 0169119 and 2002 0193301). Betacellulin is a potent mitogen for retinal pigment epithelial cells and vascular smooth muscle cells (Shing et al., Science (1993) 259:1604-1607).

IGFs can also be used to treat cardiac conditions in accordance with the invention. Members of the IGF family have been reported to have a wide range of actions on different tissues, including stimulating anabolism, stimulating acute metabolic effects, enhancing cell proliferation and differentiation, and protecting cells from apoptosis. The role of the growth hormone (GH) IGF-I axis in regulating cardiac growth, structure, and function has been reviewed by Isgaard et al, Horm. Metab. Res. (1999) 31(2-3):50-54. Mechanisms of action of the IGF family on cardiomyocytes include regenerative and anti-apoptosis effects and the interplay between heat shock protein and IGF-I receptor signaling (Saetrum et al., Growth Horm. IGF Res. (2005) 15(2):89-94).

Members of the PDGF family can be used to treat cardiac conditions in accordance with the invention. Enhancing PDGF signaling pathways provides cardioprotection and has been reported to reduce the extent of myocardial injury following coronary occlusion (Edelberg et al., Cardiovasc. Toxicol. (2003) 3(1):27-35). PDGF-AA has been reported to have a mitogenic effect on cardiac myocytes (Simm et al., Basic. Res. Cardiol. (1998) 93 Suppl 3:40-43). PDGF-BB induces increased synthesis of both PDGF α- and β-receptor protein, and binds the PDGF β-receptor with high affinity (Eriksson et al., J. Biol. Chem. (1991) 266:21138-21144). Stimulating cultured neonatal rat cardiomyocytes with PDGF-BB was reported to induce myocardial hypertrophy in spontaneously hypertensive rats, suggesting that PDGF-BB plays a role in mediating cardiomyocyte proliferation (Liu et al., Sheng Li Xue Bao. (2002) 54(2):159-164. PDGF-DD is secreted as a disulfide-linked homodimer with latent activity that is activated by extracellular proteases (Bergsten et al., Nat. Cell Biol. (2001) 3(5):512-516). PDGF-DD is specific for the PDGF receptor beta isoform (Fredriksson et al., Cytokine Growth Factor Rev. (2004) 15(4):197-204). However, as described by Raines et al., Cytokine Growth Factor Rev. (2004) 15(4):237-254, PDGFs can, under certain conditions, contribute to cardiovascular disease.

Most growth factors have other actions in addition to inducing cell growth or proliferation, for example, they may influence survival, differentiation, migration, or other cellular functions. Growth factors can have complex effects on their targets, for example, they may act on some cells to stimulate cell division, and on others to inhibit it. They may stimulate growth at one concentration, and inhibit at another.

Growth factors of the invention may protect the heart against oxidative stress, such as FGFs, IGFs, EGFs, hepatocyte growth factors, endothelin-1, and transforming growth factors (Suzuki, Antioxid. Redox Signal. (2003) 5:741-749). Other therapeutic polypeptides that can be used in the instant invention are angiotensin II, which stimulates myocyte growth (Sen, Hypertension (1997) 30:209-216) and FGF-2, which protects the myocardium from tissue loss and dysfunction when administered before or during ischemia (Detillieux et al., Cardiovasc. Res. (2003) 57:8-19; Jiang et al., Cardiovasc. Res. (2004) 62:154-166).

Thymosin β4 is a small protein with a diverse range of activities which has been reported to enhance the survival and repair of embryonic and postnatal cardiomyocytes (Bock-Marquette et al., Nature (2004) 432:466-72). It is hypothesized to integrate the actin cytoskeleton with growth factor signal transduction cascades (Bubb et al., Vitam. Horm. (2003) 66:297-316). It is present in a number of tissues, including heart muscle, spleen, thymus, brain, lung, and liver (Hannappel et al., Proc. Natl. Acad. Sci. USA (1982) 79:2172).

The invention also provides treatment with survival factors, such as IGF1 and cardiotrophin-1. These factors, alone or in combination with other factors, can provide protection to adult cardiomyocytes and neonatal cardiomyocytes, as well as other types of cells, such as renal cells and neuronal cells. The invention also provides combinations of growth factors that have synergistic effects. For example, one or more FGFs may be combined with one or more IGF, HGF, Wnt (ligands for receptors with seven transmembrane regions that comprise the "frizzled" gene family), or bone morphogenic protein, with synergistic effects.

The mechanisms through which cardiomyocytes respond to stimuli such as stress are complex. Cardiomyocytes respond to a variety of stimuli, and their response depends on a number of factors, including, but not limited to, the stimulus involved and their stage of development. For example, in response to growth stimuli, cardiomyocytes of an adult myocardium increase their cellular mass but do not proliferate, in contrast to immature cardiomyocytes. Neonatal cardiomyocytes respond to mechanical stretching via an angiotensin II- and endothelin-mechanism that does not operate in adult cardiomyocytes (Schlüter and Piper, FASEB J. (1999) 13 Suppl.:S17-22). The signal transduction mechanisms behind these responses involve distinct signaling pathways, each of which contributes a component to the overall response. For example, activation of a pathway including the mitogen-activated protein kinase can lead to re-expression of fetal genes, whereas activation of a pathway including PI3-kinase and p70$^{s6k}$ can lead to a general activation of protein synthesis and cellular growth (Schlüter and Piper, FASEB J. (1999) 13 Suppl.:S17-22). An understanding of these pathways, their timing and the steps and components involved, can lead to effective strategies for treating injury arising from stress, including ischemic cardiac injury and other cardiac conditions.

Growth factors described herein, such as PDGF-BB, EGF, FGF-4, and FGF-9, can be used to stimulate proliferation of cardiomyocyte progenitor cells (for example, cardiac stem cells) and thus treat ischemic cardiac injury or other cardiac condition in a patient. As described in more detail in the Examples, PDGF-BB, FGF-4, FGF-9, and EGF have been found to increase the number of cardiospheres, which are clusters of undifferentiated cells generated from subcultures of heart specimens that can differentiate into cardiomyocytes (Messina et al., Circ. Res. (2004) 95:911-921). Present in the heart are stem cells that can differentiate into cardiomyocytes (Messina et al., Circ. Res. (2004) 95:911-921; Beltrami et al., Cell (2003) 114:763-776; Oh et al., Proc. Natl. Acad. Sci. (2003) 100:12,313-12,318; Laugwitz et al., Nature (2005) 433:647-653), such that myocardial repair and treatment of ischemic cardiac injury and other cardiac conditions can be accomplished by locally administering substances that cause proliferation and differentiation of these stem cells. This strategy does not involve cellular transplantation, a procedure that is fraught with challenges, as described by Lovell and Mathur, Cell Prolif. (2004) 37:67-87.

Multiple pathways operate in concert to enable cardiomyocytes to adapt to oxidative stress or to mount a hypertophic response. Similarly, complex and multi-step pathways govern differentiation and proliferation of cardiomyocytes. Growth factors, enzymes, substrates, transcription factors, and other substances involved in these pathways can be used to treat ischemic cardiac injury and other cardiac conditions in a patient by ensuring that pathways for cardiomyocyte survival, growth, proliferation, and differentiation operate as needed. They include 18 kDa FGF-2, 21-34 kDa FGF-2 (hi-FGF-2), activator protein-1 (AP-1), acidic fibroblast growth factor (or FGF-1 or aFGF), Akt, angiotensin II receptor, axin, $β_1$ integrin, Bcl-2, Bcl-X$_L$, Ca$^{2+}$-calmodulin dependent kinase, calcineurin, calmodulin, catalase, catecholamine, c-Jun N-terminal kinase, connexin 43, Csx/Nkx-2.5 transcription factor, diacylglycerol, Egr-1 (early growth response protein), E1F-4E (peptide chain initiation factor), Elk-1 transcription factor, ErbB2 receptor, ErbB4 receptor, ERK (extracellular signal regulated kinase), ERK-1, ERK-2, estrogen, extracellular signal regulated kinase, FGFR-1 receptor, FGFR-1 tyrosine kinase, fibroblast growth factor 8b, FOG-2 (friend of GATA-2), Frat1, Fyn, $G_{αi}$ protein, $G_{αq}$ protein, GATA (includes members GATA-1, -2, -3, -4, -5, and -6), GATA-1, GATA-2, GATA-4, GATA-6, $G_i$ protein, gp130-signal transducer and activator of transcription, $G_q$ protein, Grb2, glial growth factor 2, glycogen synthase kinase-3 inhibitor, inducible nitric oxide synthase (iNOS), inositol-1,4,5-triphosphate, insulin, insulin-like growth factor, insulin-like growth factor II, insulin-like growth factor II receptor, integrin, Janus kinase, MAPK (mitogen-activated protein kinase), MAPK phosphatase-1, MGF (mechano-growth factor), MEF2 (myocyte enhancer factor-2), MEK (mitogen-activated protein kinase kinase), MEK1, MEK2, mitogen-activated protein kinase, MKK (MAPK kinase), neuregulin, neuregulin-1 (also known as neu differentiation factor, heregulin, glial growth factor, and acetylcholine receptor-inducing activity), neuropeptide Y, NFAT (nuclear factor of activated T-cells), NF-AT3 (nuclear factor of activated T-cells 3), NF-κβ (nuclear factor κβ), nitric oxide, ornithine decarboxylase, p70$^{s6k}$, PD098059, phenylephrine, phosphatidylinositol 3'-kinase (PI 3-kinase), phospholipase C, PKCe, protein kinase B, protein kinase C, protein phosphatase 2A, protein tyrosine kinase, protein tyrosine phosphatase, Rac GTPase, Raf/MKKK (MAPK kinase kinase), Ras GTPase, RhoA GTPase, Shc, Sos, Src homology domain-containing protein tyrosine phosphatase 1, SRF (serum response factor), Stat (signal transducer and activator of transcription), steroid receptor coactivator-1, superoxide dismutase, thymosin β4, transforming growth factor β, transforming growth factor β1, tumor necrosis factor, Wnt-3a protein, YY1 transcription factor, β-catenin, and variants thereof. Variants that can be used in the invention include constitutively active forms and activated forms, including, but not limited to, constitutively active Akt, constitutively active PI 3-kinase, activated calcineurin mutant, gain-of-function β-catenin, and activated β-catenin.

Additional variants that can be used in the invention include biotinylated forms, e.g., biotinylated IGF-1 in conjunction with streptavidin and biotinylated self-assembling peptide nanofibers (Davis et al., "Targeted delivery of IGF-1 with biotinylated self-assembling peptide nanofibers," presented at the Keystone Symposium on Molecular Biology of Cardiac Diseases and Regeneration (D2), Steamboat Springs, Colo., USA, Apr. 3-8, 2005), and truncated forms, e.g., E-domain of mechano-growth factor (MGF) (Geenen et al., "Systemic application of a locally expressed IGF-I splice variant preserves cardiac function following myocardial infarction," presented at the Keystone Symposium on Molecular Biology of Cardiac Diseases and Regeneration (D2), Steamboat Springs, Colo., USA, Apr. 4, 2005). Also, neuregulin, neuregulin derivatives and related compounds may be used for cardiomyocyte growth and/or differentiation and for the treatment or management of heart disease and heart failure, according to PCT application WO 00/037095, published on Jun. 29, 2000.

Substances that stabilize β-catenin can be used as therapeutic agents in the instant invention. Pathways leading to stabilization of β-catenin have been studied, e.g., by Haq et al., Proc. Natl. Acad. Sci. USA (2003) 100:4610-4615. Substances that stabilize β-catenin are known in the art, and include, but are not limited to, insulin, insulin-like growth factor-1, phenylephrine, wnt proteins, and hypertrophic stimuli. Protein kinase B (PKB) can also be used to stabilize β-catenin since inhibition of GSK-3β, via phosphorylation of Ser-9 by PKB, appears to be the mechanism by which β-catenin is stabilized (Haq et al., Proc. Natl. Acad. Sci. USA (2003) 100:4610-4615).

The therapeutic methods of the invention can modulate physiologic and pathologic processes. This modulation can encompass an increase or a decrease, a stimulation, inhibition, or blockage in the measured activity when compared to a suitable control. Modulation of expression levels includes increasing the level and decreasing the level of an mRNA or polypeptide of interest encoded by a polynucleotide of the invention when compared to a control lacking the agent being tested. In some embodiments, agents of particular interest are those which inhibit a biological activity of a subject polypeptide, and/or which reduce a level of a subject polypeptide in a cell, and/or which reduce a level of a subject mRNA in a cell, and/or which reduce the release of a subject polypeptide from a eukaryotic cell, and/or which reduce the symptoms (e.g., cell death and damage) associated with a medical condition. In other embodiments, agents of interest are those that increase polypeptide activity. Modulating a level of an active subject polypeptide can include increasing or decreasing the activity of a subject polypeptide; increasing or decreasing a level of active polypeptide; and increasing or decreasing a level of mRNA encoding active subject polypeptide. In some embodiments, an agent is a subject polypeptide, where the subject polypeptide itself is administered to an individual. In some embodiments, an agent is an antibody specific for a subject polypeptide.

Specifically, the invention provides compositions and methods for treating a cardiac condition, for example, ischemic cardiac injury, in a patient by providing a composition comprising a therapeutic polypeptide, or biologically active fragment thereof, including, but not limited to, a fibroblast growth factor (FGF), such as FGF-1, FGF-2, FGF-4, FGF-5, FGF-6, FGF-8, FGF-9, FGF-16, and FGF-17; an insulin-like growth factor (IGF), such as IGF-1, IGF-2, IGF1e and MGF; a vascular endothelial growth factor (VEGF), such as VEGF-C; an epidermal growth factor (EGF) family member such as a neuregulin (NRG), such as NRG-1α, NRG-1β, amphiregulin, Epigen, epiregulin, HB-EGF, EGF, betacellulin and a betacellulin splice variant (SEQ ID NO: 180); a platelet-derived growth factor (PDGF) such as PDGF-A, PDGF-B, PDGF-C, PDGF-D, and a PDGF composed of two polypeptides of A, B, C, or D polypeptides, such as PDGF-AA, PDGF-BB, PDGF-CC, PDGF-DD, and PDGF-AB; oncostatin M; a hepatocyte growth factor (HGF); a transforming growth factor (TGF) such as TGFα, TGFβ2 and TGFβ3; endothelin-1; hypothetical protein XP-098916 (SEQ ID NO: 20); TNF-α and TNF-β; interferon-α1; a member of the trefoil factor family, such as trefoil factor 2; leukemia inhibitory factor (LIF); an interleukin, such as IL-1α, IL-1β, IL-6, and IL-11; a G-CSF splice variant (SEQ ID NO: 183); chro10orf58; sushi-repeat-containing protein-X-linked 2; thymosin β4; and/or angiotensin-II; and administering the composition to the patient, for example, with a catheter to deliver the composition specifically to a VAR for treating ischemic cardiac injury.

Variant and Mutant Polypeptides

It is to be understood that the therapeutic polypeptides covered by the instant invention include biologically active fragments and analogs of therapeutic polypeptides specifically identified, such as the growth factors and proteins mentioned above. Thus, for example, a reference to EGF encompasses not only the full-length EGF, but also biologically active fragments and analogs of EGF. A biologically active fragment or analog is capable of treating ischemic cardiac injury or other cardiac conditions. Analogs of a particular therapeutic polypeptide can differ from the therapeutic polypeptide by amino acid sequence differences, or by modifications (e.g., post-translational modifications), which do not affect sequence, or by both. Analogs of the invention will generally exhibit at least 80%, at least 85%, at least 90%, or at least 99% amino acid identity with all or part of the amino acid sequence of a therapeutic polypeptide. Methods for assaying the capacity of biologically active fragments and analogs to treat ischemic cardiac injury or other cardiac conditions are known in the art, e.g., those described herein.

Protein engineering may be employed to improve or alter the characteristics of the therapeutic polypeptides of the invention. Recombinant DNA technology known to those skilled in the art can be used to create novel mutant proteins or "muteins" including single or multiple amino acid substitutions, deletions, additions, or fusion proteins. Such modified polypeptides can show desirable properties, such as enhanced activity or increased stability. In addition, they may be purified in higher yields and show better solubility than the corresponding natural polypeptide, at least under certain purification and storage conditions.

N-Terminal and C-Terminal Deletion Mutants

For instance, for many proteins, including the extracellular domain of a membrane associated protein or the mature form(s) of a secreted protein, it is known in the art that one or more amino acids may be deleted from the N-terminus or C-terminus without substantial loss of biological function. For instance, Ron et al., J. Biol. Chem. (1993) 268:2984-2988, reported modified KGF proteins that had heparin binding activity even if 3, 8, or 27 amino-terminal amino acid residues were missing.

However, even if deletion of one or more amino acids from the N-terminus of a protein results in modification or loss of one or more biological functions of the protein, other biological activities may still be retained. Thus, the ability of the shortened protein to induce and/or bind to antibodies which recognize the complete or mature from of the protein generally will be retained when less than the majority of the residues of the complete or mature protein are removed from the N-terminus. Whether a particular polypeptide lacking N-terminal residues of a complete protein retains such immunologic activities can be determined by routine methods described herein and otherwise known in the art. Accordingly, the present invention further provides polypeptides having one or more residues deleted from the amino terminus of the amino acid sequences of the molecules shown in the Sequence Listing.

Similarly, many examples of biologically functional C-terminal deletion muteins are known. For instance, interferon gamma increases in activity as much as ten fold when 8-10 amino acid residues are deleted from the carboxy terminus of the protein, see, for example, Dobeli et al., J. Biotechnology (1988) 7:199-216.

However, even if deletion of one or more amino acids from the C-terminus of a protein results in modification of loss of one or more biological functions of the protein, other biological activities may still be retained. Thus, the ability of the shortened protein to induce and/or bind to antibodies which recognize the complete or mature form of the protein generally will be retained when less than the majority of the residues of the complete or mature protein are removed from the C-terminus. Whether a particular polypeptide lacking C-terminal residues of a complete protein retains such immunologic activities can be determined by routine methods described herein and otherwise known in the art.

Other Mutants

In addition to terminal deletion forms of the protein discussed above, it also will be recognized by one of ordinary skill in the art that some amino acid sequences of the therapeutic polypeptides of the invention can be varied without significant effect of the structure or function of the protein. If such differences in sequence are contemplated, it should be remembered that there will be critical areas on the protein which determine activity.

Thus, the invention further includes variations of the therapeutic polypeptides of the invention which show substantial biological activity. Such mutants include deletions, insertions, inversions, repeats, and type substitutions, selected according to general rules known in the art, so as have little effect on activity. For example, guidance concerning how to make phenotypically silent amino acid substitutions is provided in Bowie et al., Science (1990) 247:1306-1310, wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections, or screens, to identify sequences that maintain functionality.

These studies report that proteins are surprisingly tolerant of amino acid substitutions. The authors further indicate which amino acid changes are likely to be permissive at a certain position of the protein. For example, most buried amino acid residues require nonpolar side chains, whereas few features of surface side chains are generally conserved. Other such phenotypically silent substitutions are described in Bowie, et al., supra, and the references cited therein. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg, and replacements between the aromatic residues Phe and Tyr.

Thus, a fragment, derivative, or analog of a polypeptide of the Sequence Listing or polypeptide encoded by a nucleic acid sequence of the Sequence Listing may be (i) one in which one or more of the amino acid residues are substituted with a conserved or non-conserved amino acid residue; such a substituted amino acid residue may or may not be one encoded by the genetic code; (ii) one in which one or more of the amino acid residues includes a substituent group; (iii) one in which the mature polypeptide is fused with another compound, such as a compound to increase the half-life of the polypeptide (for example, polyethylene glycol); or (iv) one in which the additional amino acids are fused to the above form of the polypeptide, such as an IgG Fc fusion region peptide, a leader or secretory sequence, a sequence employed to purify the above form of the polypeptide, or a proprotein sequence. Such fragments, derivatives, and analogs are deemed to be within the scope of those skilled in the art from the teachings herein.

Thus, the therapeutic polypeptides of the invention may include one or more amino acid substitutions, deletions, or additions, either from natural mutations or human manipulation. As indicated, these changes may be of a minor nature, such as conservative amino acid substitutions, that do not significantly affect the folding or activity of the protein. Conservative amino acid substitutions include the aromatic substitutions Phe, Trp, and Tyr; the hydrophobic substitutions Leu, Iso, and Val; the polar substitutions Glu and Asp; the basic substitutions Arg, Lys, and His; the acidic substitutions Asp and Glu; and the small amino acid substations Ala, Ser, Thr, Met, and Gly.

Amino acids essential for the functions of the therapeutic polypeptides of the invention can be identified by methods known in the art, such as site-directed mutagenesis or alanine-scanning mutagenesis, see, for example, Cunningham and Wells, Science (1989) 244:1081-1085. The latter procedure introduces single alanine mutations. The resulting mutant molecules are then tested for biological activity such as receptor binding, or in vitro or in vitro proliferative activity.

Of special interest are substitutions of charged amino acids with other charged or neutral amino acids which may produce proteins with highly desirable improved characteristics, such as less aggregation. Aggregation may not only reduce activity but also be problematic when preparing pharmaceutical formulations, because, for example, aggregates can be immunogenic, Pinckard et al., Clin. Exp. Immunol. (1967) 2:331-340; Robbins et al., Diabetes (1987) 36:838-845; Cleland et al., Crit. Rev. Therapeutic Drug Carrier Systems (1993) 10:307-377.

Replacing amino acids can also change the selectivity of the binding of a ligand to cell surface receptors. For example, Ostade et al., Nature (1993) 361:266-268 describes mutations resulting in selective binding of TNF-α to only one of the two known types of TNF receptors. Sites that are critical for ligand-receptor binding can also be determined by structural analysis such as crystallization, nuclear magnetic resonance, or photoaffinity labeling, for example, Smith et al., J. Mol. Biol. (1992) 224:899-904 and de Vos et al., Science (1992) 255:306-312.

The locations and disulfide bonding properties of the growth factors of the invention are known by those of skill in the art. In an embodiment, the invention provides compositions comprising mutant growth factor molecules with cysteine serine mutated to serine. These constructs may be cloned into any suitable vector, as known in the art, for example, the pTT5-G vector. These muteins may provide a composition with improved therapeutic properties.

The therapeutic agent can be administered to the patient through various means, e.g., intravenously, intracardially, and intraperitoneally, and in a variety of formulations, e.g., with or without material that slowly releases the therapeutic agent, with or without matrix material that serves as scaffold, and with or without certain kinds of stem cells including cardiac stem cells. Various materials can be used as matrix material, including, but not limited to, collagen (e.g., rat tail collagen, Roche cat #1 179 179), nanofiber, and alginate. In some embodiments, the therapeutic agent can be administered with or without use of devices such as catheters, and with or without monitoring, e.g., via echocardiography. The therapeutic agent can be used to treat patients, including, but not limited to, patients with pathological conditions including, but not limited to, heart failure, myocardial infarction, coronary artery disease, and cardiomyopathy.

Therapeutic Fusion Molecules

As one of skill in the art will appreciate, therapeutic polypeptides of the invention can be combined with heterologous molecules, for example, polypeptides, resulting in chimeric polypeptide molecules. These fusion molecules may facilitate purification. They provide an increased half-life in vivo. This increase has been reported, for example, in chimeric proteins consisting of the first two domains of the human CD4-polypeptide and various domains of the constant regions of the heavy or light chains of mammalian immunoglobulins, for example, EP 0 394 827; Traunecker et al., Nature (1988) 331:84-86. Fusion proteins with a disulfide-linked dimeric structure due to an immunoglobulin portion can also be more efficient in binding and neutralizing other molecules than the therapeutic protein or protein fragment alone, for example, as described by Fountoulakis et al., J. Biochem. (1995) 270:3958-3964. Suitable chemical moieties for derivatization of a heterologous polypeptide include, for example, polymers, such as water soluble polymers, succinyl groups, the constant domain of immunoglobulins, all or part of human serum albumin; fetuin A; fetuin B; a leucine zipper domain; a tetranectin trimerization domain; mannose binding protein (also known as mannose binding lectin), for example, mannose binding protein 1; and an Fc region, as described herein and further described in U.S. Pat. No. 6,686,179, and U.S. Application Nos. 60/589,788 and 60/654,229. Methods of making fusion proteins are well-known to the skilled artisan.

For example, the short plasma half-life of unmodified interferon alpha makes frequent dosing necessary over an extended period of time, in order to treat viral and proliferative disorders. Interferon alpha fused with HSA has a longer half life and requires less frequent dosing than unmodified interferon alpha; the half-life was 18-fold longer and the clearance rate was approximately 140 times slower (Osborn et al., J. Pharmacol. Exp. Ther. (2002) 303:540-548). Interferon beta fused with HSA also has favorable pharmacokinetic properties; its half life was reported to be 36-40 hours, compared to 8 hours for unmodified interferon beta (Sung et al., J. Interferon Cytokine Res. (2003) 23:25-36). A HSA-interleukin-2 fusion protein has been reported to have both a longer half-life and favorable biodistribution compared to unmodified interleukin-2. This fusion protein was observed to target tissues where lymphocytes reside to a greater extent than unmodified interleukin 2, suggesting that it exerts greater efficacy (Yao et al., Cancer Immunol. Immunother. (2004) 53:404-410).

The Fc receptor of human immunoglobulin G subclass 1 has also been used as a fusion partner for a therapeutic molecule. It has been recombinantly linked to two soluble p75 tumor necrosis factor (TNF) receptor molecules. This fusion protein has been reported to have a longer circulating half-life than monomeric soluble receptors, and to inhibit TNFα-induced proinflammatory activity in the joints of patients with rheumatoid arthritis (Goldenberg, Clin. Ther. (1999) 21:75-87). This fusion protein has been used clinically to treat rheumatoid arthritis, juvenile rheumatoid arthritis, psoriatic arthritis, and ankylosing spondylitis (Nanda and Bathon, Expert Opin. Pharmacother. (2004) 5:1175-1186).

Polymers, for example, water soluble polymers, are useful in the present invention as the polypeptide to which each polymer is attached will not precipitate in an aqueous environment, such as typically found in a physiological environment. Polymers employed in the invention will be pharmaceutically acceptable for the preparation of a therapeutic product or composition. One skilled in the art will be able to select the desired polymer based on such considerations as whether the polymer/protein conjugate will be used therapeutically and, if so, the desired dosage, circulation time, and resistance to proteolysis.

Suitable, clinically acceptable, water soluble polymers include, but are not limited to, polyethylene glycol (PEG), polyethylene glycol propionaldehyde, copolymers of ethylene glycol/propylene glycol, monomethoxy-polyethylene glycol, carboxymethylcellulose, dextran, polyvinyl alcohol (PVA), polyvinyl pyrrolidone, poly-1,3-dioxolane, poly-1,3,6-trioxane, ethylene/maleic anhydride copolymer, poly (β-amino acids) (either homopolymers or random copolymers), poly(n-vinyl pyrrolidone) polyethylene glycol, polypropylene glycol homopolymers (PPG) and other polyakylene oxides, polypropylene oxide/ethylene oxide copolymers, polyoxyethylated polyols (POG) (for example, glycerol) and other polyoxyethylated polyols, polyoxyethylated sorbitol, or polyoxyethylated glucose, colonic acids or other carbohydrate polymers, Ficoll, or dextran and mixtures thereof.

As used herein, polyethylene glycol (PEG) is meant to encompass any of the forms that have been used to derivatize other proteins, such as mono-(C1-C10) alkoxy- or aryloxy-polyethylene glycol. Polyethylene glycol propionaldehyde may have advantages in manufacturing due to its stability in water.

Specifically, a modified heterologous polypeptide of the invention may be prepared by attaching polyaminoacids or branch point amino acids to the polypeptide. For example, the polyaminoacid may be a carrier protein that serves to increase the circulation half life of the polypeptide (in addition to the advantages achieved via a fusion molecule). For the therapeutic purpose of the present invention, such polyaminoacids should ideally be those that have or do not create neutralizing antigenic response, or other adverse responses. Such polyaminoacids may be chosen from serum album (such as human serum albumin), an additional antibody or portion thereof, for example the Fc region, fetuin A, fetuin B, leucine zipper nuclear factor erythroid derivative-2 (NFE2), neuroretinal leucine zipper, tetranectin, or other polyaminoacids, for example, lysines. As described herein, the location of attachment of the polyaminoacid may be at the N-terminus, or C-terminus, or other places in between, and also may be connected by a chemical linker moiety to the selected molecule.

Polymers used herein, for example water soluble polymers, may be of any molecular weight and may be branched or unbranched. The polymers each typically have an average molecular weight of between about 2 kDa to about 100 kDa (the term "about" indicating that in preparations of a polymer, some molecules will weigh more, some less, than the stated molecular weight). The average molecular weight of each polymer may be between about 5 kDa and about 50 kDa, or between about 12 kDa and about 25 kDa. Generally, the higher the molecular weight or the more branches, the higher the polymer:protein ratio. Other sizes may also be used, depending on the desired therapeutic profile; for example, the duration of sustained release; the effects, if any, on biological activity; the ease in handling; the degree or lack of antigenicity; and other known effects of a polymer on a modified molecule of the invention.

Polymers employed in the present invention are typically attached to a heterologous polypeptide with consideration of effects on functional or antigenic domains of the polypeptide. In general, chemical derivatization may be performed under any suitable condition used to react a protein with an activated polymer molecule. Activating groups which can be used to link the polymer to the active moieties include sulfone, maleimide, sulfhydryl, thiol, triflate, tresylate, azidirine, oxirane, and 5-pyridyl.

Polymers of the invention are typically attached to a heterologous polypeptide at the alpha (α) or epsilon (ε) amino groups of amino acids or a reactive thiol group, but it is also contemplated that a polymer group could be attached to any reactive group of the protein that is sufficiently reactive to become attached to a polymer group under suitable reaction conditions. Thus, a polymer may be covalently bound to a heterologous polypeptide via a reactive group, such as a free amino or carboxyl group. The amino acid residues having a free amino group may include lysine residues and the N-terminal amino acid residue. Those having a free carboxyl group may include aspartic acid residues, glutamic acid residues, and the C-terminal amino acid residue. Those having a reactive thiol group include cysteine residues.

Methods for preparing fusion molecules conjugated with polymers, such as water soluble polymers, will each generally involve (a) reacting a heterologous polypeptide with a polymer under conditions whereby the polypeptide becomes attached to one or more polymers and (b) obtaining the reaction product. Reaction conditions for each conjugation may be selected from any of those known in the art or those subsequently developed, but should be selected to avoid or limit exposure to reaction conditions such as temperatures, solvents, and pH levels that would inactivate the protein to be modified. In general, the optimal reaction conditions for the reactions will be determined case-by-case based on known parameters and the desired result. For example, the larger the ratio of polymer:polypeptide conjugate, the greater the percentage of conjugated product. The optimum ratio (in terms of efficiency of reaction in that there is no excess unreacted polypeptide or polymer) may be determined by factors such as the desired degree of derivatization (for example, mono-, di- tri- etc.), the molecular weight of the polymer selected, whether the polymer is branched or unbranched and the reaction conditions used. The ratio of polymer (for example, PEG) to a polypeptide will generally range from 1:1 to 100:1. One or more purified conjugates may be prepared from each mixture by standard purification techniques, including among others, dialysis, salting-out, ultrafiltration, ion-exchange chromatography, gel filtration chromatography, and electrophoresis.

One may specifically desire an N-terminal chemically modified protein. One may select a polymer by molecular weight, branching, etc., the proportion of polymers to protein (polypeptide or peptide) molecules in the reaction mix, the type of reaction to be performed, and the method of obtaining the selected N-terminal chemically modified protein. The method of obtaining the N-terminal chemically modified protein preparation (separating this moiety from other monoderivatized moieties if necessary) may be by purification of the N-terminal chemically modified protein material from a population of chemically modified protein molecules.

Selective N-terminal chemical modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved. For example, one may selectively attach a polymer to the N-terminus of the protein by performing the reaction at a pH which allows one to take advantage of the pKa differences between the $\epsilon$-amino group of the lysine residues and that of the $\alpha$-amino group of the N-terminal residue of the protein. By such selective derivatization, attachment of a polymer to a protein is controlled: the conjugation with the polymer takes place predominantly at the N-terminus of the protein and no significant modification of other reactive groups, such as the lysine side chain amino groups, occurs. Using reductive alkylation, the polymer may be of the type described above and should have a single reactive aldehyde for coupling to the protein. Polyethylene glycol propionaldehyde, containing a single reactive aldehyde, may also be used.

In one embodiment, the present invention contemplates the chemically derivatized polypeptide to include mono- or poly- (for example, 2-4) PEG moieties. Pegylation may be carried out by any of the pegylation reactions known in the art.

Methods for preparing a pegylated protein product will generally include (a) reacting a polypeptide with polyethylene glycol (such as a reactive ester or aldehyde derivative of PEG) under conditions whereby the protein becomes attached to one or more PEG groups; and (b) obtaining the reaction product(s). In general, the optimal reaction conditions for the reactions will be determined case by case based on known parameters and the desired result.

There are a number of PEG attachment methods available to those skilled in the art. See, for example, EP 0 401 384; Malik et al., Exp. Hematol. (1992) 20:1028-1035; Francis, Focus on Growth Factors (1992) 3(2):4-10; EP 0 154 316; EP 0 401 384; WO 92/16221; WO 95/34326; and the other publications cited herein that relate to pegylation.

The step of pegylation as described herein may be carried out via an acylation reaction or an alkylation reaction with a reactive polyethylene glycol molecule. Thus, protein products according to the present invention include pegylated proteins wherein the PEG group(s) is (are) attached via acyl or alkyl groups. Such products may be mono-pegylated or poly-pegylated (for example, those containing 2-6 or 2-5 PEG groups). The PEG groups are generally attached to the protein at the $\alpha$- or $\epsilon$-amino groups of amino acids, but it is also contemplated that the PEG groups could be attached to any amino group attached to the protein that is sufficiently reactive to become attached to a PEG group under suitable reaction conditions.

Pegylation by acylation generally involves reacting an active ester derivative of polyethylene glycol (PEG) with a polypeptide of the invention. For acylation reactions, the polymer(s) selected typically have a single reactive ester group. Any known or subsequently discovered reactive PEG molecule may be used to carry out the pegylation reaction. An example of a suitable activated PEG ester is PEG esterified to N-hydroxysuccinimide (NHS). As used herein, acylation is contemplated to include, without limitation, the following types of linkages between the therapeutic protein and a polymer such as PEG: amide, carbamate, urethane, and the like, see for example, Chamow, Bioconjugate Chem. (1994) 5:133-140. Reaction conditions may be selected from any of those known in the pegylation art or those subsequently developed, but should avoid conditions such as temperature, solvent, and pH that would inactivate the polypeptide to be modified.

Pegylation by acylation will generally result in a poly-pegylated protein. The connecting linkage may be an amide. The resulting product may be substantially only (for example, >95%) mono, di- or tri-pegylated. However, some species with higher degrees of pegylation may be formed in amounts depending on the specific reaction conditions used. If desired, more purified pegylated species may be separated from the mixture (particularly unreacted species) by standard purification techniques, including among others, dialysis, salting-out, ultrafiltration, ion-exchange chromatography, gel filtration chromatography and electrophoresis.

Pegylation by alkylation generally involves reacting a terminal aldehyde derivative of PEG with a polypeptide in the presence of a reducing agent. For the reductive alkylation reaction, the polymer(s) selected should have a single reactive aldehyde group. An exemplary reactive PEG aldehyde is polyethylene glycol propionaldehyde, which is water stable, or mono C1-C10 alkoxy or aryloxy derivatives thereof, see for example, U.S. Pat. No. 5,252,714.

Additionally, heterologous polypeptides of the present invention and the epitope-bearing fragments thereof described herein can be combined with parts of the constant domain of immunoglobulins (IgG), resulting in chimeric polypeptides. These particular fusion molecules facilitate purification and show an increased half-life in vivo, This has been shown, for example, in chimeric proteins consisting of the first two domains of the human CD4-polypeptide and various domains of the constant regions of the heavy or light chains of mammalian immunoglobulins, such as EP 0 394 827; Traunecker et al., Nature (1988) 331:84-86. Fusion molecules that have a disulfide-linked dimeric structure due to the IgG part can also be more efficient in binding and neutralizing other molecules than, for example, a monomeric polypeptide or polypeptide fragment alone; see, for example, Fountoulakis et al., J. Biochem. (1995) 270:3958-3964.

In another described embodiment, a human serum albumin fusion molecule may also be prepared as described herein and as further described in U.S. Pat. No. 6,686,179.

Moreover, the polypeptides of the present invention can be fused to marker sequences, such as a peptide that facilitates purification of the fused polypeptide. The marker amino acid sequence may be a hexa-histidine peptide such as the tag provided in a pQE vector (Qiagen, Mississauga, Ontario, Canada), among others, many of which are commercially available. As described in Gentz et al., Proc. Natl. Acad. Sci. (1989) 86:821-824, for instance, hexa-histidine provides for convenient purification of the fusion protein. Another peptide tag useful for purification, the hemagglutinin HA tag, corresponds to an epitope derived from the influenza hemagglutinin protein (Wilson et al., Cell (1984) 37:767-78). Any of these above fusions can be engineered using the polynucleotides or the polypeptides of the present invention.

Delivery of Therapeutic Agents

Catheterization

Cardiac catheterization is an example of a method of local delivery to the heart that involves the passage of a catheter (typically, a thin flexible tube) into the right or left side of the heart. Generally this procedure is performed to obtain diagnostic information about the heart or its blood vessels or to provide therapeutic interventions in certain types of heart conditions, such as in balloon angioplasty. Cardiac catheterization can be used to determine pressure and blood flow in the heart's chambers, collect blood samples from the heart, and examine the arteries of the heart with an X-ray technique called fluoroscopy. It can also be done on infants and children to examine or treat congenital heart defects. The technique has not been used in methods for local delivery of therapeutic agents to the myocardium for treating cardiac conditions, as disclosed in the instant invention.

The therapeutic agent may be delivered by introducing a catheter into either a vein or an artery, which is then advanced into a heart chamber and ultimately to an affected area in the myocardium, for example, areas that have sustained ischemic cardiac injury. In one embodiment of the invention, a catheter can be inserted into a femoral vein and then advanced from the femoral vein into the right atrium, and from the right atrium into the myocardium of the affected area; or from the right atrium to the right ventricle and into the myocardium of the affected area. In another embodiment, a catheter can be introduced into a femoral artery and advanced from the femoral artery into the aorta and left ventricle and then into the myocardium of the affected area; or from the left ventricle to the left atrium into the myocardium of the affected area.

Cardiac catheterization has been described in detail elsewhere, for example, Baim & Grossman (2000) Grossman's Cardiac Catheterization, Angiography, and Intervention. 6$^{th}$ ed., Lippincott, Williams, & Wilkins.

A variety of catheters and delivery routes can be used to achieve intracoronary delivery, as is known in the art (see, for example, Textbook of Interventional Cardiology (1994) E. J. Topol, ed., 2$^{nd}$ ed., W.B. Saunders Co.; Vascular Surgery (1989) R. B. Rutherford, ed., 3$^{rd}$ ed., W.B. Saunders Co.; Cecil Textbook of Medicine (1992) J. B. Wyngaarden et al., eds., 19$^{th}$ ed., W.B. Saunders Co.; and Textbook of Surgery (1991) D. Sabiston, ed., 14$^{th}$ ed., W.B. Saunders Co.). Direct intracoronary (or graft vessel) injection can be performed using standard percutaneous catheter based methods under fluoroscopic guidance. Any variety of coronary catheter, or a Stack perfusion catheter, for example, can be used in the present invention. A variety of general purpose catheters and modified catheters can also be used in the instant invention. They are available commercially, for example, from Advanced Cardiovascular Systems (ACS), Target Therapeutics, Boston Scientific and Cordis. Where delivery to the myocardium is achieved by injection directly into a coronary artery, a number of approaches can be used to introduce a catheter into the coronary artery, as is known in the art. For example, a catheter can be conveniently introduced into a femoral artery and threaded retrograde through the iliac artery and abdominal aorta and into a coronary artery. Alternatively, a catheter can be first introduced into a brachial or carotid artery and threaded retrograde to a coronary artery. The capillary bed of the myocardium can also be reached by retrograde perfusion, for example, from a catheter placed in the coronary sinus. Such a catheter can include a proximal balloon to prevent or reduce anterograde flow as a means of facilitating retrograde perfusion.

A therapeutic composition of the invention can be adapted to be delivered to the cardiac area by catheter.

The therapeutic agent can be administered locally at the time of cardiac surgery, while treating a cardiac event, or while performing a diagnostic procedure. The therapeutic agent can also be delivered in anticipation of events that can result in ischemic cardiac injury or other cardiac conditions. In this regard, the therapeutic agent serves to prevent ischemic cardiac injury or other cardiac conditions. For example, the therapeutic agent can be delivered a plurality of days prior to non-cardiac surgery, complex percutaneous revascularization, or complex cardiac surgery. The therapeutic agent can also be delivered to donor hearts prior to cardiac transplantation to prevent any ischemic cardiac injury or other cardiac conditions that may arise during the entire transplantation process (explantation, transport, implantation). The therapeutic agent can also be useful in providing myocardial protection to patients with diffuse, nonrevascularizable coronary artery disease. For these patients, a life-long regimen of the therapeutic agent may be needed.

Direct Injection

Therapeutic compositions have also been delivered to the heart by direct injection into the cardiac muscle (myocardium). Direct injection may be performed during open heart surgery. Surgical visualization of the heart facilitates accurate implantation into the myocardium. Direct injection may also be performed without surgical access to the heart by injecting the therapeutic composition through the chest wall, guided by the use of an imaging procedure. Any known imaging technique which provides information in real time is suitable for use with the methods disclosed herein of injecting therapeutic compositions of the invention into the myocardium. For example, echocardiography and other real-time imaging techniques can be used to guide direct injection.

In an embodiment, the therapeutic agent is delivered to the heart by direct intracoronary injection using standard percutaneous catheter-based methods under fluoroscopic guidance. The injection can be made substantially (such as at least 1 cm) into the lumen of the coronary arteries or one or more saphenous veins or internal mammary artery grafts or other conduits delivering blood to the myocardium. Any coronary artery can be injected. Any suitable variety of coronary catheter, or a Stack perfusion catheter, can be used in accordance with the present invention.

In some embodiments, the instant invention employs a catheter suitable for injecting therapeutic agents into specific parts of the heart, for example, the VAR region, presumptive VAR region, pericardial space, myocardium, or pericardium. Magnetic resonance (MR) may be used to precisely guide delivery of therapeutic agents to defined locations within the infarct or elsewhere in the heart. A catheter as described by Karmarkar et al., Magnetic Resonance in Medicine (2004) 51:1163-1172 or by U.S. Pat. No. 6,304,769, can be used. The components of such a catheter can be arranged to form a loopless RF antenna receiver coil that enables tracking by magnetic resonance imaging (MRI). Different types of RF receiver antennas (for example, loop, loopless, opposed solenoid, etc.) can be used to enable active tracking. Myocardial delayed-enhancement (MDE) imaging can identify the infarcted myocardium, and real-time MRI can be used to guide catheterization. The distal end of the catheter can be seen under MRI with a bright signal at the distal tip of the catheter. Using MRI tracking, the catheter can be steered into position and the needle advanced to inject the therapeutic agent intramyocardially or into the pericardial space or into any other desired location in the heart.

Other systems may be suitable for delivery of the therapeutic agent, such as, for example, the "Noga" system developed by Johnson & Johnson; the "Myocath" device and system developed by BioHeart, Inc.; the "Stilleto" catheter device and system developed by Boston Scientific Corporation; and a catheter device and system commercially developed by BioCardia. Deflectable intravascular catheters with an infusion needle generally can be used. Methods of delivery and catheters described in U.S. Pat. Nos. 6,297,219; 5,797,870; 5,698,531; 5,707,969; 5,328,470; 5,049,132; and WO 00/44443 can be adapted for use in the present invention.

Using the catheterization delivery methods of the instant invention, the therapeutic agent can be delivered to specific areas of the heart. The therapeutic agent can be delivered to the injury site, the VAR region, or presumptive VAR region. In other embodiments, the therapeutic agent is delivered to the pericardial space. The pericardial space may potentially serve as a convenient, safe, and effective drug delivery reservoir that might be used to administer therapeutic agents to the heart, as described in U.S. Pat. No. 6,759,386 B2. Intrapericardial delivery of basic fibroblast growth factor (bFGF) is described by Laham et al. (1999) Clin. Cardiol. 22 (Suppl. I):I-6-I-9. The pericardial space can be accessed by transthoracic devices (for example, needles or catheters) or by a transventricular approach using a catheter. The pericardial space can also be accessed transvenously via the right auricle, as described by U.S. Pat. No. 5,269,326 and U.S. Patent Application 2004/0215168 A1.

A therapeutic composition of the invention can be adapted to be delivered to the cardiac area by direct injection.

Other Delivery Methods

The therapeutic agent can be delivered in a gel composition. A gel composition provides the advantage of controlled and sustained release of the therapeutic agent over time. A gel composition can comprise a biocompatible polymer and a solvent that dissolves the polymer to form a gel. The gel composition can also contain other substances including surfactants, viscosity controlling agents, complexing agents, antioxidants, other polymers, etc. Viscosity of the gel can be altered, for example, by changing the concentration of the polymer, to accommodate desired release kinetics of the therapeutic agent. Using a temperature-sensitive polymer, the gel composition can be liquid before administration to the patient and become a gel inside the patient. Biocompatible polymers that can be used may be biodegradable and may include, but are not limited to polylactides, polyglycolides, polycaprolactones, polyanhydrides, polyamines, polyurethanes, polyesteramides, polyorthoesters, polydioxanones, poloxamers, polyacetals, polyketals, polycarbonates, polyorthocarbonates, polyphosphazenes, succinates, poly(malic acid), poly(amino acids), polyvinylpyrrolidone, polyethylene glycol, polyhydroxycellulose, chitin, chitosan, and copolymers, terpolymers, and mixtures thereof.

Biodegradable carriers can be used to deliver the therapeutic agent. In one embodiment, the carrier comprises a cross-linked first and second polysaccharide, as described by U.S. Pat. No. 6,303,585 B1. The first and second polysaccharides are each a derivative of a member selected from the group consisting of hyaluronic acid, dextran, dextran sulfate, chondroitin sulfate, dermatan sulfate, keratan sulfate, heparin, heparin sulfate, and alginate. Aldehyde groups of the first polysaccharide derived from oxidized sugar rings can form covalent imine crosslinks with the second polysaccharide amine derivative at amine sites. The ratios of the first and second polysaccharides determine both the physical and biological properties of the carrier. For example, the ratio can be manipulated to provide unreacted but active aldehydes for covalent linkage to a therapeutic agent, if desired. Advantages of such cross-linked polysaccharide drug carriers include a prolonged bio-degradation rate, controlled release of the therapeutic agent, and flexibility of formulation in gel-like or sponge-like form to accommodate desired therapeutic intervention. Other carriers that can be used in the instant invention include heparin-alginate polymer and alginate as described in Harada et al., J. Clin. Invest. (1994) 94:623-630 and references cited therein.

To assist in determining the fate and location of the therapeutic agent within the patient, a biomarker can be co-administered with the composition containing the therapeutic agent. In one embodiment, the composition containing the therapeutic agent includes the biomarker. Biomarkers can be visualized or detected by a variety of methods, including, but not limited to, x-rays, computed tomography (CT), magnetic resonance imaging (MRI), molecular imaging, or nuclear medicine techniques such as positron emission tomography (PET). Biomarkers that can be used in the present invention, and methods of making and using them, are known in the art.

The therapeutic agent can be delivered in a matrix composition. The matrix material may serve as scaffold. It may or may not comprise cardiac progenitor cells, including cardiac stem cells. Various materials can be used as matrix material, including, but not limited to, collagen (for example, rat tail collagen, Roche cat# 1 179 179), nanofiber, and alginate. In some embodiments, the therapeutic agent can be administered with or without use of devices such as catheters, and with or without monitoring, for example, via echocardiography.

In response to an ischemic episode or a potentially ischemic episode, or in anticipation thereof, the therapeutic agent may be delivered once or a plurality of times. The frequency of treatment and amount of therapeutic agent delivered per treatment will depend on a number of variables, including, but not limited to, the extent and nature of the injury; the potency, toxicity, half-life, solubility, and side effects of the therapeutic agent; and the degree of cardiomyocyte function desired. Those of skill will readily appreciate that dose levels can vary as a function of the specific compound, the severity of the symptoms, and the susceptibility of the subject to side effects. A person of ordinary skill in the art, without undue experimentation, will be able to determine the appropriate frequency and amount of therapeutic agent to use for a particular situation. Suitable dosages for a given compound are readily determinable by those of skill in the art by a variety of means. For example, the invention provides FGF2 to human subjects. The dose ranges stated herein are based on a 70 kg person and may be adjusted to treat patients of greater or lesser weight. The invention provides FGF2 at doses of from about 20 micrograms to about 3 milligrams. The invention provides FGF2 at doses of from about 30 micrograms to about 3.5 milligrams. The invention provides FGF2 at doses of from about 40 micrograms to about 4 milligrams. The invention provides FGF2 at doses of from about 50 micrograms to about 4.5 milligrams. The invention provides FGF2 at doses of from about 100 micrograms to about 5 milligrams. The invention provides FGF2 at doses of from about 136 micrograms to about 5.5 milligrams. Multiple doses may be provided in one container, such as a vial or a syringe. Thus, the invention provides doses on multiples of those listed above, intended to be provided in multiple doses, for example, two or three doses per container.

The dose may be administered through a variety of routes, including, but not limited to, intracardiac, intracoronary, intravenous, subcutaneous, intramuscular, intrapulmonary, inhaled, intranasal, transdermal, etc. Dosing frequency can be once, twice, thrice, once every other month, once every three months, once every six months, once a year, once monthly, once weekly, twice weekly, thrice weekly, every other day, or daily. The dose may be given in one injection, or a plurality of injections, for example, two, three, four, five, six, seven, eight, nine, or ten injections in a given session. The dose may range from 1 nanogram to 10 milligrams.

To determine efficacy of the treatment, various parameters may be monitored using a variety of techniques. For example, magnetic resonance imaging may be used to monitor changes in infarct size, wall motion and thickening, and myocardial perfusion (van der Wall et al., Circulation (1995) 92:2723-2739). Echocardiography and microscopic analysis may also be used. Apoptotic cell death can be detected in vivo as described by Blankenberg et al., J. Nucl. Cardiol. (1999) 6:531-539.

The therapeutic agent can be delivered over a period of time by a pump. This delivery may be performed before, simultaneously with, or, or following an acute procedure, such as catheterization, injection, or surgery. The period of time may be in the range of minutes, hours, days, weeks, or months. The pump may be any biocompatible pump, for example, an osmotic pump. The delivery of the agent by a pump my comprise the primary mode of therapy or an adjunctive therapy.

Additional methods that detect or measure DNA damage, cell death, or apoptosis that may be useful in evaluating efficacy of a particular treatment for ischemic cardiac injury or other cardiac conditions can be employed, for example, in animal studies or on biopsy tissue. DNA damage can be detected using any known method, including, but not limited to, a Comet assay (commercially available from Trevigen, Inc.), which is based on alkaline lysis of labile DNA at sites of damage; and immunological assays using antibodies specific for aberrant DNA structures, for example, 8-OHdG.

Cell death can be measured using any known method, and is generally measured using any of a variety of known methods for measuring cell viability. Such assays are generally based on entry into the cell of a detectable compound (or a compound that becomes detectable upon interacting with, or being acted on by, an intracellular component) that would normally be excluded from a normal, living cell by its intact cell membrane. Such compounds include substrates for intracellular enzymes, including, but not limited to, a fluorescent substrate for esterase; dyes that are excluded from living cells, including, but not limited to, trypan blue; and DNA-binding compounds, including, but not limited to, an ethidium compound such as ethidium bromide and ethidium homodimer, and propidium iodide.

Apoptosis can be assayed using any known method. Assays can be conducted on cell populations or an individual cell, and include morphological assays and biochemical assays. A non-limiting example of a method of determining the level of apoptosis in a cell population is TUNEL (TdT-mediated dUTP nick-end labeling) labeling of the 3'-OH free end of DNA fragments produced during apoptosis (Gavrieli et al. (1992) J. Cell Biol. 119:493). The TUNEL method consists of catalytically adding a nucleotide, which has been conjugated to a chromogen system or a to a fluorescent tag, to the 3'-OH end of the 180-bp (base pair) oligomer DNA fragments in order to detect the fragments. The presence of a DNA ladder of 180-bp oligomers is indicative of apoptosis. Procedures to detect cell death based on the TUNEL method are available commercially, for example, from Boehringer Mannheim (Cell Death Kit) and Oncor (Apoptag Plus). Another marker that is currently available is annexin, sold under the trademark APOPTEST™. This marker is used in the "Apoptosis Detection Kit," which is also commercially available, for example, from R&D Systems. During apoptosis, a cell membrane's phospholipid asymmetry changes such that the phospholipids are exposed on the outer membrane. Annexins are a homologous group of proteins that bind phospholipids in the presence of calcium. A second reagent, propidium iodide (PI), is a DNA binding fluorochrome. When a cell population is exposed to both reagents, apoptotic cells stain positive for annexin and negative for PI, necrotic cells stain positive for both, live cells stain negative for both. Other methods of testing for apoptosis are known in the art and can be used, including, for example, the method disclosed in U.S. Pat. No. 6,048,703.

The therapeutic agent may be delivered alone or in combination with one or more other therapeutic agents. The exact formulation and combination will depend on a number of factors, including, but not limited to, the extent and nature of the injury; mode of action of the therapeutic agents; and any interactions between the therapeutic agents. A person of ordinary skill in the art, without undue experimentation, will be able to determine the appropriate combination for a particular situation.

Kits

The invention further provides a kit comprising a device suitable for use according to the instant invention, for example, in local delivery, including cardiac catheterization or direct injection of a therapeutic agent to the myocardium to treat ischemic cardiac injury. The device may be pre-packaged in a sterile container ready for use. The kit may further include a therapeutic agent and other substances needed to prepare the final composition to be used to treat a cardiac condition. In an embodiment, the kit includes unit doses of the therapeutic agent in injectable form. Unit dosage forms for injection may comprise the therapeutic agent in a composition as a solution in sterile water, normal saline, or another pharmaceutically acceptable carrier. In an embodiment, the kit includes unit doses of a therapeutic agent for treating a cardiac condition in a patient, for example, a fibroblast growth factor (FGF), such as FGF-1, FGF-2, FGF-4, FGF-5, FGF-6, FGF-8, FGF-9, FGF-16, and FGF-17; an insulin-like growth factor (IGF), such as IGF-1, IGF-2, IGF1e and MGF;

a vascular endothelial growth factor (VEGF), such as VEGF-C; an epidermal growth factor (EGF) family member such as a neuregulin (NRG), such as NRG-1α, NRG-1β, amphiregulin, Epigen, epiregulin, HB-EGF, EGF, betacellulin and a betacellulin splice variant (SEQ ID NO: 180); a platelet-derived growth factor (PDGF) such as PDGF-A, PDGF-B, PDGF-C, PDGF-D, and a PDGF composed of two polypeptides of A, B, C, or D polypeptides, such as PDGF-AA, PDGF-BB, PDGF-CC, PDGF-DD, and PDGF-AB; oncostatin M; a hepatocyte growth factor (HGF); a transforming growth factor (TGF) such as TGFα, TGFβ2 and TGFβ3; endothelin-1; hypothetical protein XP-098916 (SEQ ID NO: 20); TNF-α and TNF-β; interferon-α1; a member of the trefoil factor family, such as trefoil factor 2; leukemia inhibitory factor (LIF); an interleukin, such as IL-1α, IL-1β, IL-6, and IL-11; a G-CSF splice variant (SEQ ID NO: 183); chr10orf58; sushi-repeat-containing protein-X-linked 2; thymosin β4; angiotensin-II; and/or biologically active fragments or variants thereof. In an embodiment, the kit includes instructions for its use. These instructions may describe the attendant benefits of the therapeutic agent in treating the cardiac condition and may be provided in a variety of forms. Suitable forms include printed information, a compact disc, and the like. Suitable devices, including catheters; therapeutic agents; and unit doses are those described herein.

EXAMPLES

The examples, which are intended to be purely exemplary of the invention and should therefore not be considered to limit the invention in any way, also describe and detail aspects and embodiments of the invention discussed above. The examples are not intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

While the present invention has been described with reference to the specific embodiments thereof, it should be understood by those skilled in the art that various changes may be made and equivalents may be substituted without departing from the true spirit and scope of the invention. In addition, many modifications can be made to adapt a particular situation, material, composition of matter, process, process step or steps, to the objective, spirit and scope of the present invention. All such modifications are intended to be within the scope of the claims appended hereto.

Example 1

Isolation and Expansion of Adult Cardiac Stem Cells

Adult mouse (strain C57BL/6J, Jackson Laboratory, Bar Harbor, Me.) cardiac stem cells were isolated and expanded using the method described by Messina et al., Circ. Res. (2004) 95:911-921. Briefly, isolated myocardial tissue was cut into 1- to 2-mm$^3$ pieces, washed with $Ca^{2+}$—$Mg^{2+}$-free phosphate-buffered solution (PBS) (cat# 21-031-CM, Mediatech, Herndon, Va.), and digested with trypsin (cat# 15090-046, Invitrogen, Carlsbad, Calif.) and collagenase IV (cat# M1927, Sigma, St. Louis, Mo.). The cells thus obtained were discarded. The remaining tissue fragments were washed with complete explant medium (CEM), which contained Iscove's Modified Dulbecco's Medium (IMDM) (cat#12440, Invitrogen, Carlsbad, Calif.), fetal bovine serum (FBS) (cat# 35-015-CV, Mediatech, Herndon, Va.), penicillin and streptomycin (cat#15140-122, Invitrogen, Carlsbad, Calif.), L-glutamine (cat#25030-081, Invitrogen, Carlsbad, Calif.), and 2-mecaptoethanol (cat#M6250, Sigma, St. Louis, Mo.). The washed tissue fragments were cultured as explants in CEM. After a few weeks, small, phase-bright cells migrated to the layer of fibroblast-like cells that was generated from adherent explants. The phase-bright cells were collected by washing, using $Ca^{2+}$—$Mg^{2+}$-free PBS, versene (cat#15040-066, Invitrogen, Carlsbad, Calif.), trypsin, and EDTA.

Example 2

Effect of Various Growth Factors on Cardiosphere Proliferation In Vitro

Figure 10:
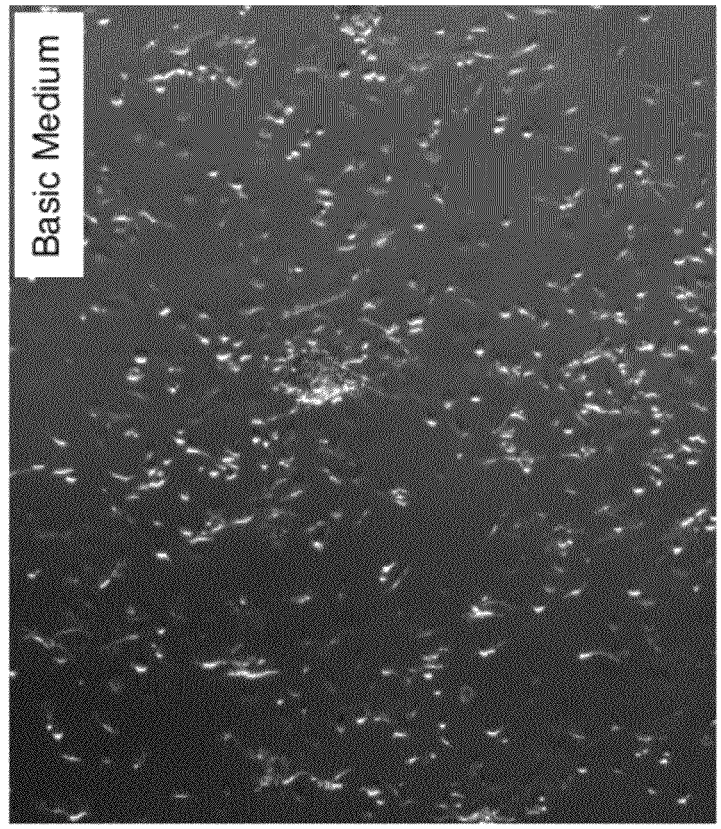
FIG. 10 shows a set of photographs of the cell cultures resulting from incubation with the indicated treatments for ten days as described further in Example 2. The treatments shown are: (1) complete medium; (2) basal medium (basic medium); (3) basal medium supplemented with FGF-4 (FGF4); (4) basal medium supplemented with EGF (EGF); (5) basal medium supplemented with FGF-9 (FGF9); (6) conditioned medium (CM) from 293 cells (S-control); (7) pool of CM with human FGF-1, FGF-2, FGF-3, FGF-4, and FGF-5 (S1); (8) pool of CM with human FGF-6, FGF-7, FGF-8, FGF-9, and FGF-10 (S2); and (9) pool of CM with human FGF-11, FGF-12, FGF-13-1A, FGF-13-1B, and FGF-13SV1 (splice variant 1) (S3).
Figure 10:
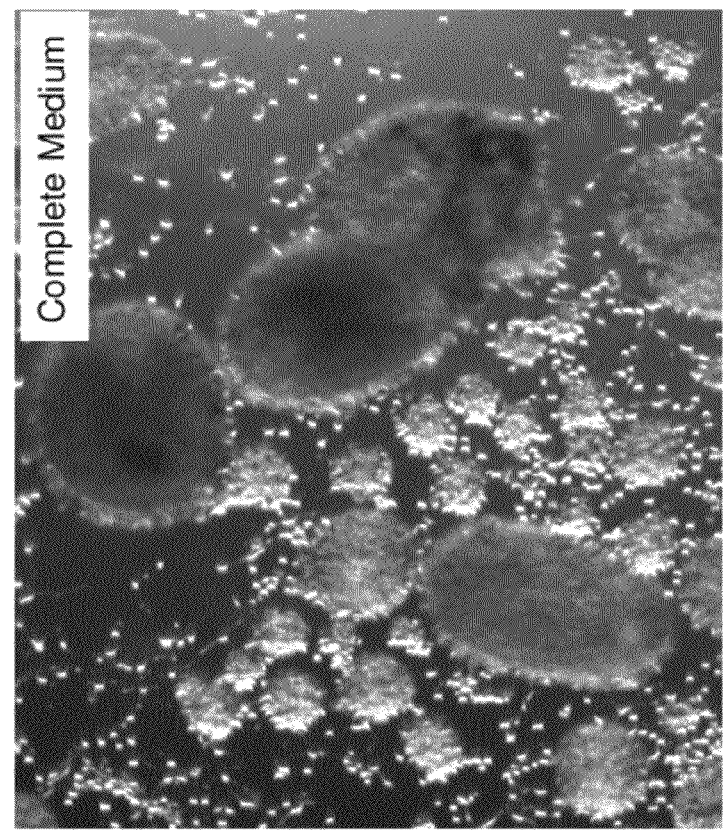
Figure 11:
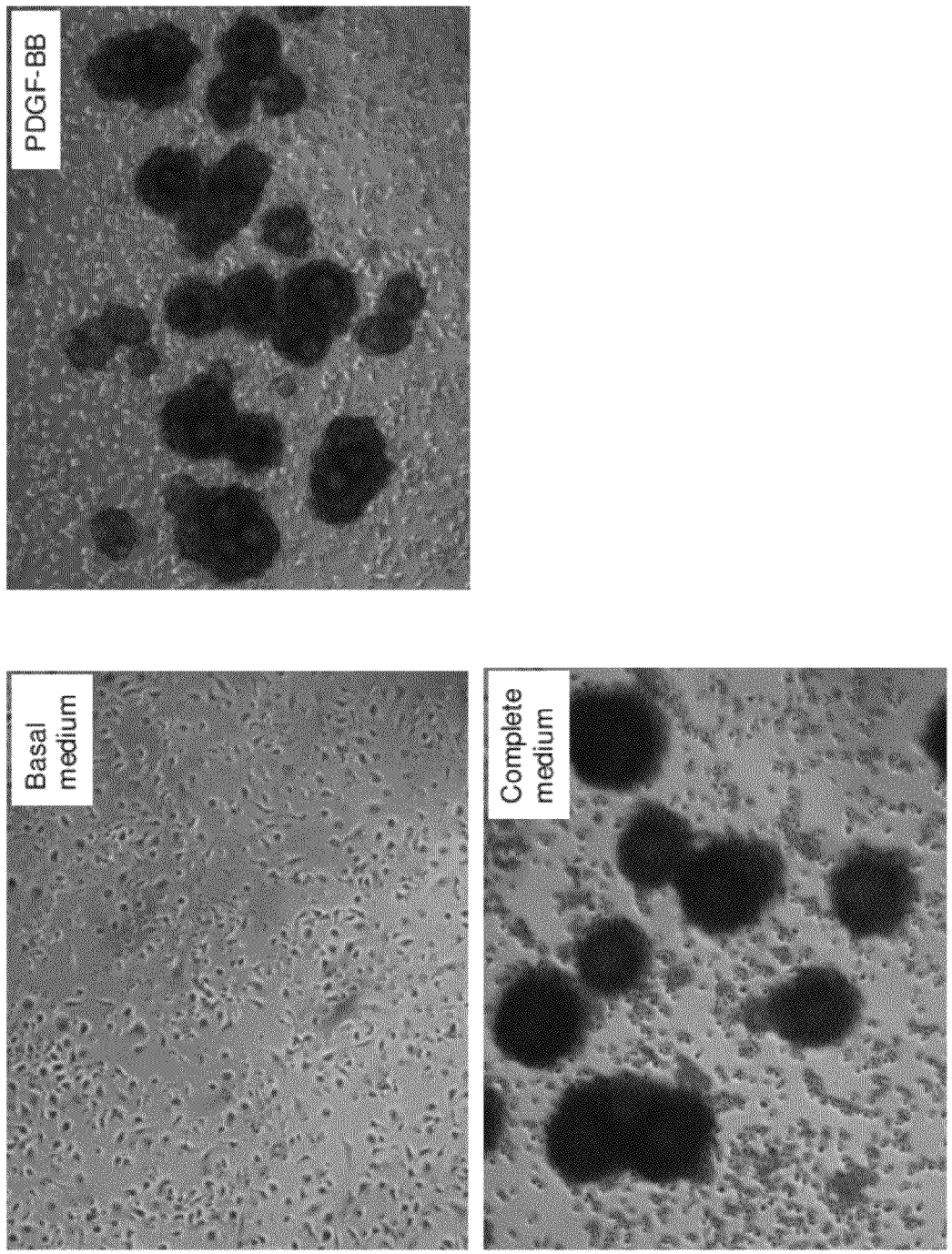
FIG. 11 shows a set of photographs of the cell cultures resulting from incubation with the indicated treatments for ten days, as described further in Example 3. The treatments shown are: (1) basal medium; (2) complete medium; and (3) platelet-derived growth factor-BB (PDGF-BB).
Figure 12:
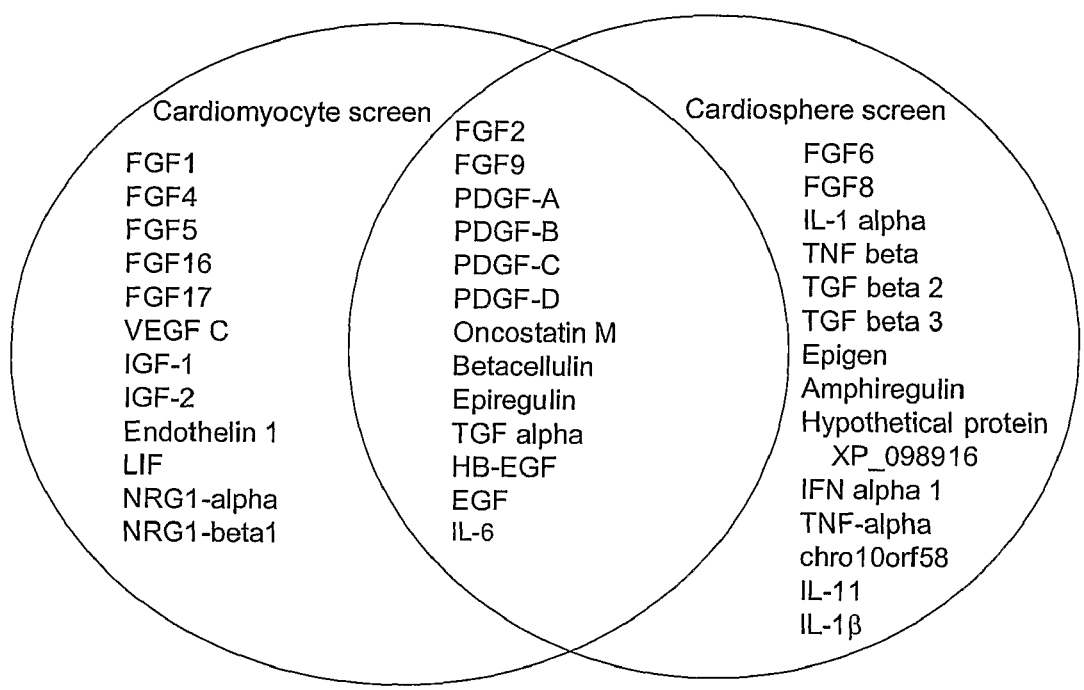
FIG. 12 summarizes the results of cardiomyocyte and cardiosphere assays performed as described in FIGS. 1-11. Agents which increased the phosphorylation of Akt, STAT3 and ERK1/2 in cardiomyocytes in vitro and are thus identified as agents which can increase cardiomyocyte cell survival are listed within the oval on the left. Agents which increased the proliferation of cardiospheres in vitro are listed within the oval on the right. Thirteen agents both increased the phosphorylation of Akt, STAT3 and ERK1/2 in cardiomyocytes and increased cardiomyocyte cell survival. They are listed in the overlapping ovals.

To test the effect of different substances, including a variety of growth factors, on cardiosphere proliferation, the small, phase-bright cells collected in Example 1 were seeded at a density of $1 \times 10^5$ cells per well in poly-D-lysine coated 24-well cell culture plates (cat#354414, Becton Dickinson (BD), Franklin Lakes, N.J.) containing cardiosphere-growing medium (CGM) (Messina et al., Circ. Res. (2004) 95:911-921). The medium CGM included IMDM, DMEM/F12 medium (cat#11330-032, Invitrogen, Carlsbad, Calif.), B27 (cat#17504, Invitrogen, Carlsbad, Calif.), 2-mercaptoethanol, epidermal growth factor (EGF) (cat#13247-051, Invitrogen, Carlsbad, Calif.), basic fibroblast growth factor (bFGF) (cat#13256-029, Invitrogen, Carlsbad, Calif.), cardiotrophin-1 (cat#438-CT-050, R&D, Minneapolis, Minn.), and thrombin (cat#1473-SE-010, R&D, Minneapolis, Minn.). The cells were incubated overnight at 37° C. with 5% $CO_2$. After the overnight incubation, the CGM was replaced with basal medium containing 35% IMDM/65% DMEM Ham F12 mix supplemented with 2% B27 without serum or growth factor ("basal medium" treatment which served as negative control) or with individual test growth factors (e.g., EGF, FGF-1, FGF-2, FGF-3, FGF-4, FGF-5, FGF-7, FGF-9, FGF-10; obtained from R&D, Minneapolis, Minn., except for EGF, which was obtained from Invitrogen, Carlsbad, Calif.) at 100 ng/ml each. As a positive control, some cells were incubated in CGM. The cells were maintained in these different treatments for ten days. On day five of the ten-day incubation, the cells were transferred to fresh media. On day ten of the ten-day incubation, the number of cardiospheres in suspension was counted (FIG. 9), and photographs of the cultures were taken (FIGS. 10 and 11).

The effect of various pools of human FGFs on cardiosphere proliferation was also determined. To prepare various conditioned media (CM) with different pools of human FGFs, FGF-containing supernatants were obtained using stable 293E cell lines (ATCC, Manassas, Va.) expressing individual human FGFs. These cells ($1-2 \times 10^7$) were grown to confluence in DMEM with 10% FBS and 1% P/S (typically, one or two days). The cells were then split, and 10% of the cells were incubated in serum-free media (DMEM with 10 mM Hepes and 0.1% BSA) for 3 days at 37° C. to collect the supernatant containing an FGF of interest. The other 90% of the cells was maintained in DMEM with 10% FBS and 1% P/S until the next round of supernatant collection. Supernatants from cells grown in the presence of one FGF were pooled to form supernatants containing multiple FGFs, as described in greater detail below.

Photographs of the cultures were obtained using an Axio-Cam HRc digital camera (Carl Zeiss, Oberkochen, Germany) attached to a light microscope with Zeiss KS300 3.0 photography software (Carl Zeiss, Oberkochen, Germany). Cardiosphere survival assays were performed by measuring the number of viable cells using the CellTiter-Glo ATP assay according to the manufacturer's instructions (see, e.g., Crouch et al., J. Immunol. Meth. (1993) 160:81-8; Zhelev et al., Cancer Chemother. Pharmacol. (2004) 53(3):267-75). Briefly, an equal volume of CellTiter-Glo Reagent (cat#G7570, Promega, Madison, Wis.) was mixed with the culture media covering a monolayer of cells by shaking the cell plate, for example, a multiwell plate, for two minutes to induce cell lysis. The plate was then incubated at room temperature for ten minutes to stabilize the luminescence signal. Luminescence was read using an Lmax microplate reader (Molecular Devices, Sunnyvale, Calif.) with an integration time of 0.1 second.

Figure 9:
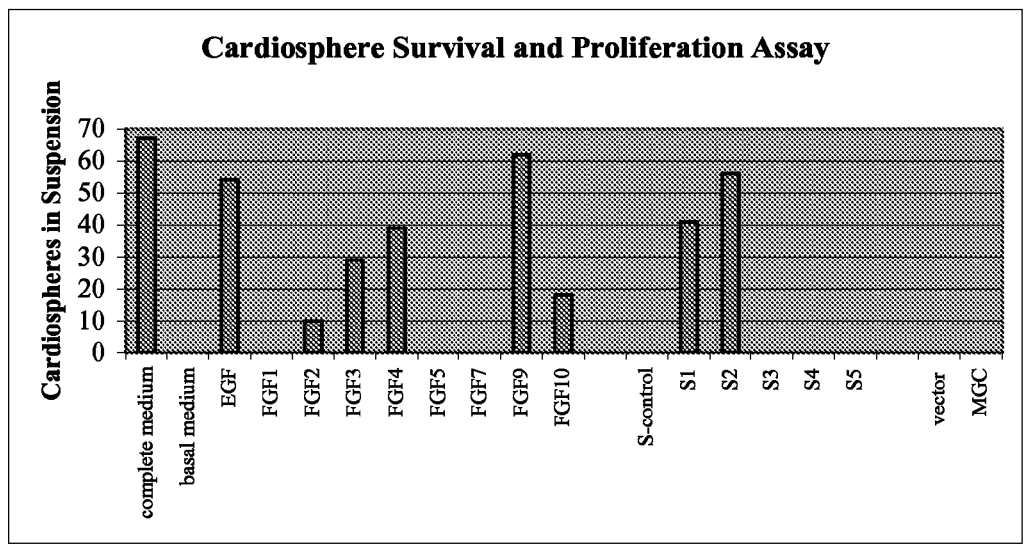
FIG. 9 shows the results of the cardiosphere survival ATP assay for the total number of viable cells (FIG. 9A) and the cardiosphere survival and proliferation in suspension assay (FIGS. 9B and 9C), as further described in Example 2. Cardiosphere survival and proliferation was measured in the presence of (1) complete medium; (2) basal medium; (3) basal medium supplemented with EGF (EGF); (4) basal medium supplemented with FGF-1 (FGF1); (5) basal medium supplemented with FGF-2 (FGF2); (6) basal medium supplemented with FGF-3 (FGF3); (7) basal medium supplemented with FGF-4 (FGF4); (8) basal medium supplemented with FGF-5 (FGF5); (9) basal medium supplemented with FGF-7 (FGF7); (10) basal medium supplemented with FGF-9 (FGF9); (11) basal medium supplemented with FGF-10 (FGF10); (12) conditioned medium (CM) from 293 cells (S-control); (13) pool of CM with human FGF-1, FGF-2, FGF-3, FGF-4, and FGF-5 (S1); (14) pool of CM with human FGF-6, FGF-7, FGF-8, FGF-9, and FGF-10 (S2); (15) pool of CM with human FGF-11, FGF-12, FGF-13-1A, FGF-13-1B, and FGF-13SV1 (splice variant 1) (S3); (16) pool of CM with human FGF-13SV2 (splice variant 2), FGF-14, FGF-16, FGF-17, and FGF-18 (no FGF-15) (S4); (17) pool of CM with human FGF-19, FGF-20, FGF-21, FGF-22, and FGF-23 (S 5); (18) empty vector negative control (vector); and (19) an irrelevant vector negative control (MGC).
Figure 9:
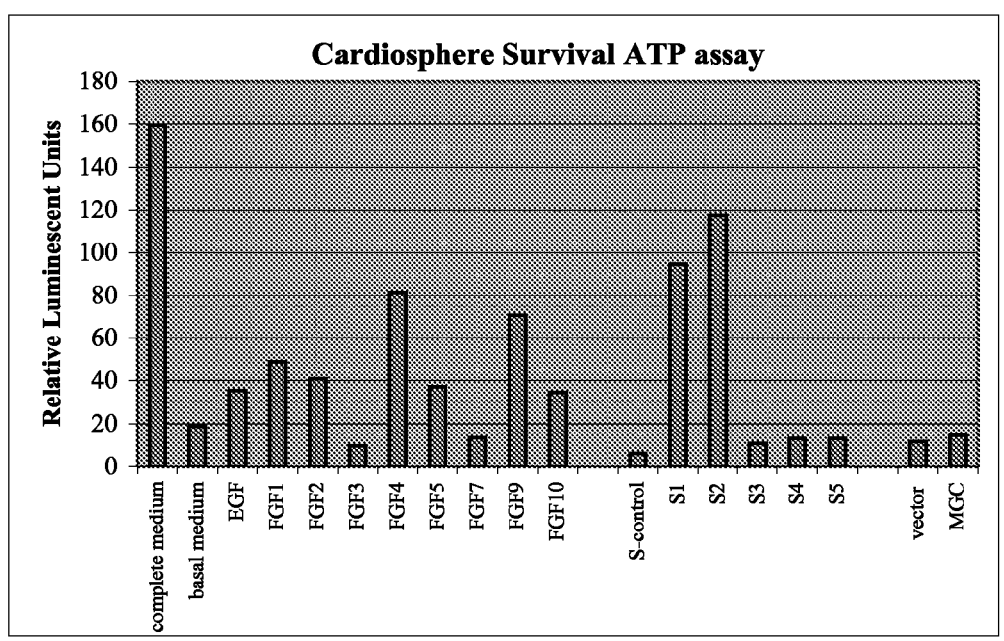
Figure 9:
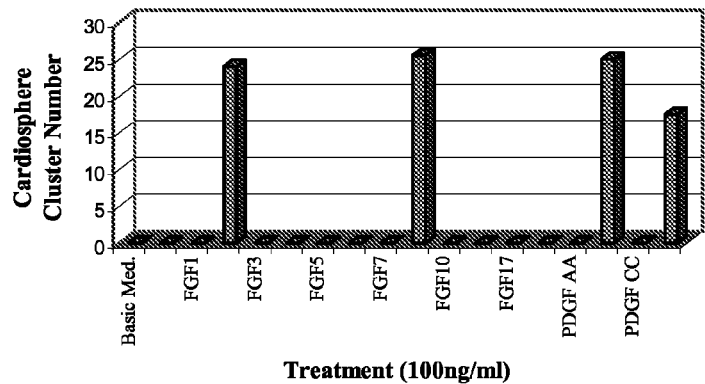

FIG. 9B shows the results of the cardiosphere survival ATP assay, showing the total number of viable cells expressed in terms of relative luminescent units, as described above, following the indicated treatments. "Complete medium" refers to CGM as described above. "Basal medium" is also described above. "EGF," "FGF1," "FGF2," "FGF3," "FGF4," "FGF5," "FGF7," "FGF9," and "FGF10" refer to basal medium supplemented with the indicated growth factors, which were recombinantly produced and commercially obtained, as described above. "S-control" refers to conditioned medium (CM) from 293 cells. "S1" refers to a pool of CM with human FGF-1, FGF-2, FGF-3, FGF-4, and FGF-5. "S2" refers to a pool of CM with human FGF-6, FGF-7, FGF-8, FGF-9, and FGF-10. "S3" refers to a pool of CM with human FGF-11, FGF-12, FGF-13-1A, FGF-13-1B, and FGF-13SV1 (splice variant 1). "S4" refers to a pool of CM with FGF-13SV2 (splice variant 2), FGF-14, FGF-16, FGF-17, and FGF-18 (no FGF-15). "S5" refers to a pool of CM with human FGF-19, FGF-20, FGF-21, FGF-22, and FGF-23. Negative controls shown in FIG. 9 also include the empty vector "vector" and an irrelevant vector "MGC."

FIGS. 9A and 9C show the results of the suspension culture assay for cardiosphere proliferation. Suspension cultures were grown as described above. Treatment designations are the same as in FIG. 9B. FIG. 9A shows that EGF, FGF-4, and FGF-9 each increased the number of cardiospheres in suspension. In addition, FGF-4 and FGF-9 enhanced overall cell survival. "S1" and "S2" increased cardiosphere survival and total cell viability to a greater extent than "S-control." The survival-promoting effects of "S1" and "S2" may be attributed to the effect of FGF-4 and FGF-9, respectively. FIG. 9C shows that FGF-4, FGF-9, PDGF-BB, and PDGF-DD each enhance both cardiosphere survival and cardiosphere proliferation.

FIG. 10 shows the effects of the indicated treatments on cardiosphere culture morphology. Cardiospheres are observed in these photographs as clusters of small, round, phase-bright cells. No cardiospheres developed in basal medium ("Basic Medium"). In contrast, cultures grown in complete medium or basic medium supplemented with FGF-4, FGF-9, or EGF generated numerous cardiospheres. In some of the cardiospheres, dark zones within the inner mass can be seen. FIG. 10 also shows that the supernatant pool control ("S-control") and the cultures grown in the "S3" pool generated only a few small cardiospheres. By comparison, cultures grown in the "S1" and "S2" pools generated cardiospheres which were more numerous and larger in size.

The results of the cardiosphere survival and proliferation assays shown in the Figures and described in the Examples herein are indicative of the ability of these growth factors to enhance survival and proliferation of cardiomyocytes in vivo.

Example 3

Effect of PDGF-BB on Cardiosphere Proliferation In Vitro

In a separate experiment, the effect of PDGF-BB (100 ng/ml) (R&D, Minneapolis, Minn.) on cardiosphere proliferation in vitro was determined using the method described in Example 2. The results are shown in FIG. 11, along with the positive and negative controls, "Complete medium" and "Basal medium," respectively. No cardiospheres developed in basal medium, whereas the culture grown in complete medium generated numerous cardiospheres. The culture grown in the presence of PDGF-BB also generated numerous cardiospheres, indicating that PDGF-BB stimulated cardiosphere proliferation.

Example 4

Effect of EGF Family Members on Cardiosphere Proliferation in Vitro

The effect of various EGF family members on cardiosphere proliferation was investigated. Cardiospheres obtained using the method in Example 1 were detached and dissociated with trypsin, and seeded at a density of $1\text{-}2\times10^5$ cells per well in poly-D-lysine coated 24-well cell culture plates (cat#354414, Becton Dickinson (BD), Franklin Lakes, N.J.) containing basal medium (BM) with 35% IMDM/65% DMEM Ham F12 mix supplemented with 2% B27. Alternatively, cardiospheres obtained by the method of Example 1 were expanded on fibronectin-coated plates, then seeded at a density of $1\text{-}2\times10^5$ cells per well in poly-D-lysine coated 24-well cell culture plates (cat#354414, Becton Dickinson (BD), Franklin Lakes, N.J.) containing basal medium (BM). The cultures were incubated at 37° C. with 5% $CO_2$ overnight or over two days. Each of the EGF family members to be tested was then added to separate cultures at 100 ng/ml. The EGF family members that were tested were obtained from R&D, Minneapolis, Minn. and included: amphiregulin (cat#262-AR), Epigen (cat#1127-EP), epiregulin (cat#1195-EP), HB-EGF (cat#259-HE), TGFα (cat#239-A), EGF (cat#236-EG), betacellulin (cat#261-CE), heregulin α (cat#296-HR), and NRG-1-β1'-HRG-β1 (cat#396-HB). As a positive control, some cells were incubated in CGM. The cultures were incubated for 5-7 days. The cardiosphere clusters in each culture were then counted. Pictures of culture morphology were obtained using an AxioCam HRc digital camera (Carl Zeiss, Oberkochen, Germany) attached to a light microscope with Zeiss KS300 3.0 photography software (Carl Zeiss, Oberkochen, Germany).

Figure 7:
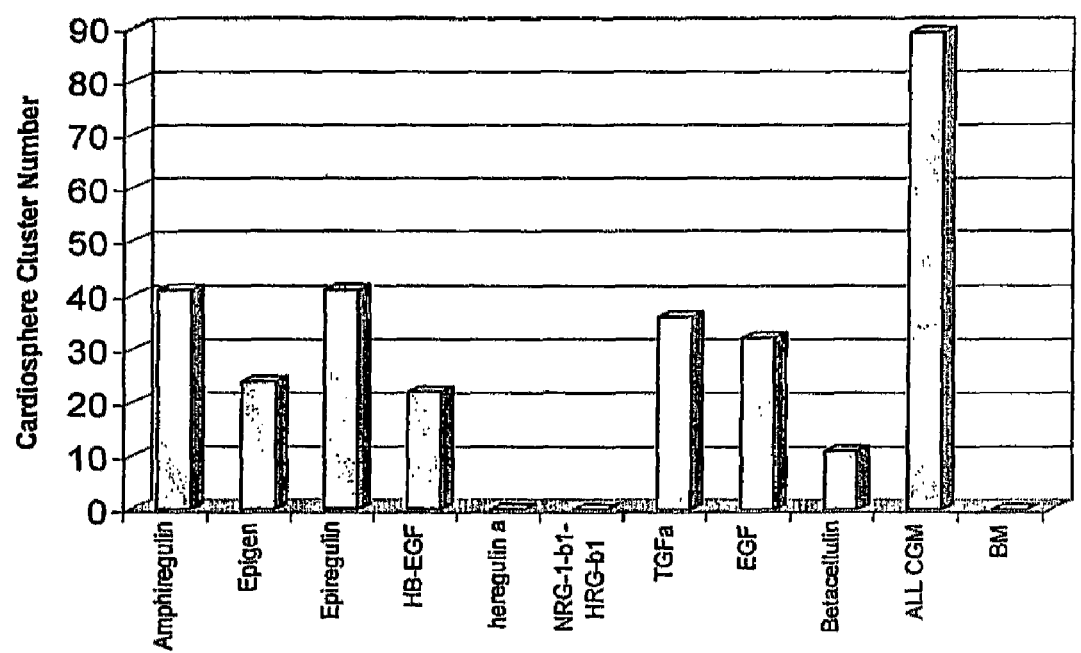
FIG. 7 shows a graph of the number of cardiospheres resulting from treatment with EGF family members, as further described in Example 4. The treatments compared are: (1) basal medium supplemented with amphiregulin (Amphiregulin); (2) basal medium supplemented with Epigen (Epigen); (3) basal medium supplemented with epiregulin (Epiregulin); (4) basal medium supplemented with heparin-binding EGF-like growth factor (HB-EGF); (5) basal medium supplemented with truncated heregulin α (heregulin a); (6) basal medium supplemented with truncated neuregulin NRG-1-β1-HRG-β1 (NRG-1-b1-HRG-b1); (7) basal medium supplemented with transforming growth factor α (TGFa); (8) basal medium supplemented with epidermal growth factor (EGF); (9) basal medium supplemented with betacellulin (Betacellulin); (10) complete medium (ALL CGM); and (11) basal medium (BM).

The results are shown in FIG. 7, which plots the number of cardiospheres ("cardiosphere cluster number") observed in response to treatments with the indicated EGF family members. As described in Examples 2 and 3, no cardiospheres developed in basal medium, whereas the culture grown in complete medium generated numerous cardiospheres. Amphiregulin, Epigen, epiregulin, HB-EGF, TGFα, EGF, and betacellulin promoted cardiosphere proliferation (FIG. 7). By comparison, heregulin a and NRG-1-β1-HRG-β1 did not promote cardiosphere development. The heregulin α and NRG-1-β1-HRG-β1 preparations that were tested did not contain the full-length proteins, but only primarily the EFG domains.

Example 5

Isolation of Rat Neonatal Cardiomyocytes

Portions of heart ventricles from day one new born rats were collected. Digestion working solutions including D1, D2, and D3 working solutions were prepared using a neonatal rat/mouse cardiomyocyte isolation kit purchased from Cellutronlife Technologies (cat#nc-60631, Highland Park, N.J.). Specifically, the D1 working solution was prepared with 5 ml of D1 stock solution and 45 ml of sterile water. Two D2 working solutions were prepared. Each D2 working solution contained 20 ml of D2 stock solution, 28 ml sterile water, 2 ml of EC (Enzyme Collagenase) buffer, mixed and filtered with a 0.22 micrometer (μm) filter. Two D3 working solutions were prepared. Each D3 working solution contained 25 ml of NS (Neonatal Seeding) medium, one (1) bottle of 15 ml D3 stock solution and brought to a final volume of 40 ml.

Once these solutions were prepared, the heart portions were transferred to a culture dish containing D1 working solution and cut once or twice. The cut heart pieces were then transferred to a separate culture dish containing D1 solution until all the hearts were cut. The cut heart pieces were then transferred to a flask containing 12 ml of D2 working solution and stirred on a stir plate for 12 minutes at a stir speed setting between #2-3 (about 300-600 rpm) (Fisher Scientific, Houston, Tex., cat#1150049S). The supernatant containing isolated cells was then transferred to a 15 ml tube and placed in a centrifuge (Kendro, Germany, cat#75004377). The supernatant was spun at room temperature at 1200 rpm for two minutes to yield a cell pellet. The cell pellet was resuspended in 5-10 ml of a D3 working solution and left at room temperature until the end of the isolation procedure. The steps described above with the D1, D2, and D3 working solutions were repeated between five and eleven separate times until all of the processed heart tissues were digested. The digested cells were filtered with a cell strainer and the cells were pipetted from the top of the filter by moving the pipette around on the surface of the filter.

The cells were subsequently incubated for about 1.5 hours at 37° C. with 5% $CO_2$ by seeding eight uncoated 100 mm Coring cell culture dishes (Corning Incorporated, Corning, N.Y., cat#430167) to remove the fibroblasts. The supernatants containing neonatal cardiomyocytes were subsequently collected and the cells thus obtained were counted.

Example 6

Rat Neonatal Cardiomyocyte pAkt, pSTAT3 and Perk Assays

Collected cells, from Example 5, were diluted to a density of $6 \times 10^5$ cells/ml in a NS (Neonatal Seeding) medium (Cellutronlife Technologies, Highland Park, N.J., cat# M-8031) supplemented with 0.1 millimolar (mM) bromodeoxyuridin (BrdU) solution (Sigma, Steinheim, Germany, cat#B5002-250 mg). The diluted cells were then plated at a volume of 100 microliters (μl)/well in 96-well Primaria™ plates (Becton Dickinson, Franklin Lakes, N.J., cat #353872) and incubated at 37° C. with 5% $CO_2$ overnight on day one.

The next day (day two), the media were changed to fresh NS medium containing 0.1 mM BrdU at 150 ul/well, and the cells were incubated at 37° C. with 5% $CO_2$ overnight. On day three, the media were changed to starvation medium with 150 ul/well, and the cells were incubated at 37° C. with 5% $CO_2$. The starvation medium contained: DMEM-glc-pry+10 mM HEPES+0.1% BSA+1× Penicillin-Streptomycin. The DMEM-glc-pry contained DMEM without glucose and without pyruvate (Gibco/Invitrogen Corporation, Grand Island, N.Y., cat#11966-025). HEPES was purchased from Mediatech Inc., Herndon, Va. (cat#25-060-Cl, 1M). Bovine Albumin Fr. V Fatty Acid Free (BSA) was purchased from Serologicals Protein Inc., Kankakee, Ill. (cat#82-002-4), and Penicillin-Streptomycin was purchased from Mediatech Inc., Herndon, Va. (cat#30-002-Cl, 100X).

On day four after the overnight incubation, the 96 wells of the plates were aspirated and washed with 150 μl/well of fresh starvation media, and an additional 50 μl/well of fresh starve media were added to each well. The cells in columns 2-11 of the 96 well plate(s) were subsequently treated by adding 50 μl of protein conditioned medium. Positive controls of 300 nanograms (ng)/mL rhIGF1 were added to wells A-D of column 1, positive controls of 20 ng/mL rhLIF were added to wells A-H of column 12, and negative controls, vector only conditioned medium, were added to wells E-H of column 1.

The plates were subsequently incubated at 37° C. with 5% $CO_2$ for fifteen minutes. After the incubation, the solutions in the wells were removed by aspiration. The wells were subsequently washed with 150 μl/well of ice-cold 1×PBS, and 40 μl of ice-cold lysis buffer (Cell Signaling Technology Inc., Beverly, Mass., cat#9803) containing 1 mM PMSF (Sigma, Steinheim, Germany, cat#P7626) were added to each well. The plates were kept on ice for ten minutes. The plates were then ready for the Luminex Phosphor-protein Detection Assay (see, for example, Example 7).

Figure 4:
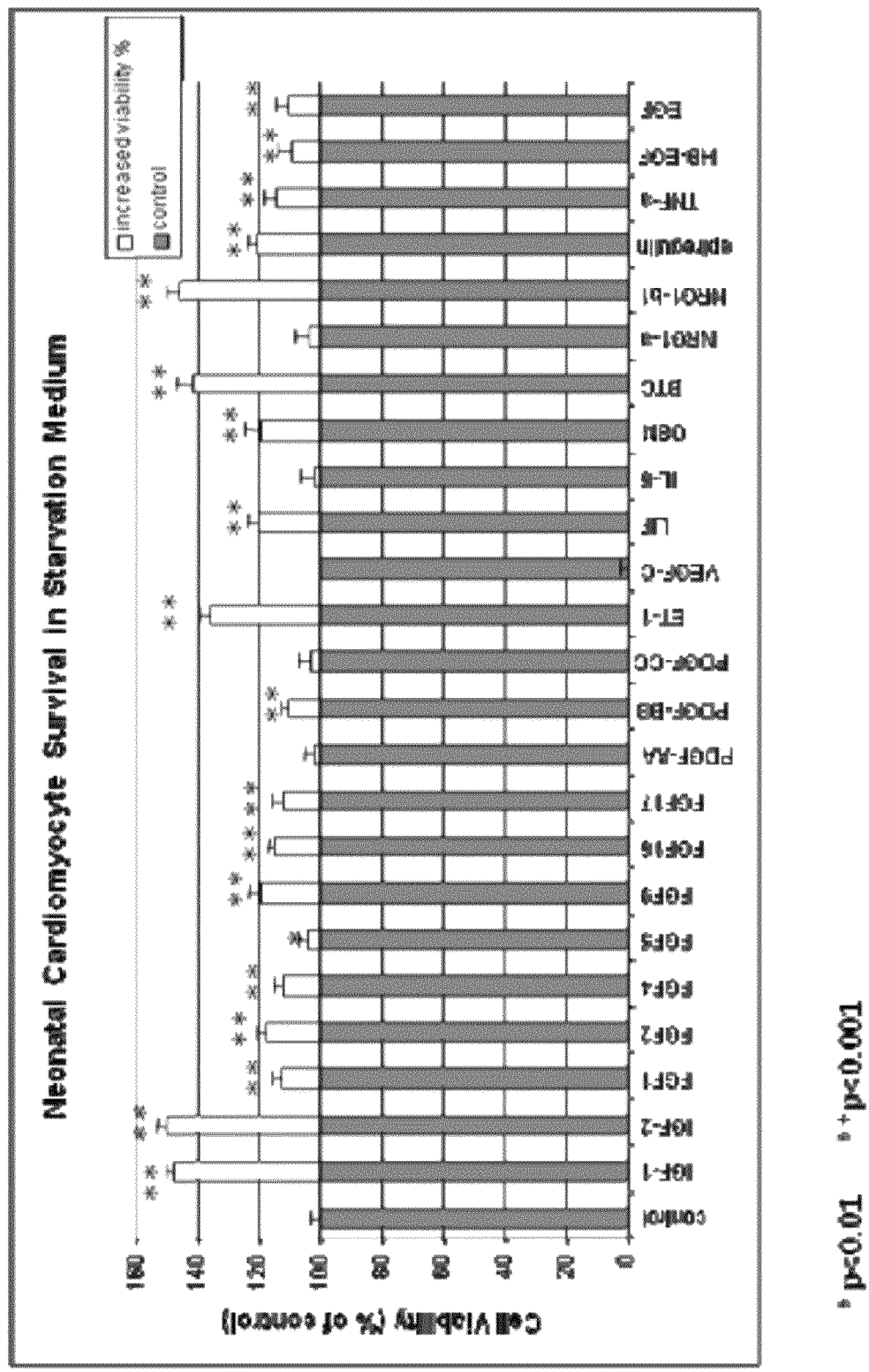
FIG. 4 shows the effects of selected recombinant proteins on rat neonatal cardiomyocyte viability in starvation medium, as further described in Example 6. Rat neonatal cardiomyocytes were treated with different recombinant proteins at a concentration of 100 ng/ml in starvation medium for about 40 hours. Each bar represents the results of six replicate luminescent ATP assays of the indicated recombinant protein. The height of the bar (y-axis) indicates cell viability as a percentage of the control. FGF-1, FGF-2, FGF-4, FGF-5, FGF-9, FGF-16, FGF-17, PDGF-BB, ET-1, IGF-1, IGF-2, LIF, OSM, BTC, NRG1-beta1, epiregulin, TNF-α, HB-EGF, and EGF, but not PDGF-AA, PDGF-CC, VEGF-C, IL-6 and NRG1-alpha, enhanced cardiomyocyte survival in starvation medium to a statistically significant extent; ** denotes ($p<0.001$) and * denotes ($p<0.01$).

Rat neonatal cardiomyocytes were also assayed for their ability to survive under starvation conditions. On day one, rat neonatal cardiomyocytes were seeded at a density of $2 \times 10^4$ cells per well in 100 ul of NS medium (Cellutron Life Technologies, Highland Park, N.J., cat#M-8031) supplemented with 0.1 mM bromodeoxyuridin (BrdU) solution (Sigma, Steinheim, Germany, cat#B5002) in 96-well Primaria™ tissue culture plates (Becton Dickinson, Franklin Lakes, N.J., cat#353872). The plates were sealed with Breathe Easy Sealing Tape (E&K Scientific, Santa Clara, Calif., cat#1796200) and then incubated overnight at 37° C. with 5% $CO_2$. On day two, the medium was replaced with 150 ul fresh NS medium supplemented with 0.1 mM BrdU, the plate sealed with sealing tape, and the cells incubated for another 24-48 hours. The medium was replaced with 100 ul starvation medium containing recombinant test proteins. Starvation medium contained 10 mM HEPES (Mediatech Inc., Herndon, Va., cat#25-060-Cl, 1M), 0.1% bovine albumin fraction V, fatty acid free (Serologicals Protein Inc., Kankakee, Ill., cat#82-002-4), 1× penicillin-streptomycin (Mediatech Inc., Herndon, Va., cat#25-060-Cl, 1M) in DMEM-glc-pyr (DMEM without glucose or pyruvate) (Gibco/Invitrogen Corporation, Grand Island, N.Y., cat#11966-025). After incubating for about forty hours, 100 ul CellTiter-Glo assay buffer (Promega, Madison, Wis., cat#G7573) were added to the medium in each well and the plates were shaken in the dark at room temperature for ten minutes. A portion of the contents of each well (100 ul) was transferred to a 96-well ½ area assay plate (Corning Incorporated, Corning, N.Y., cat#3688), and the luminescent signal determined using a Lmax luminescent plate reader. FIG. 4 shows the results for some of the proteins tested.

Figure 5A:
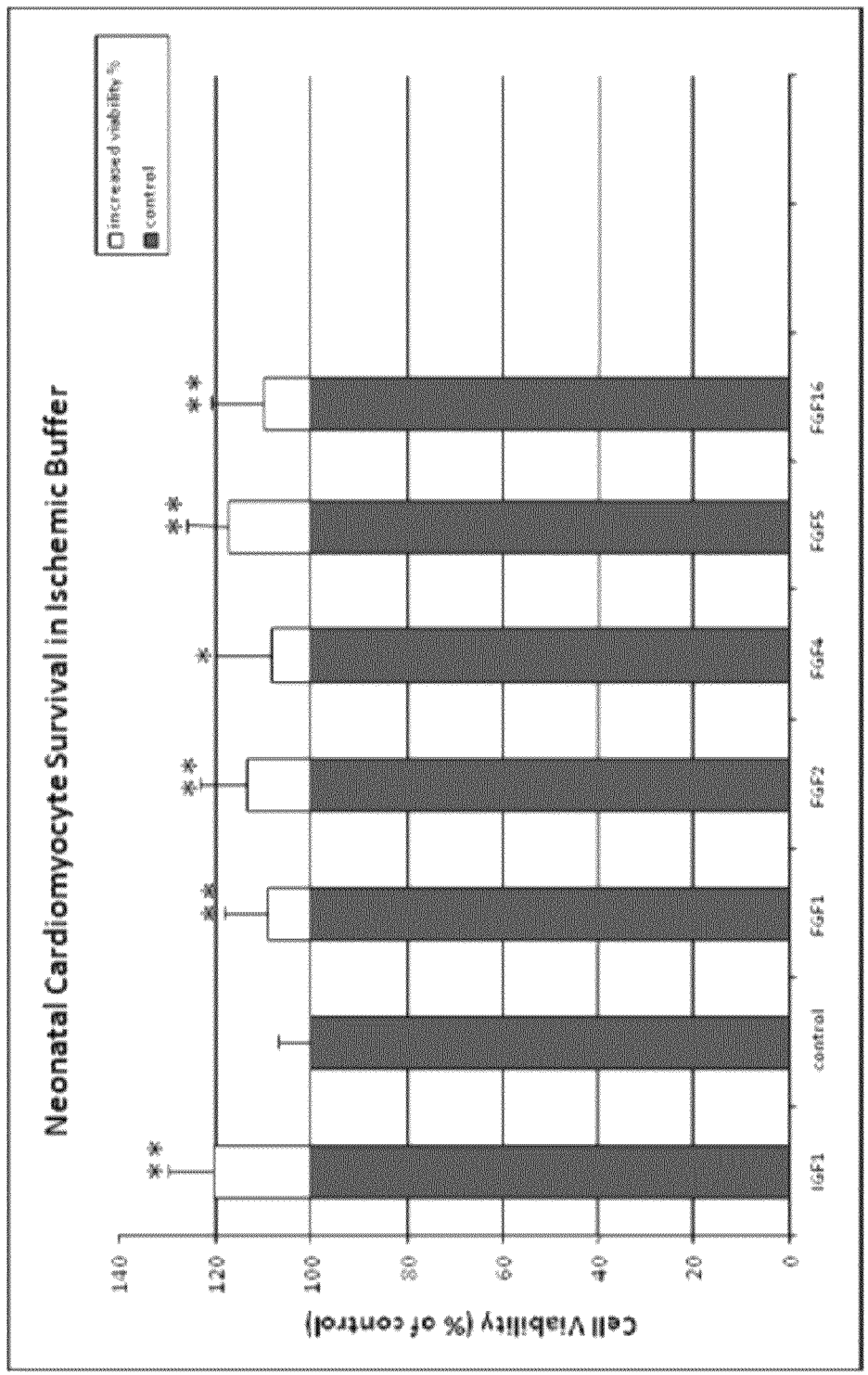
FIGS. 5A and 5B show the effects of selected recombinant proteins on rat neonatal cardiomyocyte viability in ischemic buffer, as further described in Example 6. Rat neonatal cardiomyocytes were treated with different recombinant proteins at a concentration of 100 ng/ml in ischemic buffer for three hours. Each bar represents the results of 24 replicate luminescent ATP assays of the indicated recombinant protein. The height of the bar (y-axis) indicates cell viability as a percentage of the control. FGF-1, FGF-2, FGF-4, FGF-5, FGF-9, FGF-16, FGF-17, and IGF-1 each enhanced cardiomyocyte survival in ischemic buffer to a statistically significant extent; ** denotes ($p<0.001$) and * denotes ($p<0.01$).
Figure 5B:
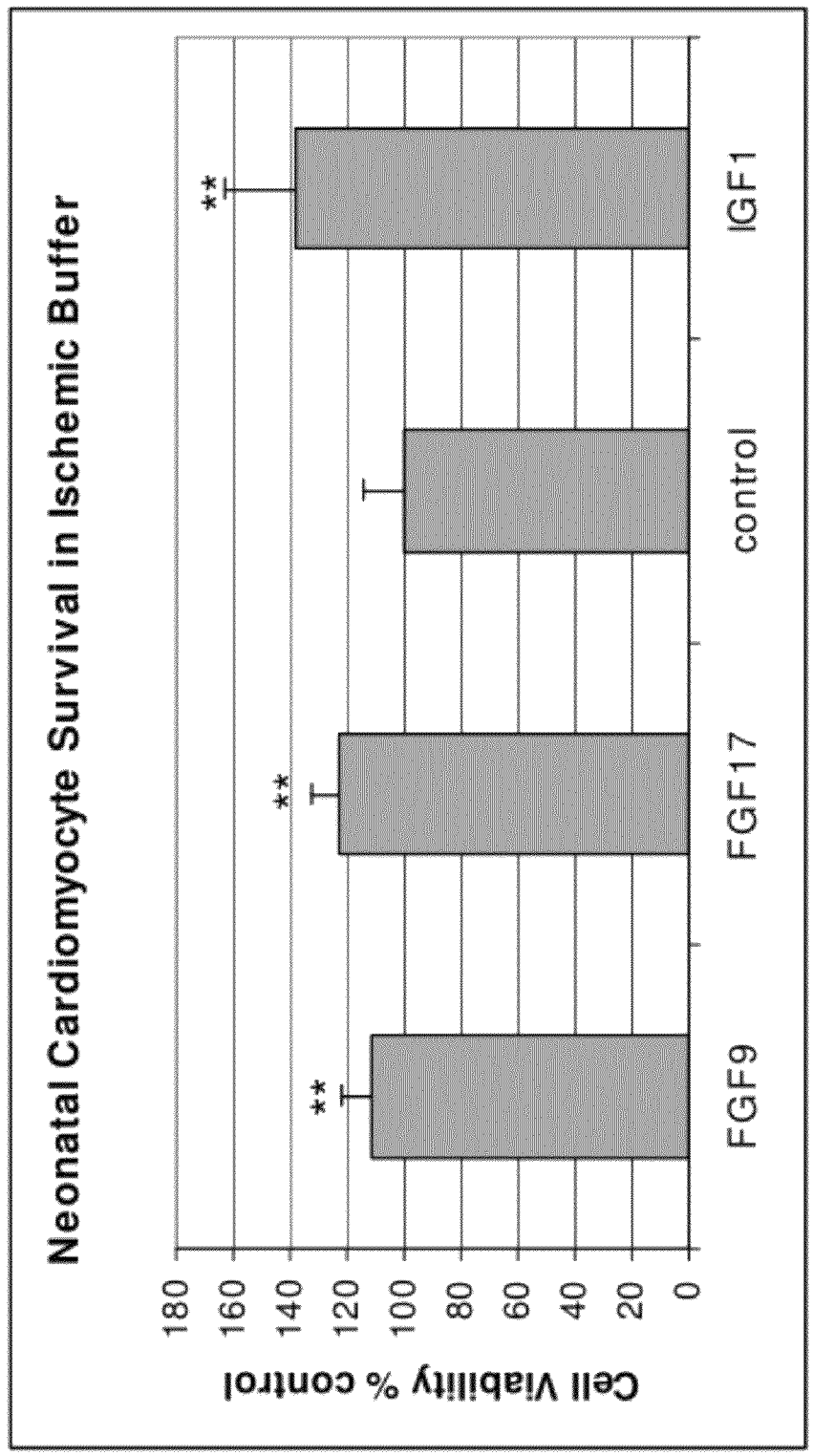

Rat neonatal cardiomyocytes were further assayed for their ability to survive under ischemic conditions. On day one, rat neonatal cardiomyocytes were seeded at a density of $2 \times 10^4$ cells per well in 100 ul of NS medium (Cellutron Life Technologies, Highland Park, N.J., cat#M-8031) supplemented with 0.1 mM bromodeoxyuridine (BrdU) solution (Sigma, Steinheim, Germany, cat#B5002) in 96-well Primaria™ tissue culture plates (Becton Dickinson, Franklin Lakes, N.J., cat#353872). The plates were sealed with Breathe Easy Sealing Tape (E&K Scientific, Santa Clara, Calif., cat#1796200) and then incubated overnight at 37° C. with 5% $CO_2$. On day two, the medium was replaced with 150 ul fresh NS medium supplemented with 0.1 mM BrdU, the plate sealed with sealing tape, and the cells incubated overnight. On day three, the medium was replaced with starvation medium, as described above, the plate sealed with sealing tape, and the cells incubated overnight. The medium was replaced with 100 ul Esumi Ischemic Buffer (EIB) containing recombinant test proteins. EIB contained 137 mM NaCl, 12 mM KCl, 0.9 mM $CaCl_2.2H_2O$, 4 mM HEPES, 10 mM deoxyglucose, 20 mM sodium lactate, and 0.49 mM $MgCl_2$, at pH 6.7. After incubating for about three hours, 100 ul CellTiter-Glo assay buffer (Promega, Madison, Wis., cat#G7573) were added to the medium in each well and the plates were shaken in the dark at room temperature for ten minutes. A portion (100 ul) of the contents of each well was transferred to a 96-well ½ area assay plate (Corning Incorporated, Corning, N.Y., cat#3688), and the luminescent signal determined using a Lmax luminescent plate reader. FIGS. 5A and 5B show the results for some of the proteins tested.

Example 7

Luminex Phosphor-Protein Detection Assay

Assay Filter Plates (96-well; cat#MSBVN1250, Millipore, Molsheim, France) were washed with 100 µl of assay buffer, and then vacuumed. The assay buffer contained Dulbecco's Phosphate-Buffered Saline (DPBS) without calcium & magnesium (Mediatech Inc., Herndon, Va., cat#21-031-CV) and 0.2% BSA (Serologicals Protein Inc. Kankakee, Ill., cat#82-002-4).

The bead suspensions of αpAkt beads (UpState Inc., Lake Placid, N.Y., cat#46-601), αpERK beads (UpState Inc., cat#46-602), and αpStat3 beads (UpState Inc., cat#46-623) were diluted in assay buffer with a 1:40 dilution for the αpAkt Beads and a 1:50 dilution for both the αpERK beads and the αpStat3 beads. The three-bead mixture (25 µl) was added to each well of the Assay Filter plate. Additionally, 25 µl of cell lysate prepared using lysis buffer as described in Example 6 were added to each well of the Assay Filter plate. The plates were subsequently incubated on a shaker at 4° C. overnight in the dark with black lids.

After incubation, the plates were vacuumed to remove liquid in the wells and were then washed twice with 200 µl of assay buffer. The biotinylated reporters for αpAkt (UpState Inc., Lake Placid, N.Y., cat#46-601), αpERK (UpState Inc., cat#46-602), and αpStat3 (UpState Inc., cat# 46-623) were diluted with assay buffer accordingly: a 1:40 dilution for the αpAkt biotinylated reporter and a 1:50 dilution for both the αpERK and αpStat3 biotinylated reporters. The prepared biotinylated reporters were mixed and a volume of 25 µl of the mixed reporters was added to each well of a plate after the plate was vacuumed. The plates were then incubated on a shaker at room temperature for ninety minutes in the dark. After ninety minutes, the liquid was vacuumed from the wells and washed twice with 200 µl of assay buffer. Streptavidin-PE (BD PharMingen, San Diego, Calif., cat#554061) was subsequently prepared with assay buffer at 1:200 dilution and 25 µl of diluted streptavidin-PE were added to each well. The plates were then incubated on a shaker at room temperature for fifteen minutes in the dark. Enhancer Solution (UpState Inc., Lake Placid, N.Y., cat#43-024) was prepared with assay buffer (1:1) and 25 µl were added to each well. The plates were incubated for thirty minutes on a shaker at room temperature in the dark. The liquid was vacuumed and washed once with 200 µl of assay buffer. Finally, 100 µl of assay buffer were added to each well to suspend the beads, and the plates were placed on a shaker at room temperature for ten minutes in the dark. The plates were then ready to be read on a Luminex Reader using "pAkt, pERK, pStat3" Program.

Example 8

$^3$H-Deoxyglucose Uptake in Rat Neonatal Cardiomyocytes

On day one, rat neonatal cardiomyocytes were seeded at a density of $3 \times 10^4$ cells per well in 100 ul of NS medium (Cellutron Life Technologies, Highland Park, N.J., cat#M-8031) in 96-well white/clear bottom tissue culture plates (BD Biosciences, Bedford, Mass., cat#353947). Following seeding, the plates remained in the tissue culture hood for thirty minutes to minimize the edge effect, and then placed in an incubator at 37° C. with 5% $CO_2$ overnight. On day two, the medium was replaced with 90 ul per well of starvation medium (1% BSA in low glucose (5 mM) DMEM) for six hours. The starvation medium was replaced with ten ul negative control medium, positive control medium containing insulin, or test medium containing test factors for twenty minutes of incubation. The control or test medium was replaced with 50 ul of $^3$H labeling medium containing 1 uCi $^3$H-deoxyglucose in 50 ul labeling medium (PerkinElmer Life Science, Boston, Mass., cat#NET-331A), 1% BSA, and 10 uM cold deoxyglucose (Sigma, Steinheim, Germany, cat#D-3179) in glucose-free DMEM. The cells were labeled for fifteen minutes and then the cells were washed three times with ice-cold PBS with calcium and magnesium. Following the wash step, the PBS was replaced with 50 ul 0.05N NaOH, which was applied to each well to lyse the cells. Then 150 ul of microscint 40 (PerkinElmer Life Science, Boston, Mass., cat#D-6013641) were slowly added to each well, the plate sealed with sealing tape (PerkinElmer Life Science, Boston, Mass., cat#6005185), and the bottom of the plate covered with white Backing tape (PerkinElmer Life Science, Boston, Mass., cat#6005199). The radioactivity of each well was measured using TopCount NXT with Windows XP®-based operating software (PerkinElmer Life Science, Boston, Mass.). The results are shown in FIG. 8C.

Example 9

Effect of Growth Factors on Adult Mouse Cardiosphere Proliferation

Adult mouse cardiac stem cells (cardiospheres) were isolated and expanded as described in Example 1, according to Messina at al., Circ. Res. (2004) 95(9):911-921. The effects of FGF9, epiregulin, and PDGF-BB, both individually and in combination, on cardiosphere proliferation were measured in vitro. Cardiospheres were detached and dissociated with trypsin, and then seeded onto poly-D-lysine coated culture plates at a density of $4 \times 10^4$ cells per well in 96-well plates or $1-2 \times 10^5$ cells per well in 24-well plates. Cardiospheres were maintained in basal medium (BM) containing 35% IMDM/65% DMEM Ham F12 mix supplemented with 2% B27. Alternatively, the cardiospheres obtained by the method of Example 1 were expanded on fibronectin-coated plates, and then seeded in basal medium onto poly-D-lysine coated culture plates at a density of $4 \times 10^4$ cells per well in 96-well plates or $1-2 \times 10^5$ cells per well in 24-well plates. The cultures were incubated at 37° C. with 5% $CO_2$ overnight or for two days.

Figure 6:
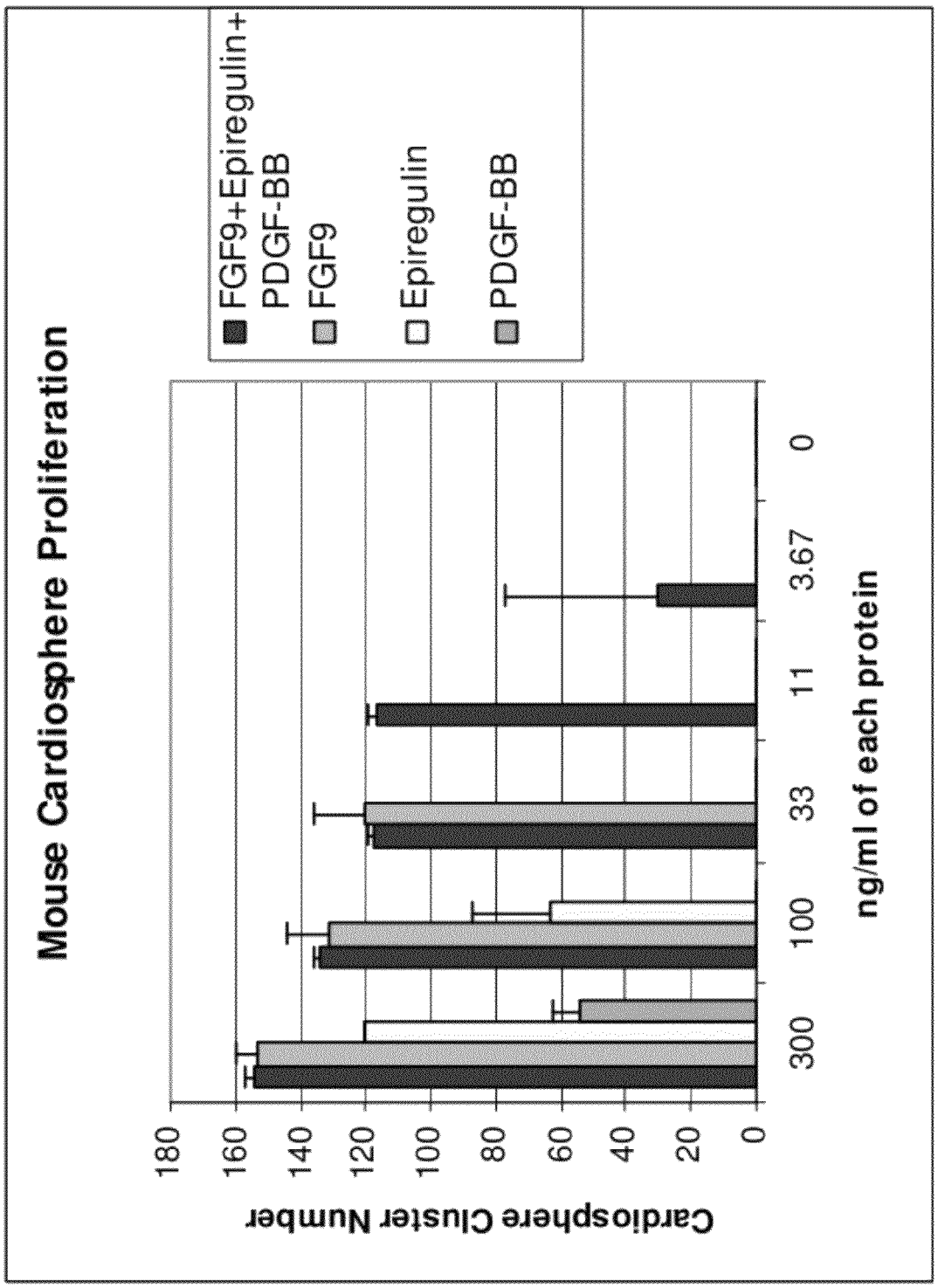
FIG. 6 shows the proliferative effects of FGF9, epiregulin, and PDGF-BB alone and in combination, on adult mouse cardiospheres. Cardiospheres were prepared on fibronectin-coated plates then dissociated into single cells as described in Examples 1, 2, and 9, then plated onto 96-well poly-D-lysine coated cell culture plates at a density of $4\times10^4$ cells/well in complete growth medium, and incubated at 37° C. with 5% $CO_2$ overnight. The next day, the cells were treated with FGF9, epiregulin, and PDGF-BB alone or in combination, in basal medium. After five days, the cardiosphere cluster number was counted for each well. Each bar shows the result of three replicate experiments.

As shown in FIG. 6, growth factors were added at concentrations ranging from 0 to 300 ng/ml in complete growth medium (CGM) (Messina at al., Circ. Res. (2004) 95(9):911-921) and incubated for five to seven days. The cultures were photographed with an AxioCam HRc (Carl Zeiss, Germany) attached to a light microscope using Zeiss KS300 3.0 software, the morphology assessed, and the number of cardiospheres counted.

At a concentration of 3.67 ng/ml or 11 ng/ml, none of the recombinant growth factors promoted cardiosphere proliferation, when added alone (FIG. 6). However, when FGF9, epiregulin, and PDGF-BB were combined at a concentration of 3.67 ng/ml or 11 ng/ml each, the combination dramatically promoted cardiosphere proliferation (FIG. 6). Thus, the effect of FGF9, epiregulin, and PDGF-BB on cardiosphere proliferation was synergistic.

At higher protein concentrations, 33 ng/ml, 100 ng/ml and 300 ng/ml, the effect of FGF9 alone was similar to that of the combination of the three proteins (FIG. 6), suggesting that the signal may be saturated at these higher protein concentrations. Alternatively, because the cluster number is a semi-quantitative measure and does not indicate the size of each cluster, the clusters formed after combination treatment may be larger than those formed in response to only one growth factor.

Example 10

Treatment of Cardiac Conditions with Growth Factors

A patient with a cardiac condition can be treated with the therapeutic pharmaceutical compositions and methods of the invention. To determine the pharmaceutical composition to be administered and the frequency and dosage the pharmaceutical composition is to be given, various factors are considered, including, but not limited to, the severity of the cardiac condition, the underlying cause of the cardiac condition, and the physical, metabolic, and immunological characteristics of the patient. The pharmaceutical composition can be administered using a catheter, by direct injection to the myocardium, or by systemic injection. The patient is monitored for any changes in the cardiac condition, and the pharmaceutical compositions and methods used for treatment are modified as needed.

It is to be understood that the foregoing description of the invention is exemplary and explanatory only and is not restrictive of the invention, as claimed. Moreover, it must be understood that the invention is not limited to the particular embodiments described, as such may, of course, vary. Further, the terminology used to describe particular embodiments is not intended to be limiting, since the scope of the present invention will be limited only by its claims.

With respect to ranges of values, the invention encompasses each intervening value between the upper and lower limits of the range to at least a tenth of the lower limit's unit, unless the context clearly indicates otherwise. Further, the invention encompasses any other stated intervening values. Moreover, the invention also encompasses ranges excluding either or both of the upper and lower limits of the range, unless specifically excluded from the stated range.

Unless defined otherwise, the meanings of all technical and scientific terms used herein are those commonly understood by one of ordinary skill in the art to which this invention belongs. One of ordinary skill in the art will also appreciate that any methods and materials similar or equivalent to those described herein can also be used to practice or test the invention. Further, all publications mentioned herein are incorporated by reference.

It must be noted that, as used herein and in the appended claims, the singular forms "a," "or," and "the" include plural referents unless the context clearly dictates otherwise. Thus, for example, reference to "a subject polypeptide" includes a plurality of such polypeptides and reference to "the agent" includes reference to one or more agents and equivalents thereof known to those skilled in the art, and so forth.

Further, all numbers expressing quantities of ingredients, reaction conditions, % purity, polypeptide and polynucleotide lengths, and so forth, used in the specification, are modified by the term "about," unless otherwise indicated. Accordingly, the numerical parameters set forth in the specification are approximations that may vary depending upon the desired properties of the present invention. At the very least, and not as an attempt to limit the application of the doctrine of equivalents to the scope of the claims, each numerical parameter should at least be construed in light of the number of reported significant digits, applying ordinary rounding techniques. Nonetheless, the numerical values set forth in the specific examples are reported as precisely as possible. Any numerical value, however, inherently contains certain errors from the standard deviation of its experimental measurement.

The specification is most thoroughly understood in light of the cited patents and other references. The disclosures of the patents and other references cited herein are herein incorporated by reference in their entireties.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Tables

TABLE 1

| FP ID | SEQ. ID. NO. (N1) | SEQ. ID. NO. (P1) | Source ID |
|---|---|---|---|
| HG1015480 | SEQ. ID. NO. 1 | SEQ. ID. NO. 175 | CLN00235738 |
| HG1015481 | SEQ. ID. NO. 2 | SEQ. ID. NO. 176 | CLN00358501 |
| HG1015482 | SEQ. ID. NO. 3 | SEQ. ID. NO. 177 | NP_000600 |
| HG1015490 | SEQ. ID. NO. 4 | SEQ. ID. NO. 178 | NP_003317 |
| HG1015494 | SEQ. ID. NO. 5 | SEQ. ID. NO. 179 | NP_001235 |
| HG1015496 | SEQ. ID. NO. 6 | SEQ. ID. NO. 180 | CLN00211466 |
| HG1015498 | SEQ. ID. NO. 7 | SEQ. ID. NO. 181 | NP_001720 |
| HG1015509 | SEQ. ID. NO. 8 | SEQ. ID. NO. 182 | CLN00235738_22-140 |
| HG1015527 | SEQ. ID. NO. 9 | SEQ. ID. NO. 183 | CLN00489695 |
| HG1015531 | SEQ. ID. NO. 10 | SEQ. ID. NO. 184 | NP_000750 |
| HG1015712 | SEQ. ID. NO. 11 | SEQ. ID. NO. 185 | NP_002300_23-202 |
| HG1018346 | SEQ. ID. NO. 12 | SEQ. ID. NO. 186 | NP_000591 |
| HG1018401 | SEQ. ID. NO. 13 | SEQ. ID. NO. 187 | NP_002300 |

TABLE 1-continued

| FP ID | SEQ. ID. NO. (N1) | SEQ. ID. NO. (P1) | Source ID |
|---|---|---|---|
| HG1019038 | SEQ. ID. NO. 14 | SEQ. ID. NO. 188 | NP_003801 |
| HG1019751 | SEQ. ID. NO. 15 | SEQ. ID. NO. 189 | 122742__10-155 |
| HG1019752 | SEQ. ID. NO. 16 | SEQ. ID. NO. 190 | 12652749__279-390 |
| HG1019753 | SEQ. ID. NO. 17 | SEQ. ID. NO. 191 | 12652749__30-390 |
| HG1019754 | SEQ. ID. NO. 18 | SEQ. ID. NO. 192 | 13637763__18-268 |
| HG1019755 | SEQ. ID. NO. 19 | SEQ. ID. NO. 193 | 13637763__4-268 |
| HG1019756 | SEQ. ID. NO. 20 | SEQ. ID. NO. 194 | 18573061__18-117 |
| HG1019757 | SEQ. ID. NO. 21 | SEQ. ID. NO. 195 | 21362994__26-174 |
| HG1019758 | SEQ. ID. NO. 22 | SEQ. ID. NO. 196 | 22761542__24-218 |
| HG1019759 | SEQ. ID. NO. 23 | SEQ. ID. NO. 197 | 298591__18-212 |
| HG1019760 | SEQ. ID. NO. 24 | SEQ. ID. NO. 198 | 298591__53-73 |
| HG1019761 | SEQ. ID. NO. 25 | SEQ. ID. NO. 199 | 298591__53-90 |
| HG1019762 | SEQ. ID. NO. 26 | SEQ. ID. NO. 200 | 9789758__1-361 |
| HG1019763 | SEQ. ID. NO. 27 | SEQ. ID. NO. 201 | NP_000020__34-41 |
| HG1019764 | SEQ. ID. NO. 28 | SEQ. ID. NO. 202 | NP_000020__34-43 |
| HG1019765 | SEQ. ID. NO. 29 | SEQ. ID. NO. 203 | NP_000020__34-485 |
| HG1019766 | SEQ. ID. NO. 30 | SEQ. ID. NO. 204 | NP_000020__35-41 |
| HG1019767 | SEQ. ID. NO. 31 | SEQ. ID. NO. 205 | NP_000065__113-261 |
| HG1019768 | SEQ. ID. NO. 32 | SEQ. ID. NO. 206 | NP_000065__47-261 |
| HG1019769 | SEQ. ID. NO. 33 | SEQ. ID. NO. 207 | NP_000451__22-353 |
| HG1019770 | SEQ. ID. NO. 34 | SEQ. ID. NO. 208 | NP_000585__57-233 |
| HG1019771 | SEQ. ID. NO. 35 | SEQ. ID. NO. 209 | NP_000585__77-233 |
| HG1019772 | SEQ. ID. NO. 36 | SEQ. ID. NO. 210 | NP_000586__35-205 |
| HG1019773 | SEQ. ID. NO. 37 | SEQ. ID. NO. 211 | NP_000591__30-212 |
| HG1019774 | SEQ. ID. NO. 38 | SEQ. ID. NO. 212 | NP_000592__32-494 |
| HG1019775 | SEQ. ID. NO. 39 | SEQ. ID. NO. 213 | NP_000592__495-728 |
| HG1019776 | SEQ. ID. NO. 40 | SEQ. ID. NO. 214 | NP_000600__22-93 |
| HG1019777 | SEQ. ID. NO. 41 | SEQ. ID. NO. 215 | NP_000603__25-180 |
| HG1019778 | SEQ. ID. NO. 42 | SEQ. ID. NO. 216 | NP_000603__25-91 |
| HG1019779 | SEQ. ID. NO. 43 | SEQ. ID. NO. 217 | NP_000609__49-118 |
| HG1019780 | SEQ. ID. NO. 44 | SEQ. ID. NO. 218 | NP_000630__103-281 |
| HG1019781 | SEQ. ID. NO. 45 | SEQ. ID. NO. 219 | NP_000630__130-281 |
| HG1019782 | SEQ. ID. NO. 46 | SEQ. ID. NO. 220 | NP_000750__30-207 |
| HG1019783 | SEQ. ID. NO. 47 | SEQ. ID. NO. 221 | NP_000791__16-155 |
| HG1019784 | SEQ. ID. NO. 48 | SEQ. ID. NO. 222 | NP_000896__29-64 |
| HG1019785 | SEQ. ID. NO. 49 | SEQ. ID. NO. 223 | NP_000896__29-97 |
| HG1019786 | SEQ. ID. NO. 50 | SEQ. ID. NO. 224 | NP_001235__63-234 |
| HG1019787 | SEQ. ID. NO. 51 | SEQ. ID. NO. 225 | NP_001243__39-193 |
| HG1019788 | SEQ. ID. NO. 52 | SEQ. ID. NO. 226 | NP_001390__160-391 |
| HG1019789 | SEQ. ID. NO. 53 | SEQ. ID. NO. 227 | NP_001390__63-391 |
| HG1019790 | SEQ. ID. NO. 54 | SEQ. ID. NO. 228 | NP_001423__60-108 |
| HG1019791 | SEQ. ID. NO. 55 | SEQ. ID. NO. 229 | NP_001423__63-108 |
| HG1019792 | SEQ. ID. NO. 56 | SEQ. ID. NO. 230 | NP_001648__101-184 |
| HG1019793 | SEQ. ID. NO. 57 | SEQ. ID. NO. 231 | NP_001648__19-198 |
| HG1019794 | SEQ. ID. NO. 58 | SEQ. ID. NO. 232 | NP_001720__32-111 |
| HG1019795 | SEQ. ID. NO. 59 | SEQ. ID. NO. 233 | NP_001936__20-160 |
| HG1019796 | SEQ. ID. NO. 60 | SEQ. ID. NO. 234 | NP_001936__63-148 |
| HG1019797 | SEQ. ID. NO. 61 | SEQ. ID. NO. 235 | NP_001947__18-212 |
| HG1019798 | SEQ. ID. NO. 62 | SEQ. ID. NO. 236 | NP_001947__49-69 |
| HG1019799 | SEQ. ID. NO. 63 | SEQ. ID. NO. 237 | NP_001954__23-1032 |
| HG1019800 | SEQ. ID. NO. 64 | SEQ. ID. NO. 238 | NP_001954__971-1023 |
| HG1019801 | SEQ. ID. NO. 65 | SEQ. ID. NO. 239 | NP_001998__31-206 |
| HG1019802 | SEQ. ID. NO. 66 | SEQ. ID. NO. 240 | NP_001998__54-206 |
| HG1019803 | SEQ. ID. NO. 67 | SEQ. ID. NO. 241 | NP_001998__57-206 |
| HG1019804 | SEQ. ID. NO. 68 | SEQ. ID. NO. 242 | NP_001998__68-206 |
| HG1019805 | SEQ. ID. NO. 69 | SEQ. ID. NO. 243 | NP_001998__71-206 |
| HG1019806 | SEQ. ID. NO. 70 | SEQ. ID. NO. 244 | NP_002001__4-208 |
| HG1019807 | SEQ. ID. NO. 71 | SEQ. ID. NO. 245 | NP_002332__49-244 |
| HG1019808 | SEQ. ID. NO. 72 | SEQ. ID. NO. 246 | NP_002598__87-211 |
| HG1019809 | SEQ. ID. NO. 73 | SEQ. ID. NO. 247 | NP_002599__82-190 |
| HG1019810 | SEQ. ID. NO. 74 | SEQ. ID. NO. 248 | NP_003093__19-240 |
| HG1019811 | SEQ. ID. NO. 75 | SEQ. ID. NO. 249 | NP_003227__1-98 |
| HG1019812 | SEQ. ID. NO. 76 | SEQ. ID. NO. 250 | NP_003227__24-98 |
| HG1019813 | SEQ. ID. NO. 77 | SEQ. ID. NO. 251 | NP_003227__40-89 |
| HG1019814 | SEQ. ID. NO. 78 | SEQ. ID. NO. 252 | NP_003317__51-183 |
| HG1019815 | SEQ. ID. NO. 79 | SEQ. ID. NO. 253 | NP_003692__140-317 |
| HG1019816 | SEQ. ID. NO. 80 | SEQ. ID. NO. 254 | NP_003692__69-317 |
| HG1019817 | SEQ. ID. NO. 81 | SEQ. ID. NO. 255 | NP_003799__105-250 |
| HG1019818 | SEQ. ID. NO. 82 | SEQ. ID. NO. 256 | NP_003800__43-249 |
| HG1019819 | SEQ. ID. NO. 83 | SEQ. ID. NO. 257 | NP_003800__94-249 |
| HG1019820 | SEQ. ID. NO. 84 | SEQ. ID. NO. 258 | NP_003801__39-281 |
| HG1019821 | SEQ. ID. NO. 85 | SEQ. ID. NO. 259 | NP_003802__50-254 |
| HG1019822 | SEQ. ID. NO. 86 | SEQ. ID. NO. 260 | NP_003858__23-216 |
| HG1019823 | SEQ. ID. NO. 87 | SEQ. ID. NO. 261 | NP_004874__112-405 |
| HG1019824 | SEQ. ID. NO. 88 | SEQ. ID. NO. 262 | NP_005083__50-177 |
| HG1019825 | SEQ. ID. NO. 89 | SEQ. ID. NO. 263 | NP_005414__24-129 |
| HG1019826 | SEQ. ID. NO. 90 | SEQ. ID. NO. 264 | NP_005420__112-227 |
| HG1019827 | SEQ. ID. NO. 91 | SEQ. ID. NO. 265 | NP_006174__151-163 |

TABLE 1-continued

| FP ID | SEQ. ID. NO. (N1) | SEQ. ID. NO. (P1) | Source ID |
| --- | --- | --- | --- |
| HG1019828 | SEQ. ID. NO. 92 | SEQ. ID. NO. 266 | NP_006174__24-148 |
| HG1019829 | SEQ. ID. NO. 93 | SEQ. ID. NO. 267 | NP_006564__134-285 |
| HG1019830 | SEQ. ID. NO. 94 | SEQ. ID. NO. 268 | NP_006564__68-285 |
| HG1019831 | SEQ. ID. NO. 95 | SEQ. ID. NO. 269 | NP_006844__20-250 |
| HG1019832 | SEQ. ID. NO. 96 | SEQ. ID. NO. 270 | NP_039253__101-296 |
| HG1019833 | SEQ. ID. NO. 97 | SEQ. ID. NO. 271 | NP_039258__177-241 |
| HG1019834 | SEQ. ID. NO. 98 | SEQ. ID. NO. 272 | NP_039258__19-241 |
| HG1019835 | SEQ. ID. NO. 99 | SEQ. ID. NO. 273 | NP_055282__23-465 |
| HG1019836 | SEQ. ID. NO. 100 | SEQ. ID. NO. 274 | NP_057289__15-345 |
| HG1019837 | SEQ. ID. NO. 101 | SEQ. ID. NO. 275 | NP_062825__20-211 |
| HG1019838 | SEQ. ID. NO. 102 | SEQ. ID. NO. 276 | NP_065391__26-209 |
| HG1019839 | SEQ. ID. NO. 103 | SEQ. ID. NO. 277 | NP_065391__26-234 |
| HG1019840 | SEQ. ID. NO. 104 | SEQ. ID. NO. 278 | NP_066276__38-208 |
| HG1019841 | SEQ. ID. NO. 105 | SEQ. ID. NO. 279 | NP_079484__19-370 |
| HG1019842 | SEQ. ID. NO. 106 | SEQ. ID. NO. 280 | NP_149122__25-352 |
| HG1019843 | SEQ. ID. NO. 107 | SEQ. ID. NO. 281 | NP_149353__23-233 |
| HG1019844 | SEQ. ID. NO. 108 | SEQ. ID. NO. 282 | NP_612640__1-62 |
| HG1019845 | SEQ. ID. NO. 109 | SEQ. ID. NO. 283 | NP_659196__51-282 |
| HG1019846 | SEQ. ID. NO. 110 | SEQ. ID. NO. 284 | NP_766638__21-988 |
| HG1019847 | SEQ. ID. NO. 111 | SEQ. ID. NO. 285 | 122742 |
| HG1019848 | SEQ. ID. NO. 112 | SEQ. ID. NO. 286 | 12652749 |
| HG1019849 | SEQ. ID. NO. 113 | SEQ. ID. NO. 287 | 13637763 |
| HG1019850 | SEQ. ID. NO. 114 | SEQ. ID. NO. 288 | 18573061 |
| HG1019851 | SEQ. ID. NO. 115 | SEQ. ID. NO. 289 | 21362994 |
| HG1019852 | SEQ. ID. NO. 116 | SEQ. ID. NO. 290 | 22761542 |
| HG1019853 | SEQ. ID. NO. 117 | SEQ. ID. NO. 291 | 298591 |
| HG1019854 | SEQ. ID. NO. 118 | SEQ. ID. NO. 292 | 51464450 |
| HG1019855 | SEQ. ID. NO. 119 | SEQ. ID. NO. 293 | 9789758 |
| HG1019856 | SEQ. ID. NO. 120 | SEQ. ID. NO. 294 | NP_000020 |
| HG1019857 | SEQ. ID. NO. 121 | SEQ. ID. NO. 295 | NP_000065 |
| HG1019858 | SEQ. ID. NO. 122 | SEQ. ID. NO. 296 | NP_000451 |
| HG1019859 | SEQ. ID. NO. 123 | SEQ. ID. NO. 297 | NP_000585 |
| HG1019860 | SEQ. ID. NO. 124 | SEQ. ID. NO. 298 | NP_000586 |
| HG1019861 | SEQ. ID. NO. 125 | SEQ. ID. NO. 299 | NP_000592 |
| HG1019862 | SEQ. ID. NO. 126 | SEQ. ID. NO. 300 | NP_000603 |
| HG1019863 | SEQ. ID. NO. 127 | SEQ. ID. NO. 301 | NP_000609 |
| HG1019864 | SEQ. ID. NO. 128 | SEQ. ID. NO. 302 | NP_000630 |
| HG1019865 | SEQ. ID. NO. 129 | SEQ. ID. NO. 303 | NP_000791 |
| HG1019866 | SEQ. ID. NO. 130 | SEQ. ID. NO. 304 | NP_000896 |
| HG1019867 | SEQ. ID. NO. 131 | SEQ. ID. NO. 305 | NP_001243 |
| HG1019868 | SEQ. ID. NO. 132 | SEQ. ID. NO. 306 | NP_001390 |
| HG1019869 | SEQ. ID. NO. 133 | SEQ. ID. NO. 307 | NP_001423 |
| HG1019870 | SEQ. ID. NO. 134 | SEQ. ID. NO. 308 | NP_001648 |
| HG1019871 | SEQ. ID. NO. 135 | SEQ. ID. NO. 309 | NP_001936 |
| HG1019872 | SEQ. ID. NO. 136 | SEQ. ID. NO. 310 | NP_001947 |
| HG1019873 | SEQ. ID. NO. 137 | SEQ. ID. NO. 311 | NP_001954 |
| HG1019874 | SEQ. ID. NO. 138 | SEQ. ID. NO. 312 | NP_001998 |
| HG1019875 | SEQ. ID. NO. 139 | SEQ. ID. NO. 313 | NP_002001 |
| HG1019876 | SEQ. ID. NO. 140 | SEQ. ID. NO. 314 | NP_002332 |
| HG1019877 | SEQ. ID. NO. 141 | SEQ. ID. NO. 315 | NP_002598 |
| HG1019878 | SEQ. ID. NO. 142 | SEQ. ID. NO. 316 | NP_002599 |
| HG1019879 | SEQ. ID. NO. 143 | SEQ. ID. NO. 317 | NP_003093 |
| HG1019880 | SEQ. ID. NO. 144 | SEQ. ID. NO. 318 | NP_003227 |
| HG1019881 | SEQ. ID. NO. 145 | SEQ. ID. NO. 319 | NP_003692 |
| HG1019882 | SEQ. ID. NO. 146 | SEQ. ID. NO. 320 | NP_003799 |
| HG1019883 | SEQ. ID. NO. 147 | SEQ. ID. NO. 321 | NP_003800 |
| HG1019884 | SEQ. ID. NO. 148 | SEQ. ID. NO. 322 | NP_003802 |
| HG1019885 | SEQ. ID. NO. 149 | SEQ. ID. NO. 323 | NP_003858 |
| HG1019886 | SEQ. ID. NO. 150 | SEQ. ID. NO. 324 | NP_003859 |
| HG1019887 | SEQ. ID. NO. 151 | SEQ. ID. NO. 325 | NP_004874 |
| HG1019888 | SEQ. ID. NO. 152 | SEQ. ID. NO. 326 | NP_005083 |
| HG1019889 | SEQ. ID. NO. 153 | SEQ. ID. NO. 327 | NP_005414 |
| HG1019890 | SEQ. ID. NO. 154 | SEQ. ID. NO. 328 | NP_005420 |
| HG1019891 | SEQ. ID. NO. 155 | SEQ. ID. NO. 329 | NP_005535 |
| HG1019892 | SEQ. ID. NO. 156 | SEQ. ID. NO. 330 | NP_006174 |
| HG1019893 | SEQ. ID. NO. 157 | SEQ. ID. NO. 331 | NP_006564 |
| HG1019894 | SEQ. ID. NO. 158 | SEQ. ID. NO. 332 | NP_006844 |
| HG1019895 | SEQ. ID. NO. 159 | SEQ. ID. NO. 333 | NP_039253 |
| HG1019896 | SEQ. ID. NO. 160 | SEQ. ID. NO. 334 | NP_039258 |
| HG1019897 | SEQ. ID. NO. 161 | SEQ. ID. NO. 335 | NP_055282 |
| HG1019898 | SEQ. ID. NO. 162 | SEQ. ID. NO. 336 | NP_057289 |
| HG1019899 | SEQ. ID. NO. 163 | SEQ. ID. NO. 337 | NP_062825 |
| HG1019900 | SEQ. ID. NO. 164 | SEQ. ID. NO. 338 | NP_065391 |
| HG1019901 | SEQ. ID. NO. 165 | SEQ. ID. NO. 339 | NP_066276 |
| HG1019902 | SEQ. ID. NO. 166 | SEQ. ID. NO. 340 | NP_079484 |
| HG1019903 | SEQ. ID. NO. 167 | SEQ. ID. NO. 341 | NP_149122 |
| HG1019904 | SEQ. ID. NO. 168 | SEQ. ID. NO. 342 | NP_149353 |
| HG1019905 | SEQ. ID. NO. 169 | SEQ. ID. NO. 343 | NP_612640 |

TABLE 1-continued

| FP ID | SEQ. ID. NO. (N1) | SEQ. ID. NO. (P1) | Source ID |
|---|---|---|---|
| HG1019906 | SEQ. ID. NO. 170 | SEQ. ID. NO. 344 | NP_659196 |
| HG1019907 | SEQ. ID. NO. 171 | SEQ. ID. NO. 345 | NP_766638 |
| HG1019908 | SEQ. ID. NO. 172 | SEQ. ID. NO. 346 | CLN00211466_32-129 |
| HG1019909 | SEQ. ID. NO. 173 | SEQ. ID. NO. 347 | CLN00358501_22-119 |
| HG1019910 | SEQ. ID. NO. 174 | SEQ. ID. NO. 348 | CLN00489695_23-164 |

TABLE 2

| FP ID | Source ID | Pfam Domain | Location |
|---|---|---|---|
| HG1015480 | CLN00235738 | IL8 | (22-87) |
| HG1015481 | CLN00358501 | IL8 | (22-87) |
| HG1015482 | NP_000600 | IL8 | (22-87) |
| HG1015490 | NP_003317 | TNF | (77-182) |
| HG1015494 | NP_001235 | TNF | (113-230) |
| HG1015498 | NP_001720 | EGF | (69-104) |
| HG1015509 | CLN00235738_22-140 | IL8 | (1-66) |
| HG1015527 | CLN00489695 | IL6 | (62-159) |
| HG1015531 | NP_000750 | IL6 | (51-202) |
| HG1015712 | NP_002300_23-202 | LIF_OSM | (1-180) |
| HG1018346 | NP_000591 | IL6 | (57-210) |
| HG1018401 | NP_002300 | LIF_OSM | (2-202) |
| HG1019038 | NP_003801 | TNF | (152-280) |
| HG1019751 | 122742_10-155 | FGF | (19-140) |
| HG1019752 | 12652749_279-390 | TGF_beta | (12-112) |
| HG1019753 | 12652749_30-390 | TGF_beta | (261-361) |
| HG1019753 | 12652749_30-390 | TGFb_propeptide | (4-223) |
| HG1019754 | 13637763_18-268 | FGF | (70-199) |
| HG1019755 | 13637763_4-268 | FGF | (84-213) |
| HG1019757 | 21362994_26-174 | TNF | (15-149) |
| HG1019759 | 298591_18-212 | Endothelin | (31-61) |
| HG1019760 | 298591_53-73 | Endothelin | (1-21) |
| HG1019761 | 298591_53-90 | Endothelin | (1-26) |
| HG1019762 | 9789758_1-361 | EGF | (290-328) |
| HG1019765 | NP_000020_34-485 | Serpin | (66-448) |
| HG1019767 | NP_000065_113-261 | TNF | (26-149) |
| HG1019768 | NP_000065_47-261 | TNF | (92-215) |
| HG1019769 | NP_000451_22-353 | EPO_TPO | (1-167) |
| HG1019770 | NP_000585_57-233 | TNF | (46-177) |
| HG1019771 | NP_000585_77-233 | TNF | (26-157) |
| HG1019772 | NP_000586_35-205 | TNF | (43-171) |
| HG1019773 | NP_000591_30-212 | IL6 | (28-181) |
| HG1019774 | NP_000592_32-494 | Kringle | (274-352) |
| HG1019774 | NP_000592_32-494 | Kringle | (180-257) |
| HG1019774 | NP_000592_32-494 | Kringle | (97-175) |
| HG1019774 | NP_000592_32-494 | Kringle | (360-438) |
| HG1019774 | NP_000592_32-494 | PAN | (3-93) |
| HG1019775 | NP_000592_495-728 | Trypsin | (1-222) |
| HG1019776 | NP_000600_22-93 | IL8 | (1-66) |
| HG1019777 | NP_000603_25-180 | Insulin | (6-60) |
| HG1019778 | NP_000603_25-91 | Insulin | (6-60) |
| HG1019779 | NP_000609_49-118 | Insulin | (3-61) |
| HG1019780 | NP_000630_103-281 | TNF | (58-179) |
| HG1019781 | NP_000630_130-281 | TNF | (31-152) |
| HG1019782 | NP_000750_30-207 | IL6 | (22-173) |
| HG1019783 | NP_000791_16-155 | FGF | (10-133) |
| HG1019784 | NP_000896_29-64 | Hormone_3 | (1-36) |
| HG1019785 | NP_000896_29-64 | Hormone_3 | (1-36) |
| HG1019786 | NP_001235_63-234 | TNF | (51-168) |
| HG1019787 | NP_001243_39-193 | TNF | (35-153) |
| HG1019788 | NP_001390_160-391 | TNF | (113-226) |
| HG1019789 | NP_001390_63-391 | TNF | (210-323) |
| HG1019790 | NP_001423_60-108 | EGF | (9-44) |
| HG1019791 | NP_001423_63-108 | EGF | (6-41) |
| HG1019792 | NP_001648_101-184 | EGF | (46-81) |
| HG1019793 | NP_001648_19-198 | EGF | (128-163) |
| HG1019794 | NP_001720_32-111 | EGF | (38-73) |
| HG1019795 | NP_001936_20-160 | EGF | (89-124) |
| HG1019796 | NP_001936_63-148 | EGF | (46-81) |
| HG1019797 | NP_001947_18-212 | Endothelin | (28-57) |
| HG1019798 | NP_001947_49-69 | Endothelin | (1-21) |
| HG1019799 | NP_001954_23-1032 | EGF | (379-414) |
| HG1019799 | NP_001954_23-1032 | EGF | (954-990) |
| HG1019799 | NP_001954_23-1032 | EGF | (813-846) |
| HG1019799 | NP_001954_23-1032 | EGF | (723-758) |
| HG1019799 | NP_001954_23-1032 | EGF | (296-332) |
| HG1019799 | NP_001954_23-1032 | EGF | (338-373) |
| HG1019799 | NP_001954_23-1032 | EGF | (865-888) |
| HG1019799 | NP_001954_23-1032 | EGF | (894-929) |
| HG1019799 | NP_001954_23-1032 | EGF_CA | (848-888) |
| HG1019799 | NP_001954_23-1032 | EGF_CA | (890-918) |
| HG1019799 | NP_001954_23-1032 | EGF_CA | (334-373) |
| HG1019799 | NP_001954_23-1032 | Ldl_recept_b | (632-672) |
| HG1019799 | NP_001954_23-1032 | Ldl_recept_b | (545-586) |
| HG1019799 | NP_001954_23-1032 | Ldl_recept_b | (502-543) |
| HG1019799 | NP_001954_23-1032 | Ldl_recept_b | (588-630) |
| HG1019800 | NP_001954_971-1023 | EGF | (6-42) |
| HG1019801 | NP_001998_31-206 | FGF | (52-173) |
| HG1019802 | NP_001998_54-206 | FGF | (29-150) |
| HG1019803 | NP_001998_57-206 | FGF | (26-147) |
| HG1019804 | NP_001998_68-206 | FGF | (15-136) |
| HG1019805 | NP_001998_71-206 | FGF | (12-133) |
| HG1019806 | NP_002001_4-208 | FGF | (59-165) |
| HG1019807 | NP_002332_49-244 | TNF | (54-195) |
| HG1019808 | NP_002598_87-211 | PDGF | (10-93) |
| HG1019809 | NP_002599_82-190 | PDGF | (16-99) |
| HG1019809 | NP_002599_82-190 | PDGF_N | (1-15) |
| HG1019810 | NP_003093_19-240 | Sod_Cu | (46-196) |
| HG1019811 | NP_003227_1-98 | EGF | (47-82) |
| HG1019812 | NP_003227_24-98 | EGF | (24-59) |
| HG1019813 | NP_003227_40-89 | EGF | (8-43) |
| HG1019814 | NP_003317_51-183 | TNF | (27-132) |
| HG1019815 | NP_003692_140-317 | TNF | (46-174) |
| HG1019816 | NP_003692_69-317 | TNF | (117-245) |
| HG1019817 | NP_003799_105-250 | TNF | (32-146) |
| HG1019818 | NP_003800_43-249 | TNF | (89-206) |
| HG1019819 | NP_003800_94-249 | TNF | (38-155) |
| HG1019820 | NP_003801_39-281 | TNF | (114-242) |
| HG1019821 | NP_003802_50-254 | TNF | (58-191) |
| HG1019822 | NP_003858_23-216 | FGF | (31-156) |
| HG1019823 | NP_004874_112-405 | EGF | (234-270) |
| HG1019823 | NP_004874_112-405 | ig | (139-202) |
| HG1019823 | NP_004874_112-405 | I-set | (128-218) |
| HG1019824 | NP_005083_50-177 | TNF | (18-121) |
| HG1019825 | NP_005414_24-129 | Trefoil | (7-49) |
| HG1019825 | NP_005414_24-129 | Trefoil | (57-98) |
| HG1019826 | NP_005420_112-227 | PDGF | (20-100) |
| HG1019827 | NP_006174_151-163 | Pro-NT_NN | (1-13) |
| HG1019828 | NP_006174_24-148 | Pro-NT_NN | (1-125) |
| HG1019829 | NP_006564_134-285 | TNF | (33-151) |
| HG1019830 | NP_006564_68-285 | TNF | (99-217) |
| HG1019831 | NP_006844_20-250 | Trypsin | (3-224) |
| HG1019832 | NP_039253_101-296 | EGF | (137-176) |
| HG1019833 | NP_039258_177-241 | EGF | (6-45) |
| HG1019834 | NP_039258_19-241 | EGF | (164-203) |
| HG1019834 | NP_039258_19-241 | ig | (32-96) |
| HG1019834 | NP_039258_19-241 | I-set | (18-112) |
| HG1019835 | NP_055282_23-465 | HYR | (155-237) |
| HG1019835 | NP_055282_23-465 | Sushi | (100-154) |
| HG1019835 | NP_055282_23-465 | Sushi | (37-95) |
| HG1019835 | NP_055282_23-465 | Sushi | (242-297) |
| HG1019836 | NP_057289_15-345 | CUB | (39-154) |
| HG1019836 | NP_057289_15-345 | PDGF | (255-323) |
| HG1019837 | NP_062825_20-211 | FGF | (46-172) |
| HG1019838 | NP_065391_26-209 | LIF_OSM | (1-184) |
| HG1019839 | NP_065391_26-234 | LIF_OSM | (1-184) |
| HG1019840 | NP_066276_38-208 | FGF | (47-168) |
| HG1019841 | NP_079484_19-370 | CUB | (43-149) |

TABLE 2-continued

| FP ID | Source ID | Pfam Domain | Location |
|---|---|---|---|
| HG1019842 | NP_149122_25-352 | wnt | (17-328) |
| HG1019843 | NP_149353_23-233 | FGF | (59-185) |
| HG1019844 | NP_612640_1-62 | EGF | (9-45) |
| HG1019845 | NP_659196_51-282 | Trypsin | (4-225) |
| HG1019846 | NP_766638_21-988 | CUB | (778-816) |
| HG1019846 | NP_766638_21-988 | CUB | (855-887) |
| HG1019846 | NP_766638_21-988 | EGF | (17-52) |
| HG1019846 | NP_766638_21-988 | EGF | (101-136) |
| HG1019846 | NP_766638_21-988 | EGF | (346-381) |
| HG1019846 | NP_766638_21-988 | EGF | (266-301) |
| HG1019846 | NP_766638_21-988 | EGF | (225-260) |
| HG1019846 | NP_766638_21-988 | EGF | (186-221) |
| HG1019846 | NP_766638_21-988 | EGF | (146-182) |
| HG1019846 | NP_766638_21-988 | EGF_CA | (13-52) |
| HG1019846 | NP_766638_21-988 | EGF_CA | (303-340) |
| HG1019846 | NP_766638_21-988 | EGF_CA | (342-371) |
| HG1019846 | NP_766638_21-988 | EGF_CA | (97-136) |
| HG1019846 | NP_766638_21-988 | EGF_CA | (262-301) |
| HG1019846 | NP_766638_21-988 | GCC2_GCC3 | (726-773) |
| HG1019846 | NP_766638_21-988 | GCC2_GCC3 | (670-717) |
| HG1019846 | NP_766638_21-988 | GCC2_GCC3 | (616-663) |
| HG1019847 | 122742 | FGF | (28-149) |
| HG1019848 | 12652749 | TGF_beta | (290-390) |
| HG1019848 | 12652749 | TGFb_propeptide | (33-252) |
| HG1019849 | 13637763 | FGF | (87-216) |
| HG1019851 | 21362994 | TNF | (40-174) |
| HG1019853 | 298591 | Endothelin | (48-78) |
| HG1019854 | 51464450 | EGF | (60-95) |
| HG1019855 | 9789758 | EGF | (290-328) |
| HG1019855 | 9789758 | neuregulin | (353-397) |
| HG1019856 | NP_000020 | Serpin | (99-481) |
| HG1019857 | NP_000065 | TNF | (138-261) |
| HG1019858 | NP_000451 | EPO_TPO | (5-188) |
| HG1019859 | NP_000585 | TNF | (102-233) |
| HG1019860 | NP_000586 | TNF | (77-205) |
| HG1019861 | NP_000592 | Kringle | (305-383) |
| HG1019861 | NP_000592 | Kringle | (211-288) |
| HG1019861 | NP_000592 | Kringle | (128-206) |
| HG1019861 | NP_000592 | Kringle | (391-469) |
| HG1019861 | NP_000592 | PAN | (34-124) |
| HG1019861 | NP_000592 | Trypsin | (495-716) |
| HG1019862 | NP_000603 | Insulin | (30-84) |
| HG1019863 | NP_000609 | Insulin | (51-109) |
| HG1019864 | NP_000630 | TNF | (160-281) |
| HG1019865 | NP_000791 | FGF | (25-148) |
| HG1019866 | NP_000896 | Hormone_3 | (29-64) |
| HG1019867 | NP_001243 | TNF | (73-191) |
| HG1019868 | NP_001390 | TNF | (272-385) |
| HG1019869 | NP_001423 | EGF | (68-103) |
| HG1019870 | NP_001648 | EGF | (146-181) |
| HG1019871 | NP_001936 | EGF | (108-143) |
| HG1019872 | NP_001947 | Endothelin | (45-74) |
| HG1019873 | NP_001954 | EGF | (401-436) |
| HG1019873 | NP_001954 | EGF | (976-1012) |
| HG1019873 | NP_001954 | EGF | (835-868) |
| HG1019873 | NP_001954 | EGF | (745-780) |
| HG1019873 | NP_001954 | EGF | (318-354) |
| HG1019873 | NP_001954 | EGF | (360-395) |
| HG1019873 | NP_001954 | EGF | (887-910) |
| HG1019873 | NP_001954 | EGF | (916-951) |
| HG1019873 | NP_001954 | EGF_CA | (870-910) |
| HG1019873 | NP_001954 | EGF_CA | (912-940) |
| HG1019873 | NP_001954 | EGF_CA | (356-395) |
| HG1019873 | NP_001954 | Ldl_recept_b | (654-694) |
| HG1019873 | NP_001954 | Ldl_recept_b | (567-608) |
| HG1019873 | NP_001954 | Ldl_recept_b | (524-565) |
| HG1019873 | NP_001954 | Ldl_recept_b | (610-652) |
| HG1019874 | NP_001998 | FGF | (82-203) |
| HG1019875 | NP_002001 | FGF | (62-188) |
| HG1019876 | NP_002332 | TNF | (102-243) |
| HG1019877 | NP_002598 | PDGF | (96-179) |
| HG1019877 | NP_002598 | PDGF_N | (21-95) |
| HG1019878 | NP_002599 | PDGF | (97-180) |
| HG1019878 | NP_002599 | PDGF_N | (21-96) |
| HG1019879 | NP_003093 | Sod_Cu | (64-214) |
| HG1019880 | NP_003227 | EGF | (47-82) |
| HG1019881 | NP_003692 | TNF | (185-313) |
| HG1019882 | NP_003799 | TNF | (136-250) |
| HG1019883 | NP_003800 | TNF | (131-248) |
| HG1019884 | NP_003802 | TNF | (107-240) |
| HG1019885 | NP_003858 | FGF | (53-178) |
| HG1019886 | NP_003859 | FGF | (61-187) |
| HG1019887 | NP_004874 | EGF | (345-381) |
| HG1019887 | NP_004874 | ig | (250-313) |
| HG1019887 | NP_004874 | I-set | (239-329) |
| HG1019887 | NP_004874 | neuregulin | (398-648) |
| HG1019887 | NP_004874 | neuregulin | (699-769) |
| HG1019888 | NP_005083 | TNF | (67-170) |
| HG1019889 | NP_005414 | Trefoil | (30-72) |
| HG1019889 | NP_005414 | Trefoil | (80-121) |
| HG1019890 | NP_005420 | PDGF | (131-211) |
| HG1019891 | NP_005535 | IRS | (160-262) |
| HG1019891 | NP_005535 | PH | (13-115) |
| HG1019892 | NP_006174 | Pro-NT_NN | (2-170) |
| HG1019893 | NP_006564 | TNF | (166-284) |
| HG1019894 | NP_006844 | Trypsin | (22-243) |
| HG1019895 | NP_039253 | EGF | (237-276) |
| HG1019896 | NP_039258 | EGF | (182-221) |
| HG1019896 | NP_039258 | ig | (50-114) |
| HG1019896 | NP_039258 | I-set | (36-130) |
| HG1019896 | NP_039258 | neuregulin | (235-630) |
| HG1019897 | NP_055282 | HYR | (177-259) |
| HG1019897 | NP_055282 | Sushi | (122-176) |
| HG1019897 | NP_055282 | Sushi | (59-117) |
| HG1019897 | NP_055282 | Sushi | (264-319) |
| HG1019898 | NP_057289 | CUB | (53-148) |
| HG1019898 | NP_057289 | PDGF | (269-337) |
| HG1019899 | NP_062825 | FGF | (65-191) |
| HG1019900 | NP_065391 | LIF_OSM | (2-209) |
| HG1019901 | NP_066276 | FGF | (84-205) |
| HG1019902 | NP_079484 | CUB | (61-167) |
| HG1019903 | NP_149122 | wnt | (41-352) |
| HG1019904 | NP_149353 | FGF | (81-207) |
| HG1019905 | NP_612640 | EGF | (9-45) |
| HG1019906 | NP_659196 | Trypsin | (54-275) |
| HG1019907 | NP_766638 | CUB | (798-836) |
| HG1019907 | NP_766638 | CUB | (875-907) |
| HG1019907 | NP_766638 | EGF | (37-72) |
| HG1019907 | NP_766638 | EGF | (121-156) |
| HG1019907 | NP_766638 | EGF | (366-401) |
| HG1019907 | NP_766638 | EGF | (286-321) |
| HG1019907 | NP_766638 | EGF | (245-280) |
| HG1019907 | NP_766638 | EGF | (206-241) |
| HG1019907 | NP_766638 | EGF | (166-202) |
| HG1019907 | NP_766638 | EGF_CA | (33-72) |
| HG1019907 | NP_766638 | EGF_CA | (323-360) |
| HG1019907 | NP_766638 | EGF_CA | (362-391) |
| HG1019907 | NP_766638 | EGF_CA | (117-156) |
| HG1019907 | NP_766638 | EGF_CA | (282-321) |
| HG1019907 | NP_766638 | GCC2_GCC3 | (746-793) |
| HG1019907 | NP_766638 | GCC2_GCC3 | (690-737) |
| HG1019907 | NP_766638 | GCC2_GCC3 | (636-683) |
| HG1019909 | CLN00358501_22-119 | IL8 | (1-66) |
| HG1019910 | CLN00489695_23-164 | IL6 | (40-137) |

TABLE 3

| FP ID | Predicted Protein Length | Treevote | Signal Peptide Coordinates | Mature Protein Coordinates | Alternative Signal Peptide Coordinates | Alternate Mature Protein Coordinates | Hydrophobicity Coordinates | TM | TM Coordinates | non-TM Coordinates |
|---|---|---|---|---|---|---|---|---|---|---|
| HG1015480 | 140 | 0.98 | (1-21) | (22-140) | (5-17)(7-19)(9-21) | (18-259)(20-259)(22-259) | (9-21) | 0 | | (1-140) |
| HG1015481 | 119 | 0.98 | (1-21) | (22-119) | (5-17)(7-19)(9-21) | (18-217)(20-217)(22-217) | (9-21) | 0 | | (1-119) |
| HG1015482 | 93 | 1 | (1-21) | (22-93) | (5-17)(7-19) | (18-93)(20-93) | (9-21) | 0 | | (1-93) |
| HG1015490 | 183 | 0 | | (1-183) | | | (23-35) | 1 | (24-46) | (1-23)(47-183) |
| HG1015494 | 234 | 0 | | (1-234) | | | | 1 | (39-61) | (1-38)(62-234) |
| HG1015496 | 129 | 0.92 | (1-31) | (32-129) | (14-26)(10-22)(19-31) | (27-227)(23-227)(32-227) | (19-31) | 1 | (7-29) | (1-6)(30-129) |
| HG1015498 | 178 | 0 | (1-31) | (32-178) | (14-26)(10-22) | (27-178)(23-178) | (19-31) | 2 | (9-31)(119-141) | (1-8)(32-118)(142-178) |
| HG1015509 | 119 | 0.2 | | (1-119) | | | | 0 | | (1-119) |
| HG1015527 | 164 | 0.87 | | (1-164) | | | | 0 | | (1-164) |
| HG1015531 | 207 | 1 | (13-30) | (31-207) | (14-26) | (27-207) | (14-26) | 0 | | (1-207) |
| HG1015712 | 180 | 0.02 | | (1-180) | | | | 0 | | (1-180) |
| HG1018346 | 212 | 1 | (1-25) | (26-212) | (12-24)(15-27) | (25-212)(28-212) | (15-27) | 0 | | (1-212) |
| HG1018401 | 202 | 1 | (1-22) | (23-202) | (11-23) | (24-202) | (11-23) | 0 | | (1-202) |
| HG1019038 | 281 | 0.64 | (3-33) | (34-281) | (22-34)(18-30)(20-32) | (35-281)(31-281)(33-281) | (20-32) | 1 | (15-37) | (1-14)(38-281) |
| HG1019751 | 146 | 0.3 | | (1-146) | | | | 0 | | (1-146) |
| HG1019752 | 112 | 0.01 | | (1-112) | | | | 0 | | (1-112) |
| HG1019753 | 361 | 0 | | (1-361) | (25-37) | (38-361) | (25-37) | 0 | | (1-361) |
| HG1019754 | 251 | 0.36 | | (1-251) | | | | 0 | | (1-251) |
| HG1019755 | 265 | 0.99 | (3-18) | (19-265) | (1-13)(3-15)(7-19)(5-17)(2-14) | (14-265)(16-265)(20-265)(18-265)(15-265) | (2-14) | 0 | | (1-265) |
| HG1019756 | 100 | 0.01 | | (1-100) | | | | 0 | | (1-100) |
| HG1019757 | 149 | 0.1 | | (1-149) | | | | 0 | | (1-149) |
| HG1019758 | 195 | 0.02 | | (1-195) | | | | 0 | | (1-195) |
| HG1019759 | 195 | 0.01 | | (1-195) | | | | 0 | | (1-195) |
| HG1019762 | 361 | 0.06 | | (1-361) | | | (24-36) | 1 | (69-91) | (1-68)(92-361) |
| HG1019765 | 452 | 0.03 | | (1-452) | | | | 0 | | (1-452) |
| HG1019767 | 149 | 0.01 | | (1-149) | | | | 0 | | (1-149) |
| HG1019768 | 215 | 0 | | (1-215) | | | | 0 | | (1-215) |
| HG1019769 | 332 | 0.06 | | (1-332) | | | | 0 | | (1-332) |
| HG1019770 | 177 | 0.26 | (12-25) | (26-177) | (11-23) | (24-177) | (11-23) | 0 | | (1-177) |
| HG1019771 | 157 | 0 | | (1-157) | | | | 0 | | (1-157) |
| HG1019772 | 171 | 0.03 | | (1-171) | | | | 0 | | (1-171) |
| HG1019773 | 183 | 0.72 | | (1-183) | | | | 0 | | (1-183) |
| HG1019774 | 463 | 0 | | (1-463) | | | | 0 | | (1-463) |
| HG1019775 | 234 | 0 | | (1-234) | | | | 0 | | (1-234) |
| HG1019776 | 72 | 0.02 | | (1-72) | | | | 0 | | (1-72) |
| HG1019777 | 156 | 0.01 | | (1-156) | | | | 0 | | (1-156) |
| HG1019779 | 70 | 0 | | (1-70) | | | | 0 | | (1-70) |
| HG1019780 | 179 | 0 | | (1-179) | | | | 0 | | (1-179) |
| HG1019781 | 152 | 0 | | (1-152) | | | | 0 | | (1-152) |
| HG1019782 | 178 | 0.59 | | (1-178) | | | | 0 | | (1-178) |
| HG1019783 | 140 | 0.23 | | (1-140) | | | | 0 | | (1-140) |
| HG1019786 | 172 | 0.03 | | (1-172) | | | | 0 | | (1-172) |
| HG1019787 | 155 | 0 | | (1-155) | | | | 0 | | (1-155) |
| HG1019788 | 232 | 0.01 | | (1-232) | | | | 0 | | (1-232) |
| HG1019789 | 329 | 0 | | (1-329) | | | | 0 | | (1-329) |
| HG1019792 | 84 | 0 | | (1-84) | | | | 0 | | (1-84) |
| HG1019793 | 180 | 0 | | (1-180) | | | | 0 | | (1-180) |
| HG1019794 | 80 | 0.01 | | (1-80) | | | | 0 | | (1-80) |
| HG1019795 | 141 | 0.02 | | (1-141) | | | | 0 | | (1-141) |
| HG1019796 | 86 | 0.1 | | (1-86) | | | (10-22) | 0 | | (1-86) |
| HG1019797 | 161 | 0.01 | | (1-161) | | | | 0 | | (1-161) |
| HG1019799 | 1010 | 0.01 | | (1-1010) | | | | 0 | | (1-1010) |
| HG1019801 | 176 | 0.59 | (19-33) | (34-176) | (20-32) | (33-176) | (20-32) | 0 | | (1-176) |
| HG1019802 | 153 | 0.49 | | (1-153) | | | | 0 | | (1-153) |
| HG1019803 | 150 | 0.5 | | (1-150) | | | | 0 | | (1-150) |
| HG1019804 | 139 | 0.48 | | (1-139) | | | | 0 | | (1-139) |
| HG1019805 | 136 | 0.47 | | (1-136) | | | | 0 | | (1-136) |
| HG1019806 | 205 | 0.79 | | (1-205) | | | | 0 | | (1-205) |
| HG1019807 | 196 | 0.03 | | (1-196) | | | (5-17) | 0 | | (1-196) |
| HG1019808 | 125 | 0 | | (1-125) | | | | 0 | | (1-125) |
| HG1019809 | 109 | 0 | | (1-109) | | | | 0 | | (1-109) |
| HG1019810 | 222 | 0 | | (1-222) | | | | 0 | | (1-222) |
| HG1019811 | 98 | 0.97 | (1-22) | (23-98) | (6-18) | (19-98) | (10-22) | 0 | | (1-98) |

TABLE 3-continued

| FP ID | Pre-dicted Protein Length | Treevote | Signal Peptide Coordinates | Mature Protein Coordinates | Alternative Signal Peptide Coordinates | Alternate Mature Protein Coordinates | Hydro-phobicity Coordinates | TM | TM Coordinates | non-TM Coordinates |
|---|---|---|---|---|---|---|---|---|---|---|
| HG1019812 | 75 | 0.01 | | (1-75) | | | | 0 | | (1-75) |
| HG1019814 | 133 | 0.01 | | (1-133) | | | | 0 | | (1-133) |
| HG1019815 | 178 | 0.02 | | (1-178) | | | | 0 | | (1-178) |
| HG1019816 | 249 | 0.01 | | (1-249) | | | | 0 | | (1-249) |
| HG1019817 | 146 | 0.01 | | (1-146) | | | | 0 | | (1-146) |
| HG1019818 | 207 | 0 | | (1-207) | | | | 0 | | (1-207) |
| HG1019819 | 156 | 0.02 | | (1-156) | | | | 0 | | (1-156) |
| HG1019820 | 243 | 0.01 | | (1-243) | | | | 0 | | (1-243) |
| HG1019821 | 205 | 0.01 | | (1-205) | | | (5-17) | 0 | | (1-205) |
| HG1019822 | 194 | 0.24 | | (1-194) | | | | 0 | | (1-194) |
| HG1019823 | 294 | 0 | | (1-294) | | | | 0 | | (1-294) |
| HG1019824 | 128 | 0.03 | | (1-128) | | | | 0 | | (1-128) |
| HG1019825 | 106 | 0 | | (1-106) | | | | 0 | | (1-106) |
| HG1019826 | 116 | 0.02 | | (1-116) | | | | 0 | | (1-116) |
| HG1019828 | 125 | 0 | | (1-125) | | | | 0 | | (1-125) |
| HG1019829 | 152 | 0.03 | | (1-152) | | | | 0 | | (1-152) |
| HG1019830 | 218 | 0.02 | | (1-218) | | | | 0 | | (1-218) |
| HG1019831 | 231 | 0 | | (1-231) | | | | 0 | | (1-231) |
| HG1019832 | 196 | 0.06 | | (1-196) | | | | 0 | | (1-196) |
| HG1019834 | 223 | 0 | | (1-223) | | | | 0 | | (1-223) |
| HG1019835 | 443 | 0.01 | | (1-443) | | | | 0 | | (1-443) |
| HG1019836 | 331 | 0 | | (1-331) | | | | 0 | | (1-331) |
| HG1019837 | 192 | 0.48 | | (1-192) | | | | 0 | | (1-192) |
| HG1019838 | 184 | 0 | | (1-184) | | | | 0 | | (1-184) |
| HG1019839 | 209 | 0.01 | | (1-209) | | | | 0 | | (1-209) |
| HG1019840 | 171 | 0.7 | | (1-171) | | | | 0 | | (1-171) |
| HG1019841 | 352 | 0.01 | | (1-352) | | | | 0 | | (1-352) |
| HG1019842 | 328 | 0.03 | | (1-328) | | | | 0 | | (1-328) |
| HG1019843 | 211 | 0.5 | | (1-211) | | | | 0 | | (1-211) |
| HG1019845 | 232 | 0.01 | | (1-232) | | | | 0 | | (1-232) |
| HG1019846 | 968 | 0 | | (1-968) | | | | 0 | | (1-968) |
| HG1019847 | 155 | 0.84 | | (1-155) | | | | 0 | | (1-155) |
| HG1019848 | 390 | 1 | | (1-390) | | | | 0 | | (1-390) |
| HG1019849 | 268 | 0.99 | | (1-268) | (1-13)(3-15)(7-19)(5-17)(2-14) | (14-784)(16-784)(20-784)(18-784)(15-784) | (2-14) | 0 | | (1-268) |
| HG1019850 | 117 | 0.56 | (1-17) | (18-117) | (7-19)(5-17) | (20-217)(18-217) | (5-17) | 0 | | (1-117) |
| HG1019851 | 174 | 0.68 | (13-30) | (31-174) | (15-27) | (28-323) | (15-27) | 0 | | (1-174) |
| HG1019852 | 218 | 0.83 | (1-24) | (25-218) | (9-21)(11-23) | (22-413)(24-413) | (11-23) | 0 | | (1-218) |
| HG1019853 | 212 | 1 | (1-17) | (18-212) | (3-15)(4-16)(5-17) | (16-466)(17-466)(18-466) | (5-17) | 0 | | (1-212) |
| HG1019854 | 154 | 0.39 | (1-18) | (19-154) | | | | 1 | (111-133) | (1-110)(134-154) |
| HG1019855 | 720 | 0.04 | | (1-720) | | | (24-36) | 3 | (69-91)(430-452)(722-744) | (1-68)(92-429)(453-721) |
| HG1019856 | 485 | 1 | (10-33) | (34-485) | (16-28)(19-31)(20-32) | (29-485)(32-485)(33-485) | (21-33) | 0 | | (1-485) |
| HG1019857 | 261 | 0 | (21-35) | (36-261) | | | | 1 | (23-45) | (1-22)(46-261) |
| HG1019858 | 353 | 1 | (1-21) | (22-353) | (8-20)(3-15)(11-23)(6-18) | (21-353)(16-353)(24-353)(19-353) | (9-21) | 0 | | (1-353) |
| HG1019859 | 233 | 0 | (16-44) | (45-233) | | | | 1 | (35-57) | (1-34)(58-233) |
| HG1019860 | 205 | 0.99 | (1-34) | (35-205) | (17-29)(24-36)(25-37)(21-33)(18-30)(19-31) | (30-205)(37-205)(38-205)(34-205)(31-205)(32-205) | (22-34) | 1 | (7-29) | (1-6)(30-205) |
| HG1019861 | 728 | 0.96 | (1-32) | (33-728) | (15-27)(19-31) | (28-728)(32-728) | (19-31) | 1 | (7-29) | (1-6)(30-728) |
| HG1019862 | 180 | 1 | (1-24) | (25-180) | (13-25)(7-19)(10-22)(9-21) | (26-180)(20-180)(23-180)(22-180) | (12-24) | 0 | | (1-180) |
| HG1019863 | 153 | 0 | (24-49) | (50-153) | | | | 0 | | (1-153) |
| HG1019864 | 281 | 0 | | (1-281) | | | | 1 | (80-102) | (1-79)(103-281) |
| H01019865 | 155 | 0.81 | | (1-155) | | | | 0 | | (1-155) |
| HG1019866 | 97 | 1 | (1-30) | (31-97) | (12-24)(11-23)(16-28)(14-26) | (25-97)(24-97)(29-97)(27-97) | (14-26) | 1 | (7-29) | (1-6)(30-97) |
| HG1019867 | 193 | 0 | (1-34) | (35-193) | (21-33)(17-29) | (34-193)(30-193) | (17-29) | 1 | (21-43) | (1-20)(44-193) |

TABLE 3-continued

| FP ID | Predicted Protein Length | Treevote | Signal Peptide Coordinates | Mature Protein Coordinates | Alternative Signal Peptide Coordinates | Alternate Mature Protein Coordinates | Hydrophobicity Coordinates | TM | TM Coordinates | non-TM Coordinates |
|---|---|---|---|---|---|---|---|---|---|---|
| HG1019868 | 391 | 0 | | (1-391) | | | | 1 | (40-62) | (1-39)(63-391) |
| HG1019869 | 169 | 0 | (12-29) | (30-169) | (20-32) | (33-169) | (17-29) | 2 | (13-35)(118-140) | (1-12)(36-117)(141-169) |
| HG1019870 | 252 | 0.1 | (1-24) | (25-252) | (14-26)(9-21) | (27-252)(22-252) | (9-21) | 1 | (199-221) | (1-198)(222-252) |
| HG1019871 | 208 | 0 | (1-25) | (26-208) | (6-18)(7-19)(11-23) | (19-208)(20-208)(24-208) | (11-23) | 1 | (162-184) | (1-161)(185-208) |
| HG1019872 | 178 | 1 | (1-24) | (25-178) | | | (12-24) | 0 | | (1-178) |
| HG1019873 | 1207 | 0.04 | | (1-1207) | (1-13) | (14-1207) | (1-13) | 1 | (1033-1055) | (1-1032)(1056-1207) |
| HG1019874 | 206 | 0.96 | (1-25) | (26-206) | (17-29)(8-20)(15-27) | (30-206)(21-206)(28-206) | (15-27) | 1 | (7-24) | (1-6)(25-206) |
| HG1019875 | 208 | 0.8 | | (1-208) | | | | 0 | | (1-208) |
| HG1019876 | 244 | 0 | (1-31) | (32-244) | (23-35)(16-28) | (36-244)(29-244) | (16-28) | 1 | (21-43) | (1-20)(44-244) |
| HG1019877 | 211 | 1 | (1-20) | (21-211) | | (21-241) | (8-20) | 0 | | (1-211) |
| HG1019878 | 241 | 1 | (1-22) | (23-241) | (8-20) | (21-241) | (8-20) | 0 | | (1-241) |
| HG1019879 | 240 | 1 | (1-21) | (22-240) | (1-13)(8-20)(6-18)(4-16)(2-14)(3-15) | (14-240)(21-240)(19-240)(17-240)(15-240)(16-240) | (3-15) | 0 | | (1-240) |
| HG1019880 | 160 | 0 | (1-22) | (23-160) | (6-18) | (19-160) | (10-22) | 1 | (99-121) | (1-98)(122-160) |
| HG1019881 | 317 | 0 | | (1-317) | | | | 1 | (48-70) | (1-47)(71-317) |
| HG1019882 | 250 | 0.13 | (18-41) | (42-250) | | | | 1 | (28-50) | (1-27)(51-250) |
| HG1019883 | 249 | 0.16 | (1-35) | (36-249) | (19-31)(24-36)(21-33) | (32-249)(37-249)(34-249) | (21-33) | 1 | (20-42) | (1-19)(43-249) |
| HG1019884 | 254 | 0 | (24-46) | (47-254) | | | | 1 | (29-51) | (1-28)(52-254) |
| HG1019885 | 216 | 1 | (1-25) | (26-216) | (11-23)(10-22) | (24-216)(23-216) | (10-22) | 0 | | (1-216) |
| HG1019886 | 207 | 0.88 | | (1-207) | | | | 0 | | (1-207) |
| HG1019887 | 850 | 0.02 | | (1-850) | | | | 1 | (406-428) | (1-405)(429-850) |
| HG1019888 | 177 | 0 | (9-42) | (43-177) | | | | 1 | (27-49) | (1-26)(50-177) |
| HG1019889 | 129 | 1 | (1-24) | (25-129) | (10-22)(7-19)(8-20)(9-21)(11-23) | (23-129)(20-129)(21-129)(22-129)(24-129) | (11-23) | 0 | | (1-129) |
| HG1019890 | 419 | 0.99 | (1-19) | (20-419) | (3-15)(4-16)(8-20) | (16-419)(17-419)(21-419) | (8-20) | 0 | | (1-419) |
| HG1019891 | 1242 | 0 | | (1-1242) | | | | 0 | | (1-1242) |
| HG1019892 | 170 | 1 | (5-23) | (24-170) | (12-24)(14-26)(9-21) | (25-170)(27-170)(22-170) | (11-23) | 0 | | (1-170) |
| HG1019893 | 285 | 0 | | (1-285) | | | | 1 | (48-70) | (1-47)(71-285) |
| HG1019894 | 250 | 1 | (1-18) | (19-250) | (5-17)(2-14) | (18-250)(15-250) | (6-18) | 0 | | (1-250) |
| HG1019895 | 296 | 0 | | (1-296) | | | | 1 | (76-98) | (1-75)(99-296) |
| HG1019896 | 640 | 0 | | (1-640) | | | | 1 | (243-265) | (1-242)(266-640) |
| HG1019897 | 465 | 0.99 | (1-22) | (23-465) | (12-24)(11-23) | (25-465)(24-465) | (10-22) | 0 | | (1-465) |
| HG1019898 | 345 | 0.98 | (1-18) | (19-345) | (4-16)(3-15)(2-14) | (17-345)(16-345)(15-345) | (2-14) | 0 | | (1-345) |
| HG1019899 | 211 | 0.9 | (1-19) | (20-211) | | | | 0 | | (1-211) |
| HG1019900 | 252 | 1 | (10-24) | (25-252) | (17-29)(14-26)(4-16)(8-20)(11-23) | (30-252)(27-252)(17-252)(21-252)(24-252) | (11-23) | 0 | | (1-252) |
| HG1019901 | 208 | 0.81 | (11-33) | (34-208) | (25-37) | (38-208) | (25-37) | 1 | (20-42) | (1-19)(43-208) |
| HG1019902 | 370 | 0.82 | (1-17) | (18-370) | (6-18) | (19-370) | (6-18) | 0 | | (1-370) |
| HG1019903 | 352 | 1 | (1-18) | (19-352) | (7-19) | (20-352) | (6-18) | 0 | | (1-352) |
| HG1019904 | 244 | 0.99 | (1-25) | (26-244) | (15-27)(9-21)(7-19)(10-22) | (28-244)(22-244)(20-244)(23-244) | (10-22) | 0 | | (1-244) |
| HG1019905 | 115 | 0 | | (1-115) | | | | 1 | (61-83) | (1-60)(84-115) |
| HG1019906 | 282 | 0 | (20-53) | (54-282) | | | | 0 | | (1-282) |

TABLE 3-continued

| FP ID | Predicted Protein Length | Treevote | Signal Peptide Coordinates | Mature Protein Coordinates | Alternative Signal Peptide Coordinates | Alternate Mature Protein Coordinates | Hydrophobicity Coordinates | TM | TM Coordinates | non-TM Coordinates |
|---|---|---|---|---|---|---|---|---|---|---|
| HG1019907 | 988 | 0.96 | (1-24) | (25-988) | (8-20) | (21-988) | (8-20) | 0 | | (1-988) |
| HG1019908 | 98 | 0 | | (1-98) | | | | 0 | | (1-98) |
| HG1019909 | 98 | 0.06 | | (1-98) | | | | 0 | | (1-98) |
| HG1019910 | 142 | 0.42 | | (1-142) | | | | 0 | | (1-142) |

TABLE 4

| FP ID | Chemicon | confirmed in pAkt | confirmed in pERK | confirmed in pSTAT3 | SwissProt ID | WT | Assayed Clone | Representative Protein of clone | Cluster ID | Cluster Annotation |
|---|---|---|---|---|---|---|---|---|---|---|
| HG1015496 | none | RecProt/clone | RecProt/clone | RecProt/clone | LIF_HUMAN | NP_002300 | LIF1010 | LIF1010 | 186999 | leukemia inhibitory factor (cholinergic differentiation factor) immunoglobulin kappa variable 2-10 |
| HG1015498 | none | RecProt/clone | none | clone | BTC_HUMAN | NP_001720 | CLN00795087 | CLN00211466 | 183727 | betacellulin |
| HG1015527 | none | none | RecProt/clone | none | BTC_HUMAN | NP_001720 | CLN00736345 | NP_001720 | 183727 | betacellulin |
|  |  |  | none | clone | CSF3_HUMAN | NP_000750 | CLN00800080 | CLN00489695 | 216616 | colony stimulating factor 3 (granulocyte) |
| HG1015712 | none | RecProt/clone | RecProt/clone | RecProt/clone | LIF_HUMAN | NP_002300 | NP_002300_23-202 | NP_002300_23-202 | 186999 | leukemia inhibitory factor (cholinergic differentiation factor) immunoglobulin kappa variable 2-10 |
| HG1018346 | none | none | none | clone | IL6_HUMAN | NP_000591 | CLN00547801 | NP_000591 | 301353 | interleukin 6 (interferon, beta 2) |
| HG1018401 | none | RecProt/clone | RecProt/clone | RecProt/clone | LIF_HUMAN | NP_002300 | CLN00658121 | NP_002300 | 186999 | leukemia inhibitory factor (cholinergic differentiation factor) immunoglobulin kappa variable 2-10 |
| HG1019751 | none | none | RecProt/clone | none | FGF2_HUMAN | 122742 | 122742_10-155 | 122742_10-155 | 200403 | fibroblast growth factor 2 (basic) |
| HG1019754 | none | none | RecProt | none | FGF5_HUMAN | 13637763 | 13637763_4-268 | 13637763_18-268 | 204218 | fibroblast growth factor-5 precursor (FGF-5) |
| HG1019755 | none | none | RecProt | none | FGF5_HUMAN | 13637763 | 13637763_4-268 | 13637763_4-268 | 204218 | fibroblast growth factor-5 precursor (FGF-5) |
| HG1019756 | none | none | clone | clone | NA | 18573061 | CLN00837199 | 18573061_18-117 | 300718 | hypothetical protein XP_098916 |
| HG1019758 | none | none | none | none | NA | 22761542 | CLN00528140 | 22761542_24-218 | 182320 | chromosome 10 open reading frame 58 |
| HG1019759 | none | none | clone | none | EDN1_HUMAN | 298591 | CLN00529143 | 298591_18-212 | 211961 | endothelin 1 |
| HG1019760 | none | none | clone | none | EDN1_HUMAN | 298591 | CLN00529143 | 298591_53-73 | 211961 | endothelin 1 |
| HG1019761 | none | none | clone | none | EDN1_HUMAN | 298591 | CLN00529143 | 298591_53-90 | 211961 | endothelin 1 |
| HG1019769 | none | none | none | none | TPO_HUMAN | NP_000451 | CLN00886240 | NP_000451_22-353 | 306968 | thrombopoietin (myeloproliferative leukemia virus oncogene ligand, megakaryocyte growth and development factor) |
| HG1019770 | none | none | none | none | TNFA_HUMAN | NP_000585 | CLN00871329 | NP_000585_57-233 | 330470 | tumor necrosis factor (TNF superfamily, member 2) topoisomerase (DNA) III beta, 2 |

TABLE 4-continued

| FP ID | confirmed in pAkt | confirmed in pERK | confirmed in pSTAT3 | SwissProt ID | WT | Assayed Clone | Representative Protein of clone | Cluster ID | Cluster Annotation |
|---|---|---|---|---|---|---|---|---|---|
| HG1019771 | none | none | none | TNFA_HUMAN | NP_000585 | CLN00871329 | NP_000585_77-233 | 330470 | tumor necrosis factor (TNF superfamily, member 2) topoisomerase (DNA) III beta, 2 |
| HG1019773 | none | clone | none | IL6_HUMAN | NP_000591 | CLN00547801 | NP_000591_30-212 | 301353 | interleukin 6 (interferon, beta 2) |
| HG1019777 | clone | none | none | IGF2_HUMAN | NP_000603 | CLN00823293 | NP_000603_25-180 | 305535 | insulin-like growth factor 2 (somatomedin A) |
| HG1019778 | clone | none | none | IGF2_HUMAN | NP_000603 | CLN00823293 | NP_000603_25-91 | 305535 | insulin-like growth factor 2 (somatomedin A) |
| HG1019779 | RecProt/clone | none | none | IGF1B_HUMAN | 32992 | NP_000609_49-118 | NP_000609_49-118 | 181818 | insulin-like growth factor 1 (somatomedin C) |
| HG1019782 | none | none | none | CSF3_HUMAN | NP_000750 | NP_000750_30-207 | NP_000750_30-207 | 216616 | colony stimulating factor 3 (granulocyte) |
| HG1019783 | RecProt/clone | none | none | FGF1_HUMAN | NP_000791 | NP_000791_16-155 | NP_000791_16-155 | 212275 | fibroblast growth factor 1 (acidic) |
| HG1019790 | RecProt | none | none | EREG_HUMAN | NP_001423 | NP_001423_60-108 | NP_001423_60-108 | 196083 | epiregulin precursor |
| HG1019791 | RecProt | none | none | EREG_HUMAN | NP_001423 | NP_001423_63-108 | NP_001423_63-108 | 196083 | epiregulin precursor |
| HG1019794 | RecProt/clone | none | none | BTC_HUMAN | NP_001720 | NP_001720_32-111 | NP_001720_32-111 | 183727 | betacellulin |
| HG1019795 | none | none | none | HBEGF_HUMAN | NP_001936 | CLN00870460 | NP_001936_20-160 | 195302 | heparin-binding EGF-like growth factor |
| HG1019796 | none | none | none | HBEGF_HUMAN | NP_001936 | CLN00870460 | NP_001936_63-148 | 195302 | heparin-binding EGF-like growth factor |
| HG1019797 | clone | none | none | EDN2_HUMAN | NP_001947 | CLN00547043 | NP_001947_18-212 | 185682 | endothelin 2 |
| HG1019798 | clone | none | none | EDN2_HUMAN | NP_001947 | CLN00547043 | NP_001947_49-69 | 185682 | endothelin 2 |
| HG1019801 | RecProt | none | none | FGF4_HUMAN | NP_001998 | NP_001998_31-206 | NP_001998_31-206 | 303930 | fibroblast growth factor-4 precursor (FGF-4) |
| HG1019802 | RecProt | none | none | FGF4_HUMAN | NP_001998 | NP_001998_54-206 | NP_001998_54-206 | 303930 | fibroblast growth factor-4 precursor (FGF-4) |
| HG1019803 | RecProt | none | none | FGF4_HUMAN | NP_001998 | NP_001998_57-206 | NP_001998_57-206 | 303930 | fibroblast growth factor-4 precursor (FGF-4) |
| HG1019804 | RecProt | none | none | FGF4_HUMAN | NP_001998 | NP_001998_68-206 | NP_001998_68-206 | 303930 | fibroblast growth factor-4 precursor (FGF-4) |
| HG1019805 | RecProt | none | none | FGF4_HUMAN | NP_001998 | NP_001998_71-206 | NP_001998_71-206 | 303930 | fibroblast growth factor-4 precursor (FGF-4) |
| HG1019806 | RecProt/clone | none | none | FGF9_HUMAN | NP_002001 | CLN00528241 | NP_002001_4-208 | 199622 | fibroblast growth factor 9 (glia-activating factor) |

TABLE 4-continued

| FP ID | confirmed in pAkt | confirmed in pERK | confirmed in pSTAT3 | SwissProt ID | WT | Assayed Clone | Representative Protein of clone | Cluster ID | Cluster Annotation |
|---|---|---|---|---|---|---|---|---|---|
| HG1019809 | clone | none | none | PDGFB_HUMAN | NP_002599 | CLN00528015 | NP_002599_82-190 | 302092 | platelet-derived growth factor beta polypeptide (simian sarcoma viral (v-sis) oncogene homolog) |
| HG1019811 | none | none | none | TGFA_HUMAN | NP_003227 | CLN00870219 | NP_003227_1-98 | 301061 | transforming growth factor, alpha |
| HG1019812 | none | none | none | TGFA_HUMAN | NP_003227 | CLN00870219 | NP_003227_24-98 | 301061 | transforming growth factor, alpha |
| HG1019813 | none | none | none | TGFA_HUMAN | NP_003227 | CLN00870219 | NP_003227_40-89 | 301061 | transforming growth factor, alpha |
| HG1019822 | none | RecProt | none | FGF17_HUMAN | NP_003858 | NP_003858_23-216 | NP_003858_23-216 | 212528 | fibroblast growth factor-17 precursor (FGF-17) |
| HG1019825 | clone | clone | clone | TFF2_HUMAN | NP_005414 | CLN00658140 | NP_005414_24-129 | 185354 | trefoil factor 2 (spasmolytic protein 1) |
| HG1019826 | clone | clone | none | VEGFC_HUMAN | NP_005420 | CLN00542783 | NP_005420_112-227 | 205141 | vascular endothelial growth factor C |
| HG1019827 | none | none | none | NEUT_HUMAN | NP_006174 | CLN00583185 | NP_006174_151-163 | 199873 | neurotensin |
| HG1019828 | none | none | none | NEUT_HUMAN | NP_006174 | CLN00583185 | NP_006174_24-148 | 199873 | neurotensin |
| HG1019831 | none | none | none | KLK11_HUMAN | NP_006844 | CLN00823025 | NP_006844_20-250 | 213251 | kallikrein 11 |
| HG1019833 | RecProt | RecProt | none | NRG1_HUMAN | NP_039258 | NP_039258_177-241 | NP_039258_177-241 | 306450 | neuregulin-1 |
| HG1019834 | RecProt | RecProt | none | NRG1_HUMAN | NP_039258 | NP_039258_19-241 | NP_039258_19-241 | 306450 | neuregulin-1 |
| HG1019835 | none | none | none | NA | NP_055282 | CLN00554545 | NP_055282_23-465 | 184982 | sushi-repeat-containing protein, X-linked 2 |
| HG1019836 | clone | none | none | NA | NP_057289 | CLN00795285 | NP_057289_15-345 | 217307 | platelet derived growth factor C |
| HG1019837 | none | none | none | FGF20_HUMAN | NP_062825 | CLN00878867 | NP_062825_20-211 | 213313 | fibroblast growth factor 20 |
| HG1019838 | RecProt/clone | RecProt/clone | none | ONCM_HUMAN | NP_065391 | NP_065391_26-209 | NP_065391_26_209 | 206932 | oncostatin M |
| HG1019839 | RecProt/clone | RecProt/clone | none | ONCM_HUMAN | NP_065391 | NP_065391_26-234 | NP_065391_26_234 | 206932 | oncostatin M |
| HG1019840 | none | none | none | FGF6_HUMAN | NP_066276 | CLN00878854 | NP_066276_38-208 | 193768 | fibroblast growth factor 6 |
| HG1019841 | clone | clone | none | NA | NP_079484 | CLN00529196 | NP_079484_19-370 | 196403 | platelet derived growth factor D |
| HG1019843 | none | none | none | FGF8_HUMAN | NP_149354 | CLN00878877 | NP_149353_23-233 | 206766 | fibroblast growth factor 8 (androgen-induced) similar to prohibitin (B-cell receptor associated protein 32)(BAP 32) |
| HG1019845 | none | none | none | KLK11_HUMAN | NP_006844 | CLN00623004 | NP_659196_51-282 | 213251 | kallikrein 11 |
| HG1019846 | none | none | none | NA | NP_766638 | CLN00582867 | NP_766638_21-988 | 301463 | signal peptide, CUB domain, EGF-like 1 |

TABLE 4-continued

| FP ID | confirmed in pAkt | confirmed in pERK | confirmed in pSTAT3 | SwissProt ID | WT | Assayed Clone | Representative Protein of clone | Cluster ID | Cluster Annotation |
|---|---|---|---|---|---|---|---|---|---|
| HG1019847 | none | RecProt/clone | none | FGF2_HUMAN | 122742 | CLN00542792 | 122742 | 200403 | fibroblast growth factor 2 (basic) |
| HG1019849 | none | RecProt | none | FGF5_HUMAN | 13637763 | 13637763 | 13637763 | 204218 | fibroblast growth factor-5 precursor (FGF-5) |
| HG1019850 | none | clone | clone | NA | 18573061 | CLN00837199 | 18573061 | 300718 | hypothetical protein XP_098916 |
| HG1019852 | none | none | none | NA | 22761542 | CLN00528140 | 22761542 | 182320 | chromosome 10 open reading frame 58 |
| HG1019853 | none | clone | none | EDN1_HUMAN | 298591 | CLN00529143 | 298591 | 211961 | endothelin 1 |
| HG1019858 | none | none | none | TPO_HUMAN | NP_000451 | CLN00886240 | NP_000451 | 306968 | thrombopoietin (myeloproliferative leukemia virus oncogene ligand, megakaryocyte growth and development factor) |
| HG1019859 | none | none | none | TNFA_HUMAN | NP_000585 | CLN00871329 | NP_000585 | 330470 | tumor necrosis factor (TNF superfamily, member 2) topoisomerase (DNA) III beta, 2 |
| HG1019862 | clone | none | none | IGF2_HUMAN | NP_000603 | CLN00823293 | NP_000603 | 305535 | insulin-like growth factor 2 (somatomedin A) |
| HG1019863 | RecProt/clone | none | none | IGF1B_HUMAN | 32992 | CLN00547277 | NP_000609 | 181818 | insulin-like growth factor 1 (somatomedin C) |
| HG1019865 | none | RecProt/clone | none | FGF1_HUMAN | NP_000791 | CLN00554547 | NP_000791 | 212275 | fibroblast growth factor 1 (acidic) |
| HG1019869 | none | RecProt | none | EREG_HUMAN | NP_001423 | NP_001423 | NP_001423 | 196083 | epiregulin precursor |
| HG1019871 | none | none | none | HBEGF_HUMAN | NP_001936 | CLN00870460 | NP_001936 | 195302 | heparin-binding EGF-like growth factor |
| HG1019871 | none | none | none | HBEGF_HUMAN | NP_001936 | CLN00870460 | NP_001936 | 195302 | heparin-binding EGF-like growth factor |
| HG1019872 | none | clone | none | EDN2_HUMAN | NP_001947 | CLN00547043 | NP_001947 | 185682 | endothelin 2 |
| HG1019874 | none | RecProt | none | FGF4_HUMAN | NP_001998 | NP_001998 | NP_001998 | 303930 | fibroblast growth factor-4 precursor (FGF-4) |
| HG1019875 | none | RecProt/clone | none | FGF9_HUMAN | NP_002001 | CLN00528241 | NP_002001 | 199622 | fibroblast growth factor 9 (glia-activating factor) |
| HG1019878 | clone | none | none | PDGFB_HUMAN | NP_002599 | CLN00528015 | NP_002599 | 302092 | platelet-derived growth factor beta polypeptide (simian sarcoma viral (v-sis) oncogene homolog) |
| HG1019880 | none | none | none | TGFA_HUMAN | NP_003227 | CLN00870219 | NP_003227 | 301061 | transforming growth factor, alpha |

TABLE 4-continued

| FP ID | confirmed in pAkt | confirmed in pERK | confirmed in pSTAT3 | SwissProt ID | WT | Assayed Clone | Representative Protein of clone | Cluster ID | Cluster Annotation |
|---|---|---|---|---|---|---|---|---|---|
| HG1019885 | none | RecProt | none | FGF17_HUMAN | NP_003858 | NP_003858 | NP_003858 | 212528 | fibroblast growth factor-17 precursor (FGF-17) |
| HG1019886 | none | RecProt | none | FGF16_HUMAN | NP_003859 | NP_003859 | NP_003859 | 208481 | fibroblast growth factor-16 (FGF-16) |
| HG1019889 | clone | clone | clone | TFF2_HUMAN | NP_005414 | CLN00658140 | NP_005414 | 185354 | trefoil factor 2 (spasmolytic protein 1) |
| HG1019890 | clone | clone | none | VEGFC_HUMAN | NP_005420 | CLN00542783 | NP_005420 | 205141 | vascular endothelial growth factor C |
| HG1019891 | none | none | none | IRS1_HUMAN | NP_005535 | CLN00543000 | NP_005535 | 199067 | insulin receptor substrate 1 |
| HG1019891 | none | none | none | IRS1_HUMAN | NP_005535 | CLN00543028 | NP_005535 | 199067 | insulin receptor substrate 1 |
| HG1019892 | none | none | none | NEUT_HUMAN | NP_006174 | CLN00583185 | NP_006174 | 199873 | neurotensin |
| HG1019894 | none | none | none | KLK11_HUMAN | NP_006844 | CLN00823025 | NP_006844 | 213251 | kallikrein 11 |
| HG1019896 | RecProt | RecProt | none | NRG1_HUMAN | NP_039258 | NP_039258 | NP_039258 | 306450 | neuregulin-1 |
| HG1019897 | none | none | none | NA | NP_055282 | CLN00554545 | NP_055282 | 184982 | sushi-repeat-containing protein, X-linked 2 |
| HG1019898 | clone | none | none | NA | NP_057289 | CLN00795285 | NP_057289 | 217307 | platelet derived growth factor C |
| HG1019899 | none | none | none | FGF20_HUMAN | NP_062825 | CLN00878867 | NP_062825 | 213313 | fibroblast growth factor 20 |
| HG1019900 | RecProt/clone | RecProt/clone | none | ONCM_HUMAN | NP_065391 | CLN00529286 | NP_065391 | 206932 | oncostatin M |
| HG1019901 | none | none | none | FGF6_HUMAN | NP_066276 | CLN00878854 | NP_066276 | 193768 | fibroblast growth factor 6 |
| HG1019902 | clone | clone | none | NA | NP_079484 | CLN00529196 | NP_079484 | 196403 | platelet derived growth factor D |
| HG1019904 | none | none | none | FGF8_HUMAN | NP_149354 | CLN00878877 | NP_149353 | 206766 | fibroblast growth factor 8 (androgen-induced; similar to prohibitin (B-cell receptor associated protein 32)(BAP 32) |
| HG1019906 | none | none | none | KLK11_HUMAN | NP_006844 | CLN00623004 | NP_659196 | 213251 | kallikrein 11 |
| HG1019907 | none | clone | none | NA | NP_766638 | CLN00582867 | NP_766638 | 301463 | signal peptide, CUB domain, EGF-like 1 |
| HG1019908 | clone | clone | none | BTC_HUMAN | NP_001720 | CLN00795087 | CLN00211466_32-129 | 183727 | betacellulin |
| HG1019910 | none | clone | none | CSF3_HUMAN | NP_000750 | CLN00800080 | CLN00489695_23-164 | 216616 | colony stimulating factor 3 (granulocyte) |
| R&D | RecProt/clone | none | none | FGF9_HUMAN | NP_002001 | 273-F9-025 | 273-F9-025 | 199622 | fibroblast growth factor 9 (glia-activating factor) |
| R&D | RecProt/clone | none | none | ONCM_HUMAN | NP_065391 | 295-OM-010 | 295-OM-010 | 206932 | oncostatin M |
| R&D | RecProt/clone | none | none | FGF2_HUMAN | 122742 | 234-FSE-025 | 234-FSE-025 | 200403 | fibroblast growth factor 2 (basic) |
| R&D | RecProt/clone | none | none | IGF1B_HUMAN | 32992 | 291-G1-050 | 291-G1-050 | 181818 | insulin-like growth factor 1 (somatomedin C) |
| R&D | RecProt/clone | none | none | FGF1_HUMAN | NP_000791 | 232-FA-025 | 232-FA-025 | 212275 | fibroblast growth factor 1 (acidic) |
| R&D | RecProt/clone | none | none | BTC_HUMAN | NP_001720 | 261-CE-050 | 261-CE-050 | 183727 | betacellulin |

TABLE 4-continued

| FP ID | confirmed in pAkt | confirmed in pERK | confirmed in pSTAT3 | SwissProt ID | WT | Assayed Clone | Representative Protein of clone | Cluster ID | Cluster Annotation |
|---|---|---|---|---|---|---|---|---|---|
| R&D | none | none | none | CSF3_HUMAN | NP_000750 | 214-CS-025 | 214-CS-025 | 216616 | colony stimulating factor 3 (granulocyte) |
| R&D | none | RecProt | none | FGF16_HUMAN | NP_003859 | 1212-FG-025 | 1212-FG-025 | 208481 | fibroblast growth factor-16 (FGF-16) |
| R&D | none | RecProt | none | FGF17_HUMAN | NP_003858 | 319-FG-025 | 319-FG-025 | 212528 | fibroblast growth factor-17 precursor (FGF-17) |
| R&D | none | RecProt | none | FGF4_HUMAN | NP_001998 | 235-F4-025 | 235-F4-025 | 303930 | fibroblast growth factor-4 precursor (FGF-4) |
| R&D | none | RecProt | none | FGF5_HUMAN | 13637763 | 237-F5-050 | 237-F5-050 | 204218 | fibroblast growth factor-5 precursor (FGF-5) |
| R&D | RecProt | RecProt | none | NRG1_HUMAN | NP_039258 | 296-HR-050 | 296-HR-050 | 306450 | neuregulin-1 |
| R&D | none | RecProt | none | EREG_HUMAN | NP_001423 | 1195-EP-025 | 1195-EP-025 | 196083 | epiregulin precursor |
| R&D | none | none | none | FGF6_HUMAN | NP_066276 | 238-F6-025 | 238-F6-025 | 193768 | fibroblast growth factor 6 |
| Short | none | none | none | NEUT_HUMAN | NP_006174 | CLN00583185 | NP_006174_144-148 | 199873 | neurotensin |
| Short | none | none | none | NEUT_HUMAN | NP_149354 | CLN00583185 | NP_006174_166-170 | 199873 | neurotensin |
| Sigma | none | none | none | NA | NP_149354 | F1802 | F1802 | NA | fibroblast growth factor 8c, mouse |

TABLE 5

| Expressed Protein | Clone | Representative Annotation | Sigma from Median | Activity Percentage | Well Position | Read Category |
|---|---|---|---|---|---|---|
| | | clones from two transfections | | | | |
| PRN00000538 | CLN00528015 | platelet-derived growth factor beta polypeptide (simian sarcoma viral (v-sis) oncogene homolog) | 3.4 | 25 | C3 | pAkt |
| PRN00000538 | CLN00528015 | platelet-derived growth factor beta polypeptide (simian sarcoma viral (v-sis) oncogene homolog) | 4.3 | 34 | C3 | pAkt |
| PRN00000538 | CLN00528015 | platelet-derived growth factor beta polypeptide (simian sarcoma viral (v-sis) oncogene homolog) | 7.3 | 32 | C3 | pAkt |
| PRN00000538 | CLN00528015 | platelet-derived growth factor beta polypeptide (simian sarcoma viral (v-sis) oncogene homolog) | 5.7 | 18 | C3 | pAkt |
| PRN00000538 | CLN00528015 | platelet-derived growth factor beta polypeptide (simian sarcoma viral (v-sis) oncogene homolog) | 2.9 | 25 | C3 | pERK |
| PRN00000538 | CLN00528015 | platelet-derived growth factor beta polypeptide (simian sarcoma viral (v-sis) oncogene homolog) | 5.3 | 42 | C3 | pERK |
| PRN00000590 | CLN00528241 | fibroblast growth factor 9 (glia-activating factor) | 3.8 | 24 | A7 | pERK |
| PRN00000590 | CLN00528241 | fibroblast growth factor 9 (glia-activating factor) | 4.7 | 26 | A7 | pERK |
| PRN00000590 | CLN00528241 | fibroblast growth factor 9 (glia-activating factor) | 4.0 | 24 | A9 | pERK |
| PRN00000590 | CLN00528241 | fibroblast growth factor 9 (glia-activating factor) | 9.2 | 46 | A9 | pERK |
| PRN00000745 | CLN00529143 | endothelin 1 | 15.2 | 153 | H11 | pERK |
| PRN00000745 | CLN00529143 | endothelin 1 | 10.7 | 88 | H11 | pERK |
| PRN00000745 | CLN00529143 | endothelin 1 | 8.5 | 73 | G11 | pERK |
| PRN00000745 | CLN00529143 | endothelin 1 | 9.7 | 77 | G11 | pERK |
| PRN00000732 | CLN00529196 | platelet derived growth factor D | 3.8 | 28 | G5 | pAkt |
| PRN00000732 | CLN00529196 | platelet derived growth factor D | 2.4 | 24 | G5 | pERK |
| PRN00000732 | CLN00529196 | platelet derived growth factor D | 4.7 | 37 | G5 | pAkt |
| PRN00000732 | CLN00529196 | platelet derived growth factor D | 2.5 | 21 | G5 | pERK |
| PRN00000732 | CLN00529196 | platelet derived growth factor D | 9.3 | 41 | G5 | pAkt |
| PRN00000732 | CLN00529196 | platelet derived growth factor D | 5.1 | 44 | G5 | pERK |
| PRN00000732 | CLN00529196 | platelet derived growth factor D | 3.4 | 27 | G5 | pERK |
| PRN00000732 | CLN00529196 | platelet derived growth factor D | 5.0 | 16 | G5 | pAkt |
| PRN00000736 | CLN00529286 | oncostatin M | 3.8 | 38 | F7 | pERK |
| PRN00000736 | CLN00529286 | oncostatin M | 4.3 | 32 | F7 | pAkt |
| PRN00000736 | CLN00529286 | oncostatin M | 110.2 | 76 | F7 | pStat3 |
| PRN00000736 | CLN00529286 | oncostatin M | 215.9 | 79 | F7 | pStat3 |
| PRN00000736 | CLN00529286 | oncostatin M | 5.0 | 39 | F7 | pAkt |
| PRN00000736 | CLN00529286 | oncostatin M | 5.4 | 44 | F7 | pERK |
| PRN00000736 | CLN00529286 | oncostatin M | 7.5 | 64 | F7 | pERK |
| PRN00000736 | CLN00529286 | oncostatin M | 5.2 | 23 | F7 | pAkt |
| PRN00000736 | CLN00529286 | oncostatin M | 284.7 | 106 | F7 | pStat3 |
| PRN00000736 | CLN00529286 | oncostatin M | 228.4 | 99 | F7 | pStat3 |
| PRN00000736 | CLN00529286 | oncostatin M | 2.5 | 8 | F7 | pAkt |
| PRN00000736 | CLN00529286 | oncostatin M | 8.4 | 67 | F7 | pERK |
| PRN00000835 | CLN00542783 | vascular endothelial growth factor C | 5.5 | 27 | D9 | pAkt |
| PRN00000835 | CLN00542783 | vascular endothelial growth factor C | 3.0 | 20 | D9 | pERK |
| PRN00000835 | CLN00542783 | vascular endothelial growth factor C | 4.3 | 23 | D9 | pERK |
| PRN00000835 | CLN00542783 | vascular endothelial growth factor C | 5.2 | 50 | D9 | pAkt |
| PRN00000835 | CLN00542783 | vascular endothelial growth factor C | 4.6 | 30 | D9 | pERK |
| PRN00000835 | CLN00542783 | vascular endothelial growth factor C | 6.7 | 21 | D9 | pAkt |
| PRN00000835 | CLN00542783 | vascular endothelial growth factor C | 13.4 | 78 | D9 | pAkt |
| PRN00000835 | CLN00542783 | vascular endothelial growth factor C | 7.4 | 44 | D9 | pERK |
| PRN00000816 | CLN00542792 | fibroblast growth factor 2 (basic) | 2.9 | 19 | D10 | pERK |
| PRN00000816 | CLN00542792 | fibroblast growth factor 2 (basic) | 6.4 | 2 | D10 | pStat3 |
| PRN00000816 | CLN00542792 | fibroblast growth factor 2 (basic) | 4.1 | 23 | D10 | pERK |
| PRN00000816 | CLN00542792 | fibroblast growth factor 2 (basic) | 3.6 | 1 | D10 | pStat3 |
| PRN00000816 | CLN00542792 | fibroblast growth factor 2 (basic) | 2.0 | 12 | A10 | pERK |
| PRN00000816 | CLN00542792 | fibroblast growth factor 2 (basic) | 4.1 | 2 | A10 | pStat3 |
| PRN00000816 | CLN00542792 | fibroblast growth factor 2 (basic) | 4.2 | 1 | A10 | pStat3 |
| PRN00000816 | CLN00542792 | fibroblast growth factor 2 (basic) | 5.3 | 26 | A10 | pERK |
| PRN00000897 | CLN00547043 | endothelin 2 | 11.9 | 162 | H6 | pERK |
| PRN00000897 | CLN00547043 | endothelin 2 | 14.9 | | H6 | pERK |
| PRN00000897 | CLN00547043 | endothelin 2 | 11.0 | | H6 | pERK |
| PRN00000897 | CLN00547043 | endothelin 2 | 12.0 | 98 | H6 | pERK |
| PRN00001182 | CLN00547277 | insulin-like growth factor 1 (somatomedin C) | 3.7 | 37 | H4 | pERK |
| PRN00001182 | CLN00547277 | insulin-like growth factor 1 (somatomedin C) | 18.4 | 137 | H4 | pAkt |
| PRN00001182 | CLN00547277 | insulin-like growth factor 1 (somatomedin C) | 7.9 | 62 | H4 | pAkt |
| PRN00001182 | CLN00547277 | insulin-like growth factor 1 (somatomedin C) | 3.0 | 25 | H4 | pERK |
| PRN00001182 | CLN00547277 | insulin-like growth factor 1 (somatomedin C) | 16.1 | 78 | H4 | pAkt |
| PRN00001182 | CLN00547277 | insulin-like growth factor 1 (somatomedin C) | 4.9 | 33 | H4 | pERK |
| PRN00001182 | CLN00547277 | insulin-like growth factor 1 (somatomedin C) | 5.6 | 54 | H4 | pAkt |
| PRN00001182 | CLN00547277 | insulin-like growth factor 1 (somatomedin C) | 2.9 | 16 | H4 | pERK |
| PRN00001887 | CLN00547801 | interleukin 6 (interferon, beta 2) | 49.9 | 21 | B3 | pStat3 |
| PRN00001887 | CLN00547801 | interleukin 6 (interferon, beta 2) | 40.3 | 15 | B3 | pStat3 |
| PRN00001887 | CLN00547801 | interleukin 6 (interferon, beta 2) | 46.8 | 24 | E4 | pStat3 |
| PRN00001887 | CLN00547801 | interleukin 6 (interferon, beta 2) | 58.5 | 26 | E4 | pStat3 |
| PRN00002737 | CLN00554547 | fibroblast growth factor 1 (acidic) | 7.7 | 57 | G3 | pERK |
| PRN00002737 | CLN00554547 | fibroblast growth factor 1 (acidic) | 5.5 | 2 | G3 | pStat3 |

TABLE 5-continued

| Expressed Protein | Clone | Representative Annotation | Sigma from Median | Activity Percentage | Well Position | Read Category |
|---|---|---|---|---|---|---|
| PRN00002737 | CLN00554547 | fibroblast growth factor 1 (acidic) | 5.8 | 52 | G3 | pERK |
| PRN00002737 | CLN00554547 | fibroblast growth factor 1 (acidic) | 4.6 | 2 | G3 | pStat3 |
| PRN00002737 | CLN00554547 | fibroblast growth factor 1 (acidic) | 6.7 | 50 | D2 | pERK |
| PRN00002737 | CLN00554547 | fibroblast growth factor 1 (acidic) | 6.5 | 3 | D2 | pStat3 |
| PRN00002737 | CLN00554547 | fibroblast growth factor 1 (acidic) | 5.8 | 43 | D2 | pERK |
| PRN00002737 | CLN00554547 | fibroblast growth factor 1 (acidic) | 6.6 | 3 | D2 | pStat3 |
| PRN00002518 | CLN00658121 | leukemia inhibitory factor (cholinergic differentiation factor) | 9.5 | 37 | H2 | pAkt |
| PRN00002518 | CLN00658121 | leukemia inhibitory factor (cholinergic differentiation factor) | 14.3 | 64 | H2 | pERK |
| PRN00002518 | CLN00658121 | leukemia inhibitory factor (cholinergic differentiation factor) | 220.6 | 92 | H2 | pStat3 |
| PRN00002518 | CLN00658121 | leukemia inhibitory factor (cholinergic differentiation factor) | 9.2 | 68 | H2 | pERK |
| PRN00002518 | CLN00658121 | leukemia inhibitory factor (cholinergic differentiation factor) | 216.9 | 102 | H2 | pStat3 |
| PRN00002518 | CLN00658121 | leukemia inhibitory factor (cholinergic differentiation factor) | 6.4 | 41 | H2 | pAkt |
| PRN00002518 | CLN00658121 | leukemia inhibitory factor (cholinergic differentiation factor) | 6.0 | 35 | H2 | pAkt |
| PRN00002518 | CLN00658121 | leukemia inhibitory factor (cholinergic differentiation factor) | 12.8 | 94 | H2 | pERK |
| PRN00002518 | CLN00658121 | leukemia inhibitory factor (cholinergic differentiation factor) | 27.5 | 101 | H2 | pStat3 |
| PRN00002518 | CLN00658121 | leukemia inhibitory factor (cholinergic differentiation factor) | 31.3 | 105 | H2 | pStat3 |
| PRN00002518 | CLN00658121 | leukemia inhibitory factor (cholinergic differentiation factor) | 10.8 | 74 | H2 | pERK |
| PRN00002518 | CLN00658121 | leukemia inhibitory factor (cholinergic differentiation factor) | 2.3 | 20 | H2 | pAkt |
| PRN00002517 | CLN00658140 | trefoil factor 2 (spasmolytic protein 1) | 3.6 | 16 | H3 | pERK |
| PRN00002517 | CLN00658140 | trefoil factor 2 (spasmolytic protein 1) | 206.4 | 86 | H3 | pStat3 |
| PRN00002517 | CLN00658140 | trefoil factor 2 (spasmolytic protein 1) | 2.4 | 18 | H3 | pERK |
| PRN00002517 | CLN00658140 | trefoil factor 2 (spasmolytic protein 1) | 204.8 | 96 | H3 | pStat3 |
| PRN00002517 | CLN00658140 | trefoil factor 2 (spasmolytic protein 1) | 25.8 | 95 | A4 | pStat3 |
| PRN00002517 | CLN00658140 | trefoil factor 2 (spasmolytic protein 1) | 3.9 | 29 | A4 | pERK |
| PRN00002517 | CLN00658140 | trefoil factor 2 (spasmolytic protein 1) | 27.8 | 93 | A4 | pStat3 |
| PRN00002517 | CLN00658140 | trefoil factor 2 (spasmolytic protein 1) | 2.8 | 19 | A4 | pERK |
| PRN00002007 | CLN00736345 | betacellulin | 15.7 | 116 | F3 | pERK |
| PRN00002007 | CLN00736345 | betacellulin | 14.5 | 61 | F3 | pAkt |
| PRN00002007 | CLN00736345 | betacellulin | 15.1 | 137 | F3 | pERK |
| PRN00002007 | CLN00736345 | betacellulin | 16.4 | 73 | F3 | pAkt |
| PRN00002007 | CLN00736345 | betacellulin | 12.7 | 95 | C2 | pERK |
| PRN00002007 | CLN00736345 | betacellulin | 20.0 | 70 | C2 | pAkt |
| PRN00002007 | CLN00736345 | betacellulin | 15.2 | 112 | C2 | pERK |
| PRN00002007 | CLN00736345 | betacellulin | 19.7 | 86 | C2 | pAkt |
| PRN00002685 | CLN00795285 | platelet derived growth factor C | 2.6 | 11 | E10 | pAkt |
| PRN00002685 | CLN00795285 | platelet derived growth factor C | 4.2 | 19 | E10 | pAkt |
| PRN00002685 | CLN00795285 | platelet derived growth factor C | 2.5 | 9 | C10 | pAkt |
| PRN00002685 | CLN00795285 | platelet derived growth factor C | 4.4 | 19 | C10 | pAkt |
| PRN00002685 | CLN00795285 | platelet derived growth factor C | 2.6 | 20 | C10 | pERK |
| PRN00002685 | CLN00795285 | platelet derived growth factor C | 7.6 | 56 | C10 | pERK |
| PRN00002516 | CLN00800080 | Splice Variant CLN00489695 (CSF3) | 2.6 | 19 | G2 | pERK |
| PRN00002516 | CLN00800080 | Splice Variant CLN00489695 | 2.6 | 9 | G2 | pStat3 |
| PRN00002516 | CLN00800080 | Splice Variant CLN00489695 | 3.1 | 21 | G2 | pERK |
| PRN00002516 | CLN00800080 | Splice Variant CLN00489695 | 2.3 | 8 | G2 | pStat3 |
| PRN00002766 | CLN00823293 | insulin-like growth factor 2 (somatomedin A) | 16.8 | 100 | E5 | pAkt |
| PRN00002766 | CLN00823293 | insulin-like growth factor 2 (somatomedin A) | 16.3 | 76 | E5 | pAkt |
| PRN00002766 | CLN00823293 | insulin-like growth factor 2 (somatomedin A) | 21.6 | 73 | F5 | pAkt |
| PRN00002766 | CLN00823293 | insulin-like growth factor 2 (somatomedin A) | 15.9 | 80 | F5 | pAkt |
| PRN00004262 | CLN00870219 | shed_construct of TGF-alpha | 6.4 | 39 | D10 | pERK |
| PRN00004262 | CLN00870219 | shed_construct of TGF-alpha | 8.8 | 42 | D10 | pERK |
| PRN00004262 | CLN00870219 | shed_construct of TGF-alpha | 7.0 | 56 | D10 | pERK |
| PRN00004262 | CLN00870219 | shed_construct of TGF-alpha | 7.4 | 48 | D10 | pERK |
| PRN00004248 | CLN00870460 | shed_construct of HB-EGF | 4.1 | 13 | C5 | pAkt |
| PRN00004248 | CLN00870460 | shed_construct of HB-EGF | 3.4 | 10 | C5 | pAkt |
| PRN00004248 | CLN00870460 | shed_construct of HB-EGF | 3.0 | 9 | C5 | pAkt |
| PRN00004248 | CLN00870460 | shed_construct of HB-EGF | 2.7 | 9 | C5 | pAkt |
| PRN00004319 | CLN00871329 | shed_construct of TNF-alpha | 5.1 | 26 | C2 | pERK |
| PRN00004319 | CLN00871329 | shed_construct of TNF-alpha | 6.0 | 27 | C2 | pERK |
| PRN00004319 | CLN00871329 | shed_construct of TNF-alpha | 4.1 | 1 | C2 | pStat3 |
| PRN00004319 | CLN00871329 | shed_construct of TNF-alpha | 5.1 | 2 | C2 | pStat3 |
| PRN00004319 | CLN00871329 | shed_construct of TNF-alpha | 3.7 | 1 | C2 | pStat3 |
| PRN00004319 | CLN00871329 | shed_construct of TNF-alpha | 3.7 | 1 | C2 | pStat3 |
| PRN00004452 | CLN00878752 | fibroblast growth factor 16 | 6.2 | 37 | C8 | pERK |
| PRN00004452 | CLN00878752 | fibroblast growth factor 16 | 3.4 | 23 | C8 | pERK |
| PRN00004452 | CLN00878752 | fibroblast growth factor 16 | 3.8 | 37 | C8 | pERK |
| PRN00004452 | CLN00878752 | fibroblast growth factor 16 | 3.4 | 34 | C8 | pERK |
| PRN00004433 | CLN00878854 | fibroblast growth factor 6 | 3.6 | 21 | A10 | pERK |
| PRN00004433 | CLN00878854 | fibroblast growth factor 6 | 2.4 | 16 | A10 | pERK |
| PRN00004433 | CLN00878854 | fibroblast growth factor 6 | 4.4 | 1 | A10 | pStat3 |
| PRN00004433 | CLN00878854 | fibroblast growth factor 6 | 3.1 | 1 | A10 | pStat3 |
| PRN00004433 | CLN00878854 | fibroblast growth factor 6 | 3.7 | 1 | A10 | pStat3 |
| PRN00004433 | CLN00878854 | fibroblast growth factor 6 | 2.5 | 1 | A10 | pStat3 |
| PRN00004298 | CLN00878867 | fibroblast growth factor 20 | 4.5 | 23 | H10 | pERK |
| PRN00004298 | CLN00878867 | fibroblast growth factor 20 | 3.0 | 14 | H10 | pERK |
| PRN00004298 | CLN00878867 | fibroblast growth factor 20 | 3.4 | 37 | H10 | pERK |
| PRN00004298 | CLN00878867 | fibroblast growth factor 20 | 4.2 | 39 | H10 | pERK |

TABLE 5-continued

| Expressed Protein | Clone | Representative Annotation | Sigma from Median | Activity Percentage | Well Position | Read Category |
|---|---|---|---|---|---|---|
| PRN00004299 | CLN00878877 | fibroblast growth factor 8 (androgen-induced) | 7.5 | 2 | H11 | pStat3 |
| PRN00004299 | CLN00878877 | fibroblast growth factor 8 (androgen-induced) | 10.6 | 54 | H11 | pERK |
| PRN00004299 | CLN00878877 | fibroblast growth factor 8 (androgen-induced) | 3.3 | 15 | H11 | pERK |
| PRN00004299 | CLN00878877 | fibroblast growth factor 8 (androgen-induced) | 2.1 | 1 | H11 | pStat3 |
| PRN00004299 | CLN00878877 | fibroblast growth factor 8 (androgen-induced) | 5.1 | 56 | H11 | pERK |
| PRN00004299 | CLN00878877 | fibroblast growth factor 8 (androgen-induced) | 4.6 | 2 | H11 | pStat3 |
| PRN00004299 | CLN00878877 | fibroblast growth factor 8 (androgen-induced) | 3.7 | 1 | H11 | pStat3 |
| PRN00004299 | CLN00878877 | fibroblast growth factor 8 (androgen-induced) | 6.7 | 61 | H11 | pERK |
| | | clones from one transfection | | | | |
| PRN00002899 | CLN00837200 | interferon, alpha 13 | 37.2 | 10 | D11 | pStat3 |
| PRN00002899 | CLN00837200 | interferon, alpha 13 | 22.5 | 10 | D11 | pStat3 |
| PRN00002968 | CLN00837199 | gi\|18573061\|ref\|XP_098916.1\|hypothetical protein XP_098916 [*Homo sapiens*] | 21.0 | 6 | E10 | pStat3 |
| PRN00002968 | CLN00837199 | gi\|18573061\|ref\|XP_098916.1\|hypothetical protein XP_098916 [*Homo sapiens*] | 7.8 | 4 | E10 | pStat3 |
| PRN00005561 | CLN00891196 | Splice Variant CLN00541754 (neuregulin) | 2.7 | 24 | D4 | pERK |
| PRN00005561 | CLN00891196 | Splice Variant CLN00541754 | 2.4 | | D4 | pERK |
| | | tested using recombinant proteins | | | | |
| | | FGF4 | | | | pERK |
| | | FGF5 | | | | pERK |
| | | FGF17 | | | | pERK |
| | | PDGF-A | | | | pAkt |
| | | NRG1-alpha (EGF domain) | | | | pAkt |
| | | NRG1-alpha (EGF domain) | | | | pERK |
| | | NRG1-beta1 (EGF domain) | | | | pAkt |
| | | NRG1-beta1 (EGF domain) | | | | pERK |
| | | epiregulin | | | | pERK |
| | | EGF | | | | pERK |

The invention claimed is:

1. A method of treating a cardiac condition in a subject in need thereof, comprising local administration of an effective amount of a pharmaceutical composition to the heart of the subject, wherein the pharmaceutical composition is not delivered to a coronary artery of the subject, wherein the pharmaceutical composition comprises FGF9 and betacellulin, and wherein the cardiac condition is one or more of cardiac ischemia, ischemic cardiac injury, congestive heart failure, myocardial infarction, coronary artery disease, and cardiomyopathy, and wherein the pharmaceutical composition treats the cardiac condition.

2. The method of claim 1, wherein the local administration comprises administering the composition to a volume at risk.

3. The method of claim 1, further comprising administering the composition systemically.

4. A method of treating a cardiac condition in a subject in need thereof, comprising administering an effective dose of a pharmaceutical composition to the subject, wherein the pharmaceutical composition comprises FGF9 and betacellulin, and wherein the cardiac condition is one or more of cardiac ischemia, ischemic cardiac injury, congestive heart failure, myocardial infarction, coronary artery disease, and cardiomyopathy, and wherein the pharmaceutical composition treats the cardiac condition.

5. The method of claim 4, wherein the subject is administered a dose in the range of about 1 ng to about 10 mg.

6. The method of claim 4, comprising administering the pharmaceutical composition systemically.

7. The method of claim 1, wherein the pharmaceutical composition treats the cardiac condition by:
   (a) promoting survival of cardiac cells; and/or
   (b) promoting differentiation of cardiac cells; and/or
   (c) promoting proliferation of cardiac cells.

8. The method of claim 1, wherein the administration is by a catheter.

9. The method of claim 1, wherein the administration is by direct injection.

10. The method of claim 1, wherein at least one of the FGF9 or the betacellulin comprises at least one fusion partner.

11. The method of claim 10, wherein the at least one fusion partner comprises a polymer, an Fc polypeptide, or human serum albumin.

12. The method of claim 1, wherein the pharmaceutical composition increases cardiomyocyte cell survival in vitro and/or increases the proliferation of cardiospheres in vitro.

13. The method of claim 4, wherein the pharmaceutical composition treats the cardiac condition by:
(a) promoting survival of cardiac cells; and/or
(b) promoting differentiation of cardiac cells; and/or
(c) promoting proliferation of cardiac cells.

14. The method of claim 4, wherein the pharmaceutical composition is administered by injection.

15. The method of claim 4, wherein the pharmaceutical composition is administered intravenously.

16. The method of claim 4, wherein at least one of the FGF9 or the betacellulin comprises at least one fusion partner.

17. The method of claim 16, wherein the at least one fusion partner comprises a polymer, an Fc polypeptide, or human serum albumin.

18. The method of claim 4, wherein the pharmaceutical composition increases cardiomyocyte cell survival in vitro and/or increases the proliferation of cardiospheres in vitro.

* * * * *

SEQUENCE LISTING

<160> NUMBER OF SEQ ID NOS: 348

<210> SEQ ID NO 1
<211> LENGTH: 423
<212> TYPE: DNA
<213> ORGANISM: Homo sapiens

<400> SEQUENCE: 1

```
atgaacgcca aggtcgtggt cgtgctggtc ctcgtgctga ccgcgctctg cctcagcgac      60
gggaagcccg tcagcctgag ctacagatgc ccatgccgat tcttcgaaag ccatgttgcc     120
agagccaacg tcaagcatct caaaattctc aacactccaa actgtgccct tcagattgta     180
gcccggctga gaacaacaa cagacaagtg tgcattgacc cgaagctaaa gtggattcag     240
gagtacctgg agaaagcttt aaacaacctg atcagcgccg caccagccgg aagagggtg     300 attgctgggg ctcgtgcccct gcatccctct cctcccaggg cctgcccac agctcgggcc     360 ctctgtgaga tccgtctttg gcctcctcca gaatggagct ggccctctcc tggggatgtg     420
taa                                                                   423
```

<210> SEQ ID NO 2
<211> LENGTH: 360
<212> TYPE: DNA
<213> ORGANISM: Homo sapiens

<400> SEQUENCE: 2

```
atgaacgcca aggtcgtggt cgtgctggtc ctcgtgctga ccgcgctctg cctcagcgac      60
gggaagcccg tcagcctgag ctacagatgc ccatgccgat tcttcgaaag ccatgttgcc     120
```

| | |
|---|---|
| agagccaacg tcaagcatct caaaattctc aacactccaa actgtgccct tcagattgta | 180 |
| gcccggctga agaacaacaa cagacaagtg tgcattgacc cgaagctaaa gtggattcag | 240 |
| gagtacctgg agaaagcttt aaacaagggg cgcagagaag aaaaagtggg gaaaaaagaa | 300 |
| aagataggaa aaagaagcg acagaagaag agaaaggctg cccagaaaag gaaaaactag | 360 |

<210> SEQ ID NO 3
<211> LENGTH: 282
<212> TYPE: DNA
<213> ORGANISM: Homo sapiens

<400> SEQUENCE: 3

| | |
|---|---|
| atgaacgcca aggtcgtggt cgtgctggtc ctcgtgctga ccgcgctctg cctcagcgac | 60 |
| gggaagcccg tcagcctgag ctacagatgc ccatgccgat tcttcgaaag ccatgttgcc | 120 |
| agagccaacg tcaagcatct caaaattctc aacactccaa actgtgccct tcagattgta | 180 |
| gcccggctga agaacaacaa cagacaagtg tgcattgacc cgaagctaaa gtggattcag | 240 |
| gagtacctgg agaaagcttt aaacaagagg ttcaagatgt ga | 282 |

<210> SEQ ID NO 4
<211> LENGTH: 552
<212> TYPE: DNA
<213> ORGANISM: Homo sapiens

<400> SEQUENCE: 4

| | |
|---|---|
| atggaaaggg tccaacccct ggaagagaat gtgggaaatg cagccaggcc aagattcgag | 60 |
| aggaacaagc tattgctggt ggcctctgta attcagggac tggggctgct cctgtgcttc | 120 |
| acctacatct gcctgcactt ctctgctctt caggtatcac atcggtatcc tcgaattcaa | 180 |
| agtatcaaag tacaatttac cgaatataag aaggagaaag gtttcatcct cacttcccaa | 240 |
| aaggaggatg aaatcatgaa ggtgcagaac aactcagtca tcatcaactg tgatgggttt | 300 |
| tatctcatct ccctgaaggg ctacttctcc caggaagtca acattagcct tcattaccag | 360 |
| aaggatgagg agccccctct tccaactgaa aaggtcaggt ctgtcaactc cttgatggtg | 420 |
| gcctctctga cttacaaaga caaagtctac ttgaatgtga ccactgacaa tacctccctg | 480 |
| gatgacttcc atgtgaatgg cggagaactg attcttatcc atcaaaatcc tggtgaattc | 540 |
| tgtgtccttt ga | 552 |

<210> SEQ ID NO 5
<211> LENGTH: 705
<212> TYPE: DNA
<213> ORGANISM: Homo sapiens

<400> SEQUENCE: 5

| | |
|---|---|
| atggacccag ggctgcagca agcactcaac ggaatggccc ctcctggaga cacagccatg | 60 |
| catgtgccgg cgggctccgt ggccagccac ctggggacca cgagccgcag ctatttctat | 120 |
| ttgaccacag ccactctggc tctgtgcctt gtcttcacgg tggccactat tatggtgttg | 180 |
| gtcgttcaga ggacggactc cattcccaac tcacctgaca cgtcccctt caaaggagga | 240 |
| aattgctcag aagacctctt atgtatcctg aaaagggctc cattcaagaa gtcatgggcc | 300 |
| tacctccaag tggcaaagca tctaaacaaa ccaagttgt cttggaacaa agatggcatt | 360 |
| ctccatggag tcagatatca ggatgggaat ctggtgatcc aattccctgg tttgtacttc | 420 |
| atcatttgcc aactgcagtt tcttgtacaa tgcccaaata attctgtcga tctgaagttg | 480 |
| gagcttctca tcaacaagca tatcaaaaaa caggccctgg tgacagtgtg tgagtctgga | 540 |

```
atgcaaacga aacacgtata ccagaatctc tctcaattct tgctggatta cctgcaggtc    600
aacaccacca tatcagtcaa tgtggataca ttccagtaca tagatacaag cacctttcct    660
cttgagaatg tgttgtccat cttcttatac agtaattcag actga                    705
```

<210> SEQ ID NO 6
<211> LENGTH: 390
<212> TYPE: DNA
<213> ORGANISM: Homo sapiens

<400> SEQUENCE: 6

```
atggaccggg ccgcccggtg cagcggcgcc agctccctgc cactgctcct ggcccttgcc     60
ctgggtctag tgatccttca ctgtgtggtg gcagatggga attccaccag aagtcctgaa    120
actaatggcc tcctctgtgg agaccctgag gaaaactgtg cagctaccac cacacaatca    180
aagcggaaag gccacttctc taggtgcccc aagcaataca agcattactg catcaaaggg    240
agatgccgct cgtggtggc cgagcagacg ccctcctgtg tccctcttcg gaaacgtcgt    300
aaaagaaaga gaaagaaga agaaatggaa actctgggta agatataac tcctatcaat     360 gaagatattg aagagacaaa tattgcttaa                                     390
```

<210> SEQ ID NO 7
<211> LENGTH: 537
<212> TYPE: DNA
<213> ORGANISM: Homo sapiens

<400> SEQUENCE: 7

```
atggaccggg ccgcccggtg cagcggcgcc agctccctgc cactgctcct ggcccttgcc     60
ctgggtctag tgatccttca ctgtgtggtg gcagatggga attccaccag aagtcctgaa    120
actaatggcc tcctctgtgg agaccctgag gaaaactgtg cagctaccac cacacaatca    180
aagcggaaag gccacttctc taggtgcccc aagcaataca agcattactg catcaaaggg    240
agatgccgct cgtggtggc cgagcagacg ccctcctgtg tctgtgatga aggctacatt    300
ggagcaaggt gtgagagagt tgacttgttt tacctaagag gagacagagg acagattctg    360
gtgatttgtt tgatagcagt tatggtagtt tttattattt tggtcatcgg tgtctgcaca    420
tgctgtcacc ctcttcggaa acgtcgtaaa agaagaaga aagaagaaga atggaaact    480 ctgggtaaag atataactcc tatcaatgaa gatattgaag acaaatat tgcttaa        537
```

<210> SEQ ID NO 8
<211> LENGTH: 119
<212> TYPE: PRT
<213> ORGANISM: Homo sapiens

<400> SEQUENCE: 8

```
Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Asn Leu Ile Ser Ala Ala Pro Ala Gly Lys Arg Val Ile
65                  70                  75                  80

Ala Gly Ala Arg Ala Leu His Pro Ser Pro Pro Arg Ala Cys Pro Thr
                85                  90                  95
```

Ala Arg Ala Leu Cys Glu Ile Arg Leu Trp Pro Pro Glu Trp Ser
            100                 105                 110

Trp Pro Ser Pro Gly Asp Val
        115

<210> SEQ ID NO 9
<211> LENGTH: 495
<212> TYPE: DNA
<213> ORGANISM: Homo sapiens

<400> SEQUENCE: 9

| | | |
|---|---|---|
| atgtctcctg agcccgctct gtccccagcc ctgcagctgc tgctgtggca cagtgcactc | 60 |
| tggacagtgc aggaagccac ccccctgggc cctgccagct ccctgcccca gagcttcctg | 120 |
| ctcaagtgct agagcaagt gaggaagatc cagggcgatg cgcagcgct ccaggagaag | 180 |
| ctggcaggct gcttgagcca actccatagc ggccttttcc tctaccaggg gctcctgcag | 240 |
| gccctggaag ggatctcccc cgagttgggt cccaccttgg acacactgca gctggacgtc | 300 |
| gccgactttg ccaccaccat ctggcagcag atggaagaac tgggaatggc ccctgccctg | 360 |
| cagcccaccc aggtgccat gccggccttc gcctctgctt tccagcgccg ggcaggaggg | 420 |
| gtcctggttg cctcccatct gcagagcttc ctggaggtgt cgtaccgcgt tctacgccac | 480 |
| cttgcccagc cctga | 495 |

<210> SEQ ID NO 10
<211> LENGTH: 624
<212> TYPE: DNA
<213> ORGANISM: Homo sapiens

<400> SEQUENCE: 10

| | | |
|---|---|---|
| atggctggac ctgccaccca gagccccatg aagctgatgg ccctgcagct gctgctgtgg | 60 |
| cacagtgcac tctggacagt gcaggaagcc acccccctgg gccctgccag ctccctgccc | 120 |
| cagagcttcc tgctcaagtg cttagagcaa gtgaggaaga tccagggcga tgcgcagcg | 180 |
| ctccaggaga agctggtgag tgagtgtgcc acctacaagc tgtgccaccc cgaggagctg | 240 |
| gtgctgctcg acactctct gggcatcccc tgggctcccc tgagcagctg ccccagccag | 300 |
| gccctgcagc tggcaggctg cttgagccac tccatagcg gccttttcct ctaccagggg | 360 |
| ctcctgcagg ccctggaagg gatctccccc gagttgggtc ccaccttgga cacactgcag | 420 |
| ctggacgtcg ccgactttgc caccaccatc tggcagcaga tggaagaact gggaatggcc | 480 |
| cctgccctgc agcccaccca gggtgccatg ccggccttcg cctctgcttt ccagcgccgg | 540 |
| gcaggagggg tcctggttgc ctcccatctg cagagcttcc tggaggtgtc gtaccgcgtt | 600 |
| ctacgccacc ttgcccagcc ctga | 624 |

<210> SEQ ID NO 11
<211> LENGTH: 540
<212> TYPE: DNA
<213> ORGANISM: Homo sapiens

<400> SEQUENCE: 11

| | | |
|---|---|---|
| agccccctcc ccatcacccc tgtcaacgcc acctgtgcca tacgccaccc atgtcacaac | 60 |
| aacctcatga accagatcag gagccaactg cacagctca atggcagtgc caatgccctc | 120 |
| tttattctct attacacagc ccaggggggag ccgttcccca caacctggga caagctatgt | 180 |
| ggccccaacg tgacggactt cccgcccttc cacgccaacg gcacggagaa ggccaagctg | 240 |
| gtggagctgt accgcatagt cgtgtacctt ggcacctccc tgggcaacat cacccgggac | 300 |

```
cagaagatcc tcaaccccag tgccctcagc ctccacagca agctcaacgc caccgccgac    360
atcctgcgag gcctccttag caacgtgctg tgccgcctgt gcagcaagta ccacgtgggc    420
catgtggacg tgacctacgg ccctgacacc tcgggtaagg atgtcttcca gaagaagaag    480
ctgggctgtc aactcctggg gaagtataag cagatcatcg ccgtgttggc ccaggccttc    540

<210> SEQ ID NO 12
<211> LENGTH: 639
<212> TYPE: DNA
<213> ORGANISM: Homo sapiens

<400> SEQUENCE: 12
atgaactcct tctccacaag cgccttcggt ccagttgcct tctccctggg gctgctcctg     60
gtgttgcctg ctgccttccc tgccccagta cccccaggag aagattccaa agatgtagcc    120
gccccacaca gacagccact cacctcttca gaacgaattg acaaacaaat tcggtacatc    180
ctcgacggca tctcagccct gagaaaggag acatgtaaca gagtaacat gtgtgaaagc    240 agcaaagagg cactggcaga aaacaacctg aaccttccaa agatggctga aaaagatgga    300
tgcttccaat ctggattcaa tgaggagact tgcctggtga aaatcatcac tggtctttg    360 gagtttgagg tatacctaga gtacctccag aacagatttg agagtagtga ggaacaagcc    420
agagctgtgc agatgagtac aaaagtcctg atccagttcc tgcagaaaaa ggcaaagaat    480
ctagatgcaa taaccacccc tgacccaacc acaaatgcca gcctgctgac gaagctgcag    540
gcacagaacc agtggctgca ggacatgaca actcatctca ttctgcgcag cttaaggag    600 ttcctgcagt ccagcctgag ggctcttcgg caaatgtag                           639

<210> SEQ ID NO 13
<211> LENGTH: 609
<212> TYPE: DNA
<213> ORGANISM: Homo sapiens

<400> SEQUENCE: 13
atgaaggtct tggcggcagg agttgtgccc ctgctgttgg ttctgcactg gaaacatggg     60
gcggggagcc ccctccccat caccccctgtc aacgccacct gtgccatacg ccacccatgt    120
cacaacaacc tcatgaacca gatcaggagc caactggcac agctcaatgg cagtgccaat    180 gccctctttta ttctctatta cacagcccag ggggagccgt tccccaacaa cctggacaag    240
ctatgtggcc caacgtgac ggacttcccg cccttccacg ccaacggcac ggagaaggcc     300
aagctggtgg agctgtaccg catagtcgtg taccttggca cctccctggg caacatcacc    360
cgggaccaga agatcctcaa ccccagtgcc ctcagcctcc acagcaagct caacgccacc    420
gccgacatcc tgcgaggcct ccttagcaac gtgctgtgcc gcctgtgcag caagtaccac    480
gtgggccatg tggacgtgac ctacggccct gacacctcgg gtaaggatgt cttccagaag    540
aagaagctgg gctgtcaact cctggggaag tataagcaga tcatcgccgt gttggcccag    600
gccttctag                                                            609

<210> SEQ ID NO 14
<211> LENGTH: 846
<212> TYPE: DNA
<213> ORGANISM: Homo sapiens

<400> SEQUENCE: 14
atggctatga tggaggtcca gggggggaccc agcctgggac agacctgcgt gctgatcgtg     60
atcttcacag tgctcctgca gtctctctgt gtggctgtaa cttacgtgta ctttaccaac    120
```

```
gagctgaagc agatgcagga caagtactcc aaaagtggca ttgcttgttt cttaaaagaa      180
gatgacagtt attgggaccc caatgacgaa gagagtatga acagccctg ctggcaagtc       240 aagtggcaac tccgtcagct cgttagaaag atgattttga gaacctctga ggaaaccatt      300
tctacagttc aagaaaagca acaaaatatt tctcccctag tgagagaaag aggtcctcag      360
agagtagcag ctcacataac tgggaccaga ggaagaagca acacattgtc ttctccaaac      420
tccaagaatg aaaaggctct gggccgcaaa ataaactcct gggaatcatc aaggagtggg      480
cattcattcc tgagcaactt gcacttgagg aatggtgaac tggtcatcca tgaaaaaggg      540
ttttactaca tctattccca aacatacttt cgatttcagg aggaaataaa agaaaacaca      600
aagaacgaca acaaatggt ccaatatatt tacaaataca caagttatcc tgaccctata      660
ttgttgatga aaagtgctag aaatagttgt tggtctaaag atgcagaata tggactctat      720
tccatctatc aaggggaat atttgagctt aaggaaaatg acagaatttt tgtttctgta      780
acaaatgagc acttgataga catggaccat gaagccagtt ttttcggggc ctttttagtt      840
ggctaa                                                                  846

<210> SEQ ID NO 15
<211> LENGTH: 438
<212> TYPE: DNA
<213> ORGANISM: Homo sapiens

<400> SEQUENCE: 15
cccgccttgc ccgaggatgg cggcagcggc gccttcccgc ccggccactt caaggacccc       60
aagcggctgt actgcaaaaa cggggggcttc ttcctgcgca tccaccccga cggccgagtt     120
gacggggtcc gggagaagag cgaccctcac atcaagctac aacttcaagc agaagagaga      180
ggagttgtgt ctatcaaagg agtgtgtgct aaccgttacc tggctatgaa ggaagatgga      240
agattactgg cttctaaatg tgttacggat gagtgtttct tttttgaacg attggaatct      300
aataactaca atacttaccg gtcaaggaaa tacaccagtt ggtatgtggc actgaaacga      360
actgggcagt ataaacttgg atccaaaaca ggacctgggc agaaagctat acttttcttt     420
ccaatgtctg ctaagagc                                                    438

<210> SEQ ID NO 16
<211> LENGTH: 336
<212> TYPE: DNA
<213> ORGANISM: Homo sapiens

<400> SEQUENCE: 16
gccctggaca ccaactattg cttcagctcc acggagaaga actgctgcgt gcggcagctg       60
tacattgact ccgcaagga cctcggctgg aagtggatcc acgagcccaa gggctaccat      120
gccaacttct gcctcgggcc ctgcccctac atttggagcc tggacacgca gtacagcaag      180
gtcctggccc tgtacaacca gcataacccg ggcgcctcgg cggcgccgtg ctgcgtgccg      240
caggcgctgg agccgctgcc catcgtgtac tacgtgggcc gcaagcccaa ggtggagcag      300
ctgtccaaca tgatcgtgcg ctcctgcaag tgcagc                                336

<210> SEQ ID NO 17
<211> LENGTH: 1083
<212> TYPE: DNA
<213> ORGANISM: Homo sapiens

<400> SEQUENCE: 17
ctatccacct gcaagactat cgacatggag ctggtgaagc ggaagcgcat cgaggccatc       60
```

```
cgcggccaga tcctgtccaa gctgcggctc gccagccccc cgagccaggg ggaggtgccg      120
cccggcccgc tgcccgaggc cgtgctcgcc ctgtacaaca gcacccgcga ccgggtggcc      180
ggggagagtg cagaaccgga gcccgagcct gaggccgact actacgccaa ggaggtcacc      240
cgcgtgctaa tggtggaaac ccacaacgaa atctatgaca agttcaagca gagtacacac      300
agcatatata tgttcttcaa cacatcagag ctccgagaag cggtacctga acccgtgttg      360
ctctcccggg cagagctgcg tctgctgagg ctcaagttaa aagtggagca gcacgtggag      420
ctgtaccaga aatacagcaa caattcctgg cgatacctca gcaaccggct gctggcaccc      480
agcgactcgc cagagtggtt atcttttgat gtcaccggag ttgtgcggca gtggttgagc      540
cgtggagggg aaattgaggg cttcgccctt agcgcccact gctcctgtga cagcagggat      600
aacacactgc aagtggacat caacgggttc actaccggcc gccgaggtga cctggccacc      660
attcatggca tgaaccggcc tttcctgctt ctcatggcca ccccgctgga gagggcccag      720
catctgcaaa gctcccggca ccgccgagcc ctggacacca actattgctt cagctccacg      780
gagaagaact gctgcgtgcg gcagctgtac attgacttcc gcaaggacct cggctggaag      840
tggatccacg agcccaaggg ctaccatgcc aacttctgcc tcgggccctg cccctacatt      900
tggagcctgg acacgcagta cagcaaggtc ctggccctgt acaaccagca taacccgggc      960
gcctcggcgg cgccgtgctg cgtgccgcag gcgctggagc cgctgcccat cgtgtactac     1020
gtgggccgca gcccaaggt ggagcagctg tccaacatga tcgtgcgctc ctgcaagtgc     1080
agc                                                                   1083

<210> SEQ ID NO 18
<211> LENGTH: 753
<212> TYPE: DNA
<213> ORGANISM: Homo sapiens

<400> SEQUENCE: 18
gcctgggctc acggggagaa gcgtctcgcc cccaaagggc aacccggacc cgctgccact       60
gataggaacc ctataggctc agcagcaga cagagcagca gtagcgctat gtcttcctct      120
tctgcctcct cctcccccgc agcttctctg ggcagccaag gaagtggctt ggagcagagc      180
agtttccagt ggagcccctc ggggcgccgg accggcagcc tctactgcag agtgggcatc      240
ggtttccatc tgcagatcta cccggatggc aaagtcaatg gatcccacga agccaatatg      300
ttaagtgttt tggaaatatt tgctgtgtct caggggattg taggaatacg aggagttttc      360
agcaacaaat tttagcgat gtcaaaaaaa ggaaaactcc atgcaagtgc caagttcaca      420
gatgactgca agttcaggga gcgttttcaa gaaaatagct ataatacctg tgcctcagca      480
atacatagaa ctgaaaaaac agggcgggag tggtatgttg ccctgaataa agaggaaaa      540 gccaaacgag ggtgcagccc ccgggttaaa ccccagcata tctctaccca ttttcttcca      600
agattcaagc agtcggagca gccagaactt tcttcacgg ttactgttcc tgaaaagaaa      660
aatccaccta gccctatcaa gtcaaagatt cccctttctg cacctcggaa aaataccaac      720
tcagtgaaat acagactcaa gtttcgcttt gga                                   753

<210> SEQ ID NO 19
<211> LENGTH: 795
<212> TYPE: DNA
<213> ORGANISM: Homo sapiens

<400> SEQUENCE: 19
tccttcctcc tcctcctctt cttcagccac ctgatcctca gcgcctgggc tcacggggag       60
```

```
aagcgtctcg cccccaaagg gcaacccgga cccgctgcca ctgataggaa ccctataggc    120
tccagcagca gacagagcag cagtagcgct atgtcttcct cttctgcctc ctcctccccc    180
gcagcttctc tgggcagcca aggaagtggc ttggagcaga gcagtttcca gtggagcccc    240
tcggggcgcc ggaccggcag cctctactgc agagtgggca tcggtttcca tctgcagatc    300
tacccggatg caaagtcaa tggatcccac gaagccaata tgttaagtgt tttggaaata     360
tttgctgtgt ctcaggggat gtaggaata cgaggagttt tcagcaacaa attttagcg      420 atgtcaaaaa aaggaaaact ccatgcaagt gccaagttca cagatgactg caagttcagg    480
gagcgttttc aagaaaatag ctataatacc tatgcctcag caatacatag aactgaaaaa    540
acagggcggg agtggtatgt tgccctgaat aaaagaggaa aagccaaacg agggtgcagc    600
ccccgggtta aacccagca tatctctacc cattttcttc caagattcaa gcagtcggag     660
cagccagaac tttctttcac ggttactgtt cctgaaaaga aaaatccacc tagccctatc    720
aagtcaaaga ttcccctttc tgcacctcgg aaaaatacca actcagtgaa atacagactc    780
aagtttcgct ttgga                                                      795

<210> SEQ ID NO 20
<211> LENGTH: 300
<212> TYPE: DNA
<213> ORGANISM: Homo sapiens

<400> SEQUENCE: 20
cggtgcaagc ttgtaaccgc tttaattgcc ccccagcctg gtaccctgca cagtggcagc     60
cgtgttccag aacgtgtggc gggggtgttc agaaacgtga ggttctttgc aagcagcgca    120
tggctgatgg cagcttcctg gagcttcctg agaccttctg ttcagcttca aaacctgcct    180
gccagcaagc atgcaagaaa gatgactgtc ccagcgagtg gcttctctca gactggacag    240
agtgttccac aagctgcggg gaaggcaccc agactcgaag cgccatttgc cgaaagatgc    300

<210> SEQ ID NO 21
<211> LENGTH: 447
<212> TYPE: DNA
<213> ORGANISM: Homo sapiens

<400> SEQUENCE: 21
agacaaactc ccacacagca ctttaaaaat cagttcccag ctctgcactg gaacatgaa      60 ctaggcctgg ccttcaccaa gaaccgaatg aactatacca caaaattcct gctgatccca    120
gagtcgggag actacttcat ttactcccag gtcacattcc gtgggatgac ctctgagtgc    180
agtgaaatca gacaagcagg ccgaccaaac aagccagact ccatcactgt ggtcatcacc    240
aaggtaacag cagctaccc tgagccaacc cagctcctca tggggaccaa gtctgtatgc     300
gaagtaggta gcaactggtt ccagcccatc tacctcggag ccatgttctc cttgcaagaa    360
ggggacaagc taatggtgaa cgtcagtgac atctctttgg tggattacac aaaagaagat    420
aaaaccttct ttggagcctt cttacta                                        447

<210> SEQ ID NO 22
<211> LENGTH: 585
<212> TYPE: DNA
<213> ORGANISM: Homo sapiens

<400> SEQUENCE: 22
gacgtgtttc tgtccaagcc ccagaaagcg gccctggagt acctggagga tatagacctg     60
aaaacactgg agaaggaacc aaggactttc aaagcaaagg agctatggga aaaaaatgga    120
```

```
gctgtgatta tggccgtgcg gaggccaggc tgtttcctct gtcgagagga agctgcggat      180
ctgtcctccc tgaaaagcat gttggaccag ctgggcgtcc ccctctatgc agtggtaaag      240
gagcacatca ggactgaagt gaaggatttc cagccttatt tcaaaggaga aatcttcctg      300
gatgaaaaga aaagttcta tggtccacaa aggcggaaga tgatgtttat gggatttatc       360
cgtctgggag tgtggtacaa cttcttccga gcctggaacg gaggcttctc tggaaacctg      420
gaaggagaag gcttcatcct tgggggagtt ttcgtggtgg gatcaggaaa gcagggcatt      480
cttcttgagc accgagaaaa agaatttgga gacagagtaa acctacttc tgttctggaa       540 gctgctaaga tgatcaaacc acagactttg gcctcagaga aaaa                      585

<210> SEQ ID NO 23
<211> LENGTH: 585
<212> TYPE: DNA
<213> ORGANISM: Homo sapiens

<400> SEQUENCE: 23
gctccagaaa cagcagtctt aggcgctgag ctcagcgcgg tgggtgagaa cggcggggag      60
aaacccactc ccagtccacc ctggcggctc cgccggtcca agcgctgctc ctgtcgtcc      120 ctgatggata aagagtgtgt ctacttctgc cacctggaca tcatttgggt caacactccc      180
gagcacgttg ttccgtatgg acttggaagc cctaggtcca agagagcctt ggagaattta      240
cttcccacaa aggcaacaga ccgtgagaat agatgccaat gtgctagcca aaaagacaag      300
aagtgctgga ttttttgcca agcaggaaaa gaactcaggg ctgaagacat tatgagaaaa      360
gactggaata atcataagaa aggaaaagac tgttccaagc ttgggaaaaa gtgtatttat      420
cagcagttag tgagaggaag aaaaatcaga agaagttcag aggaacacct aagcaaaacc      480
aggtcggaga ccatgagaaa cagcgtcaaa tcatctttc atgatcccaa gctgaaaggc      540
aagccctcca gagagcgtta tgtgacccac aaccgagcac attgg                     585

<210> SEQ ID NO 24
<211> LENGTH: 63
<212> TYPE: DNA
<213> ORGANISM: Homo sapiens

<400> SEQUENCE: 24
tgctcctgct cgtccctgat ggataaagag tgtgtctact tctgccacct ggacatcatt      60
tgg                                                                   63

<210> SEQ ID NO 25
<211> LENGTH: 114
<212> TYPE: DNA
<213> ORGANISM: Homo sapiens

<400> SEQUENCE: 25
tgctcctgct cgtccctgat ggataaagag tgtgtctact tctgccacct ggacatcatt      60
tgggtcaaca ctcccgagca cgttgttccg tatggacttg aagccctag gtcc            114

<210> SEQ ID NO 26
<211> LENGTH: 1083
<212> TYPE: DNA
<213> ORGANISM: Homo sapiens

<400> SEQUENCE: 26
atgagtgaag gggcggccgc tgcctcgcca cctggtgccg cttcggcagc cgccgcctcg      60
gccgaggagg gcaccgcggc ggctgcggcg gcggcagcgg cgggcggggg cccggacggc      120
```

```
ggcggcgaag gggcggccga gcccccccgg gagttacgct gtagcgactg catcgtgtgg      180
aaccggcagc agacgtggct gtgcgtggta cctctgttca tcggcttcat cggcctgggg      240
ctcagcctca tgcttctcaa atggatcgtg gtgggctccg tcaaggagta cgtgcccacc      300
gacctagtgg actccaaggg gatgggccag gaccccttct tcctctccaa gcccagctct      360
ttccccaagg ccatggagac caccaccact accacttcca ccacgtcccc cgccacccccc     420 tccgccgggg gtgccgcctc ctccaggacg cccaaccgga ttagcactcg cctgaccacc      480
atcacgcggg cgcccactcg cttccccggg caccgggtgc ccatccgggc cagcccgcgc      540
tccaccacag cacggaacac tgcggcccct gcgacggtcc cgtccaccac ggccccgttc      600
ttcagtagca gcacgctggg ctcccgaccc ccggtgccag gaactccaag tacccaggca      660
atgccctcct ggcctactgc ggcatacgct acctcctcct accttcacga ttctactccc      720
tcctggaccc tgtctccctt tcaggatgct gcctcctctt cttcctcttc ttcctcctcc      780
gctaccacca ccacaccaga aactagcacc agccccaaat tcatacgac gacatattcc       840 acagagcgat ccgagcactt caaaccctgc cgagacaagg accttgcata ctgtctcaat      900
gatggcgagt gctttgtgat cgaaaccctg accggatccc ataaacactg tcggtgcaaa      960
gaaggctacc aaggagtccg ttgtgatcaa tttctgccga aaactgattc catcttatcg     1020
gatccaacag accacttggg gattgaattc atggagagtg aagaagttta tcaaaggcag     1080
gtg                                                                   1083

<210> SEQ ID NO 27
<211> LENGTH: 24
<212> TYPE: DNA
<213> ORGANISM: Homo sapiens

<400> SEQUENCE: 27
gaccgggtgt acatacaccc cttc                                              24

<210> SEQ ID NO 28
<211> LENGTH: 30
<212> TYPE: DNA
<213> ORGANISM: Homo sapiens

<400> SEQUENCE: 28
gaccgggtgt acatacaccc cttccacctc                                        30

<210> SEQ ID NO 29
<211> LENGTH: 1356
<212> TYPE: DNA
<213> ORGANISM: Homo sapiens

<400> SEQUENCE: 29
gaccgggtgt acatacaccc cttccacctc gtcatccaca atgagagtac ctgtgagcag       60
ctggcaaagg ccaatgccgg gaagcccaaa gaccccacct tcatacctgc tccaattcag      120
gccaagacat cccctgtgga tgaaaaggcc ctacaggacc agctggtgct agtcgctgca      180
aaacttgaca ccgaagacaa gttgagggcc gcaatggtcg gatgctggc caacttcttg       240 ggcttccgta tatatggcat gcacagtgag ctatggggcg tggtccatgg ggccaccgtc      300
ctctccccaa cggctgtctt tggcaccctg gcctctctct atctgggagc cttggaccac      360
acagctgaca ggctacaggc aatcctgggt gttccttgga aggacaagaa ctgcacctcc      420
cggctggatg cgcacaaggt cctgtctgcc ctgcaggctg tacagggcct gctagtggcc      480
cagggcaggg ctgatagcca ggcccagctg ctgctgtcca cggtggtggg cgtgttcaca      540
```

```
gccccaggcc tgcacctgaa gcagccgttt gtgcagggcc tggctctcta taccctgtg    600 gtcctcccac gctctctgga cttcacagaa ctggatgttg ctgctgagaa gattgacagg    660
ttcatgcagg ctgtgacagg atggaagact ggctgctccc tgatgggagc cagtgtggac    720
agcaccctgg ctttcaacac ctacgtccac ttccaaggga agatgaaggg cttctccctg    780
ctggccgagc cccaggagtt ctgggtggac aacagcacct cagtgtctgt tcccatgctc    840
tctggcatgg gcaccttcca gcactggagt gacatccagg acaacttctc ggtgactcaa    900
gtgcccttca ctgagagcgc ctgcctgctg ctgatccagc ctcactatgc ctctgacctg    960
gacaaggtgg agggtctcac tttccagcaa aactccctca actggatgaa gaaactgtct    1020
ccccggacca tccacctgac catgccccaa ctggtgctgc aaggatctta tgacctgcag    1080
gacctgctcg cccaggctga gctgcccgcc attctgcaca ccgagctgaa cctgcaaaaa    1140
ttgagcaatg accgcatcag ggtgggggag gtgctgaaca gcatttttt tgagcttgaa    1200 gcggatgaga gagagcccac agagtctacc caacagctta caagcctga ggtcttggag    1260 gtgaccctga accgcccatt cctgtttgct gtgtatgatc aaagcgccac tgccctgcac    1320
ttcctgggcc gcgtggccaa cccgctgagc acagca                              1356

<210> SEQ ID NO 30
<211> LENGTH: 21
<212> TYPE: DNA
<213> ORGANISM: Homo sapiens

<400> SEQUENCE: 30
cgggtgtaca tacaccccctt c                                              21

<210> SEQ ID NO 31
<211> LENGTH: 447
<212> TYPE: DNA
<213> ORGANISM: Homo sapiens

<400> SEQUENCE: 31
atgcaaaaag gtgatcagaa tcctcaaatt gcggcacatg tcataagtga ggccagcagt    60
aaaacaacat ctgtgttaca gtgggctgaa aaaggatact acaccatgag caacaacttg    120
gtaaccctgg aaaatgggaa acagctgacc gttaaaagac aaggactcta ttatatctat    180
gcccaagtca ccttctgttc caatcgggaa gcttcgagtc aagctccatt tatagccagc    240
ctctgcctaa agtcccccgg tagattcgag agaatcttac tcagagctgc aaatacccac    300
agttccgcca aaccttgcgg gcaacaatcc attcacttgg gaggagtatt tgaattgcaa    360
ccaggtgctt cggtgtttgt caatgtgact gatccaagcc aagtgagcca tggcactggc    420
ttcacgtcct ttggcttact caaactc                                         447

<210> SEQ ID NO 32
<211> LENGTH: 645
<212> TYPE: DNA
<213> ORGANISM: Homo sapiens

<400> SEQUENCE: 32
catagaaggt tggacaagat agaagatgaa aggaatcttc atgaagattt tgtattcatg    60
aaaacgatac agagatgcaa cacaggagaa agatccttat ccttactgaa ctgtgaggag    120
attaaaagcc agtttgaagg ctttgtgaag gatataatgt taaacaaaga ggagacgaag    180
aaagaaaaca gctttgaaat gcaaaaaggt gatcagaatc ctcaaattgc ggcacatgtc    240
ataagtgagg ccagcagtaa aacaacatct gtgttacagt gggctgaaaa aggatactac    300
```

```
accatgagca acaacttggt aaccctggaa aatgggaaac agctgaccgt taaaagacaa    360
ggactctatt atatctatgc ccaagtcacc ttctgttcca atcgggaagc ttcgagtcaa    420
gctccattta tagccagcct ctgcctaaag tcccccggta gattcgagag aatcttactc    480
agagctgcaa atacccacag ttccgccaaa ccttgcgggc aacaatccat tcacttggga    540
ggagtatttg aattgcaacc aggtgcttcg gtgtttgtca atgtgactga tccaagccaa    600
gtgagccatg gcactggctt cacgtccttt ggcttactca aactc                   645
```

```
<210> SEQ ID NO 33
<211> LENGTH: 996
<212> TYPE: DNA
<213> ORGANISM: Homo sapiens

<400> SEQUENCE: 33
agcccggctc ctcctgcttg tgacctccga gtcctcagta aactgcttcg tgactcccat     60
gtccttcaca gcagactgag ccagtgccca gaggttcacc ctttgcctac acctgtcctg    120
ctgcctgctg tggactttag cttgggagaa tggaaaaccc agatggagga gaccaaggca    180
caggacattc tgggagcagt gacccttctg ctggagggag tgatggcagc acggggacaa    240
ctgggaccca cttgcctctc atccctcctg ggcagctttt ctggacaggt ccgtctcctc    300 cttgggccc tgcagagcct ccttggaacc cagcttcctc cacagggcag gaccacagct    360
cacaaggatc ccaatgccat cttcctgagc ttccaacacc tgctccgagg aaaggtgcgt    420
ttcctgatgc ttgtaggagg gtccacccte tgcgtcaggc gggccccacc caccacagct    480
gtccccagca gaacctctct agtcctcaca ctgaacgagc tcccaaacag gacttctgga    540
ttgttggaga caaacttcac tgcctcagcc agaactactg gctctgggct tctgaagtgg    600
cagcagggat tcagagccaa gattcctggt ctgctgaacc aaaacctccag gtccctggac    660 caaatccccg gatacctgaa caggatacac gaactcttga atggaactcg tggactcttt    720 cctggacccet cacgcaggac cctaggagcc ccggacattt cctcaggaac atcagacaca    780
ggctccctgc cacccaacct ccagcctgga tattctcctt ccccaaccca tcctcctact    840
ggacagtata cgctcttccc tcttccacce accttgccca cccctgtggt ccagctccac    900
cccctgcttc ctgacccttc tgctccaacg cccaccccta ccagccctct tctaaacaca    960
tcctacaccc actcccagaa tctgtctcag gaaggg                              996
```

```
<210> SEQ ID NO 34
<211> LENGTH: 531
<212> TYPE: DNA
<213> ORGANISM: Homo sapiens

<400> SEQUENCE: 34 ggccccccaga gggaagagtt ccccagggac ctctctctaa tcagccctct ggcccaggca     60
gtcagatcat cttctcgaac cccgagtgac aagcctgtag cccatgttgt agcaaaccct    120
caagctgagg ggcagctcca gtggctgaac cgccgggcca atgccctcct ggccaatggc    180
gtggagctga gagataacca gctggtggtg ccatcagagg gcctgtacct catctactcc    240
caggtcctct tcaagggcca aggctgcccc tccacccatg tgctcctcac ccacaccatc    300
agccgcatcg ccgtctccta ccagaccaag gtcaacctcc tctctgccat caagagcccc    360
tgccagaggg agacccccaga ggggctgag gccaagccct ggtatgagcc catctatctg    420
ggaggggtct tccagctgga gaagggtgac cgactcagcg ctgagatcaa tcggcccgac    480
tatctcgact ttgccgagtc tgggcaggtc tactttggga tcattgccct g              531
```

```
<210> SEQ ID NO 35
<211> LENGTH: 471
<212> TYPE: DNA
<213> ORGANISM: Homo sapiens

<400> SEQUENCE: 35
gtcagatcat cttctcgaac cccgagtgac aagcctgtag cccatgttgt agcaaaccct      60
caagctgagg ggcagctcca gtggctgaac cgccgggcca atgccctcct ggccaatggc     120
gtggagctga gagataacca gctggtggtg ccatcagagg gcctgtacct catctactcc     180
caggtcctct tcaagggcca aggctgcccc tccacccatg tgctcctcac ccacaccatc     240
agccgcatcg ccgtctccta ccagaccaag gtcaacctcc tctctgccat caagagcccc     300
tgccagaggg agaccccaga gggggctgag gccaagccct ggtatgagcc catctatctg     360
ggaggggtct tccagctgga aagggtgacc cgactcagcg ctgagatcaa tcggcccgac     420
tatctcgact tgccgagtc tgggcaggtc tactttggga tcattgccct g                471

<210> SEQ ID NO 36
<211> LENGTH: 513
<212> TYPE: DNA
<213> ORGANISM: Homo sapiens

<400> SEQUENCE: 36
ctccctggtg ttggcctcac accttcagct gcccagactg cccgtcagca ccccaagatg      60
catcttgccc acagcaccct caaacctgct gctcacctca ttggagaccc cagcaagcag     120
aactcactgc tctggagagc aaacacggac cgtgccttcc tccaggatgg tttctccttg     180
agcaacaatt ctctcctggt ccccaccagt ggcatctact tcgtctactc ccaggtggtc     240
ttctctggga aagcctactc tcccaaggcc acctcctccc cactctacct ggcccatgag     300
gtccagctct tctcctccca gtacccctc catgtgcctc tcctcagctc ccagaagatg     360
gtgtatccag ggctgcagga accctggctg cactcgatgt accacggggc tgcgttccag     420
ctcacccagg gagaccagct atccaccac acagatggca tcccccacct agtcctcagc     480
cctagtactg tcttctttgg agccttcgct ctg                                   513

<210> SEQ ID NO 37
<211> LENGTH: 549
<212> TYPE: DNA
<213> ORGANISM: Homo sapiens

<400> SEQUENCE: 37 gtaccccag gagaagattc aaagatgta gccgccccac acagacagcc actcacctct      60
tcagaacgaa ttgacaaaca aattcggtac atcctgacg gcatctcagc cctgagaaag     120
gagacatgta acaagagtaa catgtgtgaa agcagcaaag aggcactggc agaaaacaac     180
ctgaaccttc caaagatggc tgaaaaagat ggatgcttcc aatctggatt caatgaggag     240
acttgcctgg tgaaaatcat cactggtctt ttggagtttg aggtatacct agagtacctc     300
cagaacagat ttgagagtag tgaggaacaa gccagagctg tgcagatgag tacaaaagtc     360
ctgatccagt tcctgcagaa aaaggcaaag aatctagatg caataaccac ccctgaccca     420
accacaaatg ccagcctgct gacgaagctg caggcacaga accagtggct gcaggacatg     480
acaactcatc tcattctgcg cagctttaag gagttcctgc agtccagcct gagggctctt     540
cggcaaatg                                                              549

<210> SEQ ID NO 38
```

```
<211> LENGTH: 1389
<212> TYPE: DNA
<213> ORGANISM: Homo sapiens

<400> SEQUENCE: 38
caaaggaaaa gaagaaatac aattcatgaa ttcaaaaaat cagcaaagac tacccctaatc    60 aaaatagatc cagcactgaa gataaaaacc aaaaaagtga atactgcaga ccaatgtgct   120
aatagatgta ctaggaataa aggacttcca ttcacttgca aggcttttgt ttttgataaa   180
gcaagaaaac aatgcctctg gttccccttc aatagcatgt caagtggagt gaaaaaagaa   240
tttggccatg aatttgacct ctatgaaaac aaagactaca ttagaaactg catcattggt   300
aaaggacgca gctacaaggg aacagtatct atcactaaga gtggcatcaa atgtcagccc   360
tggagttcca tgataccaca cgaacacagc tttttgcctt cgagctatcg ggtaaagac    420 ctacaggaaa actactgtcg aaatcctcga ggggaagaag ggggaccctg tgtttcaca    480 agcaatccag aggtacgcta cgaagtctgt gacattcctc agtgttcaga gttgaatgc    540 atgacctgca atggggagag ttatcgaggt ctcatggatc atacagaatc aggcaagatt   600
tgtcagcgct gggatcatca gacaccacac cggcacaaat tcttgcctga agatatccc    660 gacaagggct tgatgataa ttattgccgc aatcccgatg ccagccgag gccatggtgc    720 tatactcttg accctcacac ccgctgggag tactgtgcaa ttaaaacatg cgctgacaat   780
actatgaatg acactgatgt tcctttggaa acaactgaat gcatccaagg tcaaggagaa   840
ggctacaggg gcactgtcaa taccatttgg aatggaattc catgtcagcg ttgggattct   900
cagtatcctc acgagcatga catgactcct gaaaatttca gtgcaagga cctacgagaa   960 aattactgcc gaaatccaga tgggtctgaa tcaccctggt gttttaccac tgatccaaac  1020
atccgagttg gctactgctc ccaaattcca actgtgata tgtcacatgg acaagattgt  1080
tatcgtggga atggcaaaaa ttatatgggc aacttatccc aaacaagatc tggactaaca  1140
tgttcaatgt gggacaagaa catggaagac ttacatcgtc atatcttctg gaaccagat   1200 gcaagtaagc tgaatgagaa ttactgccga aatccagatg atgatgctca tggaccctgg  1260
tgctacacgg gaaatccact cattccttgg gattattgcc ctatttctcg ttgtgaaggt  1320
gataccacac ctacaatagt caatttagac catcccgtaa tatcttgtgc caaaacgaaa  1380
caattgcga                                                         1389

<210> SEQ ID NO 39
<211> LENGTH: 702
<212> TYPE: DNA
<213> ORGANISM: Homo sapiens

<400> SEQUENCE: 39
gttgtaaatg ggattccaac acgaacaaac ataggatgga tggttagttt gagatacaga    60
aataaacata tctgcggagg atcattgata aaggagagtt gggttcttac tgcacgacag   120
tgtttccctt ctcgagactt gaaagattat gaagcttggc ttggaattca tgatgtccac   180
ggaagaggag atgagaaatg caacaggtt ctcaatgttt cccagctggt atatggccct   240
gaaggatcag atctggtttt aatgaagctt gccaggcctg ctgtcctgga tgattttgtt   300
agtacgattg atttacctaa ttatggatgc acaattcctg aaaagaccag ttgcagtgtt   360
tatggctggg gctacactgg attgatcaac tatgatggcc tattacgagt ggcacatctc   420
tatataatgg gaaatgagaa atgcagccag catcatcgag ggaaggtgac tctgaatgag   480
tctgaaatat gtgctggggc tgaaaagatt ggatcaggac catgtgaggg ggattatggt   540
```

-continued

```
ggcccacttg tttgtgagca acataaaatg agaatggttc ttggtgtcat tgttcctggt    600
cgtggatgtg ccattccaaa tcgtcctggt attttttgtcc gagtagcata ttatgcaaaa   660
tggatacaca aaattatttt aacatataag gtaccacagt ca                       702
```

<210> SEQ ID NO 40
<211> LENGTH: 216
<212> TYPE: DNA
<213> ORGANISM: Homo sapiens

<400> SEQUENCE: 40

```
aagcccgtca gcctgagcta cagatgccca tgccgattct tcgaaagcca tgttgccaga    60
gccaacgtca agcatctcaa aattctcaac actccaaact gtgcccttca gattgtagcc   120
cggctgaaga acaacaacag acaagtgtgc attgacccga agctaaagtg gattcaggag   180
tacctggaga aagcttttaaa caagaggttc aagatg                             216
```

<210> SEQ ID NO 41
<211> LENGTH: 468
<212> TYPE: DNA
<213> ORGANISM: Homo sapiens

<400> SEQUENCE: 41

```
gcttaccgcc ccagtgagac cctgtgcggc ggggagctgg tggacaccct ccagttcgtc    60
tgtggggacc gcggcttcta cttcagcagg cccgcaagcc gtgtgagccg tcgcagccgt   120
ggcatcgttg aggagtgctg tttccgcagc tgtgacctgg ccctcctgga gacgtactgt   180 gctaccccg ccaagtccga gagggacgtg tcgacccctc cgaccgtgct tccggacaac   240
ttccccagat accccgtggg caagttcttc caatatgaca cctggaagca gtccacccag   300
cgcctgcgca ggggcctgcc tgccctcctg cgtgcccgcc ggggtcacgt gctcgccaag   360
gagctcgagg cgttcaggga ggccaaacgt caccgtcccc tgattgctct acccacccaa   420
gaccccgccc acgggggcgc cccccagag atggccagca atcggaag                  468
```

<210> SEQ ID NO 42
<211> LENGTH: 201
<212> TYPE: DNA
<213> ORGANISM: Homo sapiens

<400> SEQUENCE: 42

```
gcttaccgcc ccagtgagac cctgtgcggc ggggagctgg tggacaccct ccagttcgtc    60
tgtggggacc gcggcttcta cttcagcagg cccgcaagcc gtgtgagccg tcgcagccgt   120
ggcatcgttg aggagtgctg tttccgcagc tgtgacctgg ccctcctgga gacgtactgt   180 gctaccccg ccaagtccga g                                               201
```

<210> SEQ ID NO 43
<211> LENGTH: 210
<212> TYPE: DNA
<213> ORGANISM: Homo sapiens

<400> SEQUENCE: 43

```
ggaccggaga cgctctgcgg ggctgagctg gtggatgctc ttcagttcgt gtgtggagac    60 agggggctttt atttcaacaa gcccacaggg tatggctcca gcagtcggag ggcgcctcag   120
acaggcatcg tggatgagtg ctgcttccgg agctgtgatc taaggaggct ggagatgtat   180
tgcgcacccc tcaagcctgc caagtcagct                                     210
```

<210> SEQ ID NO 44

<211> LENGTH: 537
<212> TYPE: DNA
<213> ORGANISM: Homo sapiens

<400> SEQUENCE: 44

```
cagctcttcc acctacagaa ggagctggca gaactccgag agtctaccag ccagatgcac    60
acagcatcat ctttggagaa gcaaataggc cacccccagtc cacccccctga aaaaaggag  120
ctgaggaaag tggcccattt aacaggcaag tccaactcaa ggtccatgcc tctggaatgg  180
gaagacacct atggaattgt cctgctttct ggagtgaagt ataagaaggg tggccttgtg  240
atcaatgaaa ctgggctgta ctttgtatat tccaaagtat acttccgggg tcaatcttgc  300
aacaacctgc ccctgagcca aaggtctac atgaggaact ctaagtatcc caggatctg   360
gtgatgatgg aggggaagat gatgagctac tgcactactg gcagatgtg ggcccgcagc  420
agctacctgg gggcagtgtt caatcttacc agtgctgatc atttatatgt caacgtatct  480
gagctctctc tggtcaattt tgaggaatct cagacgttttt tcggcttata taagctc    537
```

<210> SEQ ID NO 45
<211> LENGTH: 456
<212> TYPE: DNA
<213> ORGANISM: Homo sapiens

<400> SEQUENCE: 45

```
caaataggcc accccagtcc acccccctgaa aaaaggagc tgaggaaagt ggcccattta    60
acaggcaagt ccaactcaag gtccatgcct ctggaatggg aagacaccta tggaattgtc  120
ctgctttctg gagtgaagta taagaagggt ggccttgtga tcaatgaaac tgggctgtac  180
tttgtatatt ccaaagtata cttccggggt caatcttgca acaacctgcc cctgagccac  240
aaggtctaca tgaggaactc taagtatccc aggatctggt tgatgatgga ggggaagatg  300
atgagctact gcactactgg gcagatgtgg gcccgcagca gctacctggg ggcagtgttc  360
aatcttacca gtgctgatca tttatatgtc aacgtatctg agctctctct ggtcaatttt  420
gaggaatctc agacgttttt cggcttatat aagctc                           456
```

<210> SEQ ID NO 46
<211> LENGTH: 534
<212> TYPE: DNA
<213> ORGANISM: Homo sapiens

<400> SEQUENCE: 46

```
gccacccccc tgggccctgc cagctccctg ccccagagct tcctgctcaa gtgcttagag    60
caagtgagga agatccaggg cgatggcgca gcgctccagg agaagctggt gagtgagtgt  120
gccacctaca agctgtgcca ccccgaggag ctggtgctgc tcggacactc tctgggcatc  180
ccctgggctc ccctgagcag ctgccccagc caggccctgc agctggcagg ctgcttgagc  240
caactccata gcggccttt cctctaccag gggctcctgc aggccctgga agggatctcc  300
cccgagttgg gtcccacctt ggacacactg cagctggacg tcgccgactt tgccaccacc  360
atctggcagc agatggaaga actgggaatg gcccctgccc tgcagcccac ccagggtgcc  420
atgccggcct tcgcctctgc tttccagcgc cgggcaggag gggtcctggt tgcctcccat  480
ctgcagagct tcctggaggt gtcgtaccgc gttctacgcc accttgccca gccc        534
```

<210> SEQ ID NO 47
<211> LENGTH: 420
<212> TYPE: DNA
<213> ORGANISM: Homo sapiens

<400> SEQUENCE: 47

```
tttaatctgc ctccagggaa ttacaagaag cccaaactcc tctactgtag caacgggggc    60
cacttcctga ggatccttcc ggatggcaca gtggatggga caagggacag gagcgaccag   120
cacattcagc tgcagctcag tgcggaaagc gtggggaggt gtatataaa gagtaccgag    180
actggccagt acttggccat ggacaccgac gggctttat acggctcaca gacaccaaat   240
gaggaatgtt tgttcctgga aaggctggag gagaaccatt acaacaccta tatatccaag  300
aagcatgcag agaagaattg gtttgttggc ctcaagaaga atgggagctg caaacgcggt   360
cctcggactc actatggcca gaaagcaatc ttgtttctcc ccctgccagt ctcttctgat   420
```

<210> SEQ ID NO 48
<211> LENGTH: 108
<212> TYPE: DNA
<213> ORGANISM: Homo sapiens

<400> SEQUENCE: 48

```
taccctcca agccggacaa cccgggcgag gacgcaccag cggaggacat ggccagatac    60
tactcggcgc tgcgacacta catcaacctc atcaccaggc agagatat                108
```

<210> SEQ ID NO 49
<211> LENGTH: 207
<212> TYPE: DNA
<213> ORGANISM: Homo sapiens

<400> SEQUENCE: 49

```
taccctcca agccggacaa cccgggcgag gacgcaccag cggaggacat ggccagatac    60
tactcggcgc tgcgacacta catcaacctc atcaccaggc agagatatgg aaaacgatcc  120
agcccagaga cactgatttc agacctcttg atgagagaaa gcacagaaaa tgttcccaga  180
actcggcttg aagaccctgc aatgtgg                                      207
```

<210> SEQ ID NO 50
<211> LENGTH: 516
<212> TYPE: DNA
<213> ORGANISM: Homo sapiens

<400> SEQUENCE: 50

```
cagaggacgg actccattcc caactcacct gacaacgtcc ccctcaaagg aggaaattgc    60
tcagaagacc tcttatgtat cctgaaaagg gctccattca agaagtcatg ggcctacctc   120
caagtggcaa agcatctaaa caaaaccaag ttgtcttgga acaaagatgg cattctccat   180
ggagtcagat atcaggatgg gaatctggtg atccaattcc ctggtttgta cttcatcatt   240
tgccaactgc agtttcttgt acaatgccca ataattctg tcgatctgaa gttggagctt   300
ctcatcaaca agcatatcaa aaaacaggcc ctggtgacag tgtgtgagtc tggaatgcaa   360
acgaaacacg tataccagaa tctctctcaa ttcttgctgg attacctgca ggtcaacacc   420
accatatcag tcaatgtgga tacattccag tacatagata caagcacctt tcctcttgag   480
aatgtgttgt ccatcttctt atacagtaat tcagac                            516
```

<210> SEQ ID NO 51
<211> LENGTH: 465
<212> TYPE: DNA
<213> ORGANISM: Homo sapiens

<400> SEQUENCE: 51

```
cagcgcttcg cacaggctca gcagcagctg ccgctcgagt cacttgggtg ggacgtagct    60
```

| | |
|---|---|
| gagctgcagc tgaatcacac aggacctcag caggacccca ggctatactg cagggggc | 120 |
| ccagcactgg gccgctcctt cctgcatgga ccagagctgg acaaggggca gctacgtatc | 180 |
| catcgtgatg gcatctacat ggtacacatc caggtgacgc tggccatctg ctcctccacg | 240 |
| acggcctcca ggcaccaccc caccaccctg gccgtgggaa tctgctctcc cgcctcccgt | 300 |
| agcatcagcc tgctgcgtct cagcttccac caaggttgta ccattgcctc cagcgcctg | 360 |
| acgcccctgg cccgagggga cacactctgc accaacctca ctgggacact tttgccttcc | 420 |
| cgaaacactg atgagacctt ctttggagtg cagtgggtgc gcccc | 465 |

<210> SEQ ID NO 52
<211> LENGTH: 696
<212> TYPE: DNA
<213> ORGANISM: Homo sapiens

<400> SEQUENCE: 52

| | |
|---|---|
| agcaaaagca atgaaggagc agatggccca gttaaaaaca agaaaaaggg aaagaaagca | 60 |
| ggacctcctg gacccaatgg ccctccagga cccccaggac ctccaggacc ccagggaccc | 120 |
| ccaggaattc cagggattcc tggaattcca ggaacaactg ttatgggacc acctggtcct | 180 |
| ccaggtcctc ctggtcctca aggacccct ggcctccagg accttctgg tgctgctgat | 240 |
| aaagctggaa ctcgagaaaa ccagccagct gtggtgcatc tacagggcca agggtcagca | 300 |
| attcaagtca agaatgatct ttcaggtgga gtgctcaatg actggtctcg catcactatg | 360 |
| aaccccaagg tgtttaagct acatcccgc agcggggagc tggaggtact ggtggacggc | 420 |
| acctacttca tctatagtca ggtagaagta tactacatca acttcactga cttttgccagc | 480 |
| tatgaggtgg tggtggatga aagcccttc ctgcagtgca cacgcagcat cgagacgggc | 540 |
| aagaccaact acaacacttg ctataccgca ggcgtctgcc tcctcaaggc ccggcagaag | 600 |
| atcgccgtca agatggtgca cgctgacatc tccatcaaca tgagcaagca caccacgttc | 660 |
| tttggggcca tcaggctggg tgaagcccct gcatcc | 696 |

<210> SEQ ID NO 53
<211> LENGTH: 987
<212> TYPE: DNA
<213> ORGANISM: Homo sapiens

<400> SEQUENCE: 53

| | |
|---|---|
| gagttgcgct cggagttgcg gcgggaacgt ggagccgagt cccgccttgg cggctcgggc | 60 |
| acccctggca cctctggcac cctaagcagc ctcggtggcc tcgaccctga cagccccatc | 120 |
| accagtcacc ttgggcagcc gtcacctaag cagcagccat ggaaccggg agaagccgca | 180 |
| ctccactctg actcccagga cgggcaccag atggccctat tgaatttctt cttccctgat | 240 |
| gaaaagccat actctgaaga gaaagtaggc gtgttcgcc gcaataaaag aagcaaaagc | 300 |
| aatgaaggag cagatggccc agttaaaaac aagaaaaagg gaaagaaagc aggacctcct | 360 |
| ggacccaatg gccctccagg accccagga cctccaggac cccagggacc cccaggaatt | 420 |
| ccagggattc ctggaattcc aggaacaact gttatgggac cacctggtcc tccaggtcct | 480 |
| cctggtcctc aaggaccccc tggcctccag gaccttctg gtgctgctga taaagctgga | 540 |
| actcgagaaa accagccagc tgtggtgcat ctacagggcc aagggtcagc aattcaagtc | 600 |
| aagaatgatc tttcaggtgg agtgctcaat gactggtctc gcatcactat gaaccccaag | 660 |
| gtgtttaagc tacatcccg cagcggggag ctggaggtac tggtggacgg cacctacttc | 720 |
| atctatagtc aggtagaagt atactacatc aacttcactg acttttgccag ctatgaggtg | 780 |

```
gtggtggatg agaagccctt cctgcagtgc acacgcagca tcgagacggg caagaccaac    840
tacaacactt gctataccgc aggcgtctgc ctcctcaagg cccggcagaa gatcgccgtc    900
aagatggtgc acgctgacat ctccatcaac atgagcaagc acaccacgtt ctttggggcc    960
atcaggctgg gtgaagcccc tgcatcc                                        987

<210> SEQ ID NO 54
<211> LENGTH: 147
<212> TYPE: DNA
<213> ORGANISM: Homo sapiens

<400> SEQUENCE: 54
gtggctcaag tgtcaataac aaagtgtagc tctgacatga atggctattg tttgcatgga     60
cagtgcatct atctggtgga catgagtcaa aactactgca ggtgtgaagt gggttatact    120
ggtgtccgat gtgaacactt cttttta                                        147

<210> SEQ ID NO 55
<211> LENGTH: 138
<212> TYPE: DNA
<213> ORGANISM: Homo sapiens

<400> SEQUENCE: 55
gtgtcaataa caaagtgtag ctctgacatg aatggctatt gtttgcatgg acagtgcatc     60
tatctggtgg acatgagtca aaactactgc aggtgtgaag tgggttatac tggtgtccga    120
tgtgaacact tcttttta                                                  138

<210> SEQ ID NO 56
<211> LENGTH: 252
<212> TYPE: DNA
<213> ORGANISM: Homo sapiens

<400> SEQUENCE: 56
tcagtcagag ttgaacaggt agttaagccc ccccaaaaca agacggaaag tgaaaatact     60
tcagataaac ccaaaagaaa gaaaagggga ggcaaaaatg gaaaaaatag aagaaacaga    120
aagaagaaaa atccatgtaa tgcagaattt caaaatttct gcattcacgg agaatgcaaa    180
tatatagagc acctggaagc agtaacatgc aaatgtcagc aagaatattt cggtgaacgg    240
tgtggggaaa ag                                                        252

<210> SEQ ID NO 57
<211> LENGTH: 540
<212> TYPE: DNA
<213> ORGANISM: Homo sapiens

<400> SEQUENCE: 57
ggctcaggcc attatgctgc tggattggac ctcaatgaca cctactctgg gaagcgtgaa     60 ccatttctg gggaccacag tgctgatgga tttgaggtta cctcaagaag tgagatgtct    120
tcagggagtg agatttcccc tgtgagtgaa atgccttcta gtagtgaacc gtcctcggga    180
gccgactatg actactcaga agagtatgat aacgaaccac aaatacctgg ctatattgtc    240
gatgattcag tcagagttga acaggtagtt aagcccccc aaaacaagac ggaaagtgaa    300
aatacttcag ataaacccaa agaaagaaa agggaggca aaaatggaaa aatagaaga    360 aacagaaaga gaaaaatcc atgtaatgca gaatttcaaa atttctgcat tcacggagaa    420
tgcaaatata tagagcacct ggaagcagta acatgcaaat gtcagcaaga atatttcggt    480
gaacggtgtg gggaaaagtc catgaaaact cacagcatga ttgacagtag tttatcaaaa    540
```

<210> SEQ ID NO 58
<211> LENGTH: 240
<212> TYPE: DNA
<213> ORGANISM: Homo sapiens

<400> SEQUENCE: 58

```
gatgggaatt ccaccagaag tcctgaaact aatggcctcc tctgtggaga ccctgaggaa      60
aactgtgcag ctaccaccac acaatcaaag cggaaaggcc acttctctag gtgcccaag     120
caatacaagc attactgcat caaagggaga tgccgcttcg tggtggccga gcagacgccc    180
tcctgtgtct gtgatgaagg ctacattgga gcaaggtgtg agagagttga cttgttttac    240
```

<210> SEQ ID NO 59
<211> LENGTH: 423
<212> TYPE: DNA
<213> ORGANISM: Homo sapiens

<400> SEQUENCE: 59

```
ctggtgactg gcgagagcct ggagcggctt cggagagggc tagctgctgg aaccagcaac      60
ccggacccct ccactgtatc cacggaccag ctgctacccc taggaggcgg ccggaccgg     120
aaagtccgtg acttgcaaga ggcagatctg daccttttga gagtcacttt atcctccaag    180
ccacaagcac tggccacacc aaacaaggag agcacgggaa aagaaagaa gaaaggcaag    240
gggctaggga agaagaggga cccatgtctt cggaaataca aggacttctg catccatgga    300
gaatgcaaat atgtgaagga gctccgggct ccctcctgca tctgccaccc gggttaccat    360
ggagagaggt gtcatgggct gagcctccca gtggaaaatc gcttatatac ctatgaccac    420
aca                                                                   423
```

<210> SEQ ID NO 60
<211> LENGTH: 258
<212> TYPE: DNA
<213> ORGANISM: Homo sapiens

<400> SEQUENCE: 60

```
gacttgcaag aggcagatct ggacctttg agagtcactt tatcctccaa gccacaagca      60
ctggccacac caaacaagga ggagcacggg aaaagaaaga gaaaggcaa ggggctaggg     120
aagaagaggg acccatgtct tcggaaatac aaggacttct gcatccatgg agaatgcaaa    180
tatgtgaagg agctccgggc tccctcctgc atctgccacc cgggttacca tggagagagg    240
tgtcatgggc tgagcctc                                                   258
```

<210> SEQ ID NO 61
<211> LENGTH: 483
<212> TYPE: DNA
<213> ORGANISM: Homo sapiens

<400> SEQUENCE: 61

```
gccctgcatg aagggaaggg ccaggctgct gccaccctgg agcagccagc gtcctcatct      60
catgcccaag gcacccacct tcggcttcgc cgttgctcct gcagctcctg gctcgacaag    120
gagtgcgtct acttctgcca cttggacatc atctgggtga acactcctga acagacagct    180
ccttacggcc tgggaaaccc gccaagacgc cggcgccgct ccctgccaag gcgctgtcag    240
tgctccagtg ccagggaccc cgcctgtgcc accttctgcc ttcgaaggcc ctggactgaa    300
gccggggcag tcccaagccg gaagtcccct gcagacgtgt tccagactgg caagacaggg    360
gccactacag gagagcttct ccaaaggctg agggacattt ccacagtcaa gagcctcttt    420
```

```
gccaagcgac aacaggaggc catgcgggag cctcggtcca cacattccag gtggaggaag    480
aga                                                                  483

<210> SEQ ID NO 62
<211> LENGTH: 63
<212> TYPE: DNA
<213> ORGANISM: Homo sapiens

<400> SEQUENCE: 62
tgctcctgca gctcctggct cgacaaggag tgcgtctact tctgccactt ggacatcatc     60
tgg                                                                   63

<210> SEQ ID NO 63
<211> LENGTH: 3030
<212> TYPE: DNA
<213> ORGANISM: Homo sapiens

<400> SEQUENCE: 63
ccgcagcact ggagctgtcc tgaaggtact ctcgcaggaa atgggaattc tacttgtgtg     60
ggtcctgcac ccttcttaat tttctcccat ggaaatagta tctttaggat tgacacagaa    120
ggaaccaatt atgagcaatt ggtggtggat gctggtgtct cagtgatcat ggattttcat    180
tataatgaga aaagaatcta ttgggtggat ttagaaagac aacttttgca aagagttttt    240
ctgaatgggt caaggcaaga gagagtatgt aatatagaga aaaatgtttc tggaatggca    300
ataaattgga taaatgaaga agttatttgg tcaaatcaac aggaaggaat cattacagta    360
acagatatga aggaaataa ttcccacatt cttttaagtg ctttaaaata tcctgcaaat    420
gtagcagttg atccagtaga aaggtttata ttttggtctt cagaggtggc tggaagcctt    480
tatagagcag atctcgatgg tgtgggagtg aaggctctgt tggagacatc agagaaaata    540
acagctgtgt cattggatgt gcttgataag cggctgtttt ggattcagta caacagagaa    600
ggaagcaatt ctcttatttg ctcctgtgat tatgatggag gttctgtcca cattagtaaa    660
catccaacac agcataattt gtttgcaatg tccctttttg gtgaccgtat cttctattca    720
acatggaaaa tgaagacaat ttggatagcc aacaaacaca ctggaaagga catggttaga    780
attaacctcc attcatcatt tgtaccactt ggtgaactga agtagtgca tccacttgca    840 caacccaagg cagaagatga cacttgggag cctgagcaga aactttgcaa attgaggaaa    900
ggaaactgca gcagcactgt gtgtgggcaa gacctccagt cacacttgtg catgtgtgca    960
gagggatacg ccctaagtcg agaccggaag tactgtgaag atgttaatga atgtgctttt    1020
tggaatcatg gctgtactct tgggtgtaaa acaccccctg gatcctatta ctgcacgtgc    1080
cctgtaggat ttgttctgct tcctgatggg aaacgatgtc atcaacttgt ttcctgtcca    1140
cgcaatgtgt ctgaatgcag ccatgactgt gttctgacat cagaaggtcc cttatgtttc    1200
tgtcctgaag gctcagtgct tgagagagat gggaaaacat gtagcggttg ttcctcaccc    1260
gataatggtg gatgtagcca gctctgcgtt cctcttagcc cagtatcctg ggaatgtgat    1320
tgctttcctg gtatgaccct acaactggat gaaaaaagct gtgcagcttc aggaccacaa    1380
ccatttttgc tgtttgccaa ttctcaagat attcgacaca tgcattttga tggaacagac    1440
tatggaactc tgctcagcca gcagatggga atggtttatg ccctagatca tgaccctgtg    1500
gaaaataaga tatactttgc ccatacagcc ctgaagtgga tagagagagc taatatggat    1560
ggttcccagc gagaaaggct tattgaggaa ggagtagatg tgccagaagg tcttgctgtg    1620
gactggattg gccgtagatt ctattggaca gacagaggga atctctgat tggaaggagt    1680
```

| | |
|---|---|
| gatttaaatg ggaaacgttc caaaataatc actaaggaga acatctctca accacgagga | 1740 |
| attgctgttc atccaatggc caagagatta ttctggactg atacagggat taatccacga | 1800 |
| attgaaagtt cttccctcca aggccttggc cgtctggtta tagccagctc tgatctaatc | 1860 |
| tggcccagtg gaataacgat tgacttctta actgacaagt tgtactggtg cgatgccaag | 1920 |
| cagtctgtga ttgaaatggc caatctggat ggttcaaaac gccgaagact tacccagaat | 1980 |
| gatgtaggtc acccatttgc tgtagcagtg tttgaggatt atgtgtggtt ctcagattgg | 2040 |
| gctatgccat cagtaataag agtaaacaag aggactggca agatagagt acgtctccaa | 2100 |
| ggcagcatgc tgaagccctc atcactggtt gtggttcatc cattggcaaa accaggagca | 2160 |
| gatccctgct tatatcaaaa cggaggctgt gaacatattt gcaaaagag cttggaact | 2220 |
| gcttggtgtt cgtgtcgtga aggttttatg aaagcctcag atgggaaaac gtgtctggct | 2280 |
| ctggatggtc atcagctgtt ggcaggtggt gaagttgatc taaagaacca agtaacacca | 2340 |
| ttggacatct tgtccaagac tagagtgtca gaagataaca ttacagaatc tcaacacatg | 2400 |
| ctagtggctg aaatcatggt gtcagatcaa gatgactgtg ctcctgtggg atgcagcatg | 2460 |
| tatgctcggt gtatttcaga gggagaggat gccacatgtc agtgtttgaa aggatttgct | 2520 |
| ggggatggaa aactatgttc tgatatagat gaatgtgaga tgggtgtccc agtgtgcccc | 2580 |
| cctgcctcct ccaagtgcat caacaccgaa ggtggttatg tctgccggtg ctcagaaggc | 2640 |
| taccaaggag atgggattca ctgtcttgat attgatgagt gccaactggg ggtgcacagc | 2700 |
| tgtggagaga atgccagctg cacaaataca gagggaggct atacctgcat gtgtgctgga | 2760 |
| cgcctgtctg aaccaggact gatttgccct gactctactc cacccctca cctcagggaa | 2820 |
| gatgaccacc actattccgt aagaaatagt gactctgaat gtccctgtc ccacgatggg | 2880 |
| tactgcctcc atgatggtgt gtgcatgtat attgaagcat tggacaagta tgcatgcaac | 2940 |
| tgtgttgttg gctacatcgg ggagcgatgt cagtaccgag acctgaagtg gtgggaactg | 3000 |
| cgccacgctg gccacgggca gcagcagaag | 3030 |

<210> SEQ ID NO 64
<211> LENGTH: 159
<212> TYPE: DNA
<213> ORGANISM: Homo sapiens

<400> SEQUENCE: 64

| | |
|---|---|
| aatagtgact ctgaatgtcc cctgtcccac gatgggtact gcctccatga tggtgtgtgc | 60 |
| atgtatattg aagcattgga caagtatgca tgcaactgtg ttgttggcta catcggggag | 120 |
| cgatgtcagt accgagacct gaagtggtgg gaactgcgc | 159 |

<210> SEQ ID NO 65
<211> LENGTH: 528
<212> TYPE: DNA
<213> ORGANISM: Homo sapiens

<400> SEQUENCE: 65

| | |
|---|---|
| gcacccactg cacccaacgg cacgctggag gccgagctgg agcgccgctg ggagagcctg | 60 |
| gtggcgctct cgttggcgcg cctgccggtg gcagcgcagc ccaaggaggc ggccgtccag | 120 |
| agcggcgccg cgactacct gctgggcatc aagcggctgc ggcggctcta ctgcaacgtg | 180 |
| ggcatcggct ccacctcca ggcgctcccc gacgccgca tcgcggcgc gcacgcggac | 240 |
| acccgcgaca gctgctgga gctctcgccc gtggagcggg gcgtggtgag catcttcggc | 300 |
| gtggccagcc ggttcttcgt ggccatgagc agcaagggca agctctatgg ctcgcccttc | 360 |

```
ttcaccgatg agtgcacgtt caaggagatt ctccttccca acaactacaa cgcctacgag    420
tcctacaagt accccggcat gttcatcgcc ctgagcaaga atgggaagac caagaagggg    480
aaccgagtgt cgcccaccat gaaggtcacc cacttcctcc ccaggctg                 528
```

<210> SEQ ID NO 66
<211> LENGTH: 459
<212> TYPE: DNA
<213> ORGANISM: Homo sapiens

<400> SEQUENCE: 66

```
tcgttggcgc gcctgccggt ggcagcgcag cccaaggagg cggccgtcca gagcggcgcc     60
ggcgactacc tgctgggcat caagcggctg cggcggctct actgcaacgt gggcatcggc    120
ttccacctcc aggcgctccc cgacggccgc atcggcggcg cgcacgcgga cacccgcgac    180
agcctgctgg agctctcgcc cgtggagcgg ggcgtggtga gcatcttcgg cgtggccagc    240
cggttcttcg tggccatgag cagcaagggc aagctctatg gctcgccctt cttcaccgat    300
gagtgcacgt tcaaggagat tctccttccc aacaactaca acgcctacga gtcctacaag    360
taccccggca tgttcatcgc cctgagcaag aatgggaaga ccaagaaggg gaaccgagtg    420
tcgcccacca tgaaggtcac ccacttcctc cccaggctg                           459
```

<210> SEQ ID NO 67
<211> LENGTH: 450
<212> TYPE: DNA
<213> ORGANISM: Homo sapiens

<400> SEQUENCE: 67

```
cgcctgccgg tggcagcgca gcccaaggag gcggccgtcc agagcggcgc cggcgactac     60
ctgctgggca tcaagcggct gcggcggctc tactgcaacg tgggcatcgg cttccacctc    120
caggcgctcc ccgacggccg catcggcggc gcgcacgcgg acacccgcga cagcctgctg    180
gagctctcgc ccgtggagcg gggcgtggtg agcatcttcg gcgtggccag ccggttcttc    240
gtggccatga gcagcaaggg caagctctat ggctcgccct tcttcaccga tgagtgcacg    300
ttcaaggaga ttctccttcc caacaactac aacgcctacg agtcctacaa gtaccccggc    360
atgttcatcg ccctgagcaa gaatgggaag accaagaagg ggaaccgagt gtcgcccacc    420
atgaaggtca cccacttcct ccccaggctg                                     450
```

<210> SEQ ID NO 68
<211> LENGTH: 417
<212> TYPE: DNA
<213> ORGANISM: Homo sapiens

<400> SEQUENCE: 68

```
gccgtccaga gcggcgccgg cgactacctg ctgggcatca agcggctgcg gcggctctac     60
tgcaacgtgg gcatcggctt ccacctccag gcgctccccg acggccgcat cggcggcgcg    120
cacgcggaca cccgcgacag cctgctggag ctctcgcccg tggagcgggg cgtggtgagc    180
atcttcggcg tggccagccg gttcttcgtg gccatgagca gcaagggcaa gctctatggc    240
tcgcccttct tcaccgatga gtgcacgttc aaggagattc cttcccaa caactacaac    300 gcctacgagt cctacaagta ccccggcatg ttcatcgccc tgagcaagaa tgggaagacc    360
aagaagggga accgagtgtc gcccaccatg aaggtcaccc acttcctccc caggctg       417
```

<210> SEQ ID NO 69
<211> LENGTH: 408
<212> TYPE: DNA

<213> ORGANISM: Homo sapiens

<400> SEQUENCE: 69

```
agcggcgccg gcgactacct gctgggcatc aagcggctgc ggcggctcta ctgcaacgtg      60
ggcatcggct tccacctcca ggcgctcccc gacggccgca tcggcggcgc gcacgcggac     120
acccgcgaca gcctgctgga gctctcgccc gtggagcggg gcgtggtgag catcttcggc     180
gtggccagcc ggttcttcgt ggccatgagc agcaagggca agctctatgg ctcgcccttc     240
ttcaccgatg agtgcacgtt caaggagatt ctccttccca caaactacaa cgcctacgag     300
tcctacaagt accccggcat gttcatcgcc ctgagcaaga atgggaagac caagaagggg     360
aaccgagtgt cgcccaccat gaaggtcacc cacttcctcc ccaggctg                  408
```

<210> SEQ ID NO 70
<211> LENGTH: 615
<212> TYPE: DNA
<213> ORGANISM: Homo sapiens

<400> SEQUENCE: 70

```
ttaggtgaag ttgggaacta tttcggtgtg caggatgcgg taccgtttgg gaatgtgccc      60
gtgttgccgg tggacagccc ggttttgtta agtgaccacc tgggtcagtc cgaagcaggg     120
gggctcccca ggggacccgc agtcacggac ttggatcatt taaaggggat tctcaggcgg     180
aggcagctat actgcaggac tggatttcac ttagaaatct tccccaatgg tactatccag     240
ggaaccagga agaccacag ccgatttggc attctggaat ttatcagtat agcagtgggc     300
ctggtcagca ttcgaggcgt ggacagtgga ctctacctcg ggatgaatga aagggggag      360
ctgtatggat cagaaaaact aacccaagag tgtgtattca gagaacagtt cgaagaaaac     420
tggtataata cgtactcgtc aaacctatat aagcacgtgg acactggaag gcgatactat     480
gttgcattaa ataaagatgg gaccccgaga gaagggacta ggactaaacg gcaccagaaa     540
ttcacacatt ttttacctag accagtggac cccgacaaag tacctgaact gtataaggat     600
attctaagcc aaagt                                                      615
```

<210> SEQ ID NO 71
<211> LENGTH: 588
<212> TYPE: DNA
<213> ORGANISM: Homo sapiens

<400> SEQUENCE: 71

```
caggatcagg gaggactggt aacggagacg gccgaccccg gggcacaggc ccagcaagga      60
ctggggtttc agaagctgcc agaggaggag ccagaaacag atctcagccc cgggctccca     120
gctgcccacc tcataggcgc tccgctgaag gggcagggc taggctggga gacgacgaag      180
gaacaggcgt ttctgacgag cgggacgcag ttctcggacg ccgaggggct ggcgctcccg     240
caggacggcc tctattacct ctactgtctc gtcggctacc ggggccgggc gccccctggc     300
ggcggggacc cccagggccg ctcggtcacg ctgcgcagct ctctgtaccg gcggggggc      360
gcctacgggc cgggcactcc cgagctgctg ctcgagggcg ccgagacggt gactccagtg     420
ctggacccgg ccaggagaca agggtacggg cctctctggt acacgagcgt ggggttcggc     480
ggcctggtgc agctccggag gggcgagagg gtgtacgtca acatcagtca ccccgatatg     540
gtggacttcg cgagagggaa gaccttcttt ggggccgtga tggtgggg                  588
```

<210> SEQ ID NO 72
<211> LENGTH: 375
<212> TYPE: DNA

-continued

<213> ORGANISM: Homo sapiens

<400> SEQUENCE: 72

```
agcatcgagg aagctgtccc cgctgtctgc aagaccagga cggtcattta cgagattcct      60
cggagtcagg tcgaccccac gtccgccaac ttcctgatct ggcccccgtg cgtggaggtg     120
aaacgctgca ccggctgctg caacacgagc agtgtcaagt gccagccctc ccgcgtccac     180
caccgcagcg tcaaggtggc caaggtggaa tacgtcagga agaagccaaa attaaaagaa     240
gtccaggtga ggttagagga gcatttggag tgcgcctgcg cgaccacaag cctgaatccg     300
gattatcggg aagaggacac gggaaggcct agggagtcag gtaaaaaacg gaaaagaaaa     360
aggttaaaac ccacc                                                      375
```

<210> SEQ ID NO 73
<211> LENGTH: 327
<212> TYPE: DNA
<213> ORGANISM: Homo sapiens

<400> SEQUENCE: 73

```
agcctgggtt ccctgaccat tgctgagccg gccatgatcg ccgagtgcaa gacgcgcacc      60
gaggtgttcg agatctcccg gcgcctcata gaccgcacca acgccaactt cctggtgtgg     120
ccgcccgtgtg tggaggtgca gcgctgctcc ggctgctgca caaccgcaa cgtgcagtgc     180
cgccccaccc aggtgcagct gcgacctgtc caggtgagaa agatcgagat tgtgcggaag     240
aagccaatct ttaagaaggc cacggtgacg ctggaagacc acctggcatg caagtgtgag     300
acagtggcag ctgcacggcc tgtgacc                                         327
```

<210> SEQ ID NO 74
<211> LENGTH: 666
<212> TYPE: DNA
<213> ORGANISM: Homo sapiens

<400> SEQUENCE: 74

```
tggacgggcg aggactcggc ggagcccaac tctgactcgg cggagtggat ccgagacatg      60
tacgccaagg tcacggagat ctggcaggag gtcatgcagc ggcgggacga cgacggcacg     120
ctccacgccg cctgccaggt gcagccgtcg gccacgctgg acgccgcgca gccccgggtg     180
accggcgtcg tcctcttccg gcagcttgcg ccccgcgcca agctcgacgc cttcttcgcc     240
ctggagggct tcccgaccga gccgaacagc tccagccgcg ccatccacgt gcaccagttc     300
ggggacctga gccagggctg cgagtccacc gggccccact acaacccgct ggccgtgccg     360
cacccgcagc acccgggcga cttcggcaac ttcgcggtcc gcgacggcag cctctggagg     420
taccgcgccg gcctggccgc ctcgctcgcg ggcccgcact ccatcgtggg ccgggccgtg     480
gtcgtccacg ctggcgagga cgacctgggc cgcggcggca accaggccag cgtggagaac     540
gggaacgcgg gccggcggct ggcctgctgc gtggtgggcg tgtgcgggcc cgggctctgg     600
gagcgccagg cgcgggagca ctcagagcgc aagaagcggc ggcgcgagag cgagtgcaag     660
gccgcc                                                                666
```

<210> SEQ ID NO 75
<211> LENGTH: 294
<212> TYPE: DNA
<213> ORGANISM: Homo sapiens

<400> SEQUENCE: 75

```
atggtcccct cggctggaca gctcgccctg ttcgctctgg gtattgtgtt ggctgcgtgc      60
```

```
caggccttgg agaacagcac gtccccgctg agtgcagacc cgcccgtggc tgcagcagtg    120
gtgtcccatt ttaatgactg cccagattcc cacactcagt tctgcttcca tggaacctgc    180 aggttttttgg tgcaggagga caagccagca tgtgtctgcc attctgggta cgttggtgca   240
cgctgtgagc atgcggacct cctggccgtg gtggctgcca gccagaagaa gcag          294

<210> SEQ ID NO 76
<211> LENGTH: 225
<212> TYPE: DNA
<213> ORGANISM: Homo sapiens

<400> SEQUENCE: 76
gagaacagca cgtccccgct gagtgcagac ccgcccgtgg ctgcagcagt ggtgtcccat     60
tttaatgact gcccagattc ccacactcag ttctgcttcc atggaacctg caggttttttg   120 gtgcaggagg acaagccagc atgtgtctgc cattctgggt acgttggtgc acgctgtgag    180
catgcggacc tcctggccgt ggtggctgcc agccagaaga agcag                     225

<210> SEQ ID NO 77
<211> LENGTH: 150
<212> TYPE: DNA
<213> ORGANISM: Homo sapiens

<400> SEQUENCE: 77
gtggtgtccc attttaatga ctgcccagat tcccacactc agttctgctt ccatggaacc    60
tgcaggtttt tggtgcagga ggacaagcca gcatgtgtct gccattctgg gtacgttggt   120
gcacgctgtg agcatgcgga cctcctggcc                                     150

<210> SEQ ID NO 78
<211> LENGTH: 399
<212> TYPE: DNA
<213> ORGANISM: Homo sapiens

<400> SEQUENCE: 78
caggtatcac atcggtatcc tcgaattcaa agtatcaaag tacaatttac cgaatataag     60
aaggagaaag gtttcatcct cacttcccaa aaggaggatg aaatcatgaa ggtgcagaac    120
aactcagtca tcatcaactg tgatgggttt tatctcatct ccctgaaggg ctacttctcc    180
caggaagtca acattagcct tcattaccag aaggatgagg agcccctctt ccaactgaag    240
aaggtcaggt ctgtcaactc cttgatggtg gcctctctga cttacaaaga caaagtctac    300
ttgaatgtga ccactgacaa tacctccctg atgacttcc atgtgaatgg cggagaactg     360
attcttatcc atcaaaatcc tggtgaattc tgtgtccctt                          399

<210> SEQ ID NO 79
<211> LENGTH: 534
<212> TYPE: DNA
<213> ORGANISM: Homo sapiens

<400> SEQUENCE: 79
atcagagcag agaaagcgat ggtggatggc tcatggttag atctggccaa gaggagcaag     60
cttgaagctc agccttttgc tcatctcact attaatgcca ccgacatccc atctggttcc    120
cataaagtga gtctgtcctc ttggtaccat gatcggggtt gggccaagat ctccaacatg    180
acttttagca atggaaaact aatagttaat caggatggct tttattacct gtatgccaac    240
atttgctttc gacatcatga acttcagga gacctagcta cagagtatct tcaactaatg    300
gtgtacgtca ctaaaaccag catcaaaatc ccaagttctc ataccctgat gaaaggagga    360
```

| | |
|---|---|
| agcaccaagt attggtcagg gaattctgaa ttccattttt attccataaa cgttggtgga | 420 |
| ttttttaagt tacggtctgg agaggaaatc agcatcgagg tctccaaccc ctccttactg | 480 |
| gatccggatc aggatgcaac atactttggg gcttttaaag ttcgagatat agat | 534 |

<210> SEQ ID NO 80
<211> LENGTH: 747
<212> TYPE: DNA
<213> ORGANISM: Homo sapiens

<400> SEQUENCE: 80

| | |
|---|---|
| tatttcagag cgcagatgga tcctaataga atatcagaag atggcactca ctgcatttat | 60 |
| agaattttga gactccatga aaatgcagat tttcaagaca caactctgga gagtcaagat | 120 |
| acaaaattaa tacctgattc atgtaggaga attaaacagg cctttcaagg agctgtgcaa | 180 |
| aaggaattac aacatatcgt tggatcacag cacatcagag cagagaaagc gatggtggat | 240 |
| ggctcatggt tagatctggc caagaggagc aagcttgaag ctcagccttt tgctcatctc | 300 |
| actattaatg ccaccgacat cccatctggt tcccataaag tgagtctgtc ctcttggtac | 360 |
| catgatcggg gttgggccaa gatctccaac atgactttta gcaatggaaa actaatagtt | 420 |
| aatcaggatg gcttttatta cctgtatgcc aacatttgct ttcgacatca tgaaacttca | 480 |
| ggagacctag ctacagagta tcttcaacta atggtgtacg tcactaaaac cagcatcaaa | 540 |
| atcccaagtt ctcatacccc tgatgaaagga ggaagcacca gtattggtc agggaattct | 600 |
| gaattccatt tttattccat aaacgttggt ggattttta agttacggtc tggagaggaa | 660 |
| atcagcatcg aggtctccaa cccctcctta ctggatccgg atcaggatgc aacatacttt | 720 |
| ggggctttta aagttcgaga tatagat | 747 |

<210> SEQ ID NO 81
<211> LENGTH: 438
<212> TYPE: DNA
<213> ORGANISM: Homo sapiens

<400> SEQUENCE: 81

| | |
|---|---|
| gcagtgctca cccaaaaaca gaagaagcag cactctgtcc tgcacctggt tcccattaac | 60 |
| gccacctcca aggatgactc cgatgtgaca gaggtgatgt ggcaaccagc tcttaggcgt | 120 |
| gggagaggcc tacaggccca aggatatggt gtccgaatcc aggatgctgg agtttatctg | 180 |
| ctgtatagcc aggtcctgtt tcaagacgtg actttcacca tgggtcaggt ggtgtctcga | 240 |
| gaaggccaag gaaggcagga gactctattc cgatgtataa gaagtatgcc ctcccacccg | 300 |
| gaccgggcct acaacagctg ctatagcgca ggtgtcttcc atttacacca agggatatt | 360 |
| ctgagtgtca taattccccg ggcaagggcg aaacttaacc tctctccaca tggaaccttc | 420 |
| ctggggtttg tgaaactg | 438 |

<210> SEQ ID NO 82
<211> LENGTH: 621
<212> TYPE: DNA
<213> ORGANISM: Homo sapiens

<400> SEQUENCE: 82

| | |
|---|---|
| agtttgggga gccgggcatc gctgtccgcc caggagcctg cccaggagga gctggtggca | 60 |
| gaggaggacc aggacccgtc ggaactgaat ccccagacag aagaaagcca ggatcctgcg | 120 |
| cctttcctga accgactagt tcggcctcgc agaagtgcac ctaaaggccg gaaaacacgg | 180 |
| gctcgaagag cgatcgcagc ccattatgaa gttcatccac gacctggaca ggacggagcg | 240 |

```
caggcaggtg tggacgggac agtgagtggc tgggaggaag ccagaatcaa cagctccagc    300
cctctgcgct acaaccgcca gatcgggag tttatagtca cccgggctgg gctctactac    360
```
```
caggcaggtg tggacgggac agtgagtggc tgggaggaag ccagaatcaa cagctccagc    300
cctctgcgct acaaccgcca gatcgggag  tttatagtca cccgggctgg gctctactac    360
ctgtactgtc aggtgcactt tgatgagggg aaggctgtct acctgaagct ggacttgctg    420
gtggatggtg tgctggccct cgctgcctg  gaggaattct cagccactgc ggcgagttcc    480
ctcgggcccc agctccgcct ctgccaggtg tctgggctgt ggccctgcg  gccagggtcc    540 tccctgcgga tccgcaccct ccctggggc  catctcaagg ctgccccctt cctcacctac    600
ttcggactct tccaggttca c                                              621

<210> SEQ ID NO 83
<211> LENGTH: 468
<212> TYPE: DNA
<213> ORGANISM: Homo sapiens

<400> SEQUENCE: 83
agtgcaccta aaggccggaa aacacgggct cgaagagcga tcgcagccca ttatgaagtt     60
catccacgac ctggacagga cggagcgcag gcaggtgtgg acgggacagt gagtggctgg    120
gaggaagcca gaatcaacag ctccagccct ctgcgctaca accgccagat cggggagttt    180
atagtcaccc gggctgggct ctactacctg tactgtcagg tgcactttga tgaggggaag    240
gctgtctacc tgaagctgga cttgctggtg gatggtgtgc tggccctgcg ctgcctggag    300
gaattctcag ccactgcggc gagttccctc gggccccagc tccgcctctg ccaggtgtct    360
gggctgttgg ccctgcggcc agggtcctcc ctgcggatcc gcaccctccc ctgggcccat    420
ctcaaggctg ccccccttcct cacctacttc ggactcttcc aggttcac               468

<210> SEQ ID NO 84
<211> LENGTH: 729
<212> TYPE: DNA
<213> ORGANISM: Homo sapiens

<400> SEQUENCE: 84
accaacgagc tgaagcagat gcaggacaag tactccaaaa gtggcattgc ttgtttctta     60
aaagaagatg acagttattg ggaccccaat gacgaagaga gtatgaacag cccctgctgg    120
caagtcaagt ggcaactccg tcagctcgtt agaaagatga ttttgagaac ctctgaggaa    180
accatttcta cagttcaaga aaagcaacaa atatttctc ccctagtgag agaaagaggt    240
cctcagagag tagcagctca cataactggg accagaggaa gaagcaacac attgtcttct    300
ccaaactcca agaatgaaaa ggctctgggc cgcaaaataa actcctggga atcatcaagg    360
agtgggcatt cattcctgag caacttgcac ttgaggaatg gtgaactggt catccatgaa    420 aaaggggtttt actacatcta ttcccaaaca tactttcgat tcaggagga  aataaaagaa    480 aacacaaaga acgacaaaca aatggtccaa tatatttaca aatacacaag ttatcctgac    540
cctatattgt tgatgaaaag tgctagaaat agttgttggt ctaaagatgc agaatatgga    600
ctctattcca tctatcaagg gggaatattt gagcttaagg aaaatgacag aattttttgtt    660 tctgtaacaa atgagcactt gatagacatg gaccatgaag ccagttttttt cggggccttt    720 ttagttggc                                                            729

<210> SEQ ID NO 85
<211> LENGTH: 615
<212> TYPE: DNA
<213> ORGANISM: Homo sapiens

<400> SEQUENCE: 85
```

```
gcctgcccct gggccgtgtc cggggctcgc gcctcgcccg gctccgcggc cagcccgaga     60
ctccgcgagg gtcccgagct ttcgcccgac gatcccgccg gcctcttgga cctgcggcag    120
ggcatgtttg cgcagctggt ggcccaaaat gttctgctga tcgatgggcc cctgagctgg    180
tacagtgacc caggcctggc aggcgtgtcc ctgacggggg gcctgagcta caaagaggac    240
acgaaggagc tggtggtggc caaggctgga gtctactatg tcttctttca actagagctg    300
cggcgcgtgg tggccggcga gggctcaggc tccgtttcac ttgcgctgca cctgcagcca    360
ctgcgctctg ctgctggggc cgccgccctg gctttgaccg tggacctgcc accgcctcc     420 tccgaggctc ggaactcggc cttcggtttc cagggccgct tgctgcacct gagtgccggc    480
cagcgcctgg gcgtccatct tcacactgag gccagggcac gccatgcctg cagcttacc     540 cagggcgcca cagtcttggg actcttccgg gtgaccccg aaatcccagc cggactccct     600
tcaccgaggt cggaa                                                    615
```

<210> SEQ ID NO 86
<211> LENGTH: 582
<212> TYPE: DNA
<213> ORGANISM: Homo sapiens

<400> SEQUENCE: 86

```
actcagggg agaatcaccc gtctcctaat tttaaccagt acgtgaggga ccagggcgcc      60
atgaccgacc agctgagcag gcggcagatc cgcgagtacc aactctacag caggaccagt    120
ggcaagcacg tgcaggtcac cgggcgtcgc atctccgcca ccgccgagga cggcaacaag    180
tttgccaagc tcatagtgga gacggacacg tttggcagcc gggttcgcat caaagggct     240 gagagtgaga agtacatctg tatgaacaag aggggcaagc tcatcgggaa gcccagcggg    300
aagagcaaag actgcgtgtt cacggagatc gtgctggaga caactatac ggccttccag     360 aacgcccggc acgagggctg gttcatggcc ttcacgcggc aggggcggcc ccgccaggct    420
tcccgcagcc gccagaacca gcgcgaggcc cacttcatca gcgcctcta ccaaggccag    480 ctgcccttcc ccaaccacgc cgagaagcag aagcagttcg agtttgtggg ctccgccccc    540
acccgccgga ccaagcgcac acggcggccc cagcccctca cg                      582
```

<210> SEQ ID NO 87
<211> LENGTH: 882
<212> TYPE: DNA
<213> ORGANISM: Homo sapiens

<400> SEQUENCE: 87

```
tgctactcgc ccagcctcaa gtcagtgcag gaccaggcgt acaaggcacc cgtggtggtg      60
gagggcaagg tacaggggct ggtcccagcc ggcggctcca gctccaacag cacccgagag    120
ccgcccgcct cgggtcgggt ggcgttggta aaggtgctgg acaagtggcc gctccggagc    180 gggggggctgc agcgcgagca ggtgatcagc gtgggctcct gtgtgccgct cgaaaggaac    240
cagcgctaca tcttttttcct ggagcccacg gaacagccct tagtctttaa gacggccttt    300
gcccccctcg ataccaacgg caaaaatctc aagaaagagg tggcaagat cctgtgcact     360 gactgcgcca cccggcccaa gttgaagaag atgaagagcc agacgggaca ggtgggtgag    420
aagcaatcgc tgaagtgtga ggcagcagcc ggtaatcccc agccttccta ccgttggttc    480
aaggatggca aggagctcaa ccgcagccga gacattcgca tcaaatatgg caacggcaga    540
aagaactcac gactacagtt caacaaggtg aaggtgagg acgctgggga gtatgtctgc    600
gaggccgaga acatcctggg gaaggacacc gtccgggggcc ggctttacgt caacagcgtg    660
```

```
agcaccaccc tgtcatcctg gtcggggcac gcccggaagt gcaacgagac agccaagtcc    720
tattgcgtca atggaggcgt ctgctactac atcgagggca tcaaccagct ctcctgcaaa    780
tgtccaaatg gattcttcgg acagagatgt ttggagaaac tgcctttgcg attgtacatg    840
ccagatccta agcaaaaagc cgaggagctg taccagaaga gg                       882

<210> SEQ ID NO 88
<211> LENGTH: 384
<212> TYPE: DNA
<213> ORGANISM: Homo sapiens

<400> SEQUENCE: 88
caattagaga ctgctaagga gccctgtatg gctaagtttg gaccattacc ctcaaaatgg    60
caaatggcat cttctgaacc tccttgcgtg aataaggtgt ctgactggaa gctggagata    120
cttcagaatg gcttatattt aatttatggc caagtggctc ccaatgcaaa ctacaatgat    180
gtagctcctt ttgaggtgcg gctgtataaa aacaaagaca tgatacaaac tctaacaaac    240
aaatctaaaa tccaaaatgt aggagggact tatgaattgc atgttgggga caccatagac    300
ttgatattca actctgagca tcaggttcta aaaaataata catactgggg tatcatttta    360
ctagcaaatc cccaattcat ctcc                                           384

<210> SEQ ID NO 89
<211> LENGTH: 318
<212> TYPE: DNA
<213> ORGANISM: Homo sapiens

<400> SEQUENCE: 89
gagaaaccct cccctgcca gtgctccagg ctgagccccc ataacaggac gaactgcggc    60
ttccctggaa tcaccagtga ccagtgtttt gacaatggat gctgtttcga ctccagtgtc    120 actgggtcc cctggtgttt cccccccctc ccaaagcaag agtcggatca gtgcgtcatg    180
gaggtctcag accgaagaaa ctgtggctac ccgggcatca gccccgagga atgcgcctct    240
cggaagtgct gcttctccaa cttcatcttt gaagtgccct ggtgcttctt cccgaagtct    300
gtggaagact gccattac                                                  318

<210> SEQ ID NO 90
<211> LENGTH: 348
<212> TYPE: DNA
<213> ORGANISM: Homo sapiens

<400> SEQUENCE: 90
gcacattata atacagagat cttgaaaagt attgataatg agtggagaaa gactcaatgc    60
atgccacggg aggtgtgtat agatgtgggg aaggagtttg gagtcgcgac aaacaccttc    120
tttaaacctc catgtgtgtc cgtctacaga tgtgggggtt gctgcaatag tgaggggctg    180
cagtgcatga acaccagcac gagctacctc agcaagacgt tatttgaaat tacagtgcct    240
ctctctcaag gccccaaacc agtaacaatc agttttgcca atcacacttc ctgccgatgc    300
atgtctaaac tggatgttta cagacaagtt cattccatta ttagacgt                 348

<210> SEQ ID NO 91
<211> LENGTH: 39
<212> TYPE: DNA
<213> ORGANISM: Homo sapiens

<400> SEQUENCE: 91
cagctgtatg agaataaacc cagaagaccc tacatactc                            39
```

<210> SEQ ID NO 92
<211> LENGTH: 375
<212> TYPE: DNA
<213> ORGANISM: Homo sapiens

<400> SEQUENCE: 92

```
tcagattcag aagaggaaat gaaagcatta gaagcagatt tcttgaccaa tatgcataca      60
tcaaagatta gtaaagcaca tgttccctct tggaagatga ctctgctaaa tgtttgcagt     120
cttgtaaata atttgaacag cccagctgag gaaacaggag aagttcatga agaggagctt     180
gttgcaagaa ggaaacttcc tactgcttta gatggcttta gcttggaagc aatgttgaca     240
atataccagc tccacaaaat ctgtcacagc agggcttttc aacactggga gttaatccag     300
gaagatattc ttgatactgg aaatgacaaa atggaaagg aagaagtcat aaagagaaaa      360
attccttata ttctg                                                       375
```

<210> SEQ ID NO 93
<211> LENGTH: 456
<212> TYPE: DNA
<213> ORGANISM: Homo sapiens

<400> SEQUENCE: 93

```
gccgttcagg gtccagaaga aacagtcact caagactgct tgcaactgat tgcagacagt      60
gaaacaccaa ctatacaaaa aggatcttac acatttgttc catggcttct cagctttaaa     120
aggggaagtg ccctagaaga aaagagaat aaaatattgg tcaaagaaac tggttacttt      180
tttatatatg gtcaggtttt atatactgat aagacctacg ccatgggaca tctaattcag     240
aggaagaagg tccatgtctt tggggatgaa ttgagtctgg tgactttgtt tcgatgtatt     300
caaaatatgc ctgaaacact acccaataat tcctgctatt cagctggcat tgcaaaactg     360
gaagaaggag atgaactcca acttgcaata ccaagagaaa atgcacaaat atcactggat     420
ggagatgtca cattttttgg tgcattgaaa ctgctg                                456
```

<210> SEQ ID NO 94
<211> LENGTH: 654
<212> TYPE: DNA
<213> ORGANISM: Homo sapiens

<400> SEQUENCE: 94

```
caggtggccg ccctgcaagg ggacctggcc agcctccggg cagagctgca gggccaccac      60
gcggagaagc tgccagcagg agcaggagcc cccaaggccg gctggagga agctccagct      120
gtcaccgcgg gactgaaaat cttttgaacca ccagctccag gagaaggcaa ctccagtcag     180
aacagcagaa ataagcgtgc cgttcagggt ccagaagaaa cagtcactca agactgcttg     240
caactgattg cagacagtga aacaccaact atacaaaaag gatcttacac atttgttcca     300
tggcttctca gctttaaaag gggaagtgcc ctagaagaaa agagaataa atattggtc       360
aaagaaactg gttactttt tatatatggt caggttttat atactgataa gacctacgcc      420
atgggacatc taattcagag gaagaaggtc catgtctttg gggatgaatt gagtctggtg     480
actttgtttc gatgtattca aaatatgcct gaaacactac ccaataattc ctgctattca     540
gctggcattg caaaactgga agaaggagat gaactccaac ttgcaatacc aagagaaaat     600
gcacaaatat cactggatgg agatgtcaca ttttttggtg cattgaaact gctg            654
```

<210> SEQ ID NO 95
<211> LENGTH: 693
<212> TYPE: DNA

<213> ORGANISM: Homo sapiens

<400> SEQUENCE: 95

| | | | | | |
|---|---|---|---|---|---|
| accaggatca | tcaagggggtt | cgagtgcaag | cctcactccc | agccctggca | ggcagccctg | 60 |
| ttcgagaaga | cgcggctact | ctgtggggcg | acgctcatcg | ccccagatg | gctcctgaca | 120 |
| gcagcccact | gcctcaagcc | ccgctacata | gttcacctgg | ggcagcacaa | cctccagaag | 180 |
| gaggagggct | gtgagcagac | ccggacagcc | actgagtcct | tcccccaccc | cggcttcaac | 240 |
| aacagcctcc | ccaacaaaga | ccaccgcaat | gacatcatgc | tggtgaagat | ggcatcgcca | 300 |
| gtctccatca | cctgggctgt | gcgacccctc | accctctcct | cacgctgtgt | cactgctggc | 360 |
| accagctgcc | tcatttccgg | ctggggcagc | acgtccagcc | cccagttacg | cctgcctcac | 420 |
| accttgcgat | gcgccaacat | caccatcatt | gagcaccaga | agtgtgagaa | cgcctacccc | 480 |
| ggcaacatca | cagacaccat | ggtgtgtgcc | agcgtgcagg | aaggggggcaa | ggactcctgc | 540 |
| cagggtgact | ccgggggccc | tctggtctgt | aaccagtctc | ttcaaggcat | tatctcctgg | 600 |
| ggccaggatc | cgtgtgcgat | cacccgaaag | cctggtgtct | acacgaaagt | ctgcaaatat | 660 |
| gtggactgga | tccaggagac | gatgaagaac | aat | | | 693 |

<210> SEQ ID NO 96
<211> LENGTH: 588
<212> TYPE: DNA
<213> ORGANISM: Homo sapiens

<400> SEQUENCE: 96

| | | | | | |
|---|---|---|---|---|---|
| gacaagatct | ttgaatatga | ctctcctact | caccttgacc | ctggggggtt | aggccaggac | 60 |
| cctattattt | ctctggacgc | aactgctgcc | tcagctgtgt | gggtgtcgtc | tgaggcatac | 120 |
| acttcacctg | tctctagggc | tcaatctgaa | agtgaggttc | aagttacagt | gcaaggtgac | 180 |
| aaggctgttg | tctcctttga | accatcagcg | gcaccgacac | cgaagaatcg | tatttttgcc | 240 |
| ttttctttct | tgccgtccac | tgcgccatcc | ttcccttcac | ccacccggaa | ccctgaggtg | 300 |
| agaacgccca | gtcagcaac | tcagccacaa | acaacagaaa | ctaatctcca | aactgctcct | 360 |
| aaactttcta | catctacatc | caccactggg | acaagccatc | ttgtaaaatg | tgcggagaag | 420 |
| gagaaaactt | tctgtgtgaa | tggagggggag | tgcttcatgg | tgaaagacct | ttcaaacccc | 480 |
| tcgagatact | tgtgcaagtg | cccaaatgag | tttactggtg | atcgctgcca | aaactacgta | 540 |
| atggccagct | tctacagtac | gtccactccc | tttctgtctc | tgcctgaa | | 588 |

<210> SEQ ID NO 97
<211> LENGTH: 195
<212> TYPE: DNA
<213> ORGANISM: Homo sapiens

<400> SEQUENCE: 97

| | | | | | |
|---|---|---|---|---|---|
| agccatcttg | taaaatgtgc | ggagaaggag | aaaactttct | gtgtgaatgg | aggggagtgc | 60 |
| ttcatggtga | aagacctttc | aaaccccctcg | agatacttgt | gcaagtgcca | acctggattc | 120 |
| actggagcaa | gatgtactga | gaatgtgccc | atgaaagtcc | aaaaccaaga | aaaggcggag | 180 |
| gagctgtacc | agaag | | | | | 195 |

<210> SEQ ID NO 98
<211> LENGTH: 669
<212> TYPE: DNA
<213> ORGANISM: Homo sapiens

<400> SEQUENCE: 98

| | |
|---|---|
| ggctccggca agaagccgga gtccgcggcg ggcagccaga gcccagcctt gcctccccga | 60 |
| ttgaaagaga tgaaaagcca ggaatcggct gcaggttcca aactagtcct tcggtgtgaa | 120 |
| accagttctg aatactcctc tctcagattc aagtggttca agaatgggaa tgaattgaat | 180 |
| cgaaaaaaca aaccacaaaa tatcaagata caaaaaaagc cagggaagtc agaacttcgc | 240 |
| attaacaaag catcactggc tgattctgga gagtatatgt gcaaagtgat cagcaaatta | 300 |
| ggaaatgaca gtgcctctgc caatatcacc atcgtggaat caaacgagat catcactggt | 360 |
| atgccagcct caactgaagg agcatatgtg tcttcagagt ctcccattag aatatcagta | 420 |
| tccacagaag gagcaaatac ttcttcatct acatctacat ccaccactgg gacaagccat | 480 |
| cttgtaaaat gtgcggagaa ggagaaaact ttctgtgtga atggagggga gtgcttcatg | 540 |
| gtgaaagacc tttcaaaccc ctcgagatac ttgtgcaagt gccaacctgg attcactgga | 600 |
| gcaagatgta ctgagaatgt gcccatgaaa gtccaaaacc aagaaaaggc ggaggagctg | 660 |
| taccagaag | 669 |

<210> SEQ ID NO 99
<211> LENGTH: 1329
<212> TYPE: DNA
<213> ORGANISM: Homo sapiens

<400> SEQUENCE: 99

| | |
|---|---|
| ccaacatggt atgcaggttc tggctactat ccggatgaaa gctacaatga agtatatgca | 60 |
| gaggaggtcc cacaggctcc tgccctggac taccgagtcc cccgatggtg ttatacatta | 120 |
| aatatccagg atgcagaagc cacatgctac tcaccgaagg gaggaaatta tcacagcagc | 180 |
| ctggcacgc gttgtgagct ctcctgtgac cggggctttc gattgattgg aaggaggtcg | 240 |
| gtgcaatgcc tgccaagccg tcgttggtct ggaactgcct actgcaggca gatgagatgc | 300 |
| cacgcactac cattcatcac tagtggcact tacacctgca caaatggagt gcttcttgac | 360 |
| tctcgctgtg actacagctg ttccagtggc taccacctgg aaggtgatcg cagccgaatc | 420 |
| tgcatggaag atgggagatg gagtggaggc gagcctgtat gtgtagacat agatccccc | 480 |
| aagatccgct gtcccactc acgtgagaag atggcagagc cagagaaatt gactgctcga | 540 |
| gtatactggg acccaccgtt ggtgaaagat tctgctgatg gtaccatcac cagggtgaca | 600 |
| cttcggggcc ctgagcctgg ctctcacttt cccgaaggag agcatgtgat tcgttacact | 660 |
| gcctatgacc gagcctacaa ccgggccagc tgcaagttca ttgtgaaagt acaagtgaga | 720 |
| cgctgcccaa ctctgaaacc tccgcagcac ggctacctca cctgcacctc agcggggac | 780 |
| aactatggtg ccacctgtga ataccactgt gatggcggtt atgatcgcca ggggacaccc | 840 |
| tcccgggtct gtcagtccag ccgccagtgg tcaggttcac caccaatctg tgctcctatg | 900 |
| aagattaacg tcaacgtcaa ctcagctgct ggtctcttgg atcaattcta tgagaaacag | 960 |
| cgactcctca tcatctcagc tcctgatcct tccaaccgat attataaaat gcagatctct | 1020 |
| atgctacagc aatccaccctg tggactggat ttgcggcatg tgaccatcat tgaactggtg | 1080 |
| ggacagccac ctcaggaggt ggggcgcatc cgggagcaac agctgtcagc caacatcatc | 1140 |
| gaggagctca ggcaatttca gcgcctcact cgctcctact tcaacatggt gttgattgac | 1200 |
| aagcagggta ttgaccgaga ccgctacatg gaacctgtca cccccgagga aatcttcaca | 1260 |
| ttcattgatg actacctact gagcaatcag gagttgaccc agcgtcggga gcaaagggac | 1320 |
| atatgcgag | 1329 |

<210> SEQ ID NO 100

<211> LENGTH: 993
<212> TYPE: DNA
<213> ORGANISM: Homo sapiens

<400> SEQUENCE: 100

| | | | | | |
|---|---|---|---|---|---|
| ggccagagac | aggggactca | ggcggaatcc | aacctgagta | gtaaattcca | gttttccagc | 60 |
| aacaaggaac | agaacggagt | acaagatcct | cagcatgaga | gaattattac | tgtgtctact | 120 |
| aatggaagta | ttcacagccc | aaggtttcct | catacttatc | caagaaatac | ggtcttggta | 180 |
| tggagattag | tagcagtaga | ggaaaatgta | tggatacaac | ttacgtttga | tgaaagattt | 240 |
| gggcttgaag | acccagaaga | tgacatatgc | aagtatgatt | tgtagaagt | tgaggaaccc | 300 |
| agtgatggaa | ctatattagg | gcgctggtgt | ggttctggta | ctgtaccagg | aaaacagatt | 360 |
| tctaaaggaa | atcaaattag | gataagattt | gtatctgatg | aatattttcc | ttctgaacca | 420 |
| gggttctgca | tccactacaa | cattgtcatg | ccacaattca | cagaagctgt | gagtccttca | 480 |
| gtgctacccc | cttcagcttt | gccactggac | ctgcttaata | atgctataac | tgcctttagt | 540 |
| accttggaag | accttattcg | atatcttgaa | ccagagagat | ggcagttgga | cttagaagat | 600 |
| ctatataggc | caacttggca | acttcttggc | aaggcttttg | ttttggaag | aaaatccaga | 660 |
| gtggtggatc | tgaaccttct | aacagaggag | gtaagattat | acagctgcac | acctcgtaac | 720 |
| ttctcagtgt | ccataaggga | agaactaaag | agaaccgata | ccattttctg | gccaggttgt | 780 |
| ctcctggtta | aacgctgtgg | tgggaactgt | gcctgttgtc | tccacaattg | caatgaatgt | 840 |
| caatgtgtcc | caagcaaagt | tactaaaaaa | taccacgagg | tccttcagtt | gagaccaaag | 900 |
| accggtgtca | ggggattgca | caaatcactc | accgacgtgg | ccctggagca | ccatgaggag | 960 |
| tgtgactgtg | tgtgcagagg | gagcacagga | gga | | | 993 |

<210> SEQ ID NO 101
<211> LENGTH: 576
<212> TYPE: DNA
<213> ORGANISM: Homo sapiens

<400> SEQUENCE: 101

| | | | | | |
|---|---|---|---|---|---|
| caggtgggtt | cgcatttcct | gttgcctcct | gccggggagc | ggccgccgct | gctgggcgag | 60 |
| cgcaggagcg | cggcggagcg | gagcgcccgc | ggcgggccgg | gggctgcgca | gctggcgcac | 120 |
| ctgcacggca | tcctgcgccg | ccggcagctc | tattgccgca | ccggcttcca | cctgcagatc | 180 |
| ctgcccgacg | gcagcgtgca | gggcacccgg | caggaccaca | gcctcttcgg | tatcttggaa | 240 |
| ttcatcagtg | tggcagtggg | actggtcagt | attagaggtg | tggacagtgg | tctctatctt | 300 |
| ggaatgaatg | acaaaggaga | actctatgga | tcagagaaac | ttacttccga | atgcatcttt | 360 |
| agggagcagt | ttgaagagaa | ctggtataac | acctattcat | ctaacatata | taaacatgga | 420 |
| gacactggcc | gcaggtattt | tgtggcactt | aacaaagacg | gaactccaag | agatggcgcc | 480 |
| aggtccaaga | ggcatcagaa | atttacacat | ttcttaccta | gaccagtgga | tccagaaaga | 540 |
| gttccagaat | tgtacaagga | cctactgatg | tacact | | | 576 |

<210> SEQ ID NO 102
<211> LENGTH: 552
<212> TYPE: DNA
<213> ORGANISM: Homo sapiens

<400> SEQUENCE: 102

| | | | | | |
|---|---|---|---|---|---|
| gcggctatag | gcagctgctc | gaaagagtac | cgcgtgctcc | ttggccagct | ccagaagcag | 60 |
| acagatctca | tgcaggacac | cagcagactc | ctggacccct | atatacgtat | ccaaggcctg | 120 |

```
gatgttccta aactgagaga gcactgcagg gagcgccccg gggccttccc cagtgaggag      180
accctgaggg ggctgggcag gcggggcttc ctgcagaccc tcaatgccac actgggctgc      240
gtcctgcaca gactggccga cttagagcag cgcctcccca aggcccagga tttggagagg      300
tctgggctga acatcgagga cttggagaag ctgcagatgg cgaggccgaa catcctcggg      360
ctcaggaaca acatctactg catggcccag ctgctggaca actcagacac ggctgagccc      420
acgaaggctg gccgggggc ctctcagccg cccaccccca cccctgcctc ggatgctttt       480
cagcgcaagc tggagggctg caggttcctg catggctacc atcgcttcat gcactcagtg      540
gggcgggtct tc                                                          552

<210> SEQ ID NO 103
<211> LENGTH: 627
<212> TYPE: DNA
<213> ORGANISM: Homo sapiens

<400> SEQUENCE: 103
gcggctatag gcagctgctc gaaagagtac cgcgtgctcc ttggccagct ccagaagcag       60
acagatctca tgcaggacac cagcagactc ctggacccct atatacgtat ccaaggcctg      120
gatgttccta aactgagaga gcactgcagg gagcgccccg gggccttccc cagtgaggag      180
accctgaggg ggctgggcag gcggggcttc ctgcagaccc tcaatgccac actgggctgc      240
gtcctgcaca gactggccga cttagagcag cgcctcccca aggcccagga tttggagagg      300
tctgggctga acatcgagga cttggagaag ctgcagatgg cgaggccgaa catcctcggg      360
ctcaggaaca acatctactg catggcccag ctgctggaca actcagacac ggctgagccc      420
acgaaggctg gccgggggc ctctcagccg cccaccccca cccctgcctc ggatgctttt       480
cagcgcaagc tggagggctg caggttcctg catggctacc atcgcttcat gcactcagtg      540
gggcgggtct tcagcaagtg gggggagagc ccgaaccgga gccggagaca cagcccccac      600
caggccctga ggaagggggt gcgcagg                                          627

<210> SEQ ID NO 104
<211> LENGTH: 513
<212> TYPE: DNA
<213> ORGANISM: Homo sapiens

<400> SEQUENCE: 104
tcgcctgcag gcacccgtgc caacaacacg ctgctggact cgaggggctg gggcaccctg       60
ctgtccaggt ctcgcgcggg gctagctgga gagattgccg gggtgaactg gaaagtggc      120 tatttggtgg ggatcaagcg gcagcggagg ctctactgca acgtgggcat cggctttcac      180
ctccaggtgc tccccgacgg ccggatcagc gggacccacg aggagaaccc ctacagcctg      240
ctggaaattt ccactgtgga gcgaggcgtg gtgagtctct ttggagtgag aagtgccctc      300
ttcgttgcca tgaacagtaa aggaagattg tacgcaacgc ccagcttcca agaagaatgc      360
aagttcagag aaaccctcct gcccaacaat tacaatgcct acgagtcaga cttgtaccaa      420 ggacctaca ttgcccctgag caaatacgga cgggtaaagc ggggcagcaa ggtgtccccg      480
atcatgactg tcactcattt ccttcccagg atc                                  513

<210> SEQ ID NO 105
<211> LENGTH: 1056
<212> TYPE: DNA
<213> ORGANISM: Homo sapiens

<400> SEQUENCE: 105
```

```
cgggacactt ctgcaacccc gcagagcgca tccatcaaag ctttgcgcaa cgccaacctc    60
aggcgagatg agagcaatca cctcacagac ttgtaccgaa gagatgagac catccaggtg   120
aaaggaaacg gctacgtgca gagtcctaga ttcccgaaca gctacccag gaacctgctc    180 ctgacatggc ggcttcactc tcaggagaat acacggatac agctagtgtt tgacaatcag   240
tttggattag aggaagcaga aaatgatatc tgtaggtatg attttgtgga agttgaagat   300
atatccgaaa ccagtaccat tattagagga cgatggtgtg gacacaagga agttcctcca   360
aggataaaat caagaacgaa ccaaattaaa atcacattca agtccgatga ctactttgtg   420
gctaaacctg gattcaagat ttattattct ttgctggaag atttccaacc cgcagcagct   480
tcagagacca actgggaatc tgtcacaagc tctatttcag gggtatccta taactctcca   540
tcagtaacgg atcccactct gattgcggat gctctggaca aaaaaattgc agaatttgat   600
acagtggaag atctgctcaa gtacttcaat ccagagtcat ggcaagaaga tcttgagaat   660
atgtatctgg acacccctcg gtatcgaggc aggtcatacc atgaccggaa gtcaaaagtt   720
gacctggata ggctcaatga tgatgccaag cgttacagtt gcactcccag gaattactcg   780
gtcaatataa gagaagagct gaagttggcc aatgtggtct tctttccacg ttgcctcctc   840
gtgcagcgct gtggaggaaa ttgtggctgt ggaactgtca actggaggtc ctgcacatgc   900
aattcaggga aaaccgtgaa aaagtatcat gaggtattac agtttgagcc tggccacatc   960
aagaggaggg gtagagctaa gaccatggct ctagttgaca tccagttgga tcaccatgaa  1020
cgatgtgatt gtatctgcag ctcaagacca cctcga                           1056
```

<210> SEQ ID NO 106
<211> LENGTH: 984
<212> TYPE: DNA
<213> ORGANISM: Homo sapiens

<400> SEQUENCE: 106

```
tcgctggctg ttgggccaca gtattcctcc ctgggctcgc agcccatcct gtgtgccagc    60
atcccgggcc tggtccccaa gcagctccgc ttctgcagga actacgtgga gatcatgccc   120
agcgtggccg agggcatcaa gattggcatc caggagtgcc agcaccagtt ccgcggccgc   180
cggtggaact gcaccaccgt ccacgacagc ctggccatct tcgggcccgt gctggacaaa   240
gctaccaggg agtcggcctt tgtccacgcc attgcctcag ccggtgtggc ctttgcagtg   300
acacgctcat gtgcagaagg cacggccgcc atctgtggct gcagcagccg ccaccagggc   360
tcaccaggca agggctggaa gtggggtggc tgtagcgagg acatcgagtt tggtgggatg   420
gtgtctcggg agttcgccga cgcccgggag aaccggccag atgcccgctc agccatgaac   480
cgccacaaca acgaggctgg gcgccaggcc atcgccagcc acatgcacct caagtgcaag   540
tgccacgggc tgtcgggcag ctgcgaggtg aagacatgct ggtggtcgca acccgacttc   600
cgcgccatcg tgacttcct caaggacaag tacgacagcg cctcggagat ggtggtggag   660
aagcaccggg agtcccgcgg ctgggtggag accctgcggc cgcgctacac ctacttcaag   720
gtgcccacgg agcgcgacct ggtctactac gaggcctcgc ccaacttctg cgagcccaac   780
cctgagacgg gctccttcgg cacgcgcgac cgcacctgca acgtcagctc gcacggcatc   840
gacggctgcg acctgctgtg ctgcggccgc ggccacaacg cgcgagcgga gcggcgccgg   900
gagaagtgcc gctgcgtgtt ccactggtgc tgctacgtca gctgccagga gtgcacgcgc   960
gtctacgacg tgcacacctg caag                                         984
```

<210> SEQ ID NO 107

```
<211> LENGTH: 633
<212> TYPE: DNA
<213> ORGANISM: Homo sapiens

<400> SEQUENCE: 107
caggaaggcc cgggcagggg ccctgcgctg ggcagggagc tcgcttccct gttccgggct      60
ggccgggagc cccagggtgt ctcccaacag gtaactgttc agtcctcacc taattttaca     120
cagcatgtga gggagcagag cctggtgacg gatcagctca gccgccgcct catccggacc     180
taccaactct acagccgcac cagcgggaag cacgtgcagg tcctggccaa caagcgcatc     240
aacgccatgg cagaggacgg cgaccccttc gcaaagctca tcgtggagac ggacaccttt     300
ggaagcagag tccgagtccg aggagccgag acgggcctct acatctgcat gaacaagaag     360
gggaagctga tcgccaagag caacggcaaa ggcaaggact cgtcttcac ggagattgtg       420 ctggagaaca actacacagc gctgcagaat gccaagtacg agggctggta catggccttc     480
acccgcaagg gccggccccg caagggctcc aagacgcggc agcaccagcg tgaggtccac     540
ttcatgaagc ggctgccccg gggccaccac accaccgagc agagcctgcg cttcgagttc     600
ctcaactacc cgcccttcac gcgcagcctg cgc                                  633

<210> SEQ ID NO 108
<211> LENGTH: 186
<212> TYPE: DNA
<213> ORGANISM: Homo sapiens

<400> SEQUENCE: 108
atgccaacag atcacgaaga gccctgtggt cccagtcaca agtcgttttg cctgaatggg      60
gggctttgtt atgtgatacc tactattccc agcccatttt gtaggtgcgt tgaaaactat     120
acaggagctc gttgtgaaga ggttttctc ccaggctcca gcatccaaac taaaagtaac      180
ctgttt                                                                186

<210> SEQ ID NO 109
<211> LENGTH: 696
<212> TYPE: DNA
<213> ORGANISM: Homo sapiens

<400> SEQUENCE: 109
gagaccagga tcatcaaggg gttcgagtgc aagcctcact cccagccctg gcaggcagcc      60
ctgttcgaga agacgcggct actctgtggg gcgacgctca tcgccccag atggctcctg      120 acagcagccc actgcctcaa gcccgctac atagttcacc tggggcagca aacctccag       180 aaggaggagg gctgtgagca gacccggaca gccactgagt ccttcccca ccccggcttc      240 aacaacagcc tccccaacaa agaccaccgc aatgacatca tgctggtgaa gatggcatcg     300
ccagtctcca tcacctgggc tgtgcgaccc ctcaccctct cctcacgctg tgtcactgct     360
ggcaccagct gcctcatttc cggctgggc agcacgtcca gccccagtt acgcctgcct       420 cacaccttgc gatgcgccaa catcaccatc attgagcacc agaagtgtga gaacgcctac     480
cccggcaaca tcagacacac catggtgtgt gccagcgtgc aggaagggggg caaggactcc     540 tgccagggtg actccggggg ccctctggtc tgtaaccagt ctcttcaagg cattatctcc     600
tggggccagg atccgtgtgc gatcacccga aagcctggtg tctacacgaa agtctgcaaa     660
tatgtggact ggatccagga gacgatgaag aacaat                               696

<210> SEQ ID NO 110
<211> LENGTH: 2904
<212> TYPE: DNA
```

<213> ORGANISM: Homo sapiens

<400> SEQUENCE: 110

```
cggctggccg ggggcagcgg gctcccaggg tcagtcgacg tggatgagtg ctcagagggc      60
acagatgact gccacatcga tgccatctgt cagaacgcgc ccaagtccta caaatgcctc     120
tgcaagccag gctacaaggg ggaaggcaag cagtgtggag acattgacga gtgtgagaat     180
gactactaca atgggggctg tgtccacgag tgcatcaaca tcccggggaa ctacaggtgt     240
acctgctttg atggcttcat gctggcacac gatggacaca actgcctgga tgtggacgag     300
tgtcaggaca taatggtgg ctgccagcag atctgcgtca atgccatggg cagctacgag      360
tgtcagtgcc acagtggctt cttccttagt gacaaccagc atacctgcat ccaccgctcc     420
aatgagggta tgaactgcat gaacaaagac catggctgtg cccacatctg ccgggagacg     480
cccaaaggtg gggtggcctg cgactgcagg cccggctttg accttgccca aaaccagaag     540
gactgcacac taacctgtaa ttatggaaac ggaggctgcc agcacagctg tgaggacaca     600
gacacaggcc ccacgtgtgg ttgccaccag aagtacgccc ccactcaga cggtcgcacg       660
tgcatcgaga cgtgcgcagt caataacgga ggctgcgacc ggacatgcaa ggacacagcc     720
actggcgtgc gatgcagctg ccccgttgga ttcacactgc agccggacgg aagacatgc      780
aaagacatca cgagtgcct ggtcaacaac ggaggctgcg accacttctg ccgcaacacc       840
gtaggcagct tcgagtgcgg ctgccggaag ggctacaagc tgctcaccga cgagcgcacc     900
tgccaggaca tcgacgagtg ctccttcgag cggacctgtg accacatctg catcaactcc     960
ccgggcagct tccagtgcct gtgtcaccgc ggctacatcc tctacgggac aacccactgc    1020
ggagatgtgg acgagtgcag catgagcaac gggagctgtg accagggctg cgtcaacacc    1080
aagggcagct acgagtgcgt ctgtccccg gggaggcggc tccactggaa ccggaaggat      1140
tgcgtggaga caggcaagtg tcttttctcgc gccaagacct ccccccgggc ccagctgtcc    1200
tgcagcaagg caggcggtgt ggagagctgc ttcctttcct gcccggctca cacactcttc    1260
gtgccagact cggaaaatag ctacgtcctg agctgcggag ttccagggcc gcagggcaag    1320
gcgctgcaga acgcaacgg caccagctct ggcctcgggc ccagctgctc agatgccccc     1380
accaccccca tcaaacagaa ggcccgcttc aagatccgag atgccaagtg ccacctccgg    1440
ccccacagcc aggcacgagc aaaggagacc gccaggcagc cgctgctgga ccactgccat    1500
gtgactttcg tgaccctcaa gtgtgactcc tccaagaaga ggcgccgtgg ccgcaagtcc    1560
ccatccaagg aggtgtccca cattacagca gagtttgaga tcgagacaaa gatgcaagag    1620
gcctcagaca catgcgaagc ggactgcttg cggaagcgag cagaacagag cctgcaggcc    1680
gccatcaaga ccctgcgcaa gtccatcggc cggcagcagt tctatgtcca ggtctcaggc    1740
actgagtacg aggtagccca gaggccagcc aaggcgctgg agggggaggg gcatgtggc     1800
gcaggccagg tgctacagga cagcaaatgc gttgcctgtg ggcctggcac ccacttcggt    1860
ggtgagctcg ccagtgtgt gccatgtatg ccaggaacat accaggacat ggaaggccag     1920
ctcagttgca caccgtgccc cagcagcgac gggcttggtc tgcctggtgc ccgcaacgtg    1980
tcggaatgtg gaggccagtg ttctccaggc ttcttctcgg ccgatggctt caagccctgc    2040
caggcctgcc ccgtgggcac gtaccagcct gagcccgggc gcaccggctg cttccctgt     2100
ggaggggggtt tgctcaccaa acacgaaggc accacctcct tccaggactg cgaggctaaa    2160
gtgcactgct ccccccggcca ccactacaac accaccaccc accgctgcat ccgctgcccc    2220
gtcggcacct accagcccga gtttggccag aaccactgca tcacctgtcc gggcaacacc    2280
```

| | |
|---|---|
| agcacagact tcgatggctc caccaacgtc acacactgca aaaaccagca ctgcggcggc | 2340 |
| gagcttggtg actacaccgg ctacatcgag tcccccaact accctggcga ctacccagcc | 2400 |
| aacgctgaat gcgtctggca catcgcacct cccccaaagc gcaggatcct catcgtggtc | 2460 |
| cctgagatct tcctgcccat cgaggatgag tgcggcgatg ttctggtcat gaggaagagt | 2520 |
| gcctctccca cgtccatcac cacctatgag acctgccaga cctacgagag gcccatcgcc | 2580 |
| ttcacctccc gctcccgcaa gctctggatc cagttcaaat ccaatgaagg caacagcggc | 2640 |
| aaaggcttcc aagtgcccta tgtcacctac gatgaggact accagcaact catagaggac | 2700 |
| atcgtgcgcg atgggcgcct gtacgcctcg gagaaccacc aggaaatttt gaaagacaag | 2760 |
| aagctgatca aggccctctt cgacgtgctg gcgcatcccc agaactactt caagtacaca | 2820 |
| gcccaggaat ccaaggagat gttcccacgg tccttcatca aactgctgcg ctccaaagtg | 2880 |
| tctcggttcc tgcggcccta caaa | 2904 |

<210> SEQ ID NO 111
<211> LENGTH: 468
<212> TYPE: DNA
<213> ORGANISM: Homo sapiens

<400> SEQUENCE: 111

| | |
|---|---|
| atggcagccg ggagcatcac cacgctgccc gccttgcccg aggatggcgg cagcggcgcc | 60 |
| ttcccgcccg gccacttcaa ggaccccaag cggctgtact gcaaaaacgg gggcttcttc | 120 |
| ctgcgcatcc accccgacgg ccgagttgac ggggtccggg agaagagcga ccctcacatc | 180 |
| aagctacaac ttcaagcaga agagagagga gttgtgtcta tcaaaggagt gtgtgctaac | 240 |
| cgttacctgg ctatgaagga agatggaaga ttactggctt ctaaatgtgt tacggatgag | 300 |
| tgtttctttt ttgaacgatt ggaatctaat aactacaata cttaccggtc aaggaaatac | 360 |
| accagttggt atgtggcact gaaacgaact gggcagtata aacttggatc caaaacagga | 420 |
| cctgggcaga aagctatact tttcttcca atgtctgcta agagctga | 468 |

<210> SEQ ID NO 112
<211> LENGTH: 1173
<212> TYPE: DNA
<213> ORGANISM: Homo sapiens

<400> SEQUENCE: 112

| | |
|---|---|
| atgccgccct ccgggctgcg gctgctgctg ctgctgctac cgctgctgtg gctactggtg | 60 |
| ctgacgcctg gccggccggc cgcgggacta tccacctgca agactatcga catggagctg | 120 |
| gtgaagcgga agcgcatcga ggccatccgc ggccagatcc tgtccaagct gcggctcgcc | 180 |
| agcccccga gccaggggga ggtgccgccc ggccgctgc cgaggccgt gctcgccctg | 240 |
| tacaacagca cccgcgaccg ggtggccggg agagtgcag aaccggagcc cgagcctgag | 300 |
| gccgactact acgccaagga ggtcaccgc gtgctaatgg tggaaacccca aacgaaatc | 360 |
| tatgacaagt tcaagcagag tacacacagc atatatatgt tcttcaacac atcagagctc | 420 |
| cgagaagcgg tacctgaacc cgtgttgctc tcccggcag agctgcgtct gctgaggctc | 480 |
| aagttaaaag tggagcagca cgtggagctg taccagaaat acagcaacaa ttcctggcga | 540 |
| tacctcagca accggctgct ggcacccagc gactcgccag agtggttatc ttttgatgtc | 600 |
| accggagttg tgcggcagtg gttgagccgt ggaggggaaa ttgagggctt tcgccttagc | 660 |
| gcccactgct cctgtgacag cagggataac acactgcaag tggacatcaa cgggttcact | 720 |
| accggccgcc gaggtgacct ggccaccatt catggcatga accggccttt cctgcttctc | 780 |

| | |
|---|---|
| atggccaccc cgctggagag ggcccagcat ctgcaaagct cccggcaccg ccgagccctg | 840 |
| gacaccaact attgcttcag ctccacggag aagaactgct gcgtgcggca gctgtacatt | 900 |
| gacttccgca aggacctcgg ctggaagtgg atccacgagc caagggcta ccatgccaac | 960 |
| ttctgcctcg ggcccgcgcc ctacatttgg agcctggaca cgcagtacag caaggtcctg | 1020 |
| gccctgtaca accagcataa cccgggcgcc tcggcggcgc cgtgctgcgt gccgcaggcg | 1080 |
| ctggagccgc tgcccatcgt gtactacgtg ggccgcaagc ccaaggtgga gcagctgtcc | 1140 |
| aacatgatcg tgcgctcctg caagtgcagc tga | 1173 |

<210> SEQ ID NO 113
<211> LENGTH: 807
<212> TYPE: DNA
<213> ORGANISM: Homo sapiens

<400> SEQUENCE: 113

| | |
|---|---|
| atgagcttgt ccttcctcct cctcctcttc ttcagccacc tgatcctcag cgcctgggct | 60 |
| cacggggaga agcgtctcgc ccccaaaggg caacccggac ccgctgccac tgataggaac | 120 |
| cctataggct ccagcagcag acagagcagc agtagcgcta tgtcttcctc ttctgcctcc | 180 |
| tcctcccccg cagcttctct gggcagccaa ggaagtggct tggagcagag cagtttccag | 240 |
| tggagcccct cggggcgccg gaccggcagc ctctactgca gagtgggcat cggtttccat | 300 |
| ctgcagatct acccggatgg caaagtcaat ggatcccacg aagccaatat gttaagtgtt | 360 |
| ttggaaatat ttgctgtgtc tcaggggatt gtaggaatac gaggagtttt cagcaacaaa | 420 |
| tttttagcga tgtcaaaaaa aggaaaactc catgcaagtg ccaagttcac agatgactgc | 480 |
| aagttcaggg agcgttttca agaaaatagc tataatacct atgcctcagc aatacataga | 540 |
| actgaaaaaa cagggcggga gtggtatgtt gccctgaata aagaggaaa agccaaacga | 600 |
| gggtgcagcc cccgggttaa accccagcat atctctaccc attttcttcc aagattcaag | 660 |
| cagtcggagc agccagaact ttcttttcacg gttactgttc ctgaaaagaa aaatccacct | 720 |
| agccctatca gtcaaagat tccccttttct gcacctcgga aaaataccaa ctcagtgaaa | 780 |
| tacagactca agtttcgctt tggataa | 807 |

<210> SEQ ID NO 114
<211> LENGTH: 354
<212> TYPE: DNA
<213> ORGANISM: Homo sapiens

<400> SEQUENCE: 114

| | |
|---|---|
| atgaaacagt catcctggct gatgagctgt gtcgccagcc caagcccagc acggtgcaag | 60 |
| cttgtaaccg ctttaattgc ccccagcct ggtaccctgc acagtggcag ccgtgttcca | 120 |
| gaacgtgtgg cggggtgtt cagaaacgtg aggttctttg caagcagcgc atggctgatg | 180 |
| gcagcttcct ggagcttcct gagaccttct gttcagcttc aaaacctgcc tgccagcaag | 240 |
| catgcaagaa agatgactgt cccagcgagt ggcttctctc agactggaca gagtgttcca | 300 |
| caagctgcgg ggaaggcacc cagactcgaa gcgccatttg ccgaaagatg ctga | 354 |

<210> SEQ ID NO 115
<211> LENGTH: 525
<212> TYPE: DNA
<213> ORGANISM: Homo sapiens

<400> SEQUENCE: 115

| | |
|---|---|
| atgagacgct ttttaagcaa agtctacagt ttcccaatga gaaaattaat cctctttctt | 60 |

```
gtctttccag ttgtgagaca aactcccaca cagcacttta aaaatcagtt cccagctctg    120
cactgggaac atgaactagg cctggccttc accaagaacc gaatgaacta taccaacaaa    180
ttcctgctga tcccagagtc gggagactac ttcatttact cccaggtcac attccgtggg    240
atgacctctg agtgcagtga atcagacaa gcaggccgac caaacaagcc agactccatc    300
actgtggtca tcaccaaggt aacagacagc taccctgagc caacccagct cctcatgggg    360
accaagtctg tatgcgaagt aggtagcaac tggttccagc ccatctacct cggagccatg    420
ttctccttgc aagaagggga caagctaatg gtgaacgtca gtgacatctc tttggtggat    480
tacacaaaag aagataaaac cttctttgga gccttcttac tatag                     525

<210> SEQ ID NO 116
<211> LENGTH: 657
<212> TYPE: DNA
<213> ORGANISM: Homo sapiens

<400> SEQUENCE: 116
atggggatgt ggtccattgg tgcaggagcc ctgggggctg ctgccttggc attgctgctt     60
gccaacacag acgtgtttct gtccaagccc agaaagcgg ccctggagta cctggaggat    120
atagacctga aacactgga gaaggaacca aggactttca agcaaagga gctatgggaa     180 aaaaatggag ctgtgattat ggccgtgcgg aggccaggct gtttcctctg tcgagaggaa    240
gctgcggatc tgtcctccct gaaaagcatg ttggaccagc tgggcgtccc cctctatgca    300
gtggtaaagg agcacatcag gactgaagtg aaggatttcc agcccttattt caaaggagaa    360 atcttcctgg atgaaaagaa aaagttctat ggtccacaaa ggcggaagat gatgtttatg    420
ggatttatcc gtctgggagt gtggtacaac ttcttccgag cctggaacgg aggcttctct    480
ggaaacctgg aaggagaagg cttcatcctt gggggagttt cgtggtggg atcaggaaag     540 cagggcattc ttcttgagca ccgagaaaaa gaatttggag acagagtaaa cctactttct    600
gttctggaag ctgctaagat gatcaaacca cagactttgg cctcagagaa aaaatga       657

<210> SEQ ID NO 117
<211> LENGTH: 639
<212> TYPE: DNA
<213> ORGANISM: Homo sapiens

<400> SEQUENCE: 117
atggattatt tgctcatgat tttctctctg ctgtttgtgg cttgccaagg agctccagaa     60
acagcagtct taggcgctga gctcagcgcg gtgggtgaga acggcgggga gaaacccact    120
cccagtccac cctggcggct ccgccggtcc aagcgctgct cctgctcgtc cctgatggat    180
aaagagtgtg tctacttctg ccacctggac atcatttggg tcaacactcc cgagcacgtt    240
gttccgtatg gacttggaag ccctaggtcc aagagagcct tggagaattt acttcccaca    300
aaggcaacag accgtgagaa tagatgccaa tgtgctagcc aaaaagacaa gaagtgctgg    360 aattttttgcc aagcaggaaa agaactcagg gctgaagaca ttatggagaa agactggaat    420
aatcataaga aggaaaaga ctgttccaag cttgggaaaa agtgtattta tcagcagtta    480
gtgagaggaa gaaaaatcag aagaagttca gaggaacacc taagacaaac caggtcggag    540
accatgagaa acagcgtcaa atcatctttt catgatccca agctgaaagg caagccctcc    600
agagagcgtt atgtgaccca caaccgagca cattggtga                            639

<210> SEQ ID NO 118
<211> LENGTH: 465
<212> TYPE: DNA
```

<213> ORGANISM: Homo sapiens

<400> SEQUENCE: 118

```
atggctttgg gagttccaat atcagtctat cttttattca acgcaatgac agcactgacc    60
gaagaggcag ccgtgactgt aacacctcca atcacagccc agcaaggtaa ctggacagtt   120
aacaaaacag aagctgacaa catagaagga cccatagcct tgaagttctc acacctttgc   180
ctggaagatc ataacagtta ctgcatcaac ggtgcttgtg cattccacca tgagctagag   240
aaagccatct gcaggtgttt tactggttat actggagaaa ggtgtgagca cttgacttta   300
acttcatatg ctgtggattc ttatgaaaaa tacattgcaa tgggattgg tgttggatta   360
ctattaagtg gttttcttgt tatttttac tgctatataa gaaagaggtg tctaaaattg   420
aaatcgcctt acaatgtctg ttctggagaa agacgaccac tgtga                    465
```

<210> SEQ ID NO 119
<211> LENGTH: 2163
<212> TYPE: DNA
<213> ORGANISM: Homo sapiens

<400> SEQUENCE: 119

```
atgagtgaag gggcggccgc tgcctcgcca cctggtgccg cttcggcagc cgccgcctcg    60
gccgaggagg gcaccgcggc ggctgcggcg cggcagcgg cggcggggg cccggacggc   120
ggcggcgaag gggcggccga gccccccgg gagttacgct gtagcgactg catcgtgtgg   180
aaccggcagc agacgtggct gtgcgtggta cctctgttca tcggcttcat cggcctgggg   240
ctcagcctca tgcttctcaa atggatcgtg gtgggctccg tcaaggagta cgtgcccacc   300
gacctagtgg actccaaggg gatgggccag gaccccttct tcctctccaa gcccagctct   360
ttccccaagg ccatggagac caccaccact accacttcca ccacgtcccc cgccacccc    420
tccgccgggg gtgccgcctc ctccaggacg cccaaccgga ttagcactcg cctgaccacc   480
atcacgcggg cgcccactcg cttccccggg caccgggtgc ccatccgggc cagcccgcgc   540
tccaccacag cacggaacac tgcggcccct gcgacggtcc cgtccaccac ggccccgttc   600
ttcagtagca gcacgctggg ctcccgaccc ccggtgccag gaactccaag tacccaggca   660
atgccctcct ggcctactgc ggcatacgct acctcctcct accttcacga ttctactccc   720
tcctggaccc tgtctccctt tcaggatgct gcctcctctt cttcctcttc ttcctcctcc   780
gctaccacca ccacaccaga aactagcacc agccccaaat tcatacgac gacatattcc   840
acagagcgat ccgagcactt caaaccctgc gagacaagg accttgcata ctgtctcaat   900
gatggcgagt gctttgtgat cgaaaccctg accggatccc ataaacactg tcggtgcaaa   960
gaaggctacc aaggagtccg ttgtgatcaa tttctgccga aaactgattc catcttatcg  1020
gatccaacag accacttggg gattgaattc atggagagtg aagaagttta tcaaaggcag  1080
gtgctgtcaa tttcatgtat catctttgga attgtcatcg tgggcatgtt ctgtgcagca  1140
ttctacttca aaagcaagaa acaagctaaa caaatccaag agcagctgaa agtgccacaa  1200
aatggtaaaa gctacagtct caaagcatcc agcacaatgg caaagtcaga gaacttggtg  1260
aagagccatg tccagctgca aaattattca aaggtggaaa ggcatcctgt gactgcattg  1320
gagaaaatga tggagtcaag ttttgtcggc ccccagtcat tccctgaggt cccttctcct  1380
gacagaggaa gccagtctgt caaacaccac aggagtctat cctcttgctg cagcccaggg  1440
caaagaagtg gcatgctcca taggaatgcc ttcagaagga cacccccgtc accccgaagt  1500
aggctaggtg gaattgtggg accagcatat cagcaactcg aagaatcaag gatcccagac  1560
```

```
caggatacga taccttgcca agggatagag gtcaggaaga ctatatccca cctgcctata    1620
cagctgtggt gtgttgaaag accctggac ttaaagtatt catccagtgg tttaaaaacc     1680
caacgaaata catcaataaa tatgcaactg ccttcaagag agacaaaccc ctattttaat    1740
agcttggagc aaaaggacct ggtgggctat tcatccacaa gggccagttc tgtgcccatc    1800
atcccttcag tgggtttaga ggaaacctgc ctgcaaatgc cagggatttc tgaagtcaaa    1860
agcatcaaat ggtgcaaaaa ctcctattca gctgacgttg tcaatgtgag tattccagtc    1920
agcgattgtc ttatagcaga acaacaagaa gtgaaaatat tgctagaaac tgtccaggag    1980
cagatccgaa ttctgactga tgccagacgg tcagaagact acgaactggc cagcgtagaa    2040
accgaggaca gtgcaagcga aaacacagcc tttctccccc tgagtccac agccaaatca     2100 gaacgagagg cgcaatttgt cttaagaaat gaaatacaaa gagactctgc attgaccaag    2160
tga                                                                  2163

<210> SEQ ID NO 120
<211> LENGTH: 1458
<212> TYPE: DNA
<213> ORGANISM: Homo sapiens

<400> SEQUENCE: 120
atgcggaagc gagcacccca gtctgagatg gctcctgccg gtgtgagcct gagggccacc      60
atcctctgcc tcctggcctg ggctggcctg gctgcaggtg accgggtgta catacacccc     120
ttccacctcg tcatccacaa tgagagtacc tgtgagcagc tggcaaaggc caatgccggg     180
aagcccaaag accccacctt catacctgct ccaattcagg ccaagacatc ccctgtggat     240
gaaaaggccc tacaggacca gctggtgcta gtcgctgcaa aacttgacac cgaagacaag     300
ttgagggccg caatggtcgg gatgctgccc aacttcttgg gcttccgtat atatggcatg     360
cacagtgagc tatggggcgt ggtccatggg gccaccgtcc tctccccaac ggctgtcttt     420
ggcaccctgg cctctctcta tctggggagcc ttggaccaca cagctgacag gctacaggca     480
atcctgggtg ttccttggaa ggacaagaac tgcacctccc ggctggatgc gcacaaggtc     540
ctgtctgccc tgcaggctgt acagggcctg ctagtggccc agggcagggc tgatagccag     600
gcccagctgc tgctgtccac ggtggtgggc gtgttcacag ccccaggcct gcacctgaag     660
cagccgtttg tgcagggcct ggctctctat accctgtgg tcctcccacg ctctctggac      720
ttcacagaac tggatgttgc tgctgagaag attgacaggt tcatgcaggc tgtgacagga     780
tggaagactg gctgctccct gatgggagcc agtgtgacac gcaccctggc tttcaacacc     840
tacgtccact tccaagggaa gatgaagggc ttctcctgc tggccgagcc ccaggagttc      900
tgggtggaca cagcaccctc agtgtctgtt cccatgctct ctggcatggg caccttccag     960
cactggagtg acatccagga caacttctcg gtgactcaag tgcccttcac tgagagcgcc    1020
tgcctgctgc tgatccagcc tcactatgcc tctgacctgg acaaggtgga gggtctcact    1080
ttccagcaaa actccctcaa ctggatgaag aaactgtctc cccggaccat ccacctgacc    1140 atgcccaac tggtgctgca aggatcttat gacctgcagg acctgctcgc ccaggctgag    1200 ctgccccgcca ttctgcacac cgagctgaac ctgcaaaaat tgagcaatga ccgcatcagg    1260 gtggggagg tgctgaacag catttttttt gagcttgaag cggatgagag agagcccaca    1320
gagtctaccc aacagcttaa caagcctgag gtcttggagg tgaccctgaa ccgcccattc    1380
ctgtttgctg tgtatgatca aagcgccact gccctgcact tcctgggccg cgtggccaac    1440
ccgctgagca cagcatga                                                  1458
```

<210> SEQ ID NO 121
<211> LENGTH: 786
<212> TYPE: DNA
<213> ORGANISM: Homo sapiens

<400> SEQUENCE: 121

```
atgatcgaaa catacaacca aacttctccc cgatctgcgg ccactggact gcccatcagc     60
atgaaaattt ttatgtattt acttactgtt tttcttatca cccagatgat tgggtcagca    120
cttttgctg tgtatcttca tagaaggttg acaagatag aagatgaaag gaatcttcat      180
gaagattttg tattcatgaa aacgatacag agatgcaaca caggagaaag atccttatcc    240
ttactgaact gtgaggagat taaaagccag tttgaaggct ttgtgaagga tataatgtta    300
aacaaagagg agacgaagaa agaaaacagc tttgaaatgc aaaaaggtga tcagaatcct    360
caaattgcgg cacatgtcat aagtgaggcc agcagtaaaa caacatctgt gttacagtgg    420
gctgaaaaag gatactacac catgagcaac aacttggtaa ccctggaaaa tgggaaacag    480
ctgaccgtta aaagacaagg actctattat atctatgccc aagtcacctt ctgttccaat    540
cgggaagctt cgagtcaagc tccatttata gccagcctct gcctaaagtc ccccggtaga    600
ttcgagagaa tcttactcag agctgcaaat acccacagtt ccgccaaacc ttgcgggcaa    660
caatccattc acttgggagg agtatttgaa ttgcaaccag gtgcttcggt gtttgtcaat    720
gtgactgatc caagccaagt gagccatggc actggcttca cgtcctttgg cttactcaaa    780
ctctga                                                               786
```

<210> SEQ ID NO 122
<211> LENGTH: 1062
<212> TYPE: DNA
<213> ORGANISM: Homo sapiens

<400> SEQUENCE: 122

```
atggagctga ctgaattgct cctcgtggtc atgcttctcc taactgcaag gctaacgctg      60
tccagcccgg ctcctcctgc ttgtgacctc cgagtcctca gtaaactgct tcgtgactcc    120
catgtccttc acagcagact gagccagtgc ccagaggttc acccttttgcc tacacctgtc    180
ctgctgcctg ctgtggactt tagcttggga gaatggaaaa cccagatgga ggagaccaag    240
gcacaggaca ttctgggagc agtgaccctt tgctggagg gagtgatggc agcacgggga     300
caactgggac ccacttgcct ctcatccctc ctggggcagc tttctggaca ggtccgtctc    360
ctccttgggg ccctgcagag cctccttgga acccagcttc ctccacaggg caggaccaca    420
gctcacaagg atcccaatgc catcttcctg agcttccaac acctgctccg aggaaaggtg    480
cgtttcctga tgcttgtagg agggtccacc ctctgcgtca ggcgggcccc acccaccaca    540
gctgtcccca gcagaacctc tctagtcctc acactgaacg agctcccaaa caggacttct    600
ggattgttgg agacaaactt cactgcctca gccagaacta ctggctctgg gcttctgaag    660
tggcagcagg gattcagagc caagattcct ggtctgctga ccaaacctc caggtccctg     720
gaccaaatcc ccggatacct gaacaggata cacgaactct tgaatggaac tcgtggactc    780
tttcctggac cctcacgcag gaccctagga gccccggaca tttcctcagg aacatcagac    840
acaggctccc tgccacccaa cctccagcct ggatattctc cttccccaac ccatcctcct    900
actggacagt atacgctctt ccctcttcca cccaccttgc ccaccctgt ggtccagctc    960
cacccctgc ttcctgaccc ttctgctcca acgccaccc ctaccagccc tcttctaaac    1020
acatcctaca cccactccca gaatctgtct caggaagggt aa                      1062
```

```
<210> SEQ ID NO 123
<211> LENGTH: 702
<212> TYPE: DNA
<213> ORGANISM: Homo sapiens

<400> SEQUENCE: 123
atgagcactg aaagcatgat ccgggacgtg gagctggccg aggaggcgct ccccaagaag      60
acaggggggc cccagggctc caggcggtgc ttgttcctca gcctcttctc cttcctgatc     120
gtggcaggcg ccaccacgct cttctgcctg ctgcactttg gagtgatcgg cccccagagg     180
gaagagttcc ccagggacct ctctctaatc agccctctgg cccaggcagt cagatcatct     240
tctcgaaccc cgagtgacaa gcctgtagcc catgttgtag caaaccctca gctgaggggg     300
cagctccagt ggctgaaccg ccgggccaat gccctcctgg ccaatggcgt ggagctgaga     360
gataaccagc tggtggtgcc atcagagggc ctgtacctca tctactccca ggtcctcttc     420
aagggccaag ctgcccctc cacccatgtg ctcctcaccc acaccatcag ccgcatcgcc     480
gtctcctacc agaccaaggt caacctcctc tctgccatca gagcccctg ccagagggag      540 accccagagg gggctgaggc caagccctgg tatgagccca tctatctggg aggggtcttc     600
cagctggaga agggtgaccg actcagcgct gagatcaatc ggcccgacta tctcgacttt     660
gccgagtctg gcaggtcta ctttgggatc attgccctgt ga                        702

<210> SEQ ID NO 124
<211> LENGTH: 618
<212> TYPE: DNA
<213> ORGANISM: Homo sapiens

<400> SEQUENCE: 124
atgacaccac ctgaacgtct cttcctccca agggtgtgtg gcaccaccct acacctcctc      60
cttctggggc tgctgctggt tctgctgcct ggggcccagg ggctccctgg tgttggcctc     120
acaccttcag ctgcccagac tgcccgtcag caccccaaga tgcatcttgc ccacagcacc     180
ctcaaacctg ctgctcacct cattggagac cccagcaagc agaactcact gctctggaga     240
gcaaacacgg accgtgcctt cctccaggat ggtttctcct tgagcaacaa ttctctcctg     300
gtccccacca gtggcatcta cttcgtctac tcccaggtgg tcttctctgg gaaagcctac     360
tctcccaagg ccacctcctc cccactctac ctggcccatg aggtccagct cttctcctcc     420
cagtacccct tccatgtgcc tctcctcagc tcccagaaga tggtgtatcc agggctgcag     480
gaaccctggc tgcactcgat gtaccacggg gctgcgttcc agctcaccca gggagaccag     540
ctatccaccc acacagatgg catcccccac ctagtcctca gccctagtac tgtcttcttt     600
ggagccttcg ctctgtag                                                   618

<210> SEQ ID NO 125
<211> LENGTH: 2187
<212> TYPE: DNA
<213> ORGANISM: Homo sapiens

<400> SEQUENCE: 125
atgtgggtga ccaaactcct gccagccctg ctgctgcagc atgtcctcct gcatctcctc      60
ctgctcccca tcgccatccc ctatgcagag ggacaaagga aagaagaaa tacaattcat     120 gaattcaaaa aatcagcaaa gactacccta atcaaaatag atccagcact gaagataaaa     180
accaaaaaag tgaatactgc agaccaatgt gctaatagat gtactaggaa taaggacttt     240
ccattcactt gcaaggcttt tgttttttgat aaagcaagaa acaatgcct ctggttcccc     300
```

```
ttcaatagca tgtcaagtgg agtgaaaaaa gaatttggcc atgaatttga cctctatgaa      360
aacaaagact acattagaaa ctgcatcatt ggtaaaggac gcagctacaa gggaacagta      420
tctatcacta agagtggcat caaatgtcag ccctggagtt ccatgatacc acacgaacac      480 agcttttgc cttcgagcta tcggggtaaa gacctacagg aaaactactg tcgaaatcct       540 cgagggaag aaggggggacc ctggtgtttc acaagcaatc cagaggtacg ctacgaagtc      600
tgtgacattc ctcagtgttc agaagttgaa tgcatgacct gcaatgggga gagttatcga      660
ggtctcatgg atcatacaga atcaggcaag atttgtcagc gctgggatca tcagacacca      720
caccggcaca aattcttgcc tgaaagatat cccgacaagg gctttgatga taattattgc      780
cgcaatcccg atggccagcc gaggccatgg tgctatactc ttgaccctca cacccgctgg      840
gagtactgtg caattaaaac atgcgctgac aatactatga atgacactga tgttcctttg      900
gaaacaactg aatgcatcca aggtcaagga aaggctaca ggggcactgt caataccatt       960
tggaatggaa ttccatgtca gcgttgggat tctcagtatc ctcacgagca tgacatgact     1020
cctgaaaatt tcaagtgcaa ggacctacga gaaaattact gccgaaatcc agatgggtct     1080
gaatcaccct ggtgttttac cactgatcca aacatccgag ttggctactg ctcccaaatt     1140
ccaaactgtg atatgtcaca tggacaagat tgttatcgtg ggaatggcaa aaattatatg     1200
ggcaacttat cccaaacaag atctggacta acatgttcaa tgtgggacaa gaacatggaa     1260
gacttacatc gtcatatctt ctgggaacca gatgcaagta agctgaatga gaattactgc     1320
cgaaatccag atgatgatgc tcatggaccc tggtgctaca cgggaaatcc actcattcct     1380
tgggattatt gccctatttc tcgttgtgaa ggtgatacca cacctacaat agtcaattta     1440
gaccatcccg taatatcttg tgccaaaacg aaacaattgc gagttgtaaa tgggattcca     1500
acacgaacaa acataggatg gatggttagt ttgagataca gaaataaaca tatctgcgga     1560
ggatcattga taaaggagag ttgggttctt actgcacgac agtgttccc ttctcgagac      1620 ttgaaagatt atgaagcttg gcttggaatt catgatgtcc acggaagagg agatgagaaa     1680
tgcaaacagg ttctcaatgt tcccagctg gtatatggcc ctgaaggatc agatctggtt      1740
ttaatgaagc ttgccaggcc tgctgtcctg atgattttg ttagtacgat tgatttacct      1800
aattatggat gcacaattcc tgaaaagacc agttgcagtg tttatggctg gggctacact     1860
ggattgatca actatgatgg cctattacga gtggcacatc tctatataat gggaaatgag     1920
aaatgcagcc agcatcatcg agggaaggtg actctgaatg agtctgaaat atgtgctggg     1980
gctgaaaaga ttggatcagg accatgtgag gggattatg tggcccact tgtttgtgag       2040 caacataaaa tgagaatggt tcttggtgtc attgttcctg gtcgtggatg tgccattcca     2100
aatcgtcctg gtattttgt ccgagtagca tattatgcaa aatggataca caaattatt      2160 ttaacatata aggtaccaca gtcatag                                         2187
```

<210> SEQ ID NO 126
<211> LENGTH: 543
<212> TYPE: DNA
<213> ORGANISM: Homo sapiens

<400> SEQUENCE: 126

```
atgggaatcc caatggggaa gtcgatgctg gtgcttctca ccttcttggc cttcgcctcg       60
tgctgcattg ctgcttaccg ccccagtgag accctgtgcg gcggggagct ggtggacacc      120
ctccagttcg tctgtgggga ccgcggcttc tacttcagca ggcccgcaag ccgtgtgagc      180
cgtcgcagcc gtggcatcgt tgaggagtgc tgtttccgca gctgtgacct ggccctcctg     240
```

```
gagacgtact gtgctacccc cgccaagtcc gagagggacg tgtcgacccc tccgaccgtg    300
cttccggaca acttccccag ataccccgtg ggcaagttct tccaatatga cacctggaag    360
cagtccaccc agcgcctgcg caggggcctg cctgccctcc tgcgtgcccg ccggggtcac    420
gtgctcgcca aggagctcga ggcgttcagg gaggccaaac gtcaccgtcc cctgattgct    480
ctacccaccc aagacccggc ccacgggggc gcccccccag agatggccag caatcggaag    540
tga                                                                 543

<210> SEQ ID NO 127
<211> LENGTH: 462
<212> TYPE: DNA
<213> ORGANISM: Homo sapiens

<400> SEQUENCE: 127
atgggaaaaa tcagcagtct tccaacccaa ttatttaagt gctgcttttg tgatttcttg     60
aaggtgaaga tgcacaccat gtcctcctcg catctcttct acctggcgct gtgcctgctc    120
accttcacca gctctgccac ggctggaccg gagacgctct gcggggctga gctggtggat    180
gctcttcagt tcgtgtgtgg agacaggggc ttttatttca acaagcccac agggtatggc    240
tccagcagtc ggagggcgcc tcagacaggc atcgtggatg agtgctgctt ccggagctgt    300
gatctaagga ggctggagat gtattgcgca cccctcaagc ctgccaagtc agctcgctct    360
gtccgtgccc agcgccacac cgacatgccc aagacccaga aggaagtaca tttgaagaac    420
gcaagtagag ggagtgcagg aaacaagaac tacaggatgt ag                      462

<210> SEQ ID NO 128
<211> LENGTH: 846
<212> TYPE: DNA
<213> ORGANISM: Homo sapiens

<400> SEQUENCE: 128
atgcagcagc ccttcaatta cccatatccc cagatctact gggtggacag cagtgccagc     60
tctccctggg ccctccagg cacagttctt ccctgtccaa cctctgtgcc cagaaggcct    120
ggtcaaagga ggccaccacc accaccgcca ccgccaccac taccacctcc gccgccgccg    180
ccaccactgc ctccactacc gctgccaccc ctgaagaaga gagggaacca cagcacaggc    240
ctgtgtctcc ttgtgatgtt tttcatggtt ctggttgcct tggtaggatt gggcctgggg    300
atgtttcagc tcttccacct acagaaggag ctggcagaac tccgagagtc taccagccag    360
atgcacacag catcatcttt ggagaagcaa ataggccacc ccagtccacc ccctgaaaaa    420
aaggagctga ggaaagtggc ccatttaaca ggcaagtcca actcaaggtc catgcctctg    480
gaatgggaag acacctatgg aattgtcctg ctttctggag tgaagtataa gaaggtggc    540 cttgtgatca atgaaactgg gctgtacttt gtatattcca agtatactt ccggggtcaa    600 tcttgcaaca acctgcccct gagccacaag gtctacatga ggaactctaa gtatcccag    660 gatctggtga tgatggaggg gaagatgatg agctactgca ctactgggca gatgtgggcc    720
cgcagcagct acctggggc agtgttcaat cttaccagtg ctgatcattt atatgtcaac    780
gtatctgagc tctctctggt caattttgag gaatctcaga cgttttcgg cttatataag    840 ctctaa                                                              846

<210> SEQ ID NO 129
<211> LENGTH: 468
<212> TYPE: DNA
<213> ORGANISM: Homo sapiens
```

```
<400> SEQUENCE: 129
atggctgaag gggaaatcac caccttcaca gccctgaccg agaagtttaa tctgcctcca      60
gggaattaca agaagcccaa actcctctac tgtagcaacg ggggccactt cctgaggatc     120
cttccggatg gcacagtgga tgggacaagg gacaggagcg accagcacat tcagctgcag     180
ctcagtgcgg aaagcgtggg ggaggtgtat ataaagagta ccgagactgg ccagtacttg     240
gccatggaca ccgacgggct tttatacggc tcacagacac caaatgagga atgtttgttc     300
ctggaaaggc tggaggagaa ccattacaac acctatatat ccaagaagca tgcagagaag     360
aattggtttg ttggcctcaa gaagaatggg agctgcaaac gcggtcctcg gactcactat     420
ggccagaaag caatcttgtt tctcccctg ccagtctctt ctgattaa               468

<210> SEQ ID NO 130
<211> LENGTH: 294
<212> TYPE: DNA
<213> ORGANISM: Homo sapiens

<400> SEQUENCE: 130
atgctaggta caagcgact ggggctgtcc ggactcaccc tggccctgtc cctgctcgtg      60
tgcctgggtg cgctggccga ggcgtacccc tccaagccgg acaacccggg cgaggacgca     120
ccagcggagg acatggccag atactactcg gcgctgcgac actacatcaa cctcatcacc     180
aggcagagat atggaaaacg atccagccca gagacactga tttcagacct cttgatgaga     240
gaaagcacag aaaatgttcc cagaactcgg cttgaagacc ctgcaatgtg gtga           294

<210> SEQ ID NO 131
<211> LENGTH: 582
<212> TYPE: DNA
<213> ORGANISM: Homo sapiens

<400> SEQUENCE: 131
atgccggagg agggttcggg ctgctcggtg cggcgcaggc cctatgggtg cgtcctgcgg      60
gctgctttgg tcccattggt cgcgggcttg gtgatctgcc tcgtggtgtg catccagcgc     120
ttcgcacagg ctcagcagca gctgccgctc gagtcacttg ggtgggacgt agctgagctg     180
cagctgaatc acacaggacc tcagcaggac cccaggctat actggcaggg ggcccagca     240 ctgggccgct ccttcctgca tggaccgagc tggacaagg gcagctacg tatccatcgt     300 gatggcatct acatggtaca catccaggtg acgctggcca tctgctcctc cacgacggcc     360
tccaggcacc accccaccac cctggccgtg ggaatctgct ctcccgcctc ccgtagcatc     420
agcctgctgc gtctcagctt ccaccaaggt tgtaccattg cctcccagcg cctgacgccc     480
ctggcccgag gggacacact ctgcaccaac ctcactggga cttttgcc ttcccgaaac      540 actgatgaga ccttctttgg agtgcagtgg gtgcgcccct ga                       582

<210> SEQ ID NO 132
<211> LENGTH: 1176
<212> TYPE: DNA
<213> ORGANISM: Homo sapiens

<400> SEQUENCE: 132
atgggctacc cggaggtgga gcgcagggaa ctcctgcctg cagcagcgcc gcgggagcga      60
gggagccagg gctgcgggtg tggcggggcc cctgcccggg cgggcgaagg gaacagctgc     120
ctgctcttcc tgggttttct tggcctctcg ctggccctcc acctgctgac gttgtgctgc     180
tacctagagt tgcgctcgga gttgcggcgg gaacgtggag ccgagtcccg ccttggcggc     240
```

```
tcgggcaccc ctggcacctc tggcacccta agcagcctcg gtggcctcga ccctgacagc    300
cccatcacca gtcaccttgg gcagccgtca cctaagcagc agccattgga accgggagaa    360
gccgcactcc actctgactc ccaggacggg caccagatgg ccctattgaa tttcttcttc    420
cctgatgaaa agccatactc tgaagaagaa agtaggcgtg ttcgccgcaa taaaagaagc    480
aaaagcaatg aaggagcaga tggcccagtt aaaaacaaga aaagggaaa gaaagcagga    540 cctcctggac ccaatggccc tccaggaccc ccaggacctc caggacccca gggaccccca    600
ggaattccag ggattcctgg aattccagga caactgttta tgggaccacc tggtcctcca    660
ggtcctcctg gtcctcaagg acccctggc ctccagggac cttctggtgc tgctgataaa    720
gctggaactc gagaaaacca gccagctgtg gtgcatctac agggccaagg gtcagcaatt    780
caagtcaaga atgatctttc aggtggagtg ctcaatgact ggtctcgcat cactatgaac    840
cccaaggtgt ttaagctaca tccccgcagc ggggagctgg aggtactggt ggacggcacc    900
tacttcatct atagtcaggt agaagtatac tacatcaact tcactgactt tgccagctat    960
gaggtggtgg tggatgagaa gcccttcctg cagtgcacac gcagcatcga gacgggcaag   1020
accaactaca cacttgcta taccgcaggc gtctgcctcc tcaaggcccg gcagaagatc   1080
gccgtcaaga tggtgcacgc tgacatctcc atcaacatga gcaagcacac cacgttcttt   1140
ggggccatca ggctgggtga agcccctgca tcctag                              1176

<210> SEQ ID NO 133
<211> LENGTH: 510
<212> TYPE: DNA
<213> ORGANISM: Homo sapiens

<400> SEQUENCE: 133
atgaccgcgg ggaggaggat ggagatgctc tgtgccggca gggtccctgc gctgctgctc     60
tgcctgggtt ccatcttct acaggcagtc ctcagtacaa ctgtgattcc atcatgtatc    120
ccaggagagt ccagtgataa ctgcacagct ttagttcaga cagaagacaa tccacgtgtg    180
gctcaagtgt caataacaaa gtgtagctct gacatgaatg ctattgtttt gcatggacag    240
tgcatctatc tggtggacat gagtcaaaac tactgcaggt gtgaagtggg ttatactggt    300
gtccgatgtg aacacttctt tttaaccgtc caccaacctt taagcaaaga gtatgtggct    360
ttgaccgtga ttcttattat tttgtttctt atcacagtcg tcggttccac atattatttc    420
tgcagatggt acagaaatcg aaaaagtaaa gaaccaaaga aggaatatga gagagttacc    480
tcaggggatc cagagttgcc gcaagtctga                                      510

<210> SEQ ID NO 134
<211> LENGTH: 759
<212> TYPE: DNA
<213> ORGANISM: Homo sapiens

<400> SEQUENCE: 134
atgagagccc cgctgctacc gccggcgccg gtggtgctgt cgctcttgat actcggctca     60
ggccattatg ctgctggatt ggacctcaat gacaccctact ctgggaagcg tgaaccattt    120
tctggggacc acagtgctga tggatttgag gttacctcaa gaagtgagat gtcttcaggg    180
agtgagattt cccctgtgag tgaaatgcct tctagtagtg aaccgtcctc gggagccgac    240
tatgactact cagaagagta tgataacgaa ccacaaatac ctggctatat tgtcgatgat    300
tcagtcagag ttgaacaggt agttaagccc cccaaaaaca agacggaaag tgaaaatact    360
tcagataaac ccaaaagaaa gaaaagggga ggcaaaaatg gaaaaaatag aagaaacaga    420
```

```
aagaagaaaa atccatgtaa tgcagaattt caaaatttct gcattcacgg agaatgcaaa      480
tatatagagc acctggaagc agtaacatgc aaatgtcagc aagaatattt cggtgaacgg      540
tgtggggaaa agtccatgaa aactcacagc atgattgaca gtagtttatc aaaaattgca      600
ttagcagcca tagctgcctt tatgtctgct gtgatcctca cagctgttgc tgttattaca      660
gtccagctta aagacaata cgtcaggaaa tatgaaggag aagctgagga acgaaagaaa       720
cttcgacaag agaatggaaa tgtacatgct atagcataa                            759

<210> SEQ ID NO 135
<211> LENGTH: 627
<212> TYPE: DNA
<213> ORGANISM: Homo sapiens

<400> SEQUENCE: 135
atgaagctgc tgccgtcggt ggtgctgaag ctctttctgg ctgcagttct ctcggcactg       60
gtgactggcg agagcctgga gcggcttcgg agagggctag ctgctggaac cagcaacccg      120
gaccctccca ctgtatccac ggaccagctg ctacccctag gaggcggccg ggaccggaaa      180
gtccgtgact gcaagaggc agatctggac cttttgagag tcactttatc ctccaagcca      240
caagcactgg ccacaccaaa caaggaggag cacgggaaaa gaagaagaa aggcaagggg      300 ctagggaaga gagggaccc atgtcttcgg aaatacaagg acttctgcat ccatggagaa      360
tgcaaatatg tgaaggagct ccgggctccc tcctgcatct gccacccggg ttaccatgga      420
gagaggtgtc atgggctgag cctcccagtg gaaaatcgct tatataccta tgaccacaca      480
accatcctgg ccgtggtggc tgtggtgctg tcatctgtct gtctgctggt catcgtgggg      540
cttctcatgt ttaggtacca taggagagga ggttatgatg tggaaaatga agagaaagtg      600
aagttgggca tgactaattc ccactga                                         627

<210> SEQ ID NO 136
<211> LENGTH: 537
<212> TYPE: DNA
<213> ORGANISM: Homo sapiens

<400> SEQUENCE: 136
atggtctccg tgcctaccac ctggtgctcc gttgcgctag ccctgctcgt ggccctgcat       60
gaagggaagg gccaggctgc tgccaccctg gagcagccag cgtcctcatc tcatgcccaa      120
ggcacccacc ttcggcttcg ccgttgctcc tgcagctcct ggctcgacaa ggagtgcgtc      180
tacttctgcc acttggacat catctgggtg aacactcctg aacagacagc tccttacggc      240
ctgggaaacc cgccaagacg ccggcgccgc tccctgccaa ggcgctgtca gtgctccagt      300
gccagggacc ccgcctgtgc caccttctgc cttcgaaggc cctggactga agccggggca      360
gtcccaagcc ggaagtcccc tgcagacgtg ttccagactg gcaagacagg ggccactaca      420
ggagagcttc tccaaaggct gagggacatt tccacagtca agagcctctt tgccaagcga      480
caacaggagg ccatgcggga gcctcggtcc acacattcca ggtggaggaa gagatag        537

<210> SEQ ID NO 137
<211> LENGTH: 3624
<212> TYPE: DNA
<213> ORGANISM: Homo sapiens

<400> SEQUENCE: 137
atgctgctca ctcttatcat tctgttgcca gtagtttcaa aatttagttt tgttagtctc       60
tcagcaccgc agcactggag ctgtcctgaa ggtactctcg caggaaatgg gaattctact      120
```

```
tgtgtgggtc ctgcacccct cttaattttc tcccatggaa atagtatctt taggattgac    180
acagaaggaa ccaattatga gcaattggtg gtggatgctg gtgtctcagt gatcatggat    240
tttcattata atgagaaaag aatctattgg gtggatttag aaagacaact tttgcaaaga    300 gttttctga atgggtcaag gcaagagaga gtatgtaata tagagaaaaa tgtttctgga    360
atggcaataa attggataaa tgaagaagtt atttggtcaa atcaacagga aggaatcatt    420
acagtaacag atatgaaagg aaataattcc cacattcttt taagtgcttt aaaatatcct    480
gcaaatgtag cagttgatcc agtagaaagg tttatatttt ggtcttcaga ggtggctgga    540
agcctttata gagcagatct cgatggtgtg ggagtgaagg ctctgttgga gacatcagag    600
aaaataacag ctgtgtcatt ggatgtgctt gataagcggc tgttttggat tcagtacaac    660
agagaaggaa gcaattctct tatttgctcc tgtgattatg atggaggttc tgtccacatt    720
agtaaacatc caacacagca taatttgttt gcaatgtccc ttttggtga ccgtatcttc     780 tattcaacat ggaaaatgaa gacaatttgg atagccaaca acacactgg aaaggacatg     840 gttagaatta acctccattc atcatttgta ccacttggtg aactgaaagt agtgcatcca    900
cttgcacaac ccaaggcaga agatgacact tgggagcctg agcagaaact ttgcaaattg    960
aggaaaggaa actgcagcag cactgtgtgt gggcaagacc tccagtcaca cttgtgcatg    1020 tgtcagagg gatacgccct aagtcgagac cggaagtact gtgaagatgt taatgaatgt    1080 gcttttgga atcatggctg tactcttggg tgtaaaaaca ccctggatc ctattactgc     1140 acgtgccctg taggatttgt tctgcttcct gatgggaaac gatgtcatca acttgtttcc    1200
tgtccacgca atgtgtctga atgcagccat gactgtgttc tgacatcaga aggtccctta    1260
tgtttctgtc ctgaaggctc agtgcttgag agagatggga aaacatgtag cggttgttcc    1320
tcacccgata atggtggatg tagccagctc tgcgttcctc ttagcccagt atcctgggaa    1380
tgtgattgct ttcctgggta tgacctacaa ctggatgaaa aaagctgtgc agcttcagga    1440
ccacaaccat tttgctgtt tgccaattct caagatattc acacatgca ttttgatgga     1500 acagactatg gaactctgct cagccagcag atgggaatgg tttatgccct agatcatgac    1560
cctgtggaaa ataagatata ctttgcccat acagccctga gtggatagag agagctaat    1620 atggatggtt cccagcgaga aaggcttatt gaggaaggag tagatgtgcc agaaggtctt    1680
gctgtggact ggattggccg tagattctat tggacagaca gagggaaatc tctgattgga    1740
aggagtgatt taaatgggaa acgttccaaa ataatcacta aggagaacat ctctcaacca    1800
cgaggaattg ctgttcatcc aatggccaag agattattct ggactgatac agggattaat    1860
ccacgaattg aaagttcttc cctccaaggc cttggccgtc tggttatagc cagctctgat    1920
ctaatctggc ccagtggaat aacgattgac ttcttaactg acaagttgta ctggtgcgat    1980
gccaagcagt ctgtgattga atggccaat ctggatggtt caaaacgccg aagacttacc     2040
cagaatgatg taggtcaccc atttgctgta gcagtgtttg aggattatgt gtggttctca    2100
gattgggcta tgccatcagt aataagagta acaagagga ctggcaaaga tagagtacgt     2160
ctccaaggca gcatgctgaa gccctcatca ctggttgtgg ttcatccatt ggcaaaacca    2220
ggagcagatc cctgcttata tcaaaacgga ggctgtgaac atatttgcaa aaagaggctt    2280
ggaactgctt ggtgttcgtg tcgtgaaggt tttatgaaag cctcagatgg gaaaacgtgt    2340
ctggctctgg atggtcatca gctgttggca ggtggtgaag ttgatctaaa gaaccaagta    2400
acaccattgg acatcttgtc caagactaga gtgtcagaag ataacattac agaatctcaa    2460
cacatgctag tggctgaaat catggtgtca gatcaagatg actgtgctcc tgtgggatgc    2520
```

```
agcatgtatg ctcggtgtat tcagaggga gaggatgcca catgtcagtg tttgaaagga    2580
tttgctgggg atggaaaact atgttctgat atagatgaat gtgagatggg tgtcccagtg    2640 tgccccctg  cctcctccaa gtgcatcaac accgaaggtg gttatgtctg ccggtgctca    2700
gaaggctacc aaggagatgg gattcactgt cttgatattg atgagtgcca actggggggtg  2760 cacagctgtg gagagaatgc cagctgcaca aatacagagg gaggctatac ctgcatgtgt   2820
gctggacgcc tgtctgaacc aggactgatt tgccctgact ctactccacc ccctcacctc   2880
agggaagatg accaccacta ttccgtaaga aatagtgact ctgaatgtcc cctgtcccac   2940
gatgggtact gcctccatga tggtgtgtgc atgtatattg aagcattgga caagtatgca   3000
tgcaactgtg ttgttggcta catcggggag cgatgtcagt accgagacct gaagtggtgg   3060
gaactgcgcc acgctggcca cgggcagcag cagaaggtca tcgtggtggc tgtctgcgtg   3120
gtggtgcttg tcatgctgct cctcctgagc ctgtgggggg cccactacta caggactcag   3180
aagctgctat cgaaaaaccc aaagaatcct tatgaggagt cgagcagaga tgtgaggagt   3240
cgcaggcctg ctgacactga ggatgggatg tcctcttgcc ctcaaccttg gtttgtggtt   3300
ataaaagaac accaagacct caagaatggg ggtcaaccag tggctggtga ggatggccag   3360
gcagcagatg ggtcaatgca accaacttca tggaggcagg agccccagtt atgtggaatg   3420
ggcacagagc aaggctgctg gattccagta tccagtgata agggctcctg tccccaggta   3480
atggagcgaa gctttcatat gccctcctat gggacacaga cccttgaagg gggtgtcgag   3540
aagccccatt ctctcctatc agctaaccca ttatggcaac aaagggccct ggacccacca   3600
caccaaatgg agctgactca gtga                                          3624
```

<210> SEQ ID NO 138
<211> LENGTH: 621
<212> TYPE: DNA
<213> ORGANISM: Homo sapiens

<400> SEQUENCE: 138

```
atgtcggggc ccgggacggc cgcggtagcg ctgctcccgg cggtcctgct ggccttgctg     60
gcgccctggg cgggccgagg gggcgccgcc gcacccactg cacccaacgg cacgctggag   120
gccgagctgg agcgccgctg ggagagcctg gtggcgctct cgttggcgcg cctgccggtg   180
gcagcgcagc caaggaggc ggccgtccag agcggcgccg cgactacct gctgggcatc     240 aagcggctgc ggcggctcta ctgcaacgtg ggcatcggct ccacctcca ggcgctcccc    300 gacggccgca tcgcggcgc gcacgcggac cccgcgaca gctgctgga gctctcgccc      360 gtggagcggg gcgtggtgag catcttcggc gtggccagcc ggttcttcgt ggccatgagc   420
agcaagggca agctctatgg ctcgcccttc ttcaccgatg agtgcacgtt caaggagatt   480
ctccttccca caaactacaa cgcctacgag tcctacaagt accccggcat gttcatcgcc   540
ctgagcaaga atgggaagac caagaagggg aaccgagtgt cgcccaccat gaaggtcacc   600
cacttcctcc ccaggctgtg a                                             621
```

<210> SEQ ID NO 139
<211> LENGTH: 627
<212> TYPE: DNA
<213> ORGANISM: Homo sapiens

<400> SEQUENCE: 139

```
atggctccct taggtgaagt tgggaactat ttcggtgtgc aggatgcggt accgtttggg     60
aatgtgcccg tgttgccggt ggacagcccg gttttgttaa gtgaccacct gggtcagtcc    120
```

```
gaagcagggg ggctccccag gggacccgca gtcacggact tggatcattt aaaggggatt    180
ctcaggcgga ggcagctata ctgcaggact ggatttcact tagaaatctt ccccaatggt    240
actatccagg gaaccaggaa agaccacagc cgatttggca ttctggaatt tatcagtata    300
gcagtgggcc tggtcagcat tcgaggcgtg acagtggac  tctacctcgg gatgaatgag    360
aagggggagc tgtatggatc agaaaaacta acccaagagt gtgtattcag agaacagttc    420
gaagaaaact ggtataatac gtactcgtca aacctatata agcacgtgga cactggaagg    480
cgatactatg ttgcattaaa taaagatggg accccgagag aagggactag gactaaacgg    540
caccagaaat tcacacattt tttacctaga ccagtggacc ccgacaaagt acctgaactg    600
tataaggata ttctaagcca aagttga                                        627

<210> SEQ ID NO 140
<211> LENGTH: 735
<212> TYPE: DNA
<213> ORGANISM: Homo sapiens

<400> SEQUENCE: 140
atgggggcac tggggctgga gggcaggggt gggaggctcc aggggagggg ttccctcctg     60
ctagctgtgg caggagccac ttctctggtg accttgttgc tggcggtgcc tatcactgtc    120
ctggctgtgc tggccttagt gccccaggat caggaggac  tggtaacgga acgccgac     180 cccggggcac aggcccagca aggactgggg tttcagaagc tgccagagga ggagccagaa    240
acagatctca gccccgggct cccagctgcc cacctcatag gcgctccgct gaaggggcag    300
gggctaggct gggagacgac gaaggaacag gcgtttctga cgagcgggac gcagttctcg    360
gacgccgagg ggctggcgct cccgcaggac ggcctctatt acctctactg tctcgtcggc    420
taccggggcc gggcgccccc tggcggcggg accccccagg gccgctcggt cacgctgcgc    480
agctctctgt accgggcggg gggcgcctac gggccgggca ctcccgagct gctgctcgag    540
ggcgccgaga cggtgactcc agtgctggac ccggccagga caagggta  cgggcctctc    600 tggtacacga gcgtgggggtt cggcggcctg gtgcagctcc ggaggggcga gagggtgtac    660
gtcaacatca gtcaccccga tatggtggac ttcgcgagag ggaagacctt ctttggggcc    720
gtgatggtgg ggtga                                                    735

<210> SEQ ID NO 141
<211> LENGTH: 636
<212> TYPE: DNA
<213> ORGANISM: Homo sapiens

<400> SEQUENCE: 141
atgaggacct tggcttgcct gctgctcctc ggctgcggat acctcgccca tgttctggcc     60
gaggaagccg agatccccg  cgaggtgatc gagaggctgg cccgcagtca gatccacagc    120
atccgggacc tccagcgact cctggagata gactccgtag ggagtgagga ttctttggac    180
accagcctga gagctcacgg ggtccacgcc actaagcatg tgcccgagaa gcggcccctg    240
cccattcgga ggaagagaag catcgaggaa gctgtcccg  ctgtctgcaa gaccaggacg    300
gtcatttacg agattcctcg gagtcaggtc gaccccacgt ccgccaactt cctgatctgg    360
cccccgtgcg tggaggtgaa acgctgcacc ggctgctgca acacgagcag tgtcaagtgc    420
cagccctccc gcgtccacca ccgcagcgtc aaggtggcca aggtggaata cgtcaggaag    480
aagccaaaat taaagaagt  ccaggtgagg ttagaggagc attttgagtg cgcctgcgcg    540
accacaagcc tgaatccgga ttatcgggaa gaggacacgg gaaggcctag ggagtcaggt    600
```

| aaaaaacgga aaagaaaaag gttaaaaccc acctaa | 636 |

<210> SEQ ID NO 142
<211> LENGTH: 726
<212> TYPE: DNA
<213> ORGANISM: Homo sapiens

<400> SEQUENCE: 142

| atgaatcgct gctgggcgct cttcctgtct ctctgctgct acctgcgtct ggtcagcgcc | 60 |
| gaggggacc ccattcccga ggagctttat gagatgctga gtgaccactc gatccgctcc | 120 |
| tttgatgatc tccaacgcct gctgcacgga gaccccggag aggaagatgg ggccgagttg | 180 |
| gacctgaaca tgacccgctc ccactctgga ggcgagctgg agagcttggc tcgtggaaga | 240 |
| aggagcctgg gttccctgac cattgctgag ccggccatga tcgccgagtg caagacgcgc | 300 |
| accgaggtgt tcgagatctc ccggcgcctc atagaccgca ccaacgccaa cttcctggtg | 360 |
| tggccgccct gtgtggaggt gcagcgctgc tccggctgct gcaacaaccg caacgtgcag | 420 |
| tgccgcccca cccaggtgca gctgcgacct gtccaggtga aaagatcga gattgtgcgg | 480 |
| aagaagccaa tctttaagaa ggccacggtg acgctggaag accacctggc atgcaagtgt | 540 |
| gagacagtgg cagctgcacg gcctgtgacc cgaagcccgg ggggttccca ggagcagcga | 600 |
| gccaaaacgc cccaaactcg ggtgaccatt cggacggtgc gagtccgccg gcccccaag | 660 |
| ggcaagcacc ggaaattcaa gcacacgcat gacaagacgg cactgaagga gacccttgga | 720 |
| gcctag | 726 |

<210> SEQ ID NO 143
<211> LENGTH: 723
<212> TYPE: DNA
<213> ORGANISM: Homo sapiens

<400> SEQUENCE: 143

| atgctggcgc tactgtgttc ctgcctgctc ctggcagccg gtgcctcgga cgcctggacg | 60 |
| ggcgaggact cggcggagcc caactctgac tcggcggagt ggatccgaga catgtacgcc | 120 |
| aaggtcacgg agatctggca ggaggtcatg cagcggcggg acgacgacgg cacgctccac | 180 |
| gccgcctgcc aggtgcagcc gtcggccacg ctggacgccg cgcagccccg ggtgaccggc | 240 |
| gtcgtcctct ccggcagct tgcgccccgc gccaagctcg acgccttctt cgccctggag | 300 |
| ggcttcccga ccgagccgaa cagctccagc cgcgccatcc acgtgcacca gttcggggac | 360 |
| ctgagccagg gctgcgagtc caccgggccc cactacaacc cgctggccgt gccgcacccg | 420 |
| cagcacccgg gcgacttcgg caacttcgcg gtccgcgacg gcagcctctg gaggtaccgc | 480 |
| gccgcctgg ccgcctcgct cgcgggcccg cactccatcg tgggccgggc cgtggtcgtc | 540 |
| cacgctggcg aggacgacct gggccgcggc ggcaaccagg ccagcgtgga gaacgggaac | 600 |
| gcgggccggc ggctggcctg ctgcgtggtg gcgtgtgcg ggcccgggct ctgggagcgc | 660 |
| caggcgcggg agcactcaga gcgcaagaag cggcggcgcg agagcgagtg caaggccgcc | 720 |
| tga | 723 |

<210> SEQ ID NO 144
<211> LENGTH: 483
<212> TYPE: DNA
<213> ORGANISM: Homo sapiens

<400> SEQUENCE: 144

| atggtcccct cggctggaca gctcgccctg ttcgctctgg gtattgtgtt ggctgcgtgc | 60 |

```
caggccttgg agaacagcac gtccccgctg agtgcagacc cgcccgtggc tgcagcagtg      120
gtgtcccatt ttaatgactg cccagattcc cacactcagt tctgcttcca tggaacctgc      180
aggttttggt tgcaggagga caagccagca tgtgtctgcc attctgggta cgttggtgca      240
cgctgtgagc atgcggacct cctgccgtg gtggctgcca gccagaagaa gcaggccatc       300
accgccttgg tggtggtctc catcgtggcc ctggctgtcc ttatcatcac atgtgtgctg      360
atacactgct gccaggtccg aaaacactgt gagtggtgcc gggccctcat ctgccggcac      420
gagaagccca gcgccctcct gaagggaaga accgcttgct gccactcaga aacagtggtc      480
tga                                                                    483

<210> SEQ ID NO 145
<211> LENGTH: 954
<212> TYPE: DNA
<213> ORGANISM: Homo sapiens

<400> SEQUENCE: 145
atgcgccgcg ccagcagaga ctacaccaag tacctgcgtg gctcggagga gatgggcggc       60
ggccccggag ccccgcacga gggcccctg cacgcccgc cgccgcctgc gccgcaccag        120 cccccgccg cctcccgctc catgttcgtg gccctcctgg gctgggggct gggccaggtt       180
gtctgcagcg tcgccctgtt cttctatttc agagcgcaga tggatcctaa tagaatatca      240
gaagatggca ctcactgcat ttatagaatt ttgagactcc atgaaaatgc agattttcaa      300
gacacaactc tggagagtca agatacaaaa ttaatacctg attcatgtag agaaattaaa      360
caggcctttc aaggagctgt gcaaaaggaa ttacaacata tcgttggatc acagcacatc      420
agagcagaga aagcgatggt ggatggctca tggttagatc tggccaagag gagcaagctt      480
gaagctcagc cttttgctca tctcactatt aatgccaccg acatcccatc tggttcccat      540
aaagtgagtc tgtcctcttg gtaccatgat cggggttggg ccaagatctc caacatgact      600
tttagcaatg gaaaactaat agttaatcag gatggctttt attacctgta tgccaacatt      660
tgctttcgac atcatgaaac ttcaggagac ctagctacag agtatcttca actaatggtg      720
tacgtcacta aaaccagcat caaaatccca agttctcata ccctgatgaa aggaggaagc      780
accaagtatt ggtcagggaa ttctgaattc cattttatt ccataaacgt tggtggattt      840
tttaagttac ggtctggaga ggaaatcagc atcgaggtct ccaaccccte cttactggat      900 ccggatcagg atgcaacata ctttgggget tttaaagttc gagatataga ttga           954

<210> SEQ ID NO 146
<211> LENGTH: 753
<212> TYPE: DNA
<213> ORGANISM: Homo sapiens

<400> SEQUENCE: 146
atgccagcct catctccttt cttgctagcc cccaaagggc ctccaggcaa catgggggc        60 ccagtcagag agccggcact ctcagttgcc ctctggttga gttgggggc agctctgggg       120 gccgtggctt gtgccatggc tctgctgacc caacaaacag agctgcagag cctcaggaga      180
gaggtgagcc ggctgcaggg gacaggaggc ccctcccaga tggggaagg gtatccctgg       240 cagagtctcc cggagcagag ttccgatgcc ctggaagcct gggagaatgg ggagagatcc      300
cggaaaagga gagcagtgct cacccaaaaa cagaagaagc agcactctgt cctgcacctg      360
gttcccatta cgccaccte caaggatgac tccgatgtga cagaggtgat gtggcaacca      420
gctcttaggc gtgggagagg cctacaggcc caaggatatg gtgtccgaat ccaggatgct      480
```

```
ggagtttatc tgctgtatag ccaggtcctg tttcaagacg tgactttcac catgggtcag    540
gtggtgtctc gagaaggcca aggaaggcag gagactctat tccgatgtat aagaagtatg    600
ccctcccacc cggaccgggc ctacaacagc tgctatagcg caggtgtctt ccatttacac    660 caagggata ttctgagtgt cataattccc cgggcaaggg cgaaacttaa cctctctcca    720
catggaacct tcctggggtt tgtgaaactg tga                                753
```

<210> SEQ ID NO 147
<211> LENGTH: 750
<212> TYPE: DNA
<213> ORGANISM: Homo sapiens

<400> SEQUENCE: 147

```
atggccgccc gtcggagcca gaggcggagg gggcgccggg gggagccggg caccgccctg     60
ctggtcccgc tcgcgctggg cctgggcctg gcgctggcct gcctcggcct cctgctggcc    120
gtggtcagtt tggggagccg ggcatcgctg tccgcccagg agcctgccca ggaggagctg    180
gtggcagagg aggaccagga cccgtcggaa ctgaatcccc agacagaaga aagccaggat    240
cctgcgcctt tcctgaaccg actagttcgg cctcgcagaa gtgcacctaa aggcggaaa     300 acacgggctc gaagagcgat cgcagcccat tatgaagttc atccacgacc tggacaggac    360
ggagcgcagg caggtgtgga cgggacagtg agtggctggg aggaagccag aatcaacagc    420
tccagccctc tgcgctacaa ccgccagatc ggggagttta tagtcacccg ggctgggctc    480
tactacctgt actgtcaggt gcactttgat gaggggaagg ctgtctacct gaagctggac    540
ttgctggtgg atggtgtgct ggccctgcgc tgcctggagg aattctcagc cactgcggcg    600
agttccctcg gccccagct ccgcctctgc caggtgtctg ggctgttggc cctgcggcca    660
gggtcctccc tgcggatccg cacctccc tgggcccatc tcaaggctgc cccttcctc     720 acctacttcg gactcttcca ggttcactga                                     750
```

<210> SEQ ID NO 148
<211> LENGTH: 765
<212> TYPE: DNA
<213> ORGANISM: Homo sapiens

<400> SEQUENCE: 148

```
atggaatacg cctctgacgc ttcactggac cccgaagccc cgtggcctcc cgcgccccgc     60
gctcgcgcct gccgcgtact gccttgggcc ctggtcgcgg ggctgctgct gctgctgctg    120
ctcgctgccg cctgcgccgt cttcctgccc tgccctgggg ccgtgtccgg ggctcgcgcc    180
tcgcccggct ccgcggccag cccgagactc cgcgagggtc ccgagctttc gcccgacgat    240
cccgccggcc tcttggacct gcggcagggc atgtttgcgc agctggtggc ccaaaatgtt    300
ctgctgatcg atgggcccct gagctggtac agtgacccag gcctggcagg cgtgtccctg    360 acggggggc tgagctacaa agaggacacg aaggagctgg tggtggccaa ggctggagtc    420
tactatgtct tctttcaact agagctgcgg cgcgtggtgg ccggcgaggg ctcaggctcc    480
gtttcacttg cgctgcacct gcagccactg cgctctgctg ctggggccgc cgccctggct    540
ttgaccgtgg acctgccacc cgcctcctcc gaggctcgga actcggcctt cggtttccag    600
ggccgcttgc tgcacctgag tgccggccag cgcctgggcg tccatcttca cactgaggcc    660
agggcacgcc atgcctggca gcttacccag ggcgccacag tcttgggact cttccgggtg    720 accccgaaa tccagccgg actcccttca ccgaggtcgg aataa                      765
```

<210> SEQ ID NO 149

<211> LENGTH: 651
<212> TYPE: DNA
<213> ORGANISM: Homo sapiens

<400> SEQUENCE: 149

| | | | | | |
|---|---|---|---|---|---|
| atgggagccg | cccgcctgct | gcccaacctc | actctgtgct | tacagctgct | gattctctgc | 60 |
| tgtcaaactc | aggggggagaa | tcacccgtct | cctaattttta | accagtacgt | gagggaccag | 120 |
| ggcgccatga | ccgaccagct | gagcaggcgg | cagatccgcg | agtaccaact | ctacagcagg | 180 |
| accagtggca | agcacgtgca | ggtcaccggg | cgtcgcatct | ccgccaccgc | cgaggacggc | 240 |
| aacaagtttg | ccaagctcat | agtggagacg | gacacgtttg | gcagccgggt | tcgcatcaaa | 300 |
| ggggctgaga | gtgagaagta | catctgtatg | aacaagaggg | gcaagctcat | cgggaagccc | 360 |
| agcgggaaga | gcaaagactg | cgtgttcacg | gagatcgtgc | tggagaacaa | ctatacggcc | 420 |
| ttccagaacg | cccggcacga | gggctggttc | atggccttca | cgcggcaggg | gcggccccgc | 480 |
| caggcttccc | gcagccgcca | gaaccagcgc | gaggcccact | tcatcaagcg | cctctaccaa | 540 |
| ggccagctgc | ccttccccaa | ccacgccgag | aagcagaagc | agttcgagtt | tgtgggctcc | 600 |
| gcccccaccc | gccggaccaa | gcgcacacgg | cggccccagc | ccctcacgta | g | 651 |

<210> SEQ ID NO 150
<211> LENGTH: 624
<212> TYPE: DNA
<213> ORGANISM: Homo sapiens

<400> SEQUENCE: 150

| | | | | | |
|---|---|---|---|---|---|
| atggcagagg | tggggggcgt | cttcgcctcc | ttggactggg | atctacacgg | cttctcctcg | 60 |
| tctctgggga | acgtgccctt | agctgactcc | ccaggtttcc | tgaacgagcg | cctgggccaa | 120 |
| atcgagggga | agctgcagcg | tggctcaccc | acagacttcg | cccacctgaa | ggggatcctg | 180 |
| cggcgccgcc | agctctactg | ccgcaccggc | ttccacctgg | atcttccc | caacggcacg | 240 |
| gtgcacggga | cccgccacga | ccacagccgc | ttcggaatcc | tggagtttat | cagcctggct | 300 |
| gtggggctga | tcagcatccg | gggagtggac | tctggcctgt | acctaggaat | gaatgagcga | 360 |
| ggagaactct | atgggtcgaa | gaaactcaca | cgtgaatgtg | ttttccggga | acagtttgaa | 420 |
| gaaaactggt | acaacaccta | tgcctcaacc | ttgtacaaac | attcggactc | agagagacag | 480 |
| tattacgtgg | ccctgaacaa | agatggctca | ccccgggagg | gatacaggac | taaacgacac | 540 |
| cagaaattca | ctcacttttt | acccaggcct | gtagatcctt | ctaagttgcc | ctccatgtcc | 600 |
| agagacctct | ttcactatag | gtaa | | | | 624 |

<210> SEQ ID NO 151
<211> LENGTH: 2553
<212> TYPE: DNA
<213> ORGANISM: Homo sapiens

<400> SEQUENCE: 151

| | | | | | |
|---|---|---|---|---|---|
| atgcggcagg | tttgctgctc | agcgctgccg | ccgccgccac | tggagaaggg | tcggtgcagc | 60 |
| agctacagcg | acagcagcag | cagcagcagc | gagaggagca | gcagcagcag | cagcagcagc | 120 |
| agcgagagcg | gcagcagcag | caggagcagc | agcaacaaca | gcagcatctc | tcgtcccgct | 180 |
| gcgcccccag | agccgcggcc | gcagcaacag | ccgcagcccc | gcagcccgc | agcccggaga | 240 |
| gccgccgccc | gttcgcgagc | cgcagccgcc | ggcggcatga | ggcgcgaccc | ggccccggc | 300 |
| ttctccatgc | tgctcttcgg | tgtgtcgctc | gcctgctact | cgcccagcct | caagtcagtg | 360 |
| caggaccagg | cgtacaaggc | acccgtggtg | gtggagggca | aggtacaggg | gctggtccca | 420 |

| | |
|---|---|
| gccggcggct ccagctccaa cagcacccga gagccgcccg cctcgggtcg ggtggcgttg | 480 |
| gtaaaggtgc tggacaagtg gccgctccgg agcggggggc tgcagcgcga gcaggtgatc | 540 |
| agcgtgggct cctgtgtgcc gctcgaaagg aaccagcgct acatcttttt cctggagccc | 600 |
| acggaacagc ccttagtctt taagacggcc tttgcccccc tcgataccaa cggcaaaaat | 660 |
| ctcaagaaag aggtgggcaa gatcctgtgc actgactgcg ccacccggcc caagttgaag | 720 |
| aagatgaaga gccagacggg acaggtgggt gagaagcaat cgctgaagtg tgaggcagca | 780 |
| gccggtaatc cccagccttc ctaccgttgg ttcaaggatg caaggagct caaccgcagc | 840 |
| cgagacattc gcatcaaata tggcaacggc agaaagaact cacgactaca gttcaacaag | 900 |
| gtgaaggtgg aggacgctgg ggagtatgtc tgcgaggccg agaacatcct ggggaaggac | 960 |
| accgtccggg gccggcttta cgtcaacagc gtgagcacca ccctgtcatc ctggtcgggg | 1020 |
| cacgcccgga agtgcaacga gacagccaag tcctattgcg tcaatggagg cgtctgctac | 1080 |
| tacatcgagg gcatcaacca gctctcctgc aaatgtccaa atggattctt cggacagaga | 1140 |
| tgtttggaga aactgccttt gcgattgtac atgccagatc ctaagcaaaa agccgaggag | 1200 |
| ctgtaccaga gagggtcct gaccatcacg ggcatctgcg tggctctgct ggtcgtgggc | 1260 |
| atcgtctgtg tggtggccta ctgcaagacc aaaaaacagc ggaagcagat gcacaaccac | 1320 |
| ctccggcaga acatgtgccc ggcccatcag aaccggagct ggccaatgg gcccagccac | 1380 |
| ccccggctgg acccagagga gatccagatg gcagattata tttccaagaa cgtgccagcc | 1440 |
| acagaccatg tcatcaggag agaaactgag accaccttct ctgggagcca ctcctgttct | 1500 |
| ccttctcacc actgctccac agccacaccc acctccagcc acagacacga gagccacacg | 1560 |
| tggagcctgg aacgttctga gagcctgact tctgactccc agtcggggat catgctatca | 1620 |
| tcagtgggta ccagcaaatg caacagccca gcatgtgtgg aggcccgggc aaggcgggca | 1680 |
| gcagcctaca acctggagga gcggcgcagg gccaccgcgc caccctatca cgattccgtg | 1740 |
| gactcccttc gcgactcccc acacagcgag aggtacgtgt cggccctgac cacgcccgcg | 1800 |
| cgcctctcgc ccgtggactt ccactactcg ctggccacgc aggtgccaac tttcgagatc | 1860 |
| acgtccccca actcggcgca cgccgtgtcg ctgccgccgg cggcgccat cagttaccgc | 1920 |
| ctggccgagc agcagccgtt actgcggcac ccggcgcccc ccggcccggg acccggaccc | 1980 |
| gggcccgggc ccgggcccgg cgcagacatg cagcgcagct atgacagcta ctattacccc | 2040 |
| gcggcggggc ccggaccgcg cgcgggacc tgcgcgctcg gcggcagcct gggcagcctg | 2100 |
| cctgccagcc ccttccgcat ccccgaggac gacgagtacg agaccacgca ggagtgcgcg | 2160 |
| ccccgccgc cgccgcggcc gcgcgcgcg ggtgcgtccc gcaggacgtc ggcggggccc | 2220 |
| cggcgctggc gccgctcgcg cctcaacggg ctggcgcgc agcgcgcacg ggcggcgagg | 2280 |
| gactcgctgt cgctgagcag cggctcgggc ggcggctcag cctcggcgtc ggacgacgac | 2340 |
| gcggacgacg cggacggggc gctggcggcc gagagcacac cttccctggg cctgcgtggg | 2400 |
| gcgcacgacg cgctgcgctc ggactcgccg ccactgtgcc cggcggccga cagcaggact | 2460 |
| tactactcac tggacagcca cagcacgcgg gccagcagca cacacagccg cgggccgccc | 2520 |
| ccgcgggcca agcaggactc ggcgccactc tag | 2553 |

<210> SEQ ID NO 152
<211> LENGTH: 534
<212> TYPE: DNA
<213> ORGANISM: Homo sapiens

<400> SEQUENCE: 152

```
atgtgtttga gccacttgga aaatatgcct ttaagccatt caagaactca aggagctcag    60
agatcatcct ggaagctgtg gctcttttgc tcaatagtta tgttgctatt tctttgctcc   120
ttcagttggc taatctttat ttttctccaa ttagagactg ctaaggagcc ctgtatggct   180
aagtttggac cattaccctc aaaatggcaa atggcatctt ctgaacctcc ttgcgtgaat   240
aaggtgtctg actggaagct ggagatactt cagaatggct tatatttaat ttatggccaa   300
gtggctccca atgcaaacta caatgatgta gctccttttg aggtgcggct gtataaaaac   360
aaagacatga tacaaactct aacaaacaaa tctaaaatcc aaaatgtagg agggacttat   420
gaattgcatg ttggggacac catagacttg atattcaact ctgagcatca ggttctaaaa   480
aataatacat actggggtat cattttacta gcaaatcccc aattcatctc ctag         534

<210> SEQ ID NO 153
<211> LENGTH: 390
<212> TYPE: DNA
<213> ORGANISM: Homo sapiens

<400> SEQUENCE: 153
atgggacggc gagacgccca gctcctggca gcgctcctcg tcctggggct atgtgccctg    60
gcggggagtg agaaaccctc cccctgccag tgctccaggc tgagccccca taacaggacg   120
aactgcggct tccctggaat caccagtgac cagtgttttg acaatggatg ctgtttcgac   180
tccagtgtca ctggggtccc ctggtgtttc cacccctcc caaagcaaga gtcggatcag   240
tgcgtcatgg aggtctcaga ccgaagaaac tgtggctacc cggcatcag ccccgaggaa    300 tgcgcctctc ggaagtgctg cttctccaac ttcatctttg aagtgccctg gtgcttcttc   360
ccgaagtctg tggaagactg ccattactaa                                    390

<210> SEQ ID NO 154
<211> LENGTH: 1260
<212> TYPE: DNA
<213> ORGANISM: Homo sapiens

<400> SEQUENCE: 154
atgcacttgc tgggcttctt ctctgtggcg tgttctctgc tcgccgctgc gctgctcccg    60
ggtcctcgcg aggcgcccgc cgccgccgcc gccttcgagt ccggactcga cctctcggac   120
gcggagcccg acgcgggcga ggccacggct tatgcaagca agatctggga ggagcagtta   180
cggtctgtgt ccagtgtaga tgaactcatg actgtactct acccagaata ttggaaaatg   240
tacaagtgtc agctaaggaa aggaggctgg caacataaca gagaacaggc caacctcaac   300
tcaaggacag aagagactat aaaatttgct gcagcacatt ataatacaga gatcttgaaa   360
agtattgata tgagtggag aaagactcaa tgcatgccac gggaggtgtg tatagatgtg   420
gggaaggagt ttggagtcgc gacaaacacc ttctttaaac ctccatgtgt gtccgtctac   480
agatgtgggg gttgctgcaa tagtgagggg ctgcagtgca tgaacaccag cacgagctac   540
ctcagcaaga cgttatttga aattacagtg cctctctctc aaggccccaa accagtaaca   600
atcagttttg ccaatcacac ttcctgccga tgcatgtcta actgatgtgt ttacagacaa   660
gttcattcca ttattagacg ttccctgcca gcaacactac cacagtgtca ggcagcgaac   720
aagacctgcc ccaccaatta catgtggaat aatcacatct gcagatgcct ggctcaggaa   780
gattttatgt tttcctcgga tgctggagat gactcaacag atggattcca tgacatctgt   840
ggaccaaaca aggagctgga tgaagagacc tgtcagtgtg tctgcagagc ggggcttcgg   900
cctgccagct gtggacccca caagaactga gacagaaact catgccagtg tgtctgtaaa   960
```

| | | | |
|---|---|---|---|
| aacaaactct | tcccagcca atgtggggcc | aaccgagaat tgatgaaaa | cacatgccag | 1020 |
| tgtgtatgta | aaagaacctg ccccagaaat | caaccccaa atcctggaaa | atgtgcctgt | 1080 |
| gaatgtacag | aaagtccaca gaaatgcttg | ttaaaggaa agaagttcca | ccaccaaaca | 1140 |
| tgcagctgtt | acagacggcc atgtacgaac | cgccagaagg cttgtgagcc | aggattttca | 1200 |
| tatagtgaag | aagtgtgtcg ttgtgtccct | tcatattgga aaagaccaca | aatgagctaa | 1260 |

<210> SEQ ID NO 155
<211> LENGTH: 3729
<212> TYPE: DNA
<213> ORGANISM: Homo sapiens

<400> SEQUENCE: 155

| | | | |
|---|---|---|---|
| atggcgagcc | ctccggagag cgatggcttc | tcggacgtgc gcaaggtggg | ctacctgcgc | 60 |
| aaacccaaga | gcatgcacaa acgcttcttc | gtactgcgcg cggccagcga | ggctgggggc | 120 |
| ccggcgcgcc | tcgagtacta cgagaacgag | aagaagtggc ggcacaagtc | gagcgccccc | 180 |
| aaacgctcga | tccccttga gagctgcttc | aacatcaaca gcgggctga | ctccaagaac | 240 |
| aagcacctgg | tggctctcta cacccgggac | gagcactttg ccatcgcggc | ggacagcgag | 300 |
| gccgagcaag | acagctggta ccaggctctc | ctacagctgc acaaccgtgc | taagggccac | 360 |
| cacgacggag | ctgcggccct cggggcggga | ggtggtgggg gcagctgcag | cggcagctcc | 420 |
| ggccttggtg | aggctgggga ggacttgagc | tacggtgacg tgccccagg | acccgcattc | 480 |
| aaagaggtct | ggcaagtgat cctgaagccc | aagggcctgg tcagacaaa | gaacctgatt | 540 |
| ggtatctacc | gcctttgcct gaccagcaag | accatcagct tcgtgaagct | gaactcggag | 600 |
| gcagcggccg | tggtgctgca gctgatgaac | atcaggcgct gtggccactc | ggaaaacttc | 660 |
| ttcttcatcg | aggtgggccg ttctgccgtg | acggggcccg gggagttctg | gatgcaggtg | 720 |
| gatgactctg | tggtggccca gaacatgcac | gagaccatcc tggaggccat | gcgggccatg | 780 |
| agtgatgagt | tccgccctcg cagcaagagc | cagtcctcgt ccaactgctc | taaccccatc | 840 |
| agcgtccccc | tgcgccggca ccatctcaac | aatcccccgc ccagccaggt | ggggctgacc | 900 |
| cgccgatcac | gcactgagag catcaccgcc | acctccccgg ccagcatggt | gggcgggaag | 960 |
| ccaggctcct | tccgtgtccg cgcctccagt | gacggcgaag gcaccatgtc | ccgcccagcc | 1020 |
| tcggtggacg | gcagccctgt gagtcccagc | accaacagaa cccacgccca | ccggcatcgg | 1080 |
| ggcagcgccc | ggctgcaccc ccgctcaaac | acagccgct ccatcccat | gccggcttcc | 1140 |
| cgctgctcgc | cttcggccac cagccgagtc | agtctgtcgt ccagtagcac | cagtggccat | 1200 |
| ggctccacct | cggattgtct cttcccacgg | cgatctagtg cttcggtgtc | tggttccccc | 1260 |
| agcgatggcg | gtttcatctc ctcggatgag | tatggctcca gtccctgcga | tttccggagt | 1320 |
| tccttccgca | gtgtcactcc ggattccctg | gccacaccc accagcccg | cggtgaggag | 1380 |
| gagctaagca | actatatctg catggtggc | aagggccct ccaccctgac | cgcccccaac | 1440 |
| ggtcactaca | tttttgtctcg gggtggcaat | ggccaccgct gcaccccagg | aacaggcttg | 1500 |
| ggcacgagtc | cagccttggc tgggatgaa | gcagccagtg ctgcagatct | ggataatcgg | 1560 |
| ttccgaaaga | gaactcactc ggcaggcaca | tcccctacca ttacccacca | gaagaccccg | 1620 |
| tcccagtcct | cagtggcttc cattgaggag | tacacagaga tgatgcctgc | ctacccacca | 1680 |
| ggaggtggca | gtggaggccg actgccggga | cacaggcact ccgccttcgt | gcccaccgc | 1740 |
| tcctacccag | aggagggtct ggaaatgcac | ccttggagc gtcggggggg | gcaccaccgc | 1800 |
| ccagacagct | ccaccctcca cacgatgat | ggctacatgc ccatgtcccc | aggggtggcc | 1860 |

```
ccagtgccca gtggccgaaa gggcagtgga gactatatgc ccatgagccc caagagcgta    1920
tctgccccac agcagatcat caatcccatc agacgccatc cccagagagt ggaccccaat    1980
ggctacatga tgatgtcccc cagcggtggc tgctctcctg acattggagg tggccccagc    2040
agcagcagca gcagcagcaa cgccgtccct tccgggacca gctatggaaa gctgtggaca    2100
aacggggtag ggggccacca ctctcatgtc ttgcctcacc ccaaaccccc agtggagagc    2160
agcggtggta agctcttacc ttgcacaggt gactacatga acatgtcacc agtggggac    2220 tccaacacca gcagccctc cgactgctac tacggccctg aggacccca gcacaagcca    2280 gtcctctcct actactcatt gccaagatcc tttaagcaca cccagcgccc cggggagccg    2340
gaggagggtg cccggcatca gcacctccgc ctttccacta gctctggtcg ccttctctat    2400
gctgcaacag cagatgattc ttcctcttcc accagcagcg acagcctggg tggggatac    2460 tgcggggcta ggctggagcc cagccttcca catccccacc atcaggttct gcagccccat    2520
ctgcctcgaa aggtggacac agctgctcag accaatagcc gcctggcccg cccacgagg    2580 ctgtccctgg gggatcccaa ggccagcacc ttacctcggg cccgagagca gcagcagcag    2640
cagcagccct tgctgcaccc tccagagccc aagagcccgg gggaatatgt caatattgaa    2700
tttgggagtg atcagtctgg ctacttgtct ggcccggtgg ctttccacag ctcaccttct    2760
gtcaggtgtc catcccagct ccagccagct cccagagagg aagagactgg cactgaggag    2820
tacatgaaga tggacctggg gccgggccgg agggcagcct ggcaggagag cactggggtc    2880
gagatgggca gactgggccc tgcacctccc ggggctgcta gcatttgcag gcctacccgg    2940
gcagtgccca gcagccgggg tgactacatg accatgcaga tgagttgtcc ccgtcagagc    3000
tacgtggaca cctcgccagc tgcccctgta agctatgctg acatgcgaac aggcattgct    3060
gcagaggagg tgagcctgcc cagggccacc atggctgctg cctcctcatc ctcagcagcc    3120
tctgcttccc cgactgggcc tcaagggca gcagagctgg ctgccccactc gtccctgctg    3180 gggggcccac aaggacctgg gggcatgagc gccttcaccc gggtgaacct cagtcctaac    3240
cgcaaccaga gtgccaaagt gatccgtgca gacccacaag ggtgccggcg gaggcatagc    3300
tccgagactt tctcctcaac acccagtgcc acccgggtgg gcaacacagt gccctttgga    3360 gcggggcag cagtaggggg cggtggcggt agcagcagca gcagcgagga tgtgaaacgc    3420
cacagctctg cttcctttga gaatgtgtgg ctgaggcctg gggagcttgg gggagccccc    3480
aaggagccag ccaaactgtg tggggctgct gggggtttgg agaatggtct taactacata    3540
gacctggatt tggtcaagga cttcaaacag tgccctcagg agtgcacccc tgaaccgcag    3600
cctcccccac ccccaccccc tcatcaaccc ctgggcagcg gtgagagcag ctccacccgc    3660
cgctcaagtg aggatttaag cgcctatgcc agcatcagtt tccagaagca gccagaggac    3720
cgtcagtag                                                           3729

<210> SEQ ID NO 156
<211> LENGTH: 513
<212> TYPE: DNA
<213> ORGANISM: Homo sapiens

<400> SEQUENCE: 156
atgatggcag gaatgaaaat ccagcttgta tgcatgctac tcctggcttt cagctcctgg      60
agtctgtgct cagattcaga agaggaaatg aaagcattag aagcagattt cttgaccaat     120
atgcatacat caaagattag taagcacat gttccctctt ggaagatgac tctgctaaat     180
gtttgcagtc ttgtaaataa tttgaacagc ccagctgagg aaacaggaga agttcatgaa     240
```

| | |
|---|---|
| gaggagcttg ttgcaagaag gaaacttcct actgctttag atggctttag cttggaagca | 300 |
| atgttgacaa taccagct ccacaaaatc tgtcacagca gggcttttca acactgggag | 360 |
| ttaatccagg aagatattct tgatactgga aatgacaaaa atggaaagga agaagtcata | 420 |
| aagagaaaaa ttccttatat tctgaaacgg cagctgtatg agaataaacc cagaagaccc | 480 |
| tacatactca aaagagattc ttactattac tga | 513 |

<210> SEQ ID NO 157
<211> LENGTH: 858
<212> TYPE: DNA
<213> ORGANISM: Homo sapiens

<400> SEQUENCE: 157

| | |
|---|---|
| atggatgact ccacagaaag ggagcagtca cgccttactt cttgccttaa gaaaagagaa | 60 |
| gaaatgaaac tgaaggagtg tgtttccatc ctcccacgga aggaaagccc ctctgtccga | 120 |
| tcctccaaag acggaaagct gctggctgca accttgctgc tggcactgct gtcttgctgc | 180 |
| ctcacggtgg tgtctttcta ccaggtggcc gccctgcaag gggacctggc cagcctccgg | 240 |
| gcagagctgc agggccacca cgcggagaag ctgccagcag gagcaggagc cccaaggcc | 300 |
| ggcctggagg aagctccagc tgtcaccgcg ggactgaaaa tctttgaacc accagctcca | 360 |
| ggagaaggca actccagtca gaacagcaga aataagcgtg ccgttcaggg tccagaagaa | 420 |
| acagtcactc aagactgctt gcaactgatt gcagacagtg aaacaccaac tatacaaaaa | 480 |
| ggatcttaca catttgttcc atggcttctc agctttaaaa ggggaagtgc cctagaagaa | 540 |
| aaagagaata aatattggt caaagaaact ggttactttt ttatatatgg tcaggtttta | 600 |
| tatactgata agacctacgc catgggacat ctaattcaga ggaagaaggt ccatgtcttt | 660 |
| ggggatgaat tgagtctggt gactttgttt cgatgtattc aaaaatgcc tgaaacacta | 720 |
| cccaataatt cctgctattc agctggcatt gcaaaactgg aagaaggaga tgaactccaa | 780 |
| cttgcaatac aagagaaaaa tgcacaaata tcactggatg gagatgtcac attttttggt | 840 |
| gcattgaaac tgctgtga | 858 |

<210> SEQ ID NO 158
<211> LENGTH: 753
<212> TYPE: DNA
<213> ORGANISM: Homo sapiens

<400> SEQUENCE: 158

| | |
|---|---|
| atgaggattc tgcagttaat cctgcttgct ctggcaacag ggcttgtagg gggagagacc | 60 |
| aggatcatca aggggttcga gtgcaagcct cactcccagc cctggcaggc agccctgttc | 120 |
| gagaagacgc ggctactctg tggggcgacg ctcatcgccc ccagatggct cctgacagca | 180 |
| gcccactgcc tcaagccccg ctacatagtt cacctggggc agcacaacct ccagaaggag | 240 |
| gagggctgtg agcagaccog gacagccact gagtccttcc cccacccgg cttcaacaac | 300 |
| agcctcccca caaaagacca ccgcaatgac atcatgctgg tgaagatggc atcgccagtc | 360 |
| tccatcacct gggctgtgcg acccctcacc ctctcctcac gctgtgtcac tgctggcacc | 420 |
| agctgcctca tttccggctg gggcagcacg tccagccccc agttacgcct gcctcacacc | 480 |
| ttgcgatgcg ccaacatcac catcattgag caccagaagt gtgagaacgc ctaccccggc | 540 |
| aacatcacag acaccatggt gtgtgccagc gtgcaggaag ggggcaagga ctcctgccag | 600 |
| ggtgactccg ggggccctct ggtctgtaac cagtctcttc aaggcattat ctcctggggc | 660 |
| caggatccgt gtgcgatcac ccgaaagcct ggtgtctaca cgaaagtctg caaatatgtg | 720 |

| | |
|---|---|
| gactggatcc aggagacgat gaagaacaat tag | 753 |

<210> SEQ ID NO 159
<211> LENGTH: 891
<212> TYPE: DNA
<213> ORGANISM: Homo sapiens

<400> SEQUENCE: 159

| | |
|---|---|
| atggagattt attccccaga catgtctgag gtcgccgccg agaggtcctc cagcccctcc | 60 |
| actcagctga gtgcagaccc atctcttgat gggcttccgg cagcagaaga catgccagag | 120 |
| ccccagactg aagatgggag aacccctgga ctcgtgggcc tggccgtgcc ctgctgtgcg | 180 |
| tgcctagaag ctgagcgcct gagaggttgc ctcaactcag agaaaatctg cattgtcccc | 240 |
| atcctggctt gcctggtcag cctctgcctc tgcatcgccg gcctcaagtg ggtatttgtg | 300 |
| gacaagatct ttgaatatga ctctcctact caccttgacc ctgggggggtt aggccaggac | 360 |
| cctattattt ctctggacgc aactgctgcc tcagctgtgt gggtgtcgtc tgaggcatac | 420 |
| acttcacctg tctctagggc tcaatctgaa agtgaggttc aagttacagt gcaaggtgac | 480 |
| aaggctgttg tctcctttga accatcagcg gcaccgacac cgaagaatcg tattttgcc | 540 |
| ttttctttct tgccgtccac tgcgccatcc ttcccttcac ccacccggaa ccctgaggtg | 600 |
| agaacgccca gtcagcaac tcagccacaa acaacagaaa ctaatctcca aactgctcct | 660 |
| aaactttcta catctacatc caccactggg acaagccatc ttgtaaaatg tgcggagaag | 720 |
| gagaaaactt tctgtgtgaa tggaggggag tgcttcatgg tgaaagacct ttcaaacccc | 780 |
| tcgagatact tgtgcaagtg cccaaatgag tttactggtg atcgctgcca aaactacgta | 840 |
| atggccagct tctacagtac gtccactccc tttctgtctc tgcctgaata g | 891 |

<210> SEQ ID NO 160
<211> LENGTH: 1923
<212> TYPE: DNA
<213> ORGANISM: Homo sapiens

<400> SEQUENCE: 160

| | |
|---|---|
| atgtccgagc gcaaagaagg cagaggcaaa gggaagggca agaagaagga gcgaggctcc | 60 |
| ggcaagaagc cggagtccgc ggcgggcagc cagagcccag ccttgcctcc ccgattgaaa | 120 |
| gagatgaaaa gccaggaatc ggctgcaggt tccaaactag tccttcggtg tgaaaccagt | 180 |
| tctgaatact cctctctcag attcaagtgg ttcaagaatg ggaatgaatt gaatcgaaaa | 240 |
| aacaaaccac aaaatatcaa gatacaaaaa agccaggga gtcagaact cgcattaac | 300 |
| aaagcatcac tggctgattc tggagagtat atgtgcaaag tgatcagcaa attaggaaat | 360 |
| gacagtgcct ctgccaatat caccatcgtg gaatcaaacg atcatcac tggtatgcca | 420 |
| gcctcaactg aaggagcata tgtgtcttca gagtctccca ttagaatatc agtatccaca | 480 |
| gaaggagcaa atacttcttc atctacatct acatccacca ctgggacaag ccatcttgta | 540 |
| aaatgtgcgg agaaggagaa actttctgt gtgaatggag gggagtgctt catggtgaaa | 600 |
| gacctttcaa acccctcgag atacttgtgc aagtgccaac tggattcac tggagcaaga | 660 |
| tgtactgaga atgtgcccat gaaagtccaa aaccaagaaa aggcggagga gctgtaccag | 720 |
| aagagagtgc tgaccataac cggcatctgc atcgccctcc ttgtggtcgg catcatgtgt | 780 |
| gtggtggcct actgcaaaac caagaaacag cggaaaaagc tgcatgaccg tcttcggcag | 840 |
| agccttcggt ctgaacgaaa caatatgatg aacattgcca tgggcctca ccatcctaac | 900 |
| ccacccccg agaatgtcca gctggtgaat caatacgtat ctaaaacgt catctccagt | 960 |

| | |
|---|---|
| gagcatattg ttgagagaga agcagagaca tccttttcca ccagtcacta tacttccaca | 1020 |
| gcccatcact ccactactgt cacccagact cctagccaca gctggagcaa cggacacact | 1080 |
| gaaagcatcc tttccgaaag ccactctgta atcgtgatgt catccgtaga aaacagtagg | 1140 |
| cacagcagcc caactggggg cccaagagga cgtcttaatg gcacaggagg ccctcgtgaa | 1200 |
| tgtaacagct tcctcaggca tgccagagaa acccctgatt cctaccgaga ctctcctcat | 1260 |
| agtgaaaggt atgtgtcagc catgaccacc ccggctcgta tgtcacctgt agatttccac | 1320 |
| acgccaagct cccccaaatc gccccttcg gaaatgtctc cacccgtgtc cagcatgacg | 1380 |
| gtgtccatgc cttccatggc ggtcagcccc ttcatggaag aagagagacc tctacttctc | 1440 |
| gtgacaccac caaggctgcg ggagaagaag tttgaccatc accctcagca gttcagctcc | 1500 |
| ttccaccaca accccgcgca tgacagtaac agcctccctg ctagccccctt gaggatagtg | 1560 |
| gaggatgagg agtatgaaac gacccaagag tacgagccag cccaagagcc tgttaagaaa | 1620 |
| ctcgccaata gccggcgggc caaaagaacc aagcccaatg ccacattgc taacagattg | 1680 |
| gaagtggaca gcaacacaag ctcccagagc agtaactcag agagtgaaac agaagatgaa | 1740 |
| agagtaggtg aagatacgcc tttcctgggc atacagaacc ccctggcagc cagtcttgag | 1800 |
| gcaacacctg ccttccgcct ggctgacagc aggactaacc cagcaggccg cttctcgaca | 1860 |
| caggaagaaa tccaggccag gctgtctagt gtaattgcta accaagaccc tattgctgta | 1920 |
| taa | 1923 |

<210> SEQ ID NO 161
<211> LENGTH: 1398
<212> TYPE: DNA
<213> ORGANISM: Homo sapiens

<400> SEQUENCE: 161

| | |
|---|---|
| atggccagtc agctaactca aagaggagct ctctttctgc tgttcttcct aactccggca | 60 |
| gtgacaccaa catggtatgc aggttctggc tactatccgg atgaaagcta caatgaagta | 120 |
| tatgcagagg aggtcccaca ggctcctgcc ctggactacc gagtcccccg atggtgttat | 180 |
| acattaaata tccaggatgg agaagccaca tgctactcac cgaagggagg aaattatcac | 240 |
| agcagcctgg gcacgcgttg tgagctctcc tgtgaccggg ctttcgatt gattggaagg | 300 |
| aggtcggtgc aatgcctgcc aagccgtcgt tggtctggaa ctgcctactg caggcagatg | 360 |
| agatgccacg cactaccatt catcactagt ggcacttaca cctgcacaaa tggagtgctt | 420 |
| cttgactctc gctgtgacta cagctgttcc agtggctacc acctggaagg tgatcgcagc | 480 |
| cgaatctgca tggaagatgg gagatggagt ggaggcgagc ctgtatgtgt agacatagat | 540 |
| cccccccaaga tccgctgtcc ccactcacgt gagaagatgg cagagccaga gaaattgact | 600 |
| gctcgagtat actgggaccc accgttggtg aaagattctg ctgatggtac catcaccagg | 660 |
| gtgacacttc ggggccctga gcctggctct cactttcccg aaggagagca tgtgattcgt | 720 |
| tacactgcct atgaccgagc ctacaaccgg gccagctgca gttcattgt gaaagtacaa | 780 |
| gtgagacgct gccaactct gaaacctccg cagcacggct acctcacctg cacctcagcg | 840 |
| ggggacaact atggtgccac ctgtgaatac cactgtgatg gcggttatga tcgccagggg | 900 |
| acaccctccc gggtctgtca gtccagccgc cagtggtcag gttcaccacc aatctgtgct | 960 |
| cctatgaaga ttaacgtcaa cgtcaactca gctgctggtc tcttggatca attctatgag | 1020 |
| aaacagcgac tcctcatcat ctcagctcct gatccttcca accgatatta aaaatgcag | 1080 |
| atctctatgc tacagcaatc cacctgtgga ctggatttgc ggcatgtgac catcattgaa | 1140 |

```
ctggtgggac agccacctca ggaggtgggg cgcatccggg agcaacagct gtcagccaac      1200
atcatcgagg agctcaggca atttcagcgc ctcactcgct cctacttcaa catggtgttg      1260
attgacaagc agggtattga ccgagaccgc tacatggaac ctgtcacccc cgaggaaatc      1320
ttcacattca ttgatgacta cctactgagc aatcaggagt tgacccagcg tcgggagcaa      1380
agggacatat gcgagtga                                                    1398

<210> SEQ ID NO 162
<211> LENGTH: 1038
<212> TYPE: DNA
<213> ORGANISM: Homo sapiens

<400> SEQUENCE: 162
atgagcctct tcgggcttct cctgctgaca tctgccctgg ccggccagag acagggact        60 caggcggaat ccaacctgag tagtaaattc cagttttcca gcaacaagga acagaacgga      120
gtacaagatc ctcagcatga gagaattatt actgtgtcta ctaatggaag tattcacagc      180
ccaaggtttc ctcatactta tccaagaaat acggtcttgg tatggagatt agtagcagta      240
gaggaaaatg tatggataca acttacgttt gatgaaagat ttgggcttga agacccagaa      300
gatgacatat gcaagtatga ttttgtagaa gttgaggaac ccagtgatgg aactatatta      360
gggcgctggt gtggttctgg tactgtacca ggaaaacaga tttctaaagg aaatcaaatt      420
aggataagat ttgtatctga tgaatatttt ccttctgaac caggggttctg catccactac      480 aacattgtca tgcccacaat cacagaagct gtgagtcctt cagtgctacc cccttcagct      540
ttgccactgg acctgcttaa taatgctata actgccttta gtaccttgga agaccttatt      600
cgatatcttg aaccagagag atggcagttg gacttagaag atctatatag gccaacttgg      660
caacttcttg gcaaggcttt tgtttttgga agaaaatcca gagtggtgga tctgaacctt      720
ctaacagagg aggtaagatt atacagctgc acacctcgta acttctcagt gtccataagg      780
gaagaactaa agagaaccga taccattttc tggccaggtt gtctcctggt taaacgctgt      840
ggtgggaact gtgcctgttg tctccacaat tgcaatgaat gtcaatgtgt cccaagcaaa      900
gttactaaaa aataccacga ggtccttcag ttgagaccaa agaccggtgt caggggattg      960
cacaaatcac tcaccgacgt ggccctggag caccatgagg agtgtgactg tgtgtgcaga     1020
gggagcacag gaggatag                                                   1038

<210> SEQ ID NO 163
<211> LENGTH: 636
<212> TYPE: DNA
<213> ORGANISM: Homo sapiens

<400> SEQUENCE: 163
atggctccct tagccgaagt cgggggcttt ctgggcggcc tggagggctt gggccagcag       60
gtgggttcgc atttcctgtt gcctcctgcc ggggagcggc cgccgctgct gggcgagcgc      120
aggagcgcgg cggagcggag cgcccgcggc gggccggggg ctgcgcagct ggcgcacctg      180
cacggcatcc tgcgccgccg gcagctctat tgccgcaccg gcttccacct gcagatcctg      240
cccgacggca gcgtgcaggg cacccggcag gaccacagcc tcttcggtat cttggaattc      300
atcagtgtgg cagtgggact ggtcagtatt agaggtgtgg acagtggtct ctatcttgga      360
atgaatgaca aaggagaact ctatggatca gagaaactta cttccgaatg catctttagg      420
gagcagtttg aagagaactg gtataacacc tattcatcta acatatataa acatggagac      480
actggccgca ggtattttgt ggcacttaac aaagacggaa ctccaagaga tggcgccagg      540
```

```
tccaagaggc atcagaaatt tacacatttc ttacctagac cagtggatcc agaaagagtt      600
ccagaattgt acaaggacct actgatgtac acttga                                636
```

<210> SEQ ID NO 164
<211> LENGTH: 759
<212> TYPE: DNA
<213> ORGANISM: Homo sapiens

<400> SEQUENCE: 164

```
atgggggtac tgctcacaca gaggacgctg ctcagtctgg tccttgcact cctgtttcca       60
agcatggcga gcatggcggc tataggcagc tgctcgaaag agtaccgcgt gctccttggc      120
cagctccaga agcagacaga tctcatgcag gacaccagca gactcctgga ccccctatata    180 cgtatccaag gcctggatgt tcctaaactg agagagcact gcaggagcg ccccggggcc      240 ttccccagtg aggagaccct gaggggctg gcaggcggg gcttcctgca gaccctcaat      300
gccacactgg gctgcgtcct gcacagactg gccgacttag agcagcgcct ccccaaggcc      360
caggatttgg agaggtctgg gctgaacatc gaggacttgg agaagctgca gatggcgagg      420
ccgaacatcc tcgggctcag gaacaacatc tactgcatgg cccagctgct ggacaactca      480
gacacggctg agcccacgaa ggctggccgg ggggcctctc agccgcccac ccccaccct      540 gcctcggatg cttttcagcg caagctggag ggctgcaggt tcctgcatgg ctaccatcgc      600
ttcatgcact cagtggggcg ggtcttcagc aagtgggggg agagcccgaa ccggagccgg      660
agacacagcc cccaccaggc cctgaggaag ggggtgcgca ggaccagacc ctccaggaaa      720
ggcaagagac tcatgaccag gggacagctg ccccggtag                             759
```

<210> SEQ ID NO 165
<211> LENGTH: 627
<212> TYPE: DNA
<213> ORGANISM: Homo sapiens

<400> SEQUENCE: 165

```
atggccctgg acagaaaact gttcatcact atgtcccggg gagcaggacg tctgcagggc       60
acgctgtggg ctctcgtctt cctaggcatc ctagtgggca tggtggtgcc ctcgcctgca      120
ggcacccgtg ccaacaacac gctgctggac tcgaggggct ggggcaccct gctgtccagg      180
tctcgcgcgg ggctagctgg agagattgcc ggggtgaact gggaaagtgg ctatttggtg      240
gggatcaagc ggcagcggag gctctactgc aacgtgggca tcggctttca cctccaggtg      300
ctccccgacg gccggatcag cggaccccac gaggagaacc cctacagcct gctggaaatt      360
tccactgtgg agcgaggcgt ggtgagtctc tttggagtga aagtgccct cttcgttgcc      420 atgaacagta aaggaagatt gtacgcaacg cccagcttcc aagaagaatg caagttcaga      480
gaaaccctcc tgcccaacaa ttacaatgcc tacgagtcag acttgtacca agggacctac      540
attgccctga gcaaatacgg acgggtaaag cggggcagca agtgtccccc gatcatgact      600
gtcactcatt tccttcccag gatctaa                                          627
```

<210> SEQ ID NO 166
<211> LENGTH: 1113
<212> TYPE: DNA
<213> ORGANISM: Homo sapiens

<400> SEQUENCE: 166

```
atgcaccggc tcatctttgt ctacactcta atctgcgcaa acttttgcag ctgtcgggac       60
acttctgcaa ccccgcagag cgcatccatc aaagctttgc gcaacgccaa cctcaggcga      120
```

```
gatgagagca atcacctcac agacttgtac cgaagagatg agaccatcca ggtgaaagga      180
aacggctacg tgcagagtcc tagattcccg aacagctacc ccaggaacct gctcctgaca      240
tggcggcttc actctcagga gaatacacgg atacagctag tgtttgacaa tcagtttgga      300
ttagaggaag cagaaaatga tatctgtagg tatgattttg tggaagttga agatatatcc      360
gaaaccagta ccattattag aggacgatgg tgtggacaca aggaagttcc tccaaggata      420
aaatcaagaa cgaaccaaat taaaatcaca ttcaagtccg atgactactt tgtggctaaa      480
cctggattca agatttatta ttctttgctg aagatttcc aacccgcagc agcttcagag       540
accaactggg aatctgtcac aagctctatt tcaggggtat cctataactc tccatcagta      600
acggatccca ctctgattgc ggatgctctg acaaaaaaa ttgcagaatt tgatacagtg       660
gaagatctgc tcaagtactt caatccgagg tcatggcaag aagatcttga gaatatgtat      720
ctggacaccc ctcggtatcg aggcaggtca taccatgacc ggaagtcaaa agttgacctg      780
gataggctca atgatgatgc caagcgttac agttgcactc ccaggaatta ctcggtcaat      840
ataagagaag agctgaagtt ggccaatgtg gtcttctttc cacgttgcct cctcgtgcag      900
cgctgtggag gaaattgtgg ctgtggaact gtcaactgga ggtcctgcac atgcaattca      960
gggaaaaccg tgaaaaagta tcatgaggta ttacagtttg agcctggcca catcaagagg     1020 agggtagag ctaagaccat ggctctagtt gacatccagt tggatcacca tgaacgatgt      1080
gattgtatct gcagctcaag accacctcga taa                                  1113

<210> SEQ ID NO 167
<211> LENGTH: 1059
<212> TYPE: DNA
<213> ORGANISM: Homo sapiens

<400> SEQUENCE: 167
atggccccac tcggatactt cttactcctc tgcagcctga agcaggctct gggcagctac       60
ccgatctggt ggtcgctggc tgttgggcca cagtattcct ccctgggctc gcagcccatc      120
ctgtgtgcca gcatcccggg cctggtcccc aagcagctcc gcttctgcag gaactacgtg      180
gagatcatgc ccagcgtggc cgagggcatc aagattggca tccaggagtg ccagcaccag      240
ttccgcggcc gccggtggaa ctgcaccacc gtccacgaca gcctggccat cttcgggccc      300
gtgctggaca aagctaccag ggagtcggcc tttgtccacg ccattgcctc agccggtgtg      360
gcctttgcag tgacacgctc atgtgcagaa ggcacggccg ccatctgtgg ctgcagcagc      420
cgccaccagg gctcaccagg caagggctgg aagtgggggtg gctgtagcga ggacatcgag      480
tttggtggga tggtgtctcg ggagttcgcc gacgcccggg agaaccggcc agatgcccgc      540
tcagccatga accgccacaa caacgaggct gggcgccagg ccatcgccag ccacatgcac      600
ctcaagtgca gtgccacgg gctgtcgggc agctgcgagg tgaagacatg ctggtggtcg      660
caacccgact ccgcgccat cggtgacttc ctcaaggaca gtacgacag cgcctcggag       720 atggtggtgg agaagcaccg ggagtcccgc ggctgggtgg agaccctgcg gccgcgctac      780
acctacttca aggtgcccac ggagcgcgac ctggtctact acgaggcctc gccaacttc       840 tgcgagccca accctgagac gggctccttc ggcacgcgcg accgcacctg caacgtcagc      900
tcgcacggca tcgacggctg cgacctgctg tgctgcggcc gcggccacaa cgcgcgagcg      960
gagcggcgcc gggagaagtg ccgctgcgtg ttccactggt gctgctacgt cagctgccag     1020
gagtgcacgc gcgtctacga cgtgcacacc tgcaagtag                            1059

<210> SEQ ID NO 168
```

```
<211> LENGTH: 735
<212> TYPE: DNA
<213> ORGANISM: Homo sapiens

<400> SEQUENCE: 168
atgggcagcc cccgctccgc gctgagctgc ctgctgttgc acttgctggt cctctgcctc      60
caagcccagg aaggcccggg caggggccct gcgctgggca gggagctcgc ttccctgttc     120
cgggctggcc gggagcccca gggtgtctcc aacaggtaa ctgttcagtc ctcacctaat      180
tttacacagc atgtgaggga gcagagcctg gtgacggatc agctcagccg ccgcctcatc     240
cggacctacc aactctacag ccgcaccagc gggaagcacg tgcaggtcct ggccaacaag     300
cgcatcaacg ccatggcaga ggacggcgac cccttcgcaa agctcatcgt ggagacggac     360
acctttggaa gcagagtccg agtccgagga gccgagacgg cctctacat ctgcatgaac      420 aagaagggga agctgatcgc caagagcaac ggcaaaggca aggactgcgt cttcacggag     480
attgtgctgg agaacaacta cacagcgctg cagaatgcca agtacgaggg ctggtacatg     540
gccttcaccc gcaagggccg gccccgcaag ggctccaaga cgcggcagca ccagcgtgag     600
gtccacttca tgaagcggct gccccggggc caccacacca ccgagcagag cctgcgcttc     660
gagttcctca actacccgcc cttcacgcgc agcctgcgcg gcagccagag gacttgggcc     720
cccgagcccc gatag                                                     735

<210> SEQ ID NO 169
<211> LENGTH: 348
<212> TYPE: DNA
<213> ORGANISM: Homo sapiens

<400> SEQUENCE: 169
atgccaacag atcacgaaga gccctgtggt cccagtcaca agtcgttttg cctgaatggg      60
gggctttgtt atgtgatacc tactattccc agcccatttt gtaggtgcgt tgaaaactat     120
acaggagctc gttgtgaaga ggttttctc ccaggctcca gcatccaaac taaaagtaac      180
ctgtttgaag cttttgtggc attggcggtc ctagtaacac ttatcattgg agccttctac     240
ttcctttgca ggaaaggcca cttcagaga gccagttcag tccagtatga tatcaacctg     300
gtagagacga gcagtaccag tgcccaccac agtcatgaac aacactga                 348

<210> SEQ ID NO 170
<211> LENGTH: 849
<212> TYPE: DNA
<213> ORGANISM: Homo sapiens

<400> SEQUENCE: 170
atgcagaggt tgaggtggct gcgggactgg aagtcatcgg gcagaggtct cacagcagcc      60
aaggaacctg ggcccgctc ctcccccctc caggccatga ggattctgca gttaatcctg     120
cttgctctgg caacagggct tgtagggga gagaccagga tcatcaaggg gttcgagtgc     180
aagcctcact cccagccctg gcaggcagcc ctgttcgaga agacgcggct actctgtggg     240
gcgacgctca tcgcccccag atggctcctg acagcagccc actgcctcaa gcccgctac     300 atagttcacc tggggcagca caacctccag aaggaggagg gctgtgagca gacccggaca     360
gccactgagt cctcccccca cccggcttc aacaacagcc tcccaacaa agaccaccgc      420 aatgacatca tgctggtgaa gatggcatcg ccagtctcca tcacctgggc tgtgcgaccc     480
ctcaccctct cctcacgctg tgtcactgct ggcaccagct gcctcatttc cggctgggc      540 agcacgtcca gccccagtt acgcctgcct cacaccttgc gatgcgccaa catcaccatc     600
```

| | |
|---|---|
| attgagcacc agaagtgtga gaacgcctac cccggcaaca tcacagacac catggtgtgt | 660 |
| gccagcgtgc aggaagggggg caaggactcc tgccagggtg actccggggg ccctctggtc | 720 |
| tgtaaccagt ctcttcaagg cattatctcc tggggccagg atccgtgtgc gatcacccga | 780 |
| aagcctggtg tctacacgaa agtctgcaaa tatgtggact ggatccagga gacgatgaag | 840 |
| aacaattag | 849 |

<210> SEQ ID NO 171
<211> LENGTH: 2967
<212> TYPE: DNA
<213> ORGANISM: Homo sapiens

<400> SEQUENCE: 171

| | |
|---|---|
| atgggcgcgg cggccgtgcg ctggcacttg tgcgtgctgc tggccctggg cacacgcggg | 60 |
| cggctggccg ggggcagcgg gctcccaggg tcagtcgacg tggatgagtg ctcagagggc | 120 |
| acagatgact gccacatcga tgccatctgt cagaacgcgc ccaagtccta caaatgcctc | 180 |
| tgcaagccag gctacaaggg ggaaggcaag cagtgtggag acattgacga gtgtgagaat | 240 |
| gactactaca tgggggctg tgtccacgag tgcatcaaca tcccggggaa ctacaggtgt | 300 |
| acctgctttg atggcttcat gctggcacac gatggacaca actgcctgga tgtggacgag | 360 |
| tgtcaggaca taatggtgg ctgccagcag atctgcgtca atgccatggg cagctacgag | 420 |
| tgtcagtgcc acagtggctt cttccttagt gacaaccagc ataccctgcat ccaccgctcc | 480 |
| aatgagggta tgaactgcat gaacaaagac catggctgtg cccacatctg ccgggagacg | 540 |
| cccaaaggtg gggtggcctg cgactgcagg cccggctttg accttgccca aaaccagaag | 600 |
| gactgcacac taacctgtaa ttatggaaac ggaggctgcc agcacagctg tgaggacaca | 660 |
| gacacaggcc ccacgtgtgg ttgccaccag aagtacgccc ccactcaga cggtcgcacg | 720 |
| tgcatcgaga cgtgcgcagt caataacgga ggctgcgacc ggacatgcaa ggacacagcc | 780 |
| actggcgtgc gatgcagctg ccccgttgga ttcacactgc agccggacgg gaagacatgc | 840 |
| aaagacatca acgagtgcct ggtcaacaac ggaggctgcg accacttctg ccgcaacacc | 900 |
| gtaggcagct tcgagtgcgg ctgccggaag ggctacaagc tgctcaccga cgagcgcacc | 960 |
| tgccaggaca tcgacgagtg ctccttcgag cggacctgtg accacatctg catcaactcc | 1020 |
| ccgggcagct ccagtgcct tgtcaccgc ggctacatcc tctacgggac aacccactgc | 1080 |
| ggagatgtgg acgagtgcag catgagcaac gggagctgtg accagggctg cgtcaacacc | 1140 |
| aagggcagct acgagtgcgt ctgtccccg ggaggcggc tccactggaa ccggaaggat | 1200 |
| tgcgtggaga caggcaagtg tctttctcgc gccaagacct ccccccgggc ccagctgtcc | 1260 |
| tgcagcaagg caggcggtgt ggagagctgc ttccttttcct gcccggctca cactctcttc | 1320 |
| gtgccagact cggaaaatag ctacgtcctg agctgcggag ttccagggcc gcagggcaag | 1380 |
| gcgctgcaga aacgcaacgg caccagctct ggcctcgggc ccagctgctc agatgccccc | 1440 |
| accaccccca tcaaacagaa ggcccgcttc aagatccgag atgccaagtg ccacctccgg | 1500 |
| ccccacagcc aggcacgagc aaaggagacc gccaggcagc cgctgctgga ccactgccat | 1560 |
| gtgactttcg tgaccctcaa gtgtgactcc tccaagaaga ggcgccgtgg ccgcaagtcc | 1620 |
| ccatccaagg aggtgtccca cattacagca gagtttgaga tcgagacaaa gatggaagag | 1680 |
| gcctcagaca catgcgaagc ggactgcttg cggaagcgag cagaacagag cctgcaggcc | 1740 |
| gccatcaaga ccctgcgcaa gtccatcggc cggcagcagt tctatgtcca ggtctcaggc | 1800 |
| actgagtacg aggtagccca gaggccagcc aaggcgctgg aggggcaggg ggcatgtggc | 1860 |

-continued

```
gcaggccagg tgctacagga cagcaaatgc gttgcctgtg ggcctggcac ccacttcggt    1920
ggtgagctcg gccagtgtgt gccatgtatg ccaggaacat accaggacat ggaaggccag    1980
ctcagttgca caccgtgccc cagcagcgac gggcttggtc tgcctggtgc ccgcaacgtg    2040
tcggaatgtg gaggccagtg ttctccaggc ttcttctcgg ccgatggctt caagccctgc    2100
caggcctgcc ccgtgggcac gtaccagcct gagcccgggc gcaccggctg cttcccctgt    2160
ggagggggtt tgctcaccaa acacgaaggc accacctcct tccaggactg cgaggctaaa    2220
gtgcactgct ccccggcca ccactacaac accaccaccc accgctgcat ccgctgcccc    2280
gtcggcacct accagcccga gtttggccag aaccactgca tcacctgtcc gggcaacacc    2340
agcacagact tcgatggctc caccaacgtc acacactgca aaaaccagca ctgcggcggc    2400
gagcttggtg actacaccgg ctacatcgag tcccccaact accctggcga ctacccagcc    2460
aacgctgaat gcgtctggca catcgcacct ccccaaagc gcaggatcct catcgtggtc    2520
cctgagatct tcctgcccat cgaggatgag tgcggcgatg ttctggtcat gaggaagagt    2580
gcctctccca cgtccatcac cacctatgag acctgccaga cctacgagag gcccatcgcc    2640
ttcacctccc gctcccgcaa gctctggatc cagttcaaat ccaatgaagg caacagcggc    2700
aaaggcttcc aagtgcccta tgtcacctac gatgaggact accagcaact catagaggac    2760
atcgtgcgcg atgggcgcct gtacgcctcg gagaaccacc aggaaatttt gaaagacaag    2820
aagctgatca aggccctctt cgacgtgctg gcgcatcccc agaactactt caagtacaca    2880
gcccaggaat ccaaggagat gttcccacgg tccttcatca aactgctgcg ctccaaagtg    2940
tctcggttcc tgcggcccta caaataa                                         2967
```

<210> SEQ ID NO 172
<211> LENGTH: 98
<212> TYPE: PRT
<213> ORGANISM: Homo sapiens

<400> SEQUENCE: 172

```
Asp Gly Asn Ser Thr Arg Ser Pro Glu Thr Asn Gly Leu Leu Cys Gly
1               5                   10                  15

Asp Pro Glu Glu Asn Cys Ala Ala Thr Thr Thr Gln Ser Lys Arg Lys
            20                  25                  30

Gly His Phe Ser Arg Cys Pro Lys Gln Tyr Lys His Tyr Cys Ile Lys
        35                  40                  45

Gly Arg Cys Arg Phe Val Val Ala Glu Gln Thr Pro Ser Cys Val Pro
    50                  55                  60

Leu Arg Lys Arg Arg Lys Arg Lys Lys Glu Glu Met Glu Thr
65                  70                  75                  80

Leu Gly Lys Asp Ile Thr Pro Ile Asn Glu Asp Ile Glu Glu Thr Asn
                85                  90                  95

Ile Ala
```

<210> SEQ ID NO 173
<211> LENGTH: 98
<212> TYPE: PRT
<213> ORGANISM: Homo sapiens

<400> SEQUENCE: 173

```
Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30
```

```
Asn Cys Ala Leu Gln Ile Val Ala Arg Leu Lys Asn Asn Asn Arg Gln
         35                  40                  45

Val Cys Ile Asp Pro Lys Leu Lys Trp Ile Gln Glu Tyr Leu Glu Lys
 50                  55                  60

Ala Leu Asn Lys Gly Arg Arg Glu Glu Lys Val Gly Lys Lys Glu Lys
 65                  70                  75                  80

Ile Gly Lys Lys Arg Gln Lys Lys Arg Lys Ala Ala Gln Lys Arg
                 85                  90                  95

Lys Asn
```

<210> SEQ ID NO 174
<211> LENGTH: 142
<212> TYPE: PRT
<213> ORGANISM: Homo sapiens

<400> SEQUENCE: 174

```
Val Gln Glu Ala Thr Pro Leu Gly Pro Ala Ser Ser Leu Pro Gln Ser
 1               5                  10                  15

Phe Leu Leu Lys Cys Leu Glu Gln Val Arg Lys Ile Gln Gly Asp Gly
                 20                  25                  30

Ala Ala Leu Gln Glu Lys Leu Ala Gly Cys Leu Ser Gln Leu His Ser
         35                  40                  45

Gly Leu Phe Leu Tyr Gln Gly Leu Leu Gln Ala Leu Glu Gly Ile Ser
 50                  55                  60

Pro Glu Leu Gly Pro Thr Leu Asp Thr Leu Gln Leu Asp Val Ala Asp
 65                  70                  75                  80

Phe Ala Thr Thr Ile Trp Gln Gln Met Glu Glu Leu Gly Met Ala Pro
                 85                  90                  95

Ala Leu Gln Pro Thr Gln Gly Ala Met Pro Ala Phe Ala Ser Ala Phe
            100                 105                 110

Gln Arg Arg Ala Gly Gly Val Leu Val Ala Ser His Leu Gln Ser Phe
        115                 120                 125

Leu Glu Val Ser Tyr Arg Val Leu Arg His Leu Ala Gln Pro
    130                 135                 140
```

<210> SEQ ID NO 175
<211> LENGTH: 140
<212> TYPE: PRT
<213> ORGANISM: Homo sapiens

<400> SEQUENCE: 175

```
Met Asn Ala Lys Val Val Val Leu Val Leu Val Leu Thr Ala Leu
 1               5                  10                  15

Cys Leu Ser Asp Gly Lys Pro Val Ser Leu Ser Tyr Arg Cys Pro Cys
                 20                  25                  30

Arg Phe Phe Glu Ser His Val Ala Arg Ala Asn Val Lys His Leu Lys
         35                  40                  45

Ile Leu Asn Thr Pro Asn Cys Ala Leu Gln Ile Val Ala Arg Leu Lys
 50                  55                  60

Asn Asn Asn Arg Gln Val Cys Ile Asp Pro Lys Leu Lys Trp Ile Gln
 65                  70                  75                  80

Glu Tyr Leu Glu Lys Ala Leu Asn Asn Leu Ile Ser Ala Ala Pro Ala
                 85                  90                  95

Gly Lys Arg Val Ile Ala Gly Ala Arg Ala Leu His Pro Ser Pro Pro
            100                 105                 110

Arg Ala Cys Pro Thr Ala Arg Ala Leu Cys Glu Ile Arg Leu Trp Pro
        115                 120                 125
```

Pro Pro Glu Trp Ser Trp Pro Ser Pro Gly Asp Val
        130                 135                 140

<210> SEQ ID NO 176
<211> LENGTH: 119
<212> TYPE: PRT
<213> ORGANISM: Homo sapiens

<400> SEQUENCE: 176

Met Asn Ala Lys Val Val Val Leu Val Leu Val Leu Thr Ala Leu
1               5                   10                  15

Cys Leu Ser Asp Gly Lys Pro Val Ser Leu Ser Tyr Arg Cys Pro Cys
            20                  25                  30

Arg Phe Phe Glu Ser His Val Ala Arg Ala Asn Val Lys His Leu Lys
        35                  40                  45

Ile Leu Asn Thr Pro Asn Cys Ala Leu Gln Ile Val Ala Arg Leu Lys
    50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys Gly Arg Arg Glu Glu Lys Val
                85                  90                  95

Gly Lys Lys Glu Lys Ile Gly Lys Lys Arg Gln Lys Lys Arg Lys
            100                 105                 110

Ala Ala Gln Lys Arg Lys Asn
            115

<210> SEQ ID NO 177
<211> LENGTH: 93
<212> TYPE: PRT
<213> ORGANISM: Homo sapiens

<400> SEQUENCE: 177

Met Asn Ala Lys Val Val Val Leu Val Leu Val Leu Thr Ala Leu
1               5                   10                  15

Cys Leu Ser Asp Gly Lys Pro Val Ser Leu Ser Tyr Arg Cys Pro Cys
            20                  25                  30

Arg Phe Phe Glu Ser His Val Ala Arg Ala Asn Val Lys His Leu Lys
        35                  40                  45

Ile Leu Asn Thr Pro Asn Cys Ala Leu Gln Ile Val Ala Arg Leu Lys
    50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys Arg Phe Lys Met
                85                  90

<210> SEQ ID NO 178
<211> LENGTH: 183
<212> TYPE: PRT
<213> ORGANISM: Homo sapiens

<400> SEQUENCE: 178

Met Glu Arg Val Gln Pro Leu Glu Glu Asn Val Gly Asn Ala Ala Arg
1               5                   10                  15

Pro Arg Phe Glu Arg Asn Lys Leu Leu Leu Val Ala Ser Val Ile Gln
            20                  25                  30

Gly Leu Gly Leu Leu Leu Cys Phe Thr Tyr Ile Cys Leu His Phe Ser
        35                  40                  45

Ala Leu Gln Val Ser His Arg Tyr Pro Arg Ile Gln Ser Ile Lys Val

```
                50                  55                  60
Gln Phe Thr Glu Tyr Lys Lys Glu Lys Gly Phe Ile Leu Thr Ser Gln
 65                  70                  75                  80

Lys Glu Asp Glu Ile Met Lys Val Gln Asn Asn Ser Val Ile Ile Asn
                 85                  90                  95

Cys Asp Gly Phe Tyr Leu Ile Ser Leu Lys Gly Tyr Phe Ser Gln Glu
                100                 105                 110

Val Asn Ile Ser Leu His Tyr Gln Lys Asp Glu Pro Leu Phe Gln
                115                 120                 125

Leu Lys Lys Val Arg Ser Val Asn Ser Leu Met Val Ala Ser Leu Thr
130                 135                 140

Tyr Lys Asp Lys Val Tyr Leu Asn Val Thr Thr Asp Asn Thr Ser Leu
145                 150                 155                 160

Asp Asp Phe His Val Asn Gly Gly Glu Leu Ile Leu Ile His Gln Asn
                165                 170                 175

Pro Gly Glu Phe Cys Val Leu
                180

<210> SEQ ID NO 179
<211> LENGTH: 234
<212> TYPE: PRT
<213> ORGANISM: Homo sapiens

<400> SEQUENCE: 179

Met Asp Pro Gly Leu Gln Gln Ala Leu Asn Gly Met Ala Pro Pro Gly
  1               5                  10                  15

Asp Thr Ala Met His Val Pro Ala Gly Ser Val Ala Ser His Leu Gly
                 20                  25                  30

Thr Thr Ser Arg Ser Tyr Phe Tyr Leu Thr Thr Ala Thr Leu Ala Leu
                 35                  40                  45

Cys Leu Val Phe Thr Val Ala Thr Ile Met Val Leu Val Val Gln Arg
 50                  55                  60

Thr Asp Ser Ile Pro Asn Ser Pro Asp Asn Val Pro Leu Lys Gly Gly
 65                  70                  75                  80

Asn Cys Ser Glu Asp Leu Leu Cys Ile Leu Lys Arg Ala Pro Phe Lys
                 85                  90                  95

Lys Ser Trp Ala Tyr Leu Gln Val Ala Lys His Leu Asn Lys Thr Lys
                100                 105                 110

Leu Ser Trp Asn Lys Asp Gly Ile Leu His Gly Val Arg Tyr Gln Asp
                115                 120                 125

Gly Asn Leu Val Ile Gln Phe Pro Gly Leu Tyr Phe Ile Ile Cys Gln
130                 135                 140

Leu Gln Phe Leu Val Gln Cys Pro Asn Asn Ser Val Asp Leu Lys Leu
145                 150                 155                 160

Glu Leu Leu Ile Asn Lys His Ile Lys Lys Gln Ala Leu Val Thr Val
                165                 170                 175

Cys Glu Ser Gly Met Gln Thr Lys His Val Tyr Gln Asn Leu Ser Gln
                180                 185                 190

Phe Leu Leu Asp Tyr Leu Gln Val Asn Thr Thr Ile Ser Val Asn Val
                195                 200                 205

Asp Thr Phe Gln Tyr Ile Asp Thr Ser Thr Phe Pro Leu Glu Asn Val
                210                 215                 220

Leu Ser Ile Phe Leu Tyr Ser Asn Ser Asp
225                 230
```

-continued

<210> SEQ ID NO 180
<211> LENGTH: 129
<212> TYPE: PRT
<213> ORGANISM: Homo sapiens

<400> SEQUENCE: 180

Met Asp Arg Ala Ala Arg Cys Ser Gly Ala Ser Ser Leu Pro Leu Leu
1               5                   10                  15

Leu Ala Leu Ala Leu Gly Leu Val Ile Leu His Cys Val Val Ala Asp
            20                  25                  30

Gly Asn Ser Thr Arg Ser Pro Glu Thr Asn Gly Leu Leu Cys Gly Asp
        35                  40                  45

Pro Glu Glu Asn Cys Ala Ala Thr Thr Thr Gln Ser Lys Arg Lys Gly
    50                  55                  60

His Phe Ser Arg Cys Pro Lys Gln Tyr Lys His Tyr Cys Ile Lys Gly
65                  70                  75                  80

Arg Cys Arg Phe Val Val Ala Glu Gln Thr Pro Ser Cys Val Pro Leu
                85                  90                  95

Arg Lys Arg Arg Lys Arg Lys Lys Glu Glu Glu Met Glu Thr Leu
            100                 105                 110

Gly Lys Asp Ile Thr Pro Ile Asn Glu Asp Ile Glu Thr Asn Ile
            115                 120                 125

Ala

<210> SEQ ID NO 181
<211> LENGTH: 178
<212> TYPE: PRT
<213> ORGANISM: Homo sapiens

<400> SEQUENCE: 181

Met Asp Arg Ala Ala Arg Cys Ser Gly Ala Ser Ser Leu Pro Leu Leu
1               5                   10                  15

Leu Ala Leu Ala Leu Gly Leu Val Ile Leu His Cys Val Val Ala Asp
            20                  25                  30

Gly Asn Ser Thr Arg Ser Pro Glu Thr Asn Gly Leu Leu Cys Gly Asp
        35                  40                  45

Pro Glu Glu Asn Cys Ala Ala Thr Thr Thr Gln Ser Lys Arg Lys Gly
    50                  55                  60

His Phe Ser Arg Cys Pro Lys Gln Tyr Lys His Tyr Cys Ile Lys Gly
65                  70                  75                  80

Arg Cys Arg Phe Val Val Ala Glu Gln Thr Pro Ser Cys Val Cys Asp
                85                  90                  95

Glu Gly Tyr Ile Gly Ala Arg Cys Glu Arg Val Asp Leu Phe Tyr Leu
            100                 105                 110

Arg Gly Asp Arg Gly Gln Ile Leu Val Ile Cys Leu Ile Ala Val Met
            115                 120                 125

Val Val Phe Ile Ile Leu Val Ile Gly Val Cys Thr Cys Cys His Pro
        130                 135                 140

Leu Arg Lys Arg Arg Lys Arg Lys Lys Lys Glu Glu Glu Met Glu Thr
145                 150                 155                 160

Leu Gly Lys Asp Ile Thr Pro Ile Asn Glu Asp Ile Glu Glu Thr Asn
                165                 170                 175

Ile Ala

<210> SEQ ID NO 182
<211> LENGTH: 119
<212> TYPE: PRT

<213> ORGANISM: Homo sapiens

<400> SEQUENCE: 182

Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Asn Leu Ile Ser Ala Ala Pro Ala Gly Lys Arg Val Ile
65                  70                  75                  80

Ala Gly Ala Arg Ala Leu His Pro Ser Pro Pro Arg Ala Cys Pro Thr
                85                  90                  95

Ala Arg Ala Leu Cys Glu Ile Arg Leu Trp Pro Pro Glu Trp Ser
            100                 105                 110

Trp Pro Ser Pro Gly Asp Val
        115

<210> SEQ ID NO 183
<211> LENGTH: 164
<212> TYPE: PRT
<213> ORGANISM: Homo sapiens

<400> SEQUENCE: 183

Met Ser Pro Glu Pro Ala Leu Ser Pro Ala Leu Gln Leu Leu Leu Trp
1               5                   10                  15

His Ser Ala Leu Trp Thr Val Gln Glu Ala Thr Pro Leu Gly Pro Ala
            20                  25                  30

Ser Ser Leu Pro Gln Ser Phe Leu Leu Lys Cys Leu Glu Gln Val Arg
        35                  40                  45

Lys Ile Gln Gly Asp Gly Ala Ala Leu Gln Glu Lys Leu Ala Gly Cys
    50                  55                  60

Leu Ser Gln Leu His Ser Gly Leu Phe Leu Tyr Gln Gly Leu Leu Gln
65                  70                  75                  80

Ala Leu Glu Gly Ile Ser Pro Glu Leu Gly Pro Thr Leu Asp Thr Leu
                85                  90                  95

Gln Leu Asp Val Ala Asp Phe Ala Thr Thr Ile Trp Gln Gln Met Glu
            100                 105                 110

Glu Leu Gly Met Ala Pro Ala Leu Gln Pro Thr Gln Gly Ala Met Pro
        115                 120                 125

Ala Phe Ala Ser Ala Phe Gln Arg Arg Ala Gly Gly Val Leu Val Ala
    130                 135                 140

Ser His Leu Gln Ser Phe Leu Glu Val Ser Tyr Arg Val Leu Arg His
145                 150                 155                 160

Leu Ala Gln Pro

<210> SEQ ID NO 184
<211> LENGTH: 207
<212> TYPE: PRT
<213> ORGANISM: Homo sapiens

<400> SEQUENCE: 184

Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro

```
                    20                  25                  30
Leu Gly Pro Ala Ser Ser Leu Pro Gln Ser Phe Leu Leu Lys Cys Leu
            35                  40                  45

Glu Gln Val Arg Lys Ile Gln Gly Asp Gly Ala Ala Leu Gln Glu Lys
        50                  55                  60

Leu Val Ser Glu Cys Ala Thr Tyr Lys Leu Cys His Pro Glu Glu Leu
 65                  70                  75                  80

Val Leu Leu Gly His Ser Leu Gly Ile Pro Trp Ala Pro Leu Ser Ser
                85                  90                  95

Cys Pro Ser Gln Ala Leu Gln Leu Ala Gly Cys Leu Ser Gln Leu His
            100                 105                 110

Ser Gly Leu Phe Leu Tyr Gln Gly Leu Leu Gln Ala Leu Glu Gly Ile
        115                 120                 125

Ser Pro Glu Leu Gly Pro Thr Leu Asp Thr Leu Gln Leu Asp Val Ala
    130                 135                 140

Asp Phe Ala Thr Thr Ile Trp Gln Gln Met Glu Glu Leu Gly Met Ala
145                 150                 155                 160

Pro Ala Leu Gln Pro Thr Gln Gly Ala Met Pro Ala Phe Ala Ser Ala
                165                 170                 175

Phe Gln Arg Arg Ala Gly Gly Val Leu Val Ala Ser His Leu Gln Ser
            180                 185                 190

Phe Leu Glu Val Ser Tyr Arg Val Leu Arg His Leu Ala Gln Pro
        195                 200                 205

<210> SEQ ID NO 185
<211> LENGTH: 180
<212> TYPE: PRT
<213> ORGANISM: Homo sapiens

<400> SEQUENCE: 185

Ser Pro Leu Pro Ile Thr Pro Val Asn Ala Thr Cys Ala Ile Arg His
 1               5                  10                  15

Pro Cys His Asn Asn Leu Met Asn Gln Ile Arg Ser Gln Leu Ala Gln
            20                  25                  30

Leu Asn Gly Ser Ala Asn Ala Leu Phe Ile Leu Tyr Tyr Thr Ala Gln
        35                  40                  45

Gly Glu Pro Phe Pro Asn Asn Leu Asp Lys Leu Cys Gly Pro Asn Val
    50                  55                  60

Thr Asp Phe Pro Pro Phe His Ala Asn Gly Thr Glu Lys Ala Lys Leu
 65                  70                  75                  80

Val Glu Leu Tyr Arg Ile Val Val Tyr Leu Gly Thr Ser Leu Gly Asn
                85                  90                  95

Ile Thr Arg Asp Gln Lys Ile Leu Asn Pro Ser Ala Leu Ser Leu His
            100                 105                 110

Ser Lys Leu Asn Ala Thr Ala Asp Ile Leu Arg Gly Leu Leu Ser Asn
        115                 120                 125

Val Leu Cys Arg Leu Cys Ser Lys Tyr His Val Gly His Val Asp Val
    130                 135                 140

Thr Tyr Gly Pro Asp Thr Ser Gly Lys Asp Val Phe Gln Lys Lys Lys
145                 150                 155                 160

Leu Gly Cys Gln Leu Leu Gly Lys Tyr Lys Gln Ile Ile Ala Val Leu
                165                 170                 175

Ala Gln Ala Phe
            180
```

<210> SEQ ID NO 186
<211> LENGTH: 212
<212> TYPE: PRT
<213> ORGANISM: Homo sapiens

<400> SEQUENCE: 186

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30

Gly Glu Asp Ser Lys Asp Val Ala Ala Pro His Arg Gln Pro Leu Thr
        35                  40                  45

Ser Ser Glu Arg Ile Asp Lys Gln Ile Arg Tyr Ile Leu Asp Gly Ile
    50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
        115                 120                 125

Leu Gln Asn Arg Phe Glu Ser Ser Glu Glu Ala Arg Ala Val Gln
    130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
        195                 200                 205

Leu Arg Gln Met
    210

<210> SEQ ID NO 187
<211> LENGTH: 202
<212> TYPE: PRT
<213> ORGANISM: Homo sapiens

<400> SEQUENCE: 187

Met Lys Val Leu Ala Ala Gly Val Val Pro Leu Leu Leu Val Leu His
1               5                   10                  15

Trp Lys His Gly Ala Gly Ser Pro Leu Pro Ile Thr Pro Val Asn Ala
            20                  25                  30

Thr Cys Ala Ile Arg His Pro Cys His Asn Asn Leu Met Asn Gln Ile
        35                  40                  45

Arg Ser Gln Leu Ala Gln Leu Asn Gly Ser Ala Asn Ala Leu Phe Ile
    50                  55                  60

Leu Tyr Tyr Thr Ala Gln Gly Glu Pro Phe Pro Asn Asn Leu Asp Lys
65                  70                  75                  80

Leu Cys Gly Pro Asn Val Thr Asp Phe Pro Pro Phe His Ala Asn Gly
                85                  90                  95

Thr Glu Lys Ala Lys Leu Val Glu Leu Tyr Arg Ile Val Val Tyr Leu
            100                 105                 110

Gly Thr Ser Leu Gly Asn Ile Thr Arg Asp Gln Lys Ile Leu Asn Pro
        115                 120                 125

```
Ser Ala Leu Ser Leu His Ser Lys Leu Asn Ala Thr Ala Asp Ile Leu
        130                 135                 140

Arg Gly Leu Leu Ser Asn Val Leu Cys Arg Leu Cys Ser Lys Tyr His
145                 150                 155                 160

Val Gly His Val Asp Val Thr Tyr Gly Pro Thr Ser Gly Lys Asp
                165                 170                 175

Val Phe Gln Lys Lys Leu Gly Cys Gln Leu Leu Gly Lys Tyr Lys
                180                 185                 190

Gln Ile Ile Ala Val Leu Ala Gln Ala Phe
        195                 200

<210> SEQ ID NO 188
<211> LENGTH: 281
<212> TYPE: PRT
<213> ORGANISM: Homo sapiens

<400> SEQUENCE: 188

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
                20                  25                  30

Val Thr Tyr Val Tyr Phe Thr Asn Glu Leu Lys Gln Met Gln Asp Lys
            35                  40                  45

Tyr Ser Lys Ser Gly Ile Ala Cys Phe Leu Lys Glu Asp Asp Ser Tyr
        50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
    130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
    210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
            260                 265                 270

Ser Phe Phe Gly Ala Phe Leu Val Gly
        275                 280

<210> SEQ ID NO 189
```

```
<211> LENGTH: 146
<212> TYPE: PRT
<213> ORGANISM: Homo sapiens

<400> SEQUENCE: 189

Pro Ala Leu Pro Glu Asp Gly Gly Ser Gly Ala Phe Pro Pro Gly His
1               5                   10                  15

Phe Lys Asp Pro Lys Arg Leu Tyr Cys Lys Asn Gly Gly Phe Phe Leu
                20                  25                  30

Arg Ile His Pro Asp Gly Arg Val Asp Gly Val Arg Glu Lys Ser Asp
            35                  40                  45

Pro His Ile Lys Leu Gln Leu Gln Ala Glu Arg Gly Val Val Ser
    50                  55                  60

Ile Lys Gly Val Cys Ala Asn Arg Tyr Leu Ala Met Lys Glu Asp Gly
65                  70                  75                  80

Arg Leu Leu Ala Ser Lys Cys Val Thr Asp Glu Cys Phe Phe Phe Glu
                85                  90                  95

Arg Leu Glu Ser Asn Asn Tyr Asn Thr Tyr Arg Ser Arg Lys Tyr Thr
            100                 105                 110

Ser Trp Tyr Val Ala Leu Lys Arg Thr Gly Gln Tyr Lys Leu Gly Ser
        115                 120                 125

Lys Thr Gly Pro Gly Gln Lys Ala Ile Leu Phe Leu Pro Met Ser Ala
    130                 135                 140

Lys Ser
145

<210> SEQ ID NO 190
<211> LENGTH: 112
<212> TYPE: PRT
<213> ORGANISM: Homo sapiens

<400> SEQUENCE: 190

Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Trp Lys Trp
                20                  25                  30

Ile His Glu Pro Lys Gly Tyr His Ala Asn Phe Cys Leu Gly Pro Cys
            35                  40                  45

Pro Tyr Ile Trp Ser Leu Asp Thr Gln Tyr Ser Lys Val Leu Ala Leu
    50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110

<210> SEQ ID NO 191
<211> LENGTH: 361
<212> TYPE: PRT
<213> ORGANISM: Homo sapiens

<400> SEQUENCE: 191

Leu Ser Thr Cys Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
                20                  25                  30

Pro Pro Ser Gln Gly Glu Val Pro Pro Gly Pro Leu Pro Glu Ala Val
```

```
                35                  40                  45
Leu Ala Leu Tyr Asn Ser Thr Arg Asp Arg Val Ala Gly Glu Ser Ala
 50                  55                  60
Glu Pro Glu Pro Glu Pro Glu Ala Asp Tyr Tyr Ala Lys Glu Val Thr
 65                  70                  75                  80
Arg Val Leu Met Val Glu Thr His Asn Glu Ile Tyr Asp Lys Phe Lys
                 85                  90                  95
Gln Ser Thr His Ser Ile Tyr Met Phe Phe Asn Thr Ser Glu Leu Arg
            100                 105                 110
Glu Ala Val Pro Glu Pro Val Leu Leu Ser Arg Ala Glu Leu Arg Leu
        115                 120                 125
Leu Arg Leu Lys Leu Lys Val Glu Gln His Val Glu Leu Tyr Gln Lys
    130                 135                 140
Tyr Ser Asn Asn Ser Trp Arg Tyr Leu Ser Asn Arg Leu Leu Ala Pro
145                 150                 155                 160
Ser Asp Ser Pro Glu Trp Leu Ser Phe Asp Val Thr Gly Val Val Arg
                165                 170                 175
Gln Trp Leu Ser Arg Gly Gly Glu Ile Glu Gly Phe Arg Leu Ser Ala
            180                 185                 190
His Cys Ser Cys Asp Ser Arg Asp Asn Thr Leu Gln Val Asp Ile Asn
        195                 200                 205
Gly Phe Thr Thr Gly Arg Arg Gly Asp Leu Ala Thr Ile His Gly Met
    210                 215                 220
Asn Arg Pro Phe Leu Leu Leu Met Ala Thr Pro Leu Glu Arg Ala Gln
225                 230                 235                 240
His Leu Gln Ser Ser Arg His Arg Arg Ala Leu Asp Thr Asn Tyr Cys
                245                 250                 255
Phe Ser Ser Thr Glu Lys Asn Cys Cys Val Arg Gln Leu Tyr Ile Asp
            260                 265                 270
Phe Arg Lys Asp Leu Gly Trp Lys Trp Ile His Glu Pro Lys Gly Tyr
        275                 280                 285
His Ala Asn Phe Cys Leu Gly Pro Cys Pro Tyr Ile Trp Ser Leu Asp
    290                 295                 300
Thr Gln Tyr Ser Lys Val Leu Ala Leu Tyr Asn Gln His Asn Pro Gly
305                 310                 315                 320
Ala Ser Ala Ala Pro Cys Cys Val Pro Gln Ala Leu Glu Pro Leu Pro
                325                 330                 335
Ile Val Tyr Tyr Val Gly Arg Lys Pro Lys Val Glu Gln Leu Ser Asn
            340                 345                 350
Met Ile Val Arg Ser Cys Lys Cys Ser
        355                 360

<210> SEQ ID NO 192
<211> LENGTH: 251
<212> TYPE: PRT
<213> ORGANISM: Homo sapiens

<400> SEQUENCE: 192

Ala Trp Ala His Gly Glu Lys Arg Leu Ala Pro Lys Gly Gln Pro Gly
 1               5                  10                  15
Pro Ala Ala Thr Asp Arg Asn Pro Arg Gly Ser Ser Ser Arg Gln Ser
                 20                  25                  30
Ser Ser Ser Ala Met Ser Ser Ser Ala Ser Ser Pro Ala Ala
            35                  40                  45
Ser Leu Gly Ser Gln Gly Ser Gly Leu Glu Gln Ser Ser Phe Gln Trp
```

```
                 50                  55                  60
Ser Pro Ser Gly Arg Arg Thr Gly Ser Leu Tyr Cys Arg Val Gly Ile
 65                  70                  75                  80

Gly Phe His Leu Gln Ile Tyr Pro Asp Gly Lys Val Asn Gly Ser His
                 85                  90                  95

Glu Ala Asn Met Leu Ser Val Leu Glu Ile Phe Ala Val Ser Gln Gly
            100                 105                 110

Ile Val Gly Ile Arg Gly Val Phe Ser Asn Lys Phe Leu Ala Met Ser
        115                 120                 125

Lys Lys Gly Lys Leu His Ala Ser Ala Lys Phe Thr Asp Asp Cys Lys
130                 135                 140

Phe Arg Glu Arg Phe Gln Glu Asn Ser Tyr Asn Thr Tyr Ala Ser Ala
145                 150                 155                 160

Ile His Arg Thr Glu Lys Thr Gly Arg Glu Trp Tyr Val Ala Leu Asn
                165                 170                 175

Lys Arg Gly Lys Ala Lys Arg Gly Cys Ser Pro Arg Val Lys Pro Gln
            180                 185                 190

His Ile Ser Thr His Phe Leu Pro Arg Phe Lys Gln Ser Glu Gln Pro
        195                 200                 205

Glu Leu Ser Phe Thr Val Thr Val Pro Glu Lys Lys Asn Pro Pro Ser
210                 215                 220

Pro Ile Lys Ser Lys Ile Pro Leu Ser Ala Pro Arg Lys Asn Thr Asn
225                 230                 235                 240

Ser Val Lys Tyr Arg Leu Lys Phe Arg Phe Gly
                245                 250
```

<210> SEQ ID NO 193
<211> LENGTH: 265
<212> TYPE: PRT
<213> ORGANISM: Homo sapiens

<400> SEQUENCE: 193

```
Ser Phe Leu Leu Leu Phe Phe Ser His Leu Ile Leu Ser Ala Trp
 1               5                  10                  15

Ala His Gly Glu Lys Arg Leu Ala Pro Lys Gly Gln Pro Gly Pro Ala
                20                  25                  30

Ala Thr Asp Arg Asn Pro Arg Gly Ser Ser Ser Arg Gln Ser Ser Ser
            35                  40                  45

Ser Ala Met Ser Ser Ser Ser Ala Ser Ser Pro Ala Ala Ser Leu
 50                  55                  60

Gly Ser Gln Gly Ser Gly Leu Glu Gln Ser Ser Phe Gln Trp Ser Pro
 65                  70                  75                  80

Ser Gly Arg Arg Thr Gly Ser Leu Tyr Cys Arg Val Gly Ile Gly Phe
                85                  90                  95

His Leu Gln Ile Tyr Pro Asp Gly Lys Val Asn Gly Ser His Glu Ala
            100                 105                 110

Asn Met Leu Ser Val Leu Glu Ile Phe Ala Val Ser Gln Gly Ile Val
        115                 120                 125

Gly Ile Arg Gly Val Phe Ser Asn Lys Phe Leu Ala Met Ser Lys Lys
130                 135                 140

Gly Lys Leu His Ala Ser Ala Lys Phe Thr Asp Asp Cys Lys Phe Arg
145                 150                 155                 160

Glu Arg Phe Gln Glu Asn Ser Tyr Asn Thr Tyr Ala Ser Ala Ile His
                165                 170                 175

Arg Thr Glu Lys Thr Gly Arg Glu Trp Tyr Val Ala Leu Asn Lys Arg
```

```
                    180                 185                 190
Gly Lys Ala Lys Arg Gly Cys Ser Pro Arg Val Lys Pro Gln His Ile
                195                 200                 205

Ser Thr His Phe Leu Pro Arg Phe Lys Gln Ser Glu Gln Pro Glu Leu
    210                 215                 220

Ser Phe Thr Val Thr Val Pro Glu Lys Lys Asn Pro Pro Ser Pro Ile
225                 230                 235                 240

Lys Ser Lys Ile Pro Leu Ser Ala Pro Arg Lys Asn Thr Asn Ser Val
                245                 250                 255

Lys Tyr Arg Leu Lys Phe Arg Phe Gly
                260                 265

<210> SEQ ID NO 194
<211> LENGTH: 100
<212> TYPE: PRT
<213> ORGANISM: Homo sapiens

<400> SEQUENCE: 194

Arg Cys Lys Leu Val Thr Ala Leu Ile Ala Pro Gln Pro Gly Thr Leu
1               5                   10                  15

His Ser Gly Ser Arg Val Pro Glu Arg Val Ala Gly Val Phe Arg Asn
                20                  25                  30

Val Arg Phe Phe Ala Ser Ser Ala Trp Leu Met Ala Ala Ser Trp Ser
            35                  40                  45

Phe Leu Arg Pro Ser Val Gln Leu Gln Asn Leu Pro Ala Ser Lys His
        50                  55                  60

Ala Arg Lys Met Thr Val Pro Ala Ser Gly Phe Ser Gln Thr Gly Gln
65                  70                  75                  80

Ser Val Pro Gln Ala Ala Gly Lys Ala Pro Arg Leu Glu Ala Pro Phe
                85                  90                  95

Ala Glu Arg Cys
            100

<210> SEQ ID NO 195
<211> LENGTH: 149
<212> TYPE: PRT
<213> ORGANISM: Homo sapiens

<400> SEQUENCE: 195

Arg Gln Thr Pro Thr Gln His Phe Lys Asn Gln Phe Pro Ala Leu His
1               5                   10                  15

Trp Glu His Glu Leu Gly Leu Ala Phe Thr Lys Asn Arg Met Asn Tyr
                20                  25                  30

Thr Asn Lys Phe Leu Leu Ile Pro Glu Ser Gly Asp Tyr Phe Ile Tyr
            35                  40                  45

Ser Gln Val Thr Phe Arg Gly Met Thr Ser Glu Cys Ser Glu Ile Arg
        50                  55                  60

Gln Ala Gly Arg Pro Asn Lys Pro Asp Ser Ile Thr Val Val Ile Thr
65                  70                  75                  80

Lys Val Thr Asp Ser Tyr Pro Glu Pro Thr Gln Leu Leu Met Gly Thr
                85                  90                  95

Lys Ser Val Cys Glu Val Gly Ser Asn Trp Phe Gln Pro Ile Tyr Leu
            100                 105                 110

Gly Ala Met Phe Ser Leu Gln Glu Gly Asp Lys Leu Met Val Asn Val
        115                 120                 125

Ser Asp Ile Ser Leu Val Asp Tyr Thr Lys Glu Asp Lys Thr Phe Phe
130                 135                 140
```

-continued

```
Gly Ala Phe Leu Leu
145

<210> SEQ ID NO 196
<211> LENGTH: 195
<212> TYPE: PRT
<213> ORGANISM: Homo sapiens

<400> SEQUENCE: 196

Asp Val Phe Leu Ser Lys Pro Gln Lys Ala Leu Glu Tyr Leu Glu
1               5                   10                  15

Asp Ile Asp Leu Lys Thr Leu Glu Lys Glu Pro Arg Thr Phe Lys Ala
            20                  25                  30

Lys Glu Leu Trp Glu Lys Asn Gly Ala Val Ile Met Ala Val Arg Arg
        35                  40                  45

Pro Gly Cys Phe Leu Cys Arg Glu Glu Ala Ala Asp Leu Ser Ser Leu
    50                  55                  60

Lys Ser Met Leu Asp Gln Leu Gly Val Pro Leu Tyr Ala Val Val Lys
65                  70                  75                  80

Glu His Ile Arg Thr Glu Val Lys Asp Phe Gln Pro Tyr Phe Lys Gly
                85                  90                  95

Glu Ile Phe Leu Asp Glu Lys Lys Phe Tyr Gly Pro Gln Arg Arg
            100                 105                 110

Lys Met Met Phe Met Gly Phe Ile Arg Leu Gly Val Trp Tyr Asn Phe
        115                 120                 125

Phe Arg Ala Trp Asn Gly Gly Phe Ser Gly Asn Leu Glu Gly Glu Gly
    130                 135                 140

Phe Ile Leu Gly Gly Val Phe Val Val Gly Ser Gly Lys Gln Gly Ile
145                 150                 155                 160

Leu Leu Glu His Arg Glu Lys Glu Phe Gly Asp Arg Val Asn Leu Leu
                165                 170                 175

Ser Val Leu Glu Ala Ala Lys Met Ile Lys Pro Gln Thr Leu Ala Ser
            180                 185                 190

Glu Lys Lys
        195

<210> SEQ ID NO 197
<211> LENGTH: 195
<212> TYPE: PRT
<213> ORGANISM: Homo sapiens

<400> SEQUENCE: 197

Ala Pro Glu Thr Ala Val Leu Gly Ala Glu Leu Ser Ala Val Gly Glu
1               5                   10                  15

Asn Gly Gly Glu Lys Pro Thr Pro Ser Pro Pro Trp Arg Leu Arg Arg
            20                  25                  30

Ser Lys Arg Cys Ser Cys Ser Ser Leu Met Asp Lys Glu Cys Val Tyr
        35                  40                  45

Phe Cys His Leu Asp Ile Ile Trp Val Asn Thr Pro Glu His Val Val
    50                  55                  60

Pro Tyr Gly Leu Gly Ser Pro Arg Ser Lys Arg Ala Leu Glu Asn Leu
65                  70                  75                  80

Leu Pro Thr Lys Ala Thr Asp Arg Glu Asn Arg Cys Gln Cys Ala Ser
                85                  90                  95

Gln Lys Asp Lys Lys Cys Trp Asn Phe Cys Gln Ala Gly Lys Glu Leu
            100                 105                 110
```

Arg Ala Glu Asp Ile Met Glu Lys Asp Trp Asn Asn His Lys Lys Gly
            115                 120                 125

Lys Asp Cys Ser Lys Leu Gly Lys Cys Ile Tyr Gln Gln Leu Val
    130                 135                 140

Arg Gly Arg Lys Ile Arg Arg Ser Ser Glu Glu His Leu Arg Gln Thr
145                 150                 155                 160

Arg Ser Glu Thr Met Arg Asn Ser Val Lys Ser Ser Phe His Asp Pro
                165                 170                 175

Lys Leu Lys Gly Lys Pro Ser Arg Glu Arg Tyr Val Thr His Asn Arg
            180                 185                 190

Ala His Trp
        195

<210> SEQ ID NO 198
<211> LENGTH: 21
<212> TYPE: PRT
<213> ORGANISM: Homo sapiens

<400> SEQUENCE: 198

Cys Ser Cys Ser Ser Leu Met Asp Lys Glu Cys Val Tyr Phe Cys His
1               5                   10                  15

Leu Asp Ile Ile Trp
            20

<210> SEQ ID NO 199
<211> LENGTH: 38
<212> TYPE: PRT
<213> ORGANISM: Homo sapiens

<400> SEQUENCE: 199

Cys Ser Cys Ser Ser Leu Met Asp Lys Glu Cys Val Tyr Phe Cys His
1               5                   10                  15

Leu Asp Ile Ile Trp Val Asn Thr Pro Glu His Val Val Pro Tyr Gly
            20                  25                  30

Leu Gly Ser Pro Arg Ser
        35

<210> SEQ ID NO 200
<211> LENGTH: 361
<212> TYPE: PRT
<213> ORGANISM: Homo sapiens

<400> SEQUENCE: 200

Met Ser Glu Gly Ala Ala Ala Ser Pro Gly Ala Ala Ser Ala
1               5                   10                  15

Ala Ala Ser Ala Glu Glu Gly Thr Ala Ala Ala Ala Ala Ala
            20                  25                  30

Ala Ala Gly Gly Gly Pro Asp Gly Gly Glu Gly Ala Ala Glu Pro
                35                  40                  45

Pro Arg Glu Leu Arg Cys Ser Asp Cys Ile Val Trp Asn Arg Gln Gln
    50                  55                  60

Thr Trp Leu Cys Val Val Pro Leu Phe Ile Gly Phe Ile Gly Leu Gly
65                  70                  75                  80

Leu Ser Leu Met Leu Leu Lys Trp Ile Val Val Gly Ser Val Lys Glu
                85                  90                  95

Tyr Val Pro Thr Asp Leu Val Asp Ser Lys Gly Met Gly Gln Asp Pro
            100                 105                 110

Phe Phe Leu Ser Lys Pro Ser Ser Phe Pro Lys Ala Met Glu Thr Thr
        115                 120                 125

```
Thr Thr Thr Thr Ser Thr Ser Pro Ala Thr Pro Ser Ala Gly Gly
        130                 135                 140

Ala Ala Ser Ser Arg Thr Pro Asn Arg Ile Ser Thr Arg Leu Thr Thr
145                 150                 155                 160

Ile Thr Arg Ala Pro Thr Arg Phe Pro Gly His Arg Val Pro Ile Arg
                165                 170                 175

Ala Ser Pro Arg Ser Thr Thr Ala Arg Asn Thr Ala Ala Pro Ala Thr
            180                 185                 190

Val Pro Ser Thr Thr Ala Pro Phe Phe Ser Ser Thr Leu Gly Ser
        195                 200                 205

Arg Pro Pro Val Pro Gly Thr Pro Ser Thr Gln Ala Met Pro Ser Trp
        210                 215                 220

Pro Thr Ala Ala Tyr Ala Thr Ser Ser Tyr Leu His Asp Ser Thr Pro
225                 230                 235                 240

Ser Trp Thr Leu Ser Pro Phe Gln Asp Ala Ala Ser Ser Ser Ser
                245                 250                 255

Ser Ser Ser Ser Ala Thr Thr Thr Pro Glu Thr Ser Thr Ser Pro
            260                 265                 270

Lys Phe His Thr Thr Thr Tyr Ser Thr Glu Arg Ser Glu His Phe Lys
                275                 280                 285

Pro Cys Arg Asp Lys Asp Leu Ala Tyr Cys Leu Asn Asp Gly Glu Cys
        290                 295                 300

Phe Val Ile Glu Thr Leu Thr Gly Ser His Lys His Cys Arg Cys Lys
305                 310                 315                 320

Glu Gly Tyr Gln Gly Val Arg Cys Asp Gln Phe Leu Pro Lys Thr Asp
                325                 330                 335

Ser Ile Leu Ser Asp Pro Thr Asp His Leu Gly Ile Glu Phe Met Glu
            340                 345                 350

Ser Glu Glu Val Tyr Gln Arg Gln Val
        355                 360

<210> SEQ ID NO 201
<211> LENGTH: 8
<212> TYPE: PRT
<213> ORGANISM: Homo sapiens

<400> SEQUENCE: 201

Asp Arg Val Tyr Ile His Pro Phe
1               5

<210> SEQ ID NO 202
<211> LENGTH: 10
<212> TYPE: PRT
<213> ORGANISM: Homo sapiens

<400> SEQUENCE: 202

Asp Arg Val Tyr Ile His Pro Phe His Leu
1               5                   10

<210> SEQ ID NO 203
<211> LENGTH: 452
<212> TYPE: PRT
<213> ORGANISM: Homo sapiens

<400> SEQUENCE: 203

Asp Arg Val Tyr Ile His Pro Phe His Leu Val Ile His Asn Glu Ser
1               5                   10                  15

Thr Cys Glu Gln Leu Ala Lys Ala Asn Ala Gly Lys Pro Lys Asp Pro
```

-continued

```
               20                  25                  30
Thr Phe Ile Pro Ala Pro Ile Gln Ala Lys Thr Ser Pro Val Asp Glu
            35                  40                  45
Lys Ala Leu Gln Asp Gln Leu Val Leu Val Ala Ala Lys Leu Asp Thr
 50                  55                  60
Glu Asp Lys Leu Arg Ala Ala Met Val Gly Met Leu Ala Asn Phe Leu
 65                  70                  75                  80
Gly Phe Arg Ile Tyr Gly Met His Ser Glu Leu Trp Gly Val Val His
                85                  90                  95
Gly Ala Thr Val Leu Ser Pro Thr Ala Val Phe Gly Thr Leu Ala Ser
            100                 105                 110
Leu Tyr Leu Gly Ala Leu Asp His Thr Ala Asp Arg Leu Gln Ala Ile
        115                 120                 125
Leu Gly Val Pro Trp Lys Asp Lys Asn Cys Thr Ser Arg Leu Asp Ala
        130                 135                 140
His Lys Val Leu Ser Ala Leu Gln Ala Val Gln Gly Leu Leu Val Ala
145                 150                 155                 160
Gln Gly Arg Ala Asp Ser Gln Ala Gln Leu Leu Leu Ser Thr Val Val
                165                 170                 175
Gly Val Phe Thr Ala Pro Gly Leu His Leu Lys Gln Pro Phe Val Gln
            180                 185                 190
Gly Leu Ala Leu Tyr Thr Pro Val Val Leu Pro Arg Ser Leu Asp Phe
        195                 200                 205
Thr Glu Leu Asp Val Ala Ala Glu Lys Ile Asp Arg Phe Met Gln Ala
        210                 215                 220
Val Thr Gly Trp Lys Thr Gly Cys Ser Leu Met Gly Ala Ser Val Asp
225                 230                 235                 240
Ser Thr Leu Ala Phe Asn Thr Tyr Val His Phe Gln Gly Lys Met Lys
                245                 250                 255
Gly Phe Ser Leu Leu Ala Glu Pro Gln Glu Phe Trp Val Asp Asn Ser
            260                 265                 270
Thr Ser Val Ser Val Pro Met Leu Ser Gly Met Gly Thr Phe Gln His
        275                 280                 285
Trp Ser Asp Ile Gln Asp Asn Phe Ser Val Thr Gln Val Pro Phe Thr
        290                 295                 300
Glu Ser Ala Cys Leu Leu Leu Ile Gln Pro His Tyr Ala Ser Asp Leu
305                 310                 315                 320
Asp Lys Val Glu Gly Leu Thr Phe Gln Gln Asn Ser Leu Asn Trp Met
                325                 330                 335
Lys Lys Leu Ser Pro Arg Thr Ile His Leu Thr Met Pro Gln Leu Val
            340                 345                 350
Leu Gln Gly Ser Tyr Asp Leu Gln Asp Leu Leu Ala Gln Ala Glu Leu
        355                 360                 365
Pro Ala Ile Leu His Thr Glu Leu Asn Leu Gln Lys Leu Ser Asn Asp
        370                 375                 380
Arg Ile Arg Val Gly Glu Val Leu Asn Ser Ile Phe Phe Glu Leu Glu
385                 390                 395                 400
Ala Asp Glu Arg Glu Pro Thr Glu Ser Thr Gln Gln Leu Asn Lys Pro
                405                 410                 415
Glu Val Leu Glu Val Thr Leu Asn Arg Pro Phe Leu Phe Ala Val Tyr
            420                 425                 430
Asp Gln Ser Ala Thr Ala Leu His Phe Leu Gly Arg Val Ala Asn Pro
        435                 440                 445
```

```
Leu Ser Thr Ala
    450

<210> SEQ ID NO 204
<211> LENGTH: 7
<212> TYPE: PRT
<213> ORGANISM: Homo sapiens

<400> SEQUENCE: 204

Arg Val Tyr Ile His Pro Phe
1               5

<210> SEQ ID NO 205
<211> LENGTH: 149
<212> TYPE: PRT
<213> ORGANISM: Homo sapiens

<400> SEQUENCE: 205

Met Gln Lys Gly Asp Gln Asn Pro Gln Ile Ala Ala His Val Ile Ser
1               5                   10                  15

Glu Ala Ser Ser Lys Thr Thr Ser Val Leu Gln Trp Ala Glu Lys Gly
            20                  25                  30

Tyr Tyr Thr Met Ser Asn Asn Leu Val Thr Leu Glu Asn Gly Lys Gln
        35                  40                  45

Leu Thr Val Lys Arg Gln Gly Leu Tyr Tyr Ile Tyr Ala Gln Val Thr
    50                  55                  60

Phe Cys Ser Asn Arg Glu Ala Ser Ser Gln Ala Pro Phe Ile Ala Ser
65                  70                  75                  80

Leu Cys Leu Lys Ser Pro Gly Arg Phe Glu Arg Ile Leu Leu Arg Ala
                85                  90                  95

Ala Asn Thr His Ser Ser Ala Lys Pro Cys Gly Gln Gln Ser Ile His
            100                 105                 110

Leu Gly Gly Val Phe Glu Leu Gln Pro Gly Ala Ser Val Phe Val Asn
        115                 120                 125

Val Thr Asp Pro Ser Gln Val Ser His Gly Thr Gly Phe Thr Ser Phe
    130                 135                 140

Gly Leu Leu Lys Leu
145

<210> SEQ ID NO 206
<211> LENGTH: 215
<212> TYPE: PRT
<213> ORGANISM: Homo sapiens

<400> SEQUENCE: 206

His Arg Arg Leu Asp Lys Ile Glu Asp Glu Arg Asn Leu His Glu Asp
1               5                   10                  15

Phe Val Phe Met Lys Thr Ile Gln Arg Cys Asn Thr Gly Glu Arg Ser
            20                  25                  30

Leu Ser Leu Leu Asn Cys Glu Glu Ile Lys Ser Gln Phe Glu Gly Phe
        35                  40                  45

Val Lys Asp Ile Met Leu Asn Lys Glu Glu Thr Lys Lys Glu Asn Ser
    50                  55                  60

Phe Glu Met Gln Lys Gly Asp Gln Asn Pro Gln Ile Ala Ala His Val
65                  70                  75                  80

Ile Ser Glu Ala Ser Ser Lys Thr Thr Ser Val Leu Gln Trp Ala Glu
                85                  90                  95

Lys Gly Tyr Tyr Thr Met Ser Asn Asn Leu Val Thr Leu Glu Asn Gly
            100                 105                 110
```

```
Lys Gln Leu Thr Val Lys Arg Gln Gly Leu Tyr Tyr Ile Tyr Ala Gln
            115                 120                 125

Val Thr Phe Cys Ser Asn Arg Glu Ala Ser Ser Gln Ala Pro Phe Ile
        130                 135                 140

Ala Ser Leu Cys Leu Lys Ser Pro Gly Arg Phe Glu Arg Ile Leu Leu
145                 150                 155                 160

Arg Ala Ala Asn Thr His Ser Ser Ala Lys Pro Cys Gly Gln Gln Ser
                165                 170                 175

Ile His Leu Gly Gly Val Phe Glu Leu Gln Pro Gly Ala Ser Val Phe
            180                 185                 190

Val Asn Val Thr Asp Pro Ser Gln Val Ser His Gly Thr Gly Phe Thr
        195                 200                 205

Ser Phe Gly Leu Leu Lys Leu
        210                 215
```

<210> SEQ ID NO 207
<211> LENGTH: 332
<212> TYPE: PRT
<213> ORGANISM: Homo sapiens

<400> SEQUENCE: 207

```
Ser Pro Ala Pro Pro Ala Cys Asp Leu Arg Val Leu Ser Lys Leu Leu
1               5                   10                  15

Arg Asp Ser His Val Leu His Ser Arg Leu Ser Gln Cys Pro Glu Val
                20                  25                  30

His Pro Leu Pro Thr Pro Val Leu Leu Pro Ala Val Asp Phe Ser Leu
            35                  40                  45

Gly Glu Trp Lys Thr Gln Met Glu Glu Thr Lys Ala Gln Asp Ile Leu
        50                  55                  60

Gly Ala Val Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
            100                 105                 110

Pro Pro Gln Gly Arg Thr Thr Ala His Lys Asp Pro Asn Ala Ile Phe
        115                 120                 125

Leu Ser Phe Gln His Leu Leu Arg Gly Lys Val Arg Phe Leu Met Leu
130                 135                 140

Val Gly Gly Ser Thr Leu Cys Val Arg Arg Ala Pro Pro Thr Thr Ala
145                 150                 155                 160

Val Pro Ser Arg Thr Ser Leu Val Leu Thr Leu Asn Glu Leu Pro Asn
                165                 170                 175

Arg Thr Ser Gly Leu Leu Glu Thr Asn Phe Thr Ala Ser Ala Arg Thr
            180                 185                 190

Thr Gly Ser Gly Leu Leu Lys Trp Gln Gln Gly Phe Arg Ala Lys Ile
        195                 200                 205

Pro Gly Leu Leu Asn Gln Thr Ser Arg Ser Leu Asp Gln Ile Pro Gly
        210                 215                 220

Tyr Leu Asn Arg Ile His Glu Leu Leu Asn Gly Thr Arg Gly Leu Phe
225                 230                 235                 240

Pro Gly Pro Ser Arg Arg Thr Leu Gly Ala Pro Asp Ile Ser Ser Gly
                245                 250                 255

Thr Ser Asp Thr Gly Ser Leu Pro Pro Asn Leu Gln Pro Gly Tyr Ser
            260                 265                 270
```

```
Pro Ser Pro Thr His Pro Pro Thr Gly Gln Tyr Thr Leu Phe Pro Leu
        275                 280                 285

Pro Pro Thr Leu Pro Thr Pro Val Val Gln Leu His Pro Leu Leu Pro
        290                 295                 300

Asp Pro Ser Ala Pro Thr Pro Thr Pro Thr Ser Pro Leu Leu Asn Thr
305                 310                 315                 320

Ser Tyr Thr His Ser Gln Asn Leu Ser Gln Glu Gly
            325                 330
```

<210> SEQ ID NO 208
<211> LENGTH: 177
<212> TYPE: PRT
<213> ORGANISM: Homo sapiens

<400> SEQUENCE: 208

```
Gly Pro Gln Arg Glu Glu Phe Pro Arg Asp Leu Ser Leu Ile Ser Pro
1               5                   10                  15

Leu Ala Gln Ala Val Arg Ser Ser Arg Thr Pro Ser Asp Lys Pro
            20                  25                  30

Val Ala His Val Val Ala Asn Pro Gln Ala Glu Gly Gln Leu Gln Trp
        35                  40                  45

Leu Asn Arg Arg Ala Asn Ala Leu Leu Ala Asn Gly Val Glu Leu Arg
    50                  55                  60

Asp Asn Gln Leu Val Val Pro Ser Glu Gly Leu Tyr Leu Ile Tyr Ser
65                  70                  75                  80

Gln Val Leu Phe Lys Gly Gln Gly Cys Pro Ser Thr His Val Leu Leu
                85                  90                  95

Thr His Thr Ile Ser Arg Ile Ala Val Ser Tyr Gln Thr Lys Val Asn
            100                 105                 110

Leu Leu Ser Ala Ile Lys Ser Pro Cys Gln Arg Glu Thr Pro Glu Gly
        115                 120                 125

Ala Glu Ala Lys Pro Trp Tyr Glu Pro Ile Tyr Leu Gly Gly Val Phe
    130                 135                 140

Gln Leu Glu Lys Gly Asp Arg Leu Ser Ala Glu Ile Asn Arg Pro Asp
145                 150                 155                 160

Tyr Leu Asp Phe Ala Glu Ser Gly Gln Val Tyr Phe Gly Ile Ile Ala
                165                 170                 175

Leu
```

<210> SEQ ID NO 209
<211> LENGTH: 157
<212> TYPE: PRT
<213> ORGANISM: Homo sapiens

<400> SEQUENCE: 209

```
Val Arg Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
```

```
                    85                  90                  95

Ile Lys Ser Pro Cys Gln Arg Glu Thr Pro Glu Gly Ala Glu Ala Lys
                100                 105                 110

Pro Trp Tyr Glu Pro Ile Tyr Leu Gly Gly Val Phe Gln Leu Glu Lys
            115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155

<210> SEQ ID NO 210
<211> LENGTH: 171
<212> TYPE: PRT
<213> ORGANISM: Homo sapiens

<400> SEQUENCE: 210

Leu Pro Gly Val Gly Leu Thr Pro Ser Ala Ala Gln Thr Ala Arg Gln
1               5                   10                  15

His Pro Lys Met His Leu Ala His Ser Thr Leu Lys Pro Ala Ala His
            20                  25                  30

Leu Ile Gly Asp Pro Ser Lys Gln Asn Ser Leu Leu Trp Arg Ala Asn
        35                  40                  45

Thr Asp Arg Ala Phe Leu Gln Asp Gly Phe Ser Leu Ser Asn Asn Ser
    50                  55                  60

Leu Leu Val Pro Thr Ser Gly Ile Tyr Phe Val Tyr Ser Gln Val Val
65                  70                  75                  80

Phe Ser Gly Lys Ala Tyr Ser Pro Lys Ala Thr Ser Ser Pro Leu Tyr
                85                  90                  95

Leu Ala His Glu Val Gln Leu Phe Ser Ser Gln Tyr Pro Phe His Val
                100                 105                 110

Pro Leu Leu Ser Ser Gln Lys Met Val Tyr Pro Gly Leu Gln Glu Pro
            115                 120                 125

Trp Leu His Ser Met Tyr His Gly Ala Ala Phe Gln Leu Thr Gln Gly
    130                 135                 140

Asp Gln Leu Ser Thr His Thr Asp Gly Ile Pro His Leu Val Leu Ser
145                 150                 155                 160

Pro Ser Thr Val Phe Phe Gly Ala Phe Ala Leu
                165                 170

<210> SEQ ID NO 211
<211> LENGTH: 183
<212> TYPE: PRT
<213> ORGANISM: Homo sapiens

<400> SEQUENCE: 211

Val Pro Pro Gly Glu Asp Ser Lys Asp Val Ala Ala Pro His Arg Gln
1               5                   10                  15

Pro Leu Thr Ser Ser Glu Arg Ile Asp Lys Gln Ile Arg Tyr Ile Leu
            20                  25                  30

Asp Gly Ile Ser Ala Leu Arg Lys Glu Thr Cys Asn Lys Ser Asn Met
        35                  40                  45

Cys Glu Ser Ser Lys Glu Ala Leu Ala Glu Asn Asn Leu Asn Leu Pro
    50                  55                  60

Lys Met Ala Glu Lys Asp Gly Cys Phe Gln Ser Gly Phe Asn Glu Glu
65                  70                  75                  80

Thr Cys Leu Val Lys Ile Ile Thr Gly Leu Leu Glu Phe Glu Val Tyr
                85                  90                  95
```

```
Leu Glu Tyr Leu Gln Asn Arg Phe Glu Ser Ser Glu Gln Ala Arg
            100                 105                 110

Ala Val Gln Met Ser Thr Lys Val Leu Ile Gln Phe Leu Gln Lys Lys
            115                 120                 125

Ala Lys Asn Leu Asp Ala Ile Thr Thr Pro Asp Pro Thr Thr Asn Ala
130                 135                 140

Ser Leu Leu Thr Lys Leu Gln Ala Gln Asn Gln Trp Leu Gln Asp Met
145                 150                 155                 160

Thr Thr His Leu Ile Leu Arg Ser Phe Lys Glu Phe Leu Gln Ser Ser
                165                 170                 175

Leu Arg Ala Leu Arg Gln Met
            180

<210> SEQ ID NO 212
<211> LENGTH: 463
<212> TYPE: PRT
<213> ORGANISM: Homo sapiens

<400> SEQUENCE: 212

Gln Arg Lys Arg Arg Asn Thr Ile His Glu Phe Lys Lys Ser Ala Lys
1               5                   10                  15

Thr Thr Leu Ile Lys Ile Asp Pro Ala Leu Lys Ile Lys Thr Lys Lys
            20                  25                  30

Val Asn Thr Ala Asp Gln Cys Ala Asn Arg Cys Thr Arg Asn Lys Gly
        35                  40                  45

Leu Pro Phe Thr Cys Lys Ala Phe Val Phe Asp Lys Ala Arg Lys Gln
    50                  55                  60

Cys Leu Trp Phe Pro Phe Asn Ser Met Ser Ser Gly Val Lys Lys Glu
65                  70                  75                  80

Phe Gly His Glu Phe Asp Leu Tyr Glu Asn Lys Asp Tyr Ile Arg Asn
                85                  90                  95

Cys Ile Ile Gly Lys Gly Arg Ser Tyr Lys Gly Thr Val Ser Ile Thr
            100                 105                 110

Lys Ser Gly Ile Lys Cys Gln Pro Trp Ser Ser Met Ile Pro His Glu
        115                 120                 125

His Ser Phe Leu Pro Ser Ser Tyr Arg Gly Lys Asp Leu Gln Glu Asn
    130                 135                 140

Tyr Cys Arg Asn Pro Arg Gly Glu Glu Gly Gly Pro Trp Cys Phe Thr
145                 150                 155                 160

Ser Asn Pro Glu Val Arg Tyr Glu Val Cys Asp Ile Pro Gln Cys Ser
                165                 170                 175

Glu Val Glu Cys Met Thr Cys Asn Gly Glu Ser Tyr Arg Gly Leu Met
            180                 185                 190

Asp His Thr Glu Ser Gly Lys Ile Cys Gln Arg Trp Asp His Gln Thr
        195                 200                 205

Pro His Arg His Lys Phe Leu Pro Glu Arg Tyr Pro Asp Lys Gly Phe
    210                 215                 220

Asp Asp Asn Tyr Cys Arg Asn Pro Asp Gly Gln Pro Arg Pro Trp Cys
225                 230                 235                 240

Tyr Thr Leu Asp Pro His Thr Arg Trp Glu Tyr Cys Ala Ile Lys Thr
                245                 250                 255

Cys Ala Asp Asn Thr Met Asn Asp Thr Asp Val Pro Leu Glu Thr Thr
            260                 265                 270

Glu Cys Ile Gln Gly Gln Gly Glu Gly Tyr Arg Gly Thr Val Asn Thr
        275                 280                 285
```

```
Ile Trp Asn Gly Ile Pro Cys Gln Arg Trp Asp Ser Gln Tyr Pro His
    290                 295                 300

Glu His Asp Met Thr Pro Glu Asn Phe Lys Cys Lys Asp Leu Arg Glu
305                 310                 315                 320

Asn Tyr Cys Arg Asn Pro Asp Gly Ser Glu Ser Pro Trp Cys Phe Thr
                325                 330                 335

Thr Asp Pro Asn Ile Arg Val Gly Tyr Cys Ser Gln Ile Pro Asn Cys
            340                 345                 350

Asp Met Ser His Gly Gln Asp Cys Tyr Arg Gly Asn Gly Lys Asn Tyr
        355                 360                 365

Met Gly Asn Leu Ser Gln Thr Arg Ser Gly Leu Thr Cys Ser Met Trp
    370                 375                 380

Asp Lys Asn Met Glu Asp Leu His Arg His Ile Phe Trp Glu Pro Asp
385                 390                 395                 400

Ala Ser Lys Leu Asn Glu Asn Tyr Cys Arg Asn Pro Asp Asp Asp Ala
                405                 410                 415

His Gly Pro Trp Cys Tyr Thr Gly Asn Pro Leu Ile Pro Trp Asp Tyr
            420                 425                 430

Cys Pro Ile Ser Arg Cys Glu Gly Asp Thr Thr Pro Thr Ile Val Asn
        435                 440                 445

Leu Asp His Pro Val Ile Ser Cys Ala Lys Thr Lys Gln Leu Arg
    450                 455                 460

<210> SEQ ID NO 213
<211> LENGTH: 234
<212> TYPE: PRT
<213> ORGANISM: Homo sapiens

<400> SEQUENCE: 213

Val Val Asn Gly Ile Pro Thr Arg Thr Asn Ile Gly Trp Met Val Ser
1               5                   10                  15

Leu Arg Tyr Arg Asn Lys His Ile Cys Gly Gly Ser Leu Ile Lys Glu
                20                  25                  30

Ser Trp Val Leu Thr Ala Arg Gln Cys Phe Pro Ser Arg Asp Leu Lys
            35                  40                  45

Asp Tyr Glu Ala Trp Leu Gly Ile His Asp Val His Gly Arg Gly Asp
    50                  55                  60

Glu Lys Cys Lys Gln Val Leu Asn Val Ser Gln Leu Val Tyr Gly Pro
65                  70                  75                  80

Glu Gly Ser Asp Leu Val Leu Met Lys Leu Ala Arg Pro Ala Val Leu
                85                  90                  95

Asp Asp Phe Val Ser Thr Ile Asp Leu Pro Asn Tyr Gly Cys Thr Ile
            100                 105                 110

Pro Glu Lys Thr Ser Cys Ser Val Tyr Gly Trp Gly Tyr Thr Gly Leu
        115                 120                 125

Ile Asn Tyr Asp Gly Leu Leu Arg Val Ala His Leu Tyr Ile Met Gly
    130                 135                 140

Asn Glu Lys Cys Ser Gln His His Arg Gly Lys Val Thr Leu Asn Glu
145                 150                 155                 160

Ser Glu Ile Cys Ala Gly Ala Glu Lys Ile Gly Ser Gly Pro Cys Glu
                165                 170                 175

Gly Asp Tyr Gly Gly Pro Leu Val Cys Glu Gln His Lys Met Arg Met
            180                 185                 190

Val Leu Gly Val Ile Val Pro Gly Arg Gly Cys Ala Ile Pro Asn Arg
        195                 200                 205
```

Pro Gly Ile Phe Val Arg Val Ala Tyr Tyr Ala Lys Trp Ile His Lys
    210                 215                 220

Ile Ile Leu Thr Tyr Lys Val Pro Gln Ser
225                 230

<210> SEQ ID NO 214
<211> LENGTH: 72
<212> TYPE: PRT
<213> ORGANISM: Homo sapiens

<400> SEQUENCE: 214

Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys Arg Phe Lys Met
65                  70

<210> SEQ ID NO 215
<211> LENGTH: 156
<212> TYPE: PRT
<213> ORGANISM: Homo sapiens

<400> SEQUENCE: 215

Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro Ala
            20                  25                  30

Ser Arg Val Ser Arg Arg Ser Arg Gly Ile Val Glu Glu Cys Cys Phe
        35                  40                  45

Arg Ser Cys Asp Leu Ala Leu Leu Glu Thr Tyr Cys Ala Thr Pro Ala
    50                  55                  60

Lys Ser Glu Arg Asp Val Ser Thr Pro Pro Thr Val Leu Pro Asp Asn
65                  70                  75                  80

Phe Pro Arg Tyr Pro Val Gly Lys Phe Phe Gln Tyr Asp Thr Trp Lys
                85                  90                  95

Gln Ser Thr Gln Arg Leu Arg Arg Gly Leu Pro Ala Leu Leu Arg Ala
            100                 105                 110

Arg Arg Gly His Val Leu Ala Lys Glu Leu Glu Ala Phe Arg Glu Ala
        115                 120                 125

Lys Arg His Arg Pro Leu Ile Ala Leu Pro Thr Gln Asp Pro Ala His
    130                 135                 140

Gly Gly Ala Pro Pro Glu Met Ala Ser Asn Arg Lys
145                 150                 155

<210> SEQ ID NO 216
<211> LENGTH: 67
<212> TYPE: PRT
<213> ORGANISM: Homo sapiens

<400> SEQUENCE: 216

Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro Ala

Ser Arg Val Ser Arg Arg Ser Arg Gly Ile Val Glu Glu Cys Cys Phe
            35                  40                  45

Arg Ser Cys Asp Leu Ala Leu Leu Glu Thr Tyr Cys Ala Thr Pro Ala
        50                  55                  60

Lys Ser Glu
65

<210> SEQ ID NO 217
<211> LENGTH: 70
<212> TYPE: PRT
<213> ORGANISM: Homo sapiens

<400> SEQUENCE: 217

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
            35                  40                  45

Phe Arg Ser Cys Asp Leu Arg Arg Leu Glu Met Tyr Cys Ala Pro Leu
        50                  55                  60

Lys Pro Ala Lys Ser Ala
65                  70

<210> SEQ ID NO 218
<211> LENGTH: 179
<212> TYPE: PRT
<213> ORGANISM: Homo sapiens

<400> SEQUENCE: 218

Gln Leu Phe His Leu Gln Lys Glu Leu Ala Glu Leu Arg Glu Ser Thr
1               5                   10                  15

Ser Gln Met His Thr Ala Ser Ser Leu Glu Lys Gln Ile Gly His Pro
            20                  25                  30

Ser Pro Pro Pro Glu Lys Lys Glu Leu Arg Lys Val Ala His Leu Thr
            35                  40                  45

Gly Lys Ser Asn Ser Arg Ser Met Pro Leu Glu Trp Glu Asp Thr Tyr
        50                  55                  60

Gly Ile Val Leu Leu Ser Gly Val Lys Tyr Lys Lys Gly Gly Leu Val
65                  70                  75                  80

Ile Asn Glu Thr Gly Leu Tyr Phe Val Tyr Ser Lys Val Tyr Phe Arg
                85                  90                  95

Gly Gln Ser Cys Asn Asn Leu Pro Leu Ser His Lys Val Tyr Met Arg
            100                 105                 110

Asn Ser Lys Tyr Pro Gln Asp Leu Val Met Met Glu Gly Lys Met Met
        115                 120                 125

Ser Tyr Cys Thr Thr Gly Gln Met Trp Ala Arg Ser Ser Tyr Leu Gly
    130                 135                 140

Ala Val Phe Asn Leu Thr Ser Ala Asp His Leu Tyr Val Asn Val Ser
145                 150                 155                 160

Glu Leu Ser Leu Val Asn Phe Glu Glu Ser Gln Thr Phe Phe Gly Leu
                165                 170                 175

Tyr Lys Leu

<210> SEQ ID NO 219
<211> LENGTH: 152

```
<212> TYPE: PRT
<213> ORGANISM: Homo sapiens

<400> SEQUENCE: 219

Gln Ile Gly His Pro Ser Pro Pro Glu Lys Lys Glu Leu Arg Lys
1               5                   10                  15

Val Ala His Leu Thr Gly Lys Ser Asn Ser Arg Ser Met Pro Leu Glu
                20                  25                  30

Trp Glu Asp Thr Tyr Gly Ile Val Leu Leu Ser Gly Val Lys Tyr Lys
            35                  40                  45

Lys Gly Gly Leu Val Ile Asn Glu Thr Gly Leu Tyr Phe Val Tyr Ser
50                  55                  60

Lys Val Tyr Phe Arg Gly Gln Ser Cys Asn Asn Leu Pro Leu Ser His
65                  70                  75                  80

Lys Val Tyr Met Arg Asn Ser Lys Tyr Pro Gln Asp Leu Val Met Met
                85                  90                  95

Glu Gly Lys Met Met Ser Tyr Cys Thr Thr Gly Gln Met Trp Ala Arg
            100                 105                 110

Ser Ser Tyr Leu Gly Ala Val Phe Asn Leu Thr Ser Ala Asp His Leu
        115                 120                 125

Tyr Val Asn Val Ser Glu Leu Ser Leu Val Asn Phe Glu Glu Ser Gln
130                 135                 140

Thr Phe Phe Gly Leu Tyr Lys Leu
145                 150

<210> SEQ ID NO 220
<211> LENGTH: 178
<212> TYPE: PRT
<213> ORGANISM: Homo sapiens

<400> SEQUENCE: 220

Ala Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
                20                  25                  30

Gln Glu Lys Leu Val Ser Glu Cys Ala Thr Tyr Lys Leu Cys His Pro
            35                  40                  45

Glu Glu Leu Val Leu Leu Gly His Ser Leu Gly Ile Pro Trp Ala Pro
        50                  55                  60

Leu Ser Ser Cys Pro Ser Gln Ala Leu Gln Leu Ala Gly Cys Leu Ser
65                  70                  75                  80

Gln Leu His Ser Gly Leu Phe Leu Tyr Gln Gly Leu Leu Gln Ala Leu
                85                  90                  95

Glu Gly Ile Ser Pro Glu Leu Gly Pro Thr Leu Asp Thr Leu Gln Leu
            100                 105                 110

Asp Val Ala Asp Phe Ala Thr Thr Ile Trp Gln Gln Met Glu Glu Leu
        115                 120                 125

Gly Met Ala Pro Ala Leu Gln Pro Thr Gln Gly Ala Met Pro Ala Phe
130                 135                 140

Ala Ser Ala Phe Gln Arg Arg Ala Gly Gly Val Leu Val Ala Ser His
145                 150                 155                 160

Leu Gln Ser Phe Leu Glu Val Ser Tyr Arg Val Leu Arg His Leu Ala
                165                 170                 175

Gln Pro

<210> SEQ ID NO 221
```

<211> LENGTH: 140
<212> TYPE: PRT
<213> ORGANISM: Homo sapiens

<400> SEQUENCE: 221

Phe Asn Leu Pro Pro Gly Asn Tyr Lys Lys Pro Lys Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
            100                 105                 110

Lys Asn Gly Ser Cys Lys Arg Gly Pro Arg Thr His Tyr Gly Gln Lys
        115                 120                 125

Ala Ile Leu Phe Leu Pro Leu Pro Val Ser Ser Asp
    130                 135                 140

<210> SEQ ID NO 222
<211> LENGTH: 36
<212> TYPE: PRT
<213> ORGANISM: Homo sapiens

<400> SEQUENCE: 222

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
        35

<210> SEQ ID NO 223
<211> LENGTH: 69
<212> TYPE: PRT
<213> ORGANISM: Homo sapiens

<400> SEQUENCE: 223

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr Gly Lys Arg Ser Ser Pro Glu Thr Leu Ile Ser Asp
        35                  40                  45

Leu Leu Met Arg Glu Ser Thr Glu Asn Val Pro Arg Thr Arg Leu Glu
50                  55                  60

Asp Pro Ala Met Trp
65

<210> SEQ ID NO 224
<211> LENGTH: 172
<212> TYPE: PRT
<213> ORGANISM: Homo sapiens

<400> SEQUENCE: 224

Gln Arg Thr Asp Ser Ile Pro Asn Ser Pro Asp Asn Val Pro Leu Lys
1               5                   10                  15

Gly Gly Asn Cys Ser Glu Asp Leu Leu Cys Ile Leu Lys Arg Ala Pro
            20                  25                  30

Phe Lys Lys Ser Trp Ala Tyr Leu Gln Val Ala Lys His Leu Asn Lys
        35                  40                  45

Thr Lys Leu Ser Trp Asn Lys Asp Gly Ile Leu His Gly Val Arg Tyr
    50                  55                  60

Gln Asp Gly Asn Leu Val Ile Gln Phe Pro Gly Leu Tyr Phe Ile Ile
65              70                  75                  80

Cys Gln Leu Gln Phe Leu Val Gln Cys Pro Asn Asn Ser Val Asp Leu
            85                  90                  95

Lys Leu Glu Leu Leu Ile Asn Lys His Ile Lys Lys Gln Ala Leu Val
        100                 105                 110

Thr Val Cys Glu Ser Gly Met Gln Thr Lys His Val Tyr Gln Asn Leu
    115                 120                 125

Ser Gln Phe Leu Leu Asp Tyr Leu Gln Val Asn Thr Thr Ile Ser Val
130                 135                 140

Asn Val Asp Thr Phe Gln Tyr Ile Asp Thr Ser Thr Phe Pro Leu Glu
145                 150                 155                 160

Asn Val Leu Ser Ile Phe Leu Tyr Ser Asn Ser Asp
            165                 170

<210> SEQ ID NO 225
<211> LENGTH: 155
<212> TYPE: PRT
<213> ORGANISM: Homo sapiens

<400> SEQUENCE: 225

Gln Arg Phe Ala Gln Ala Gln Gln Leu Pro Leu Glu Ser Leu Gly
1               5                   10                  15

Trp Asp Val Ala Glu Leu Gln Leu Asn His Thr Gly Pro Gln Gln Asp
            20                  25                  30

Pro Arg Leu Tyr Trp Gln Gly Gly Pro Ala Leu Gly Arg Ser Phe Leu
        35                  40                  45

His Gly Pro Glu Leu Asp Lys Gly Gln Leu Arg Ile His Arg Asp Gly
    50                  55                  60

Ile Tyr Met Val His Ile Gln Val Thr Leu Ala Ile Cys Ser Ser Thr
65              70                  75                  80

Thr Ala Ser Arg His His Pro Thr Thr Leu Ala Val Gly Ile Cys Ser
            85                  90                  95

Pro Ala Ser Arg Ser Ile Ser Leu Leu Arg Leu Ser Phe His Gln Gly
        100                 105                 110

Cys Thr Ile Ala Ser Gln Arg Leu Thr Pro Leu Ala Arg Gly Asp Thr
    115                 120                 125

Leu Cys Thr Asn Leu Thr Gly Thr Leu Leu Pro Ser Arg Asn Thr Asp
130                 135                 140

Glu Thr Phe Phe Gly Val Gln Trp Val Arg Pro
145                 150                 155

<210> SEQ ID NO 226
<211> LENGTH: 232
<212> TYPE: PRT
<213> ORGANISM: Homo sapiens

<400> SEQUENCE: 226

```
Ser Lys Ser Asn Glu Gly Ala Asp Gly Pro Val Lys Asn Lys Lys Lys
1               5                   10                  15

Gly Lys Lys Ala Gly Pro Pro Gly Pro Asn Gly Pro Pro Gly Pro Pro
                20                  25                  30

Gly Pro Pro Gly Pro Gln Gly Pro Pro Gly Ile Pro Gly Ile Pro Gly
                35                  40                  45

Ile Pro Gly Thr Thr Val Met Gly Pro Gly Pro Pro Gly Pro Pro
 50                  55                  60

Gly Pro Gln Gly Pro Pro Gly Leu Gln Gly Pro Ser Gly Ala Ala Asp
 65                  70                  75                  80

Lys Ala Gly Thr Arg Glu Asn Gln Pro Ala Val Val His Leu Gln Gly
                85                  90                  95

Gln Gly Ser Ala Ile Gln Val Lys Asn Asp Leu Ser Gly Gly Val Leu
                100                 105                 110

Asn Asp Trp Ser Arg Ile Thr Met Asn Pro Lys Val Phe Lys Leu His
                115                 120                 125

Pro Arg Ser Gly Glu Leu Glu Val Leu Val Asp Gly Thr Tyr Phe Ile
 130                 135                 140

Tyr Ser Gln Val Glu Val Tyr Tyr Ile Asn Phe Thr Asp Phe Ala Ser
145                 150                 155                 160

Tyr Glu Val Val Val Asp Glu Lys Pro Phe Leu Gln Cys Thr Arg Ser
                165                 170                 175

Ile Glu Thr Gly Lys Thr Asn Tyr Asn Thr Cys Tyr Thr Ala Gly Val
                180                 185                 190

Cys Leu Leu Lys Ala Arg Gln Lys Ile Ala Val Lys Met Val His Ala
                195                 200                 205

Asp Ile Ser Ile Asn Met Ser Lys His Thr Thr Phe Phe Gly Ala Ile
210                 215                 220

Arg Leu Gly Glu Ala Pro Ala Ser
225                 230

<210> SEQ ID NO 227
<211> LENGTH: 329
<212> TYPE: PRT
<213> ORGANISM: Homo sapiens

<400> SEQUENCE: 227

Glu Leu Arg Ser Glu Leu Arg Arg Glu Arg Gly Ala Glu Ser Arg Leu
1               5                   10                  15

Gly Gly Ser Gly Thr Pro Gly Thr Ser Gly Thr Leu Ser Ser Leu Gly
                20                  25                  30

Gly Leu Asp Pro Asp Ser Pro Ile Thr Ser His Leu Gly Gln Pro Ser
                35                  40                  45

Pro Lys Gln Gln Pro Leu Glu Pro Gly Glu Ala Ala Leu His Ser Asp
 50                  55                  60

Ser Gln Asp Gly His Gln Met Ala Leu Leu Asn Phe Phe Phe Pro Asp
 65                  70                  75                  80

Glu Lys Pro Tyr Ser Glu Glu Glu Ser Arg Arg Val Arg Arg Asn Lys
                85                  90                  95

Arg Ser Lys Ser Asn Glu Gly Ala Asp Gly Pro Val Lys Asn Lys Lys
                100                 105                 110

Lys Gly Lys Lys Ala Gly Pro Pro Gly Pro Asn Gly Pro Pro Gly Pro
                115                 120                 125

Pro Gly Pro Pro Gly Pro Gln Gly Pro Pro Gly Ile Pro Gly Ile Pro
 130                 135                 140
```

```
Gly Ile Pro Gly Thr Thr Val Met Gly Pro Pro Gly Pro Pro Gly Pro
145                 150                 155                 160

Pro Gly Pro Gln Gly Pro Pro Gly Leu Gln Gly Pro Ser Gly Ala Ala
            165                 170                 175

Asp Lys Ala Gly Thr Arg Glu Asn Gln Pro Ala Val Val His Leu Gln
            180                 185                 190

Gly Gln Gly Ser Ala Ile Gln Val Lys Asn Asp Leu Ser Gly Gly Val
            195                 200                 205

Leu Asn Asp Trp Ser Arg Ile Thr Met Asn Pro Lys Val Phe Lys Leu
210                 215                 220

His Pro Arg Ser Gly Glu Leu Glu Val Leu Val Asp Gly Thr Tyr Phe
225                 230                 235                 240

Ile Tyr Ser Gln Val Glu Val Tyr Tyr Ile Asn Phe Thr Asp Phe Ala
                245                 250                 255

Ser Tyr Glu Val Val Val Asp Glu Lys Pro Phe Leu Gln Cys Thr Arg
                260                 265                 270

Ser Ile Glu Thr Gly Lys Thr Asn Tyr Asn Thr Cys Tyr Thr Ala Gly
                275                 280                 285

Val Cys Leu Leu Lys Ala Arg Gln Lys Ile Ala Val Lys Met Val His
                290                 295                 300

Ala Asp Ile Ser Ile Asn Met Ser Lys His Thr Thr Phe Phe Gly Ala
305                 310                 315                 320

Ile Arg Leu Gly Glu Ala Pro Ala Ser
                325

<210> SEQ ID NO 228
<211> LENGTH: 49
<212> TYPE: PRT
<213> ORGANISM: Homo sapiens

<400> SEQUENCE: 228

Val Ala Gln Val Ser Ile Thr Lys Cys Ser Ser Asp Met Asn Gly Tyr
1               5                   10                  15

Cys Leu His Gly Gln Cys Ile Tyr Leu Val Asp Met Ser Gln Asn Tyr
            20                  25                  30

Cys Arg Cys Glu Val Gly Tyr Thr Gly Val Arg Cys Glu His Phe Phe
        35                  40                  45

Leu

<210> SEQ ID NO 229
<211> LENGTH: 46
<212> TYPE: PRT
<213> ORGANISM: Homo sapiens

<400> SEQUENCE: 229

Val Ser Ile Thr Lys Cys Ser Ser Asp Met Asn Gly Tyr Cys Leu His
1               5                   10                  15

Gly Gln Cys Ile Tyr Leu Val Asp Met Ser Gln Asn Tyr Cys Arg Cys
            20                  25                  30

Glu Val Gly Tyr Thr Gly Val Arg Cys Glu His Phe Phe Leu
        35                  40                  45

<210> SEQ ID NO 230
<211> LENGTH: 84
<212> TYPE: PRT
<213> ORGANISM: Homo sapiens

<400> SEQUENCE: 230
```

```
Ser Val Arg Val Glu Gln Val Val Lys Pro Pro Gln Asn Lys Thr Glu
1               5                   10                  15

Ser Glu Asn Thr Ser Asp Lys Pro Lys Arg Lys Lys Lys Gly Gly Lys
                20                  25                  30

Asn Gly Lys Asn Arg Arg Asn Arg Lys Lys Lys Asn Pro Cys Asn Ala
            35                  40                  45

Glu Phe Gln Asn Phe Cys Ile His Gly Glu Cys Lys Tyr Ile Glu His
    50                  55                  60

Leu Glu Ala Val Thr Cys Lys Cys Gln Gln Glu Tyr Phe Gly Glu Arg
65                  70                  75                  80

Cys Gly Glu Lys

<210> SEQ ID NO 231
<211> LENGTH: 180
<212> TYPE: PRT
<213> ORGANISM: Homo sapiens

<400> SEQUENCE: 231

Gly Ser Gly His Tyr Ala Ala Gly Leu Asp Leu Asn Asp Thr Tyr Ser
1               5                   10                  15

Gly Lys Arg Glu Pro Phe Ser Gly Asp His Ser Ala Asp Gly Phe Glu
                20                  25                  30

Val Thr Ser Arg Ser Glu Met Ser Ser Gly Ser Glu Ile Ser Pro Val
            35                  40                  45

Ser Glu Met Pro Ser Ser Ser Glu Pro Ser Ser Gly Ala Asp Tyr Asp
    50                  55                  60

Tyr Ser Glu Glu Tyr Asp Asn Glu Pro Gln Ile Pro Gly Tyr Ile Val
65                  70                  75                  80

Asp Asp Ser Val Arg Val Glu Gln Val Val Lys Pro Pro Gln Asn Lys
                85                  90                  95

Thr Glu Ser Glu Asn Thr Ser Asp Lys Pro Lys Arg Lys Lys Lys Gly
            100                 105                 110

Gly Lys Asn Gly Lys Asn Arg Arg Asn Arg Lys Lys Lys Asn Pro Cys
        115                 120                 125

Asn Ala Glu Phe Gln Asn Phe Cys Ile His Gly Glu Cys Lys Tyr Ile
    130                 135                 140

Glu His Leu Glu Ala Val Thr Cys Lys Cys Gln Gln Glu Tyr Phe Gly
145                 150                 155                 160

Glu Arg Cys Gly Glu Lys Ser Met Lys Thr His Ser Met Ile Asp Ser
                165                 170                 175

Ser Leu Ser Lys
            180

<210> SEQ ID NO 232
<211> LENGTH: 80
<212> TYPE: PRT
<213> ORGANISM: Homo sapiens

<400> SEQUENCE: 232

Asp Gly Asn Ser Thr Arg Ser Pro Glu Thr Asn Gly Leu Leu Cys Gly
1               5                   10                  15

Asp Pro Glu Glu Asn Cys Ala Ala Thr Thr Thr Gln Ser Lys Arg Lys
                20                  25                  30

Gly His Phe Ser Arg Cys Pro Lys Gln Tyr Lys His Tyr Cys Ile Lys
            35                  40                  45

Gly Arg Cys Arg Phe Val Val Ala Glu Gln Thr Pro Ser Cys Val Cys
        50                  55                  60
```

Asp Glu Gly Tyr Ile Gly Ala Arg Cys Glu Arg Val Asp Leu Phe Tyr
65                  70                  75                  80

<210> SEQ ID NO 233
<211> LENGTH: 141
<212> TYPE: PRT
<213> ORGANISM: Homo sapiens

<400> SEQUENCE: 233

Leu Val Thr Gly Glu Ser Leu Glu Arg Leu Arg Arg Gly Leu Ala Ala
1               5                   10                  15

Gly Thr Ser Asn Pro Asp Pro Thr Val Ser Thr Asp Gln Leu Leu
            20                  25                  30

Pro Leu Gly Gly Gly Arg Asp Arg Lys Val Arg Asp Leu Gln Glu Ala
        35                  40                  45

Asp Leu Asp Leu Leu Arg Val Thr Leu Ser Ser Lys Pro Gln Ala Leu
50                  55                  60

Ala Thr Pro Asn Lys Glu Glu His Gly Lys Arg Lys Lys Gly Lys
65                  70                  75                  80

Gly Leu Gly Lys Lys Arg Asp Pro Cys Leu Arg Lys Tyr Lys Asp Phe
            85                  90                  95

Cys Ile His Gly Glu Cys Lys Tyr Val Lys Glu Leu Arg Ala Pro Ser
            100                 105                 110

Cys Ile Cys His Pro Gly Tyr His Gly Glu Arg Cys His Gly Leu Ser
            115                 120                 125

Leu Pro Val Glu Asn Arg Leu Tyr Thr Tyr Asp His Thr
        130                 135                 140

<210> SEQ ID NO 234
<211> LENGTH: 86
<212> TYPE: PRT
<213> ORGANISM: Homo sapiens

<400> SEQUENCE: 234

Asp Leu Gln Glu Ala Asp Leu Asp Leu Leu Arg Val Thr Leu Ser Ser
1               5                   10                  15

Lys Pro Gln Ala Leu Ala Thr Pro Asn Lys Glu Glu His Gly Lys Arg
            20                  25                  30

Lys Lys Lys Gly Lys Gly Leu Gly Lys Lys Arg Asp Pro Cys Leu Arg
        35                  40                  45

Lys Tyr Lys Asp Phe Cys Ile His Gly Glu Cys Lys Tyr Val Lys Glu
50                  55                  60

Leu Arg Ala Pro Ser Cys Ile Cys His Pro Gly Tyr His Gly Glu Arg
65                  70                  75                  80

Cys His Gly Leu Ser Leu
            85

<210> SEQ ID NO 235
<211> LENGTH: 161
<212> TYPE: PRT
<213> ORGANISM: Homo sapiens

<400> SEQUENCE: 235

Ala Leu His Glu Gly Lys Gly Gln Ala Ala Thr Leu Glu Gln Pro
1               5                   10                  15

Ala Ser Ser Ser His Ala Gln Gly Thr His Leu Arg Leu Arg Arg Cys
            20                  25                  30

Ser Cys Ser Ser Trp Leu Asp Lys Glu Cys Val Tyr Phe Cys His Leu

```
                   35                  40                  45
Asp Ile Ile Trp Val Asn Thr Pro Glu Gln Thr Ala Pro Tyr Gly Leu
        50                  55                  60

Gly Asn Pro Pro Arg Arg Arg Arg Ser Leu Pro Arg Arg Cys Gln
65                  70                  75                  80

Cys Ser Ser Ala Arg Asp Pro Ala Cys Ala Thr Phe Cys Leu Arg Arg
                85                  90                  95

Pro Trp Thr Glu Ala Gly Ala Val Pro Ser Arg Lys Ser Pro Ala Asp
            100                 105                 110

Val Phe Gln Thr Gly Lys Thr Gly Ala Thr Thr Gly Glu Leu Leu Gln
            115                 120                 125

Arg Leu Arg Asp Ile Ser Thr Val Lys Ser Leu Phe Ala Lys Arg Gln
130                 135                 140

Gln Glu Ala Met Arg Glu Pro Arg Ser Thr His Ser Arg Trp Arg Lys
145                 150                 155                 160

Arg
```

<210> SEQ ID NO 236
<211> LENGTH: 21
<212> TYPE: PRT
<213> ORGANISM: Homo sapiens

<400> SEQUENCE: 236

```
Cys Ser Cys Ser Ser Trp Leu Asp Lys Glu Cys Val Tyr Phe Cys His
1               5                   10                  15

Leu Asp Ile Ile Trp
            20
```

<210> SEQ ID NO 237
<211> LENGTH: 1010
<212> TYPE: PRT
<213> ORGANISM: Homo sapiens

<400> SEQUENCE: 237

```
Pro Gln His Trp Ser Cys Pro Glu Gly Thr Leu Ala Gly Asn Gly Asn
1               5                   10                  15

Ser Thr Cys Val Gly Pro Ala Pro Phe Leu Ile Phe Ser His Gly Asn
            20                  25                  30

Ser Ile Phe Arg Ile Asp Thr Glu Gly Thr Asn Tyr Glu Gln Leu Val
            35                  40                  45

Val Asp Ala Gly Val Ser Val Ile Met Asp Phe His Tyr Asn Glu Lys
        50                  55                  60

Arg Ile Tyr Trp Val Asp Leu Glu Arg Gln Leu Leu Gln Arg Val Phe
65                  70                  75                  80

Leu Asn Gly Ser Arg Gln Glu Arg Val Cys Asn Ile Glu Lys Asn Val
                85                  90                  95

Ser Gly Met Ala Ile Asn Trp Ile Asn Glu Glu Val Ile Trp Ser Asn
            100                 105                 110

Gln Gln Glu Gly Ile Ile Thr Val Thr Asp Met Lys Gly Asn Asn Ser
            115                 120                 125

His Ile Leu Leu Ser Ala Leu Lys Tyr Pro Ala Asn Val Ala Val Asp
            130                 135                 140

Pro Val Glu Arg Phe Ile Phe Trp Ser Ser Glu Val Ala Gly Ser Leu
145                 150                 155                 160

Tyr Arg Ala Asp Leu Asp Gly Val Gly Val Lys Ala Leu Leu Glu Thr
                165                 170                 175
```

```
Ser Glu Lys Ile Thr Ala Val Ser Leu Asp Val Leu Asp Lys Arg Leu
            180                 185                 190

Phe Trp Ile Gln Tyr Asn Arg Glu Gly Ser Asn Ser Leu Ile Cys Ser
        195                 200                 205

Cys Asp Tyr Asp Gly Gly Ser Val His Ile Ser Lys His Pro Thr Gln
    210                 215                 220

His Asn Leu Phe Ala Met Ser Leu Phe Gly Asp Arg Ile Phe Tyr Ser
225                 230                 235                 240

Thr Trp Lys Met Lys Thr Ile Trp Ile Ala Asn Lys His Thr Gly Lys
                245                 250                 255

Asp Met Val Arg Ile Asn Leu His Ser Ser Phe Val Pro Leu Gly Glu
            260                 265                 270

Leu Lys Val Val His Pro Leu Ala Gln Pro Lys Ala Glu Asp Asp Thr
        275                 280                 285

Trp Glu Pro Glu Gln Lys Leu Cys Lys Leu Arg Lys Gly Asn Cys Ser
    290                 295                 300

Ser Thr Val Cys Gly Gln Asp Leu Gln Ser His Leu Cys Met Cys Ala
305                 310                 315                 320

Glu Gly Tyr Ala Leu Ser Arg Asp Arg Lys Tyr Cys Glu Asp Val Asn
                325                 330                 335

Glu Cys Ala Phe Trp Asn His Gly Cys Thr Leu Gly Cys Lys Asn Thr
            340                 345                 350

Pro Gly Ser Tyr Tyr Cys Thr Cys Pro Val Gly Phe Val Leu Leu Pro
        355                 360                 365

Asp Gly Lys Arg Cys His Gln Leu Val Ser Cys Pro Arg Asn Val Ser
    370                 375                 380

Glu Cys Ser His Asp Cys Val Leu Thr Ser Glu Gly Pro Leu Cys Phe
385                 390                 395                 400

Cys Pro Glu Gly Ser Val Leu Glu Arg Asp Gly Lys Thr Cys Ser Gly
                405                 410                 415

Cys Ser Ser Pro Asp Asn Gly Gly Cys Ser Gln Leu Cys Val Pro Leu
            420                 425                 430

Ser Pro Val Ser Trp Glu Cys Asp Cys Phe Pro Gly Tyr Asp Leu Gln
        435                 440                 445

Leu Asp Glu Lys Ser Cys Ala Ala Ser Gly Pro Gln Pro Phe Leu Leu
    450                 455                 460

Phe Ala Asn Ser Gln Asp Ile Arg His Met His Phe Asp Gly Thr Asp
465                 470                 475                 480

Tyr Gly Thr Leu Leu Ser Gln Gln Met Gly Met Val Tyr Ala Leu Asp
                485                 490                 495

His Asp Pro Val Glu Asn Lys Ile Tyr Phe Ala His Thr Ala Leu Lys
            500                 505                 510

Trp Ile Glu Arg Ala Asn Met Asp Gly Ser Gln Arg Glu Arg Leu Ile
        515                 520                 525

Glu Glu Gly Val Asp Val Pro Glu Gly Leu Ala Val Asp Trp Ile Gly
    530                 535                 540

Arg Arg Phe Tyr Trp Thr Asp Arg Gly Lys Ser Leu Ile Gly Arg Ser
545                 550                 555                 560

Asp Leu Asn Gly Lys Arg Ser Lys Ile Ile Thr Lys Glu Asn Ile Ser
                565                 570                 575

Gln Pro Arg Gly Ile Ala Val His Pro Met Ala Lys Arg Leu Phe Trp
            580                 585                 590

Thr Asp Thr Gly Ile Asn Pro Arg Ile Glu Ser Ser Ser Leu Gln Gly
        595                 600                 605
```

```
Leu Gly Arg Leu Val Ile Ala Ser Ser Asp Leu Ile Trp Pro Ser Gly
    610                 615                 620

Ile Thr Ile Asp Phe Leu Thr Asp Lys Leu Tyr Trp Cys Asp Ala Lys
625                 630                 635                 640

Gln Ser Val Ile Glu Met Ala Asn Leu Asp Gly Ser Lys Arg Arg Arg
                645                 650                 655

Leu Thr Gln Asn Asp Val Gly His Pro Phe Ala Val Ala Val Phe Glu
                660                 665                 670

Asp Tyr Val Trp Phe Ser Asp Trp Ala Met Pro Ser Val Ile Arg Val
            675                 680                 685

Asn Lys Arg Thr Gly Lys Asp Arg Val Arg Leu Gln Gly Ser Met Leu
        690                 695                 700

Lys Pro Ser Ser Leu Val Val His Pro Leu Ala Lys Pro Gly Ala
705                 710                 715                 720

Asp Pro Cys Leu Tyr Gln Asn Gly Gly Cys Glu His Ile Cys Lys Lys
                725                 730                 735

Arg Leu Gly Thr Ala Trp Cys Ser Cys Arg Glu Gly Phe Met Lys Ala
                740                 745                 750

Ser Asp Gly Lys Thr Cys Leu Ala Leu Asp Gly His Gln Leu Leu Ala
            755                 760                 765

Gly Gly Glu Val Asp Leu Lys Asn Gln Val Thr Pro Leu Asp Ile Leu
770                 775                 780

Ser Lys Thr Arg Val Ser Glu Asp Asn Ile Thr Glu Ser Gln His Met
785                 790                 795                 800

Leu Val Ala Glu Ile Met Val Ser Asp Gln Asp Cys Ala Pro Val
                805                 810                 815

Gly Cys Ser Met Tyr Ala Arg Cys Ile Ser Glu Gly Asp Ala Thr
                820                 825                 830

Cys Gln Cys Leu Lys Gly Phe Ala Gly Asp Gly Lys Leu Cys Ser Asp
            835                 840                 845

Ile Asp Glu Cys Glu Met Gly Val Pro Val Cys Pro Pro Ala Ser Ser
        850                 855                 860

Lys Cys Ile Asn Thr Glu Gly Gly Tyr Val Cys Arg Cys Ser Glu Gly
865                 870                 875                 880

Tyr Gln Gly Asp Gly Ile His Cys Leu Asp Ile Asp Glu Cys Gln Leu
                885                 890                 895

Gly Val His Ser Cys Gly Glu Asn Ala Ser Cys Thr Asn Thr Glu Gly
            900                 905                 910

Gly Tyr Thr Cys Met Cys Ala Gly Arg Leu Ser Glu Pro Gly Leu Ile
        915                 920                 925

Cys Pro Asp Ser Thr Pro Pro His Leu Arg Glu Asp His His
930                 935                 940

Tyr Ser Val Arg Asn Ser Asp Ser Glu Cys Pro Leu Ser His Asp Gly
945                 950                 955                 960

Tyr Cys Leu His Asp Gly Val Cys Met Tyr Ile Glu Ala Leu Asp Lys
                965                 970                 975

Tyr Ala Cys Asn Cys Val Val Gly Tyr Ile Gly Glu Arg Cys Gln Tyr
            980                 985                 990

Arg Asp Leu Lys Trp Trp Glu Leu Arg His Ala Gly His Gly Gln Gln
        995                 1000                1005

Gln Lys
    1010
```

```
<210> SEQ ID NO 238
<211> LENGTH: 53
<212> TYPE: PRT
<213> ORGANISM: Homo sapiens

<400> SEQUENCE: 238

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg
    50

<210> SEQ ID NO 239
<211> LENGTH: 176
<212> TYPE: PRT
<213> ORGANISM: Homo sapiens

<400> SEQUENCE: 239

Ala Pro Thr Ala Pro Asn Gly Thr Leu Glu Ala Leu Glu Arg Arg
1               5                   10                  15

Trp Glu Ser Leu Val Ala Leu Ser Leu Ala Arg Leu Pro Val Ala Ala
            20                  25                  30

Gln Pro Lys Glu Ala Ala Val Gln Ser Gly Ala Gly Asp Tyr Leu Leu
        35                  40                  45

Gly Ile Lys Arg Leu Arg Arg Leu Tyr Cys Asn Val Gly Ile Gly Phe
    50                  55                  60

His Leu Gln Ala Leu Pro Asp Gly Arg Ile Gly Gly Ala His Ala Asp
65                  70                  75                  80

Thr Arg Asp Ser Leu Leu Glu Leu Ser Pro Val Glu Arg Gly Val Val
                85                  90                  95

Ser Ile Phe Gly Val Ala Ser Arg Phe Phe Val Ala Met Ser Ser Lys
            100                 105                 110

Gly Lys Leu Tyr Gly Ser Pro Phe Phe Thr Asp Glu Cys Thr Phe Lys
        115                 120                 125

Glu Ile Leu Leu Pro Asn Asn Tyr Asn Ala Tyr Glu Ser Tyr Lys Tyr
    130                 135                 140

Pro Gly Met Phe Ile Ala Leu Ser Lys Asn Gly Lys Thr Lys Lys Gly
145                 150                 155                 160

Asn Arg Val Ser Pro Thr Met Lys Val Thr His Phe Leu Pro Arg Leu
                165                 170                 175

<210> SEQ ID NO 240
<211> LENGTH: 153
<212> TYPE: PRT
<213> ORGANISM: Homo sapiens

<400> SEQUENCE: 240

Ser Leu Ala Arg Leu Pro Val Ala Ala Gln Pro Lys Glu Ala Ala Val
1               5                   10                  15

Gln Ser Gly Ala Gly Asp Tyr Leu Leu Gly Ile Lys Arg Leu Arg Arg
            20                  25                  30

Leu Tyr Cys Asn Val Gly Ile Gly Phe His Leu Gln Ala Leu Pro Asp
        35                  40                  45

Gly Arg Ile Gly Gly Ala His Ala Asp Thr Arg Asp Ser Leu Leu Glu
    50                  55                  60
```

```
Leu Ser Pro Val Glu Arg Gly Val Val Ser Ile Phe Gly Val Ala Ser
 65                  70                  75                  80

Arg Phe Phe Val Ala Met Ser Ser Lys Gly Lys Leu Tyr Gly Ser Pro
                 85                  90                  95

Phe Phe Thr Asp Glu Cys Thr Phe Lys Glu Ile Leu Leu Pro Asn Asn
            100                 105                 110

Tyr Asn Ala Tyr Glu Ser Tyr Lys Tyr Pro Gly Met Phe Ile Ala Leu
        115                 120                 125

Ser Lys Asn Gly Lys Thr Lys Lys Gly Asn Arg Val Ser Pro Thr Met
130                 135                 140

Lys Val Thr His Phe Leu Pro Arg Leu
145                 150

<210> SEQ ID NO 241
<211> LENGTH: 150
<212> TYPE: PRT
<213> ORGANISM: Homo sapiens

<400> SEQUENCE: 241

Arg Leu Pro Val Ala Ala Gln Pro Lys Glu Ala Val Gln Ser Gly
1               5                   10                  15

Ala Gly Asp Tyr Leu Leu Gly Ile Lys Arg Leu Arg Arg Leu Tyr Cys
                20                  25                  30

Asn Val Gly Ile Gly Phe His Leu Gln Ala Leu Pro Asp Gly Arg Ile
            35                  40                  45

Gly Gly Ala His Ala Asp Thr Arg Asp Ser Leu Leu Glu Leu Ser Pro
        50                  55                  60

Val Glu Arg Gly Val Val Ser Ile Phe Gly Val Ala Ser Arg Phe Phe
65                  70                  75                  80

Val Ala Met Ser Ser Lys Gly Lys Leu Tyr Gly Ser Pro Phe Phe Thr
                85                  90                  95

Asp Glu Cys Thr Phe Lys Glu Ile Leu Leu Pro Asn Asn Tyr Asn Ala
            100                 105                 110

Tyr Glu Ser Tyr Lys Tyr Pro Gly Met Phe Ile Ala Leu Ser Lys Asn
        115                 120                 125

Gly Lys Thr Lys Lys Gly Asn Arg Val Ser Pro Thr Met Lys Val Thr
    130                 135                 140

His Phe Leu Pro Arg Leu
145                 150

<210> SEQ ID NO 242
<211> LENGTH: 139
<212> TYPE: PRT
<213> ORGANISM: Homo sapiens

<400> SEQUENCE: 242

Ala Val Gln Ser Gly Ala Gly Asp Tyr Leu Leu Gly Ile Lys Arg Leu
1               5                   10                  15

Arg Arg Leu Tyr Cys Asn Val Gly Ile Gly Phe His Leu Gln Ala Leu
                20                  25                  30

Pro Asp Gly Arg Ile Gly Gly Ala His Ala Asp Thr Arg Asp Ser Leu
            35                  40                  45

Leu Glu Leu Ser Pro Val Glu Arg Gly Val Val Ser Ile Phe Gly Val
        50                  55                  60

Ala Ser Arg Phe Phe Val Ala Met Ser Ser Lys Gly Lys Leu Tyr Gly
65                  70                  75                  80

Ser Pro Phe Phe Thr Asp Glu Cys Thr Phe Lys Glu Ile Leu Leu Pro
```

```
                      85                  90                  95
Asn Asn Tyr Asn Ala Tyr Glu Ser Tyr Lys Tyr Pro Gly Met Phe Ile
                100                 105                 110

Ala Leu Ser Lys Asn Gly Lys Thr Lys Lys Gly Asn Arg Val Ser Pro
            115                 120                 125

Thr Met Lys Val Thr His Phe Leu Pro Arg Leu
        130                 135

<210> SEQ ID NO 243
<211> LENGTH: 136
<212> TYPE: PRT
<213> ORGANISM: Homo sapiens

<400> SEQUENCE: 243

Ser Gly Ala Gly Asp Tyr Leu Leu Gly Ile Lys Arg Leu Arg Arg Leu
1               5                   10                  15

Tyr Cys Asn Val Gly Ile Gly Phe His Leu Gln Ala Leu Pro Asp Gly
            20                  25                  30

Arg Ile Gly Gly Ala His Ala Asp Thr Arg Asp Ser Leu Leu Glu Leu
        35                  40                  45

Ser Pro Val Glu Arg Gly Val Val Ser Ile Phe Gly Val Ala Ser Arg
    50                  55                  60

Phe Phe Val Ala Met Ser Ser Lys Gly Lys Leu Tyr Gly Ser Pro Phe
65                  70                  75                  80

Phe Thr Asp Glu Cys Thr Phe Lys Glu Ile Leu Leu Pro Asn Asn Tyr
                85                  90                  95

Asn Ala Tyr Glu Ser Tyr Lys Tyr Pro Gly Met Phe Ile Ala Leu Ser
                100                 105                 110

Lys Asn Gly Lys Thr Lys Lys Gly Asn Arg Val Ser Pro Thr Met Lys
            115                 120                 125

Val Thr His Phe Leu Pro Arg Leu
        130                 135

<210> SEQ ID NO 244
<211> LENGTH: 205
<212> TYPE: PRT
<213> ORGANISM: Homo sapiens

<400> SEQUENCE: 244

Leu Gly Glu Val Gly Asn Tyr Phe Gly Val Gln Asp Ala Val Pro Phe
1               5                   10                  15

Gly Asn Val Pro Val Leu Pro Val Asp Ser Pro Val Leu Leu Ser Asp
            20                  25                  30

His Leu Gly Gln Ser Glu Ala Gly Gly Leu Pro Arg Gly Pro Ala Val
        35                  40                  45

Thr Asp Leu Asp His Leu Lys Gly Ile Leu Arg Arg Arg Gln Leu Tyr
    50                  55                  60

Cys Arg Thr Gly Phe His Leu Glu Ile Phe Pro Asn Gly Thr Ile Gln
65                  70                  75                  80

Gly Thr Arg Lys Asp His Ser Arg Phe Gly Ile Leu Glu Phe Ile Ser
                85                  90                  95

Ile Ala Val Gly Leu Val Ser Ile Arg Gly Val Asp Ser Gly Leu Tyr
                100                 105                 110

Leu Gly Met Asn Glu Lys Gly Glu Leu Tyr Gly Ser Glu Lys Leu Thr
            115                 120                 125

Gln Glu Cys Val Phe Arg Glu Gln Phe Glu Glu Asn Trp Tyr Asn Thr
        130                 135                 140
```

```
Tyr Ser Ser Asn Leu Tyr Lys His Val Asp Thr Gly Arg Arg Tyr Tyr
145                 150                 155                 160

Val Ala Leu Asn Lys Asp Gly Thr Pro Arg Glu Gly Thr Arg Thr Lys
                165                 170                 175

Arg His Gln Lys Phe Thr His Phe Leu Pro Arg Pro Val Asp Pro Asp
            180                 185                 190

Lys Val Pro Glu Leu Tyr Lys Asp Ile Leu Ser Gln Ser
        195                 200                 205
```

<210> SEQ ID NO 245
<211> LENGTH: 196
<212> TYPE: PRT
<213> ORGANISM: Homo sapiens

<400> SEQUENCE: 245

```
Gln Asp Gln Gly Gly Leu Val Thr Glu Thr Ala Asp Pro Gly Ala Gln
1               5                   10                  15

Ala Gln Gln Gly Leu Gly Phe Gln Lys Leu Pro Glu Glu Pro Glu
            20                  25                  30

Thr Asp Leu Ser Pro Gly Leu Pro Ala Ala His Leu Ile Gly Ala Pro
                35                  40                  45

Leu Lys Gly Gln Gly Leu Gly Trp Glu Thr Thr Lys Glu Gln Ala Phe
50                  55                  60

Leu Thr Ser Gly Thr Gln Phe Ser Asp Ala Glu Gly Leu Ala Leu Pro
65                  70                  75                  80

Gln Asp Gly Leu Tyr Tyr Leu Tyr Cys Leu Val Gly Tyr Arg Gly Arg
                85                  90                  95

Ala Pro Pro Gly Gly Gly Asp Pro Gln Gly Arg Ser Val Thr Leu Arg
                100                 105                 110

Ser Ser Leu Tyr Arg Ala Gly Gly Ala Tyr Gly Pro Gly Thr Pro Glu
            115                 120                 125

Leu Leu Leu Glu Gly Ala Glu Thr Val Thr Pro Val Leu Asp Pro Ala
130                 135                 140

Arg Arg Gln Gly Tyr Gly Pro Leu Trp Tyr Thr Ser Val Gly Phe Gly
145                 150                 155                 160

Gly Leu Val Gln Leu Arg Arg Gly Glu Arg Val Tyr Val Asn Ile Ser
                165                 170                 175

His Pro Asp Met Val Asp Phe Ala Arg Gly Lys Thr Phe Phe Gly Ala
                180                 185                 190

Val Met Val Gly
        195
```

<210> SEQ ID NO 246
<211> LENGTH: 125
<212> TYPE: PRT
<213> ORGANISM: Homo sapiens

<400> SEQUENCE: 246

```
Ser Ile Glu Glu Ala Val Pro Ala Val Cys Lys Thr Arg Thr Val Ile
1               5                   10                  15

Tyr Glu Ile Pro Arg Ser Gln Val Asp Pro Thr Ser Ala Asn Phe Leu
            20                  25                  30

Ile Trp Pro Pro Cys Val Glu Val Lys Arg Cys Thr Gly Cys Cys Asn
            35                  40                  45

Thr Ser Ser Val Lys Cys Gln Pro Ser Arg Val His His Arg Ser Val
50                  55                  60
```

```
Lys Val Ala Lys Val Glu Tyr Val Arg Lys Lys Pro Lys Leu Lys Glu
 65                  70                  75                  80

Val Gln Val Arg Leu Glu Glu His Leu Glu Cys Ala Cys Ala Thr Thr
                 85                  90                  95

Ser Leu Asn Pro Asp Tyr Arg Glu Glu Asp Thr Gly Arg Pro Arg Glu
            100                 105                 110

Ser Gly Lys Lys Arg Lys Arg Lys Leu Lys Pro Thr
        115                 120                 125

<210> SEQ ID NO 247
<211> LENGTH: 109
<212> TYPE: PRT
<213> ORGANISM: Homo sapiens

<400> SEQUENCE: 247

Ser Leu Gly Ser Leu Thr Ile Ala Glu Pro Ala Met Ile Ala Glu Cys
  1               5                  10                  15

Lys Thr Arg Thr Glu Val Phe Glu Ile Ser Arg Arg Leu Ile Asp Arg
             20                  25                  30

Thr Asn Ala Asn Phe Leu Val Trp Pro Pro Cys Val Glu Val Gln Arg
         35                  40                  45

Cys Ser Gly Cys Cys Asn Asn Arg Asn Val Gln Cys Arg Pro Thr Gln
 50                  55                  60

Val Gln Leu Arg Pro Val Gln Val Arg Lys Ile Glu Ile Val Arg Lys
 65                  70                  75                  80

Lys Pro Ile Phe Lys Lys Ala Thr Val Thr Leu Glu Asp His Leu Ala
             85                  90                  95

Cys Lys Cys Glu Thr Val Ala Ala Ala Arg Pro Val Thr
            100                 105

<210> SEQ ID NO 248
<211> LENGTH: 222
<212> TYPE: PRT
<213> ORGANISM: Homo sapiens

<400> SEQUENCE: 248

Trp Thr Gly Glu Asp Ser Ala Glu Pro Asn Ser Asp Ser Ala Glu Trp
  1               5                  10                  15

Ile Arg Asp Met Tyr Ala Lys Val Thr Glu Ile Trp Gln Glu Val Met
             20                  25                  30

Gln Arg Arg Asp Asp Asp Gly Thr Leu His Ala Ala Cys Gln Val Gln
         35                  40                  45

Pro Ser Ala Thr Leu Asp Ala Ala Gln Pro Arg Val Thr Gly Val Val
 50                  55                  60

Leu Phe Arg Gln Leu Ala Pro Arg Ala Lys Leu Asp Ala Phe Phe Ala
 65                  70                  75                  80

Leu Glu Gly Phe Pro Thr Glu Pro Asn Ser Ser Arg Ala Ile His
             85                  90                  95

Val His Gln Phe Gly Asp Leu Ser Gln Gly Cys Glu Ser Thr Gly Pro
            100                 105                 110

His Tyr Asn Pro Leu Ala Val Pro His Pro Gln His Pro Gly Asp Phe
        115                 120                 125

Gly Asn Phe Ala Val Arg Asp Gly Ser Leu Trp Arg Tyr Arg Ala Gly
    130                 135                 140

Leu Ala Ala Ser Leu Ala Gly Pro His Ser Ile Val Gly Arg Ala Val
145                 150                 155                 160

Val Val His Ala Gly Glu Asp Asp Leu Gly Arg Gly Gly Asn Gln Ala
```

```
                          165                 170                 175
Ser Val Glu Asn Gly Asn Ala Gly Arg Arg Leu Ala Cys Cys Val Val
            180                 185                 190

Gly Val Cys Gly Pro Gly Leu Trp Glu Arg Gln Ala Arg Glu His Ser
        195                 200                 205

Glu Arg Lys Lys Arg Arg Arg Glu Ser Glu Cys Lys Ala Ala
210                 215                 220

<210> SEQ ID NO 249
<211> LENGTH: 98
<212> TYPE: PRT
<213> ORGANISM: Homo sapiens

<400> SEQUENCE: 249

Met Val Pro Ser Ala Gly Gln Leu Ala Leu Phe Ala Leu Gly Ile Val
1               5                   10                  15

Leu Ala Ala Cys Gln Ala Leu Glu Asn Ser Thr Ser Pro Leu Ser Ala
            20                  25                  30

Asp Pro Pro Val Ala Ala Ala Val Val Ser His Phe Asn Asp Cys Pro
        35                  40                  45

Asp Ser His Thr Gln Phe Cys Phe His Gly Thr Cys Arg Phe Leu Val
    50                  55                  60

Gln Glu Asp Lys Pro Ala Cys Val Cys His Ser Gly Tyr Val Gly Ala
65                  70                  75                  80

Arg Cys Glu His Ala Asp Leu Leu Ala Val Val Ala Ala Ser Gln Lys
                85                  90                  95

Lys Gln

<210> SEQ ID NO 250
<211> LENGTH: 75
<212> TYPE: PRT
<213> ORGANISM: Homo sapiens

<400> SEQUENCE: 250

Glu Asn Ser Thr Ser Pro Leu Ser Ala Asp Pro Pro Val Ala Ala Ala
1               5                   10                  15

Val Val Ser His Phe Asn Asp Cys Pro Asp Ser His Thr Gln Phe Cys
            20                  25                  30

Phe His Gly Thr Cys Arg Phe Leu Val Gln Glu Asp Lys Pro Ala Cys
        35                  40                  45

Val Cys His Ser Gly Tyr Val Gly Ala Arg Cys Glu His Ala Asp Leu
    50                  55                  60

Leu Ala Val Val Ala Ala Ser Gln Lys Lys Gln
65                  70                  75

<210> SEQ ID NO 251
<211> LENGTH: 50
<212> TYPE: PRT
<213> ORGANISM: Homo sapiens

<400> SEQUENCE: 251

Val Val Ser His Phe Asn Asp Cys Pro Asp Ser His Thr Gln Phe Cys
1               5                   10                  15

Phe His Gly Thr Cys Arg Phe Leu Val Gln Glu Asp Lys Pro Ala Cys
            20                  25                  30

Val Cys His Ser Gly Tyr Val Gly Ala Arg Cys Glu His Ala Asp Leu
        35                  40                  45

Leu Ala
```

<210> SEQ ID NO 252
<211> LENGTH: 133
<212> TYPE: PRT
<213> ORGANISM: Homo sapiens

<400> SEQUENCE: 252

```
Gln Val Ser His Arg Tyr Pro Arg Ile Gln Ser Ile Lys Val Gln Phe
 1               5                  10                  15

Thr Glu Tyr Lys Lys Glu Lys Gly Phe Ile Leu Thr Ser Gln Lys Glu
            20                  25                  30

Asp Glu Ile Met Lys Val Gln Asn Asn Ser Val Ile Ile Asn Cys Asp
        35                  40                  45

Gly Phe Tyr Leu Ile Ser Leu Lys Gly Tyr Phe Ser Gln Glu Val Asn
    50                  55                  60

Ile Ser Leu His Tyr Gln Lys Asp Glu Glu Pro Leu Phe Gln Leu Lys
65                  70                  75                  80

Lys Val Arg Ser Val Asn Ser Leu Met Val Ala Ser Leu Thr Tyr Lys
                85                  90                  95

Asp Lys Val Tyr Leu Asn Val Thr Thr Asp Asn Thr Ser Leu Asp Asp
            100                 105                 110

Phe His Val Asn Gly Gly Glu Leu Ile Leu Ile His Gln Asn Pro Gly
        115                 120                 125

Glu Phe Cys Val Leu
    130
```

<210> SEQ ID NO 253
<211> LENGTH: 178
<212> TYPE: PRT
<213> ORGANISM: Homo sapiens

<400> SEQUENCE: 253

```
Ile Arg Ala Glu Lys Ala Met Val Asp Gly Ser Trp Leu Asp Leu Ala
 1               5                  10                  15

Lys Arg Ser Lys Leu Glu Ala Gln Pro Phe Ala His Leu Thr Ile Asn
            20                  25                  30

Ala Thr Asp Ile Pro Ser Gly Ser His Lys Val Ser Leu Ser Ser Trp
        35                  40                  45

Tyr His Asp Arg Gly Trp Ala Lys Ile Ser Asn Met Thr Phe Ser Asn
    50                  55                  60

Gly Lys Leu Ile Val Asn Gln Asp Gly Phe Tyr Tyr Leu Tyr Ala Asn
65                  70                  75                  80

Ile Cys Phe Arg His His Glu Thr Ser Gly Asp Leu Ala Thr Glu Tyr
                85                  90                  95

Leu Gln Leu Met Val Tyr Val Thr Lys Thr Ser Ile Lys Ile Pro Ser
            100                 105                 110

Ser His Thr Leu Met Lys Gly Gly Ser Thr Lys Tyr Trp Ser Gly Asn
        115                 120                 125

Ser Glu Phe His Phe Tyr Ser Ile Asn Val Gly Gly Phe Phe Lys Leu
    130                 135                 140

Arg Ser Gly Glu Glu Ile Ser Ile Glu Val Ser Asn Pro Ser Leu Leu
145                 150                 155                 160

Asp Pro Asp Gln Asp Ala Thr Tyr Phe Gly Ala Phe Lys Val Arg Asp
                165                 170                 175

Ile Asp
```

<210> SEQ ID NO 254
<211> LENGTH: 249
<212> TYPE: PRT
<213> ORGANISM: Homo sapiens

<400> SEQUENCE: 254

Tyr Phe Arg Ala Gln Met Asp Pro Asn Arg Ile Ser Glu Asp Gly Thr
1               5                   10                  15

His Cys Ile Tyr Arg Ile Leu Arg Leu His Glu Asn Ala Asp Phe Gln
            20                  25                  30

Asp Thr Thr Leu Glu Ser Gln Asp Thr Lys Leu Ile Pro Asp Ser Cys
        35                  40                  45

Arg Arg Ile Lys Gln Ala Phe Gln Gly Ala Val Gln Lys Glu Leu Gln
    50                  55                  60

His Ile Val Gly Ser Gln His Ile Arg Ala Glu Lys Ala Met Val Asp
65                  70                  75                  80

Gly Ser Trp Leu Asp Leu Ala Lys Arg Ser Lys Leu Glu Ala Gln Pro
                85                  90                  95

Phe Ala His Leu Thr Ile Asn Ala Thr Asp Ile Pro Ser Gly Ser His
            100                 105                 110

Lys Val Ser Leu Ser Ser Trp Tyr His Asp Arg Gly Trp Ala Lys Ile
        115                 120                 125

Ser Asn Met Thr Phe Ser Asn Gly Lys Leu Ile Val Asn Gln Asp Gly
    130                 135                 140

Phe Tyr Tyr Leu Tyr Ala Asn Ile Cys Phe Arg His His Glu Thr Ser
145                 150                 155                 160

Gly Asp Leu Ala Thr Glu Tyr Leu Gln Leu Met Val Tyr Val Thr Lys
                165                 170                 175

Thr Ser Ile Lys Ile Pro Ser Ser His Thr Leu Met Lys Gly Gly Ser
            180                 185                 190

Thr Lys Tyr Trp Ser Gly Asn Ser Glu Phe His Phe Tyr Ser Ile Asn
        195                 200                 205

Val Gly Gly Phe Phe Lys Leu Arg Ser Gly Glu Glu Ile Ser Ile Glu
    210                 215                 220

Val Ser Asn Pro Ser Leu Leu Asp Pro Asp Gln Asp Ala Thr Tyr Phe
225                 230                 235                 240

Gly Ala Phe Lys Val Arg Asp Ile Asp
                245

<210> SEQ ID NO 255
<211> LENGTH: 146
<212> TYPE: PRT
<213> ORGANISM: Homo sapiens

<400> SEQUENCE: 255

Ala Val Leu Thr Gln Lys Gln Lys Gln His Ser Val Leu His Leu
1               5                   10                  15

Val Pro Ile Asn Ala Thr Ser Lys Asp Asp Ser Asp Val Thr Glu Val
            20                  25                  30

Met Trp Gln Pro Ala Leu Arg Arg Gly Arg Gly Leu Gln Ala Gln Gly
        35                  40                  45

Tyr Gly Val Arg Ile Gln Asp Ala Gly Val Tyr Leu Leu Tyr Ser Gln
    50                  55                  60

Val Leu Phe Gln Asp Val Thr Phe Thr Met Gly Gln Val Val Ser Arg
65                  70                  75                  80

Glu Gly Gln Gly Arg Gln Glu Thr Leu Phe Arg Cys Ile Arg Ser Met

-continued

```
                85                  90                  95
Pro Ser His Pro Asp Arg Ala Tyr Asn Ser Cys Tyr Ser Ala Gly Val
            100                 105                 110

Phe His Leu His Gln Gly Asp Ile Leu Ser Val Ile Ile Pro Arg Ala
            115                 120                 125

Arg Ala Lys Leu Asn Leu Ser Pro His Gly Thr Phe Leu Gly Phe Val
            130                 135                 140

Lys Leu
145

<210> SEQ ID NO 256
<211> LENGTH: 207
<212> TYPE: PRT
<213> ORGANISM: Homo sapiens

<400> SEQUENCE: 256

Ser Leu Gly Ser Arg Ala Ser Leu Ser Ala Gln Glu Pro Ala Gln Glu
1               5                   10                  15

Glu Leu Val Ala Glu Glu Asp Gln Asp Pro Ser Glu Leu Asn Pro Gln
            20                  25                  30

Thr Glu Glu Ser Gln Asp Pro Ala Pro Phe Leu Asn Arg Leu Val Arg
        35                  40                  45

Pro Arg Arg Ser Ala Pro Lys Gly Arg Lys Thr Arg Ala Arg Arg Ala
    50                  55                  60

Ile Ala Ala His Tyr Glu Val His Pro Arg Pro Gly Gln Asp Gly Ala
65                  70                  75                  80

Gln Ala Gly Val Asp Gly Thr Val Ser Gly Trp Glu Glu Ala Arg Ile
                85                  90                  95

Asn Ser Ser Pro Leu Arg Tyr Asn Arg Gln Ile Gly Glu Phe Ile
            100                 105                 110

Val Thr Arg Ala Gly Leu Tyr Tyr Leu Tyr Cys Gln Val His Phe Asp
            115                 120                 125

Glu Gly Lys Ala Val Tyr Leu Lys Leu Asp Leu Leu Val Asp Gly Val
            130                 135                 140

Leu Ala Leu Arg Cys Leu Glu Glu Phe Ser Ala Thr Ala Ala Ser Ser
145                 150                 155                 160

Leu Gly Pro Gln Leu Arg Leu Cys Gln Val Ser Gly Leu Leu Ala Leu
                165                 170                 175

Arg Pro Gly Ser Ser Leu Arg Ile Arg Thr Leu Pro Trp Ala His Leu
            180                 185                 190

Lys Ala Ala Pro Phe Leu Thr Tyr Phe Gly Leu Phe Gln Val His
            195                 200                 205

<210> SEQ ID NO 257
<211> LENGTH: 156
<212> TYPE: PRT
<213> ORGANISM: Homo sapiens

<400> SEQUENCE: 257

Ser Ala Pro Lys Gly Arg Lys Thr Arg Ala Arg Ala Ile Ala Ala
1               5                   10                  15

His Tyr Glu Val His Pro Arg Pro Gly Gln Asp Gly Ala Gln Ala Gly
            20                  25                  30

Val Asp Gly Thr Val Ser Gly Trp Glu Glu Ala Arg Ile Asn Ser Ser
        35                  40                  45

Ser Pro Leu Arg Tyr Asn Arg Gln Ile Gly Glu Phe Ile Val Thr Arg
    50                  55                  60
```

```
Ala Gly Leu Tyr Tyr Leu Tyr Cys Gln Val His Phe Asp Glu Gly Lys
 65                  70                  75                  80

Ala Val Tyr Leu Lys Leu Asp Leu Leu Val Asp Gly Val Leu Ala Leu
                 85                  90                  95

Arg Cys Leu Glu Glu Phe Ser Ala Thr Ala Ala Ser Ser Leu Gly Pro
            100                 105                 110

Gln Leu Arg Leu Cys Gln Val Ser Gly Leu Leu Ala Leu Arg Pro Gly
        115                 120                 125

Ser Ser Leu Arg Ile Arg Thr Leu Pro Trp Ala His Leu Lys Ala Ala
    130                 135                 140

Pro Phe Leu Thr Tyr Phe Gly Leu Phe Gln Val His
145                 150                 155
```

<210> SEQ ID NO 258
<211> LENGTH: 243
<212> TYPE: PRT
<213> ORGANISM: Homo sapiens

<400> SEQUENCE: 258

```
Thr Asn Glu Leu Lys Gln Met Gln Asp Lys Tyr Ser Lys Ser Gly Ile
 1               5                  10                  15

Ala Cys Phe Leu Lys Glu Asp Asp Ser Tyr Trp Asp Pro Asn Asp Glu
                 20                  25                  30

Glu Ser Met Asn Ser Pro Cys Trp Gln Val Lys Trp Gln Leu Arg Gln
             35                  40                  45

Leu Val Arg Lys Met Ile Leu Arg Thr Ser Glu Thr Ile Ser Thr
 50                  55                  60

Val Gln Glu Lys Gln Gln Asn Ile Ser Pro Leu Val Arg Glu Arg Gly
 65                  70                  75                  80

Pro Gln Arg Val Ala Ala His Ile Thr Gly Thr Arg Gly Arg Ser Asn
                 85                  90                  95

Thr Leu Ser Ser Pro Asn Ser Lys Asn Glu Lys Ala Leu Gly Arg Lys
            100                 105                 110

Ile Asn Ser Trp Glu Ser Ser Arg Ser Gly His Ser Phe Leu Ser Asn
        115                 120                 125

Leu His Leu Arg Asn Gly Glu Leu Val Ile His Glu Lys Gly Phe Tyr
    130                 135                 140

Tyr Ile Tyr Ser Gln Thr Tyr Phe Arg Phe Gln Glu Glu Ile Lys Glu
145                 150                 155                 160

Asn Thr Lys Asn Asp Lys Gln Met Val Gln Tyr Ile Tyr Lys Tyr Thr
                165                 170                 175

Ser Tyr Pro Asp Pro Ile Leu Leu Met Lys Ser Ala Arg Asn Ser Cys
            180                 185                 190

Trp Ser Lys Asp Ala Glu Tyr Gly Leu Tyr Ser Ile Tyr Gln Gly Gly
        195                 200                 205

Ile Phe Glu Leu Lys Glu Asn Asp Arg Ile Phe Val Ser Val Thr Asn
    210                 215                 220

Glu His Leu Ile Asp Met Asp His Glu Ala Ser Phe Phe Gly Ala Phe
225                 230                 235                 240

Leu Val Gly
```

<210> SEQ ID NO 259
<211> LENGTH: 205
<212> TYPE: PRT
<213> ORGANISM: Homo sapiens

<400> SEQUENCE: 259

```
Ala Cys Pro Trp Ala Val Ser Gly Ala Arg Ala Ser Pro Gly Ser Ala
1               5                   10                  15

Ala Ser Pro Arg Leu Arg Glu Gly Pro Glu Leu Ser Pro Asp Asp Pro
            20                  25                  30

Ala Gly Leu Leu Asp Leu Arg Gln Gly Met Phe Ala Gln Leu Val Ala
        35                  40                  45

Gln Asn Val Leu Leu Ile Asp Gly Pro Leu Ser Trp Tyr Ser Asp Pro
50                  55                  60

Gly Leu Ala Gly Val Ser Leu Thr Gly Leu Ser Tyr Lys Glu Asp
65                  70                  75                  80

Thr Lys Glu Leu Val Val Ala Lys Ala Gly Val Tyr Tyr Val Phe Phe
                85                  90                  95

Gln Leu Glu Leu Arg Arg Val Val Ala Gly Glu Gly Ser Gly Ser Val
            100                 105                 110

Ser Leu Ala Leu His Leu Gln Pro Leu Arg Ser Ala Ala Gly Ala Ala
        115                 120                 125

Ala Leu Ala Leu Thr Val Asp Leu Pro Pro Ala Ser Ser Glu Ala Arg
130                 135                 140

Asn Ser Ala Phe Gly Phe Gln Gly Arg Leu Leu His Leu Ser Ala Gly
145                 150                 155                 160

Gln Arg Leu Gly Val His Leu His Thr Glu Ala Arg Ala Arg His Ala
                165                 170                 175

Trp Gln Leu Thr Gln Gly Ala Thr Val Leu Gly Leu Phe Arg Val Thr
            180                 185                 190

Pro Glu Ile Pro Ala Gly Leu Pro Ser Pro Arg Ser Glu
            195                 200                 205
```

<210> SEQ ID NO 260
<211> LENGTH: 194
<212> TYPE: PRT
<213> ORGANISM: Homo sapiens

<400> SEQUENCE: 260

```
Thr Gln Gly Glu Asn His Pro Ser Pro Asn Phe Asn Gln Tyr Val Arg
1               5                   10                  15

Asp Gln Gly Ala Met Thr Asp Gln Leu Ser Arg Gln Ile Arg Glu
            20                  25                  30

Tyr Gln Leu Tyr Ser Arg Thr Ser Gly Lys His Val Gln Val Thr Gly
        35                  40                  45

Arg Arg Ile Ser Ala Thr Ala Glu Asp Gly Asn Lys Phe Ala Lys Leu
50                  55                  60

Ile Val Glu Thr Asp Thr Phe Gly Ser Arg Val Arg Ile Lys Gly Ala
65                  70                  75                  80

Glu Ser Glu Lys Tyr Ile Cys Met Asn Lys Arg Gly Lys Leu Ile Gly
                85                  90                  95

Lys Pro Ser Gly Lys Ser Lys Asp Cys Val Phe Thr Glu Ile Val Leu
            100                 105                 110

Glu Asn Asn Tyr Thr Ala Phe Gln Asn Ala Arg His Glu Gly Trp Phe
        115                 120                 125

Met Ala Phe Thr Arg Gln Gly Arg Pro Arg Gln Ala Ser Arg Ser Arg
130                 135                 140

Gln Asn Gln Arg Glu Ala His Phe Ile Lys Arg Leu Tyr Gln Gly Gln
145                 150                 155                 160

Leu Pro Phe Pro Asn His Ala Glu Lys Gln Lys Gln Phe Glu Phe Val
```

165                 170                 175
Gly Ser Ala Pro Thr Arg Arg Thr Lys Arg Thr Arg Arg Pro Gln Pro
                180                 185                 190

Leu Thr

<210> SEQ ID NO 261
<211> LENGTH: 294
<212> TYPE: PRT
<213> ORGANISM: Homo sapiens

<400> SEQUENCE: 261

Cys Tyr Ser Pro Ser Leu Lys Ser Val Gln Asp Gln Ala Tyr Lys Ala
1               5                   10                  15

Pro Val Val Glu Gly Lys Val Gln Gly Leu Val Pro Ala Gly Gly
            20                  25                  30

Ser Ser Ser Asn Ser Thr Arg Glu Pro Pro Ala Ser Gly Arg Val Ala
            35                  40                  45

Leu Val Lys Val Leu Asp Lys Trp Pro Leu Arg Ser Gly Gly Leu Gln
        50                  55                  60

Arg Glu Gln Val Ile Ser Val Gly Ser Cys Val Pro Leu Glu Arg Asn
65                  70                  75                  80

Gln Arg Tyr Ile Phe Phe Leu Glu Pro Thr Glu Gln Pro Leu Val Phe
                85                  90                  95

Lys Thr Ala Phe Ala Pro Leu Asp Thr Asn Gly Lys Asn Leu Lys Lys
            100                 105                 110

Glu Val Gly Lys Ile Leu Cys Thr Asp Cys Ala Thr Arg Pro Lys Leu
        115                 120                 125

Lys Lys Met Lys Ser Gln Thr Gly Gln Val Gly Glu Lys Gln Ser Leu
130                 135                 140

Lys Cys Glu Ala Ala Ala Gly Asn Pro Gln Pro Ser Tyr Arg Trp Phe
145                 150                 155                 160

Lys Asp Gly Lys Glu Leu Asn Arg Ser Arg Asp Ile Arg Ile Lys Tyr
                165                 170                 175

Gly Asn Gly Arg Lys Asn Ser Arg Leu Gln Phe Asn Lys Val Lys Val
            180                 185                 190

Glu Asp Ala Gly Glu Tyr Val Cys Glu Ala Glu Asn Ile Leu Gly Lys
        195                 200                 205

Asp Thr Val Arg Gly Arg Leu Tyr Val Asn Ser Val Ser Thr Thr Leu
    210                 215                 220

Ser Ser Trp Ser Gly His Ala Arg Lys Cys Asn Glu Thr Ala Lys Ser
225                 230                 235                 240

Tyr Cys Val Asn Gly Gly Val Cys Tyr Tyr Ile Glu Gly Ile Asn Gln
                245                 250                 255

Leu Ser Cys Lys Cys Pro Asn Gly Phe Phe Gly Gln Arg Cys Leu Glu
            260                 265                 270

Lys Leu Pro Leu Arg Leu Tyr Met Pro Asp Pro Lys Gln Lys Ala Glu
        275                 280                 285

Glu Leu Tyr Gln Lys Arg
    290

<210> SEQ ID NO 262
<211> LENGTH: 128
<212> TYPE: PRT
<213> ORGANISM: Homo sapiens

<400> SEQUENCE: 262

```
Gln Leu Glu Thr Ala Lys Glu Pro Cys Met Ala Lys Phe Gly Pro Leu
1               5                   10                  15

Pro Ser Lys Trp Gln Met Ala Ser Ser Glu Pro Pro Cys Val Asn Lys
            20                  25                  30

Val Ser Asp Trp Lys Leu Glu Ile Leu Gln Asn Gly Leu Tyr Leu Ile
            35                  40                  45

Tyr Gly Gln Val Ala Pro Asn Ala Asn Tyr Asn Asp Val Ala Pro Phe
50                  55                  60

Glu Val Arg Leu Tyr Lys Asn Lys Asp Met Ile Gln Thr Leu Thr Asn
65                  70                  75                  80

Lys Ser Lys Ile Gln Asn Val Gly Gly Thr Tyr Glu Leu His Val Gly
                85                  90                  95

Asp Thr Ile Asp Leu Ile Phe Asn Ser Glu His Gln Val Leu Lys Asn
            100                 105                 110

Asn Thr Tyr Trp Gly Ile Ile Leu Leu Ala Asn Pro Gln Phe Ile Ser
            115                 120                 125
```

<210> SEQ ID NO 263
<211> LENGTH: 106
<212> TYPE: PRT
<213> ORGANISM: Homo sapiens

<400> SEQUENCE: 263

```
Glu Lys Pro Ser Pro Cys Gln Cys Ser Arg Leu Ser Pro His Asn Arg
1               5                   10                  15

Thr Asn Cys Gly Phe Pro Gly Ile Thr Ser Asp Gln Cys Phe Asp Asn
            20                  25                  30

Gly Cys Cys Phe Asp Ser Ser Val Thr Gly Val Pro Trp Cys Phe His
            35                  40                  45

Pro Leu Pro Lys Gln Glu Ser Asp Gln Cys Val Met Glu Val Ser Asp
50                  55                  60

Arg Arg Asn Cys Gly Tyr Pro Gly Ile Ser Pro Glu Cys Ala Ser
65                  70                  75                  80

Arg Lys Cys Cys Phe Ser Asn Phe Ile Phe Glu Val Pro Trp Cys Phe
                85                  90                  95

Phe Pro Lys Ser Val Glu Asp Cys His Tyr
            100                 105
```

<210> SEQ ID NO 264
<211> LENGTH: 116
<212> TYPE: PRT
<213> ORGANISM: Homo sapiens

<400> SEQUENCE: 264

```
Ala His Tyr Asn Thr Glu Ile Leu Lys Ser Ile Asp Asn Glu Trp Arg
1               5                   10                  15

Lys Thr Gln Cys Met Pro Arg Glu Val Cys Ile Asp Val Gly Lys Glu
            20                  25                  30

Phe Gly Val Ala Thr Asn Thr Phe Phe Lys Pro Pro Cys Val Ser Val
            35                  40                  45

Tyr Arg Cys Gly Gly Cys Cys Asn Ser Glu Gly Leu Gln Cys Met Asn
50                  55                  60

Thr Ser Thr Ser Tyr Leu Ser Lys Thr Leu Phe Glu Ile Thr Val Pro
65                  70                  75                  80

Leu Ser Gln Gly Pro Lys Pro Val Thr Ile Ser Phe Ala Asn His Thr
                85                  90                  95

Ser Cys Arg Cys Met Ser Lys Leu Asp Val Tyr Arg Gln Val His Ser
```

```
                100                 105                 110

Ile Ile Arg Arg
        115

<210> SEQ ID NO 265
<211> LENGTH: 13
<212> TYPE: PRT
<213> ORGANISM: Homo sapiens

<400> SEQUENCE: 265

Gln Leu Tyr Glu Asn Lys Pro Arg Arg Pro Tyr Ile Leu
1               5                   10

<210> SEQ ID NO 266
<211> LENGTH: 125
<212> TYPE: PRT
<213> ORGANISM: Homo sapiens

<400> SEQUENCE: 266

Ser Asp Ser Glu Glu Met Lys Ala Leu Glu Ala Asp Phe Leu Thr
1               5                   10                  15

Asn Met His Thr Ser Lys Ile Ser Lys Ala His Val Pro Ser Trp Lys
            20                  25                  30

Met Thr Leu Leu Asn Val Cys Ser Leu Val Asn Asn Leu Asn Ser Pro
        35                  40                  45

Ala Glu Glu Thr Gly Glu Val His Glu Glu Leu Val Ala Arg Arg
    50                  55                  60

Lys Leu Pro Thr Ala Leu Asp Gly Phe Ser Leu Glu Ala Met Leu Thr
65                  70                  75                  80

Ile Tyr Gln Leu His Lys Ile Cys His Ser Arg Ala Phe Gln His Trp
            85                  90                  95

Glu Leu Ile Gln Glu Asp Ile Leu Asp Thr Gly Asn Asp Lys Asn Gly
            100                 105                 110

Lys Glu Glu Val Ile Lys Arg Lys Ile Pro Tyr Ile Leu
            115                 120                 125

<210> SEQ ID NO 267
<211> LENGTH: 152
<212> TYPE: PRT
<213> ORGANISM: Homo sapiens

<400> SEQUENCE: 267

Ala Val Gln Gly Pro Glu Glu Thr Val Thr Gln Asp Cys Leu Gln Leu
1               5                   10                  15

Ile Ala Asp Ser Glu Thr Pro Thr Ile Gln Lys Gly Ser Tyr Thr Phe
            20                  25                  30

Val Pro Trp Leu Leu Ser Phe Lys Arg Gly Ser Ala Leu Glu Glu Lys
        35                  40                  45

Glu Asn Lys Ile Leu Val Lys Glu Thr Gly Tyr Phe Phe Ile Tyr Gly
            50                  55                  60

Gln Val Leu Tyr Thr Asp Lys Thr Tyr Ala Met Gly His Leu Ile Gln
65                  70                  75                  80

Arg Lys Lys Val His Val Phe Gly Asp Glu Leu Ser Leu Val Thr Leu
            85                  90                  95

Phe Arg Cys Ile Gln Asn Met Pro Glu Thr Leu Pro Asn Asn Ser Cys
            100                 105                 110

Tyr Ser Ala Gly Ile Ala Lys Leu Glu Glu Gly Asp Glu Leu Gln Leu
            115                 120                 125
```

```
Ala Ile Pro Arg Glu Asn Ala Gln Ile Ser Leu Asp Gly Asp Val Thr
            130                 135                 140

Phe Phe Gly Ala Leu Lys Leu Leu
145                 150
```

<210> SEQ ID NO 268
<211> LENGTH: 218
<212> TYPE: PRT
<213> ORGANISM: Homo sapiens

<400> SEQUENCE: 268

```
Gln Val Ala Ala Leu Gln Gly Asp Leu Ala Ser Leu Arg Ala Glu Leu
1               5                   10                  15

Gln Gly His His Ala Glu Lys Leu Pro Ala Gly Ala Gly Ala Pro Lys
                20                  25                  30

Ala Gly Leu Glu Glu Ala Pro Ala Val Thr Ala Gly Leu Lys Ile Phe
            35                  40                  45

Glu Pro Pro Ala Pro Gly Glu Gly Asn Ser Ser Gln Asn Ser Arg Asn
50                  55                  60

Lys Arg Ala Val Gln Gly Pro Glu Glu Thr Val Thr Gln Asp Cys Leu
65                  70                  75                  80

Gln Leu Ile Ala Asp Ser Glu Thr Pro Thr Ile Gln Lys Gly Ser Tyr
                85                  90                  95

Thr Phe Val Pro Trp Leu Leu Ser Phe Lys Arg Gly Ser Ala Leu Glu
            100                 105                 110

Glu Lys Glu Asn Lys Ile Leu Val Lys Glu Thr Gly Tyr Phe Phe Ile
        115                 120                 125

Tyr Gly Gln Val Leu Tyr Thr Asp Lys Thr Tyr Ala Met Gly His Leu
130                 135                 140

Ile Gln Arg Lys Lys Val His Val Phe Gly Asp Glu Leu Ser Leu Val
145                 150                 155                 160

Thr Leu Phe Arg Cys Ile Gln Asn Met Pro Glu Thr Leu Pro Asn Asn
                165                 170                 175

Ser Cys Tyr Ser Ala Gly Ile Ala Lys Leu Glu Glu Gly Asp Glu Leu
            180                 185                 190

Gln Leu Ala Ile Pro Arg Glu Asn Ala Gln Ile Ser Leu Asp Gly Asp
        195                 200                 205

Val Thr Phe Phe Gly Ala Leu Lys Leu Leu
210                 215
```

<210> SEQ ID NO 269
<211> LENGTH: 231
<212> TYPE: PRT
<213> ORGANISM: Homo sapiens

<400> SEQUENCE: 269

```
Thr Arg Ile Ile Lys Gly Phe Glu Cys Lys Pro His Ser Gln Pro Trp
1               5                   10                  15

Gln Ala Ala Leu Phe Glu Lys Thr Arg Leu Leu Cys Gly Ala Thr Leu
                20                  25                  30

Ile Ala Pro Arg Trp Leu Leu Thr Ala Ala His Cys Leu Lys Pro Arg
            35                  40                  45

Tyr Ile Val His Leu Gly Gln His Asn Leu Gln Lys Glu Glu Gly Cys
50                  55                  60

Glu Gln Thr Arg Thr Ala Thr Glu Ser Phe Pro His Pro Gly Phe Asn
65                  70                  75                  80

Asn Ser Leu Pro Asn Lys Asp His Arg Asn Asp Ile Met Leu Val Lys
```

```
            85                  90                  95
Met Ala Ser Pro Val Ser Ile Thr Trp Ala Val Arg Pro Leu Thr Leu
            100                 105                 110

Ser Ser Arg Cys Val Thr Ala Gly Thr Ser Cys Leu Ile Ser Gly Trp
            115                 120                 125

Gly Ser Thr Ser Ser Pro Gln Leu Arg Leu Pro His Thr Leu Arg Cys
            130                 135                 140

Ala Asn Ile Thr Ile Ile Glu His Gln Lys Cys Glu Asn Ala Tyr Pro
145                 150                 155                 160

Gly Asn Ile Thr Asp Thr Met Val Cys Ala Ser Val Gln Glu Gly Gly
                    165                 170                 175

Lys Asp Ser Cys Gln Gly Asp Ser Gly Gly Pro Leu Val Cys Asn Gln
            180                 185                 190

Ser Leu Gln Gly Ile Ile Ser Trp Gly Gln Asp Pro Cys Ala Ile Thr
            195                 200                 205

Arg Lys Pro Gly Val Tyr Thr Lys Val Cys Lys Tyr Val Asp Trp Ile
            210                 215                 220

Gln Glu Thr Met Lys Asn Asn
225                 230

<210> SEQ ID NO 270
<211> LENGTH: 196
<212> TYPE: PRT
<213> ORGANISM: Homo sapiens

<400> SEQUENCE: 270

Asp Lys Ile Phe Glu Tyr Asp Ser Pro Thr His Leu Asp Pro Gly Gly
1               5                   10                  15

Leu Gly Gln Asp Pro Ile Ile Ser Leu Asp Ala Thr Ala Ala Ser Ala
            20                  25                  30

Val Trp Val Ser Ser Glu Ala Tyr Thr Ser Pro Val Ser Arg Ala Gln
            35                  40                  45

Ser Glu Ser Glu Val Gln Val Thr Val Gln Gly Asp Lys Ala Val Val
            50                  55                  60

Ser Phe Glu Pro Ser Ala Ala Pro Thr Pro Lys Asn Arg Ile Phe Ala
65                  70                  75                  80

Phe Ser Phe Leu Pro Ser Thr Ala Pro Ser Phe Pro Ser Pro Thr Arg
            85                  90                  95

Asn Pro Glu Val Arg Thr Pro Lys Ser Ala Thr Gln Pro Gln Thr Thr
            100                 105                 110

Glu Thr Asn Leu Gln Thr Ala Pro Lys Leu Ser Thr Ser Thr Ser Thr
            115                 120                 125

Thr Gly Thr Ser His Leu Val Lys Cys Ala Glu Lys Glu Lys Thr Phe
            130                 135                 140

Cys Val Asn Gly Gly Glu Cys Phe Met Val Lys Asp Leu Ser Asn Pro
145                 150                 155                 160

Ser Arg Tyr Leu Cys Lys Cys Pro Asn Glu Phe Thr Gly Asp Arg Cys
            165                 170                 175

Gln Asn Tyr Val Met Ala Ser Phe Tyr Ser Thr Ser Thr Pro Phe Leu
            180                 185                 190

Ser Leu Pro Glu
            195

<210> SEQ ID NO 271
<211> LENGTH: 65
<212> TYPE: PRT
```

<213> ORGANISM: Homo sapiens

<400> SEQUENCE: 271

Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Gln Pro Gly Phe Thr Gly Ala Arg Cys Thr Glu Asn
        35                  40                  45

Val Pro Met Lys Val Gln Asn Gln Glu Lys Ala Glu Glu Leu Tyr Gln
    50                  55                  60

Lys
65

<210> SEQ ID NO 272
<211> LENGTH: 223
<212> TYPE: PRT
<213> ORGANISM: Homo sapiens

<400> SEQUENCE: 272

Gly Ser Gly Lys Lys Pro Glu Ser Ala Ala Gly Ser Gln Ser Pro Ala
1               5                   10                  15

Leu Pro Pro Arg Leu Lys Glu Met Lys Ser Gln Glu Ser Ala Ala Gly
            20                  25                  30

Ser Lys Leu Val Leu Arg Cys Glu Thr Ser Ser Glu Tyr Ser Ser Leu
        35                  40                  45

Arg Phe Lys Trp Phe Lys Asn Gly Asn Glu Leu Asn Arg Lys Asn Lys
    50                  55                  60

Pro Gln Asn Ile Lys Ile Gln Lys Lys Pro Gly Lys Ser Glu Leu Arg
65                  70                  75                  80

Ile Asn Lys Ala Ser Leu Ala Asp Ser Gly Glu Tyr Met Cys Lys Val
                85                  90                  95

Ile Ser Lys Leu Gly Asn Asp Ser Ala Ser Ala Asn Ile Thr Ile Val
            100                 105                 110

Glu Ser Asn Glu Ile Ile Thr Gly Met Pro Ala Ser Thr Glu Gly Ala
        115                 120                 125

Tyr Val Ser Ser Glu Ser Pro Ile Arg Ile Ser Val Ser Thr Glu Gly
    130                 135                 140

Ala Asn Thr Ser Ser Ser Thr Ser Thr Ser Thr Thr Gly Thr Ser His
145                 150                 155                 160

Leu Val Lys Cys Ala Glu Lys Glu Lys Thr Phe Cys Val Asn Gly Gly
                165                 170                 175

Glu Cys Phe Met Val Lys Asp Leu Ser Asn Pro Ser Arg Tyr Leu Cys
            180                 185                 190

Lys Cys Gln Pro Gly Phe Thr Gly Ala Arg Cys Thr Glu Asn Val Pro
        195                 200                 205

Met Lys Val Gln Asn Gln Glu Lys Ala Glu Glu Leu Tyr Gln Lys
    210                 215                 220

<210> SEQ ID NO 273
<211> LENGTH: 443
<212> TYPE: PRT
<213> ORGANISM: Homo sapiens

<400> SEQUENCE: 273

Pro Thr Trp Tyr Ala Gly Ser Gly Tyr Tyr Pro Asp Glu Ser Tyr Asn
1               5                   10                  15

```
Glu Val Tyr Ala Glu Val Pro Gln Ala Pro Ala Leu Asp Tyr Arg
            20              25              30

Val Pro Arg Trp Cys Tyr Thr Leu Asn Ile Gln Asp Gly Glu Ala Thr
        35              40              45

Cys Tyr Ser Pro Lys Gly Gly Asn Tyr His Ser Ser Leu Gly Thr Arg
50              55              60

Cys Glu Leu Ser Cys Asp Arg Gly Phe Arg Leu Ile Gly Arg Arg Ser
65              70              75              80

Val Gln Cys Leu Pro Ser Arg Arg Trp Ser Gly Thr Ala Tyr Cys Arg
            85              90              95

Gln Met Arg Cys His Ala Leu Pro Phe Ile Thr Ser Gly Thr Tyr Thr
            100             105             110

Cys Thr Asn Gly Val Leu Leu Asp Ser Arg Cys Asp Tyr Ser Cys Ser
            115             120             125

Ser Gly Tyr His Leu Glu Gly Asp Arg Ser Arg Ile Cys Met Glu Asp
            130             135             140

Gly Arg Trp Ser Gly Gly Glu Pro Val Cys Val Asp Ile Asp Pro Pro
145             150             155             160

Lys Ile Arg Cys Pro His Ser Arg Glu Lys Met Ala Glu Pro Glu Lys
            165             170             175

Leu Thr Ala Arg Val Tyr Trp Asp Pro Pro Leu Val Lys Asp Ser Ala
            180             185             190

Asp Gly Thr Ile Thr Arg Val Thr Leu Arg Gly Pro Glu Pro Gly Ser
            195             200             205

His Phe Pro Glu Gly Glu His Val Ile Arg Tyr Thr Ala Tyr Asp Arg
            210             215             220

Ala Tyr Asn Arg Ala Ser Cys Lys Phe Ile Val Lys Val Gln Val Arg
225             230             235             240

Arg Cys Pro Thr Leu Lys Pro Pro Gln His Gly Tyr Leu Thr Cys Thr
            245             250             255

Ser Ala Gly Asp Asn Tyr Gly Ala Thr Cys Glu Tyr His Cys Asp Gly
            260             265             270

Gly Tyr Asp Arg Gln Gly Thr Pro Ser Arg Val Cys Gln Ser Ser Arg
            275             280             285

Gln Trp Ser Gly Ser Pro Pro Ile Cys Ala Pro Met Lys Ile Asn Val
            290             295             300

Asn Val Asn Ser Ala Ala Gly Leu Leu Asp Gln Phe Tyr Glu Lys Gln
305             310             315             320

Arg Leu Leu Ile Ile Ser Ala Pro Asp Pro Ser Asn Arg Tyr Tyr Lys
            325             330             335

Met Gln Ile Ser Met Leu Gln Gln Ser Thr Cys Gly Leu Asp Leu Arg
            340             345             350

His Val Thr Ile Ile Glu Leu Val Gly Gln Pro Pro Gln Glu Val Gly
            355             360             365

Arg Ile Arg Glu Gln Gln Leu Ser Ala Asn Ile Ile Glu Glu Leu Arg
            370             375             380

Gln Phe Gln Arg Leu Thr Arg Ser Tyr Phe Asn Met Val Leu Ile Asp
385             390             395             400

Lys Gln Gly Ile Asp Arg Asp Arg Tyr Met Glu Pro Val Thr Pro Glu
            405             410             415

Glu Ile Phe Thr Phe Ile Asp Asp Tyr Leu Leu Ser Asn Gln Glu Leu
            420             425             430

Thr Gln Arg Arg Glu Gln Arg Asp Ile Cys Glu
            435             440
```

<210> SEQ ID NO 274
<211> LENGTH: 331
<212> TYPE: PRT
<213> ORGANISM: Homo sapiens

<400> SEQUENCE: 274

Gly Gln Arg Gln Gly Thr Gln Ala Glu Ser Asn Leu Ser Ser Lys Phe
1               5                   10                  15

Gln Phe Ser Ser Asn Lys Glu Gln Asn Gly Val Gln Asp Pro Gln His
            20                  25                  30

Glu Arg Ile Ile Thr Val Ser Thr Asn Gly Ser Ile His Ser Pro Arg
        35                  40                  45

Phe Pro His Thr Tyr Pro Arg Asn Thr Val Leu Val Trp Arg Leu Val
    50                  55                  60

Ala Val Glu Glu Asn Val Trp Ile Gln Leu Thr Phe Asp Glu Arg Phe
65                  70                  75                  80

Gly Leu Glu Asp Pro Glu Asp Ile Cys Lys Tyr Asp Phe Val Glu
            85                  90                  95

Val Glu Glu Pro Ser Asp Gly Thr Ile Leu Gly Arg Trp Cys Gly Ser
            100                 105                 110

Gly Thr Val Pro Gly Lys Gln Ile Ser Lys Gly Asn Gln Ile Arg Ile
            115                 120                 125

Arg Phe Val Ser Asp Glu Tyr Phe Pro Ser Glu Pro Gly Phe Cys Ile
130                 135                 140

His Tyr Asn Ile Val Met Pro Gln Phe Thr Glu Ala Val Ser Pro Ser
145                 150                 155                 160

Val Leu Pro Pro Ser Ala Leu Pro Leu Asp Leu Leu Asn Asn Ala Ile
            165                 170                 175

Thr Ala Phe Ser Thr Leu Glu Asp Leu Ile Arg Tyr Leu Glu Pro Glu
            180                 185                 190

Arg Trp Gln Leu Asp Leu Glu Asp Leu Tyr Arg Pro Thr Trp Gln Leu
            195                 200                 205

Leu Gly Lys Ala Phe Val Phe Gly Arg Lys Ser Arg Val Val Asp Leu
        210                 215                 220

Asn Leu Leu Thr Glu Glu Val Arg Leu Tyr Ser Cys Thr Pro Arg Asn
225                 230                 235                 240

Phe Ser Val Ser Ile Arg Glu Glu Leu Lys Arg Thr Asp Thr Ile Phe
                245                 250                 255

Trp Pro Gly Cys Leu Leu Val Lys Arg Cys Gly Gly Asn Cys Ala Cys
            260                 265                 270

Cys Leu His Asn Cys Asn Glu Cys Gln Cys Val Pro Ser Lys Val Thr
        275                 280                 285

Lys Lys Tyr His Glu Val Leu Gln Leu Arg Pro Lys Thr Gly Val Arg
    290                 295                 300

Gly Leu His Lys Ser Leu Thr Asp Val Ala Leu Glu His His Glu Glu
305                 310                 315                 320

Cys Asp Cys Val Cys Arg Gly Ser Thr Gly Gly
                325                 330

<210> SEQ ID NO 275
<211> LENGTH: 192
<212> TYPE: PRT
<213> ORGANISM: Homo sapiens

<400> SEQUENCE: 275

Gln Val Gly Ser His Phe Leu Leu Pro Pro Ala Gly Glu Arg Pro Pro
1               5                   10                  15

Leu Leu Gly Glu Arg Arg Ser Ala Ala Glu Arg Ser Ala Arg Gly Gly
            20                  25                  30

Pro Gly Ala Ala Gln Leu Ala His Leu His Gly Ile Leu Arg Arg Arg
            35                  40                  45

Gln Leu Tyr Cys Arg Thr Gly Phe His Leu Gln Ile Leu Pro Asp Gly
50                  55                  60

Ser Val Gln Gly Thr Arg Gln Asp His Ser Leu Phe Gly Ile Leu Glu
65                  70                  75                  80

Phe Ile Ser Val Ala Val Gly Leu Val Ser Ile Arg Gly Val Asp Ser
                85                  90                  95

Gly Leu Tyr Leu Gly Met Asn Asp Lys Gly Glu Leu Tyr Gly Ser Glu
            100                 105                 110

Lys Leu Thr Ser Glu Cys Ile Phe Arg Glu Gln Phe Glu Glu Asn Trp
            115                 120                 125

Tyr Asn Thr Tyr Ser Ser Asn Ile Tyr Lys His Gly Asp Thr Gly Arg
            130                 135                 140

Arg Tyr Phe Val Ala Leu Asn Lys Asp Gly Thr Pro Arg Asp Gly Ala
145                 150                 155                 160

Arg Ser Lys Arg His Gln Lys Phe Thr His Phe Leu Pro Arg Pro Val
                165                 170                 175

Asp Pro Glu Arg Val Pro Glu Leu Tyr Lys Asp Leu Leu Met Tyr Thr
            180                 185                 190

<210> SEQ ID NO 276
<211> LENGTH: 184
<212> TYPE: PRT
<213> ORGANISM: Homo sapiens

<400> SEQUENCE: 276

Ala Ala Ile Gly Ser Cys Ser Lys Glu Tyr Arg Val Leu Leu Gly Gln
1               5                   10                  15

Leu Gln Lys Gln Thr Asp Leu Met Gln Asp Thr Ser Arg Leu Leu Asp
            20                  25                  30

Pro Tyr Ile Arg Ile Gln Gly Leu Asp Val Pro Lys Leu Arg Glu His
            35                  40                  45

Cys Arg Glu Arg Pro Gly Ala Phe Pro Ser Glu Thr Leu Arg Gly
50                  55                  60

Leu Gly Arg Arg Gly Phe Leu Gln Thr Leu Asn Ala Thr Leu Gly Cys
65                  70                  75                  80

Val Leu His Arg Leu Ala Asp Leu Glu Gln Arg Leu Pro Lys Ala Gln
                85                  90                  95

Asp Leu Glu Arg Ser Gly Leu Asn Ile Glu Asp Leu Glu Lys Leu Gln
            100                 105                 110

Met Ala Arg Pro Asn Ile Leu Gly Leu Arg Asn Asn Ile Tyr Cys Met
            115                 120                 125

Ala Gln Leu Leu Asp Asn Ser Asp Thr Ala Glu Pro Thr Lys Ala Gly
130                 135                 140

Arg Gly Ala Ser Gln Pro Pro Thr Pro Thr Pro Ala Ser Asp Ala Phe
145                 150                 155                 160

Gln Arg Lys Leu Glu Gly Cys Arg Phe Leu His Gly Tyr His Arg Phe
                165                 170                 175

Met His Ser Val Gly Arg Val Phe
            180

<210> SEQ ID NO 277
<211> LENGTH: 209
<212> TYPE: PRT
<213> ORGANISM: Homo sapiens

<400> SEQUENCE: 277

Ala Ala Ile Gly Ser Cys Ser Lys Glu Tyr Arg Val Leu Leu Gly Gln
1               5                   10                  15

Leu Gln Lys Gln Thr Asp Leu Met Gln Asp Thr Ser Arg Leu Leu Asp
            20                  25                  30

Pro Tyr Ile Arg Ile Gln Gly Leu Asp Val Pro Lys Leu Arg Glu His
        35                  40                  45

Cys Arg Glu Arg Pro Gly Ala Phe Pro Ser Glu Glu Thr Leu Arg Gly
    50                  55                  60

Leu Gly Arg Arg Gly Phe Leu Gln Thr Leu Asn Ala Thr Leu Gly Cys
65                  70                  75                  80

Val Leu His Arg Leu Ala Asp Leu Glu Gln Arg Leu Pro Lys Ala Gln
                85                  90                  95

Asp Leu Glu Arg Ser Gly Leu Asn Ile Glu Asp Leu Glu Lys Leu Gln
            100                 105                 110

Met Ala Arg Pro Asn Ile Leu Gly Leu Arg Asn Asn Ile Tyr Cys Met
        115                 120                 125

Ala Gln Leu Leu Asp Asn Ser Asp Thr Ala Glu Pro Thr Lys Ala Gly
    130                 135                 140

Arg Gly Ala Ser Gln Pro Pro Thr Pro Thr Pro Ala Ser Asp Ala Phe
145                 150                 155                 160

Gln Arg Lys Leu Glu Gly Cys Arg Phe Leu His Gly Tyr His Arg Phe
                165                 170                 175

Met His Ser Val Gly Arg Val Phe Ser Lys Trp Gly Glu Ser Pro Asn
            180                 185                 190

Arg Ser Arg Arg His Ser Pro His Gln Ala Leu Arg Lys Gly Val Arg
        195                 200                 205

Arg

<210> SEQ ID NO 278
<211> LENGTH: 171
<212> TYPE: PRT
<213> ORGANISM: Homo sapiens

<400> SEQUENCE: 278

Ser Pro Ala Gly Thr Arg Ala Asn Asn Thr Leu Leu Asp Ser Arg Gly
1               5                   10                  15

Trp Gly Thr Leu Leu Ser Arg Ser Arg Ala Gly Leu Ala Gly Glu Ile
            20                  25                  30

Ala Gly Val Asn Trp Glu Ser Gly Tyr Leu Val Gly Ile Lys Arg Gln
        35                  40                  45

Arg Arg Leu Tyr Cys Asn Val Gly Ile Gly Phe His Leu Gln Val Leu
    50                  55                  60

Pro Asp Gly Arg Ile Ser Gly Thr His Glu Glu Asn Pro Tyr Ser Leu
65                  70                  75                  80

Leu Glu Ile Ser Thr Val Glu Arg Gly Val Val Ser Leu Phe Gly Val
                85                  90                  95

Arg Ser Ala Leu Phe Val Ala Met Asn Ser Lys Gly Arg Leu Tyr Ala
            100                 105                 110

Thr Pro Ser Phe Gln Glu Glu Cys Lys Phe Arg Glu Thr Leu Leu Pro
        115                 120                 125

```
Asn Asn Tyr Asn Ala Tyr Glu Ser Asp Leu Tyr Gln Gly Thr Tyr Ile
    130                 135                 140

Ala Leu Ser Lys Tyr Gly Arg Val Lys Arg Gly Ser Lys Val Ser Pro
145                 150                 155                 160

Ile Met Thr Val Thr His Phe Leu Pro Arg Ile
                165                 170

<210> SEQ ID NO 279
<211> LENGTH: 352
<212> TYPE: PRT
<213> ORGANISM: Homo sapiens

<400> SEQUENCE: 279

Arg Asp Thr Ser Ala Thr Pro Gln Ser Ala Ser Ile Lys Ala Leu Arg
1               5                   10                  15

Asn Ala Asn Leu Arg Arg Asp Glu Ser Asn His Leu Thr Asp Leu Tyr
                20                  25                  30

Arg Arg Asp Glu Thr Ile Gln Val Lys Gly Asn Gly Tyr Val Gln Ser
            35                  40                  45

Pro Arg Phe Pro Asn Ser Tyr Pro Arg Asn Leu Leu Leu Thr Trp Arg
50                  55                  60

Leu His Ser Gln Glu Asn Thr Arg Ile Gln Leu Val Phe Asp Asn Gln
65                  70                  75                  80

Phe Gly Leu Glu Glu Ala Glu Asn Asp Ile Cys Arg Tyr Asp Phe Val
                85                  90                  95

Glu Val Glu Asp Ile Ser Glu Thr Ser Thr Ile Ile Arg Gly Arg Trp
            100                 105                 110

Cys Gly His Lys Glu Val Pro Pro Arg Ile Lys Ser Arg Thr Asn Gln
        115                 120                 125

Ile Lys Ile Thr Phe Lys Ser Asp Asp Tyr Phe Val Ala Lys Pro Gly
130                 135                 140

Phe Lys Ile Tyr Tyr Ser Leu Leu Glu Asp Phe Gln Pro Ala Ala Ala
145                 150                 155                 160

Ser Glu Thr Asn Trp Glu Ser Val Thr Ser Ser Ile Ser Gly Val Ser
                165                 170                 175

Tyr Asn Ser Pro Ser Val Thr Asp Pro Thr Leu Ile Ala Asp Ala Leu
            180                 185                 190

Asp Lys Lys Ile Ala Glu Phe Asp Thr Val Glu Asp Leu Leu Lys Tyr
        195                 200                 205

Phe Asn Pro Glu Ser Trp Gln Glu Asp Leu Glu Asn Met Tyr Leu Asp
    210                 215                 220

Thr Pro Arg Tyr Arg Gly Arg Ser Tyr His Asp Arg Lys Ser Lys Val
225                 230                 235                 240

Asp Leu Asp Arg Leu Asn Asp Asp Ala Lys Arg Tyr Ser Cys Thr Pro
                245                 250                 255

Arg Asn Tyr Ser Val Asn Ile Arg Glu Glu Leu Lys Leu Ala Asn Val
            260                 265                 270

Val Phe Phe Pro Arg Cys Leu Leu Val Gln Arg Cys Gly Gly Asn Cys
        275                 280                 285

Gly Cys Gly Thr Val Asn Trp Arg Ser Cys Thr Cys Asn Ser Gly Lys
    290                 295                 300

Thr Val Lys Lys Tyr His Glu Val Leu Gln Phe Glu Pro Gly His Ile
305                 310                 315                 320

Lys Arg Arg Gly Arg Ala Lys Thr Met Ala Leu Val Asp Ile Gln Leu
                325                 330                 335
```

```
Asp His His Glu Arg Cys Asp Cys Ile Cys Ser Ser Arg Pro Pro Arg
            340                 345                 350

<210> SEQ ID NO 280
<211> LENGTH: 328
<212> TYPE: PRT
<213> ORGANISM: Homo sapiens

<400> SEQUENCE: 280

Ser Leu Ala Val Gly Pro Gln Tyr Ser Ser Leu Gly Ser Gln Pro Ile
1               5                   10                  15

Leu Cys Ala Ser Ile Pro Gly Leu Val Pro Lys Gln Leu Arg Phe Cys
            20                  25                  30

Arg Asn Tyr Val Glu Ile Met Pro Ser Val Ala Glu Gly Ile Lys Ile
        35                  40                  45

Gly Ile Gln Glu Cys Gln His Gln Phe Arg Gly Arg Trp Asn Cys
    50                  55                  60

Thr Thr Val His Asp Ser Leu Ala Ile Phe Gly Pro Val Leu Asp Lys
65                  70                  75                  80

Ala Thr Arg Glu Ser Ala Phe Val His Ala Ile Ala Ser Ala Gly Val
                85                  90                  95

Ala Phe Ala Val Thr Arg Ser Cys Ala Glu Gly Thr Ala Ala Ile Cys
            100                 105                 110

Gly Cys Ser Ser Arg His Gln Gly Ser Pro Gly Lys Gly Trp Lys Trp
        115                 120                 125

Gly Gly Cys Ser Glu Asp Ile Glu Phe Gly Gly Met Val Ser Arg Glu
    130                 135                 140

Phe Ala Asp Ala Arg Glu Asn Arg Pro Asp Ala Arg Ser Ala Met Asn
145                 150                 155                 160

Arg His Asn Asn Glu Ala Gly Arg Gln Ala Ile Ala Ser His Met His
                165                 170                 175

Leu Lys Cys Lys Cys His Gly Leu Ser Gly Ser Cys Glu Val Lys Thr
            180                 185                 190

Cys Trp Trp Ser Gln Pro Asp Phe Arg Ala Ile Gly Asp Phe Leu Lys
        195                 200                 205

Asp Lys Tyr Asp Ser Ala Ser Glu Met Val Val Glu Lys His Arg Glu
    210                 215                 220

Ser Arg Gly Trp Val Glu Thr Leu Arg Pro Arg Tyr Thr Tyr Phe Lys
225                 230                 235                 240

Val Pro Thr Glu Arg Asp Leu Val Tyr Tyr Glu Ala Ser Pro Asn Phe
                245                 250                 255

Cys Glu Pro Asn Pro Glu Thr Gly Ser Phe Gly Thr Arg Asp Arg Thr
            260                 265                 270

Cys Asn Val Ser Ser His Gly Ile Asp Gly Cys Asp Leu Leu Cys Cys
        275                 280                 285

Gly Arg Gly His Asn Ala Arg Ala Glu Arg Arg Arg Glu Lys Cys Arg
    290                 295                 300

Cys Val Phe His Trp Cys Cys Tyr Val Ser Cys Gln Glu Cys Thr Arg
305                 310                 315                 320

Val Tyr Asp Val His Thr Cys Lys
                325

<210> SEQ ID NO 281
<211> LENGTH: 211
<212> TYPE: PRT
<213> ORGANISM: Homo sapiens
```

<400> SEQUENCE: 281

Gln Glu Gly Pro Gly Arg Gly Pro Ala Leu Gly Arg Glu Leu Ala Ser
1               5                   10                  15

Leu Phe Arg Ala Gly Arg Glu Pro Gln Gly Val Ser Gln Gln Val Thr
                20                  25                  30

Val Gln Ser Ser Pro Asn Phe Thr Gln His Val Arg Glu Gln Ser Leu
            35                  40                  45

Val Thr Asp Gln Leu Ser Arg Arg Leu Ile Arg Thr Tyr Gln Leu Tyr
        50                  55                  60

Ser Arg Thr Ser Gly Lys His Val Gln Val Leu Ala Asn Lys Arg Ile
65                  70                  75                  80

Asn Ala Met Ala Glu Asp Gly Asp Pro Phe Ala Lys Leu Ile Val Glu
                85                  90                  95

Thr Asp Thr Phe Gly Ser Arg Val Arg Val Arg Gly Ala Glu Thr Gly
            100                 105                 110

Leu Tyr Ile Cys Met Asn Lys Lys Gly Lys Leu Ile Ala Lys Ser Asn
        115                 120                 125

Gly Lys Gly Lys Asp Cys Val Phe Thr Glu Ile Val Leu Glu Asn Asn
130                 135                 140

Tyr Thr Ala Leu Gln Asn Ala Lys Tyr Glu Gly Trp Tyr Met Ala Phe
145                 150                 155                 160

Thr Arg Lys Gly Arg Pro Arg Lys Gly Ser Lys Thr Arg Gln His Gln
                165                 170                 175

Arg Glu Val His Phe Met Lys Arg Leu Pro Arg Gly His Thr Thr
            180                 185                 190

Glu Gln Ser Leu Arg Phe Glu Phe Leu Asn Tyr Pro Pro Phe Thr Arg
        195                 200                 205

Ser Leu Arg
    210

<210> SEQ ID NO 282
<211> LENGTH: 62
<212> TYPE: PRT
<213> ORGANISM: Homo sapiens

<400> SEQUENCE: 282

Met Pro Thr Asp His Glu Glu Pro Cys Gly Pro Ser His Lys Ser Phe
1               5                   10                  15

Cys Leu Asn Gly Gly Leu Cys Tyr Val Ile Pro Thr Ile Pro Ser Pro
                20                  25                  30

Phe Cys Arg Cys Val Glu Asn Tyr Thr Gly Ala Arg Cys Glu Glu Val
            35                  40                  45

Phe Leu Pro Gly Ser Ser Ile Gln Thr Lys Ser Asn Leu Phe
        50                  55                  60

<210> SEQ ID NO 283
<211> LENGTH: 232
<212> TYPE: PRT
<213> ORGANISM: Homo sapiens

<400> SEQUENCE: 283

Glu Thr Arg Ile Ile Lys Gly Phe Glu Cys Lys Pro His Ser Gln Pro
1               5                   10                  15

Trp Gln Ala Ala Leu Phe Glu Lys Thr Arg Leu Leu Cys Gly Ala Thr
                20                  25                  30

Leu Ile Ala Pro Arg Trp Leu Leu Thr Ala Ala His Cys Leu Lys Pro

```
                35                  40                  45
Arg Tyr Ile Val His Leu Gly Gln His Asn Leu Gln Lys Glu Glu Gly
 50                  55                  60

Cys Glu Gln Thr Arg Thr Ala Thr Glu Ser Phe Pro His Pro Gly Phe
 65                  70                  75                  80

Asn Asn Ser Leu Pro Asn Lys Asp His Arg Asn Asp Ile Met Leu Val
                 85                  90                  95

Lys Met Ala Ser Pro Val Ser Ile Thr Trp Ala Val Arg Pro Leu Thr
            100                 105                 110

Leu Ser Ser Arg Cys Val Thr Ala Gly Thr Ser Cys Leu Ile Ser Gly
        115                 120                 125

Trp Gly Ser Thr Ser Ser Pro Gln Leu Arg Leu Pro His Thr Leu Arg
130                 135                 140

Cys Ala Asn Ile Thr Ile Ile Glu His Gln Lys Cys Glu Asn Ala Tyr
145                 150                 155                 160

Pro Gly Asn Ile Thr Asp Thr Met Val Cys Ala Ser Val Gln Glu Gly
                165                 170                 175

Gly Lys Asp Ser Cys Gln Gly Asp Ser Gly Gly Pro Leu Val Cys Asn
            180                 185                 190

Gln Ser Leu Gln Gly Ile Ile Ser Trp Gly Gln Asp Pro Cys Ala Ile
        195                 200                 205

Thr Arg Lys Pro Gly Val Tyr Thr Lys Val Cys Lys Tyr Val Asp Trp
210                 215                 220

Ile Gln Glu Thr Met Lys Asn Asn
225                 230

<210> SEQ ID NO 284
<211> LENGTH: 968
<212> TYPE: PRT
<213> ORGANISM: Homo sapiens

<400> SEQUENCE: 284

Arg Leu Ala Gly Gly Ser Gly Leu Pro Gly Ser Val Asp Val Asp Glu
1               5                   10                  15

Cys Ser Glu Gly Thr Asp Asp Cys His Ile Asp Ala Ile Cys Gln Asn
                20                  25                  30

Ala Pro Lys Ser Tyr Lys Cys Leu Cys Lys Pro Gly Tyr Lys Gly Glu
            35                  40                  45

Gly Lys Gln Cys Gly Asp Ile Asp Glu Cys Glu Asn Asp Tyr Tyr Asn
        50                  55                  60

Gly Gly Cys Val His Glu Cys Ile Asn Ile Pro Gly Asn Tyr Arg Cys
65                  70                  75                  80

Thr Cys Phe Asp Gly Phe Met Leu Ala His Asp Gly His Asn Cys Leu
                85                  90                  95

Asp Val Asp Glu Cys Gln Asp Asn Asn Gly Gly Cys Gln Gln Ile Cys
            100                 105                 110

Val Asn Ala Met Gly Ser Tyr Glu Cys Gln Cys His Ser Gly Phe Phe
        115                 120                 125

Leu Ser Asp Asn Gln His Thr Cys Ile His Arg Ser Asn Glu Gly Met
130                 135                 140

Asn Cys Met Asn Lys Asp His Gly Cys Ala His Ile Cys Arg Glu Thr
145                 150                 155                 160

Pro Lys Gly Gly Val Ala Cys Asp Cys Arg Pro Gly Phe Asp Leu Ala
                165                 170                 175

Gln Asn Gln Lys Asp Cys Thr Leu Thr Cys Asn Tyr Gly Asn Gly Gly
```

-continued

```
            180                 185                 190
Cys Gln His Ser Cys Glu Asp Thr Asp Thr Gly Pro Thr Cys Gly Cys
            195                 200                 205
His Gln Lys Tyr Ala Pro His Ser Asp Gly Arg Thr Cys Ile Glu Thr
            210                 215                 220
Cys Ala Val Asn Asn Gly Gly Cys Asp Arg Thr Cys Lys Asp Thr Ala
225                 230                 235                 240
Thr Gly Val Arg Cys Ser Cys Pro Val Gly Phe Thr Leu Gln Pro Asp
                245                 250                 255
Gly Lys Thr Cys Lys Asp Ile Asn Glu Cys Leu Val Asn Asn Gly Gly
                260                 265                 270
Cys Asp His Phe Cys Arg Asn Thr Val Gly Ser Phe Glu Cys Gly Cys
                275                 280                 285
Arg Lys Gly Tyr Lys Leu Leu Thr Asp Glu Arg Thr Cys Gln Asp Ile
                290                 295                 300
Asp Glu Cys Ser Phe Glu Arg Thr Cys Asp His Ile Cys Ile Asn Ser
305                 310                 315                 320
Pro Gly Ser Phe Gln Cys Leu Cys His Arg Gly Tyr Ile Leu Tyr Gly
                325                 330                 335
Thr Thr His Cys Gly Asp Val Asp Glu Cys Ser Met Ser Asn Gly Ser
                340                 345                 350
Cys Asp Gln Gly Cys Val Asn Thr Lys Gly Ser Tyr Glu Cys Val Cys
                355                 360                 365
Pro Pro Gly Arg Arg Leu His Trp Asn Arg Lys Asp Cys Val Glu Thr
                370                 375                 380
Gly Lys Cys Leu Ser Arg Ala Lys Thr Ser Pro Arg Ala Gln Leu Ser
385                 390                 395                 400
Cys Ser Lys Ala Gly Gly Val Glu Ser Cys Phe Leu Ser Cys Pro Ala
                405                 410                 415
His Thr Leu Phe Val Pro Asp Ser Glu Asn Ser Tyr Val Leu Ser Cys
                420                 425                 430
Gly Val Pro Gly Pro Gln Gly Lys Ala Leu Gln Lys Arg Asn Gly Thr
                435                 440                 445
Ser Ser Gly Leu Gly Pro Ser Cys Ser Asp Ala Pro Thr Thr Pro Ile
450                 455                 460
Lys Gln Lys Ala Arg Phe Lys Ile Arg Asp Ala Lys Cys His Leu Arg
465                 470                 475                 480
Pro His Ser Gln Ala Arg Ala Lys Glu Thr Ala Arg Gln Pro Leu Leu
                485                 490                 495
Asp His Cys His Val Thr Phe Val Thr Leu Lys Cys Asp Ser Ser Lys
                500                 505                 510
Lys Arg Arg Arg Gly Arg Lys Ser Pro Ser Lys Glu Val Ser His Ile
                515                 520                 525
Thr Ala Glu Phe Glu Ile Glu Thr Lys Met Glu Ala Ser Asp Thr
                530                 535                 540
Cys Glu Ala Asp Cys Leu Arg Lys Arg Ala Glu Gln Ser Leu Gln Ala
545                 550                 555                 560
Ala Ile Lys Thr Leu Arg Lys Ser Ile Gly Arg Gln Gln Phe Tyr Val
                565                 570                 575
Gln Val Ser Gly Thr Glu Tyr Glu Val Ala Gln Arg Pro Ala Lys Ala
                580                 585                 590
Leu Glu Gly Gln Gly Ala Cys Gly Ala Gly Gln Val Leu Gln Asp Ser
                595                 600                 605
```

Lys Cys Val Ala Cys Gly Pro Gly Thr His Phe Gly Glu Leu Gly
610             615                 620

Gln Cys Val Pro Cys Met Pro Gly Thr Tyr Gln Asp Met Glu Gly Gln
625                 630                 635                 640

Leu Ser Cys Thr Pro Cys Pro Ser Ser Asp Gly Leu Gly Leu Pro Gly
                645                 650                 655

Ala Arg Asn Val Ser Glu Cys Gly Gly Gln Cys Ser Pro Gly Phe Phe
            660                 665                 670

Ser Ala Asp Gly Phe Lys Pro Cys Gln Ala Cys Pro Val Gly Thr Tyr
        675                 680                 685

Gln Pro Glu Pro Gly Arg Thr Gly Cys Phe Pro Cys Gly Gly Gly Leu
690                 695                 700

Leu Thr Lys His Glu Gly Thr Thr Ser Phe Gln Asp Cys Glu Ala Lys
705                 710                 715                 720

Val His Cys Ser Pro Gly His His Tyr Asn Thr Thr His Arg Cys
                725                 730                 735

Ile Arg Cys Pro Val Gly Thr Tyr Gln Pro Glu Phe Gly Gln Asn His
            740                 745                 750

Cys Ile Thr Cys Pro Gly Asn Thr Ser Thr Asp Phe Asp Gly Ser Thr
        755                 760                 765

Asn Val Thr His Cys Lys Asn Gln His Cys Gly Gly Glu Leu Gly Asp
770                 775                 780

Tyr Thr Gly Tyr Ile Glu Ser Pro Asn Tyr Pro Gly Asp Tyr Pro Ala
785                 790                 795                 800

Asn Ala Glu Cys Val Trp His Ile Ala Pro Pro Lys Arg Arg Ile
                805                 810                 815

Leu Ile Val Val Pro Glu Ile Phe Leu Pro Ile Glu Asp Glu Cys Gly
            820                 825                 830

Asp Val Leu Val Met Arg Lys Ser Ala Ser Pro Thr Ser Ile Thr Thr
        835                 840                 845

Tyr Glu Thr Cys Gln Thr Tyr Glu Arg Pro Ile Ala Phe Thr Ser Arg
850                 855                 860

Ser Arg Lys Leu Trp Ile Gln Phe Lys Ser Asn Glu Gly Asn Ser Gly
865                 870                 875                 880

Lys Gly Phe Gln Val Pro Tyr Val Thr Tyr Asp Glu Asp Tyr Gln Gln
                885                 890                 895

Leu Ile Glu Asp Ile Val Arg Asp Gly Arg Leu Tyr Ala Ser Glu Asn
            900                 905                 910

His Gln Glu Ile Leu Lys Asp Lys Lys Leu Ile Lys Ala Leu Phe Asp
        915                 920                 925

Val Leu Ala His Pro Gln Asn Tyr Phe Lys Tyr Thr Ala Gln Glu Ser
930                 935                 940

Lys Glu Met Phe Pro Arg Ser Phe Ile Lys Leu Leu Arg Ser Lys Val
945                 950                 955                 960

Ser Arg Phe Leu Arg Pro Tyr Lys
                965

<210> SEQ ID NO 285
<211> LENGTH: 155
<212> TYPE: PRT
<213> ORGANISM: Homo sapiens

<400> SEQUENCE: 285

Met Ala Ala Gly Ser Ile Thr Thr Leu Pro Ala Leu Pro Glu Asp Gly
1               5                   10                  15

```
Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
 50                  55                  60

Gln Ala Glu Glu Arg Gly Val Val Ser Ile Lys Gly Val Cys Ala Asn
 65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
                100                 105                 110

Asn Thr Tyr Arg Ser Arg Lys Tyr Thr Ser Trp Tyr Val Ala Leu Lys
            115                 120                 125

Arg Thr Gly Gln Tyr Lys Leu Gly Ser Lys Thr Gly Pro Gly Gln Lys
130                 135                 140

Ala Ile Leu Phe Leu Pro Met Ser Ala Lys Ser
145                 150                 155

<210> SEQ ID NO 286
<211> LENGTH: 390
<212> TYPE: PRT
<213> ORGANISM: Homo sapiens

<400> SEQUENCE: 286

Met Pro Pro Ser Gly Leu Arg Leu Leu Leu Leu Leu Pro Leu Leu
 1               5                  10                  15

Trp Leu Leu Val Leu Thr Pro Gly Arg Pro Ala Ala Gly Leu Ser Thr
            20                  25                  30

Cys Lys Thr Ile Asp Met Glu Leu Val Lys Arg Lys Arg Ile Glu Ala
        35                  40                  45

Ile Arg Gly Gln Ile Leu Ser Lys Leu Arg Leu Ala Ser Pro Pro Ser
 50                  55                  60

Gln Gly Glu Val Pro Pro Gly Pro Leu Pro Glu Ala Val Leu Ala Leu
 65                  70                  75                  80

Tyr Asn Ser Thr Arg Asp Arg Val Ala Gly Glu Ser Ala Glu Pro Glu
                85                  90                  95

Pro Glu Pro Glu Ala Asp Tyr Tyr Ala Lys Glu Val Thr Arg Val Leu
                100                 105                 110

Met Val Glu Thr His Asn Glu Ile Tyr Asp Lys Phe Lys Gln Ser Thr
            115                 120                 125

His Ser Ile Tyr Met Phe Phe Asn Thr Ser Glu Leu Arg Glu Ala Val
130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
        195                 200                 205

Ser Arg Gly Gly Glu Ile Glu Gly Phe Arg Leu Ser Ala His Cys Ser
    210                 215                 220

Cys Asp Ser Arg Asp Asn Thr Leu Gln Val Asp Ile Asn Gly Phe Thr
225                 230                 235                 240
```

```
Thr Gly Arg Arg Gly Asp Leu Ala Thr Ile His Gly Met Asn Arg Pro
            245                 250                 255

Phe Leu Leu Leu Met Ala Thr Pro Leu Glu Arg Ala Gln His Leu Gln
        260                 265                 270

Ser Ser Arg His Arg Arg Ala Leu Asp Thr Asn Tyr Cys Phe Ser Ser
    275                 280                 285

Thr Glu Lys Asn Cys Cys Val Arg Gln Leu Tyr Ile Asp Phe Arg Lys
290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
                325                 330                 335

Ser Lys Val Leu Ala Leu Tyr Asn Gln His Asn Pro Gly Ala Ser Ala
            340                 345                 350

Ala Pro Cys Cys Val Pro Gln Ala Leu Glu Pro Leu Pro Ile Val Tyr
        355                 360                 365

Tyr Val Gly Arg Lys Pro Lys Val Glu Gln Leu Ser Asn Met Ile Val
    370                 375                 380

Arg Ser Cys Lys Cys Ser
385                 390

<210> SEQ ID NO 287
<211> LENGTH: 268
<212> TYPE: PRT
<213> ORGANISM: Homo sapiens

<400> SEQUENCE: 287

Met Ser Leu Ser Phe Leu Leu Leu Phe Phe Ser His Leu Ile Leu
1               5                   10                  15

Ser Ala Trp Ala His Gly Glu Lys Arg Leu Ala Pro Lys Gly Gln Pro
            20                  25                  30

Gly Pro Ala Ala Thr Asp Arg Asn Pro Arg Gly Ser Ser Ser Arg Gln
        35                  40                  45

Ser Ser Ser Ser Ala Met Ser Ser Ser Ala Ser Ser Ser Pro Ala
    50                  55                  60

Ala Ser Leu Gly Ser Gln Gly Ser Gly Leu Glu Gln Ser Ser Phe Gln
65                  70                  75                  80

Trp Ser Pro Ser Gly Arg Arg Thr Gly Ser Leu Tyr Cys Arg Val Gly
                85                  90                  95

Ile Gly Phe His Leu Gln Ile Tyr Pro Asp Gly Lys Val Asn Gly Ser
            100                 105                 110

His Glu Ala Asn Met Leu Ser Val Leu Glu Ile Phe Ala Val Ser Gln
        115                 120                 125

Gly Ile Val Gly Ile Arg Gly Val Phe Ser Asn Lys Phe Leu Ala Met
    130                 135                 140

Ser Lys Lys Gly Lys Leu His Ala Ser Ala Lys Phe Thr Asp Asp Cys
145                 150                 155                 160

Lys Phe Arg Glu Arg Phe Gln Glu Asn Ser Tyr Asn Thr Tyr Ala Ser
                165                 170                 175

Ala Ile His Arg Thr Glu Lys Thr Gly Arg Glu Trp Tyr Val Ala Leu
            180                 185                 190

Asn Lys Arg Gly Lys Ala Lys Arg Gly Cys Ser Pro Arg Val Lys Pro
        195                 200                 205

Gln His Ile Ser Thr His Phe Leu Pro Arg Phe Lys Gln Ser Glu Gln
    210                 215                 220
```

```
Pro Glu Leu Ser Phe Thr Val Thr Val Pro Glu Lys Asn Pro Pro
225                 230                 235                 240

Ser Pro Ile Lys Ser Lys Ile Pro Leu Ser Ala Pro Arg Lys Asn Thr
                245                 250                 255

Asn Ser Val Lys Tyr Arg Leu Lys Phe Arg Phe Gly
            260                 265
```

<210> SEQ ID NO 288
<211> LENGTH: 117
<212> TYPE: PRT
<213> ORGANISM: Homo sapiens

<400> SEQUENCE: 288

```
Met Lys Gln Ser Ser Trp Leu Met Ser Cys Val Ala Ser Pro Ser Pro
1               5                   10                  15

Ala Arg Cys Lys Leu Val Thr Ala Leu Ile Ala Pro Gln Pro Gly Thr
                20                  25                  30

Leu His Ser Gly Ser Arg Val Pro Glu Arg Val Ala Gly Val Phe Arg
            35                  40                  45

Asn Val Arg Phe Phe Ala Ser Ser Ala Trp Leu Met Ala Ala Ser Trp
50                  55                  60

Ser Phe Leu Arg Pro Ser Val Gln Leu Gln Asn Leu Pro Ala Ser Lys
65                  70                  75                  80

His Ala Arg Lys Met Thr Val Pro Ala Ser Gly Phe Ser Gln Thr Gly
                85                  90                  95

Gln Ser Val Pro Gln Ala Ala Gly Lys Ala Pro Arg Leu Glu Ala Pro
            100                 105                 110

Phe Ala Glu Arg Cys
        115
```

<210> SEQ ID NO 289
<211> LENGTH: 174
<212> TYPE: PRT
<213> ORGANISM: Homo sapiens

<400> SEQUENCE: 289

```
Met Arg Arg Phe Leu Ser Lys Val Tyr Ser Phe Pro Met Arg Lys Leu
1               5                   10                  15

Ile Leu Phe Leu Val Phe Pro Val Val Arg Gln Thr Pro Thr Gln His
                20                  25                  30

Phe Lys Asn Gln Phe Pro Ala Leu His Trp Glu His Glu Leu Gly Leu
            35                  40                  45

Ala Phe Thr Lys Asn Arg Met Asn Tyr Thr Asn Lys Phe Leu Leu Ile
50                  55                  60

Pro Glu Ser Gly Asp Tyr Phe Ile Tyr Ser Gln Val Thr Phe Arg Gly
65                  70                  75                  80

Met Thr Ser Glu Cys Ser Glu Ile Arg Gln Ala Gly Arg Pro Asn Lys
                85                  90                  95

Pro Asp Ser Ile Thr Val Val Ile Thr Lys Val Thr Asp Ser Tyr Pro
            100                 105                 110

Glu Pro Thr Gln Leu Leu Met Gly Thr Lys Ser Val Cys Glu Val Gly
        115                 120                 125

Ser Asn Trp Phe Gln Pro Ile Tyr Leu Gly Ala Met Phe Ser Leu Gln
    130                 135                 140

Glu Gly Asp Lys Leu Met Val Asn Val Ser Asp Ile Ser Leu Val Asp
145                 150                 155                 160

Tyr Thr Lys Glu Asp Lys Thr Phe Phe Gly Ala Phe Leu Leu
```

165                 170

<210> SEQ ID NO 290
<211> LENGTH: 218
<212> TYPE: PRT
<213> ORGANISM: Homo sapiens

<400> SEQUENCE: 290

Met Gly Met Trp Ser Ile Gly Ala Gly Leu Gly Ala Ala Ala Leu
1               5                   10                  15

Ala Leu Leu Leu Ala Asn Thr Asp Val Phe Leu Ser Lys Pro Gln Lys
            20                  25                  30

Ala Ala Leu Glu Tyr Leu Glu Asp Ile Asp Leu Lys Thr Leu Glu Lys
        35                  40                  45

Glu Pro Arg Thr Phe Lys Ala Lys Glu Leu Trp Glu Lys Asn Gly Ala
    50                  55                  60

Val Ile Met Ala Val Arg Arg Pro Gly Cys Phe Leu Cys Arg Glu Glu
65                  70                  75                  80

Ala Ala Asp Leu Ser Ser Leu Lys Ser Met Leu Asp Gln Leu Gly Val
                85                  90                  95

Pro Leu Tyr Ala Val Val Lys Glu His Ile Arg Thr Glu Val Lys Asp
            100                 105                 110

Phe Gln Pro Tyr Phe Lys Gly Glu Ile Phe Leu Asp Glu Lys Lys Lys
        115                 120                 125

Phe Tyr Gly Pro Gln Arg Arg Lys Met Met Phe Met Gly Phe Ile Arg
130                 135                 140

Leu Gly Val Trp Tyr Asn Phe Phe Arg Ala Trp Asn Gly Gly Phe Ser
145                 150                 155                 160

Gly Asn Leu Glu Gly Glu Gly Phe Ile Leu Gly Gly Val Phe Val Val
                165                 170                 175

Gly Ser Gly Lys Gln Gly Ile Leu Leu Glu His Arg Glu Lys Glu Phe
            180                 185                 190

Gly Asp Arg Val Asn Leu Leu Ser Val Leu Glu Ala Ala Lys Met Ile
        195                 200                 205

Lys Pro Gln Thr Leu Ala Ser Glu Lys Lys
    210                 215

<210> SEQ ID NO 291
<211> LENGTH: 212
<212> TYPE: PRT
<213> ORGANISM: Homo sapiens

<400> SEQUENCE: 291

Met Asp Tyr Leu Leu Met Ile Phe Ser Leu Leu Phe Val Ala Cys Gln
1               5                   10                  15

Gly Ala Pro Glu Thr Ala Val Leu Gly Ala Glu Leu Ser Ala Val Gly
            20                  25                  30

Glu Asn Gly Gly Glu Lys Pro Thr Pro Ser Pro Pro Trp Arg Leu Arg
        35                  40                  45

Arg Ser Lys Arg Cys Ser Cys Ser Ser Leu Met Asp Lys Glu Cys Val
    50                  55                  60

Tyr Phe Cys His Leu Asp Ile Ile Trp Val Asn Thr Pro Glu His Val
65                  70                  75                  80

Val Pro Tyr Gly Leu Gly Ser Pro Arg Ser Lys Arg Ala Leu Glu Asn
                85                  90                  95

Leu Leu Pro Thr Lys Ala Thr Asp Arg Glu Asn Arg Cys Gln Cys Ala
            100                 105                 110

```
Ser Gln Lys Asp Lys Lys Cys Trp Asn Phe Cys Gln Ala Gly Lys Glu
        115                 120                 125

Leu Arg Ala Glu Asp Ile Met Glu Lys Asp Trp Asn Asn His Lys Lys
        130                 135                 140

Gly Lys Asp Cys Ser Lys Leu Gly Lys Lys Cys Ile Tyr Gln Gln Leu
145                 150                 155                 160

Val Arg Gly Arg Lys Ile Arg Arg Ser Ser Glu Glu His Leu Arg Gln
                    165                 170                 175

Thr Arg Ser Glu Thr Met Arg Asn Ser Val Lys Ser Ser Phe His Asp
            180                 185                 190

Pro Lys Leu Lys Gly Lys Pro Ser Arg Glu Arg Tyr Val Thr His Asn
        195                 200                 205

Arg Ala His Trp
    210

<210> SEQ ID NO 292
<211> LENGTH: 154
<212> TYPE: PRT
<213> ORGANISM: Homo sapiens

<400> SEQUENCE: 292

Met Ala Leu Gly Val Pro Ile Ser Val Tyr Leu Leu Phe Asn Ala Met
1               5                   10                  15

Thr Ala Leu Thr Glu Glu Ala Ala Val Thr Val Thr Pro Pro Ile Thr
            20                  25                  30

Ala Gln Gln Gly Asn Trp Thr Val Asn Lys Thr Glu Ala Asp Asn Ile
        35                  40                  45

Glu Gly Pro Ile Ala Leu Lys Phe Ser His Leu Cys Leu Glu Asp His
    50                  55                  60

Asn Ser Tyr Cys Ile Asn Gly Ala Cys Ala Phe His His Glu Leu Glu
65                  70                  75                  80

Lys Ala Ile Cys Arg Cys Phe Thr Gly Tyr Thr Gly Glu Arg Cys Glu
                85                  90                  95

His Leu Thr Leu Thr Ser Tyr Ala Val Asp Ser Tyr Glu Lys Tyr Ile
            100                 105                 110

Ala Ile Gly Ile Gly Val Gly Leu Leu Leu Ser Gly Phe Leu Val Ile
        115                 120                 125

Phe Tyr Cys Tyr Ile Arg Lys Arg Cys Leu Lys Leu Lys Ser Pro Tyr
    130                 135                 140

Asn Val Cys Ser Gly Glu Arg Arg Pro Leu
145                 150

<210> SEQ ID NO 293
<211> LENGTH: 720
<212> TYPE: PRT
<213> ORGANISM: Homo sapiens

<400> SEQUENCE: 293

Met Ser Glu Gly Ala Ala Ala Ser Pro Gly Ala Ala Ser Ala
1               5                   10                  15

Ala Ala Ala Ser Ala Glu Glu Gly Thr Ala Ala Ala Ala Ala Ala
            20                  25                  30

Ala Ala Gly Gly Gly Pro Asp Gly Gly Glu Gly Ala Ala Glu Pro
        35                  40                  45

Pro Arg Glu Leu Arg Cys Ser Asp Cys Ile Val Trp Asn Arg Gln Gln
    50                  55                  60
```

-continued

```
Thr Trp Leu Cys Val Val Pro Leu Phe Ile Gly Phe Ile Gly Leu Gly
 65                  70                  75                  80

Leu Ser Leu Met Leu Leu Lys Trp Ile Val Val Gly Ser Val Lys Glu
                 85                  90                  95

Tyr Val Pro Thr Asp Leu Val Asp Ser Lys Gly Met Gly Gln Asp Pro
            100                 105                 110

Phe Phe Leu Ser Lys Pro Ser Ser Phe Pro Lys Ala Met Glu Thr Thr
        115                 120                 125

Thr Thr Thr Thr Ser Thr Thr Ser Pro Ala Thr Pro Ser Ala Gly Gly
130                 135                 140

Ala Ala Ser Ser Arg Thr Pro Asn Arg Ile Ser Thr Arg Leu Thr Thr
145                 150                 155                 160

Ile Thr Arg Ala Pro Thr Arg Phe Pro Gly His Arg Val Pro Ile Arg
                165                 170                 175

Ala Ser Pro Arg Ser Thr Thr Ala Arg Asn Thr Ala Ala Pro Ala Thr
            180                 185                 190

Val Pro Ser Thr Thr Ala Pro Phe Phe Ser Ser Ser Thr Leu Gly Ser
        195                 200                 205

Arg Pro Pro Val Pro Gly Thr Pro Ser Thr Gln Ala Met Pro Ser Trp
210                 215                 220

Pro Thr Ala Ala Tyr Ala Thr Ser Ser Tyr Leu His Asp Ser Thr Pro
225                 230                 235                 240

Ser Trp Thr Leu Ser Pro Phe Gln Asp Ala Ala Ser Ser Ser Ser Ser
                245                 250                 255

Ser Ser Ser Ser Ala Thr Thr Thr Thr Pro Glu Thr Ser Thr Ser Pro
            260                 265                 270

Lys Phe His Thr Thr Thr Tyr Ser Thr Glu Arg Ser Glu His Phe Lys
        275                 280                 285

Pro Cys Arg Asp Lys Asp Leu Ala Tyr Cys Leu Asn Asp Gly Glu Cys
290                 295                 300

Phe Val Ile Glu Thr Leu Thr Gly Ser His Lys His Cys Arg Cys Lys
305                 310                 315                 320

Glu Gly Tyr Gln Gly Val Arg Cys Asp Gln Phe Leu Pro Lys Thr Asp
                325                 330                 335

Ser Ile Leu Ser Asp Pro Thr Asp His Leu Gly Ile Glu Phe Met Glu
            340                 345                 350

Ser Glu Glu Val Tyr Gln Arg Gln Val Leu Ser Ile Ser Cys Ile Ile
        355                 360                 365

Phe Gly Ile Val Ile Val Gly Met Phe Cys Ala Ala Phe Tyr Phe Lys
370                 375                 380

Ser Lys Lys Gln Ala Lys Gln Ile Gln Glu Gln Leu Lys Val Pro Gln
385                 390                 395                 400

Asn Gly Lys Ser Tyr Ser Leu Lys Ala Ser Ser Thr Met Ala Lys Ser
                405                 410                 415

Glu Asn Leu Val Lys Ser His Val Gln Leu Gln Asn Tyr Ser Lys Val
            420                 425                 430

Glu Arg His Pro Val Thr Ala Leu Glu Lys Met Met Glu Ser Ser Phe
        435                 440                 445

Val Gly Pro Gln Ser Phe Pro Glu Val Pro Ser Pro Asp Arg Gly Ser
450                 455                 460

Gln Ser Val Lys His His Arg Ser Leu Ser Ser Cys Cys Ser Pro Gly
465                 470                 475                 480

Gln Arg Ser Gly Met Leu His Arg Asn Ala Phe Arg Arg Thr Pro Pro
                485                 490                 495
```

```
Ser Pro Arg Ser Arg Leu Gly Gly Ile Val Gly Pro Ala Tyr Gln Gln
            500                 505                 510

Leu Glu Glu Ser Arg Ile Pro Asp Gln Asp Thr Ile Pro Cys Gln Gly
            515                 520                 525

Ile Glu Val Arg Lys Thr Ile Ser His Leu Pro Ile Gln Leu Trp Cys
530                 535                 540

Val Glu Arg Pro Leu Asp Leu Lys Tyr Ser Ser Gly Leu Lys Thr
545                 550                 555                 560

Gln Arg Asn Thr Ser Ile Asn Met Gln Leu Pro Ser Arg Glu Thr Asn
                565                 570                 575

Pro Tyr Phe Asn Ser Leu Glu Gln Lys Asp Leu Val Gly Tyr Ser Ser
            580                 585                 590

Thr Arg Ala Ser Ser Val Pro Ile Ile Pro Ser Val Gly Leu Glu Glu
            595                 600                 605

Thr Cys Leu Gln Met Pro Gly Ile Ser Glu Val Lys Ser Ile Lys Trp
610                 615                 620

Cys Lys Asn Ser Tyr Ser Ala Asp Val Val Asn Val Ser Ile Pro Val
625                 630                 635                 640

Ser Asp Cys Leu Ile Ala Glu Gln Gln Glu Val Lys Ile Leu Leu Glu
                645                 650                 655

Thr Val Gln Glu Gln Ile Arg Ile Leu Thr Asp Ala Arg Arg Ser Glu
            660                 665                 670

Asp Tyr Glu Leu Ala Ser Val Glu Thr Glu Asp Ser Ala Ser Glu Asn
            675                 680                 685

Thr Ala Phe Leu Pro Leu Ser Pro Thr Ala Lys Ser Glu Arg Glu Ala
690                 695                 700

Gln Phe Val Leu Arg Asn Glu Ile Gln Arg Asp Ser Ala Leu Thr Lys
705                 710                 715                 720

<210> SEQ ID NO 294
<211> LENGTH: 485
<212> TYPE: PRT
<213> ORGANISM: Homo sapiens

<400> SEQUENCE: 294

Met Arg Lys Arg Ala Pro Gln Ser Glu Met Ala Pro Ala Gly Val Ser
1               5                   10                  15

Leu Arg Ala Thr Ile Leu Cys Leu Leu Ala Trp Ala Gly Leu Ala Ala
            20                  25                  30

Gly Asp Arg Val Tyr Ile His Pro Phe His Leu Val Ile His Asn Glu
        35                  40                  45

Ser Thr Cys Glu Gln Leu Ala Lys Ala Asn Ala Gly Lys Pro Lys Asp
    50                  55                  60

Pro Thr Phe Ile Pro Ala Pro Ile Gln Ala Lys Thr Ser Pro Val Asp
65                  70                  75                  80

Glu Lys Ala Leu Gln Asp Gln Leu Val Leu Val Ala Ala Lys Leu Asp
                85                  90                  95

Thr Glu Asp Lys Leu Arg Ala Ala Met Val Gly Met Leu Ala Asn Phe
            100                 105                 110

Leu Gly Phe Arg Ile Tyr Gly Met His Ser Glu Leu Trp Gly Val Val
        115                 120                 125

His Gly Ala Thr Val Leu Ser Pro Thr Ala Val Phe Gly Thr Leu Ala
    130                 135                 140

Ser Leu Tyr Leu Gly Ala Leu Asp His Thr Ala Asp Arg Leu Gln Ala
145                 150                 155                 160
```

```
Ile Leu Gly Val Pro Trp Lys Asp Lys Asn Cys Thr Ser Arg Leu Asp
                165                 170                 175

Ala His Lys Val Leu Ser Ala Leu Gln Ala Val Gln Gly Leu Leu Val
            180                 185                 190

Ala Gln Gly Arg Ala Asp Ser Gln Ala Gln Leu Leu Ser Thr Val
        195                 200                 205

Val Gly Val Phe Thr Ala Pro Gly Leu His Leu Lys Gln Pro Phe Val
    210                 215                 220

Gln Gly Leu Ala Leu Tyr Thr Pro Val Val Leu Pro Arg Ser Leu Asp
225                 230                 235                 240

Phe Thr Glu Leu Asp Val Ala Ala Glu Lys Ile Asp Arg Phe Met Gln
                245                 250                 255

Ala Val Thr Gly Trp Lys Thr Gly Cys Ser Leu Met Gly Ala Ser Val
                260                 265                 270

Asp Ser Thr Leu Ala Phe Asn Thr Tyr Val His Phe Gln Gly Lys Met
            275                 280                 285

Lys Gly Phe Ser Leu Leu Ala Glu Pro Gln Glu Phe Trp Val Asp Asn
        290                 295                 300

Ser Thr Ser Val Ser Val Pro Met Leu Ser Gly Met Gly Thr Phe Gln
305                 310                 315                 320

His Trp Ser Asp Ile Gln Asp Asn Phe Ser Val Thr Gln Val Pro Phe
                325                 330                 335

Thr Glu Ser Ala Cys Leu Leu Leu Ile Gln Pro His Tyr Ala Ser Asp
                340                 345                 350

Leu Asp Lys Val Glu Gly Leu Thr Phe Gln Gln Asn Ser Leu Asn Trp
            355                 360                 365

Met Lys Lys Leu Ser Pro Arg Thr Ile His Leu Thr Met Pro Gln Leu
        370                 375                 380

Val Leu Gln Gly Ser Tyr Asp Leu Gln Asp Leu Leu Ala Gln Ala Glu
385                 390                 395                 400

Leu Pro Ala Ile Leu His Thr Glu Leu Asn Leu Gln Lys Leu Ser Asn
                405                 410                 415

Asp Arg Ile Arg Val Gly Glu Val Leu Asn Ser Ile Phe Phe Glu Leu
                420                 425                 430

Glu Ala Asp Glu Arg Glu Pro Thr Glu Ser Thr Gln Gln Leu Asn Lys
            435                 440                 445

Pro Glu Val Leu Glu Val Thr Leu Asn Arg Pro Phe Leu Phe Ala Val
        450                 455                 460

Tyr Asp Gln Ser Ala Thr Ala Leu His Phe Leu Gly Arg Val Ala Asn
465                 470                 475                 480

Pro Leu Ser Thr Ala
            485

<210> SEQ ID NO 295
<211> LENGTH: 261
<212> TYPE: PRT
<213> ORGANISM: Homo sapiens

<400> SEQUENCE: 295

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45
```

Arg Leu Asp Lys Ile Glu Asp Glu Arg Asn Leu His Glu Asp Phe Val
                50                  55                  60

Phe Met Lys Thr Ile Gln Arg Cys Asn Thr Gly Glu Arg Ser Leu Ser
 65                  70                  75                  80

Leu Leu Asn Cys Glu Glu Ile Lys Ser Gln Phe Glu Gly Phe Val Lys
                85                  90                  95

Asp Ile Met Leu Asn Lys Glu Thr Lys Lys Glu Asn Ser Phe Glu
                100                 105                 110

Met Gln Lys Gly Asp Gln Asn Pro Gln Ile Ala Ala His Val Ile Ser
                115                 120                 125

Glu Ala Ser Ser Lys Thr Thr Ser Val Leu Gln Trp Ala Glu Lys Gly
        130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
                180                 185                 190

Leu Cys Leu Lys Ser Pro Gly Arg Phe Glu Arg Ile Leu Leu Arg Ala
                195                 200                 205

Ala Asn Thr His Ser Ser Ala Lys Pro Cys Gly Gln Gln Ser Ile His
        210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
                260

<210> SEQ ID NO 296
<211> LENGTH: 353
<212> TYPE: PRT
<213> ORGANISM: Homo sapiens

<400> SEQUENCE: 296

Met Glu Leu Thr Glu Leu Leu Leu Val Val Met Leu Leu Leu Thr Ala
 1                   5                  10                  15

Arg Leu Thr Leu Ser Ser Pro Ala Pro Pro Ala Cys Asp Leu Arg Val
                20                  25                  30

Leu Ser Lys Leu Leu Arg Asp Ser His Val Leu His Ser Arg Leu Ser
                35                  40                  45

Gln Cys Pro Glu Val His Pro Leu Pro Thr Pro Val Leu Leu Pro Ala
        50                  55                  60

Val Asp Phe Ser Leu Gly Glu Trp Lys Thr Gln Met Glu Glu Thr Lys
 65                  70                  75                  80

Ala Gln Asp Ile Leu Gly Ala Val Thr Leu Leu Leu Glu Gly Val Met
                85                  90                  95

Ala Ala Arg Gly Gln Leu Gly Pro Thr Cys Leu Ser Ser Leu Leu Gly
                100                 105                 110

Gln Leu Ser Gly Gln Val Arg Leu Leu Leu Gly Ala Leu Gln Ser Leu
                115                 120                 125

Leu Gly Thr Gln Leu Pro Pro Gln Gly Arg Thr Thr Ala His Lys Asp
        130                 135                 140

Pro Asn Ala Ile Phe Leu Ser Phe Gln His Leu Leu Arg Gly Lys Val
145                 150                 155                 160

```
Arg Phe Leu Met Leu Val Gly Gly Ser Thr Leu Cys Val Arg Arg Ala
                165                 170                 175

Pro Pro Thr Thr Ala Val Pro Ser Arg Thr Ser Leu Val Leu Thr Leu
            180                 185                 190

Asn Glu Leu Pro Asn Arg Thr Ser Gly Leu Leu Glu Thr Asn Phe Thr
        195                 200                 205

Ala Ser Ala Arg Thr Thr Gly Ser Gly Leu Leu Lys Trp Gln Gln Gly
    210                 215                 220

Phe Arg Ala Lys Ile Pro Gly Leu Leu Asn Gln Thr Ser Arg Ser Leu
225                 230                 235                 240

Asp Gln Ile Pro Gly Tyr Leu Asn Arg Ile His Glu Leu Leu Asn Gly
                245                 250                 255

Thr Arg Gly Leu Phe Pro Gly Pro Ser Arg Arg Thr Leu Gly Ala Pro
            260                 265                 270

Asp Ile Ser Ser Gly Thr Ser Asp Thr Gly Ser Leu Pro Pro Asn Leu
        275                 280                 285

Gln Pro Gly Tyr Ser Pro Ser Pro Thr His Pro Pro Thr Gly Gln Tyr
    290                 295                 300

Thr Leu Phe Pro Leu Pro Pro Thr Leu Pro Thr Pro Val Val Gln Leu
305                 310                 315                 320

His Pro Leu Leu Pro Asp Pro Ser Ala Pro Thr Pro Thr Pro Thr Ser
                325                 330                 335

Pro Leu Leu Asn Thr Ser Tyr Thr His Ser Gln Asn Leu Ser Gln Glu
            340                 345                 350

Gly

<210> SEQ ID NO 297
<211> LENGTH: 233
<212> TYPE: PRT
<213> ORGANISM: Homo sapiens

<400> SEQUENCE: 297

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
    50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175
```

```
Cys Gln Arg Glu Thr Pro Glu Gly Ala Glu Ala Lys Pro Trp Tyr Glu
                180                 185                 190

Pro Ile Tyr Leu Gly Gly Val Phe Gln Leu Glu Lys Gly Asp Arg Leu
            195                 200                 205

Ser Ala Glu Ile Asn Arg Pro Asp Tyr Leu Asp Phe Ala Glu Ser Gly
        210                 215                 220

Gln Val Tyr Phe Gly Ile Ile Ala Leu
225                 230
```

<210> SEQ ID NO 298
<211> LENGTH: 205
<212> TYPE: PRT
<213> ORGANISM: Homo sapiens

<400> SEQUENCE: 298

```
Met Thr Pro Pro Glu Arg Leu Phe Leu Pro Arg Val Cys Gly Thr Thr
1               5                   10                  15

Leu His Leu Leu Leu Leu Gly Leu Leu Val Leu Leu Pro Gly Ala
            20                  25                  30

Gln Gly Leu Pro Gly Val Gly Leu Thr Pro Ser Ala Ala Gln Thr Ala
            35                  40                  45

Arg Gln His Pro Lys Met His Leu Ala His Ser Thr Leu Lys Pro Ala
50                  55                  60

Ala His Leu Ile Gly Asp Pro Ser Lys Gln Asn Ser Leu Leu Trp Arg
65                  70                  75                  80

Ala Asn Thr Asp Arg Ala Phe Leu Gln Asp Gly Phe Ser Leu Ser Asn
                85                  90                  95

Asn Ser Leu Leu Val Pro Thr Ser Gly Ile Tyr Phe Val Tyr Ser Gln
            100                 105                 110

Val Val Phe Ser Gly Lys Ala Tyr Ser Pro Lys Ala Thr Ser Ser Pro
        115                 120                 125

Leu Tyr Leu Ala His Glu Val Gln Leu Phe Ser Ser Gln Tyr Pro Phe
    130                 135                 140

His Val Pro Leu Leu Ser Ser Gln Lys Met Val Tyr Pro Gly Leu Gln
145                 150                 155                 160

Glu Pro Trp Leu His Ser Met Tyr His Gly Ala Ala Phe Gln Leu Thr
                165                 170                 175

Gln Gly Asp Gln Leu Ser Thr His Thr Asp Gly Ile Pro His Leu Val
            180                 185                 190

Leu Ser Pro Ser Thr Val Phe Phe Gly Ala Phe Ala Leu
        195                 200                 205
```

<210> SEQ ID NO 299
<211> LENGTH: 728
<212> TYPE: PRT
<213> ORGANISM: Homo sapiens

<400> SEQUENCE: 299

```
Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
            35                  40                  45

Thr Leu Ile Lys Ile Asp Pro Ala Leu Lys Ile Lys Thr Lys Lys Val
50                  55                  60

Asn Thr Ala Asp Gln Cys Ala Asn Arg Cys Thr Arg Asn Lys Gly Leu
```

```
                65                  70                  75                  80
Pro Phe Thr Cys Lys Ala Phe Val Phe Asp Lys Ala Arg Lys Gln Cys
                    85                  90                  95
Leu Trp Phe Pro Phe Asn Ser Met Ser Ser Gly Val Lys Lys Glu Phe
                100                 105                 110
Gly His Glu Phe Asp Leu Tyr Glu Asn Lys Asp Tyr Ile Arg Asn Cys
                115                 120                 125
Ile Ile Gly Lys Gly Arg Ser Tyr Lys Gly Thr Val Ser Ile Thr Lys
            130                 135                 140
Ser Gly Ile Lys Cys Gln Pro Trp Ser Ser Met Ile Pro His Glu His
145                 150                 155                 160
Ser Phe Leu Pro Ser Ser Tyr Arg Gly Lys Asp Leu Gln Glu Asn Tyr
                165                 170                 175
Cys Arg Asn Pro Arg Gly Glu Glu Gly Gly Pro Trp Cys Phe Thr Ser
                180                 185                 190
Asn Pro Glu Val Arg Tyr Glu Val Cys Asp Ile Pro Gln Cys Ser Glu
                195                 200                 205
Val Glu Cys Met Thr Cys Asn Gly Glu Ser Tyr Arg Gly Leu Met Asp
            210                 215                 220
His Thr Glu Ser Gly Lys Ile Cys Gln Arg Trp Asp His Gln Thr Pro
225                 230                 235                 240
His Arg His Lys Phe Leu Pro Glu Arg Tyr Pro Asp Lys Gly Phe Asp
                245                 250                 255
Asp Asn Tyr Cys Arg Asn Pro Asp Gly Gln Pro Arg Pro Trp Cys Tyr
                260                 265                 270
Thr Leu Asp Pro His Thr Arg Trp Glu Tyr Cys Ala Ile Lys Thr Cys
            275                 280                 285
Ala Asp Asn Thr Met Asn Asp Thr Asp Val Pro Leu Glu Thr Thr Glu
        290                 295                 300
Cys Ile Gln Gly Gln Gly Glu Gly Tyr Arg Gly Thr Val Asn Thr Ile
305                 310                 315                 320
Trp Asn Gly Ile Pro Cys Gln Arg Trp Asp Ser Gln Tyr Pro His Glu
                325                 330                 335
His Asp Met Thr Pro Glu Asn Phe Lys Cys Lys Asp Leu Arg Glu Asn
                340                 345                 350
Tyr Cys Arg Asn Pro Asp Gly Ser Glu Ser Pro Trp Cys Phe Thr Thr
            355                 360                 365
Asp Pro Asn Ile Arg Val Gly Tyr Cys Ser Gln Ile Pro Asn Cys Asp
        370                 375                 380
Met Ser His Gly Gln Asp Cys Tyr Arg Gly Asn Gly Lys Asn Tyr Met
385                 390                 395                 400
Gly Asn Leu Ser Gln Thr Arg Ser Gly Leu Thr Cys Ser Met Trp Asp
                405                 410                 415
Lys Asn Met Glu Asp Leu His Arg His Ile Phe Trp Glu Pro Asp Ala
                420                 425                 430
Ser Lys Leu Asn Glu Asn Tyr Cys Arg Asn Pro Asp Asp Asp Ala His
            435                 440                 445
Gly Pro Trp Cys Tyr Thr Gly Asn Pro Leu Ile Pro Trp Asp Tyr Cys
        450                 455                 460
Pro Ile Ser Arg Cys Glu Gly Asp Thr Thr Pro Thr Ile Val Asn Leu
465                 470                 475                 480
Asp His Pro Val Ile Ser Cys Ala Lys Thr Lys Gln Leu Arg Val Val
                485                 490                 495
```

```
Asn Gly Ile Pro Thr Arg Thr Asn Ile Gly Trp Met Val Ser Leu Arg
            500                 505                 510

Tyr Arg Asn Lys His Ile Cys Gly Ser Leu Ile Lys Glu Ser Trp
            515                 520                 525

Val Leu Thr Ala Arg Gln Cys Phe Pro Ser Arg Asp Leu Lys Asp Tyr
530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
                580                 585                 590

Phe Val Ser Thr Ile Asp Leu Pro Asn Tyr Gly Cys Thr Ile Pro Glu
                595                 600                 605

Lys Thr Ser Cys Ser Val Tyr Gly Trp Gly Tyr Thr Gly Leu Ile Asn
            610                 615                 620

Tyr Asp Gly Leu Leu Arg Val Ala His Leu Tyr Ile Met Gly Asn Glu
625                 630                 635                 640

Lys Cys Ser Gln His Arg Gly Lys Val Thr Leu Asn Glu Ser Glu
                645                 650                 655

Ile Cys Ala Gly Ala Glu Lys Ile Gly Ser Gly Pro Cys Glu Gly Asp
                660                 665                 670

Tyr Gly Gly Pro Leu Val Cys Glu Gln His Lys Met Arg Met Val Leu
            675                 680                 685

Gly Val Ile Val Pro Gly Arg Gly Cys Ala Ile Pro Asn Arg Pro Gly
            690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725

<210> SEQ ID NO 300
<211> LENGTH: 180
<212> TYPE: PRT
<213> ORGANISM: Homo sapiens

<400> SEQUENCE: 300

Met Gly Ile Pro Met Gly Lys Ser Met Leu Val Leu Leu Thr Phe Leu
1               5                   10                  15

Ala Phe Ala Ser Cys Cys Ile Ala Ala Tyr Arg Pro Ser Glu Thr Leu
            20                  25                  30

Cys Gly Gly Glu Leu Val Asp Thr Leu Gln Phe Val Cys Gly Asp Arg
        35                  40                  45

Gly Phe Tyr Phe Ser Arg Pro Ala Ser Arg Val Ser Arg Arg Ser Arg
    50                  55                  60

Gly Ile Val Glu Glu Cys Cys Phe Arg Ser Cys Asp Leu Ala Leu Leu
65                  70                  75                  80

Glu Thr Tyr Cys Ala Thr Pro Ala Lys Ser Glu Arg Asp Val Ser Thr
                85                  90                  95

Pro Pro Thr Val Leu Pro Asp Asn Phe Pro Arg Tyr Pro Val Gly Lys
            100                 105                 110

Phe Phe Gln Tyr Asp Thr Trp Lys Gln Ser Thr Gln Arg Leu Arg Arg
        115                 120                 125

Gly Leu Pro Ala Leu Leu Arg Ala Arg Arg Gly His Val Leu Ala Lys
    130                 135                 140
```

Glu Leu Glu Ala Phe Arg Glu Ala Lys Arg His Arg Pro Leu Ile Ala
145                 150                 155                 160

Leu Pro Thr Gln Asp Pro Ala His Gly Gly Ala Pro Pro Glu Met Ala
            165                 170                 175

Ser Asn Arg Lys
            180

<210> SEQ ID NO 301
<211> LENGTH: 153
<212> TYPE: PRT
<213> ORGANISM: Homo sapiens

<400> SEQUENCE: 301

Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser His Leu
                20                  25                  30

Phe Tyr Leu Ala Leu Cys Leu Leu Thr Phe Thr Ser Ser Ala Thr Ala
                35                  40                  45

Gly Pro Glu Thr Leu Cys Gly Ala Glu Leu Val Asp Ala Leu Gln Phe
50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
                100                 105                 110

Lys Pro Ala Lys Ser Ala Arg Ser Val Arg Ala Gln Arg His Thr Asp
                115                 120                 125

Met Pro Lys Thr Gln Lys Glu Val His Leu Lys Asn Ala Ser Arg Gly
130                 135                 140

Ser Ala Gly Asn Lys Asn Tyr Arg Met
145                 150

<210> SEQ ID NO 302
<211> LENGTH: 281
<212> TYPE: PRT
<213> ORGANISM: Homo sapiens

<400> SEQUENCE: 302

Met Gln Gln Pro Phe Asn Tyr Pro Tyr Pro Gln Ile Tyr Trp Val Asp
1               5                   10                  15

Ser Ser Ala Ser Ser Pro Trp Ala Pro Pro Gly Thr Val Leu Pro Cys
                20                  25                  30

Pro Thr Ser Val Pro Arg Arg Pro Gly Gln Arg Pro Pro Pro Pro Pro
                35                  40                  45

Pro Pro Pro Pro Pro Leu Pro Pro Pro Pro Pro Pro Leu Pro
50                  55                  60

Pro Leu Pro Leu Pro Pro Leu Lys Lys Arg Gly Asn His Ser Thr Gly
65                  70                  75                  80

Leu Cys Leu Leu Val Met Phe Phe Met Val Leu Val Ala Leu Val Gly
                85                  90                  95

Leu Gly Leu Gly Met Phe Gln Leu Phe His Leu Gln Lys Glu Leu Ala
                100                 105                 110

Glu Leu Arg Glu Ser Thr Ser Gln Met His Thr Ala Ser Ser Leu Glu
                115                 120                 125

Lys Gln Ile Gly His Pro Ser Pro Pro Pro Glu Lys Lys Glu Leu Arg

```
                130                 135                 140
Lys Val Ala His Leu Thr Gly Lys Ser Asn Ser Arg Ser Met Pro Leu
145                 150                 155                 160

Glu Trp Glu Asp Thr Tyr Gly Ile Val Leu Leu Ser Gly Val Lys Tyr
                165                 170                 175

Lys Lys Gly Gly Leu Val Ile Asn Glu Thr Gly Leu Tyr Phe Val Tyr
                180                 185                 190

Ser Lys Val Tyr Phe Arg Gly Gln Ser Cys Asn Asn Leu Pro Leu Ser
                195                 200                 205

His Lys Val Tyr Met Arg Asn Ser Lys Tyr Pro Gln Asp Leu Val Met
        210                 215                 220

Met Glu Gly Lys Met Met Ser Tyr Cys Thr Thr Gly Gln Met Trp Ala
225                 230                 235                 240

Arg Ser Ser Tyr Leu Gly Ala Val Phe Asn Leu Thr Ser Ala Asp His
                245                 250                 255

Leu Tyr Val Asn Val Ser Glu Leu Ser Leu Val Asn Phe Glu Glu Ser
                260                 265                 270

Gln Thr Phe Phe Gly Leu Tyr Lys Leu
                275                 280

<210> SEQ ID NO 303
<211> LENGTH: 155
<212> TYPE: PRT
<213> ORGANISM: Homo sapiens

<400> SEQUENCE: 303

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
                20                  25                  30

Asn Gly Gly His Phe Leu Arg Ile Leu Pro Asp Gly Thr Val Asp Gly
            35                  40                  45

Thr Arg Asp Arg Ser Asp Gln His Ile Gln Leu Gln Leu Ser Ala Glu
        50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
                100                 105                 110

Ile Ser Lys Lys His Ala Glu Lys Asn Trp Phe Val Gly Leu Lys Lys
            115                 120                 125

Asn Gly Ser Cys Lys Arg Gly Pro Arg Thr His Tyr Gly Gln Lys Ala
        130                 135                 140

Ile Leu Phe Leu Pro Leu Pro Val Ser Ser Asp
145                 150                 155

<210> SEQ ID NO 304
<211> LENGTH: 97
<212> TYPE: PRT
<213> ORGANISM: Homo sapiens

<400> SEQUENCE: 304

Met Leu Gly Asn Lys Arg Leu Gly Leu Ser Gly Leu Thr Leu Ala Leu
1               5                   10                  15

Ser Leu Leu Val Cys Leu Gly Ala Leu Ala Glu Ala Tyr Pro Ser Lys
                20                  25                  30
```

```
Pro Asp Asn Pro Gly Glu Asp Ala Pro Ala Glu Asp Met Ala Arg Tyr
        35                  40                  45

Tyr Ser Ala Leu Arg His Tyr Ile Asn Leu Ile Thr Arg Gln Arg Tyr
 50                  55                  60

Gly Lys Arg Ser Ser Pro Glu Thr Leu Ile Ser Asp Leu Leu Met Arg
 65                  70                  75                  80

Glu Ser Thr Glu Asn Val Pro Arg Thr Arg Leu Glu Asp Pro Ala Met
                 85                  90                  95

Trp

<210> SEQ ID NO 305
<211> LENGTH: 193
<212> TYPE: PRT
<213> ORGANISM: Homo sapiens

<400> SEQUENCE: 305

Met Pro Glu Glu Gly Ser Gly Cys Ser Val Arg Arg Arg Pro Tyr Gly
 1               5                  10                  15

Cys Val Leu Arg Ala Ala Leu Val Pro Leu Val Ala Gly Leu Val Ile
                20                  25                  30

Cys Leu Val Val Cys Ile Gln Arg Phe Ala Gln Ala Gln Gln Gln Leu
            35                  40                  45

Pro Leu Glu Ser Leu Gly Trp Asp Val Ala Glu Gln Leu Asn His
 50                  55                  60

Thr Gly Pro Gln Gln Asp Pro Arg Leu Tyr Trp Gln Gly Gly Pro Ala
 65                  70                  75                  80

Leu Gly Arg Ser Phe Leu His Gly Pro Glu Leu Asp Lys Gly Gln Leu
                85                  90                  95

Arg Ile His Arg Asp Gly Ile Tyr Met Val His Ile Gln Val Thr Leu
            100                 105                 110

Ala Ile Cys Ser Ser Thr Thr Ala Ser Arg His His Pro Thr Thr Leu
        115                 120                 125

Ala Val Gly Ile Cys Ser Pro Ala Ser Arg Ser Ile Ser Leu Leu Arg
    130                 135                 140

Leu Ser Phe His Gln Gly Cys Thr Ile Ala Ser Gln Arg Leu Thr Pro
145                 150                 155                 160

Leu Ala Arg Gly Asp Thr Leu Cys Thr Asn Leu Thr Gly Thr Leu Leu
                165                 170                 175

Pro Ser Arg Asn Thr Asp Glu Thr Phe Phe Gly Val Gln Trp Val Arg
            180                 185                 190

Pro

<210> SEQ ID NO 306
<211> LENGTH: 391
<212> TYPE: PRT
<213> ORGANISM: Homo sapiens

<400> SEQUENCE: 306

Met Gly Tyr Pro Glu Val Glu Arg Glu Leu Leu Pro Ala Ala Ala
 1               5                  10                  15

Pro Arg Glu Arg Gly Ser Gln Gly Cys Gly Cys Gly Gly Ala Pro Ala
                20                  25                  30

Arg Ala Gly Glu Gly Asn Ser Cys Leu Leu Phe Leu Gly Phe Phe Gly
            35                  40                  45

Leu Ser Leu Ala Leu His Leu Leu Thr Leu Cys Cys Tyr Leu Glu Leu
 50                  55                  60
```

```
Arg Ser Glu Leu Arg Arg Glu Arg Gly Ala Glu Ser Arg Leu Gly Gly
 65                  70                  75                  80

Ser Gly Thr Pro Gly Thr Ser Gly Thr Leu Ser Ser Leu Gly Gly Leu
                 85                  90                  95

Asp Pro Asp Ser Pro Ile Thr Ser His Leu Gly Gln Pro Ser Pro Lys
            100                 105                 110

Gln Gln Pro Leu Glu Pro Gly Glu Ala Ala Leu His Ser Asp Ser Gln
        115                 120                 125

Asp Gly His Gln Met Ala Leu Leu Asn Phe Phe Pro Asp Glu Lys
    130                 135                 140

Pro Tyr Ser Glu Glu Glu Ser Arg Arg Val Arg Arg Asn Lys Arg Ser
145                 150                 155                 160

Lys Ser Asn Glu Gly Ala Asp Gly Pro Val Lys Asn Lys Lys Gly
                165                 170                 175

Lys Lys Ala Gly Pro Pro Gly Pro Asn Gly Pro Pro Gly Pro Pro Gly
                180                 185                 190

Pro Pro Gly Pro Gln Gly Pro Pro Gly Ile Pro Gly Ile Pro Gly Ile
                195                 200                 205

Pro Gly Thr Thr Val Met Gly Pro Pro Gly Pro Pro Gly Pro Pro Gly
                210                 215                 220

Pro Gln Gly Pro Pro Gly Leu Gln Gly Pro Ser Gly Ala Ala Asp Lys
225                 230                 235                 240

Ala Gly Thr Arg Glu Asn Gln Pro Ala Val Val His Leu Gln Gly Gln
                245                 250                 255

Gly Ser Ala Ile Gln Val Lys Asn Asp Leu Ser Gly Gly Val Leu Asn
                260                 265                 270

Asp Trp Ser Arg Ile Thr Met Asn Pro Lys Val Phe Lys Leu His Pro
                275                 280                 285

Arg Ser Gly Glu Leu Glu Val Leu Val Asp Gly Thr Tyr Phe Ile Tyr
                290                 295                 300

Ser Gln Val Glu Val Tyr Tyr Ile Asn Phe Thr Asp Phe Ala Ser Tyr
305                 310                 315                 320

Glu Val Val Val Asp Glu Lys Pro Phe Leu Gln Cys Thr Arg Ser Ile
                325                 330                 335

Glu Thr Gly Lys Thr Asn Tyr Asn Thr Cys Tyr Thr Ala Gly Val Cys
                340                 345                 350

Leu Leu Lys Ala Arg Gln Lys Ile Ala Val Lys Met Val His Ala Asp
                355                 360                 365

Ile Ser Ile Asn Met Ser Lys His Thr Thr Phe Phe Gly Ala Ile Arg
                370                 375                 380

Leu Gly Glu Ala Pro Ala Ser
385                 390

<210> SEQ ID NO 307
<211> LENGTH: 169
<212> TYPE: PRT
<213> ORGANISM: Homo sapiens

<400> SEQUENCE: 307

Met Thr Ala Gly Arg Arg Met Glu Met Leu Cys Ala Gly Arg Val Pro
  1               5                  10                  15

Ala Leu Leu Leu Cys Leu Gly Phe His Leu Leu Gln Ala Val Leu Ser
                 20                  25                  30

Thr Thr Val Ile Pro Ser Cys Ile Pro Gly Glu Ser Ser Asp Asn Cys
                 35                  40                  45
```

Thr Ala Leu Val Gln Thr Glu Asp Asn Pro Arg Val Ala Gln Val Ser
            50                  55                  60

Ile Thr Lys Cys Ser Ser Asp Met Asn Gly Tyr Cys Leu His Gly Gln
 65                  70                  75                  80

Cys Ile Tyr Leu Val Asp Met Ser Gln Asn Tyr Cys Arg Cys Glu Val
                 85                  90                  95

Gly Tyr Thr Gly Val Arg Cys Glu His Phe Phe Leu Thr Val His Gln
               100                 105                 110

Pro Leu Ser Lys Glu Tyr Val Ala Leu Thr Val Ile Leu Ile Ile Leu
           115                 120                 125

Phe Leu Ile Thr Val Val Gly Ser Thr Tyr Tyr Phe Cys Arg Trp Tyr
130                 135                 140

Arg Asn Arg Lys Ser Lys Glu Pro Lys Lys Glu Tyr Glu Arg Val Thr
145                 150                 155                 160

Ser Gly Asp Pro Glu Leu Pro Gln Val
                165

<210> SEQ ID NO 308
<211> LENGTH: 252
<212> TYPE: PRT
<213> ORGANISM: Homo sapiens

<400> SEQUENCE: 308

Met Arg Ala Pro Leu Leu Pro Pro Ala Pro Val Val Leu Ser Leu Leu
 1               5                  10                  15

Ile Leu Gly Ser Gly His Tyr Ala Ala Gly Leu Asp Leu Asn Asp Thr
                20                  25                  30

Tyr Ser Gly Lys Arg Glu Pro Phe Ser Gly Asp His Ser Ala Asp Gly
             35                  40                  45

Phe Glu Val Thr Ser Arg Ser Glu Met Ser Gly Ser Glu Ile Ser
         50                  55                  60

Pro Val Ser Glu Met Pro Ser Ser Glu Pro Ser Ser Gly Ala Asp
 65                  70                  75                  80

Tyr Asp Tyr Ser Glu Glu Tyr Asp Asn Glu Pro Gln Ile Pro Gly Tyr
                 85                  90                  95

Ile Val Asp Asp Ser Val Arg Val Glu Gln Val Val Lys Pro Pro Gln
               100                 105                 110

Asn Lys Thr Glu Ser Glu Asn Thr Ser Asp Lys Pro Lys Arg Lys Lys
           115                 120                 125

Lys Gly Gly Lys Asn Gly Lys Asn Arg Arg Asn Arg Lys Lys Lys Asn
       130                 135                 140

Pro Cys Asn Ala Glu Phe Gln Asn Phe Cys Ile His Gly Glu Cys Lys
145                 150                 155                 160

Tyr Ile Glu His Leu Glu Ala Val Thr Cys Lys Cys Gln Gln Glu Tyr
                165                 170                 175

Phe Gly Glu Arg Cys Gly Glu Lys Ser Met Lys Thr His Ser Met Ile
            180                 185                 190

Asp Ser Ser Leu Ser Lys Ile Ala Leu Ala Ala Ile Ala Ala Phe Met
        195                 200                 205

Ser Ala Val Ile Leu Thr Ala Val Ala Val Ile Thr Val Gln Leu Arg
210                 215                 220

Arg Gln Tyr Val Arg Lys Tyr Glu Gly Glu Ala Glu Glu Arg Lys Lys
225                 230                 235                 240

Leu Arg Gln Glu Asn Gly Asn Val His Ala Ile Ala
                245                 250

<210> SEQ ID NO 309
<211> LENGTH: 208
<212> TYPE: PRT
<213> ORGANISM: Homo sapiens

<400> SEQUENCE: 309

Met Lys Leu Leu Pro Ser Val Val Leu Lys Leu Phe Leu Ala Ala Val
1               5                   10                  15

Leu Ser Ala Leu Val Thr Gly Glu Ser Leu Glu Arg Leu Arg Arg Gly
            20                  25                  30

Leu Ala Ala Gly Thr Ser Asn Pro Asp Pro Thr Val Ser Thr Asp
        35                  40                  45

Gln Leu Leu Pro Leu Gly Gly Arg Asp Arg Lys Val Arg Asp Leu
50                  55                  60

Gln Glu Ala Asp Leu Asp Leu Arg Val Thr Leu Ser Ser Lys Pro
65                  70                  75                  80

Gln Ala Leu Ala Thr Pro Asn Lys Glu Glu His Gly Lys Arg Lys Lys
                85                  90                  95

Lys Gly Lys Gly Leu Gly Lys Lys Arg Asp Pro Cys Leu Arg Lys Tyr
            100                 105                 110

Lys Asp Phe Cys Ile His Gly Glu Cys Lys Tyr Val Lys Glu Leu Arg
        115                 120                 125

Ala Pro Ser Cys Ile Cys His Pro Gly Tyr His Gly Glu Arg Cys His
    130                 135                 140

Gly Leu Ser Leu Pro Val Glu Asn Arg Leu Tyr Thr Tyr Asp His Thr
145                 150                 155                 160

Thr Ile Leu Ala Val Val Ala Val Val Leu Ser Ser Val Cys Leu Leu
                165                 170                 175

Val Ile Val Gly Leu Leu Met Phe Arg Tyr His Arg Arg Gly Gly Tyr
            180                 185                 190

Asp Val Glu Asn Glu Glu Lys Val Lys Leu Gly Met Thr Asn Ser His
        195                 200                 205

<210> SEQ ID NO 310
<211> LENGTH: 178
<212> TYPE: PRT
<213> ORGANISM: Homo sapiens

<400> SEQUENCE: 310

Met Val Ser Val Pro Thr Thr Trp Cys Ser Val Ala Leu Ala Leu Leu
1               5                   10                  15

Val Ala Leu His Glu Gly Lys Gly Gln Ala Ala Ala Thr Leu Glu Gln
            20                  25                  30

Pro Ala Ser Ser Ser His Ala Gln Gly Thr His Leu Arg Leu Arg Arg
        35                  40                  45

Cys Ser Cys Ser Ser Trp Leu Asp Lys Glu Cys Val Tyr Phe Cys His
    50                  55                  60

Leu Asp Ile Ile Trp Val Asn Thr Pro Glu Gln Thr Ala Pro Tyr Gly
65                  70                  75                  80

Leu Gly Asn Pro Pro Arg Arg Arg Arg Ser Leu Pro Arg Cys
                85                  90                  95

Gln Cys Ser Ser Ala Arg Asp Pro Ala Cys Ala Thr Phe Cys Leu Arg
            100                 105                 110

Arg Pro Trp Thr Glu Ala Gly Ala Val Pro Ser Arg Lys Ser Pro Ala
        115                 120                 125

-continued

Asp Val Phe Gln Thr Gly Lys Thr Gly Ala Thr Thr Gly Glu Leu Leu
         130                 135                 140

Gln Arg Leu Arg Asp Ile Ser Thr Val Lys Ser Leu Phe Ala Lys Arg
145                 150                 155                 160

Gln Gln Glu Ala Met Arg Glu Pro Arg Ser Thr His Ser Arg Trp Arg
                165                 170                 175

Lys Arg

<210> SEQ ID NO 311
<211> LENGTH: 1207
<212> TYPE: PRT
<213> ORGANISM: Homo sapiens

<400> SEQUENCE: 311

Met Leu Leu Thr Leu Ile Ile Leu Leu Pro Val Val Ser Lys Phe Ser
1               5                   10                  15

Phe Val Ser Leu Ser Ala Pro Gln His Trp Ser Cys Pro Glu Gly Thr
                20                  25                  30

Leu Ala Gly Asn Gly Asn Ser Thr Cys Val Gly Pro Ala Pro Phe Leu
            35                  40                  45

Ile Phe Ser His Gly Asn Ser Ile Phe Arg Ile Asp Thr Glu Gly Thr
    50                  55                  60

Asn Tyr Glu Gln Leu Val Val Asp Ala Gly Val Ser Val Ile Met Asp
65                  70                  75                  80

Phe His Tyr Asn Glu Lys Arg Ile Tyr Trp Val Asp Leu Glu Arg Gln
                85                  90                  95

Leu Leu Gln Arg Val Phe Leu Asn Gly Ser Arg Gln Glu Arg Val Cys
            100                 105                 110

Asn Ile Glu Lys Asn Val Ser Gly Met Ala Ile Asn Trp Ile Asn Glu
        115                 120                 125

Glu Val Ile Trp Ser Asn Gln Gln Gly Ile Ile Thr Val Thr Asp
    130                 135                 140

Met Lys Gly Asn Asn Ser His Ile Leu Leu Ser Ala Leu Lys Tyr Pro
145                 150                 155                 160

Ala Asn Val Ala Val Asp Pro Val Glu Arg Phe Ile Phe Trp Ser Ser
                165                 170                 175

Glu Val Ala Gly Ser Leu Tyr Arg Ala Asp Leu Asp Gly Val Gly Val
            180                 185                 190

Lys Ala Leu Leu Glu Thr Ser Glu Lys Ile Thr Ala Val Ser Leu Asp
        195                 200                 205

Val Leu Asp Lys Arg Leu Phe Trp Ile Gln Tyr Asn Arg Glu Gly Ser
    210                 215                 220

Asn Ser Leu Ile Cys Ser Cys Asp Tyr Asp Gly Gly Ser Val His Ile
225                 230                 235                 240

Ser Lys His Pro Thr Gln His Asn Leu Phe Ala Met Ser Leu Phe Gly
                245                 250                 255

Asp Arg Ile Phe Tyr Ser Thr Trp Lys Met Lys Thr Ile Trp Ile Ala
            260                 265                 270

Asn Lys His Thr Gly Lys Asp Met Val Arg Ile Asn Leu His Ser Ser
        275                 280                 285

Phe Val Pro Leu Gly Glu Leu Lys Val Val His Pro Leu Ala Gln Pro
    290                 295                 300

Lys Ala Glu Asp Asp Thr Trp Glu Pro Glu Gln Lys Leu Cys Lys Leu
305                 310                 315                 320

Arg Lys Gly Asn Cys Ser Ser Thr Val Cys Gly Gln Asp Leu Gln Ser

```
                       325                 330                 335
His Leu Cys Met Cys Ala Glu Gly Tyr Ala Leu Ser Arg Asp Arg Lys
                340                 345                 350

Tyr Cys Glu Asp Val Asn Glu Cys Ala Phe Trp Asn His Gly Cys Thr
                355                 360                 365

Leu Gly Cys Lys Asn Thr Pro Gly Ser Tyr Tyr Cys Thr Cys Pro Val
                370                 375                 380

Gly Phe Val Leu Leu Pro Asp Gly Lys Arg Cys His Gln Leu Val Ser
385                 390                 395                 400

Cys Pro Arg Asn Val Ser Glu Cys Ser His Asp Cys Val Leu Thr Ser
                405                 410                 415

Glu Gly Pro Leu Cys Phe Cys Pro Glu Gly Ser Val Leu Glu Arg Asp
                420                 425                 430

Gly Lys Thr Cys Ser Gly Cys Ser Ser Pro Asp Asn Gly Gly Cys Ser
                435                 440                 445

Gln Leu Cys Val Pro Leu Ser Pro Val Ser Trp Glu Cys Asp Cys Phe
                450                 455                 460

Pro Gly Tyr Asp Leu Gln Leu Asp Glu Lys Ser Cys Ala Ala Ser Gly
465                 470                 475                 480

Pro Gln Pro Phe Leu Leu Phe Ala Asn Ser Gln Asp Ile Arg His Met
                485                 490                 495

His Phe Asp Gly Thr Asp Tyr Gly Thr Leu Leu Ser Gln Gln Met Gly
                500                 505                 510

Met Val Tyr Ala Leu Asp His Asp Pro Val Glu Asn Lys Ile Tyr Phe
                515                 520                 525

Ala His Thr Ala Leu Lys Trp Ile Glu Arg Ala Asn Met Asp Gly Ser
                530                 535                 540

Gln Arg Glu Arg Leu Ile Glu Glu Gly Val Asp Val Pro Glu Gly Leu
545                 550                 555                 560

Ala Val Asp Trp Ile Gly Arg Arg Phe Tyr Trp Thr Asp Arg Gly Lys
                565                 570                 575

Ser Leu Ile Gly Arg Ser Asp Leu Asn Gly Lys Arg Ser Lys Ile Ile
                580                 585                 590

Thr Lys Glu Asn Ile Ser Gln Pro Arg Gly Ile Ala Val His Pro Met
                595                 600                 605

Ala Lys Arg Leu Phe Trp Thr Asp Thr Gly Ile Asn Pro Arg Ile Glu
                610                 615                 620

Ser Ser Ser Leu Gln Gly Leu Gly Arg Leu Val Ile Ala Ser Ser Asp
625                 630                 635                 640

Leu Ile Trp Pro Ser Gly Ile Thr Ile Asp Phe Leu Thr Asp Lys Leu
                645                 650                 655

Tyr Trp Cys Asp Ala Lys Gln Ser Val Ile Glu Met Ala Asn Leu Asp
                660                 665                 670

Gly Ser Lys Arg Arg Arg Leu Thr Gln Asn Asp Val Gly His Pro Phe
                675                 680                 685

Ala Val Ala Val Phe Glu Asp Tyr Val Trp Phe Ser Asp Trp Ala Met
                690                 695                 700

Pro Ser Val Ile Arg Val Asn Lys Arg Thr Gly Lys Asp Arg Val Arg
705                 710                 715                 720

Leu Gln Gly Ser Met Leu Lys Pro Ser Ser Leu Val Val Val His Pro
                725                 730                 735

Leu Ala Lys Pro Gly Ala Asp Pro Cys Leu Tyr Gln Asn Gly Gly Cys
                740                 745                 750
```

```
Glu His Ile Cys Lys Lys Arg Leu Gly Thr Ala Trp Cys Ser Cys Arg
        755                 760                 765

Glu Gly Phe Met Lys Ala Ser Asp Gly Lys Thr Cys Leu Ala Leu Asp
        770                 775                 780

Gly His Gln Leu Leu Ala Gly Gly Glu Val Asp Leu Lys Asn Gln Val
785                 790                 795                 800

Thr Pro Leu Asp Ile Leu Ser Lys Thr Arg Val Ser Glu Asp Asn Ile
                805                 810                 815

Thr Glu Ser Gln His Met Leu Val Ala Glu Ile Met Val Ser Asp Gln
                820                 825                 830

Asp Asp Cys Ala Pro Val Gly Cys Ser Met Tyr Ala Arg Cys Ile Ser
                835                 840                 845

Glu Gly Glu Asp Ala Thr Cys Gln Cys Leu Lys Gly Phe Ala Gly Asp
        850                 855                 860

Gly Lys Leu Cys Ser Asp Ile Asp Glu Cys Glu Met Gly Val Pro Val
865                 870                 875                 880

Cys Pro Pro Ala Ser Ser Lys Cys Ile Asn Thr Glu Gly Gly Tyr Val
                885                 890                 895

Cys Arg Cys Ser Glu Gly Tyr Gln Gly Asp Gly Ile His Cys Leu Asp
        900                 905                 910

Ile Asp Glu Cys Gln Leu Gly Val His Ser Cys Gly Glu Asn Ala Ser
        915                 920                 925

Cys Thr Asn Thr Glu Gly Gly Tyr Thr Cys Met Cys Ala Gly Arg Leu
930                 935                 940

Ser Glu Pro Gly Leu Ile Cys Pro Asp Ser Thr Pro Pro Pro His Leu
945                 950                 955                 960

Arg Glu Asp Asp His His Tyr Ser Val Arg Asn Ser Asp Ser Glu Cys
                965                 970                 975

Pro Leu Ser His Asp Gly Tyr Cys Leu His Asp Gly Val Cys Met Tyr
                980                 985                 990

Ile Glu Ala Leu Asp Lys Tyr Ala Cys Asn Cys Val Val Gly Tyr Ile
        995                 1000                1005

Gly Glu Arg Cys Gln Tyr Arg Asp Leu Lys Trp Trp Glu Leu Arg
    1010                1015                1020

His Ala Gly His Gly Gln Gln Gln Lys Val Ile Val Ala Val
    1025                1030                1035

Cys Val Val Val Leu Val Met Leu Leu Leu Ser Leu Trp Gly
    1040                1045                1050

Ala His Tyr Tyr Arg Thr Gln Lys Leu Leu Ser Lys Asn Pro Lys
    1055                1060                1065

Asn Pro Tyr Glu Glu Ser Ser Arg Asp Val Arg Ser Arg Arg Pro
    1070                1075                1080

Ala Asp Thr Glu Asp Gly Met Ser Ser Cys Pro Gln Pro Trp Phe
    1085                1090                1095

Val Val Ile Lys Glu His Gln Asp Leu Lys Asn Gly Gly Gln Pro
    1100                1105                1110

Val Ala Gly Glu Asp Gly Gln Ala Ala Asp Gly Ser Met Gln Pro
    1115                1120                1125

Thr Ser Trp Arg Gln Glu Pro Gln Leu Cys Gly Met Gly Thr Glu
    1130                1135                1140

Gln Gly Cys Trp Ile Pro Val Ser Ser Asp Lys Gly Ser Cys Pro
    1145                1150                1155

Gln Val Met Glu Arg Ser Phe His Met Pro Ser Tyr Gly Thr Gln
    1160                1165                1170
```

-continued

Thr Leu Glu Gly Gly Val Glu Lys Pro His Ser Leu Leu Ser Ala
    1175                1180                1185

Asn Pro Leu Trp Gln Gln Arg Ala Leu Asp Pro Pro His Gln Met
    1190                1195                1200

Glu Leu Thr Gln
    1205

<210> SEQ ID NO 312
<211> LENGTH: 206
<212> TYPE: PRT
<213> ORGANISM: Homo sapiens

<400> SEQUENCE: 312

Met Ser Gly Pro Gly Thr Ala Ala Val Ala Leu Leu Pro Ala Val Leu
1               5                   10                  15

Leu Ala Leu Leu Ala Pro Trp Ala Gly Arg Gly Gly Ala Ala Ala Pro
                20                  25                  30

Thr Ala Pro Asn Gly Thr Leu Glu Ala Glu Leu Glu Arg Arg Trp Glu
            35                  40                  45

Ser Leu Val Ala Leu Ser Leu Ala Arg Leu Pro Val Ala Ala Gln Pro
    50                  55                  60

Lys Glu Ala Ala Val Gln Ser Gly Ala Gly Asp Tyr Leu Leu Gly Ile
65                  70                  75                  80

Lys Arg Leu Arg Arg Leu Tyr Cys Asn Val Gly Ile Gly Phe His Leu
                85                  90                  95

Gln Ala Leu Pro Asp Gly Arg Ile Gly Gly Ala His Ala Asp Thr Arg
            100                 105                 110

Asp Ser Leu Leu Glu Leu Ser Pro Val Glu Arg Gly Val Val Ser Ile
        115                 120                 125

Phe Gly Val Ala Ser Arg Phe Phe Val Ala Met Ser Ser Lys Gly Lys
    130                 135                 140

Leu Tyr Gly Ser Pro Phe Phe Thr Asp Glu Cys Thr Phe Lys Glu Ile
145                 150                 155                 160

Leu Leu Pro Asn Asn Tyr Asn Ala Tyr Glu Ser Tyr Lys Tyr Pro Gly
                165                 170                 175

Met Phe Ile Ala Leu Ser Lys Asn Gly Lys Thr Lys Lys Gly Asn Arg
            180                 185                 190

Val Ser Pro Thr Met Lys Val Thr His Phe Leu Pro Arg Leu
        195                 200                 205

<210> SEQ ID NO 313
<211> LENGTH: 208
<212> TYPE: PRT
<213> ORGANISM: Homo sapiens

<400> SEQUENCE: 313

Met Ala Pro Leu Gly Glu Val Gly Asn Tyr Phe Gly Val Gln Asp Ala
1               5                   10                  15

Val Pro Phe Gly Asn Val Pro Val Leu Pro Val Asp Ser Pro Val Leu
                20                  25                  30

Leu Ser Asp His Leu Gly Gln Ser Glu Ala Gly Gly Leu Pro Arg Gly
            35                  40                  45

Pro Ala Val Thr Asp Leu Asp His Leu Lys Gly Ile Leu Arg Arg Arg
    50                  55                  60

Gln Leu Tyr Cys Arg Thr Gly Phe His Leu Glu Ile Phe Pro Asn Gly
65                  70                  75                  80

```
Thr Ile Gln Gly Thr Arg Lys Asp His Ser Arg Phe Gly Ile Leu Glu
                85                  90                  95

Phe Ile Ser Ile Ala Val Gly Leu Val Ser Ile Arg Gly Val Asp Ser
            100                 105                 110

Gly Leu Tyr Leu Gly Met Asn Glu Lys Gly Glu Leu Tyr Gly Ser Glu
        115                 120                 125

Lys Leu Thr Gln Glu Cys Val Phe Arg Glu Gln Phe Glu Glu Asn Trp
    130                 135                 140

Tyr Asn Thr Tyr Ser Ser Asn Leu Tyr Lys His Val Asp Thr Gly Arg
145                 150                 155                 160

Arg Tyr Tyr Val Ala Leu Asn Lys Asp Gly Thr Pro Arg Glu Gly Thr
                165                 170                 175

Arg Thr Lys Arg His Gln Lys Phe Thr His Phe Leu Pro Arg Pro Val
            180                 185                 190

Asp Pro Asp Lys Val Pro Glu Leu Tyr Lys Asp Ile Leu Ser Gln Ser
        195                 200                 205

<210> SEQ ID NO 314
<211> LENGTH: 244
<212> TYPE: PRT
<213> ORGANISM: Homo sapiens

<400> SEQUENCE: 314

Met Gly Ala Leu Gly Leu Glu Gly Arg Gly Gly Arg Leu Gln Gly Arg
1               5                   10                  15

Gly Ser Leu Leu Leu Ala Val Ala Gly Ala Thr Ser Leu Val Thr Leu
            20                  25                  30

Leu Leu Ala Val Pro Ile Thr Val Leu Ala Val Leu Ala Leu Val Pro
        35                  40                  45

Gln Asp Gln Gly Gly Leu Val Thr Glu Thr Ala Asp Pro Gly Ala Gln
    50                  55                  60

Ala Gln Gln Gly Leu Gly Phe Gln Lys Leu Pro Glu Glu Glu Pro Glu
65                  70                  75                  80

Thr Asp Leu Ser Pro Gly Leu Pro Ala Ala His Leu Ile Gly Ala Pro
                85                  90                  95

Leu Lys Gly Gln Gly Leu Gly Trp Glu Thr Thr Lys Glu Gln Ala Phe
            100                 105                 110

Leu Thr Ser Gly Thr Gln Phe Ser Asp Ala Glu Gly Leu Ala Leu Pro
        115                 120                 125

Gln Asp Gly Leu Tyr Tyr Leu Tyr Cys Leu Val Gly Tyr Arg Gly Arg
    130                 135                 140

Ala Pro Pro Gly Gly Gly Asp Pro Gln Gly Arg Ser Val Thr Leu Arg
145                 150                 155                 160

Ser Ser Leu Tyr Arg Ala Gly Gly Ala Tyr Gly Pro Gly Thr Pro Glu
                165                 170                 175

Leu Leu Leu Glu Gly Ala Glu Thr Val Thr Pro Val Leu Asp Pro Ala
            180                 185                 190

Arg Arg Gln Gly Tyr Gly Pro Leu Trp Tyr Thr Ser Val Gly Phe Gly
        195                 200                 205

Gly Leu Val Gln Leu Arg Arg Gly Glu Arg Val Tyr Val Asn Ile Ser
    210                 215                 220

His Pro Asp Met Val Asp Phe Ala Arg Gly Lys Thr Phe Phe Gly Ala
225                 230                 235                 240

Val Met Val Gly
```

-continued

```
<210> SEQ ID NO 315
<211> LENGTH: 211
<212> TYPE: PRT
<213> ORGANISM: Homo sapiens

<400> SEQUENCE: 315

Met Arg Thr Leu Ala Cys Leu Leu Leu Gly Cys Gly Tyr Leu Ala
1               5                   10                  15

His Val Leu Ala Glu Glu Ala Glu Ile Pro Arg Glu Val Ile Glu Arg
                20                  25                  30

Leu Ala Arg Ser Gln Ile His Ser Ile Arg Asp Leu Gln Arg Leu Leu
            35                  40                  45

Glu Ile Asp Ser Val Gly Ser Glu Asp Ser Leu Asp Thr Ser Leu Arg
    50                  55                  60

Ala His Gly Val His Ala Thr Lys His Val Pro Glu Lys Arg Pro Leu
65                  70                  75                  80

Pro Ile Arg Arg Lys Arg Ser Ile Glu Glu Ala Val Pro Ala Val Cys
                85                  90                  95

Lys Thr Arg Thr Val Ile Tyr Glu Ile Pro Arg Ser Gln Val Asp Pro
                100                 105                 110

Thr Ser Ala Asn Phe Leu Ile Trp Pro Pro Cys Val Glu Val Lys Arg
            115                 120                 125

Cys Thr Gly Cys Cys Asn Thr Ser Ser Val Lys Cys Gln Pro Ser Arg
        130                 135                 140

Val His His Arg Ser Val Lys Val Ala Lys Val Glu Tyr Val Arg Lys
145                 150                 155                 160

Lys Pro Lys Leu Lys Glu Val Gln Val Arg Leu Glu Glu His Leu Glu
                165                 170                 175

Cys Ala Cys Ala Thr Thr Ser Leu Asn Pro Asp Tyr Arg Glu Glu Asp
            180                 185                 190

Thr Gly Arg Pro Arg Glu Ser Gly Lys Lys Arg Lys Arg Lys Arg Leu
        195                 200                 205

Lys Pro Thr
    210

<210> SEQ ID NO 316
<211> LENGTH: 241
<212> TYPE: PRT
<213> ORGANISM: Homo sapiens

<400> SEQUENCE: 316

Met Asn Arg Cys Trp Ala Leu Phe Leu Ser Leu Cys Cys Tyr Leu Arg
1               5                   10                  15

Leu Val Ser Ala Glu Gly Asp Pro Ile Pro Glu Glu Leu Tyr Glu Met
                20                  25                  30

Leu Ser Asp His Ser Ile Arg Ser Phe Asp Asp Leu Gln Arg Leu Leu
            35                  40                  45

His Gly Asp Pro Gly Glu Glu Asp Gly Ala Glu Leu Asp Leu Asn Met
    50                  55                  60

Thr Arg Ser His Ser Gly Gly Glu Leu Glu Ser Leu Ala Arg Gly Arg
65                  70                  75                  80

Arg Ser Leu Gly Ser Leu Thr Ile Ala Glu Pro Ala Met Ile Ala Glu
                85                  90                  95

Cys Lys Thr Arg Thr Glu Val Phe Glu Ile Ser Arg Arg Leu Ile Asp
                100                 105                 110

Arg Thr Asn Ala Asn Phe Leu Val Trp Pro Pro Cys Val Glu Val Gln
            115                 120                 125
```

```
Arg Cys Ser Gly Cys Cys Asn Asn Arg Asn Val Gln Cys Arg Pro Thr
            130                 135                 140

Gln Val Gln Leu Arg Pro Val Gln Val Arg Lys Ile Glu Ile Val Arg
145                 150                 155                 160

Lys Lys Pro Ile Phe Lys Lys Ala Thr Val Thr Leu Glu Asp His Leu
                165                 170                 175

Ala Cys Lys Cys Glu Thr Val Ala Ala Arg Pro Val Thr Arg Ser
                180                 185                 190

Pro Gly Gly Ser Gln Glu Gln Arg Ala Lys Thr Pro Gln Thr Arg Val
                195                 200                 205

Thr Ile Arg Thr Val Arg Val Arg Arg Pro Pro Lys Gly Lys His Arg
210                 215                 220

Lys Phe Lys His Thr His Asp Lys Thr Ala Leu Lys Glu Thr Leu Gly
225                 230                 235                 240

Ala
```

<210> SEQ ID NO 317
<211> LENGTH: 240
<212> TYPE: PRT
<213> ORGANISM: Homo sapiens

<400> SEQUENCE: 317

```
Met Leu Ala Leu Leu Cys Ser Cys Leu Leu Leu Ala Ala Gly Ala Ser
1               5                   10                  15

Asp Ala Trp Thr Gly Glu Asp Ser Ala Glu Pro Asn Ser Asp Ser Ala
                20                  25                  30

Glu Trp Ile Arg Asp Met Tyr Ala Lys Val Thr Glu Ile Trp Gln Glu
            35                  40                  45

Val Met Gln Arg Arg Asp Asp Asp Gly Thr Leu His Ala Ala Cys Gln
50                  55                  60

Val Gln Pro Ser Ala Thr Leu Asp Ala Ala Gln Pro Arg Val Thr Gly
65                  70                  75                  80

Val Val Leu Phe Arg Gln Leu Ala Pro Arg Ala Lys Leu Asp Ala Phe
                85                  90                  95

Phe Ala Leu Glu Gly Phe Pro Thr Glu Pro Asn Ser Ser Ser Arg Ala
                100                 105                 110

Ile His Val His Gln Phe Gly Asp Leu Ser Gln Gly Cys Glu Ser Thr
            115                 120                 125

Gly Pro His Tyr Asn Pro Leu Ala Val Pro His Pro Gln His Pro Gly
130                 135                 140

Asp Phe Gly Asn Phe Ala Val Arg Asp Gly Ser Leu Trp Arg Tyr Arg
145                 150                 155                 160

Ala Gly Leu Ala Ala Ser Leu Ala Gly Pro His Ser Ile Val Gly Arg
                165                 170                 175

Ala Val Val Val His Ala Gly Glu Asp Asp Leu Gly Arg Gly Gly Asn
                180                 185                 190

Gln Ala Ser Val Glu Asn Gly Asn Ala Gly Arg Arg Leu Ala Cys Cys
            195                 200                 205

Val Val Gly Val Cys Gly Pro Gly Leu Trp Glu Arg Gln Ala Arg Glu
210                 215                 220

His Ser Glu Arg Lys Lys Arg Arg Glu Ser Glu Cys Lys Ala Ala
225                 230                 235                 240
```

<210> SEQ ID NO 318
<211> LENGTH: 160

```
<212> TYPE: PRT
<213> ORGANISM: Homo sapiens

<400> SEQUENCE: 318

Met Val Pro Ser Ala Gly Gln Leu Ala Leu Phe Ala Leu Gly Ile Val
1               5                   10                  15

Leu Ala Ala Cys Gln Ala Leu Glu Asn Ser Thr Ser Pro Leu Ser Ala
            20                  25                  30

Asp Pro Pro Val Ala Ala Ala Val Ser His Phe Asn Asp Cys Pro
        35                  40                  45

Asp Ser His Thr Gln Phe Cys Phe His Gly Thr Cys Arg Phe Leu Val
    50                  55                  60

Gln Glu Asp Lys Pro Ala Cys Val Cys His Ser Gly Tyr Val Gly Ala
65              70                  75                  80

Arg Cys Glu His Ala Asp Leu Leu Ala Val Ala Ala Ser Gln Lys
            85                  90                  95

Lys Gln Ala Ile Thr Ala Leu Val Val Val Ser Ile Val Ala Leu Ala
            100                 105                 110

Val Leu Ile Ile Thr Cys Val Leu Ile His Cys Cys Gln Val Arg Lys
        115                 120                 125

His Cys Glu Trp Cys Arg Ala Leu Ile Cys Arg His Glu Lys Pro Ser
    130                 135                 140

Ala Leu Leu Lys Gly Arg Thr Ala Cys Cys His Ser Glu Thr Val Val
145             150                 155                 160

<210> SEQ ID NO 319
<211> LENGTH: 317
<212> TYPE: PRT
<213> ORGANISM: Homo sapiens

<400> SEQUENCE: 319

Met Arg Arg Ala Ser Arg Asp Tyr Thr Lys Tyr Leu Arg Gly Ser Glu
1               5                   10                  15

Glu Met Gly Gly Gly Pro Gly Ala Pro His Glu Gly Pro Leu His Ala
            20                  25                  30

Pro Pro Pro Pro Ala Pro His Gln Pro Pro Ala Ala Ser Arg Ser Met
        35                  40                  45

Phe Val Ala Leu Leu Gly Leu Gly Leu Gly Gln Val Val Cys Ser Val
    50                  55                  60

Ala Leu Phe Phe Tyr Phe Arg Ala Gln Met Asp Pro Asn Arg Ile Ser
65              70                  75                  80

Glu Asp Gly Thr His Cys Ile Tyr Arg Ile Leu Arg Leu His Glu Asn
            85                  90                  95

Ala Asp Phe Gln Asp Thr Thr Leu Glu Ser Gln Asp Thr Lys Leu Ile
        100                 105                 110

Pro Asp Ser Cys Arg Arg Ile Lys Gln Ala Phe Gln Gly Ala Val Gln
    115                 120                 125

Lys Glu Leu Gln His Ile Val Gly Ser Gln His Ile Arg Ala Glu Lys
130             135                 140

Ala Met Val Asp Gly Ser Trp Leu Asp Leu Ala Lys Arg Ser Lys Leu
145             150                 155                 160

Glu Ala Gln Pro Phe Ala His Leu Thr Ile Asn Ala Thr Asp Ile Pro
            165                 170                 175

Ser Gly Ser His Lys Val Ser Leu Ser Ser Trp Tyr His Asp Arg Gly
        180                 185                 190

Trp Ala Lys Ile Ser Asn Met Thr Phe Ser Asn Gly Lys Leu Ile Val
```

```
                195                 200                 205
Asn Gln Asp Gly Phe Tyr Tyr Leu Tyr Ala Asn Ile Cys Phe Arg His
210                 215                 220

His Glu Thr Ser Gly Asp Leu Ala Thr Glu Tyr Leu Gln Leu Met Val
225                 230                 235                 240

Tyr Val Thr Lys Thr Ser Ile Lys Ile Pro Ser Ser His Thr Leu Met
                245                 250                 255

Lys Gly Gly Ser Thr Lys Tyr Trp Ser Gly Asn Ser Glu Phe His Phe
                260                 265                 270

Tyr Ser Ile Asn Val Gly Gly Phe Phe Lys Leu Arg Ser Gly Glu Glu
                275                 280                 285

Ile Ser Ile Glu Val Ser Asn Pro Ser Leu Leu Asp Pro Asp Gln Asp
290                 295                 300

Ala Thr Tyr Phe Gly Ala Phe Lys Val Arg Asp Ile Asp
305                 310                 315

<210> SEQ ID NO 320
<211> LENGTH: 250
<212> TYPE: PRT
<213> ORGANISM: Homo sapiens

<400> SEQUENCE: 320

Met Pro Ala Ser Ser Pro Phe Leu Leu Ala Pro Lys Gly Pro Pro Gly
1               5                   10                  15

Asn Met Gly Gly Pro Val Arg Glu Pro Ala Leu Ser Val Ala Leu Trp
                20                  25                  30

Leu Ser Trp Gly Ala Ala Leu Gly Ala Val Ala Cys Ala Met Ala Leu
                35                  40                  45

Leu Thr Gln Gln Thr Glu Leu Gln Ser Leu Arg Arg Glu Val Ser Arg
50                  55                  60

Leu Gln Gly Thr Gly Gly Pro Ser Gln Asn Gly Glu Gly Tyr Pro Trp
65                  70                  75                  80

Gln Ser Leu Pro Glu Gln Ser Ser Asp Ala Leu Glu Ala Trp Glu Asn
                85                  90                  95

Gly Glu Arg Ser Arg Lys Arg Arg Ala Val Leu Thr Gln Lys Gln Lys
                100                 105                 110

Lys Gln His Ser Val Leu His Leu Val Pro Ile Asn Ala Thr Ser Lys
                115                 120                 125

Asp Asp Ser Asp Val Thr Glu Val Met Trp Gln Pro Ala Leu Arg Arg
130                 135                 140

Gly Arg Gly Leu Gln Ala Gln Gly Tyr Gly Val Arg Ile Gln Asp Ala
145                 150                 155                 160

Gly Val Tyr Leu Leu Tyr Ser Gln Val Leu Phe Gln Asp Val Thr Phe
                165                 170                 175

Thr Met Gly Gln Val Val Ser Arg Glu Gly Gln Gly Arg Gln Glu Thr
                180                 185                 190

Leu Phe Arg Cys Ile Arg Ser Met Pro Ser His Pro Asp Arg Ala Tyr
                195                 200                 205

Asn Ser Cys Tyr Ser Ala Gly Val Phe His Leu His Gln Gly Asp Ile
                210                 215                 220

Leu Ser Val Ile Ile Pro Arg Ala Arg Ala Lys Leu Asn Leu Ser Pro
225                 230                 235                 240

His Gly Thr Phe Leu Gly Phe Val Lys Leu
                245                 250
```

-continued

<210> SEQ ID NO 321
<211> LENGTH: 249
<212> TYPE: PRT
<213> ORGANISM: Homo sapiens

<400> SEQUENCE: 321

Met Ala Ala Arg Arg Ser Gln Arg Arg Gly Arg Gly Glu Pro
1               5                   10                  15

Gly Thr Ala Leu Leu Val Pro Leu Ala Leu Gly Leu Gly Leu Ala Leu
                20                  25                  30

Ala Cys Leu Gly Leu Leu Leu Ala Val Val Ser Leu Gly Ser Arg Ala
            35                  40                  45

Ser Leu Ser Ala Gln Glu Pro Ala Gln Glu Glu Leu Val Ala Glu Glu
    50                  55                  60

Asp Gln Asp Pro Ser Glu Leu Asn Pro Gln Thr Glu Glu Ser Gln Asp
65                  70                  75                  80

Pro Ala Pro Phe Leu Asn Arg Leu Val Arg Pro Arg Arg Ser Ala Pro
                85                  90                  95

Lys Gly Arg Lys Thr Arg Ala Arg Arg Ala Ile Ala Ala His Tyr Glu
            100                 105                 110

Val His Pro Arg Pro Gly Gln Asp Gly Ala Gln Ala Gly Val Asp Gly
        115                 120                 125

Thr Val Ser Gly Trp Glu Glu Ala Arg Ile Asn Ser Ser Ser Pro Leu
130                 135                 140

Arg Tyr Asn Arg Gln Ile Gly Glu Phe Ile Val Thr Arg Ala Gly Leu
145                 150                 155                 160

Tyr Tyr Leu Tyr Cys Gln Val His Phe Asp Glu Gly Lys Ala Val Tyr
                165                 170                 175

Leu Lys Leu Asp Leu Leu Val Asp Gly Val Leu Ala Leu Arg Cys Leu
            180                 185                 190

Glu Glu Phe Ser Ala Thr Ala Ala Ser Ser Leu Gly Pro Gln Leu Arg
        195                 200                 205

Leu Cys Gln Val Ser Gly Leu Leu Ala Leu Arg Pro Gly Ser Ser Leu
    210                 215                 220

Arg Ile Arg Thr Leu Pro Trp Ala His Leu Lys Ala Ala Pro Phe Leu
225                 230                 235                 240

Thr Tyr Phe Gly Leu Phe Gln Val His
                245

<210> SEQ ID NO 322
<211> LENGTH: 254
<212> TYPE: PRT
<213> ORGANISM: Homo sapiens

<400> SEQUENCE: 322

Met Glu Tyr Ala Ser Asp Ala Ser Leu Asp Pro Glu Ala Pro Trp Pro
1               5                   10                  15

Pro Ala Pro Arg Ala Arg Ala Cys Arg Val Leu Pro Trp Ala Leu Val
                20                  25                  30

Ala Gly Leu Leu Leu Leu Leu Leu Ala Ala Ala Cys Ala Val Phe
            35                  40                  45

Leu Ala Cys Pro Trp Ala Val Ser Gly Ala Arg Ala Ser Pro Gly Ser
    50                  55                  60

Ala Ala Ser Pro Arg Leu Arg Glu Gly Pro Glu Leu Ser Pro Asp Asp
65                  70                  75                  80

Pro Ala Gly Leu Leu Asp Leu Arg Gln Gly Met Phe Ala Gln Leu Val
                85                  90                  95

```
Ala Gln Asn Val Leu Leu Ile Asp Gly Pro Leu Ser Trp Tyr Ser Asp
            100                 105                 110

Pro Gly Leu Ala Gly Val Ser Leu Thr Gly Gly Leu Ser Tyr Lys Glu
            115                 120                 125

Asp Thr Lys Glu Leu Val Val Ala Lys Ala Gly Val Tyr Tyr Val Phe
            130                 135                 140

Phe Gln Leu Glu Leu Arg Arg Val Val Ala Gly Glu Gly Ser Gly Ser
145                 150                 155                 160

Val Ser Leu Ala Leu His Leu Gln Pro Leu Arg Ser Ala Ala Gly Ala
                165                 170                 175

Ala Ala Leu Ala Leu Thr Val Asp Leu Pro Pro Ala Ser Ser Glu Ala
                180                 185                 190

Arg Asn Ser Ala Phe Gly Phe Gln Gly Arg Leu Leu His Leu Ser Ala
                195                 200                 205

Gly Gln Arg Leu Gly Val His Leu His Thr Glu Ala Arg Ala Arg His
            210                 215                 220

Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu
                245                 250

<210> SEQ ID NO 323
<211> LENGTH: 216
<212> TYPE: PRT
<213> ORGANISM: Homo sapiens

<400> SEQUENCE: 323

Met Gly Ala Ala Arg Leu Leu Pro Asn Leu Thr Leu Cys Leu Gln Leu
1               5                   10                  15

Leu Ile Leu Cys Cys Gln Thr Gln Gly Glu Asn His Pro Ser Pro Asn
            20                  25                  30

Phe Asn Gln Tyr Val Arg Asp Gln Gly Ala Met Thr Asp Gln Leu Ser
            35                  40                  45

Arg Arg Gln Ile Arg Glu Tyr Gln Leu Tyr Ser Arg Thr Ser Gly Lys
50                  55                  60

His Val Gln Val Thr Gly Arg Arg Ile Ser Ala Thr Ala Glu Asp Gly
65                  70                  75                  80

Asn Lys Phe Ala Lys Leu Ile Val Glu Thr Asp Thr Phe Gly Ser Arg
                85                  90                  95

Val Arg Ile Lys Gly Ala Glu Ser Glu Lys Tyr Ile Cys Met Asn Lys
            100                 105                 110

Arg Gly Lys Leu Ile Gly Lys Pro Ser Gly Lys Ser Lys Asp Cys Val
            115                 120                 125

Phe Thr Glu Ile Val Leu Glu Asn Asn Tyr Thr Ala Phe Gln Asn Ala
            130                 135                 140

Arg His Glu Gly Trp Phe Met Ala Phe Thr Arg Gln Gly Arg Pro Arg
145                 150                 155                 160

Gln Ala Ser Arg Ser Arg Gln Asn Gln Arg Glu Ala His Phe Ile Lys
                165                 170                 175

Arg Leu Tyr Gln Gly Gln Leu Pro Phe Pro Asn His Ala Glu Lys Gln
                180                 185                 190

Lys Gln Phe Glu Phe Val Gly Ser Ala Pro Thr Arg Arg Thr Lys Arg
            195                 200                 205

Thr Arg Arg Pro Gln Pro Leu Thr
            210                 215
```

<210> SEQ ID NO 324
<211> LENGTH: 207
<212> TYPE: PRT
<213> ORGANISM: Homo sapiens

<400> SEQUENCE: 324

Met Ala Glu Val Gly Gly Val Phe Ala Ser Leu Asp Trp Asp Leu His
1               5                   10                  15

Gly Phe Ser Ser Ser Leu Gly Asn Val Pro Leu Ala Asp Ser Pro Gly
                20                  25                  30

Phe Leu Asn Glu Arg Leu Gly Gln Ile Glu Gly Lys Leu Gln Arg Gly
            35                  40                  45

Ser Pro Thr Asp Phe Ala His Leu Lys Gly Ile Leu Arg Arg Arg Gln
50                  55                  60

Leu Tyr Cys Arg Thr Gly Phe His Leu Glu Ile Phe Pro Asn Gly Thr
65                  70                  75                  80

Val His Gly Thr Arg His Asp His Ser Arg Phe Gly Ile Leu Glu Phe
                85                  90                  95

Ile Ser Leu Ala Val Gly Leu Ile Ser Ile Arg Gly Val Asp Ser Gly
            100                 105                 110

Leu Tyr Leu Gly Met Asn Glu Arg Gly Glu Leu Tyr Gly Ser Lys Lys
        115                 120                 125

Leu Thr Arg Glu Cys Val Phe Arg Glu Gln Phe Glu Glu Asn Trp Tyr
130                 135                 140

Asn Thr Tyr Ala Ser Thr Leu Tyr Lys His Ser Asp Ser Glu Arg Gln
145                 150                 155                 160

Tyr Tyr Val Ala Leu Asn Lys Asp Gly Ser Pro Arg Glu Gly Tyr Arg
                165                 170                 175

Thr Lys Arg His Gln Lys Phe Thr His Phe Leu Pro Arg Pro Val Asp
            180                 185                 190

Pro Ser Lys Leu Pro Ser Met Ser Arg Asp Leu Phe His Tyr Arg
        195                 200                 205

<210> SEQ ID NO 325
<211> LENGTH: 850
<212> TYPE: PRT
<213> ORGANISM: Homo sapiens

<400> SEQUENCE: 325

Met Arg Gln Val Cys Cys Ser Ala Leu Pro Pro Pro Leu Glu Lys
1               5                   10                  15

Gly Arg Cys Ser Ser Tyr Ser Asp Ser Ser Ser Ser Ser Glu Arg
                20                  25                  30

Ser Ser Ser Ser Ser Ser Ser Ser Glu Ser Gly Ser Ser Arg
            35                  40                  45

Ser Ser Ser Asn Asn Ser Ser Ile Ser Arg Pro Ala Pro Pro Glu
50                  55                  60

Pro Arg Pro Gln Gln Gln Pro Gln Pro Arg Ser Pro Ala Ala Arg Arg
65                  70                  75                  80

Ala Ala Ala Arg Ser Arg Ala Ala Ala Gly Gly Met Arg Asp
                85                  90                  95

Pro Ala Pro Gly Phe Ser Met Leu Leu Phe Gly Val Ser Leu Ala Cys
            100                 105                 110

Tyr Ser Pro Ser Leu Lys Ser Val Gln Asp Gln Ala Tyr Lys Ala Pro
        115                 120                 125

-continued

```
Val Val Val Glu Gly Lys Val Gln Gly Leu Val Pro Ala Gly Gly Ser
        130             135             140
Ser Ser Asn Ser Thr Arg Glu Pro Pro Ala Ser Gly Arg Val Ala Leu
145             150             155             160
Val Lys Val Leu Asp Lys Trp Pro Leu Arg Ser Gly Gly Leu Gln Arg
            165             170             175
Glu Gln Val Ile Ser Val Gly Ser Cys Val Pro Leu Glu Arg Asn Gln
            180             185             190
Arg Tyr Ile Phe Phe Leu Glu Pro Thr Glu Gln Pro Leu Val Phe Lys
            195             200             205
Thr Ala Phe Ala Pro Leu Asp Thr Asn Gly Lys Asn Leu Lys Lys Glu
        210             215             220
Val Gly Lys Ile Leu Cys Thr Asp Cys Ala Thr Arg Pro Lys Leu Lys
225             230             235             240
Lys Met Lys Ser Gln Thr Gly Gln Val Gly Glu Lys Gln Ser Leu Lys
            245             250             255
Cys Glu Ala Ala Ala Gly Asn Pro Gln Pro Ser Tyr Arg Trp Phe Lys
            260             265             270
Asp Gly Lys Glu Leu Asn Arg Ser Arg Asp Ile Arg Ile Lys Tyr Gly
            275             280             285
Asn Gly Arg Lys Asn Ser Arg Leu Gln Phe Asn Lys Val Lys Val Glu
        290             295             300
Asp Ala Gly Glu Tyr Val Cys Glu Ala Glu Asn Ile Leu Gly Lys Asp
305             310             315             320
Thr Val Arg Gly Arg Leu Tyr Val Asn Ser Val Ser Thr Thr Leu Ser
            325             330             335
Ser Trp Ser Gly His Ala Arg Lys Cys Asn Glu Thr Ala Lys Ser Tyr
            340             345             350
Cys Val Asn Gly Gly Val Cys Tyr Tyr Ile Glu Gly Ile Asn Gln Leu
            355             360             365
Ser Cys Lys Cys Pro Asn Gly Phe Phe Gly Gln Arg Cys Leu Glu Lys
        370             375             380
Leu Pro Leu Arg Leu Tyr Met Pro Asp Pro Lys Gln Lys Ala Glu Glu
385             390             395             400
Leu Tyr Gln Lys Arg Val Leu Thr Ile Thr Gly Ile Cys Val Ala Leu
            405             410             415
Leu Val Val Gly Ile Val Cys Val Val Ala Tyr Cys Lys Thr Lys Lys
            420             425             430
Gln Arg Lys Gln Met His Asn His Leu Arg Gln Asn Met Cys Pro Ala
        435             440             445
His Gln Asn Arg Ser Leu Ala Asn Gly Pro Ser His Pro Arg Leu Asp
450             455             460
Pro Glu Glu Ile Gln Met Ala Asp Tyr Ile Ser Lys Asn Val Pro Ala
465             470             475             480
Thr Asp His Val Ile Arg Arg Glu Thr Glu Thr Thr Phe Ser Gly Ser
            485             490             495
His Ser Cys Ser Pro Ser His His Cys Ser Thr Ala Thr Pro Thr Ser
            500             505             510
Ser His Arg His Glu Ser His Thr Trp Ser Leu Glu Arg Ser Glu Ser
            515             520             525
Leu Thr Ser Asp Ser Gln Ser Gly Ile Met Leu Ser Ser Val Gly Thr
        530             535             540
Ser Lys Cys Asn Ser Pro Ala Cys Val Glu Ala Arg Ala Arg Arg Ala
545             550             555             560
```

```
Ala Ala Tyr Asn Leu Glu Glu Arg Arg Arg Thr Ala Pro Pro Tyr
                565                 570                 575

His Asp Ser Val Asp Ser Leu Arg Asp Ser Pro His Ser Glu Arg Tyr
            580                 585                 590

Val Ser Ala Leu Thr Thr Pro Ala Arg Leu Ser Pro Val Asp Phe His
            595                 600                 605

Tyr Ser Leu Ala Thr Gln Val Pro Thr Phe Glu Ile Thr Ser Pro Asn
            610                 615                 620

Ser Ala His Ala Val Ser Leu Pro Pro Ala Ala Pro Ile Ser Tyr Arg
625                 630                 635                 640

Leu Ala Glu Gln Gln Pro Leu Leu Arg His Pro Ala Pro Pro Gly Pro
                645                 650                 655

Gly Pro Gly Pro Gly Pro Gly Pro Gly Ala Asp Met Gln Arg
                660                 665                 670

Ser Tyr Asp Ser Tyr Tyr Tyr Pro Ala Ala Gly Pro Gly Pro Arg Arg
                675                 680                 685

Gly Thr Cys Ala Leu Gly Gly Ser Leu Gly Ser Leu Pro Ala Ser Pro
            690                 695                 700

Phe Arg Ile Pro Glu Asp Asp Glu Tyr Glu Thr Thr Gln Glu Cys Ala
705                 710                 715                 720

Pro Pro Pro Pro Arg Pro Arg Ala Arg Gly Ala Ser Arg Arg Thr
                725                 730                 735

Ser Ala Gly Pro Arg Arg Trp Arg Arg Ser Arg Leu Asn Gly Leu Ala
            740                 745                 750

Ala Gln Arg Ala Arg Ala Ala Arg Asp Ser Leu Ser Leu Ser Ser Gly
            755                 760                 765

Ser Gly Gly Gly Ser Ala Ser Ala Ser Asp Asp Ala Asp Ala
            770                 775                 780

Asp Gly Ala Leu Ala Ala Glu Ser Thr Pro Phe Leu Gly Leu Arg Gly
785                 790                 795                 800

Ala His Asp Ala Leu Arg Ser Asp Ser Pro Pro Leu Cys Pro Ala Ala
            805                 810                 815

Asp Ser Arg Thr Tyr Tyr Ser Leu Asp Ser His Ser Thr Arg Ala Ser
            820                 825                 830

Ser Arg His Ser Arg Gly Pro Pro Pro Arg Ala Lys Gln Asp Ser Ala
            835                 840                 845

Pro Leu
    850

<210> SEQ ID NO 326
<211> LENGTH: 177
<212> TYPE: PRT
<213> ORGANISM: Homo sapiens

<400> SEQUENCE: 326

Met Cys Leu Ser His Leu Glu Asn Met Pro Leu Ser His Ser Arg Thr
1               5                   10                  15

Gln Gly Ala Gln Arg Ser Ser Trp Lys Leu Trp Leu Phe Cys Ser Ile
            20                  25                  30

Val Met Leu Leu Phe Leu Cys Ser Phe Ser Trp Leu Ile Phe Ile Phe
            35                  40                  45

Leu Gln Leu Glu Thr Ala Lys Glu Pro Cys Met Ala Lys Phe Gly Pro
        50                  55                  60

Leu Pro Ser Lys Trp Gln Met Ala Ser Ser Glu Pro Pro Cys Val Asn
65                  70                  75                  80
```

-continued

```
Lys Val Ser Asp Trp Lys Leu Glu Ile Leu Gln Asn Gly Leu Tyr Leu
                85                  90                  95

Ile Tyr Gly Gln Val Ala Pro Asn Ala Asn Tyr Asn Asp Val Ala Pro
            100                 105                 110

Phe Glu Val Arg Leu Tyr Lys Asn Lys Asp Met Ile Gln Thr Leu Thr
        115                 120                 125

Asn Lys Ser Lys Ile Gln Asn Val Gly Gly Thr Tyr Glu Leu His Val
    130                 135                 140

Gly Asp Thr Ile Asp Leu Ile Phe Asn Ser Glu His Gln Val Leu Lys
145                 150                 155                 160

Asn Asn Thr Tyr Trp Gly Ile Ile Leu Leu Ala Asn Pro Gln Phe Ile
                165                 170                 175

Ser

<210> SEQ ID NO 327
<211> LENGTH: 129
<212> TYPE: PRT
<213> ORGANISM: Homo sapiens

<400> SEQUENCE: 327

Met Gly Arg Arg Asp Ala Gln Leu Leu Ala Leu Leu Val Leu Gly
1               5                   10                  15

Leu Cys Ala Leu Ala Gly Ser Glu Lys Pro Ser Pro Cys Gln Cys Ser
                20                  25                  30

Arg Leu Ser Pro His Asn Arg Thr Asn Cys Gly Phe Pro Gly Ile Thr
            35                  40                  45

Ser Asp Gln Cys Phe Asp Asn Gly Cys Cys Phe Asp Ser Ser Val Thr
        50                  55                  60

Gly Val Pro Trp Cys Phe His Pro Leu Pro Lys Gln Glu Ser Asp Gln
65                  70                  75                  80

Cys Val Met Glu Val Ser Asp Arg Arg Asn Cys Gly Tyr Pro Gly Ile
                85                  90                  95

Ser Pro Glu Glu Cys Ala Ser Arg Lys Cys Cys Phe Ser Asn Phe Ile
            100                 105                 110

Phe Glu Val Pro Trp Cys Phe Phe Pro Lys Ser Val Glu Asp Cys His
        115                 120                 125

Tyr

<210> SEQ ID NO 328
<211> LENGTH: 419
<212> TYPE: PRT
<213> ORGANISM: Homo sapiens

<400> SEQUENCE: 328

Met His Leu Leu Gly Phe Phe Ser Val Ala Cys Ser Leu Leu Ala Ala
1               5                   10                  15

Ala Leu Leu Pro Gly Pro Arg Glu Ala Pro Ala Ala Ala Ala Ala Phe
                20                  25                  30

Glu Ser Gly Leu Asp Leu Ser Asp Ala Glu Pro Asp Ala Gly Glu Ala
            35                  40                  45

Thr Ala Tyr Ala Ser Lys Asp Leu Glu Glu Gln Leu Arg Ser Val Ser
        50                  55                  60

Ser Val Asp Glu Leu Met Thr Val Leu Tyr Pro Glu Tyr Trp Lys Met
65                  70                  75                  80

Tyr Lys Cys Gln Leu Arg Lys Gly Gly Trp Gln His Asn Arg Glu Gln
                85                  90                  95
```

Ala Asn Leu Asn Ser Arg Thr Glu Glu Thr Ile Lys Phe Ala Ala Ala
            100                 105                 110

His Tyr Asn Thr Glu Ile Leu Lys Ser Ile Asp Asn Glu Trp Arg Lys
        115                 120                 125

Thr Gln Cys Met Pro Arg Glu Val Cys Ile Asp Val Gly Lys Glu Phe
    130                 135                 140

Gly Val Ala Thr Asn Thr Phe Phe Lys Pro Pro Cys Val Ser Val Tyr
145                 150                 155                 160

Arg Cys Gly Gly Cys Cys Asn Ser Glu Gly Leu Gln Cys Met Asn Thr
                165                 170                 175

Ser Thr Ser Tyr Leu Ser Lys Thr Leu Phe Glu Ile Thr Val Pro Leu
            180                 185                 190

Ser Gln Gly Pro Lys Pro Val Thr Ile Ser Phe Ala Asn His Thr Ser
        195                 200                 205

Cys Arg Cys Met Ser Lys Leu Asp Val Tyr Arg Gln Val His Ser Ile
    210                 215                 220

Ile Arg Arg Ser Leu Pro Ala Thr Leu Pro Gln Cys Gln Ala Ala Asn
225                 230                 235                 240

Lys Thr Cys Pro Thr Asn Tyr Met Trp Asn Asn His Ile Cys Arg Cys
                245                 250                 255

Leu Ala Gln Glu Asp Phe Met Phe Ser Ser Asp Ala Gly Asp Asp Ser
            260                 265                 270

Thr Asp Gly Phe His Asp Ile Cys Gly Pro Asn Lys Glu Leu Asp Glu
        275                 280                 285

Glu Thr Cys Gln Cys Val Cys Arg Ala Gly Leu Arg Pro Ala Ser Cys
    290                 295                 300

Gly Pro His Lys Glu Leu Asp Arg Asn Ser Cys Gln Cys Val Cys Lys
305                 310                 315                 320

Asn Lys Leu Phe Pro Ser Gln Cys Gly Ala Asn Arg Glu Phe Asp Glu
                325                 330                 335

Asn Thr Cys Gln Cys Val Cys Lys Arg Thr Cys Pro Arg Asn Gln Pro
            340                 345                 350

Leu Asn Pro Gly Lys Cys Ala Cys Glu Cys Thr Glu Ser Pro Gln Lys
        355                 360                 365

Cys Leu Leu Lys Gly Lys Lys Phe His His Gln Thr Cys Ser Cys Tyr
    370                 375                 380

Arg Arg Pro Cys Thr Asn Arg Gln Lys Ala Cys Glu Pro Gly Phe Ser
385                 390                 395                 400

Tyr Ser Glu Glu Val Cys Arg Cys Val Pro Ser Tyr Trp Lys Arg Pro
                405                 410                 415

Gln Met Ser

<210> SEQ ID NO 329
<211> LENGTH: 1242
<212> TYPE: PRT
<213> ORGANISM: Homo sapiens

<400> SEQUENCE: 329

Met Ala Ser Pro Pro Glu Ser Asp Gly Phe Ser Asp Val Arg Lys Val
1               5                   10                  15

Gly Tyr Leu Arg Lys Pro Lys Ser Met His Lys Arg Phe Phe Val Leu
            20                  25                  30

Arg Ala Ala Ser Glu Ala Gly Gly Pro Ala Arg Leu Glu Tyr Tyr Glu
        35                  40                  45

-continued

```
Asn Glu Lys Lys Trp Arg His Lys Ser Ser Ala Pro Lys Arg Ser Ile
 50                  55                  60

Pro Leu Glu Ser Cys Phe Asn Ile Asn Lys Arg Ala Asp Ser Lys Asn
 65                      70                  75                  80

Lys His Leu Val Ala Leu Tyr Thr Arg Asp Glu His Phe Ala Ile Ala
                     85                  90                  95

Ala Asp Ser Glu Ala Glu Gln Asp Ser Trp Tyr Gln Ala Leu Leu Gln
                100                 105                 110

Leu His Asn Arg Ala Lys Gly His His Asp Gly Ala Ala Ala Leu Gly
                115                 120                 125

Ala Gly Gly Gly Gly Ser Cys Ser Gly Ser Ser Gly Leu Gly Glu
    130                 135                 140

Ala Gly Glu Asp Leu Ser Tyr Gly Asp Val Pro Pro Gly Pro Ala Phe
145                 150                 155                 160

Lys Glu Val Trp Gln Val Ile Leu Lys Pro Lys Gly Leu Gly Gln Thr
                165                 170                 175

Lys Asn Leu Ile Gly Ile Tyr Arg Leu Cys Leu Thr Ser Lys Thr Ile
                180                 185                 190

Ser Phe Val Lys Leu Asn Ser Glu Ala Ala Val Val Leu Gln Leu
                195                 200                 205

Met Asn Ile Arg Arg Cys Gly His Ser Glu Asn Phe Phe Phe Ile Glu
210                 215                 220

Val Gly Arg Ser Ala Val Thr Gly Pro Gly Glu Phe Trp Met Gln Val
225                 230                 235                 240

Asp Asp Ser Val Val Ala Gln Asn Met His Gly Thr Ile Leu Glu Ala
                245                 250                 255

Met Arg Ala Met Ser Asp Glu Phe Arg Pro Arg Ser Lys Ser Gln Ser
                260                 265                 270

Ser Ser Asn Cys Ser Asn Pro Ile Ser Val Pro Leu Arg Arg His His
                275                 280                 285

Leu Asn Asn Pro Pro Ser Gln Val Gly Leu Thr Arg Arg Ser Arg
290                 295                 300

Thr Glu Ser Ile Thr Ala Thr Ser Pro Ala Ser Met Val Gly Gly Lys
305                 310                 315                 320

Pro Gly Ser Phe Arg Val Arg Ala Ser Ser Asp Gly Glu Gly Thr Met
                325                 330                 335

Ser Arg Pro Ala Ser Val Asp Gly Ser Pro Val Ser Pro Ser Thr Asn
                340                 345                 350

Arg Thr His Ala His Arg His Arg Gly Ser Ala Arg Leu His Pro Pro
                355                 360                 365

Leu Asn His Ser Arg Ser Ile Pro Met Pro Ala Ser Arg Cys Ser Pro
370                 375                 380

Ser Ala Thr Ser Pro Val Ser Leu Ser Ser Ser Thr Ser Gly His
385                 390                 395                 400

Gly Ser Thr Ser Asp Cys Leu Phe Pro Arg Arg Ser Ala Ser Val
                405                 410                 415

Ser Gly Ser Pro Ser Asp Gly Gly Phe Ile Ser Ser Asp Glu Tyr Gly
                420                 425                 430

Ser Ser Pro Cys Asp Phe Arg Ser Ser Phe Arg Ser Val Thr Pro Asp
                435                 440                 445

Ser Leu Gly His Thr Pro Pro Ala Arg Gly Glu Glu Leu Ser Asn
    450                 455                 460

Tyr Ile Cys Met Gly Gly Lys Gly Pro Ser Thr Leu Thr Ala Pro Asn
465                 470                 475                 480
```

```
Gly His Tyr Ile Leu Ser Arg Gly Gly Asn Gly His Arg Cys Thr Pro
            485                 490                 495
Gly Thr Gly Leu Gly Thr Ser Pro Ala Leu Ala Gly Asp Glu Ala Ala
            500                 505                 510
Ser Ala Ala Asp Leu Asp Asn Arg Phe Arg Lys Arg Thr His Ser Ala
            515                 520                 525
Gly Thr Ser Pro Thr Ile Thr His Gln Lys Thr Pro Ser Gln Ser Ser
            530                 535                 540
Val Ala Ser Ile Glu Glu Tyr Thr Glu Met Met Pro Ala Tyr Pro Pro
545                 550                 555                 560
Gly Gly Gly Ser Gly Gly Arg Leu Pro Gly His Arg His Ser Ala Phe
                    565                 570                 575
Val Pro Thr Arg Ser Tyr Pro Glu Glu Gly Leu Glu Met His Pro Leu
                580                 585                 590
Glu Arg Arg Gly Gly His His Arg Pro Asp Ser Ser Thr Leu His Thr
                595                 600                 605
Asp Asp Gly Tyr Met Pro Met Ser Pro Gly Val Ala Pro Val Pro Ser
            610                 615                 620
Gly Arg Lys Gly Ser Gly Asp Tyr Met Pro Met Ser Pro Lys Ser Val
625                 630                 635                 640
Ser Ala Pro Gln Gln Ile Ile Asn Pro Ile Arg Arg His Pro Gln Arg
                645                 650                 655
Val Asp Pro Asn Gly Tyr Met Met Met Ser Pro Ser Gly Gly Cys Ser
                660                 665                 670
Pro Asp Ile Gly Gly Gly Pro Ser Ser Ser Ser Ser Ser Ser Asn Ala
            675                 680                 685
Val Pro Ser Gly Thr Ser Tyr Gly Lys Leu Trp Thr Asn Gly Val Gly
            690                 695                 700
Gly His His Ser His Val Leu Pro His Pro Lys Pro Pro Val Glu Ser
705                 710                 715                 720
Ser Gly Gly Lys Leu Leu Pro Cys Thr Gly Asp Tyr Met Asn Met Ser
                725                 730                 735
Pro Val Gly Asp Ser Asn Thr Ser Ser Pro Ser Asp Cys Tyr Tyr Gly
                740                 745                 750
Pro Glu Asp Pro Gln His Lys Pro Val Leu Ser Tyr Tyr Ser Leu Pro
            755                 760                 765
Arg Ser Phe Lys His Thr Gln Arg Pro Gly Glu Pro Glu Glu Gly Ala
            770                 775                 780
Arg His Gln His Leu Arg Leu Ser Thr Ser Ser Gly Arg Leu Leu Tyr
785                 790                 795                 800
Ala Ala Thr Ala Asp Asp Ser Ser Ser Ser Thr Ser Ser Asp Ser Leu
                805                 810                 815
Gly Gly Gly Tyr Cys Gly Ala Arg Leu Glu Pro Ser Leu Pro His Pro
            820                 825                 830
His His Gln Val Leu Gln Pro His Leu Pro Arg Lys Val Asp Thr Ala
            835                 840                 845
Ala Gln Thr Asn Ser Arg Leu Ala Arg Pro Thr Arg Leu Ser Leu Gly
            850                 855                 860
Asp Pro Lys Ala Ser Thr Leu Pro Arg Ala Arg Glu Gln Gln Gln Gln
865                 870                 875                 880
Gln Gln Pro Leu Leu His Pro Pro Glu Pro Lys Ser Pro Gly Glu Tyr
                885                 890                 895
Val Asn Ile Glu Phe Gly Ser Asp Gln Ser Gly Tyr Leu Ser Gly Pro
```

```
                900             905             910
Val Ala Phe His Ser Ser Pro Ser Val Arg Cys Pro Ser Gln Leu Gln
    915                 920                 925

Pro Ala Pro Arg Glu Glu Thr Gly Thr Glu Glu Tyr Met Lys Met
    930                 935                 940

Asp Leu Gly Pro Gly Arg Arg Ala Ala Trp Gln Ser Thr Gly Val
945                 950                 955                 960

Glu Met Gly Arg Leu Gly Pro Ala Pro Gly Ala Ala Ser Ile Cys
                965                 970                 975

Arg Pro Thr Arg Ala Val Pro Ser Ser Arg Gly Asp Tyr Met Thr Met
                    980                 985                 990

Gln Met Ser Cys Pro Arg Gln Ser Tyr Val Asp Thr Ser Pro Ala Ala
                995                 1000                1005

Pro Val Ser Tyr Ala Asp Met Arg Thr Gly Ile Ala Ala Glu Glu
    1010                1015                1020

Val Ser Leu Pro Arg Ala Thr Met Ala Ala Ala Ser Ser Ser Ser
    1025                1030                1035

Ala Ala Ser Ala Ser Pro Thr Gly Pro Gln Gly Ala Ala Glu Leu
    1040                1045                1050

Ala Ala His Ser Ser Leu Leu Gly Gly Pro Gln Gly Pro Gly Gly
    1055                1060                1065

Met Ser Ala Phe Thr Arg Val Asn Leu Ser Pro Asn Arg Asn Gln
    1070                1075                1080

Ser Ala Lys Val Ile Arg Ala Asp Pro Gln Gly Cys Arg Arg Arg
    1085                1090                1095

His Ser Ser Glu Thr Phe Ser Ser Thr Pro Ser Ala Thr Arg Val
    1100                1105                1110

Gly Asn Thr Val Pro Phe Gly Ala Gly Ala Ala Val Gly Gly Gly
    1115                1120                1125

Gly Gly Ser Ser Ser Ser Glu Asp Val Lys Arg His Ser Ser
    1130                1135                1140

Ala Ser Phe Glu Asn Val Trp Leu Arg Pro Gly Glu Leu Gly Gly
    1145                1150                1155

Ala Pro Lys Glu Pro Ala Lys Leu Cys Gly Ala Ala Gly Gly Leu
    1160                1165                1170

Glu Asn Gly Leu Asn Tyr Ile Asp Leu Asp Leu Val Lys Asp Phe
    1175                1180                1185

Lys Gln Cys Pro Gln Glu Cys Thr Pro Glu Pro Gln Pro Pro
    1190                1195                1200

Pro Pro Pro Pro His Gln Pro Leu Gly Ser Gly Glu Ser Ser Ser
    1205                1210                1215

Thr Arg Arg Ser Ser Glu Asp Leu Ser Ala Tyr Ala Ser Ile Ser
    1220                1225                1230

Phe Gln Lys Gln Pro Glu Asp Arg Gln
    1235                1240

<210> SEQ ID NO 330
<211> LENGTH: 170
<212> TYPE: PRT
<213> ORGANISM: Homo sapiens

<400> SEQUENCE: 330

Met Met Ala Gly Met Lys Ile Gln Leu Val Cys Met Leu Leu Leu Ala
1               5                   10                  15

Phe Ser Ser Trp Ser Leu Cys Ser Asp Ser Glu Glu Glu Met Lys Ala
```

```
                    20                  25                  30
Leu Glu Ala Asp Phe Leu Thr Asn Met His Thr Ser Lys Ile Ser Lys
            35                  40                  45

Ala His Val Pro Ser Trp Lys Met Thr Leu Leu Asn Val Cys Ser Leu
        50                  55                  60

Val Asn Asn Leu Asn Ser Pro Ala Glu Glu Thr Gly Glu Val His Glu
65                  70                  75                  80

Glu Glu Leu Val Ala Arg Arg Lys Leu Pro Thr Ala Leu Asp Gly Phe
                85                  90                  95

Ser Leu Glu Ala Met Leu Thr Ile Tyr Gln Leu His Lys Ile Cys His
            100                 105                 110

Ser Arg Ala Phe Gln His Trp Glu Leu Ile Gln Glu Asp Ile Leu Asp
        115                 120                 125

Thr Gly Asn Asp Lys Asn Gly Lys Glu Glu Val Ile Lys Arg Lys Ile
    130                 135                 140

Pro Tyr Ile Leu Lys Arg Gln Leu Tyr Glu Asn Lys Pro Arg Arg Pro
145                 150                 155                 160

Tyr Ile Leu Lys Arg Asp Ser Tyr Tyr Tyr
                165                 170

<210> SEQ ID NO 331
<211> LENGTH: 285
<212> TYPE: PRT
<213> ORGANISM: Homo sapiens

<400> SEQUENCE: 331

Met Asp Asp Ser Thr Glu Arg Glu Gln Ser Arg Leu Thr Ser Cys Leu
1               5                   10                  15

Lys Lys Arg Glu Glu Met Lys Leu Lys Glu Cys Val Ser Ile Leu Pro
                20                  25                  30

Arg Lys Glu Ser Pro Ser Val Arg Ser Ser Lys Asp Gly Lys Leu Leu
            35                  40                  45

Ala Ala Thr Leu Leu Leu Ala Leu Leu Ser Cys Cys Leu Thr Val Val
        50                  55                  60

Ser Phe Tyr Gln Val Ala Ala Leu Gln Gly Asp Leu Ala Ser Leu Arg
65                  70                  75                  80

Ala Glu Leu Gln Gly His His Ala Glu Lys Leu Pro Ala Gly Ala Gly
                85                  90                  95

Ala Pro Lys Ala Gly Leu Glu Glu Ala Pro Ala Val Thr Ala Gly Leu
            100                 105                 110

Lys Ile Phe Glu Pro Pro Ala Pro Gly Glu Gly Asn Ser Ser Gln Asn
        115                 120                 125

Ser Arg Asn Lys Arg Ala Val Gln Gly Pro Glu Glu Thr Val Thr Gln
    130                 135                 140

Asp Cys Leu Gln Leu Ile Ala Asp Ser Glu Thr Pro Thr Ile Gln Lys
145                 150                 155                 160

Gly Ser Tyr Thr Phe Val Pro Trp Leu Leu Ser Phe Lys Arg Gly Ser
                165                 170                 175

Ala Leu Glu Glu Lys Glu Asn Lys Ile Leu Val Lys Glu Thr Gly Tyr
            180                 185                 190

Phe Phe Ile Tyr Gly Gln Val Leu Tyr Thr Asp Lys Thr Tyr Ala Met
        195                 200                 205

Gly His Leu Ile Gln Arg Lys Lys Val His Val Phe Gly Asp Glu Leu
    210                 215                 220

Ser Leu Val Thr Leu Phe Arg Cys Ile Gln Asn Met Pro Glu Thr Leu
```

```
            225                 230                 235                 240
Pro Asn Asn Ser Cys Tyr Ser Ala Gly Ile Ala Lys Leu Glu Glu Gly
                245                 250                 255

Asp Glu Leu Gln Leu Ala Ile Pro Arg Glu Asn Ala Gln Ile Ser Leu
            260                 265                 270

Asp Gly Asp Val Thr Phe Phe Gly Ala Leu Lys Leu Leu
        275                 280                 285

<210> SEQ ID NO 332
<211> LENGTH: 250
<212> TYPE: PRT
<213> ORGANISM: Homo sapiens

<400> SEQUENCE: 332

Met Arg Ile Leu Gln Leu Ile Leu Leu Ala Leu Ala Thr Gly Leu Val
1               5                   10                  15

Gly Gly Glu Thr Arg Ile Ile Lys Gly Phe Glu Cys Lys Pro His Ser
            20                  25                  30

Gln Pro Trp Gln Ala Ala Leu Phe Glu Lys Thr Arg Leu Leu Cys Gly
        35                  40                  45

Ala Thr Leu Ile Ala Pro Arg Trp Leu Leu Thr Ala Ala His Cys Leu
    50                  55                  60

Lys Pro Arg Tyr Ile Val His Leu Gly Gln His Asn Leu Gln Lys Glu
65                  70                  75                  80

Glu Gly Cys Glu Gln Thr Arg Thr Ala Thr Glu Ser Phe Pro His Pro
                85                  90                  95

Gly Phe Asn Asn Ser Leu Pro Asn Lys Asp His Arg Asn Asp Ile Met
            100                 105                 110

Leu Val Lys Met Ala Ser Pro Val Ser Ile Thr Trp Ala Val Arg Pro
        115                 120                 125

Leu Thr Leu Ser Ser Arg Cys Val Thr Ala Gly Thr Ser Cys Leu Ile
    130                 135                 140

Ser Gly Trp Gly Ser Thr Ser Ser Pro Gln Leu Arg Leu Pro His Thr
145                 150                 155                 160

Leu Arg Cys Ala Asn Ile Thr Ile Ile Glu His Gln Lys Cys Glu Asn
                165                 170                 175

Ala Tyr Pro Gly Asn Ile Thr Asp Thr Met Val Cys Ala Ser Val Gln
            180                 185                 190

Glu Gly Gly Lys Asp Ser Cys Gln Gly Asp Ser Gly Gly Pro Leu Val
        195                 200                 205

Cys Asn Gln Ser Leu Gln Gly Ile Ile Ser Trp Gly Gln Asp Pro Cys
    210                 215                 220

Ala Ile Thr Arg Lys Pro Gly Val Tyr Thr Lys Val Cys Lys Tyr Val
225                 230                 235                 240

Asp Trp Ile Gln Glu Thr Met Lys Asn Asn
                245                 250

<210> SEQ ID NO 333
<211> LENGTH: 296
<212> TYPE: PRT
<213> ORGANISM: Homo sapiens

<400> SEQUENCE: 333

Met Glu Ile Tyr Ser Pro Asp Met Ser Glu Val Ala Ala Glu Arg Ser
1               5                   10                  15

Ser Ser Pro Ser Thr Gln Leu Ser Ala Asp Pro Ser Leu Asp Gly Leu
            20                  25                  30
```

Pro Ala Ala Glu Asp Met Pro Glu Pro Gln Thr Glu Asp Gly Arg Thr
            35                  40                  45

Pro Gly Leu Val Gly Leu Ala Val Pro Cys Cys Ala Cys Leu Glu Ala
 50                  55                  60

Glu Arg Leu Arg Gly Cys Leu Asn Ser Glu Lys Ile Cys Ile Val Pro
 65                  70                  75                  80

Ile Leu Ala Cys Leu Val Ser Leu Cys Leu Cys Ile Ala Gly Leu Lys
                 85                  90                  95

Trp Val Phe Val Asp Lys Ile Phe Glu Tyr Asp Ser Pro Thr His Leu
            100                 105                 110

Asp Pro Gly Gly Leu Gly Gln Asp Pro Ile Ile Ser Leu Asp Ala Thr
            115                 120                 125

Ala Ala Ser Ala Val Trp Val Ser Ser Glu Ala Tyr Thr Ser Pro Val
        130                 135                 140

Ser Arg Ala Gln Ser Glu Ser Glu Val Gln Val Thr Val Gln Gly Asp
145                 150                 155                 160

Lys Ala Val Val Ser Phe Glu Pro Ser Ala Ala Pro Thr Pro Lys Asn
                165                 170                 175

Arg Ile Phe Ala Phe Ser Phe Leu Pro Ser Thr Ala Pro Ser Phe Pro
            180                 185                 190

Ser Pro Thr Arg Asn Pro Glu Val Arg Thr Pro Lys Ser Ala Thr Gln
            195                 200                 205

Pro Gln Thr Thr Glu Thr Asn Leu Gln Thr Ala Pro Lys Leu Ser Thr
        210                 215                 220

Ser Thr Ser Thr Thr Gly Thr Ser His Leu Val Lys Cys Ala Glu Lys
225                 230                 235                 240

Glu Lys Thr Phe Cys Val Asn Gly Gly Glu Cys Phe Met Val Lys Asp
                245                 250                 255

Leu Ser Asn Pro Ser Arg Tyr Leu Cys Lys Cys Pro Asn Glu Phe Thr
            260                 265                 270

Gly Asp Arg Cys Gln Asn Tyr Val Met Ala Ser Phe Tyr Ser Thr Ser
        275                 280                 285

Thr Pro Phe Leu Ser Leu Pro Glu
    290                 295

<210> SEQ ID NO 334
<211> LENGTH: 640
<212> TYPE: PRT
<213> ORGANISM: Homo sapiens

<400> SEQUENCE: 334

Met Ser Glu Arg Lys Glu Gly Arg Gly Lys Gly Lys Gly Lys Lys Lys
 1               5                  10                  15

Glu Arg Gly Ser Gly Lys Lys Pro Glu Ser Ala Ala Gly Ser Gln Ser
            20                  25                  30

Pro Ala Leu Pro Pro Arg Leu Lys Glu Met Lys Ser Gln Glu Ser Ala
            35                  40                  45

Ala Gly Ser Lys Leu Val Leu Arg Cys Glu Thr Ser Ser Glu Tyr Ser
        50                  55                  60

Ser Leu Arg Phe Lys Trp Phe Lys Asn Gly Asn Glu Leu Asn Arg Lys
 65                  70                  75                  80

Asn Lys Pro Gln Asn Ile Lys Ile Gln Lys Lys Pro Gly Lys Ser Glu
                 85                  90                  95

Leu Arg Ile Asn Lys Ala Ser Leu Ala Asp Ser Gly Glu Tyr Met Cys
            100                 105                 110

```
Lys Val Ile Ser Lys Leu Gly Asn Asp Ser Ala Ser Ala Asn Ile Thr
            115                 120                 125

Ile Val Glu Ser Asn Glu Ile Ile Thr Gly Met Pro Ala Ser Thr Glu
        130                 135                 140

Gly Ala Tyr Val Ser Ser Glu Ser Pro Ile Arg Ile Ser Val Ser Thr
145                 150                 155                 160

Glu Gly Ala Asn Thr Ser Ser Ser Thr Ser Ser Thr Thr Gly Thr
                    165                 170                 175

Ser His Leu Val Lys Cys Ala Glu Lys Glu Lys Thr Phe Cys Val Asn
            180                 185                 190

Gly Gly Glu Cys Phe Met Val Lys Asp Leu Ser Asn Pro Ser Arg Tyr
            195                 200                 205

Leu Cys Lys Cys Gln Pro Gly Phe Thr Gly Ala Arg Cys Thr Glu Asn
            210                 215                 220

Val Pro Met Lys Val Gln Asn Gln Glu Lys Ala Glu Glu Leu Tyr Gln
225                 230                 235                 240

Lys Arg Val Leu Thr Ile Thr Gly Ile Cys Ile Ala Leu Leu Val Val
                    245                 250                 255

Gly Ile Met Cys Val Val Ala Tyr Cys Lys Thr Lys Lys Gln Arg Lys
                260                 265                 270

Lys Leu His Asp Arg Leu Arg Gln Ser Leu Arg Ser Glu Arg Asn Asn
            275                 280                 285

Met Met Asn Ile Ala Asn Gly Pro His His Pro Asn Pro Pro Pro Glu
        290                 295                 300

Asn Val Gln Leu Val Asn Gln Tyr Val Ser Lys Asn Val Ile Ser Ser
305                 310                 315                 320

Glu His Ile Val Glu Arg Glu Ala Glu Thr Ser Phe Ser Thr Ser His
                325                 330                 335

Tyr Thr Ser Thr Ala His His Ser Thr Thr Val Thr Gln Thr Pro Ser
                340                 345                 350

His Ser Trp Ser Asn Gly His Thr Glu Ser Ile Leu Ser Glu Ser His
            355                 360                 365

Ser Val Ile Val Met Ser Ser Val Glu Asn Ser Arg His Ser Ser Pro
        370                 375                 380

Thr Gly Gly Pro Arg Gly Arg Leu Asn Gly Thr Gly Gly Pro Arg Glu
385                 390                 395                 400

Cys Asn Ser Phe Leu Arg His Ala Arg Glu Thr Pro Asp Ser Tyr Arg
                405                 410                 415

Asp Ser Pro His Ser Glu Arg Tyr Val Ser Ala Met Thr Thr Pro Ala
                420                 425                 430

Arg Met Ser Pro Val Asp Phe His Thr Pro Ser Ser Pro Lys Ser Pro
            435                 440                 445

Pro Ser Glu Met Ser Pro Pro Val Ser Ser Met Thr Val Ser Met Pro
450                 455                 460

Ser Met Ala Val Ser Pro Phe Met Glu Glu Glu Arg Pro Leu Leu Leu
465                 470                 475                 480

Val Thr Pro Pro Arg Leu Arg Glu Lys Lys Phe Asp His His Pro Gln
                485                 490                 495

Gln Phe Ser Ser Phe His His Asn Pro Ala His Asp Ser Asn Ser Leu
            500                 505                 510

Pro Ala Ser Pro Leu Arg Ile Val Glu Asp Glu Glu Tyr Glu Thr Thr
            515                 520                 525

Gln Glu Tyr Glu Pro Ala Gln Glu Pro Val Lys Lys Leu Ala Asn Ser
```

```
                530                 535                 540
Arg Arg Ala Lys Arg Thr Lys Pro Asn Gly His Ile Ala Asn Arg Leu
545                 550                 555                 560

Glu Val Asp Ser Asn Thr Ser Ser Gln Ser Ser Asn Ser Glu Ser Glu
                565                 570                 575

Thr Glu Asp Glu Arg Val Gly Glu Asp Thr Pro Phe Leu Gly Ile Gln
                580                 585                 590

Asn Pro Leu Ala Ala Ser Leu Glu Ala Thr Pro Ala Phe Arg Leu Ala
                595                 600                 605

Asp Ser Arg Thr Asn Pro Ala Gly Arg Phe Ser Thr Gln Glu Glu Ile
                610                 615                 620

Gln Ala Arg Leu Ser Ser Val Ile Ala Asn Gln Asp Pro Ile Ala Val
625                 630                 635                 640

<210> SEQ ID NO 335
<211> LENGTH: 465
<212> TYPE: PRT
<213> ORGANISM: Homo sapiens

<400> SEQUENCE: 335

Met Ala Ser Gln Leu Thr Gln Arg Gly Ala Leu Phe Leu Leu Phe Phe
1               5                   10                  15

Leu Thr Pro Ala Val Thr Pro Thr Trp Tyr Ala Gly Ser Gly Tyr Tyr
                20                  25                  30

Pro Asp Glu Ser Tyr Asn Glu Val Tyr Ala Glu Glu Val Pro Gln Ala
                35                  40                  45

Pro Ala Leu Asp Tyr Arg Val Pro Arg Trp Cys Tyr Thr Leu Asn Ile
50                  55                  60

Gln Asp Gly Glu Ala Thr Cys Tyr Ser Pro Lys Gly Asn Tyr His
65                  70                  75                  80

Ser Ser Leu Gly Thr Arg Cys Glu Leu Ser Cys Asp Arg Gly Phe Arg
                85                  90                  95

Leu Ile Gly Arg Arg Ser Val Gln Cys Leu Pro Ser Arg Arg Trp Ser
                100                 105                 110

Gly Thr Ala Tyr Cys Arg Gln Met Arg Cys His Ala Leu Pro Phe Ile
                115                 120                 125

Thr Ser Gly Thr Tyr Thr Cys Thr Asn Gly Val Leu Leu Asp Ser Arg
                130                 135                 140

Cys Asp Tyr Ser Cys Ser Ser Gly Tyr His Leu Glu Gly Asp Arg Ser
145                 150                 155                 160

Arg Ile Cys Met Glu Asp Gly Arg Trp Ser Gly Glu Pro Val Cys
                165                 170                 175

Val Asp Ile Asp Pro Pro Lys Ile Arg Cys Pro His Ser Arg Glu Lys
                180                 185                 190

Met Ala Glu Pro Glu Lys Leu Thr Ala Arg Val Tyr Trp Asp Pro Pro
                195                 200                 205

Leu Val Lys Asp Ser Ala Asp Gly Thr Ile Thr Arg Val Thr Leu Arg
                210                 215                 220

Gly Pro Glu Pro Gly Ser His Phe Pro Glu Gly Glu His Val Ile Arg
225                 230                 235                 240

Tyr Thr Ala Tyr Asp Arg Ala Tyr Asn Arg Ala Ser Cys Lys Phe Ile
                245                 250                 255

Val Lys Val Gln Val Arg Arg Cys Pro Thr Leu Lys Pro Pro Gln His
                260                 265                 270

Gly Tyr Leu Thr Cys Thr Ser Ala Gly Asp Asn Tyr Gly Ala Thr Cys
```

```
                275                 280                 285
Glu Tyr His Cys Asp Gly Gly Tyr Asp Arg Gln Gly Thr Pro Ser Arg
290                 295                 300

Val Cys Gln Ser Ser Arg Gln Trp Ser Gly Ser Pro Pro Ile Cys Ala
305                 310                 315                 320

Pro Met Lys Ile Asn Val Asn Val Asn Ser Ala Ala Gly Leu Leu Asp
                325                 330                 335

Gln Phe Tyr Glu Lys Gln Arg Leu Leu Ile Ile Ser Ala Pro Asp Pro
                340                 345                 350

Ser Asn Arg Tyr Tyr Lys Met Gln Ile Ser Met Leu Gln Gln Ser Thr
                355                 360                 365

Cys Gly Leu Asp Leu Arg His Val Thr Ile Ile Glu Leu Val Gly Gln
                370                 375                 380

Pro Pro Gln Glu Val Gly Arg Ile Arg Glu Gln Gln Leu Ser Ala Asn
385                 390                 395                 400

Ile Ile Glu Glu Leu Arg Gln Phe Gln Arg Leu Thr Arg Ser Tyr Phe
                405                 410                 415

Asn Met Val Leu Ile Asp Lys Gln Gly Ile Asp Arg Asp Arg Tyr Met
                420                 425                 430

Glu Pro Val Thr Pro Glu Glu Ile Phe Thr Phe Ile Asp Asp Tyr Leu
                435                 440                 445

Leu Ser Asn Gln Glu Leu Thr Gln Arg Arg Glu Gln Arg Asp Ile Cys
                450                 455                 460

Glu
465

<210> SEQ ID NO 336
<211> LENGTH: 345
<212> TYPE: PRT
<213> ORGANISM: Homo sapiens

<400> SEQUENCE: 336

Met Ser Leu Phe Gly Leu Leu Leu Thr Ser Ala Leu Ala Gly Gln
1               5                   10                  15

Arg Gln Gly Thr Gln Ala Glu Ser Asn Leu Ser Ser Lys Phe Gln Phe
                20                  25                  30

Ser Ser Asn Lys Glu Gln Asn Gly Val Gln Asp Pro Gln His Glu Arg
                35                  40                  45

Ile Ile Thr Val Ser Thr Asn Gly Ser Ile His Ser Pro Arg Phe Pro
50                  55                  60

His Thr Tyr Pro Arg Asn Thr Val Leu Val Trp Arg Leu Val Ala Val
65                  70                  75                  80

Glu Glu Asn Val Trp Ile Gln Leu Thr Phe Asp Glu Arg Phe Gly Leu
                85                  90                  95

Glu Asp Pro Glu Asp Asp Ile Cys Lys Tyr Asp Phe Val Glu Val Glu
                100                 105                 110

Glu Pro Ser Asp Gly Thr Ile Leu Gly Arg Trp Cys Gly Ser Gly Thr
                115                 120                 125

Val Pro Gly Lys Gln Ile Ser Lys Gly Asn Gln Ile Arg Ile Arg Phe
130                 135                 140

Val Ser Asp Glu Tyr Phe Pro Ser Glu Pro Gly Phe Cys Ile His Tyr
145                 150                 155                 160

Asn Ile Val Met Pro Gln Phe Thr Glu Ala Val Ser Pro Ser Val Leu
                165                 170                 175

Pro Pro Ser Ala Leu Pro Leu Asp Leu Leu Asn Asn Ala Ile Thr Ala
```

```
                180                 185                 190
Phe Ser Thr Leu Glu Asp Leu Ile Arg Tyr Leu Glu Pro Glu Arg Trp
        195                 200                 205
Gln Leu Asp Leu Glu Asp Leu Tyr Arg Pro Thr Trp Gln Leu Leu Gly
        210                 215                 220
Lys Ala Phe Val Phe Gly Arg Lys Ser Arg Val Val Asp Leu Asn Leu
225                 230                 235                 240
Leu Thr Glu Glu Val Arg Leu Tyr Ser Cys Thr Pro Arg Asn Phe Ser
                245                 250                 255
Val Ser Ile Arg Glu Glu Leu Lys Arg Thr Asp Thr Ile Phe Trp Pro
                260                 265                 270
Gly Cys Leu Leu Val Lys Arg Cys Gly Gly Asn Cys Ala Cys Cys Leu
                275                 280                 285
His Asn Cys Asn Glu Cys Gln Cys Val Pro Ser Lys Val Thr Lys Lys
        290                 295                 300
Tyr His Glu Val Leu Gln Leu Arg Pro Lys Thr Gly Val Arg Gly Leu
305                 310                 315                 320
His Lys Ser Leu Thr Asp Val Ala Leu Glu His His Glu Glu Cys Asp
                325                 330                 335
Cys Val Cys Arg Gly Ser Thr Gly Gly
                340                 345

<210> SEQ ID NO 337
<211> LENGTH: 211
<212> TYPE: PRT
<213> ORGANISM: Homo sapiens

<400> SEQUENCE: 337

Met Ala Pro Leu Ala Glu Val Gly Gly Phe Leu Gly Gly Leu Glu Gly
1               5                   10                  15
Leu Gly Gln Gln Val Gly Ser His Phe Leu Pro Pro Ala Gly Glu
        20                  25                  30
Arg Pro Pro Leu Leu Gly Glu Arg Ser Ala Ala Glu Arg Ser Ala
        35                  40                  45
Arg Gly Gly Pro Gly Ala Ala Gln Leu Ala His Leu His Gly Ile Leu
50                  55                  60
Arg Arg Arg Gln Leu Tyr Cys Arg Thr Gly Phe His Leu Gln Ile Leu
65                  70                  75                  80
Pro Asp Gly Ser Val Gln Gly Thr Arg Gln Asp His Ser Leu Phe Gly
                85                  90                  95
Ile Leu Glu Phe Ile Ser Val Ala Val Gly Leu Val Ser Ile Arg Gly
                100                 105                 110
Val Asp Ser Gly Leu Tyr Leu Gly Met Asn Asp Lys Gly Glu Leu Tyr
        115                 120                 125
Gly Ser Glu Lys Leu Thr Ser Glu Cys Ile Phe Arg Glu Gln Phe Glu
130                 135                 140
Glu Asn Trp Tyr Asn Thr Tyr Ser Ser Asn Ile Tyr Lys His Gly Asp
145                 150                 155                 160
Thr Gly Arg Arg Tyr Phe Val Ala Leu Asn Lys Asp Gly Thr Pro Arg
                165                 170                 175
Asp Gly Ala Arg Ser Lys Arg His Gln Lys Phe Thr His Phe Leu Pro
        180                 185                 190
Arg Pro Val Asp Pro Glu Arg Val Pro Glu Leu Tyr Lys Asp Leu Leu
        195                 200                 205
Met Tyr Thr
```

-continued

<210> SEQ ID NO 338
<211> LENGTH: 252
<212> TYPE: PRT
<213> ORGANISM: Homo sapiens

<400> SEQUENCE: 338

Met Gly Val Leu Leu Thr Gln Arg Thr Leu Leu Ser Leu Val Leu Ala
1               5                   10                  15

Leu Leu Phe Pro Ser Met Ala Ser Met Ala Ala Ile Gly Ser Cys Ser
            20                  25                  30

Lys Glu Tyr Arg Val Leu Leu Gly Gln Leu Gln Lys Gln Thr Asp Leu
        35                  40                  45

Met Gln Asp Thr Ser Arg Leu Leu Asp Pro Tyr Ile Arg Ile Gln Gly
    50                  55                  60

Leu Asp Val Pro Lys Leu Arg Glu His Cys Arg Glu Arg Pro Gly Ala
65                  70                  75                  80

Phe Pro Ser Glu Glu Thr Leu Arg Gly Leu Gly Arg Arg Gly Phe Leu
                85                  90                  95

Gln Thr Leu Asn Ala Thr Leu Gly Cys Val Leu His Arg Leu Ala Asp
            100                 105                 110

Leu Glu Gln Arg Leu Pro Lys Ala Gln Asp Leu Glu Arg Ser Gly Leu
        115                 120                 125

Asn Ile Glu Asp Leu Glu Lys Leu Gln Met Ala Arg Pro Asn Ile Leu
    130                 135                 140

Gly Leu Arg Asn Asn Ile Tyr Cys Met Ala Gln Leu Leu Asp Asn Ser
145                 150                 155                 160

Asp Thr Ala Glu Pro Thr Lys Ala Gly Arg Gly Ala Ser Gln Pro Pro
                165                 170                 175

Thr Pro Thr Pro Ala Ser Asp Ala Phe Gln Arg Lys Leu Glu Gly Cys
            180                 185                 190

Arg Phe Leu His Gly Tyr His Arg Phe Met His Ser Val Gly Arg Val
        195                 200                 205

Phe Ser Lys Trp Gly Glu Ser Pro Asn Arg Ser Arg Arg His Ser Pro
    210                 215                 220

His Gln Ala Leu Arg Lys Gly Val Arg Arg Thr Arg Pro Ser Arg Lys
225                 230                 235                 240

Gly Lys Arg Leu Met Thr Arg Gly Gln Leu Pro Arg
                245                 250

<210> SEQ ID NO 339
<211> LENGTH: 208
<212> TYPE: PRT
<213> ORGANISM: Homo sapiens

<400> SEQUENCE: 339

Met Ala Leu Gly Gln Lys Leu Phe Ile Thr Met Ser Arg Gly Ala Gly
1               5                   10                  15

Arg Leu Gln Gly Thr Leu Trp Ala Leu Val Phe Leu Gly Ile Leu Val
            20                  25                  30

Gly Met Val Val Pro Ser Pro Ala Gly Thr Arg Ala Asn Asn Thr Leu
        35                  40                  45

Leu Asp Ser Arg Gly Trp Gly Thr Leu Leu Ser Arg Ser Arg Ala Gly
    50                  55                  60

Leu Ala Gly Glu Ile Ala Gly Val Asn Trp Gly Ser Gly Tyr Leu Val
65                  70                  75                  80

Gly Ile Lys Arg Gln Arg Arg Leu Tyr Cys Asn Val Gly Ile Gly Phe
                85                  90                  95

His Leu Gln Val Leu Pro Asp Gly Arg Ile Ser Gly Thr His Glu Glu
            100                 105                 110

Asn Pro Tyr Ser Leu Leu Glu Ile Ser Thr Val Glu Arg Gly Val Val
        115                 120                 125

Ser Leu Phe Gly Val Arg Ser Ala Leu Phe Val Ala Met Asn Ser Lys
130                 135                 140

Gly Arg Leu Tyr Ala Thr Pro Ser Phe Gln Glu Glu Cys Lys Phe Arg
145                 150                 155                 160

Glu Thr Leu Leu Pro Asn Asn Tyr Asn Ala Tyr Glu Ser Asp Leu Tyr
                165                 170                 175

Gln Gly Thr Tyr Ile Ala Leu Ser Lys Tyr Gly Arg Val Lys Arg Gly
            180                 185                 190

Ser Lys Val Ser Pro Ile Met Thr Val Thr His Phe Leu Pro Arg Ile
        195                 200                 205

<210> SEQ ID NO 340
<211> LENGTH: 370
<212> TYPE: PRT
<213> ORGANISM: Homo sapiens

<400> SEQUENCE: 340

Met His Arg Leu Ile Phe Val Tyr Thr Leu Ile Cys Ala Asn Phe Cys
1               5                   10                  15

Ser Cys Arg Asp Thr Ser Ala Thr Pro Gln Ser Ala Ser Ile Lys Ala
                20                  25                  30

Leu Arg Asn Ala Asn Leu Arg Arg Asp Glu Ser Asn His Leu Thr Asp
            35                  40                  45

Leu Tyr Arg Arg Asp Glu Thr Ile Gln Val Lys Gly Asn Gly Tyr Val
        50                  55                  60

Gln Ser Pro Arg Phe Pro Asn Ser Tyr Pro Arg Asn Leu Leu Leu Thr
65                  70                  75                  80

Trp Arg Leu His Ser Gln Glu Asn Thr Arg Ile Gln Leu Val Phe Asp
                85                  90                  95

Asn Gln Phe Gly Leu Glu Glu Ala Glu Asn Asp Ile Cys Arg Tyr Asp
            100                 105                 110

Phe Val Glu Val Glu Asp Ile Ser Glu Thr Ser Thr Ile Ile Arg Gly
        115                 120                 125

Arg Trp Cys Gly His Lys Glu Val Pro Pro Arg Ile Lys Ser Arg Thr
130                 135                 140

Asn Gln Ile Lys Ile Thr Phe Lys Ser Asp Asp Tyr Phe Val Ala Lys
145                 150                 155                 160

Pro Gly Phe Lys Ile Tyr Tyr Ser Leu Leu Glu Asp Phe Gln Pro Ala
                165                 170                 175

Ala Ala Ser Glu Thr Asn Trp Glu Ser Val Thr Ser Ser Ile Ser Gly
            180                 185                 190

Val Ser Tyr Asn Ser Pro Ser Val Thr Asp Pro Thr Leu Ile Ala Asp
        195                 200                 205

Ala Leu Asp Lys Lys Ile Ala Glu Phe Asp Thr Val Glu Asp Leu Leu
210                 215                 220

Lys Tyr Phe Asn Pro Glu Ser Trp Gln Glu Asp Leu Glu Asn Met Tyr
225                 230                 235                 240

Leu Asp Thr Pro Arg Tyr Arg Gly Arg Ser Tyr His Asp Arg Lys Ser
                245                 250                 255

```
Lys Val Asp Leu Asp Arg Leu Asn Asp Asp Ala Lys Arg Tyr Ser Cys
            260                 265                 270

Thr Pro Arg Asn Tyr Ser Val Asn Ile Arg Glu Glu Leu Lys Leu Ala
        275                 280                 285

Asn Val Val Phe Phe Pro Arg Cys Leu Leu Val Gln Arg Cys Gly Gly
    290                 295                 300

Asn Cys Gly Cys Gly Thr Val Asn Trp Arg Ser Cys Thr Cys Asn Ser
305                 310                 315                 320

Gly Lys Thr Val Lys Lys Tyr His Glu Val Leu Gln Phe Glu Pro Gly
                325                 330                 335

His Ile Lys Arg Arg Gly Arg Ala Lys Thr Met Ala Leu Val Asp Ile
                340                 345                 350

Gln Leu Asp His His Glu Arg Cys Asp Cys Ile Cys Ser Ser Arg Pro
            355                 360                 365

Pro Arg
    370

<210> SEQ ID NO 341
<211> LENGTH: 352
<212> TYPE: PRT
<213> ORGANISM: Homo sapiens

<400> SEQUENCE: 341

Met Ala Pro Leu Gly Tyr Phe Leu Leu Leu Cys Ser Leu Lys Gln Ala
1               5                   10                  15

Leu Gly Ser Tyr Pro Ile Trp Trp Ser Leu Ala Val Gly Pro Gln Tyr
            20                  25                  30

Ser Ser Leu Gly Ser Gln Pro Ile Leu Cys Ala Ser Ile Pro Gly Leu
        35                  40                  45

Val Pro Lys Gln Leu Arg Phe Cys Arg Asn Tyr Val Glu Ile Met Pro
    50                  55                  60

Ser Val Ala Glu Gly Ile Lys Ile Gly Ile Gln Glu Cys Gln His Gln
65                  70                  75                  80

Phe Arg Gly Arg Arg Trp Asn Cys Thr Thr Val His Asp Ser Leu Ala
                85                  90                  95

Ile Phe Gly Pro Val Leu Asp Lys Ala Thr Arg Glu Ser Ala Phe Val
            100                 105                 110

His Ala Ile Ala Ser Ala Gly Val Ala Phe Ala Val Thr Arg Ser Cys
        115                 120                 125

Ala Glu Gly Thr Ala Ala Ile Cys Gly Cys Ser Ser Arg His Gln Gly
    130                 135                 140

Ser Pro Gly Lys Gly Trp Lys Trp Gly Gly Cys Ser Glu Asp Ile Glu
145                 150                 155                 160

Phe Gly Gly Met Val Ser Arg Glu Phe Ala Asp Ala Arg Glu Asn Arg
                165                 170                 175

Pro Asp Ala Arg Ser Ala Met Asn Arg His Asn Asn Glu Ala Gly Arg
            180                 185                 190

Gln Ala Ile Ala Ser His Met His Leu Lys Cys Lys Cys His Gly Leu
        195                 200                 205

Ser Gly Ser Cys Glu Val Lys Thr Cys Trp Trp Ser Gln Pro Asp Phe
    210                 215                 220

Arg Ala Ile Gly Asp Phe Leu Lys Asp Lys Tyr Asp Ser Ala Ser Glu
225                 230                 235                 240

Met Val Val Glu Lys His Arg Glu Ser Arg Gly Trp Val Glu Thr Leu
                245                 250                 255
```

-continued

Arg Pro Arg Tyr Thr Tyr Phe Lys Val Pro Thr Glu Arg Asp Leu Val
                260                 265                 270

Tyr Tyr Glu Ala Ser Pro Asn Phe Cys Glu Pro Asn Pro Glu Thr Gly
            275                 280                 285

Ser Phe Gly Thr Arg Asp Arg Thr Cys Asn Val Ser Ser His Gly Ile
        290                 295                 300

Asp Gly Cys Asp Leu Leu Cys Cys Gly Arg Gly His Asn Ala Arg Ala
305                 310                 315                 320

Glu Arg Arg Arg Glu Lys Cys Arg Cys Val Phe His Trp Cys Cys Tyr
                325                 330                 335

Val Ser Cys Gln Glu Cys Thr Arg Val Tyr Asp Val His Thr Cys Lys
            340                 345                 350

<210> SEQ ID NO 342
<211> LENGTH: 244
<212> TYPE: PRT
<213> ORGANISM: Homo sapiens

<400> SEQUENCE: 342

Met Gly Ser Pro Arg Ser Ala Leu Ser Cys Leu Leu Leu His Leu Leu
1               5                   10                  15

Val Leu Cys Leu Gln Ala Gln Glu Gly Pro Gly Arg Gly Pro Ala Leu
            20                  25                  30

Gly Arg Glu Leu Ala Ser Leu Phe Arg Ala Gly Arg Glu Pro Gln Gly
        35                  40                  45

Val Ser Gln Gln Val Thr Val Gln Ser Ser Pro Asn Phe Thr Gln His
    50                  55                  60

Val Arg Glu Gln Ser Leu Val Thr Asp Gln Leu Ser Arg Arg Leu Ile
65                  70                  75                  80

Arg Thr Tyr Gln Leu Tyr Ser Arg Thr Ser Gly Lys His Val Gln Val
                85                  90                  95

Leu Ala Asn Lys Arg Ile Asn Ala Met Ala Glu Asp Gly Asp Pro Phe
            100                 105                 110

Ala Lys Leu Ile Val Glu Thr Asp Thr Phe Gly Ser Arg Val Arg Val
        115                 120                 125

Arg Gly Ala Glu Thr Gly Leu Tyr Ile Cys Met Asn Lys Lys Gly Lys
    130                 135                 140

Leu Ile Ala Lys Ser Asn Gly Lys Gly Lys Asp Cys Val Phe Thr Glu
145                 150                 155                 160

Ile Val Leu Glu Asn Asn Tyr Thr Ala Leu Gln Asn Ala Lys Tyr Glu
                165                 170                 175

Gly Trp Tyr Met Ala Phe Thr Arg Lys Gly Arg Pro Arg Lys Gly Ser
            180                 185                 190

Lys Thr Arg Gln His Gln Arg Glu Val His Phe Met Lys Arg Leu Pro
        195                 200                 205

Arg Gly His His Thr Thr Glu Gln Ser Leu Arg Phe Glu Phe Leu Asn
    210                 215                 220

Tyr Pro Pro Phe Thr Arg Ser Leu Arg Gly Ser Gln Arg Thr Trp Ala
225                 230                 235                 240

Pro Glu Pro Arg

<210> SEQ ID NO 343
<211> LENGTH: 115
<212> TYPE: PRT
<213> ORGANISM: Homo sapiens

```
<400> SEQUENCE: 343

Met Pro Thr Asp His Glu Glu Pro Cys Gly Pro Ser His Lys Ser Phe
1               5                   10                  15

Cys Leu Asn Gly Gly Leu Cys Tyr Val Ile Pro Thr Ile Pro Ser Pro
            20                  25                  30

Phe Cys Arg Cys Val Glu Asn Tyr Thr Gly Ala Arg Cys Glu Glu Val
        35                  40                  45

Phe Leu Pro Gly Ser Ser Ile Gln Thr Lys Ser Asn Leu Phe Glu Ala
    50                  55                  60

Phe Val Ala Leu Ala Val Leu Val Thr Leu Ile Ile Gly Ala Phe Tyr
65                  70                  75                  80

Phe Leu Cys Arg Lys Gly His Phe Gln Arg Ala Ser Ser Val Gln Tyr
                85                  90                  95

Asp Ile Asn Leu Val Glu Thr Ser Ser Thr Ser Ala His His Ser His
            100                 105                 110

Glu Gln His
        115

<210> SEQ ID NO 344
<211> LENGTH: 282
<212> TYPE: PRT
<213> ORGANISM: Homo sapiens

<400> SEQUENCE: 344

Met Gln Arg Leu Arg Trp Leu Arg Asp Trp Lys Ser Ser Gly Arg Gly
1               5                   10                  15

Leu Thr Ala Ala Lys Glu Pro Gly Ala Arg Ser Ser Pro Leu Gln Ala
            20                  25                  30

Met Arg Ile Leu Gln Leu Ile Leu Leu Ala Leu Ala Thr Gly Leu Val
        35                  40                  45

Gly Gly Glu Thr Arg Ile Ile Lys Gly Phe Glu Cys Lys Pro His Ser
    50                  55                  60

Gln Pro Trp Gln Ala Ala Leu Phe Glu Lys Thr Arg Leu Leu Cys Gly
65                  70                  75                  80

Ala Thr Leu Ile Ala Pro Arg Trp Leu Leu Thr Ala Ala His Cys Leu
                85                  90                  95

Lys Pro Arg Tyr Ile Val His Leu Gly Gln His Asn Leu Gln Lys Glu
            100                 105                 110

Glu Gly Cys Glu Gln Thr Arg Thr Ala Thr Glu Ser Phe Pro His Pro
        115                 120                 125

Gly Phe Asn Asn Ser Leu Pro Asn Lys Asp His Arg Asn Asp Ile Met
    130                 135                 140

Leu Val Lys Met Ala Ser Pro Val Ser Ile Thr Trp Ala Val Arg Pro
145                 150                 155                 160

Leu Thr Leu Ser Ser Arg Cys Val Thr Ala Gly Thr Ser Cys Leu Ile
                165                 170                 175

Ser Gly Trp Gly Ser Thr Ser Ser Pro Gln Leu Arg Leu Pro His Thr
            180                 185                 190

Leu Arg Cys Ala Asn Ile Thr Ile Ile Glu His Gln Lys Cys Glu Asn
        195                 200                 205

Ala Tyr Pro Gly Asn Ile Thr Asp Thr Met Val Cys Ala Ser Val Gln
    210                 215                 220

Glu Gly Gly Lys Asp Ser Cys Gln Gly Asp Ser Gly Gly Pro Leu Val
225                 230                 235                 240

Cys Asn Gln Ser Leu Gln Gly Ile Ile Ser Trp Gly Gln Asp Pro Cys
```

```
                    245                 250                 255
Ala Ile Thr Arg Lys Pro Gly Val Tyr Thr Lys Val Cys Lys Tyr Val
                260                 265                 270

Asp Trp Ile Gln Glu Thr Met Lys Asn Asn
            275                 280

<210> SEQ ID NO 345
<211> LENGTH: 988
<212> TYPE: PRT
<213> ORGANISM: Homo sapiens

<400> SEQUENCE: 345

Met Gly Ala Ala Ala Val Arg Trp His Leu Cys Val Leu Ala Leu Leu
1               5                   10                  15

Gly Thr Arg Gly Arg Leu Ala Gly Gly Ser Gly Leu Pro Gly Ser Val
            20                  25                  30

Asp Val Asp Glu Cys Ser Glu Gly Thr Asp Asp Cys His Ile Asp Ala
        35                  40                  45

Ile Cys Gln Asn Ala Pro Lys Ser Tyr Lys Cys Leu Cys Lys Pro Gly
    50                  55                  60

Tyr Lys Gly Glu Gly Lys Gln Cys Gly Asp Ile Asp Glu Cys Glu Asn
65                  70                  75                  80

Asp Tyr Tyr Asn Gly Gly Cys Val His Glu Cys Ile Asn Ile Pro Gly
                85                  90                  95

Asn Tyr Arg Cys Thr Cys Phe Asp Gly Phe Met Leu Ala His Asp Gly
            100                 105                 110

His Asn Cys Leu Asp Val Asp Glu Cys Gln Asp Asn Asn Gly Gly Cys
        115                 120                 125

Gln Gln Ile Cys Val Asn Ala Met Gly Ser Tyr Glu Cys Gln Cys His
    130                 135                 140

Ser Gly Phe Phe Leu Ser Asp Asn Gln His Thr Cys Ile His Arg Ser
145                 150                 155                 160

Asn Glu Gly Met Asn Cys Met Asn Lys Asp His Gly Cys Ala His Ile
                165                 170                 175

Cys Arg Glu Thr Pro Lys Gly Gly Val Ala Cys Asp Cys Arg Pro Gly
            180                 185                 190

Phe Asp Leu Ala Gln Asn Gln Lys Asp Cys Thr Leu Thr Cys Asn Tyr
        195                 200                 205

Gly Asn Gly Gly Cys Gln His Ser Cys Glu Asp Thr Asp Thr Gly Pro
    210                 215                 220

Thr Cys Gly Cys His Gln Lys Tyr Ala Pro His Ser Asp Gly Arg Thr
225                 230                 235                 240

Cys Ile Glu Thr Cys Ala Val Asn Asn Gly Gly Cys Asp Arg Thr Cys
                245                 250                 255

Lys Asp Thr Ala Thr Gly Val Arg Cys Ser Cys Pro Val Gly Phe Thr
            260                 265                 270

Leu Gln Pro Asp Gly Lys Thr Cys Lys Asp Ile Asn Glu Cys Leu Val
        275                 280                 285

Asn Asn Gly Gly Cys Asp His Phe Cys Arg Asn Thr Val Gly Ser Phe
    290                 295                 300

Glu Cys Gly Cys Arg Lys Gly Tyr Lys Leu Leu Thr Asp Glu Arg Thr
305                 310                 315                 320

Cys Gln Asp Ile Asp Glu Cys Ser Phe Glu Arg Thr Cys Asp His Ile
                325                 330                 335

Cys Ile Asn Ser Pro Gly Ser Phe Gln Cys Leu Cys His Arg Gly Tyr
```

-continued

```
                    340                 345                 350
Ile Leu Tyr Gly Thr Thr His Cys Gly Asp Val Asp Glu Cys Ser Met
                355                 360                 365
Ser Asn Gly Ser Cys Asp Gln Gly Cys Val Asn Thr Lys Gly Ser Tyr
            370                 375                 380
Glu Cys Val Cys Pro Pro Gly Arg Arg Leu His Trp Asn Arg Lys Asp
385                 390                 395                 400
Cys Val Glu Thr Gly Lys Cys Leu Ser Arg Ala Lys Thr Ser Pro Arg
                405                 410                 415
Ala Gln Leu Ser Cys Ser Lys Ala Gly Val Glu Ser Cys Phe Leu
                420                 425                 430
Ser Cys Pro Ala His Thr Leu Phe Val Pro Asp Ser Glu Asn Ser Tyr
            435                 440                 445
Val Leu Ser Cys Gly Val Pro Gly Pro Gln Gly Lys Ala Leu Gln Lys
        450                 455                 460
Arg Asn Gly Thr Ser Ser Gly Leu Gly Pro Ser Cys Ser Asp Ala Pro
465                 470                 475                 480
Thr Thr Pro Ile Lys Gln Lys Ala Arg Phe Lys Ile Arg Asp Ala Lys
                485                 490                 495
Cys His Leu Arg Pro His Ser Gln Ala Arg Ala Lys Glu Thr Ala Arg
                500                 505                 510
Gln Pro Leu Leu Asp His Cys His Val Thr Phe Val Thr Leu Lys Cys
            515                 520                 525
Asp Ser Ser Lys Lys Arg Arg Arg Gly Arg Lys Ser Pro Ser Lys Glu
        530                 535                 540
Val Ser His Ile Thr Ala Glu Phe Glu Ile Glu Thr Lys Met Glu Glu
545                 550                 555                 560
Ala Ser Asp Thr Cys Glu Ala Asp Cys Leu Arg Lys Arg Ala Glu Gln
                565                 570                 575
Ser Leu Gln Ala Ala Ile Lys Thr Leu Arg Lys Ser Ile Gly Arg Gln
            580                 585                 590
Gln Phe Tyr Val Gln Val Ser Gly Thr Glu Tyr Glu Val Ala Gln Arg
        595                 600                 605
Pro Ala Lys Ala Leu Glu Gly Gln Gly Ala Cys Gly Ala Gly Gln Val
    610                 615                 620
Leu Gln Asp Ser Lys Cys Val Ala Cys Gly Pro Gly Thr His Phe Gly
625                 630                 635                 640
Gly Glu Leu Gly Gln Cys Val Pro Cys Met Pro Gly Thr Tyr Gln Asp
                645                 650                 655
Met Glu Gly Gln Leu Ser Cys Thr Pro Cys Pro Ser Ser Asp Gly Leu
            660                 665                 670
Gly Leu Pro Gly Ala Arg Asn Val Ser Glu Cys Gly Gly Gln Cys Ser
        675                 680                 685
Pro Gly Phe Phe Ser Ala Asp Gly Phe Lys Pro Cys Gln Ala Cys Pro
    690                 695                 700
Val Gly Thr Tyr Gln Pro Glu Pro Gly Arg Thr Gly Cys Phe Pro Cys
705                 710                 715                 720
Gly Gly Gly Leu Leu Thr Lys His Glu Gly Thr Thr Ser Phe Gln Asp
                725                 730                 735
Cys Glu Ala Lys Val His Cys Ser Pro Gly His His Tyr Asn Thr Thr
            740                 745                 750
Thr His Arg Cys Ile Arg Cys Pro Val Gly Thr Tyr Gln Pro Glu Phe
        755                 760                 765
```

```
Gly Gln Asn His Cys Ile Thr Cys Pro Gly Asn Thr Ser Thr Asp Phe
        770                 775                 780

Asp Gly Ser Thr Asn Val Thr His Cys Lys Asn Gln His Cys Gly Gly
785                 790                 795                 800

Glu Leu Gly Asp Tyr Thr Gly Tyr Ile Glu Ser Pro Asn Tyr Pro Gly
                805                 810                 815

Asp Tyr Pro Ala Asn Ala Glu Cys Val Trp His Ile Ala Pro Pro Pro
            820                 825                 830

Lys Arg Arg Ile Leu Ile Val Val Pro Glu Ile Phe Leu Pro Ile Glu
        835                 840                 845

Asp Glu Cys Gly Asp Val Leu Val Met Arg Lys Ser Ala Ser Pro Thr
    850                 855                 860

Ser Ile Thr Thr Tyr Glu Thr Cys Gln Thr Tyr Glu Arg Pro Ile Ala
865                 870                 875                 880

Phe Thr Ser Arg Ser Arg Lys Leu Trp Ile Gln Phe Lys Ser Asn Glu
                885                 890                 895

Gly Asn Ser Gly Lys Gly Phe Gln Val Pro Tyr Val Thr Tyr Asp Glu
            900                 905                 910

Asp Tyr Gln Gln Leu Ile Glu Asp Ile Val Arg Asp Gly Arg Leu Tyr
        915                 920                 925

Ala Ser Glu Asn His Gln Glu Ile Leu Lys Asp Lys Lys Leu Ile Lys
    930                 935                 940

Ala Leu Phe Asp Val Leu Ala His Pro Gln Asn Tyr Phe Lys Tyr Thr
945                 950                 955                 960

Ala Gln Glu Ser Lys Glu Met Phe Pro Arg Ser Phe Ile Lys Leu Leu
                965                 970                 975

Arg Ser Lys Val Ser Arg Phe Leu Arg Pro Tyr Lys
            980                 985

<210> SEQ ID NO 346
<211> LENGTH: 98
<212> TYPE: PRT
<213> ORGANISM: Homo sapiens

<400> SEQUENCE: 346

Asp Gly Asn Ser Thr Arg Ser Pro Glu Thr Asn Gly Leu Leu Cys Gly
1               5                   10                  15

Asp Pro Glu Glu Asn Cys Ala Ala Thr Thr Thr Gln Ser Lys Arg Lys
            20                  25                  30

Gly His Phe Ser Arg Cys Pro Lys Gln Tyr Lys His Tyr Cys Ile Lys
        35                  40                  45

Gly Arg Cys Arg Phe Val Val Ala Glu Gln Thr Pro Ser Cys Val Pro
    50                  55                  60

Leu Arg Lys Arg Arg Lys Arg Lys Lys Glu Glu Glu Met Glu Thr
65                  70                  75                  80

Leu Gly Lys Asp Ile Thr Pro Ile Asn Glu Asp Ile Glu Glu Thr Asn
                85                  90                  95

Ile Ala

<210> SEQ ID NO 347
<211> LENGTH: 98
<212> TYPE: PRT
<213> ORGANISM: Homo sapiens

<400> SEQUENCE: 347

Lys Pro Val Ser Leu Ser Tyr Arg Cys Pro Cys Arg Phe Phe Glu Ser
1               5                   10                  15
```

```
His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys Gly Arg Arg Glu Glu Lys Val Gly Lys Lys Glu Lys
65                  70                  75                  80

Ile Gly Lys Lys Lys Arg Gln Lys Lys Arg Lys Ala Ala Gln Lys Arg
            85                  90                  95

Lys Asn

<210> SEQ ID NO 348
<211> LENGTH: 142
<212> TYPE: PRT
<213> ORGANISM: Homo sapiens

<400> SEQUENCE: 348

Val Gln Glu Ala Thr Pro Leu Gly Pro Ala Ser Ser Leu Pro Gln Ser
1               5                   10                  15

Phe Leu Leu Lys Cys Leu Glu Gln Val Arg Lys Ile Gln Gly Asp Gly
            20                  25                  30

Ala Ala Leu Gln Glu Lys Leu Ala Gly Cys Leu Ser Gln Leu His Ser
        35                  40                  45

Gly Leu Phe Leu Tyr Gln Gly Leu Leu Gln Ala Leu Glu Gly Ile Ser
    50                  55                  60

Pro Glu Leu Gly Pro Thr Leu Asp Thr Leu Gln Leu Asp Val Ala Asp
65                  70                  75                  80

Phe Ala Thr Thr Ile Trp Gln Gln Met Glu Glu Leu Gly Met Ala Pro
            85                  90                  95

Ala Leu Gln Pro Thr Gln Gly Ala Met Pro Ala Phe Ala Ser Ala Phe
            100                 105                 110

Gln Arg Arg Ala Gly Gly Val Leu Val Ala Ser His Leu Gln Ser Phe
            115                 120                 125

Leu Glu Val Ser Tyr Arg Val Leu Arg His Leu Ala Gln Pro
    130                 135                 140
```